United States Patent [19]

Covacci

[11] Patent Number: 5,928,865
[45] Date of Patent: Jul. 27, 1999

[54] **COMPOSITIONS COMPRISING ISOLATED *HELICOBACTER PYLORI* CAGI POLYNUCLEOTIDES AND METHOD OF PREPARATION THEREOF**

[75] Inventor: Antonello Covacci, Siena, Italy

[73] Assignee: Chiron S.p.A., Italy

[21] Appl. No.: 08/477,451

[22] Filed: Jun. 7, 1995

Related U.S. Application Data

[62] Continuation-in-part of application No. 08/425,194, Apr. 20, 1995, abandoned, and application No. 08/471,491, Jun. 6, 1995, which is a division of application No. 08/256,848, filed as application No. PCT/EP93/00472, Mar. 2, 1993, abandoned, and application No. PCT/EP93/00158, Jan. 25, 1993, abandoned.

[30] Foreign Application Priority Data

Mar. 2, 1992 [IT] Italy ................................ FI92A0052

[51] Int. Cl.⁶ ..................................................... C12Q 1/68
[52] U.S. Cl. ............................. 435/6; 435/7.32; 536/23.1
[58] Field of Search ...................... 435/7.32, 6; 536/23.1

[56] References Cited

U.S. PATENT DOCUMENTS 5,403,924  4/1995  Cover et al. ........................... 536/23.1
5,527,678  6/1996  Blaser et al. ............................... 435/6

FOREIGN PATENT DOCUMENTS

| | | | |
|---|---|---|---|
| WO 90/040300 | 4/1990 | WIPO . | |
| 93/18150 | 9/1993 | WIPO ............................ | C12N 15/31 |
| WO 93/18150 | 9/1993 | WIPO . | |

OTHER PUBLICATIONS

Austin et al., *J. Bacteriology* (1992) 174:7470–7473.
Blaser, M. J., *Gastroenterology* (1987) 93:371–383.
Blaser, M. J., *Clinical Infect. Diseases* (1992) 15:386–393.
Covacci, A., *Proc. Natl. Acad. Sci.* (1993) 90:5791–5795.
Cover et al., *J. Bact. Chem.* (1992) 267:10570–10575.
Cover et al., *J. Clin. Invest.* (1992) 90:913–918.
Cussac et al., *J. Bacteriology* (1992) 174:2466–2473.
Dooley et al., *New Eng. J. Med.* (1989) 321:1562–66.
Drumm et al., *New Eng. J. Med.* (1990) 322:359–363.
Dunn et al., *Infect. Immun.* (1992) 60:1946–1951.
Evans et al., *Infect. Immun.* (1992) 60:2125–2127.
Goodwin et al., *Int. J. Syst. Bacteriol.* (1989) 39:397–405.
Graham et al. *New Eng. J. Med.* (1991) 100:1495–1501.
Graham et al. *Digestive Diseases and Sciences* (1991) 36:1084–1088.
Jones et., *J. Med. Microbiol.* (1986) 22:57–62.
Leunk, R.D., *Rev. of Infect. Dis.* (1991) 13:5686–89.
Leying et al., *Mol. Microbiol.* (1992) 6:2873–74.
Morris et al., *N.Z. Med. J.* (1986) 99:657–59.
Parsonnet et al., *New Eng. J. Med.* (1991) 325:1127–31.
Perez–Perez et al., *J. Infect. Immun.* (1992) 60:3658–3663.
Telford et al., *J. Exp. Med.* (1994) 179:1653–58.
Telford et al., *TibTech* (1994) 12:420–426.
Thomas, et al., *Lancet* (1992) 340:1194–1195.
Tummuru, et al., *Infect. Immun.* (1993) 61:1799–1809.
Warren, et al., Lancet (1983) vol. I:1273–75.
Orkin, S H et al, Dec. 7, 1995, Report and Recomemend. of the Panel to Assess the NIH Investment in Res. on Gene Therapy, 1995.
Covacci, A et al, Jun., Proc. Nat'l Acad. Sci, USA, vol. 90(12) pp. 5791–5795, 1993.
Xiang, Z et al, Eur. J. Clin. Microbiol. Infect. Dis Oct., pp. 739–745, vol. 12(10), 1993.
Infection & Immun, vol. (61) (5), May Tummuru et al, pp. 1799–1809, 1993.
Tummuru et al, Mol. Microbiol, vol. 18(5), pp. 867–876, 1995.

*Primary Examiner*—James C. Housel
*Assistant Examiner*—Ginny Allen Portner
*Attorney, Agent, or Firm*—Woodcock, Washburn, Kurtz, Mackiewicz & Norris; Alisa A. Harbin; Robert P. Blackburn

[57] ABSTRACT

*Helicobacter pylori* is known to cause or be a cofactor in type B gastritis, peptic ulcers, and gastric tumors. In both developed and developing countries, a high percentage of people are infected with this bacterium. The present invention relates generally to a certain *H. pylori* region located 5' to the CagA gene locus, to proteins encoded thereby, and to the use of these genes and proteins for diagnostic and vaccine applications.

6 Claims, 120 Drawing Sheets

```
                            T
                            s
      M  M              M   p
      b  b              b   5
      o  o              o   0
      I  I              I   9
      I  I              I   I
   TTTGTTCAGTGATTTCGCCTTCCATTTCTTCTTCTATGAAGTCCAATTCTTCTTTCAGTT
 1 ------------+----------+----------+----------+----------+---------- 60
   AAACAAGTCACTAAAGCGGAAGGTAAAGAAGAAGATACTTCAGGTTAAGAAGAAAGTCAA a     F  V  Q  *  F  R  L  P  F  L  L  L  *  S  P  I  L  L  S  V  -
b      L  F  S  D  F  A  F  H  H  F  F  F  Y  E  V  Q  F  F  F  Q  F  -
c       C  S  V  I  S  P  S  I  S  S  S  M  K  S  N  S  S  F  S  S  -
 1 ------------+----------+----------+----------+----------+---------- 60
d     Q  E  T  I  E  G  E  M  E  E  E  I  F  D  L  E  E  K  L  -
e      T  *  H  N  R  R  G  N  R  R  R  H  L  G  I  R  R  E  T  -
f       K  N  L  S  K  A  K  W  K  K  K  *  S  T  W  N  K  K  *  N  -

T                                          T
   s                                          s
   p                                          p
   5                                          A5
   0                                          p0
   9                                          o9
   I                                          II
                                              /
   CAAAAAGATAATTAGAAAAACTATCCAAAATCGTCAAGACATCATTTTCAAAATTTCCAA
61 ------------+----------+----------+----------+----------+---------- 120
   GTTTTTCTATTAATCTTTTTGATAGGTTTTAGCAGTTCTGTAGTAAAAGTTTTAAAGGTT a     Q  K  D  N  *  K  N  Y  P  K  S  S  R  H  H  F  Q  N  F  Q  -
b      K  K  I  I  R  K  T  I  Q  N  R  Q  D  I  I  F  K  I  S  N  -
c       K  R  *  L  E  K  L  S  K  I  V  K  T  S  F  S  K  F  P  I  -
61 ------------+----------+----------+----------+----------+---------- 120
d     E  F  L  Y  N  S  F  S  D  L  I  T  L  V  D  N  E  F  N  G  -
e      *  F  S  L  *  F  F  *  G  F  D  D  L  C  *  K  *  F  K  W  -
f       L  F  I  I  L  F  V  I  W  F  R  *  S  M  M  K  L  I  E  L  -

T           T
   s           s
   p           p        B                    B
   5           A5       s   M                c        M          B
   0           p0       e   s                e        n          a
   9           o9       R   e                8        1          e
   I           II       I   I                3        I          I
               /                              I
   TAATTTTTGTTCACGCAAATTTTGTTTCATTTTAATACTCCTCTATTTGTTGATACATTT
121 ------------+----------+----------+----------+----------+---------- 180
    ATTAAAAACAAGTGCGTTTAAAACAAAGTAAAATTATGAGGAGATAAACAACTATGTAAA a      *  F  L  F  T  Q  I  L  F  H  F  N  T  P  L  F  V  D  T  F  -
b       N  F  C  S  R  K  F  C  F  I  L  I  L  L  Y  L  L  I  H  L  -
```

FIG. 2 – SEQUENCE 1 – PAGE 1

```
c         I  F  V  H  A  N  F  V  S  F  *  Y  S  S  I  C  *  Y  I  C  -
   121   ---------+---------+---------+---------+---------+---------+ 180
d         I  I  K  T  *  A  F  K  T  E  N  *  Y  E  E  I  Q  Q  Y  M  -
e         Y  N  K  N  V  C  I  K  N  *  K  L  V  G  R  N  T  S  V  N  -
f         L  K  Q  E  R  L  N  Q  K  M  K  I  S  R  *  K  N  I  C  K  -

T
                  H                                             s
           B   C a           B                                  p
           s   vHeS          s               B                  5
           m   iaIt          a               a                  0
           A   JeIu          B               e                  9
           I   IIII          I               I                  I
                 ///
          GTCTCAAGGCCTGATATTTATCTATGATACTATGGTTTTGGATAATCTTATCAATTTCTT
   181   ---------+---------+---------+---------+---------+---------+ 240
          CAGAGTTCCGGACTATAAATAGATACTATGATACCAAAACCTATTAGAATAGTTAAAGAA a         V  S  R  P  D  I  Y  L  *  Y  Y  G  F  G  *  S  Y  Q  F  L  -
b         S  Q  G  L  I  F  I  Y  D  T  M  V  L  D  N  L  I  N  F  F  -
c         L  K  A  *  Y  L  S  M  I  L  W  F  W  I  I  L  S  I  S  L  -
   181   ---------+---------+---------+---------+---------+---------+ 240
d         Q  R  L  A  Q  Y  K  D  I  I  S  H  N  Q  I  I  K  D  I  E  -
e         T  E  L  G  S  I  *  R  H  Y  *  P  K  P  Y  D  *  *  N  R  -
f         D  *  P  R  I  N  I  *  S  V  I  T  K  S  L  R  I  L  K  K  -

T                                  T
                          s                                  s
             A            p                                  p
             l            A5            S                    5    M
             w            p0            s          B         0    s
             N            o9            p          s         9    e
             I            II            I          m         I    I
                                                   I
                           /
          TGACAAATACAGTATCTGTGGATAAAATTTTCAAATATTCTTTAGGAATGCCTCTCAAAT
   241   ---------+---------+---------+---------+---------+---------+ 300
          ACTGTTTATGTCATAGACACCTATTTTAAAAGTTTATAAGAAATCCTTACGGAGAGTTTA a         *  Q  I  Q  Y  L  W  I  K  F  S  N  I  L  *  E  C  L  S  N  -
b         D  K  Y  S  I  C  G  *  N  F  Q  I  F  F  R  N  A  S  Q  I  -
c         T  N  T  V  S  V  D  K  I  F  K  Y  S  L  G  M  P  L  K  L  -
   241   ---------+---------+---------+---------+---------+---------+ 300
d         K  V  F  V  T  D  T  S  L  I  K  L  Y  E  K  P  I  G  R  L  -
e         Q  C  I  C  Y  R  H  I  F  N  E  F  I  R  *  S  H  R  E  F  -
f         S  L  Y  L  I  Q  P  Y  F  K  *  I  N  K  L  F  A  E  *  I  -

T
                           t
                           h
                           Cl
              M    B    F  vl   B         M         B              B
              n    f    o  il   c         n         s              f
              l    a    k  JI   c         l         m              a
              I    I    I  II   I         I         F              I
                                                    I
                              /
          TAAAActagcgataaCGCTAGGGCTTCCATCCTGTTTGTAGAGGATTTTCCTATCTAGTC
   301   ---------+---------+---------+---------+---------+---------+ 360
          ATTTTgatcgctattGCGATCCCGAAGGTAGGACAAACATCTCCTAAAAGGATAGATCAG a         *  N  *  R  *  R  *  G  F  H  P  V  C  R  G  F  S  Y  L  V  -
b         K  T  S  D  N  A  R  A  S  I  L  F  V  E  D  F  P  I  *  S  -
c         K  L  A  I  T  L  G  L  P  S  C  L  *  R  I  F  L  S  S  P  -
   301   ---------+---------+---------+---------+---------+---------+ 360
d         N  F  S  A  I  V  S  P  S  G  D  Q  K  Y  L  I  K  R  D  L  -
e         *  F  *  R  Y  R  *  P  K  W  G  T  Q  L  P  N  E  *  R  T  -
f         L  V  L  S  L  A  L  A  E  M  R  N  T  S  S  K  G  I  *  D  -
```

FIG.2-SEQUENCE1-PAGE2

```
                    T
                    s
                    p
             D      A5           M             C             P             C
             d      p0           a             v             B f           j
             e      o9           e             i             s l           e
             I      II           I             J             l M           P
                                 I             I             II            I
                    /                                        /
      CCTTAGTGATGATTTCAAATTCTTTTTCTGTAACATTAGCCAATCTTTGGTAATCAGAAA
361   ---------+---------+---------+---------+---------+---------+ 420
      GGAATCACTACTAAAGTTTAAGAAAAAGACATTGTAATCGGTTAGAAACCATTAGTCTTT a        P  *  *  *  F  Q  I  L  F  L  *  H  *  P  I  F  G  N  Q  K  -
b          L  S  D  D  F  K  F  F  F  C  N  I  S  Q  S  L  V  I  R  K  -
c             L  V  M  I  S  N  S  F  S  V  T  L  A  N  L  W  *  S  E  R  -
      361   ---------+---------+---------+---------+---------+---------+ 420
d        G  K  T  I  I  E  F  E  K  E  T  V  N  A  L  R  Q  Y  D  S  -
e           G  *  H  H  N  *  I  R  K  R  Y  C  *  G  I  K  P  L  *  F  -
f              R  L  S  S  K  L  N  K  K  Q  L  M  L  W  D  K  T  I  L  F  -

C
                              B                  j
                              c                  e
                              c                  P
                              I                  I
      GATTGCCCCCATCGTTTCTCAAAAAAATCTTTGTAGGGCATTGTTCTCTAATCGTATCAG
421   ---------+---------+---------+---------+---------+---------+ 480
      CTAACGGGGGTAGCAAAGAGTTTTTTTAGAAACATCCCGTAACAAGAGATTAGCATAGTC a        D  C  P  H  R  F  S  K  K  S  L  *  G  I  V  L  *  S  Y  Q  -
b           I  A  P  I  V  S  Q  K  N  L  C  R  A  L  F  S  N  R  I  S  -
c              L  P  P  S  F  L  K  K  I  F  V  G  H  C  S  L  I  V  S  A  -
      421   ---------+---------+---------+---------+---------+---------+ 480
d        L  N  G  G  D  N  R  L  F  I  K  T  P  C  Q  E  R  I  T  D  -
e           S  Q  G  W  R  K  E  F  F  D  K  Y  P  M  T  R  *  D  Y  *  -
f              I  A  G  M  T  E  *  F  F  R  Q  L  A  N  N  E  L  R  I  L  -

S
             C  C     S  a
             a  v     f  u  D              H
             c  i     a  3  p              i             P
             8  J     N  A  n              n             l
             I  I     I  I  I              f             e
                                           I             I
      CAATAGGGCAAGCCAAAAGATCAGTGATGCTTTGAGTCGCAAGTCTGACAATAGCGTTTC
481   ---------+---------+---------+---------+---------+---------+ 540
      GTTATCCCGTTCGGTTTTCTAGTCACTACGAAACTCAGCGTTCAGACTGTTATCGCAAAG a        Q  *  G  K  P  K  D  Q  *  C  F  E  S  Q  V  *  Q  *  R  F  -
b           N  R  A  S  Q  K  I  S  D  A  L  S  R  K  S  D  N  S  V  S  -
c              I  G  Q  A  K  R  S  V  M  L  *  V  A  S  L  T  I  A  F  L  -
      481   ---------+---------+---------+---------+---------+---------+ 540
d        A  I  P  C  A  L  L  D  T  l  S  Q  T  A  L  R  V  I  A  N  -
e           C  Y  P  L  G  F  S  *  H  H  K  S  D  C  T  Q  C  Y  R  K  -
f              L  L  A  L  W  F  I  L  S  A  K  L  R  L  D  S  L  L  T  E  -

N                           S
             C           l        B                  a  C
             v           aN       s                  u  jD       A     S
             i           Is       m                  3  ep       l     s
             R           Ip       A                  A  Pn       w     p
             I           II       I                  I  II       I     I
                         /                                /
      TTTTCCTTGCAGTTTTTAGCATGTCTCTTACAAAATAAGCGACCTTTGGATcgcTAAATA
541   ---------+---------+---------+---------+---------+---------+ 600
      AAAAGGAACGTCAAAAATCGTACAGAGAATGTTTTATTCGCTGGAAACCTAgcgATTTAT
```

FIG.2-SEQUENCE1-PAGE3

```
a      F  S  L  Q  F  L  A  C  L  L  Q  N  K  R  P  L  D  R  *  I  -
b       F  P  C  S  F  *  H  V  S  Y  K  I  S  D  L  W  I  A  K  Y -
c        F  L  A  V  F  S  M  S  L  T  K  *  A  T  F  G  S  L  N  I -
   541 ----------+----------+----------+----------+----------+----------+ 600
d      R  K  R  A  T  K  L  M  D  R  V  F  Y  A  V  K  P  D  S  F  -
e       K  E  K  C  N  K  A  H  R  K  C  F  L  R  G  K  S  R  *  I -
f        K  G  Q  L  K  *  C  T  E  *  L  I  L  S  R  Q  I  A  L  Y-
```

```
         E
       c S  C                    C              B
       o c  v           D  j  F                 s              M
       R r  i           d  e  o           B  c  r              n
       I F  J           e  P  k           c  c  D              l
       I I  I           I  I  I           I  I                 I
         TTTCCAGGCTTCATCAATATCTAAGACAAATCTACGCCCATCCATTGCCTCTTGGATACG
   601 ----------+----------+----------+----------+----------+----------+ 660
         AAAGGTCCGAAGTAGTTATAGATTCTGTTTAGATGCGGGTAGGTAACGGAGAACCTATGC
```

```
a      F  P  G  F  I  N  I  *  D  K  S  T  P  I  H  C  L  L  D  T  -
b       F  Q  A  S  S  I  S  K  T  N  L  R  P  S  I  A  S  W  I  R -
c        S  R  L  H  Q  Y  L  R  Q  I  Y  A  H  P  L  P  L  G  Y  E -
   601 ----------+----------+----------+----------+----------+----------+ 660
d      I  E  L  S  *  *  Y  R  L  C  I  *  A  W  G  N  G  R  P  Y  -
e       N  G  P  K  M  L  I  *  S  L  D  V  G  M  W  Q  R  K  S  V -
f        K  W  A  E  D  I  D  L  V  F  R  R  G  D  M  A  E  Q  I  R-
```

```
                                                  D           C     B
                                                  d           j     c
                                                  e           e     c
                                                  I           I     I
         AGCGAAAAGGTAAAAACAAATAAAgggCGAAACATCATTATTGtctAAGAAACTTGACCC
   661 ----------+----------+----------+----------+----------+----------+ 720
         TCGCTTTTCCATTTTTGTTTATTTcccGCTTTGTAGTAATAACagaTTCTTTGAACTGGG
```

```
a      S  E  K  V  K  T  N  K  G  R  N  I  I  I  V  *  E  T  *  P  -
b       A  K  R  *  K  Q  I  K  G  E  T  S  L  L  S  K  K  L  D  P -
c        R  K  G  K  N  K  *  R  A  K  H  H  Y  C  L  R  N  L  T  H -
   661 ----------+----------+----------+----------+----------+----------+ 720
d      S  R  F  P  L  F  L  Y  L  A  F  C  *  *  Q  R  L  F  K  V  -
e       L  S  F  T  T  F  V  F  L  P  R  F  M  M  I  T  *  S  V  Q  G -
f        A  F  L  Y  F  C  I  F  P  S  V  D  N  N  D  L  F  S  S  G-
```

```
                         S
                         a
                         u            D             C             C
                C  D     3  D         j             v
                j  d     A  p         e             i
                e  e     I  n         P             J
                I  I        I         I             I
         ATCAACGCCAATAATCGTTTTTGAAAAATCTAAGCGAtctGTTGCTTTATTATCAAAAAG
   721 ----------+----------+----------+----------+----------+----------+ 780
         TAGTTGCGGTTATTAGCAAAAACTTTTTAGATTCGCTagaCAACGAAATAATAGTTTTTC
```

```
a      I  N  A  N  N  R  F  *  K  I  *  A  I  C  C  F  I  I  K  K  -
b       S  T  P  I  I  V  F  E  K  S  K  R  S  V  A  L  L  S  K  S -
c        Q  R  Q  *  S  F  L  K  N  L  S  D  L  L  L  Y  Y  Q  K  A -
   721 ----------+----------+----------+----------+----------+----------+ 780
d      W  *  R  W  Y  D  N  K  F  F  R  L  S  R  N  S  *  *  *  F  -
e       M  L  A  L  L  R  K  Q  F  I  *  A  I  Q  Q  K  I  I  L  F -
f        D  V  G  I  I  T  K  S  F  D  L  R  D  T  A  K  N  D  F  L-
```

```
             T
             s
             p                               H
        H    A5          C      C            Ha   M  MT HT  M    C
        p    p0          j      v            he   w  wh hh  w    v
                         e      i                               i
```

FIG.2-SEQUENCE1-PAGE4

```
                    h  o9              P          R              aI  o  oa aa     o   J
                    I  II              I          I              II  I  II II    I   I
                     /                                                   /
                    CCATTGAAATTCACCATTGGTTGATTTGCAAAAAGGCGCTAATCGCgCGACAAgcccATT
             781    ----------+---------+----------+---------+---------+----------+  840
                    GGTAACTTTAAGTGGTAACCAACTAAACGTTTTTCCGCGATTAGCGcGCTGTTcgggTAA a              P  L  K  F  T  I  G  *  F  A  K  R  R  *  S  R  D  K  P  I  -
     b               H  *  N  S  P  L  V  D  L  Q  K  G  A  N  R  A  T  S  P  L -
     c                I  E  I  H  H  W  L  I  C  K  K  A  L  I  A  R  Q  A  H  * -
             781    ----------+---------+----------+---------+---------+----------+  840
     d              A  M  S  I  *  W  Q  N  I  Q  L  F  A  S  I  A  R  C  A  W  -
     e               G  N  F  N  V  M  P  Q  N  A  F  L  R  *  D  R  S  L  G  M -
     f                W  Q  F  E  G  N  T  S  K  C  F  P  A  L  R  A  V  L  G  N -

S
                    a
                    u    D        A                  MV               B        XB   iT
                    3    p        l                  ss               c        bf   nf
                    A    n        w                  ep               c        aa   fi
                    I    I        I                  II               I        II   II
                     /                                                                 /
                    AGGATCATTGTGGTCTTTCCCGAAAGCATTAATAAGTTGAGTGATGGGATAATCTAGATT
             841    ----------+---------+----------+---------+---------+----------+  900
                    TCCTAGTAACACCAGAAAGGGCTTTCGTAATTATTCAACTCACTACCCTATTAGATCTAA a              R  I  I  V  V  F  P  E  S  I  N  K  L  S  D  G  I  I  *  I  -
     b               G  S  L  W  S  F  P  K  A  L  I  S  *  V  M  G  *  S  R  F -
     c                D  H  C  G  L  S  R  K  H  *  *  V  E  *  W  D  N  L  D  S -
             841    ----------+---------+----------+---------+---------+----------+  900
     d              *  S  *  Q  P  R  E  R  F  C  *  Y  T  S  H  H  S  L  R  S  -
     e               L  I  M  T  T  K  G  S  L  M  L  L  N  L  S  P  I  I  *  I -
     f                P  D  N  H  D  K  G  F  A  N  I  L  Q  T  I  P  Y  D  L  N -

M
                                   a              B C C           H             SC
                             B     e              HsTvMa          iT       B    fv
                             b     I              hosiwc          nf       f    ai
                             v     I              aFeRo8          fi       a    NJ
                             I     I              IIIIII          II       I    II
                                                     /                            /
                    CATATTTCCTGTGATAAGGTTGGTTACTGCGCTGCAAGCGTATTAGAATCTGCTAGGCTA
             901    ----------+---------+----------+---------+---------+----------+  960
                    GTATAAAGGACACTATTCCAACCAATGACGCGACGTTCGCATAATCTTAGACGATCCGAT a              H  I  S  C  D  K  V  G  Y  C  A  A  S  V  L  E  S  A  R  L  -
     b               I  F  P  V  I  R  L  V  T  A  L  Q  A  Y  *  N  L  L  G  * -
     c                Y  F  L  *  *  G  W  L  L  R  C  K  R  I  R  I  C  *  A  K -
             901    ----------+---------+----------+---------+---------+----------+  960
     d              E  Y  K  R  H  Y  P  Q  N  S  R  Q  L  R  I  L  I  Q  *  A  -
     e               *  I  E  Q  S  L  T  P  *  Q  A  A  L  T  N  S  D  A  L  S -
     f                M  N  G  T  I  L  N  T  V  A  S  C  A  Y  *  F  R  S  P  * -

D
                                                                   d
                                                                   e
                                                                   I
                    AAAGAGATGCTGTTGCCATTTTCATCTTTTTCATCGCTTTTAGTTGCTAAGTTTTTCACA
             961    ----------+---------+----------+---------+---------+----------+  1020
                    TTTCTCTACGACAACGGTAAAAGTAGAAAAAGTAGCGAAAATCAACGATTCAAAAAGTGT a              K  E  M  L  L  P  F  S  S  F  S  S  L  L  V  A  K  F  F  T  -
     b               K  R  C  C  H  F  H  L  F  H  R  F  *  L  L  S  F  S  Q  -
     c                R  D  A  V  A  I  F  I  F  F  I  A  F  S  C  *  V  F  H  K -
             961    ----------+---------+----------+---------+---------+----------+  1020
     d              L  L  S  A  T  A  M  K  M  K  K  M  A  K  L  Q  *  T  K  *  -
```

FIG.2-SEQUENCE1-PAGE5

```
e         F  S  I  S  N  G  N  E  D  K  E  D  S  K  T  A  L  N  K  V  -
f         F  L  H  Q  Q  W  K  *  R  K  *  R  K  *  N  S  L  K  E  C  -
                        T
                        t
                        h
             C          l           C                    C              C
             Av         l           Av                   v              v
             li         l           li                   i              i
             uJ         I           uJ                   R              R
             II                     II                   I              I
             /                      /
          AGCTCTTTGACAACAGAAATAGCTGTTTGTTTTTGCTCCATTGTTGCATTTGTTTTTTGC
    1021  ----------+----------+----------+----------+----------+---------- 1080
          TCGAGAAACTGTTGTCTTTATCGACAAACAAAAACGAGGTAACAACGTAAACAAAAAACG a         S  S  L  T  T  E  I  A  V  C  F  C  S  I  V  A  F  V  F  C  -
b         A  L  *  Q  Q  K  *  L  F  V  F  A  P  L  L  H  L  F  F  A  -
c            L  F  D  N  R  N  S  C  L  F  L  L  H  C  C  I  C  F  L  H  -
    1021  ----------+----------+----------+----------+----------+---------- 1080
d         L  S  K  S  L  L  F  L  Q  K  N  K  S  W  Q  Q  M  Q  K  K     -
e            L  E  K  V  V  S  I  A  T  Q  K  Q  E  M  T  A  N  T  K  Q  -
f               A  R  Q  C  C  F  Y  S  N  T  K  A  G  N  N  C  K  N  K  A  -
                                    T
                                    t
                                    h
          C BU                B     l                              C
          vAsb    M           sM    l                    B    Av
          icoa    w           ms    l                    f    li
          JiFJ    o           Fe    I                    a    uJ
          IIII    I           II    I                    I    II
          //                                             /
          ACACAAGCCGCCCAAGCAAAAGGATTTAATCCTGTATCTGTCCCTAGCTCAATCTTGACA
    1081  ----------+----------+----------+----------+----------+---------- 1140
          TGTGTTCGGCGGGTTCGTTTTCCTAAATTAGGACATAGACAGGGATCGAGTTAGAACTGT a         T  Q  A  A  Q  A  K  G  F  N  P  V  S  V  P  S  S  I  L  T     -
b         H  K  P  P  K  Q  K  D  L  I  L  Y  L  S  L  A  Q  S  *  H     -
c            T  S  R  P  S  K  R  I  *  S  C  I  C  P  *  L  N  L  D  I  -
    1081  ----------+----------+----------+----------+----------+---------- 1140
d         C  V  L  R  G  L  L  L  I  *  D  Q  I  Q  G  *  S  L  K  S     -
e            V  C  A  A  W  A  F  P  N  L  G  T  D  T  G  L  E  I  K  V  -
f               C  L  G  G  L  C  F  S  K  I  R  Y  R  D  R  A  *  D  Q  C  -
                            B             T              H
                            s             Sa             Ha
                            r             sq             he
                            D             pI             aI
                            I             II             II
          TACTCCCCACCCATTGCGACAATATTCCCATAAGCGCCATAATCTTTATCCATATAAACC
    1141  ----------+----------+----------+----------+----------+---------- 1200
          ATGAGGGGTGGGTAACGCTGTTATAAGGGTATTCGCGGTATTAGAAATAGGTATATTTGG a         Y  S  P  P  I  A  T  I  F  P  *  A  P  *  S  L  S  I  *  T     -
b         T  P  H  P  L  R  Q  Y  S  H  K  R  H  N  L  Y  P  Y  K  P     -
c            L  P  T  H  C  D  N  I  P  I  S  A  I  I  F  I  H  I  N  H  -
    1141  ----------+----------+----------+----------+----------+---------- 1200
d         M  S  G  V  W  Q  S  L  I  G  M  L  A  M  I  K  I  W  I  F     -
e            Y  E  G  G  M  A  V  I  N  G  Y  A  G  Y  D  K  D  M  Y  V  -
f               V  G  W  G  N  R  C  Y  E  W  L  R  W  L  R  *  G  Y  L  G  -
          T                                    T              T
          t                                    s              s
          h                                    pB             p
          l
```

FIG.2-SEQUENCE 1-PAGE 6

```
         1   Av                              5s         5
         1   li                              0m         0
         I   uJ                              9F         9
         I   II                              II         I
                /
        ATAGTGAGCTTTTGCTTGTCTTTGCTGACATTAGCAGGAAAATTATAGGCAAATTGTCCC
   1201 ----------+----------+----------+----------+----------+----------+ 1260
        TATCACTCGAAAACGAACAGAAACGACTGTAATCGTCCTTTTAATATCCGTTTAACAGGG a       I  V  S  F  C  L  S  L  L  T  L  A  G  K  L  *  A  N  C  P  -
b       *  *  A  F  A  C  L  C  *  H  *  Q  E  N  Y  R  Q  I  V  P  -
c          S  E  L  L  L  V  F  A  D  I  S  R  K  I  I  G  K  L  S  H -
   1201 ----------+----------+----------+----------+----------+----------+ 1260
d       W  L  S  S  K  S  T  K  A  S  M  L  L  F  I  I  P  L  N  D  -
e          M  T  L  K  Q  K  D  K  S  V  N  A  P  F  N  Y  A  F  Q  G -
f             Y  H  A  K  A  Q  R  Q  Q  C  *  C  S  F  *  L  C  I  T  G -

H
                                          g  BB                 C
                                          iAssM                 v
                                          Egars                 i
                                          IeWFp                 J
                                          IIIII                 I
                                             ///
        ATAGCGTTCAAGGTCATTGACATAAACACTGTCTTACCTGAACCGGTTGAGCCAAGTATC
   1261 ----------+----------+----------+----------+----------+----------+ 1320
        TATCGCAAGTTCCAGTAACTGTATTTGTGACAGAATGGACTTGGCCAACTCGGTTCATAG a       I  A  F  K  V  I  D  I  N  T  V  L  P  E  P  V  E  P  S  I  -
b       *  R  S  R  S  L  T  *  T  L  S  Y  L  N  R  L  S  Q  V  S  -
c          S  V  Q  G  H  *  H  K  H  C  L  T  *  T  G  *  A  K  Y  Q -
   1261 ----------+----------+----------+----------+----------+----------+ 1320
d       W  L  T  *  P  *  Q  C  L  C  Q  R  V  Q  V  P  Q  A  L  Y  -
e          M  A  N  L  T  M  S  M  F  V  T  K  G  S  G  T  S  G  L  I -
f             Y  R  E  L  D  N  V  Y  V  S  D  *  R  F  R  N  L  W  T  D -

E           N
                           C      D     c          1
                           Av     r     o          aNC
                    C      li     d     5          Isj
                    j      uJ     I     7          Ipe
                    e      II     I     I          III
                    I       /                       /
        AAAGTGTGTCCTGCTGAAGCTGAACCAAAATCAGTGGGCATGTGGAAGTTCAGATAAAAA
   1321 ----------+----------+----------+----------+----------+----------+ 1380
        TTTCACACAGGACGACTTCGACTTGGTTTTAGTCACCCGTACACCTTCAAGTCTATTTTT a       K  V  C  P  A  E  A  E  P  K  S  V  G  M  W  K  F  R  *  K  -
b       K  C  V  L  L  K  L  N  Q  N  Q  W  A  C  G  S  S  D  K  K  -
c          S  V  S  C  *  S  *  T  K  I  S  G  H  V  E  V  Q  I  K  R -
   1321 ----------+----------+----------+----------+----------+----------+ 1380
d       *  L  T  D  Q  Q  L  Q  V  L  I  L  P  C  T  S  T  *  I  F  -
e          L  T  H  G  A  S  A  S  G  F  D  T  P  M  H  F  N  L  Y  F -
f             F  H  T  R  S  F  S  F  W  F  *  H  A  H  P  L  E  S  L  F -

T
        s      S
        p      a
        5      u   D  H                                                C
        0      3   p  g                                                j
        9      A   n  a                                                e
        I      I   I  I                                                P
                                                                       I
        GGCGAATTGATCTCGCTTTTTAgcgTCATCACACTATTGCCCCAAGCGTTATTCTCTTGA
   1381 ----------+----------+----------+----------+----------+----------+ 1440
        CCGCTTAACTAGAGCGAAAAATcgcAGTAGTGTGATAACGGGGTTCGCAATAAGAGAACT
```

FIG.2-SEQUENCE1-PAGE7

```
a       G  E  L  I  S  L  F  S  V  I  T  L  L  P  Q  A  L  F  S  *   -
b        A  N  *  S  R  F  L  A  S  S  H  Y  C  P  K  R  Y  S  L  D  -
c          R  I  D  L  A  F  *  R  H  H  T  I  A  P  S  V  I  L  L  I  -
     1381 ---------+---------+---------+---------+---------+---------+ 1440
d       L  R  I  S  R  A  K  *  R  *  *  V  I  A  G  L  T  I  R  K    -
e        P  S  N  I  E  S  K  L  T  M  V  S  N  G  W  A  N  N  E  Q   -
f          A  F  Q  D  R  K  K  A  D  D  C  *  Q  G  L  R  *  E  R  S -
```

```
                                                    T
                                                    s                 M
              B                  C  C                p                a
              s  B               v  j  M  M  M       5                e
              a  c               i  e  w  s  n       0                I
              B  c               J  P  o  l  l       9                I
              I  I               I  I  I  I  I       I                I
        TTGCCATCAAAACTCATAGCCCTCATAGCGATGAAATCAGCAAAATTATTAGAAGTTACA
   1441 ---------+---------+---------+---------+---------+---------+ 1500
        AACGGTAGTTTTGAGTATCGGGAGTATCGCTACTTTAGTCGTTTTAATAATCTTCAATGT
```

```
a       L  P  S  K  L  I  A  L  I  A  M  K  S  A  K  L  L  E  V  T    -
b        C  H  Q  N  S  *  P  S  *  R  *  N  Q  Q  N  Y  *  K  L  H   -
c          A  I  K  T  H  S  P  H  S  D  E  I  S  K  I  I  R  S  Y  I -
     1441 ---------+---------+---------+---------+---------+---------+ 1500
d       I  A  M  L  V  *  L  G  *  L  S  S  I  L  L  I  I  L  L  *    -
e        N  G  D  F  S  M  A  R  M  A  I  F  D  A  F  N  N  S  T  V   -
f          Q  W  *  F  E  Y  G  E  Y  R  H  F  *  C  F  *  *  F  N  C -
```

```
                 T
                 t
                 h                                           T
                 1                                           s
                 1               B                           p                B
                 1               s                           5                b
                 I               r                           0                v
                 I               D                           9                I
                                 I                           I
        TCAAAAATAAAAGGAAGCGTGATAAAAGAGCAATGTTTGGCAAAAAAGTAATTTTCCATA
   1501 ---------+---------+---------+---------+---------+---------+ 1560
        AGTTTTTATTTTCCTTCGCACTATTTTCTCGTTACAAACCGTTTTTTCATTAAAAGGTAT
```

```
a       S  K  I  K  G  S  V  I  K  E  Q  C  L  A  K  K  *  F  S  I    -
b        Q  K  *  K  E  A  *  *  K  S  N  V  W  Q  K  S  N  F  P  *   -
c          K  N  K  R  K  R  D  K  R  A  M  F  G  K  K  V  I  F  H  R -
     1501 ---------+---------+---------+---------+---------+---------+ 1560
d       M  L  F  L  L  F  R  S  L  L  A  I  N  P  L  F  T  I  K  W    -
e        D  F  I  F  P  L  T  I  F  S  C  H  K  A  F  F  Y  N  E  M   -
f          *  F  Y  F  S  A  H  Y  F  L  L  T  Q  C  F  L  L  K  G  Y -
```

```
              B                                    BB
              sT    M  C                           M  ss  B           B        HM
              os    w  v                           s  mm  f           s        gs
              Fe    o  i                           e  AB  a           m        ae
              II    I  J                           I  II  I           I        II
                       I
                                                    /
        GAGAAAGTCGCTGCGTTGGCTAAAAAACCTTTAGCGTTAAGACTAGAGACGCATTCCTTA
   1561 ---------+---------+---------+---------+---------+---------+ 1620
        CTCTTTCAGCGACGCAACCGATTTTTTGGAAATCGCAATTCTGATCTCTGCGTAAGGAAT
```

```
a       E  K  V  A  A  L  A  K  K  P  L  A  L  R  L  E  T  H  S  L    -
b        R  K  S  L  R  W  L  K  N  L  *  R  *  D  *  R  R  I  P  *   -
c          E  S  R  C  V  G  *  K  T  F  S  V  K  T  R  D  A  F  L  N -
     1561 ---------+---------+---------+---------+---------+---------+ 1620
d       L  S  L  R  Q  T  P  *  F  V  K  L  T  L  V  L  S  A  N  R    -
e        S  F  T  A  A  N  A  L  F  G  K  A  N  L  S  S  V  C  E  K   -
f          L  F  D  S  R  Q  S  F  F  R  *  R  *  S  *  L  R  M  G  * -
```

FIG.2-SEQUENCE1-PAGE8

```
                                           T   t
                                           s   h
                  C                        p   l
                  Av                       5   1
                  li                       0   1
                  uJ                       9   I
                  II                       I   I
                  /
      ACGCTTTGTTTCATTTTTTCAAAGCTATCAGCAAACAGCACTAAAGAATTACCATAACTG
1621  ----------+----------+----------+----------+----------+----------+ 1680
      TGCGAAACAAAGTAAAAAAGTTTCGATAGTCGTTTGTCGTGATTTCTTAATGGTATTGAC a       T  L  C  F  I  F  S  K  L  S  A  N  S  T  K  E  L  P  *  L   -
b        R  F  V  S  F  F  Q  S  Y  Q  Q  T  A  L  K  N  Y  H  N  C  -
c         A  L  F  H  F  F  K  A  I  S  K  Q  H  *  R  I  T  I  T  A -
1621  ----------+----------+----------+----------+----------+----------+ 1680
d       L  A  K  N  *  K  K  L  A  I  L  L  C  C  *  L  I  V  M  V   -
e        V  S  Q  K  M  K  E  F  S  D  A  F  L  V  L  S  N  G  Y  S  -
f         R  K  T  E  N  K  *  L  *  *  C  V  A  S  F  F  *  W  L  Q -

T
                             T                                  t
                             s                                  h   N
                 B           p                                  l   l
          B  H   c           5                                  l   a
          f  p   e           0                                  I   I
          a  h   8           9                                  I   I
          I  I   3           I
      CCTAGCGTAATATCACCATTACCCACTAATTCGCTCAAGCAACCTAAAGTCATGCCCTGT
1681  ----------+----------+----------+----------+----------+----------+ 1740
      GGATCGCATTATAGTGGTAATGGGTGATTAAGCGAGTTCGTTGGATTTCAGTACGGGACA a       P  S  V  I  S  P  L  P  T  N  S  L  K  Q  P  K  V  M  P  C   -
b        L  A  *  Y  H  H  Y  P  L  I  R  S  S  N  L  K  S  C  P  V  -
c         *  R  N  I  T  I  I  H  *  F  A  Q  A  T  *  S  H  A  L  F -
1681  ----------+----------+----------+----------+----------+----------+ 1740
d       A  *  R  L  I  V  M  V  W  *  N  A  *  A  V  *  L  *  A  R   -
e        G  L  T  I  D  G  N  G  V  L  E  S  L  C  G  L  T  M  G  Q  -
f         R  A  Y  Y  *  W  *  G  S  I  R  E  L  L  R  F  D  H  G  T -

T
                         s
          C      M       p                     C
          v      bM      5    M   XB           vB   H         MD
          i      on      0    n   bf           is   p         sr
          J      Il      9    l   aa           Jr   h         ea
          I      II      I    I   II           II   I         II
      TCTTTAGAGCCTCCACTAATAATAATTCTTCTAGAGGTGAAAGCCAGTTTGTCCTTTAAA
1741  ----------+----------+----------+----------+----------+----------+ 1800
      AGAAATCTCGGAGGTGATTATTATTAAGAAGATCTCCACTTTCGGTCAAACAGGAAATTT a       S  L  E  P  P  L  I  I  I  L  L  E  V  K  A  S  L  S  F  K   -
b        L  *  S  L  H  *  *  *  F  F  *  R  *  K  P  V  C  P  L  K  -
c         F  R  A  S  T  N  N  N  S  S  R  G  E  S  Q  F  V  L  *  N -
1741  ----------+----------+----------+----------+----------+----------+ 1800
d       N  K  L  A  E  V  L  L  L  E  E  L  P  S  L  W  N  T  R  *   -
e        E  K  S  G  G  S  I  I  I  R  R  S  T  F  A  L  K  D  K  L  -
f         R  *  L  R  W  *  Y  Y  N  K  *  L  H  F  G  T  Q  G  K  F -

T
                        N  N           s
                     C  Cl 1           p
                     a  vaNNaS         A5             B
                     c  iIssIp         p0             f
                     8  RIipIh         o9             a
                     I  IIIIII         II             I
```

FIG.2-SEQUENCE1-PAGE9

```
                        / / /       /
            ACCTGTGAGTTTTTAGGCGAATAAGCATGCATGAAAATAAATTCGCTGTCTAGGGCGTTG
      1801  ----------+----------+----------+----------+----------+----------+ 1860
            TGGACACTCAAAAATCCGCTTATTCGTACGTACTTTTATTTAAGCGACAGATCCCGCAAC a         T  C  E  F  L  G  E  *  A  C  M  K  I  N  S  L  S  R  A  L   -
    b          P  V  S  F  *  A  N  K  H  A  *  K  *  I  R  C  L  G  R  * -
    c           L  *  V  F  R  R  I  S  M  H  E  N  K  F  A  V  *  G  V  D -
      1801  ----------+----------+----------+----------+----------+----------+ 1860
    d         F  R  H  T  K  L  R  I  L  M  C  S  F  L  N  A  T  *  P  T   -
    e          V  Q  S  N  K  P  S  Y  A  H  M  F  I  F  E  S  D  L  A  N  -
    f           G  T  L  K  *  A  F  L  C  A  H  F  Y  I  R  Q  R  P  R  Q -

T                             E
                              t                             c
                              h                             o
                              1                             4 H
                              1                             7Ha
                              1                             Ihe
                              I                             IaI
                              I                             III
            ATTTTATCAAACAAATCGCTTTGTGATTTAGGGGCGTATTCACTAATCTCAATAGCGCTA
      1861  ----------+----------+----------+----------+----------+----------+ 1920
            TAAAATAGTTTGTTTAGCGAAACACTAAATCCCCGCATAAGTGATTAGAGTTATCGCGAT a         I  L  S  N  K  S  L  C  D  L  G  A  Y  S  L  I  S  I  A  L   -
    b          F  Y  Q  T  N  R  F  V  I  *  G  R  I  H  *  S  Q  *  R  * -
    c           F  I  K  Q  I  A  L  *  F  R  G  V  F  T  N  L  N  S  A  K -
      1861  ----------+----------+----------+----------+----------+----------+ 1920
    d         S  K  I  L  C  I  A  K  H  N  L  P  T  N  V  L  R  L  L  A   -
    e          I  K  D  F  L  D  S  Q  S  K  P  A  Y  E  S  I  E  I  A  S  -
    f           N  *  *  V  F  R  K  T  I  *  P  R  I  *  *  D  *  Y  R  * -

N
                                                  l
                        S                 M       a              H
                        s                 s       p              p
                        p                 e       l              h
                        I                 I       I              I
            AAATATTTTTCACTCAAATCGTCATTTAAGATTTTTCCATGCTTATTGGCAAAATAAACT
      1921  ----------+----------+----------+----------+----------+----------+ 1980
            TTTATAAAAGTGAGTTTAGCAGTAAATTCTAAAAAGGTACGAATAACCGTTTTATTTGA a         K  Y  F  S  L  K  S  S  F  K  I  F  P  C  L  L  A  K  *  T   -
    b          N  I  F  H  S  N  R  H  L  R  F  F  H  A  Y  W  Q  N  K  L  -
    c           I  F  F  T  Q  I  V  I  *  D  F  S  M  L  I  G  K  I  N  F -
      1921  ----------+----------+----------+----------+----------+----------+ 1980
    d         L  I  N  K  V  *  I  T  M  *  S  K  E  M  S  I  P  L  I  F   -
    e          F  Y  K  E  S  L  D  D  N  L  I  K  G  H  K  N  A  F  Y  V  -
    f           F  I  K  *  E  F  R  *  K  L  N  K  W  A  *  Q  C  F  L  S -

N                             B
                        Cl                            c   C
                        vaN                           e   v
                        iIs                           8   i
                        RIi                           3   R
                        III                           I   I
                              /
            TCTTTCACCCCACCATGCATTTTTTCCTTGAGATACAAGTCTTTTCGGTTGCAAATAAAA
      1981  ----------+----------+----------+----------+----------+----------+ 2040
            AGAAAGTGGGGTGGTACGTAAAAAAGGAACTCTATGTTCAGAAAAGCCAACGTTTATTTT a         S  F  T  P  P  C  I  F  S  L  R  Y  K  S  F  R  L  Q  I  K   -
    b          L  S  P  H  H  A  F  F  P  *  D  T  S  L  F  G  C  K  *  K  -
    c           F  H  P  T  M  H  F  F  L  E  I  Q  V  F  S  V  A  N  K  R -
      1981  ----------+----------+----------+----------+----------+----------+ 2040
```

FIG.2-SEQUENCE 1-PAGE 10

```
d        K  K  *  G  V  M  C  K  K  K  R  S  I  C  T  K  E  T  A  F  L   -
e           E  K  V  G  G  H  M  K  E  K  L  Y  L  D  K  R  N  C  I  F   -
f              R  E  G  W  W  A  N  K  G  Q  S  V  L  R  K  P  Q  L  Y  F -

T
                                    T       T t
                                    s       s h
                  C                 p       p 1
                  v                 5       A 5 1                C
                  i                 0       p 0 1                j
                  J                 9       o 9 I                e
                  I                 I       I I I                I
                                    //
           GGGGCTTCATTCATTCCCAaAAGAAAATTGTAAAATTCGCATTGTTTGGAGTAAATAACG
     2041  ----------+---------+---------+---------+---------+---------+  2100
           CCCCGAAGTAAGTAAGGGTtTTCTTTTAACATTTTAAGCGTAACAAACCTCATTTATTGC a          G  A  S  F  I  P  K  R  K  L  *  N  S  H  C  L  E  *  I  T   -
b           G  L  H  S  F  P  K  E  N  C  K  I  R  I  V  W  S  K  *  R   -
c              G  F  I  H  S  Q  K  K  I  V  K  F  A  L  F  G  V  N  N  A -
     2041  ----------+---------+---------+---------+---------+---------+  2100
d          L  P  K  M  *  E  W  F  F  I  T  F  N  A  N  N  P  T  F  L   -
e           P  A  E  N  M  G  L  L  F  N  Y  F  E  C  Q  K  S  Y  I  V   -
f              P  S  *  E  N  G  F  S  F  Q  L  I  R  M  T  Q  L  L  Y  R -

A
                                        M      C          c
              B              C M    B   b      A v    E S e
              c              j s    f   o      l i    a a I
              c              e e    a   I      u J    r p I
              I              I I    I          I I    I I I
                              /                /       /
           CCATCTTTAGTGTATTCTTTTAATCTAGTGGGGTGGTATTTGCTCAACAGCTCTTCTATG
     2101  ----------+---------+---------+---------+---------+---------+  2160
           GGTAGAAATCACATAAGAAAATTAGATCACCCCACCATAAACGAGTTGTCGAGAAGATAC a          P  S  L  V  Y  S  F  N  L  V  G  W  Y  L  L  N  S  S  S  M   -
b           H  L  *  C  I  L  L  I  *  W  G  G  I  C  S  T  A  L  L  *   -
c              I  F  S  V  F  F  *  S  S  G  V  V  F  A  Q  Q  L  F  Y  E -
     2101  ----------+---------+---------+---------+---------+---------+  2160
d          A  M  K  L  T  N  K  *  D  L  P  T  T  T  N  A  *  C  S  K  * -
e           G  D  K  T  Y  E  K  L  R  T  P  H  Y  K  S  L  L  E  E  I   -
f              W  R  *  H  I  R  K  I  *  H  P  P  I  Q  E  V  A  R  R  H -

B
              s
           A  p              H
           C1B1              i
           Avwa2S            n   C    C
           1i2n8a            d   A v  v              M
           uJ1I6c            I   l i  i              b        X      E
           IIIIII            I   u J  J              o        m      a
            / ///            I   I I  I              I        n      r
               /                                                     I
           AGCTCTATCCTATCCTTGAAGTTTTCAAGCTTGGCTCTAATAATCCTTTGAAACTCTTCA
     2161  ----------+---------+---------+---------+---------+---------+  2220
           TCGAGATAGGATAGGAACTTCAAAAGTTCGAACCGAGATTATTAGGAAACTTTGAGAAGT a          S  S  I  L  S  L  K  F  S  S  L  A  L  I  I  L  *  N  S  S   -
b           A  L  S  Y  P  *  S  F  Q  A  W  L  *  *  S  F  E  T  L  Q   -
c              L  Y  P  I  L  E  V  F  K  L  G  S  N  N  P  L  K  L  F  K -
     2161  ----------+---------+---------+---------+---------+---------+  2220
d          S  S  *  G  I  R  S  T  K  L  S  P  E  L  L  G  K  F  S  K   -
e           L  E  I  R  D  K  F  N  E  L  K  A  R  I  I  R  Q  F  E  E   -
f              A  R  D  *  G  Q  L  K  *  A  Q  S  *  Y  D  K  S  V  R  * -

T
```

FIG.2-SEQUENCE 1-PAGE 11

```
                    s
                    p                    c                              B
                    5                    v                              s
                    0                    i                              c
                    9                    R                              G
                    I                    I                              I
         AAATTATTGTCTGCAAAATGCTTTTTATTCATAACGGGTTCATTGAGAGTGTCTAATAAA
    2221 ----------+---------+---------+---------+---------+---------+ 2280
         TTTAATAACAGACGTTTTACGAAAAATAAGTATTGCCCAAGTAACTCTCACAGATTATTT a        K  L  L  S  A  K  C  F  L  F  I  T  G  S  L  R  V  S  N  K   -
b         N  Y  C  L  Q  N  A  F  Y  S  *  R  V  H  *  E  C  L  I  N  -
c          I  I  V  C  K  M  L  F  I  H  N  G  F  I  E  S  V  *  *  I -
    2221 ----------+---------+---------+---------+---------+---------+ 2280
d        L  I  I  T  Q  L  I  S  K  I  *  L  P  N  M  S  L  T  *  Y   -
e         F  N  N  D  A  F  H  K  K  N  M  V  P  E  N  L  T  D  L  L  -
f          F  *  Q  R  C  F  A  K  *  E  Y  R  T  *  Q  S  H  R  I  F -

TCTTGCTCTATGGTCAGAAAAAAACTAATATCATAAAAACTTTCTCTCTTTTGCTTCTCA
    2281 ----------+---------+---------+---------+---------+---------+ 2340
         AGAACGAGATACCAGTCTTTTTTTGATTATAGTATTTTTGAAAGAGAGAAAACGAAGAGT a        S  C  S  M  V  R  K  K  L  I  S  *  K  L  S  L  F  C  F  S   -
b         L  A  L  W  S  E  K  N  *  Y  H  K  N  F  L  S  F  A  S  H  -
c          L  L  Y  G  Q  K  K  T  N  I  I  K  T  F  S  L  L  L  L  I -
    2281 ----------+---------+---------+---------+---------+---------+ 2340
d        I  K  S  *  P  *  F  F  V  L  I  M  F  V  K  E  R  K  S  R   -
e         D  Q  E  I  T  L  F  F  S  I  D  Y  F  S  E  R  K  Q  K  E  -
f          R  A  R  H  D  S  F  F  *  Y  *  L  F  K  R  E  K  A  E  *-

N
              C  C         l                B              P
              v  a         a                s              s
              i  c         I                m              h
              J  8         I                F              A
              I  I         I                I              I
         TTATAGGCTCGCATGAAATCATTAGAAAAAATAAGACCATAGTCCCTATTGCTTTCATCA
    2341 ----------+---------+---------+---------+---------+---------+ 2400
         AATATCCGAGCGTACTTTAGTAATCTTTTTTATTCTGGTATCAGGGATAACCAAAGTAGT a        L  *  A  R  M  K  S  L  E  K  I  R  P  *  S  L  L  V  S  S   -
b         Y  R  L  A  *  N  H  *  K  K  *  D  H  S  P  Y  W  F  H  Q  -
c          I  G  S  H  E  I  I  R  K  N  K  T  I  V  P  I  G  F  I  N -
    2341 ----------+---------+---------+---------+---------+---------+ 2400
d        M  I  P  E  C  S  I  M  L  F  F  L  V  M  T  G  I  P  K  M   -
e         N  Y  A  R  M  F  D  N  S  F  I  L  G  Y  D  R  N  T  E  D  -
f          *  L  S  A  H  F  *  *  F  F  Y  S  W  L  G  *  Q  N  *  *-

T     T              T
                                     s     s         M    s
                                     p     Ep        a    p
                              M      A5    Ac5       e    A5
                              s      p0    po0       I    p0
                              e      o9    oR9       I    o9
                              I      II    III       I    II
                                         /   //              /
         ATAACGATTTTCTTTTTAATAGTGTGAAAATAGAATTTGAATTCAGGGGTAACAAAATTC
    2401 ----------+---------+---------+---------+---------+---------+ 2460
         TATTGCTAAAAGAAAAATTATCACACTTTTATCTTAAACTTAAGTCCCCATTGTTTTAAG a        I  T  I  F  F  L  I  V  *  K  *  N  L  N  S  G  V  T  K  F   -
b         *  R  F  S  F  *  *  C  E  N  R  I  *  I  Q  G  *  Q  N  S  -
c          N  D  F  L  F  N  S  V  K  I  E  F  E  F  R  G  N  K  I  P -
    2401 ----------+---------+---------+---------+---------+---------+ 2460
d        L  L  S  K  R  K  L  L  T  F  I  S  N  S  N  L  P  L  L  I   -
e         I  V  I  K  K  R  I  T  H  F  Y  F  K  F  E  P  T  V  F  N  -
```

FIG.2-SEQUENCE 1-PAGE 12

FIG. 2 - SEQUENCE 1 - PAGE 13

```
f         Y   R   N   E   K   *   Y   H   S   F   L   I   Q   I   *   P   Y   C   F   E  -
                                  M               S
                              C   a               BB  a                           C
                              j   e               gs  Du                          j M
                              e   I               lt  p3                          e s
                              P   I               IY  nA                          P e
                              I   I               II  II                          I I
                                                  //                              /
          CTAAAAACGCTATAAATAGAAGCGTGTAACTCTATGAGATCTTTTTTGGAAGTGGTTAAA
     2461 ----------+---------+---------+---------+---------+---------+ 2520
          GATTTTTGCGATATTTATCTTCGCACATTGAGATACTCTAGAAAAAACCTTCACCAATTT a         L   K   T   L   *   I   E   A   C   N   S   M   R   S   F   L   E   V   V   K  -
b         *   K   R   Y   K   *   K   R   V   T   L   *   D   L   F   W   K   W   L   K  -
c             K   N   A   I   N   R   S   V   *   L   Y   E   I   F   F   G   S   G   *   K -
     2461 ----------+---------+---------+---------+---------+---------+ 2520
d         G   L   F   A   I   F   L   L   T   Y   S   *   S   I   K   K   P   L   P   *  -
e         R   F   V   S   Y   I   S   A   H   L   E   I   L   D   K   K   S   T   T   L  -
f             *   F   R   *   L   Y   F   R   T   V   R   H   S   R   K   Q   F   H   N   F -

T
              s
              p
              5
              0                                                       S
              9                                           H           a
              I                                           p           u   D
                                                          h           3   p
                                                          I           A   n
                                                                      I   I
          AAATCAATGCCCCCCAATTTGATTGTGCCTAAAAGAGAATAGTTGTTAGTAAGGATCACC
     2521 ----------+---------+---------+---------+---------+---------+ 2580
          TTTAGTTACGGGGGGTTAAACTAACACGGATTTTCTCTTATCAACAATCATTCCTAGTGG a         K   S   M   P   P   N   L   I   V   P   K   R   E   *   L   L   V   R   I   T  -
b         N   Q   C   P   P   I   *   L   C   L   K   E   N   S   C   *   *   G   S   P  -
c             I   N   A   P   Q   F   D   C   A   *   K   R   I   V   V   S   K   D   H   P -
     2521 ----------+---------+---------+---------+---------+---------+ 2580
d         F   I   L   A   G   W   N   S   Q   A   *   F   L   I   T   T   L   L   S   *  -
e         F   D   I   G   G   L   K   I   T   G   L   L   S   Y   N   N   T   L   I   V  -
f             F   *   H   G   G   I   Q   N   H   R   F   S   F   L   Q   *   Y   P   D   G -

E
                                                                      c
                                                                      o
                                                          CB  4   H   M
          AB                                      B       vs  T7  Ha  Bb B
          lc                                      f       io  s I  he  bo b
          wc                                      a       RF  e I  al  sI v
          II                                      I       II  I II I   II I
                                                          /       /
          CCATCATCTAAAAAACATTCATAGTTATTTGCTAGATAGGAGTTTGCAGCGCTCACAAGT
     2581 ----------+---------+---------+---------+---------+---------+ 2640
          GGTAGTAGATTTTTTGTAAGTATCAATAAACGATCTATCCTCAAACGTCGCGAGTGTTCA a         F   S   S   K   K   H   S   *   L   F   A   R   *   E   F   A   A   L   T   S  -
b         H   H   L   K   N   I   H   S   Y   L   L   D   R   S   L   Q   R   S   Q   V  -
c             I   I   *   K   T   F   I   V   I   C   *   I   G   V   C   S   A   H   K   S -
     2581 ----------+---------+---------+---------+---------+---------+ 2640
d         G   M   M   *   F   V   N   M   T   I   Q   *   I   P   T   Q   L   A   *   L  -
e         G   D   D   L   F   C   E   Y   N   N   A   L   Y   S   N   A   A   S   V   L  -
f             W   *   R   F   F   M   *   L   *   K   S   S   L   L   K   C   R   E   C   T -

T
          t
          h                                                                           N
          1                                         C                   C             1
          1                   M                     v F                 B v           a
```

FIG.2-SEQUENCE 1-PAGE 14

```
b              A  Q  *  Q  S  L  Q  S  K  Q  V  H  R  L  E  K  E  *  Q  I  -
c              H  N  N  N  R  Y  N  Q  N  R  F  I  G  L  K  K  N  N  R  *  -
     2821    ---------+---------+---------+---------+---------+---------+ 2880
d              L  C  L  L  L  R  *  L  *  F  L  N  M  P  K  F  F  F  L  L  -
e              L  V  I  V  I  A  V  I  L  V  P  E  Y  A  Q  F  L  I  V  S  -
f              A  C  Y  C  D  S  C  D  F  C  T  *  L  S  S  F  S  Y  C  I  -

T
                                              t
                    M                         h
                    a                         l
                    e              M          l
                    I              n          I
                    I              l          I
                    I              I          I
             AATACAATGGTTACAAACAATATAAATATAGAGGAATAAATAAAAGTTTCAGGGAAACCA
     2881    ---------+---------+---------+---------+---------+---------+ 2940
             TTATGTTACCAATGTTTGTTATATTTATATCTCCTTATTTATTTTCAAAGTCCCTTTGGT a              N  T  M  V  T  N  N  I  N  I  E  E  *  I  K  V  S  G  K  P  -
b              I  Q  W  L  Q  T  I  *  I  *  R  N  K  *  K  F  Q  G  N  Q  -
c              Y  N  G  Y  K  Q  Y  K  Y  R  G  I  N  K  S  F  R  E  T  K  -
     2881    ---------+---------+---------+---------+---------+---------+ 2940
d              Y  Y  L  P  *  L  C  Y  L  Y  L  P  I  F  L  L  K  L  S  V  -
e              L  V  I  T  V  F  L  I  F  I  S  S  Y  I  F  T  E  P  F  G  -
f              I  C  H  N  C  V  I  Y  I  Y  L  F  L  Y  F  N  *  P  F  W  -

T                    T
                        t                    t
                        h                    h                         N
                        l                    l              C          l
                        l  B                 l  MD          v          a
                        l  c                 l  st          i          I
                        I  c                 I  ea          R          I
                        I  I                 II I           I          I
             AACAACCTATTCCCCCCATCAAACAAGACTTTAAAAAAGGGATTGACACCCTTTTGCATG
     2941    ---------+---------+---------+---------+---------+---------+ 3000
             TTGTTGGATAAGGGGGGTAGTTTGTTCTGAAATTTTTTCCCTAACTGTGGGAAAACGTAC a              N  N  L  F  P  P  S  N  K  T  L  K  K  G  L  T  P  F  C  M  -
b              T  T  Y  S  P  H  Q  T  R  L  *  K  R  D  *  H  P  F  A  C  -
c              Q  P  I  P  P  I  K  Q  D  F  K  K  G  I  D  T  L  L  H  V  -
     2941    ---------+---------+---------+---------+---------+---------+ 3000
d              L  C  G  I  G  G  M  L  C  S  K  L  F  P  I  S  V  R  K  C  -
e              F  L  R  N  G  G  D  F  L  V  K  F  F  P  N  V  G  K  Q  M  -
f              V  V  *  E  G  W  *  V  L  S  *  F  L  S  Q  C  G  K  A  H  -

T
                                                                        s
                        M                        BU                     p
                   N    b  M                     Asb              M     5
                   s    o  s                     coa              n     0
                   p    I  e                     iFJ              l     9
                   I    I  I                     III              I     I
                   /                             //
             TCTGCTTTAAGTTCTTCTATTTTTTGAAACTGCCGCTTTTGAACCTCTTGCTCTATAATT
     3001    ---------+---------+---------+---------+---------+---------+ 3060
             AGACGAAATTCAAGAAGATAAAAAACTTTGACGGCGAAAACTTGGAGAACGAGATATTAA a              S  A  L  S  S  S  I  F  *  N  C  R  F  *  T  S  C  S  I  I  -
b              L  L  *  V  L  L  F  F  E  T  A  A  F  E  P  L  A  L  *  L  -
c              C  F  K  F  F  Y  F  L  K  L  P  L  L  N  L  L  L  Y  N  *  -
     3001    ---------+---------+---------+---------+---------+---------+ 3060
d              T  Q  K  L  N  K  *  K  K  F  S  G  S  K  F  R  K  S  *  L  -
e              D  A  K  L  E  E  I  K  Q  F  Q  R  K  Q  V  E  Q  E  I  I  -
f              R  S  *  T  R  R  N  K  S  V  A  A  K  S  G  R  A  R  Y  N  -
```

FIG.2-SEQUENCE 1-PAGE 15

```
                    T  T                              T
                    t  t                              t
                    h  h                              h
           C        1  1  C C    C    C               1
           A v      1  1  v a    a    a               M 1
           l i      1  1  i c    c    c               n l
           u J      I  I  J 8    8    8               l I
           I I      I  I  I I    I    I               I I
                 /                                 /
              AGCTTTTTTTGTTCATCAGCCTGCTTGCTTGCCACAAACACCTCTCTCTTTATAGATATA
       3061 ----------+----------+----------+----------+----------+----------+ 3120
              TCGAAAAAAACAAGTAGTCGGACGAACGAACGGTGTTTGTGGAGAGAGAAATATCTATAT a         S  F  F  C  S  S  A  C  L  L  A  T  N  T  S  L  F  I  D  I  -
    b          A  F  F  V  H  Q  P  A  C  L  P  Q  T  P  L  S  L  *  I  Y -
    c           L  F  L  F  I  S  L  L  A  C  H  K  H  L  S  L  Y  R  Y  T -
       3061 ----------+----------+----------+----------+----------+----------+ 3120
    d         *  S  K  K  N  M  L  R  S  A  Q  W  L  C  R  E  R  *  L  Y  -
    e          L  K  K  Q  E  D  A  Q  K  S  A  V  F  V  E  R  K  I  S  I -
    f           A  K  K  T  *  *  G  A  Q  K  G  C  V  G  R  E  K  Y  I  Y -

B
                         s
                   A p   N
                   f L   l
           A       l U   a N             B       H
           c       l I   I s             s  P    i
           i       l I   I p             m  l    n
           I       I I   I I             A  e    f
                                         I  I    I
                      /  /
              CCGCTTCACATGTAATCGTATAAAAGATTTTTTTGAGAGACTCTACGGTGCTAATATGTT
       3121 ----------+----------+----------+----------+----------+---------- 3180
              GGCGAAGTGTACATTAGCATATTTTCTAAAAAAACTCTCTGAGATGCCACGATTATACAA a         P  L  H  M  *  S  Y  K  R  F  F  *  E  T  L  R  C  *  Y  V  -
    b          R  F  T  C  N  R  I  K  D  F  F  E  R  L  Y  G  A  N  M  F -
    c           A  S  H  V  I  V  *  K  I  F  L  R  D  S  T  V  L  I  C  F -
       3121 ----------+----------+----------+----------+----------+---------- 3180
    d         V  A  E  C  T  I  T  Y  F  I  K  K  L  S  E  V  T  S  I  H  -
    e          G  S  *  M  Y  D  Y  L  L  N  K  Q  S  V  R  R  H  *  Y  T -
    f           R  K  V  H  L  R  I  F  S  K  K  S  L  S  *  P  A  L  I  N -

T
           S          S               s             H
           a          a               p            G C a           B
           u  D       u  D      A 5   Edve          c
           3  p       3  p      1 0   a i i I       e
           A  n       A  n      w 9   e I J I       f
           I  I       I  I      I I   I I I I       I
                                  /  /
              TCAAAAGATCATTAGGATCATAAGAATTGAATACGGCCAATAAAACATTATATAACTTAT
       3181 ----------+----------+----------+----------+----------+----------+ 3240
              AGTTTTCTAGTAATCCTAGTATTCTTAACTTATGCCGGTTATTTTGTAATATATTGAATA a         S  K  D  H  *  D  H  K  N  *  I  R  P  I  K  H  Y  I  T  Y  -
    b          Q  K  I  I  R  I  I  R  I  E  Y  G  Q  *  N  I  I  *  L  I -
    c           K  R  S  L  G  S  *  E  L  N  T  A  N  K  T  L  Y  N  L  S -
       3181 ----------+----------+----------+----------+----------+----------+ 3240
    d         K  L  L  D  N  P  D  Y  S  N  F  V  A  L  L  V  N  Y  L  K  -
    e          E  F  S  *  *  S  *  L  F  Q  I  R  G  I  F  C  *  I  V  * -
    f           *  F  I  M  L  I  M  L  I  S  Y  P  W  Y  F  M  I  Y  S  I -

T
                        T                                     t
                        t                                     h
                        s
```

FIG.2-SEQUENCE 1-PAGE 16

```
                                  p                              B  l  B              S
                                  A5                             s  l  sT       B     f
                                  p0             A  T  H         r  l  os       b     a
                                  o9             c  h  h         i  I  Fe       v     N
                                  II             i  a  a         I  I  II       I     I
                                                 I  I  I         /
                     CATCGCATAGAATTTCTCTTGTTTCTCCGCGCAATGACAGAAAGCAGCGTTGTTTGTTGG
              3241   ----------+----------+----------+----------+----------+----------+ 3300
                     GTAGCGTATCTTAAAGAGAACAAAGAGGCGCGTTACTGTCTTTCGTCGCAACAAACAACC a           H  R  I  E  F  L  L  F  L  R  A  M  T  E  S  S  V  V  C  W   -
         b             I  A  *  N  F  S  C  F  S  A  Q  *  Q  K  A  A  L  F  V  G -
         c               S  H  R  I  S  L  V  S  P  R  N  D  R  K  Q  R  C  L  L  V-
              3241   ----------+----------+----------+----------+----------+----------+ 3300
         d           D  D  C  L  I  E  R  T  E  G  R  L  S  L  F  C  R  Q  K  N   -
         e             *  R  M  S  N  R  K  N  R  R  A  I  V  S  L  L  T  T  Q  Q -
         f               M  A  Y  F  K  E  Q  K  E  A  C  H  C  F  A  A  N  N  T  P-

T
                                        E                                   s
                                        c                       S           p
                                        o                       a           5
                                        5                       u  D        0
                                        7                       3  p        9
                                        I                       A  n        I
                                                                I  I        I
                     TCGTGCTGATGCTTTTGAAAGTAAAAAAGTCTTTCACTTCAGGATTGATCTGTAATTCTA
              3301   ----------+----------+----------+----------+----------+----------+ 3360
                     AGCACGACTACGAAAACTTTCATTTTTTCAGAAAGTGAAGTCCTAACTAGACATTAAGAT a           S  C  *  C  F  *  K  *  K  S  L  S  L  Q  D  *  S  V  I  L   -
         b             R  A  D  A  F  E  S  K  K  V  F  H  F  R  I  D  L  *  F  Y -
         c               V  L  M  L  L  K  V  K  K  S  F  T  S  G  L  I  C  N  S  T-
              3301   ----------+----------+----------+----------+----------+----------+ 3360
         d           T  T  S  I  S  K  F  T  F  F  D  K  V  E  P  N  I  Q  L  E   -
         e             D  H  Q  H  K  Q  F  Y  F  L  R  E  S  *  S  Q  D  T  I  R -
         f               R  A  S  A  K  S  L  L  F  T  K  *  K  L  I  S  R  Y  N  *-

S
                                                           a
                                                           u  DD        A
                                                           3  sp        l
                                                           A  rn        w
                                                           I  II        I
                                                                /
                     CATTCAATCCCATTTCCTTACCCTTTTCATCAAAGATTTTTTCAATAACTGGATCGTAAT
              3361   ----------+----------+----------+----------+----------+----------+ 3420
                     GTAAGTTAGGGTAAAGGAATGGGAAAAGTAGTTTCTAAAAAAGTTATTGACCTAGCATTA a           H  S  I  P  F  P  Y  P  F  H  Q  R  F  F  Q  *  L  D  R  N   -
         b             I  Q  S  H  F  L  T  L  F  I  K  D  F  F  N  N  W  I  V  M -
         c               F  N  P  I  S  L  P  F  S  S  K  I  F  S  I  T  G  S  *  C-
              3361   ----------+----------+----------+----------+----------+----------+ 3420
         d           V  N  L  G  M  E  K  G  K  E  D  F  I  K  E  I  V  P  D  Y   -
         e             C  E  I  G  N  G  *  G  K  *  *  L  N  K  *  Y  S  S  R  L -
         f               M  *  D  W  K  R  V  R  K  M  L  S  K  K  L  L  Q  I  T  I-

H
                                  PM          i
                                  ls          n
                                  ee          f
                                  II          I
                     GCTTCAAATCCTTTATTTTTTTAAGGACTCTATTGACAATCACGAAGTCAAAAACTTCAT
              3421   ----------+----------+----------+----------+----------+----------+ 3480
                     CGAAGTTTAGGAAATAAAAAAATTCCTGAGATAACTGTTAGTGCTTCAGTTTTTGAAGTA a           A  S  N  P  L  F  F  *  G  L  Y  *  Q  S  R  S  Q  K  L  H
```

FIG.2-SEQUENCE1-PAGE17

```
       b         L  Q  I  L  Y  F  F  K  D  S  I  D  N  H  E  V  K  N  F  I   -
       c          F  K  S  F  I  F  L  R  T  L  L  T  I  T  K  S  K  T  S  S  -
              3421 ---------+---------+---------+---------+---------+---------+ 3480
       d          H  K  L  D  K  I  K  K  L  V  R  N  V  I  V  F  D  F  V  E   -
       e          A  E  F  G  K  N  K  *  P  S  *  Q  C  D  R  L  *  F  S  *   -
       f           S  *  I  R  *  K  K  L  S  E  I  S  L  *  S  T  L  F  K  M  -

T
                                         M                      s
                                         a                      p
                                         e                      A5
                                         I                      p0
                                         I                      o9
                                         I                      II
                                                                 /
                  CTTTGATAATATCGGGATTGACTTCTTTGAAAGTTACTTTCTTGTCTTTCAAATTTTTGA
              3481 ---------+---------+---------+---------+---------+---------+ 3540
                  GAAACTATTATAGCCCTAACTGAAGAAACTTTCAATGAAAGAACAGAAAGTTTAAAAACT a          L  *  *  Y  R  D  *  L  L  *  K  L  L  S  C  L  S  N  F  *   -
       b           F  D  N  I  G  I  D  F  F  E  S  Y  F  L  V  F  Q  I  F  D  -
       c            L  I  I  S  G  L  T  S  L  K  V  T  F  L  S  F  K  F  L  I -
              3481 ---------+---------+---------+---------+---------+---------+ 3540
       d          D  K  I  I  D  P  N  V  E  K  F  T. V  K  K  D  K  L  N  K   -
       e           R  Q  Y  Y  R  S  Q  S  R  Q  F  N  S  E  Q  R  E  F  K  Q  -
       f            K  S  L  I  P  I  S  K  K  S  L  *  K  R  T  K  *  I  K  S -

T
                                 s
                                 p
                                 A5      C              C
                                 p0      j              v
                                 o9      e              i
                                 II      I              J
                                                        I
                                  /
                  TAGTCGCTTTGAAACTATCAAAATCTAAATTGTATAAACAAGCCCATTGGGAGTGTTTT
              3541 ---------+---------+---------+---------+---------+---------+ 3600
                  ATCAGCGAAACTTTGATAGTTTTAGATTTAAACATATTTGTTCGGGTAACCCTCACAAAA a          *  S  L  *  N  Y  Q  N  L  N  L  Y  K  Q  A  H  W  E  C  F   -
       b           S  R  F  E  T  I  K  I  *  I  C  I  N  K  P  I  G  S  V  F  -
       c            V  A  L  K  L  S  K  S  K  F  V  *  T  S  P  L  G  V  F  F -
              3541 ---------+---------+---------+---------+---------+---------+ 3600
       d          I  T  A  K  F  S  D  F  D  L  N  T  Y  V  L  G  N  P  T  N   -
       e           Y  D  S  Q  F  *  *  F  R  F  K  Y  L  C  A  W  Q  S  H  K  -
       f            L  R  K  S  V  I  L  I  *  I  Q  I  F  L  G  M  P  L  T  K -

C
                                   C              v
                                   j              i
                                   e              J
                                   I              I
                  TTTCTTTTTCTTGTGCTTCTTTTTTGGCTTCTTTGTCATCATTTGCTAACCCATACGAAC
              3601 ---------+---------+---------+---------+---------+---------+ 3660
                  AAAGAAAAAGAACACGAAGAAAAAACCGAAGAAACAGTAGTAAACGATTGGGTATGCTTG a          F  L  F  L  V  L  L  F  W  L  L  C  H  H  L  L  T  H  T  N   -
       b           F  F  F  L  C  F  F  F  F  G  F  F  V  I  I  C  *  P  I  R  T -
       c            S  F  S  C  A  S  F  L  A  S  L  S  S  F  A  N  P  Y  E  L -
              3601 ---------+---------+---------+---------+---------+---------+ 3660
       d          K  E  K  E  Q  A  E  K  K  A  E  K  D  D  N  A  L  G  Y  S   -
       e           K  R  K  R  T  S  R  K  Q  S  R  Q  *  *  K  S  V  W  V  F  -
       f            K  K  K  K  H  K  K  K  P  K  K  T  M  M  Q  *  G  M  R  V -

B        A                 C
                           s        fM                v  D     M
```

FIG.2-SEQUENCE 1-PAGE 18

FIG.2-SEQUENCE1-PAGE19

```
                3841 ---------+---------+---------+---------+---------+---------+ 3900
            d         V  F  F  L  R  R  V  E  K  L  T  M  L  S  K  G  F  I  R  *  -
            e          R  F  V  T  A  Q  G  R  K  I  D  D  S  I  K  W  I  D  A  I -
            f           S  F  C  D  G  S  R  K  *  H  *  *  L  N  E  L  Y  G  S  H -

P
                                                f
                                                1S                  S
                              C                 1a   B         C    a
                              j        H        1u  DsP  B     j    u   D
                              e        h        03  piv  f     e    3   p
                              P        a        8A  nEu  a     P    A   n
                              I        I        II  III  I     I    I   I
                                                   /
                        CCTTTGACCCCTAAAGCGCAACCACCTACGATCGCTAGAACAGAAATGATCTGAATAACC
                3901 ---------+---------+---------+---------+---------+---------+ 3960
                        GGAAACTGGGGATTTCGCGTTGGTGGATGCTAGCGATCTTGTCTTTACTAGACTTATTGG a         P  L  T  P  K  A  Q  P  P  T  I  A  R  T  E  M  I  *  I  T  -
            b          L  *  P  L  K  R  N  H  L  R  S  L  E  Q  K  *  S  E  *  P -
            c           F  D  P  *  S  A  T  T  Y  D  R  *  N  R  N  D  L  N  N  Q -
                3901 ---------+---------+---------+---------+---------+---------+ 3960
            d         A  K  S  G  *  L  A  V  V  *  S  R  *  F  L  F  S  R  F  L  -
            e          G  K  V  G  L  A  C  G  G  V  I  A  L  V  S  I  I  Q  I  V -
            f           R  Q  G  R  F  R  L  W  R  R  D  S  S  C  F  H  D  S  Y  G -

MT
                              as                                            M
                         C    as   B         E                 B            a
                         v    ep   s         cHBS         B    As    MD     e
                         i    I4   a         ogsf         s    ci    sr     I
                         R    I5   H         Nalc         r    iE    ea     I
                         I    II   I         IIII         I    II    II     I
                             /              /            /
                        AAACCTTTAGTTGCAGTGACGCCTTCTGTAGGACTGGCGACCGCATTTAAAGGATTGGTT
                3961 ---------+---------+---------+---------+---------+---------+ 4020
                        TTTGGAAATCAACGTCACTGCGGAAGACATCCTGACCGCTGGCGTAAATTTCCTAACCAA a         K  P  L  V  A  V  T  P  S  V  G  L  A  T  A  F  K  G  L  V  -
            b          N  L  *  L  Q  *  R  L  L  *  D  W  R  P  H  L  K  D  W  L -
            c           T  F  S  C  S  D  A  F  C  R  T  G  D  R  I  *  P  I  G  C -
                3961 ---------+---------+---------+---------+---------+---------+ 4020
            d         W  V  K  L  Q  L  S  A  K  Q  L  V  P  S  R  M  *  L  I  P  -
            e          L  G  K  T  A  T  V  G  E  T  P  S  A  V  A  N  L  P  N  T -
            f           F  R  *  N  C  H  R  R  R  Y  S  Q  R  G  C  K  F  S  Q  N -

M
                                  C     a
                           B      v     e                 C      H
                           f      i     I                 Av     iT        A
                           a      J     I                 li     nf        p
                           I      I     I                 uJ     fi        o
                                                          II     II        I
                                                         /       /
                        GTTACCACTAGCCCTAAAGTTACTACAACTTTCTTGTAGCTGTCAGTGATTCTTGTAAAA
                4021 ---------+---------+---------+---------+---------+---------+ 4080
                        CAATGGTGATCGGGATTTCAATGATGTTGAAAGAACATCGACAGTCACTAAGAACATTTT a         V  T  T  S  P  K  V  T  T  T  F  L  *  L  S  V  I  L  V  K  -
            b          L  P  L  A  L  K  L  L  Q  L  S  C  S  C  Q  *  F  L  *  K -
            c           Y  H  *  P  *  S  Y  Y  N  F  L  V  A  V  S  D  S  C  K  K -
                4021 ---------+---------+---------+---------+---------+---------+ 4080
            d         Q  *  W  *  G  *  L  *  *  L  K  R  T  A  T  L  S  E  Q  L  -
            e          T  V  V  L  G  L  T  V  V  V  K  K  Y  S  D  T  I  R  T  F -
            f           N  G  S  A  R  F  N  S  C  S  E  Q  L  Q  *  H  N  K  Y  F -

T                     T
                    s          N          s                                      B
```

FIG.2-SEQUENCE1-PAGE20

```
              p         1           p                                    c
              5         a           5                                    e
              0         I           0                                    8
              9         I           9                                    3
              I                     I                                    I
              /
              AATTTCATGCGTTTCCTTTCAAATTGAAATCAATCGCTTGAGTATATCAAAAAAAAAGT
       4081   ------------+----------+----------+----------+----------+  4140
              TTAAAGTACGCAAAGGAAAGTTTAACTTTAGTTAGCGAACTCATATAGTTTTTTTTTCA a         N  F  M  R  F  L  S  N  *  N  Q  S  L  E  Y  I  K  K  K  S  -
    b          I  S  C  V  S  F  Q  I  E  I  N  R  L  S  I  S  K  K  K  V -
    c           F  H  A  P  P  F  K  L  K  S  I  A  *  V  Y  Q  K  K  K  Y-
       4081   ------------+----------+----------+----------+----------+  4140
    d         F  N  *  A  N  G  K  L  N  F  D  I  A  Q  T  Y  *  F  F  F  -
    e          F  K  M  R  K  R  E  F  Q  F  *  D  S  S  Y  I  L  F  F  L -
    f           I  E  H  T  E  K  *  I  S  I  L  R  K  L  I  D  F  F  F  T-
```

```
                                  E
                                  c
                                  o
                                  4  H            T
                                  7Ha             s
                                  Ihe             p
                                  IaI             5     MBDS                H
                                  III             0     scrw                g
                                                  9'    egaa                a
                                                  I     IIII                I
                                                        //
              ATTTTTATACTATTCATACAAGCGCTACTTTATAATTTAAATCAAAACCGACGCTTTTGC
       4141   ------------+----------+----------+----------+----------+  4200
              TAAAAATATGATAAGTATGTTCGCGATGAAATATTAAATTTAGTTTTGGCTGCGAAAACG a         I  F  I  L  F  I  Q  A  L  L  Y  N  L  N  Q  N  R  R  F  C  -
    b          F  L  Y  Y  S  Y  K  R  Y  F  I  I  *  I  K  T  D  A  F  A -
    c           F  Y  T  I  H  T  S  A  T  L  *  F  K  S  K  P  T  L  L  L-
       4141   ------------+----------+----------+----------+----------+  4200
    d         Y  K  *  V  I  *  V  L  A  V  K  Y  N  L  D  F  G  V  S  K  -
    e          I  K  I  S  N  M  C  A  S  S  *  L  K  F  *  F  R  R  K  Q -
    f           N  K  Y  *  E  Y  L  R  *  K  I  I  *  I  L  V  S  A  K  A-
```

```
                                                                B
                                           B                    c
                              B            s                    e
                              c            m                    8
                              g            F                    3
                              I            I                    I
              TCGGCAACTGACATCATTCAGGAATAGTAAACCTACTTGTCCCAACCATTTTTCTTTCTC
       4201   ------------+----------+----------+----------+----------+  4260
              AGCCGTTGACTGTAGTAAGTCCTTATCATTTGGATGAACAGGGTTGGTAAAAAGAAAGAG a         S  A  T  D  I  I  Q  E  *  *  T  Y  L  S  Q  P  F  F  F  L  -
    b          R  Q  L  T  S  F  R  N  S  K  P  T  C  P  N  H  F  S  F  S -
    c           G  N  *  H  H  S  G  I  V  N  L  L  V  P  T  I  F  L  S  Q-
       4201   ------------+----------+----------+----------+----------+  4260
    d         S  P  L  Q  C  *  E  P  I  T  F  R  S  T  G  V  M  K  R  E  -
    e          E  A  V  S  M  M  *  S  Y  Y  V  *  K  D  W  G  N  K  K  R -
    f           R  C  S  V  D  N  L  F  L  L  G  V  Q  G  L  W  K  E  K  E-
```

```
                T
                s                 S           S
                p         BB  a   Ba                              BB
                5         gsDu    suD    A            M     D     ss
                0         ltp3    t3p    l            s     d     mm
                9         IYnA    YAn    w            e     e     AB
                I         IIII    III    I            I     I     II
                         //              /
              AAGTCGTTGTAGAATTGTAGATCTTTAGGATCTTTGATGTATTTTTTAATCGTCTCAGGT
```

FIG.2-SEQUENCE1-PAGE21

```
                 4261 ----------+----------+----------+----------+----------+----------+ 4320
                      TTCAGCAACATCTTAACATCTAGAAATCCTAGAAACTACATAAAAAATTAGCAGAGTCCA
    a                  K  S  L  *  N  C  R  S  L  G  S  L  M  Y  F  L  I  V  S  G  -
    b                   S  R  C  R  I  V  D  L  *  D  L  *  C  I  F  *  S  S  Q  V  -
    c                    V  V  V  E  L  *  I  F  R  I  F  D  V  F  F  N  R  L  R  L  -
                 4261 ----------+----------+----------+----------+----------+----------+ 4320
    d                  *  T  T  T  S  N  Y  I  K  L  I  K  S  T  N  K  L  R  R  L     -
    e                   L  D  N  Y  F  Q  L  D  K  P  D  K  I  Y  K  K  I  T  E  P    -
    f                    L  R  Q  L  I  T  S  R  *  S  R  Q  H  I  K  *  D  D  *  T   -

T
                                              t
                                              h        S
                                              1   C a
                                              1   AvBuD                    C
                                              1   lic3p                    Av
                                              I   uJ1An                    li
                                              I   IIIII                    uJ
                                                    / /                    II
                                                                            /
                      TGAAACCTAAAAACAAGCAAAAACAAACCCAAGCTGATCAGAGTGAGAATAAAGCTCCAT
                 4321 ----------+----------+----------+----------+----------+----------+ 4380
                      ACTTTGGATTTTTGTTCGTTTTTGTTTGGGTTCGACTAGTCTCACTCTTATTTCGAGGTA
    a                  *  N  L  K  T  S  K  N  K  P  K  L  I  R  V  R  I  K  L  H     -
    b                   E  T  *  K  Q  A  K  T  N  P  S  *  S  E  *  E  *  S  S  I    -
    c                    K  P  K  N  K  Q  K  Q  T  Q  A  D  Q  S  E  N  K  A  P  F   -
                 4321 ----------+----------+----------+----------+----------+----------+ 4380
    d                  N  F  G  L  F  L  C  F  C  V  W  A  S  *  L  S  F  L  A  G     -
    e                   Q  F  R  F  V  L  L  F  L  G  L  S  I  L  T  L  I  F  S  W    -
    f                    S  V  *  F  C  A  F  V  F  G  L  Q  D  S  H  S  Y  L  E  M   -

C
                       M                           M                  v
                       s                           n                  i
                       e                           l                  J
                       I                           I                  I
                      TTTAAGCAACTCCATAGACCACTAAAGAAACTTTTTTTGAGGCTATCTTTGAAAATCTGT
                 4381 ----------+----------+----------+----------+----------+----------+ 4440
                      AAATTCGTTGAGGTATCTGGTGATTTCTTTGAAAAAAACTCCGATAGAAACTTTTAGACA
    a                  F  K  Q  L  H  R  P  L  K  K  L  F  L  R  L  S  L  K  I  C     -
    b                   L  S  N  S  I  D  H  *  R  N  F  F  *  G  Y  L  *  K  S  V    -
    c                    *  A  T  P  *  T  T  K  E  T  F  F  E  A  I  F  E  N  L  S   -
                 4381 ----------+----------+----------+----------+----------+----------+ 4440
    d                  N  *  A  V  G  Y  V  V  L  S  V  K  K  S  A  I  K  S  F  R     -
    e                   K  L  C  S  W  L  G  S  F  F  S  K  K  L  S  D  K  F  I  Q    -
    f                    K  L  L  E  M  S  W  *  L  F  K  K  Q  P  *  R  Q  F  D  T   -

T
                                             N        S       S                       s
                                             1  BC a          a                       p
                          C                  a  sjDu          Au D         A          M5
                          j                  I  tep3          13 p         1          s0
                          e                  I  YPnA          wA n         w          e9
                          P                  I  IIII          II I         I          II
                          I                                    /
                      CCTATTGATTTGTTTTCCATTTTGTTTCCCATGTGGATCTTGTGGATCACAAACGCTTAA
                 4441 ----------+----------+----------+----------+----------+----------+ 4500
                      GGATAACTAAACAAAAGGTAAAACAAAGGGTACACCTAGAACACCTAGTGTTTGCGAATT
    a                  P  I  D  L  F  S  I  L  F  P  M  W  I  L  W  I  T  N  A  *     -
    b                   L  L  I  C  F  P  P  F  C  F  P  C  G  S  C  G  S  Q  T  L  N -
    c                    Y  *  F  V  F  H  F  V  S  H  V  D  L  V  D  H  K  R  L  I   -
                 4441 ----------+----------+----------+----------+----------+----------+ 4500
    d                  D  *  Q  N  T  K  W  K  T  E  W  T  S  R  T  S  *  L  R  K     -
```

FIG.2-SEQUENCE1-PAGE22

```
e          G  I  S  K  N  E  M  K  N  G  M  H  I  K  H  I  V  F  A  *  -
f          R  N  I  Q  K  G  N  Q  K  G  H  P  D  Q  P  D  C  V  S  L  -

N              N                                N
           1              1                                1
           aNS            a                             H  Ma
           Isf            I                             p  wI
           Ipc            I                             h  oI
           III            I                             I  II
           //
           TTATACATGCTATAGTAAGCATGACACACAAACCAAACTATTTTTAGAACGCTTCATGTG
     4501  ----------+----------+----------+----------+----------+----------+ 4560
           AATATGTACGATATCATTCGTACTGTGTGTTTGGTTTGATAAAAATCTTGCGAAGTACAC a          L  Y  M  L  *  *  A  *  H  T  N  Q  T  I  F  R  T  L  H  V  -
b          Y  T  C  Y  S  K  H  D  T  Q  T  K  L  F  L  E  R  F  M  C  -
c             I  H  A  I  V  S  M  T  H  K  P  N  Y  F  *  N  A  S  C  A -
     4501  ----------+----------+----------+----------+----------+----------+ 4560
d          I  I  C  A  I  T  L  M  V  C  L  G  F  *  K  *  F  A  E  H  -
e          N  Y  M  S  Y  Y  A  H  C  V  F  W  V  I  K  L  V  S  *  T  -
f          *  V  H  *  L  L  C  S  V  C  V  L  S  N  K  S  R  K  M  H  -

B
           s
           Ap
           11
           w2                 B                          C  M
           28                 s                          v  b        M
           16                 a                          i  o        m
           II                 X                          R  I        e
                              I                          I  I        I
           /
           CTCACCTTGACTAACCATTTCTCCAACCATACTTTAGCGTTGCATTTGATTTCTTCAAAA
     4561  ----------+----------+----------+----------+----------+----------+ 4620
           GAGTGGAACTGATTGGTAAAGAGGTTGGTATGAAATCGCAACGTAAACTAAAGAAGTTTT a          L  T  L  T  N  H  F  S  N  H  T  L  A  L  H  L  I  S  S  K  -
b          S  P  *  L  T  I  S  P  T  I  L  *  R  C  I  *  F  L  Q  K  -
c          H  L  D  *  P  F  L  Q  P  Y  F  S  V  A  F  D  F  F  K  K  -
     4561  ----------+----------+----------+----------+----------+----------+ 4620
d          A  *  R  S  *  G  N  R  W  G  Y  K  L  T  A  N  S  K  K  L  -
e          S  V  K  V  L  W  K  E  L  W  V  K  A  N  C  K  I  E  E  F  -
f          E  G  Q  S  V  M  E  G  V  M  S  *  R  Q  M  Q  N  R  *  F  -

T           T
                                                         s           s
           H                                             p     R     p
           iT                      M                     A5    l     M5
           nf                      s                     p0    e     s0
           fi                      e                     o9    A     e9
           II                      I                     II    I     II
           /                                             /
           AGATTCATTTCTTATTTCTTGTTCTTATTAAAGTTCTTTCATTTTAGCAAATTTTTGTTA
     4621  ----------+----------+----------+----------+----------+----------+ 4680
           TCTAAGTAAAGAATAAAGAACAAGAATAATTTCAAGAAAGTAAAATCGTTTAAAAACAAT a          R  F  I  S  Y  F  L  F  L  L  K  F  F  H  F  S  K  F  L  L  -
b          D  S  F  L  I  S  C  S  Y  *  S  S  F  I  L  A  N  F  C  *  -
c             I  H  F  L  F  L  V  L  I  K  V  L  S  F  *  Q  I  F  V  N -
     4621  ----------+----------+----------+----------+----------+----------+ 4680
d          F  I  *  K  K  N  R  T  R  I  L  T  R  E  N  *  C  I  K  T  -
e          L  N  M  E  *  K  K  N  K  N  F  N  K  *  K  L  L  N  K  N  -
f             S  E  N  R  I  E  Q  E  *  *  L  E  K  M  K  A  F  K  Q  * -

S
                    H           C        B     C C    a  B       C
                    iT    B     v        s     a v H  u  DsP     v
```

FIG.2-SEQUENCE1-PAGE23

```
                            nf        f  i           a    c  i g 3 piv    i
                            fi        a  J           H    8  R a A nEu    J
                            II        I  I           I    I  I I I III    I
                           /                                 /
              ATTGTGGGTAAAAATGTGAATCGTCCTAGCCTTTAGACGCCTGCAACGATCGGGCTTTTT
    4681      ----------+----------+----------+----------+----------+----------+   4740
              TAACACCCATTTTTACACTTAGCAGGATCGGAAATCTGCGGACGTTGCTAGCCCGAAAAA a              I  V  G  K  N  V  N  R  P  S  L  *  T  P  A  T  I  G  L  F   -
b               L  W  V  K  M  *  I  V  L  A  F  R  R  L  Q  R  S  G  F  F  -
c                C  G  *  K  C  E  S  S  *  P  L  D  A  C  N  D  R  A  F  F -
    4681      ----------+----------+----------+----------+----------+----------+   4740
d              L  Q  P  Y  F  H  S  D  D  *  G  K  S  A  Q  L  S  R  A  K   -
e               I  T  P  L  F  T  F  R  G  L  R  *  V  G  A  V  I  P  S  K  -
f                N  H  T  F  I  H  I  T  R  A  K  L  R  R  C  R  D  P  K  K -
```

```
                                          T
                                          t
                                          h
                                          1
                    S MV         MV       1
                    s ss         ss       1
                    p ep         ep       I
                    I II         II       I
                    /             /
              TCAATATTAATAATGATTAATGAAAAAAAAAAAAAAATGCTTGATATTGTTGTATAATGAG
    4741      ----------+----------+----------+----------+----------+----------+   4800
              AGTTATAATTATTACTAATTACTTTTTTTTTTTTTACGAACTATAACAACATATTACTC a              S  I  L  I  M  I  N  E  K  K  K  K  C  L  I  L  L  Y  N  E   -
b               Q  Y  *  *  *  L  M  K  K  K  K  N  A  *  Y  C  C  I  M  R  -
c                N  I  N  N  D  *  *  K  K  K  K  M  L  D  I  V  V  *  *  E -
    4741      ----------+----------+----------+----------+----------+----------+   4800
d              K  L  I  L  L  S  *  H  F  F  F  F  I  S  S  I  T  T  Y  H   -
e               E  I  N  I  I  I  L  S  F  F  F  F  H  K  I  N  N  Y  L  S  -
f                *  Y  *  Y  H  N  I  F  F  F  F  F  A  Q  Y  Q  Q  I  I  L -
```

```
                              T
                         B    Ns
                         c    lp
                         e    a5
                         8    10
                         3    19
                         I    II
                         /     /
              AATGTTCAAAGACATGAATTGACTACTCAAGCGTGTAGCGATTTTTAGCAGTCTTTGACA
    4801      ----------+----------+----------+----------+----------+----------+   4860
              TTACAAGTTTCTGTACTTAACTGATGAGTTCGCACATCGCTAAAAATCGTCAGAAACTGT a              N  V  Q  R  H  E  L  T  T  Q  A  C  S  D  F  *  Q  S  L  T   -
b               M  F  K  D  M  N  *  L  L  K  R  V  A  I  F  S  S  L  *  H  -
c                C  S  K  T  *  I  D  Y  S  S  V  *  R  F  L  A  V  F  D  T -
    4801      ----------+----------+----------+----------+----------+----------+   4860
d              S  H  E  F  V  H  I  S  *  E  L  T  Y  R  N  K  A  T  K  S   -
e               F  T  *  L  C  S  N  V  V  *  A  H  L  S  K  *  C  D  K  V  -
f                I  N  L  S  M  F  Q  S  S  L  R  T  A  I  K  L  L  R  Q  C -
```

```
                                          B
                                          f
                                          a
                                          I
              CTAACAAGATACCGATAGGTATGAAACTAGGTATAGTAAGGAGAAACAATGACTAACGAA
    4861      ----------+----------+----------+----------+----------+----------+   4920
              GATTGTTCTATGGCTATCCATACTTTGATCCATATCATTCCTCTTTGTTACTGATTGCTT a              L  T  R  Y  R  *  V  *  N  *  V  *  *  G  E  T  M  T  N  E   -
```

FIG.2-SEQUENCE1-PAGE24

```
b        * Q D T D R Y E T R Y S K E K Q * L T K  -
c        N K I P I G M K L G I V R R N N D * R N  -
    4861 ---------+---------+---------+---------+---------+---------+ 4920
d        V L L I G I P I F S P I T L L F L S * R  -
e        S V L Y R Y T H F * T Y Y P S V I V L S  -
f        * C S V S L Y S V L Y L L S F C H S V F  -

T
                                     s
                  BUC          B     p    M
                  Asbv  M   A  sT   5F    b B
                  coai  s   c  os   0a    o b
                  iFJJ  e   i  Fe   9u    I v
                  IIII  I   I  II   II    I I
                   /                       /
         ACCATTGACCAACAACCACAAACCGAAGCGGCTTTTAACCCGCAGCAATTTATCAATAAT
    4921 ---------+---------+---------+---------+---------+---------+ 4980
         TGGTAACTGGTTGTTGGTGTTTGGCTTCGCCGAAAATTGGGCGTCGTTAAATAGTTATTA a        T I D Q Q P Q T E A A F N P Q Q F I N N  -
b        P L T N N H K P K R L L T R S N L S I I  -
c        H * P T T T N R S G F * P A A I Y Q * S  -
    4921 ---------+---------+---------+---------+---------+---------+ 4980
d        F W Q G V V V F R L P K * G A A I * * Y  -
e        V M S W C G C V S A A K L G C C N I L L  -
f        G N V L L W L G F R S K V R L L K D I I  -

S         S
              C                    a         B a
              Av        M          A   u  D  sBuD
              li        s          l   3  p  ac3p
              uJ        e          w   A  n  BlAn
              II        I          I   I  I  IIII
              /                                /
         CTTCAAGTAGCTTTTCTTAAAGTTGATAACGCTGTCGCTTCATACGATCCTGATCAAAAA
    4981 ---------+---------+---------+---------+---------+---------+ 5040
         GAAGTTCATCGAAAAGAATTTCAACTATTGCGACAGCGAAGTATGCTAGGACTAGTTTTT a        L Q V A F L K V D N A V A S Y D P D Q K  -
b        F K * L F L K L I T L S L H T I L I K N  -
c        S S S F S * S * * R C R F I R S * S K T  -
    4981 ---------+---------+---------+---------+---------+---------+ 5040
d        D E L L K E * L Q Y R Q R K M R D Q D F  -
e        R * T A K R L T S L A T A E Y S G S * F  -
f        K L Y S K K F N I V S D S * V I R l L F  -

H                T
                            i                s
                    Cn  C                    p
                    adAv           H         5      M
                    cIli           iT        0      s
                    8IuJ           nf        9      e
                    IIII           II        I      I
                     / /                     /
         CCAATCGTTGATAAGAACGATAGGGATAACAGGCAAGCTTTTGAAGGAATCTCGCAATTA
    5041 ---------+---------+---------+---------+---------+---------+ 5100
         GGTTAGCAACTATTCTTGCTATCCCTATTGTCCGTTCGAAAACTTCCTTAGAGCGTTAAT a        P I V D K N D R D N R Q A F E G I S Q L  -
b        Q S L I R T I G I T G K L L K E S R N *  -
c        N R * * E R * G * Q A S F * R N L A I K  -
    5041 ---------+---------+---------+---------+---------+---------+ 5100
d        V L R Q Y S R Y P Y C A L K Q L F R A I  -
e        G I T S L F S L S L L C A K S P I E C N  -
f        W D N I L V I P I V P L S K F S D R L *  -
```

FIG.2-SEQUENCE1-PAGE25

```
                                    S
                       M           aC          H                         H                      C
                       b           ujD         i                         iT                     j
                       o           3ep         n                         nf                     e
                       I           APn         4                         fi                     P
                       I           III         I                         II                     I
                                                                  /
         AGGGAAGAATACTCCAATAAAGCGATCAAAAATCCTACCAAAAAGAATCAGTATTTTTCA
   5101  ----------+----------+----------+----------+----------+----------+  5160
         TCCCTTCTTATGAGGTTATTTCGCTAGTTTTTAGGATGGTTTTTCTTAGTCATAAAAAGT a        R  E  E  Y  S  N  K  A  I  K  N  P  T  K  K  N  Q  Y  F  S    -
b         G  K  N  T  P  I  K  R  S  K  I  L  P  K  R  I  S  I  F  Q   -
c          G  R  I  L  Q  *  S  D  Q  K  S  Y  Q  K  E  S  V  F  F  R  -
   5101  ----------+----------+----------+----------+----------+----------+  5160
d        L  P  L  I  S  W  Y  L  S  *  F  D  *  W  F  S  D  T  N  K    -
e         L  S  S  Y  E  L  L  A  I  L  F  G  V  L  F  F  *  Y  K  E   -
f          P  F  F  V  G  I  F  R  D  F  I  R  G  F  L  I  L  I  K  *  -

B                                M  H  H
                               sM                                b  i iT
                               rs                                o  n nf
                               De                                I  4 fi
                               II                                I  I II
                                                                  /
         GACTTTATCAATAAGAGCAATGATTTAATCAACAAAGACAATCTCATTGATGTAGAATCT
   5161  ----------+----------+----------+----------+----------+----------+  5220
         CTGAAATAGTTATTCTCGTTACTAAATTAGTTGTTTCTGTTAGAGTAACTACATCTTAGA a        D  F  I  N  K  S  N  D  L  I  N  K  D  N  L  I  D  V  E  S    -
b         T  L  S  I  R  A  M  I  *  S  T  K  T  I  S  L  M  *  N  L   -
c          L  Y  Q  *  E  Q  *  F  N  Q  Q  R  Q  S  H  *  C  R  I  F  -
   5161  ----------+----------+----------+----------+----------+----------+  5220
d        L  S  *  *  Y  S  C  H  N  L  *  C  L  C  D  *  Q  H  L  I    -
e         S  K  I  L  L  L  L  S  K  I  L  L  S  L  R  M  S  T  S  D   -
f          V  K  D  I  L  A  I  I  *  D  V  F  V  I  E  N  I  Y  F  R  -

T                              T
                            s          S         M         s
                    C       p          a         a         p     BT
                    Av      A5         u D       eA        A5    sa
                    li      p0         3 p       Il        p0    mq
                    uJ      o9         A n       Iw        o9    Fl
                    II      II         I I       II        Il    II
                     /       /                                    /  /
         TCCACAAAGAGCTTTCAGAAATTTGGGGATCAGCGTTACCGAATTTTCACAAGTTGGGTG
   5221  ----------+----------+----------+----------+----------+----------+  5280
         AGGTGTTTCTCGAAAGTCTTTAAACCCCTAGTCGCAATGGCTTAAAAGTGTTCAACCCAC a        S  T  K  S  F  Q  K  F  G  D  Q  R  Y  R  I  F  T  S  W  V    -
b         P  Q  R  A  F  R  N  L  G  I  S  V  T  E  F  S  Q  V  G  C   -
c          H  K  E  L  S  E  I  W  G  S  A  L  P  N  F  H  K  L  G  V  -
   5221  ----------+----------+----------+----------+----------+----------+  5280
d        K  W  L  S  S  E  S  I  Q  P  D  A  N  G  F  K  *  L  N  P    -
e         E  V  F  L  K  *  F  N  P  S  *  R  *  R  I  K  V  L  Q  T   -
f          G  C  L  A  K  L  F  K  P  I  L  T  V  S  N  E  C  T  P  H  -

T
                    S                              S     S      s
                    a                         C    a  B  a      p
             B   A  u  D                      Bj   Au DsCPDuT    A5
             c   l  3  p                      se   13 pilvp3a    p0
             c   w  A  n                      bP   wA nEaunAq    o9
             I   I  I  I                      II   II IIIIII     II
              /                                 /    / //  //     /
         TCCCATCAAAACGATCCGTCTAAAATCAACACCCGATCGATCCGAAATTTTATGGAAAAT
```

FIG.2-SEQUENCE1-PAGE26

```
              5281 ----------+----------+----------+----------+----------+----------+ 5340
                   AGGGTAGTTTTGCTAGGCAGATTTTAGTTGTGGGCTAGCTAGGCTTTAAAATACCTTTTA a                  S  H  Q  N  D  P  S  K  I  N  T  R  S  I  R  N  F  M  E  N     -
b                     P  I  K  T  I  R  L  K  S  T  P  D  R  S  E  I  L  W  K  I  -
c                        P  S  K  R  S  V  *  N  Q  H  P  I  D  P  K  F  Y  G  K  Y -
              5281 ----------+----------+----------+----------+----------+----------+ 5340
d                  T  G  D  F  R  D  T  *  F  *  C  G  I  S  G  F  N  *  P  F     -
e                     D  W  *  F  S  G  D  L  I  L  V  R  D  I  R  F  K  I  S  F  -
f                        G  M  L  V  I  R  R  F  D  V  G  S  R  D  S  I  K  H  F  I -

C                                    A
                                j                                    c
                                e                                    i
                                P                                    I
                                I
                   ATCATACAACCCCCTATCCTTGATGATAAAGAGAAAGCGGAGTTTTTGAAATCTGCCAAA
              5341 ----------+----------+----------+----------+----------+----------+ 5400
                   TAGTATGTTGGGGGATAGGAACTACTATTTCTCTTTCGCCTCAAAAACTTTAGACGGTTT a                  I  I  Q  P  P  I  L  D  D  K  E  K  A  E  F  L  K  S  A  K     -
b                     S  Y  N  P  L  S  L  M  I  K  R  K  R  S  F  *  N  L  P  N  -
c                        H  T  T  P  Y  P  *  *  *  R  E  S  G  V  F  E  I  C  Q  T -
              5341 ----------+----------+----------+----------+----------+----------+ 5400
d                  Y  *  V  V  G  *  G  Q  H  Y  L  S  L  P  T  K  S  I  Q  W     -
e                     I  M  C  G  G  I  R  S  S  L  S  F  A  S  N  K  F  D  A  L  -
f                        D  Y  L  G  R  D  K  I  I  F  L  F  R  L  K  Q  F  R  G  F -

T                                          T
                                t                                          t
                                h                           S              h     N
                    C    1H                  H              a              1     1
                    v    1iT                 iT             u    D    A    l     aM
                    i    1nf                 nf             3    p    1    1     Is
                    R    Ifi                 fi             A    n    w    I     z1
                    I    III                 II             I    I    I    I     II
                              /                       /
                   CAATCTTTTGCAGGAATCATTATAGGGAATCAAATCCGAACGGATCAAAAGTTCATGGGC
              5401 ----------+----------+----------+----------+----------+----------+ 5460
                   GTTAGAAAACGTCCTTAGTAATATCCCTTAGTTTAGGCTTGCCTAGTTTTCAAGTACCCG a                  Q  S  F  A  G  I  I  I  G  N  Q  I  R  T  D  Q  K  F  M  G     -
b                     N  L  L  Q  E  S  L  *  G  I  K  S  E  R  I  K  S  S  W  A  -
c                        I  F  C  R  N  H  Y  R  E  S  N  P  N  G  S  K  V  H  G  R -
              5401 ----------+----------+----------+----------+----------+----------+ 5460
d                  V  I  K  Q  L  F  *  *  L  S  D  F  G  F  P  D  F  T  *  P     -
e                     C  D  K  A  P  I  M  I  P  F  *  I  R  V  S  *  F  N  M  P  -
f                        L  R  K  C  S  D  N  Y  P  I  L  D  S  R  I  L  L  E  H  A -

H                                           C
                           i              P                            Mv        B  B
                           n              l                            mi        s  s
                           f              e                            eJ        l  r
                           I              I                            II        I  I
                   GTGTTTGATGAGTCCTTGAAAGAAAGGCAAGAAGCAGAAAAAAATGGAGAGCCTACTGGT
              5461 ----------+----------+----------+----------+----------+----------+ 5520
                   CACAAACTACTCAGGAACTTTCTTTCCGTTCTTCGTCTTTTTTTACCTCTCGGATGACCA a                  V  F  D  E  S  L  K  E  R  Q  E  A  E  K  N  G  E  P  T  G     -
b                     C  L  M  S  P  *  K  K  G  K  K  Q  K  K  M  E  S  L  L  V  -
c                        V  *  *  V  L  E  R  K  A  R  S  R  K  K  W  R  A  Y  W  W -
              5461 ----------+----------+----------+----------+----------+----------+ 5520
d                  R  T  Q  H  T  R  S  L  F  A  L  L  L  F  F  H  L  A  *  Q     -
e                     T  N  S  S  D  K  F  S  L  C  S  A  S  F  F  P  S  G  V  P  -
f                        H  K  I  L  G  Q  F  F  P  L  F  C  F  F  I  S  L  R  S  T -
```

FIG.2-SEQUENCE 1-PAGE 27

```
                                              M
                                              b
                                              o
                                              I
                                              I
        GGGGATTGGTTGGATATTTTTCTCTCATTTATATTTGACAAAAAACAATCTTCTGATGTC
  5521  ---------+---------+---------+---------+---------+---------+  5580
        CCCCTAACCAACCTATAAAAAGAGAGTAAATATAAACTGTTTTTTGTTAGAAGACTACAG a       G  D  W  L  D  I  F  L  S  F  I  F  D  K  K  Q  S  S  D  V   -
b        G  I  G  W  I  F  F  S  H  L  Y  L  T  K  N  N  L  L  M  S  -
c         G  L  V  G  Y  F  S  L  I  Y  I  *  Q  K  T  I  F  *  C  Q -
  5521  ---------+---------+---------+---------+---------+---------+  5580
d       H  P  N  T  P  Y  K  E  R  M  *  I  Q  C  F  V  I  K  Q  H   -
e        P  S  Q  N  S  I  K  R  E  N  I  N  S  L  F  C  D  E  S  T  -
f         P  I  P  Q  I  N  K  E  *  K  Y  K  V  F  F  L  R  R  I  D -

N
              D               l                   C
              rBX             a                   v               M
              dsm             I                   i               m
              Irn             I                   J               e
              III             I                   I               I
        AAAGAAGCAATCAATCAAGAACCAGTTCCCCATGTCCAACCAGATATAGCCACTACCACC
  5581  ---------+---------+---------+---------+---------+---------+  5640
        TTTCTTCGTTAGTTAGTTCTTGGTCAAGGGGTACAGGTTGGTCTATATCGGTGATGGTGG a       K  E  A  I  N  Q  E  P  V  P  H  V  S  Q  P  D  I  A  T  T  T   -
b        K  K  Q  S  I  K  N  Q  F  P  M  S  N  Q  I  *  P  L  P  P  -
c         R  S  N  Q  S  R  T  S  S  P  C  P  T  R  Y  S  H  Y  H  H -
  5581  ---------+---------+---------+---------+---------+---------+  5640
d       *  L  L  L  *  D  L  V  L  E  G  H  G  V  L  Y  L  W  *  W   -
e        L  S  A  I  L  *  S  G  T  G  W  T  W  G  S  I  A  V  V  V  -
f         F  F  C  D  I  L  F  W  N  G  M  D  L  W  I  Y  G  S  G  G -

T
                                                            s
                C              C               E            p
                v      A       ABv             c            5
                i      c       lfi             o            0
                J      i       uaJ             5            9
                I      I       III             7            I
        ACCGACATACAAGGCTTACCGCCTGAAGCTAGAGATTTACTTGATGAAAGGGGTAATTTT
  5641  ---------+---------+---------+---------+---------+---------+  5700
        TGGCTGTATGTTCCGAATGGCGGACTTCGATCTCTAAATGAACTACTTTCCCCATTAAAA a       T  D  I  Q  G  L  P  P  E  A  R  D  L  L  D  E  R  G  N  F   -
b        P  T  Y  K  A  Y  R  L  K  L  E  I  Y  L  M  K  G  V  I  F  -
c         R  H  T  R  L  T  A  *  S  *  R  F  T  *  *  K  G  *  F  F -
  5641  ---------+---------+---------+---------+---------+---------+  5700
d       W  R  C  V  L  S  V  A  Q  L  *  L  N  V  Q  H  F  P  Y  N   -
e        V  S  M  C  P  K  G  G  S  A  L  S  K  S  S  S  L  P  L  K  -
f         G  V  Y  L  A  *  R  R  F  S  S  I  *  K  I  F  P  T  I  K -

T
         s
         p
         A5                                                 S
         p0                     M          H         AP     a    D
         o9                     n          n         11     u    3 p
         II                     l          f         we     A    n
         II                     I          I         II     I    I
        TCTAAATTCACTCTTGGCGATATGGAAATGTTAGATGTTGAGGGAGTCGCTGACATTGAT
  5701  ---------+---------+---------+---------+---------+---------+  5760
        AGATTTAAGTGAGAACCGCTATACCTTTACAATCTACAACTCCCTCAGCGACTGTAACTA
```

FIG.2-SEQUENCE1-PAGE28

```
a      S K F T L G D M E M L D V E G V A D I D   -
b       L N S L L A I W K C * M L R E S L T L I  -
c        * I H S W R Y G N V R C * G S R * H * S -
     5701 ---------+---------+---------+---------+---------+---------+ 5760
d      K * I * E Q R Y P F T L H Q P L R Q C Q   -
e       E L N V R P S I S I N S T S P T A S M S  -
f        R F E S K A I H F H * I N L S D S V N I -

T                 T
             s                 s
             p                 p
             5                 5           H           M           C
             0                 0           i T         B b         j           M
             9                 9           n f         b o         e           s
             I                 I           f i         s I         P           e
                                           I I         I I         I           I
                                              /
         CCCAATTACAAGTTCAATCAATTATTGATTCACAATAACGCTCTGTCTTCTGTGTTAATG
     5761 ---------+---------+---------+---------+---------+---------+ 5820
         GGGTTAATGTTCAAGTTAGTTAATAACTAAGTGTTATTGCGAGACAGAAGACACAATTAC a      P N Y K F N Q L L I H N N A L S S V L M   -
b       P I T S S I N Y * F T I T L C L L C * W  -
c        Q L Q V Q S I I D S Q * R S V F C V N G -
     5761 ---------+---------+---------+---------+---------+---------+ 5820
d      D W N C T * D I I S E C Y R E T K Q T L   -
e       G L * L N L * N N I * L L A R D E T N I  -
f        G I V L E I L * Q N V I V S Q R R H * H -

S E
             H           C                                   B A a c
             i           P           C                       s v u o
             n           l           j                       r a 9 R
             f           e           e                       D I 6 I
             I           I           P                       I I I I
                                     I
                                              /
         GGGAGTCATAATGGCATAGAACCTGAAAAAGTTTCATTGTTGTATGGGGGCAATGGTGGT
     5821 ---------+---------+---------+---------+---------+---------+ 5880
         CCCTCAGTATTACCGTATCTTGGACTTTTTCAAAGTAACAACATACCCCCGTTACCACCA a      G S H N G I E P E K V S L L Y G G N G G   -
b       G V I M A * N L K K F H C C M G A M V V  -
c        E S * W H R T * K S F I V V W G Q W W S -
     5821 ---------+---------+---------+---------+---------+---------+ 5880
d      P S D Y H C L V Q F L K M T T H P C H H   -
e       P L * L P M S G S F T E N N Y P P L P P  -
f        P T M I A Y F R F F N * Q Q I P A I T T -

N
             S       C       l
             c       A B v   C       a       B                   C
             r       l f i   j       I       p                   j
             F       u a J   e       I       m                   e
             I       I I I   I       I                           I
                                              /
         CCTGGAGCTAGGCATGATTGGAACGCCACCGTTGGTTATAAAGACCAACAAGGCAACAAT
     5881 ---------+---------+---------+---------+---------+---------+ 5940
         GGACCTCGATCCGTACTAACCTTGCGGTGGCAACCAATATTTCTGGTTGTTCCGTTGTTA a      P G A R H D W N A T V G Y K D Q Q G N N   -
b       L E L G M I G T P P L V I K T N K A T M  -
c        W S * A * L E R H R W L * R P T R Q Q C -
     5881 ---------+---------+---------+---------+---------+---------+ 5940
d      D Q L * A H N S R W R Q N Y L G V L C C   -
e       G P A L C S Q F A V T P * L S W C P L L  -
f        R S S P M I P V G G N T I F V L L A V I -
```

FIG.2-SEQUENCE1-PAGE29

```
                          T
                          s
              C           p                    C                    C  B        B
              v           5        MV          v  N                 vDs         c
              i           0        ss          i  d                 idp         e
              j           9        ep          R  e                 JeM         f
              I           I        II          I  I                 III         I
                                    /
          GTGGCTACAATAATTAATGTGCATATGAAAAACGGCAGTGGCTTAGTCATAGCAGGTGGT
     5941 ----------+---------+---------+---------+---------+---------+ 6000
          CACCGATGTTATTAATTACACGTATACTTTTTGCCGTCACCGAATCAGTATCGTCCACCA a         V  A  T  I  I  N  V  H  M  K  N  G  S  G  L  V  I  A  G  G    -
b          W  L  Q  *  L  M  C  I  *  K  T  A  V  A  *  S  *  Q  V  V   -
c           G  Y  N  N  *  C  A  Y  E  K  R  Q  W  L  S  H  S  R  W  *  -
     5941 ----------+---------+---------+---------+---------+---------+ 6000
d         H  P  *  L  L  *  H  A  Y  S  F  R  C  H  S  L  *  L  L  H    -
e          T  A  V  I  I  L  T  C  I  F  F  P  L  P  K  T  M  A  P  P   -
f           H  S  C  Y  N  I  H  M  H  F  V  A  T  A  *  D  Y  C  T  T  -

M  C
                HM         B                           B           b  v
                ps         f                           b           o  i
                he         a                           s           I  J
                II         I                           I           I  I
          GAGAAAGGGATTAACAACCCTAGTTTTTATCTCTACAAAGAAGACCAACTCACAGGCTCA
     6001 ----------+---------+---------+---------+---------+---------+ 6060
          CTCTTTCCCTAATTGTTGGGATCAAAAATAGAGATGTTTCTTCTGGTTGAGTGTCCGAGT a         E  K  G  I  N  N  P  S  F  Y  L  Y  K  E  D  Q  L  T  G  S    -
b          R  K  G  L  T  T  L  V  F  I  S  T  K  K  T  N  S  Q  A  H   -
c           E  R  D  *  Q  P  *  F  L  S  L  Q  R  R  P  T  H  R  L  T  -
     6001 ----------+---------+---------+---------+---------+---------+ 6060
d         H  S  L  S  *  C  G  *  N  K  D  R  C  L  L  G  V  *  L  S    -
e          S  F  P  I  L  L  G  L  K  *  R  *  L  S  S  W  S  V  P  E   -
f           L  F  P  N  V  V  R  T  K  I  E  V  F  F  V  L  E  C  A  *  -

T
                           S                            N  s
                           Ba           M               l  p              C
                  M  E  A  suD          b               aA5               v
                  s  a  l  t3p          c               lp0               i
                  e  r  w  YAn          I               Io9               R
                  I  I  I  III          I               III               I
                            /                                  /
          CAACGAGCATTAAGTCAAGAAGAGATCCAAAACAAAATAGATTTCATGGAATTTCTTGCA
     6061 ----------+---------+---------+---------+---------+---------+ 6120
          GTTGCTCGTAATTCAGTTCTTCTCTAGGTTTTGTTTTATCTAAAGTACCTTAAAGAACGT a         Q  R  A  L  S  Q  E  E  I  Q  N  K  I  D  F  M  E  F  L  A    -
b          N  E  H  *  V  K  K  R  S  K  T  K  *  I  S  W  N  F  L  H   -
c           T  S  I  K  S  R  R  D  P  K  Q  N  R  F  H  G  I  S  C  T  -
     6061 ----------+---------+---------+---------+---------+---------+ 6120
d         V  V  L  M  L  D  L  L  S  G  F  C  F  L  N  *  P  I  E  Q    -
e          C  R  A  N  L  *  S  S  I  W  F  L  I  S  K  M  S  N  R  A   -
f           L  S  C  *  T  L  F  L  D  L  V  F  Y  I  E  H  F  K  K  C  -

T                                T
                   s                                B  s
                   p                                c  p              C
                   5                                eA5               D  j
                   0                                8p0               d  e
                   9                                3o9               e  P
                   I                                III               I  I
                                                           /
```

FIG.2-SEQUENCE1-PAGE30

```
                CAAAATAATGCTAAATTAGACAACTTGAGCGAGAAAGAGAAGGAAAAATTCCGAACTGAG
         6121   ----------+---------+---------+---------+---------+---------+   6180
                GTTTTATTACGATTTAATCTGTTGAACTCGCTCTTTCTCTTCCTTTTTAAGGCTTGACTC a            Q  N  N  A  K  L  D  N  L  S  E  K  E  K  E  K  F  R  T  E   -
   b             K  I  M  L  N  *  T  T  *  A  R  K  R  R  K  N  S  E  L  R  -
   c              K  *  C  *  I  R  Q  L  E  R  E  R  E  G  K  I  P  N  *  D -
         6121   ----------+---------+---------+---------+---------+---------+   6180
   d            V  F  Y  H  *  I  L  C  S  S  R  S  L  S  P  F  I  G  F  Q   -
   e             C  F  L  A  L  N  S  L  K  L  S  F  S  F  S  F  N  R  V  S  -
   f              L  I  I  S  F  *  V  V  Q  A  L  F  L  L  F  F  E  S  S  L -

S
                              H        C  C         B   A B   a
                   M       P  i     D  v  j         s   vBsSH  u  D
                   s       l  n     d  i  a         a   rfatg  3  p
                   e       e  f     e  J  P         H   IaJya  A  n
                   I       I  I     I  I  I         I   IIIII  I  I
                                                      //
                ATTAAAGATTTCCAAAAAGACTCTAAGGCTTATTTAGACGCCCTAGGGAATGATCGTATT
         6181   ----------+---------+---------+---------+---------+---------+   6240
                TAATTTCTAAAGGTTTTTCTGAGATTCCGAATAAATCTGCGGGATCCCTTACTAGCATAA a            I  K  D  F  Q  K  D  S  K  A  Y  L  D  A  L  G  N  D  R  I   -
   b             L  K  I  S  K  K  T  L  R  L  I  *  T  P  *  G  M  I  V  L  -
   c              *  R  F  P  K  R  L  *  G  L  F  R  R  P  R  E  *  S  Y  C -
         6181   ----------+---------+---------+---------+---------+---------+   6240
   d            S  *  L  N  G  F  L  S  *  P  K  N  L  R  G  L  S  H  D  Y   -
   e             I  L  S  K  W  F  S  E  L  A  *  K  S  A  R  P  F  S  R  I  -
   f              N  F  I  E  L  F  V  R  L  S  I  *  V  G  *  P  I  I  T  N -

T
                                          s
                                      C   p
                            C      Av M5       D                      C
                            j      li s0       d                      j
                            e      uJ e9       e                      e
                            I      II II       I                      I
                                        /
                GCTTTTGTTTCTAAAAAAGACACAAAACATTCAGCTTTAATTACTGAGTTTGGTAATGGG
         6241   ----------+---------+---------+---------+---------+---------+   6300
                CGAAAACAAAGATTTTTTCTGTGTTTTGTAAGTCGAAATTAATGACTCAAACCATTACCC a            A  F  V  S  K  K  D  T  K  H  S  A  L  I  T  E  F  G  N  G   -
   b             L  L  F  L  K  K  T  Q  N  I  Q  L  *  L  L  S  L  V  M  G  -
   c              F  C  F  *  K  R  H  K  T  F  S  F  N  Y  *  V  W  *  W  G -
         6241   ----------+---------+---------+---------+---------+---------+   6300
   d            Q  K  Q  K  *  F  L  C  L  V  N  L  K  L  *  Q  T  Q  Y  H   -
   e             A  K  T  E  L  F  S  V  F  C  E  A  K  I  V  S  N  P  L  P  -
   f              S  K  N  R  F  F  V  C  F  M  *  S  *  N  S  L  K  T  I  P -

H
                                                      i
                         CH                           n  C
                         Avi                       Md Av
                         lin                       wI li
                         uJ4                       oI uJ
                         III                       II II
                          /                          /
                GATTTGAGCTACACTCTCAAAGATTATGGGAAAAAAGCAGATAAAGCTTTAGATAGGGAG
         6301   ----------+---------+---------+---------+---------+---------+   6360
                CTAAACTCGATGTGAGAGTTTCTAATACCCTTTTTTCGTCTATTTCGAAATCTATCCCTC a            D  L  S  Y  T  L  K  D  Y  G  K  K  A  D  K  A  L  D  R  E   -
   b             I  *  A  T  L  S  K  I  M  G  K  K  Q  I  K  L  *  I  G  R  -
   c              F  E  L  H  S  Q  R  L  W  E  K  S  R  *  S  F  R  *  G  E -
```

FIG.2-SEQUENCE1-PAGE31

```
                6301 ---------+---------+---------+---------+---------+---------+ 6360
              d        P  N  S  S  C  E  *  L  N  H  S  F  L  L  Y  L  K  L  Y  P  -
              e         S  K  L  *  V  R  L  S  *  P  F  F  A  S  L  A  K  S  L  S  -
              f          I  Q  A  V  S  E  F  I  I  P  F  F  C  I  F  S  *  I  P  L  -

T
                                                    t
                              M                     Nh                          T
                           M  a           C         ll                          s
                           b  e       E   v         alB                         p
                           o  I       a   i         IIc                         5
                           I  I       r   J         IIc                         0
                           I  I       I   I         III                         9
                                                                                I
                                                   /
                     AAAAATGTTACTCTTCAAGGTAGCCTAAAACATGATGGCGTGATGTTTGTTGATTATTCT
                6361 ---------+---------+---------+---------+---------+---------+ 6420
                     TTTTTACAATGAGAAGTTCCATCGGATTTTGTACTACCGCACTACAAACAACTAATAAGA a        K  N  V  T  L  Q  G  S  L  K  H  D  G  V  M  F  V  D  Y  S  -
              b         K  M  L  L  F  K  V  A  *  N  M  M  A  *  C  L  L  I  I  L  -
              c          K  C  Y  S  S  R  *  P  K  T  *  W  R  D  V  C  *  L  F  *  -
                6361 ---------+---------+---------+---------+---------+---------+ 6420
              d        S  F  H  *  E  E  L  Y  G  L  V  H  H  R  S  T  Q  Q  N  N  -
              e         F  F  T  V  R  *  P  L  R  F  C  S  P  T  I  N  T  S  *  E  -
              f          F  I  N  S  K  L  T  A  *  F  M  I  A  H  H  K  N  I  I  R  -

M
                                        H                       a
                              C         iT M        B           e    C
                              j         nf n        s           I    j
                              e         fi l        l           I    e
                              I         II I        I           I    I
                                                   /
                     AATTTCAAATACACCAACGCCTCCAAGAATCCCAATAAGGGTGTAGGCGTTACGAATGGC
                6421 ---------+---------+---------+---------+---------+---------+ 6480
                     TTAAAGTTTATGTGGTTGCGGAGGTTCTTAGGGTTATTCCCACATCCGCAATGCTTACCG a        N  F  K  Y  T  N  A  S  K  N  P  N  K  G  V  G  V  T  N  G  -
              b         I  S  N  T  P  T  P  P  R  I  P  I  R  V  *  A  L  R  M  A  -
              c          F  Q  I  H  Q  R  L  Q  E  S  Q  *  G  C  R  R  Y  E  W  R  -
                6421 ---------+---------+---------+---------+---------+---------+ 6480
              d        *  N  *  I  C  W  R  R  W  S  D  W  Y  P  H  L  P  *  S  H  -
              e         L  K  L  Y  V  L  A  E  L  F  G  L  L  P  T  P  T  V  F  P  -
              f          I  E  F  V  G  V  G  G  L  I  G  I  L  T  Y  A  N  R  I  A  -

T
                                                    s
                              C             C       p
                              v   M         Av      M5              MDS
                              i   s         li      s0              srw
                              J   e         uJ      e9              eaa
                              I   I         II      II              III
                                           /                       /
                     GTTTCCCATTTAGAAGTAGGCTTTAACAAGGTAGCTATCTTTAATTTGCCTGATTTAAAT
                6481 ---------+---------+---------+---------+---------+---------+ 6540
                     CAAAGGGTAAATCTTCATCCGAAATTGTTCCATCGATAGAAATTAAACGGACTAAATTTA a        V  S  H  L  E  V  G  F  N  K  V  A  I  F  N  L  P  D  L  N  -
              b         F  P  I  *  K  *  A  L  T  R  *  L  S  L  I  C  L  I  *  I  -
              c          F  P  F  R  S  R  L  *  Q  G  S  Y  L  *  F  A  *  F  K  *  -
                6481 ---------+---------+---------+---------+---------+---------+ 6540
              d        R  K  G  N  L  L  L  S  *  C  P  L  *  R  *  N  A  Q  N  L  -
              e         T  E  W  K  S  T  P  K  L  L  T  A  I  K  L  K  G  S  K  F  -
              f          N  G  M  *  F  Y  A  K  V  L  Y  S  D  K  I  Q  R  I  *  I  -
                                                                    T
```

FIG.2-SEQUENCE1-PAGE32

```
                            s
                            p
         SB              AE AM5                          B
         pf              cc pn0                          s
         ea              ii ol9                          m
         II              II III                          F
                              //                         I
         AATCTCGCTATCACTAGTTTCGTAAGGCGGAATTTAGAGGATAAACTAACCACTAAAGGA
    6541 ---------+---------+---------+---------+---------+---------+ 6600
         TTAGAGCGATAGTGATCAAAGCATTCCGCCTTAAATCTCCTATTTGATTGGTGATTTCCT a        N  L  A  I  T  S  F  V  R  R  N  L  E  D  K  L  T  T  K  G  -
b         I  S  L  S  L  V  S  *  G  G  I  *  R  I  N  *  P  L  K  D  -
c          S  R  Y  H  *  F  R  K  A  E  F  R  G  *  T  N  H  *  R  I -
    6541 ---------+---------+---------+---------+---------+---------+ 6600
d        Y  D  R  *  *  *  N  R  L  A  S  N  L  P  Y  V  L  W  *  L  -
e         L  R  A  I  V  L  K  T  L  R  F  K  S  S  L  S  V  V  L  P  -
f          I  E  S  D  S  T  E  Y  P  P  I  *  L  I  F  *  G  S  F  S -

H
                          i
                 C        nR  C                    B              T
                 Av       dlAv                  M  sT             s
                 li       Ieli                  m  os             p
                 uJ       IAuJ                  e  Fe             5B
                 II       IIII                  I  II             0b
                  /        /                                      9v
         TTGTCCCCACAAGAAGCTAATAAGCTTATCAAAGATTTTTTGAGCAGCAACAAAGAATTG   II
    6601 ---------+---------+---------+---------+---------+---------+ 6660
         AACAGGGGTGTTCTTCGATTATTCGAATAGTTTCTAAAAAACTCGTCGTTGTTTCTTAAC a        L  S  P  Q  E  A  N  K  L  I  K  D  F  L  S  S  N  K  E  L  -
b         C  P  H  K  K  L  I  S  L  S  K  I  F  *  A  A  T  K  N  W -
c          V  P  T  R  S  *  *  A  Y  Q  R  F  F  E  Q  Q  Q  R  I  G -
    6601 ---------+---------+---------+---------+---------+---------+ 6660
d        I  T  G  V  L  L  *  Y  A  *  *  L  N  K  S  C  C  C  L  I  -
e         N  D  G  C  S  A  L  L  S  I  L  S  K  K  L  L  L  L  S  N -
f          Q  G  W  L  F  S  I  L  K  D  F  I  K  Q  A  A  V  F  F  Q -

T
                                                                  s
                           C    C                                 p
                 MD        AvS  Av                  H             5
                 sr        lif  li                  g             0
                 ea        uJc  uJ                  a             9
                 II        III  II                  I             I
                            //   /
         GTTGGAAAAACTTTAAACTTCAATAAAGCTGTAGCTGACGCTAAAAACACAGGCAATTAT
    6661 ---------+---------+---------+---------+---------+---------+ 6720
         CAACCTTTTTGAAATTTGAAGTTATTTCGACATCGACTGCGATTTTTGTGTCCGTTAATA a        V  G  K  T  L  N  F  N  K  A  V  A  D  A  K  N  T  G  N  Y  -
b         L  E  K  L  *  T  S  I  K  L  *  L  T  L  K  T  Q  A  I  M -
c          W  K  N  F  K  L  Q  *  S  C  S  *  R  *  K  H  R  Q  L  * -
    6661 ---------+---------+---------+---------+---------+---------+ 6720
d        P  Q  F  F  K  L  S  *  Y  L  Q  L  Q  R  *  F  C  L  C  N  -
e         T  P  F  V  K  F  K  L  L  A  T  A  S  A  L  F  V  P  L  * -
f          N  S  F  S  *  V  E  I  F  S  Y  S  V  S  F  V  C  A  I  I -

S
                      C          BB  a
                      AvD        gsDu              D
                      lid        ltp3              d
                      uJe        IYnA              e
                      III        IIII              I
                       //         / /
```

FIG.2-SEQUENCE1-PAGE33

```
       GATGAAGTGAAAAAAGCTCAGAAAGATCTTGAAAAATCTCTAAGGAAACGAGAGCATTTA
  6721 ------------+----------+----------+----------+----------+---------- 6780
       CTACTTCACTTTTTTCGAGTCTTTCTAGAACTTTTTAGAGATTCCTTTGCTCTCGTAAAT a      D  E  V  K  K  A  Q  K  D  L  E  K  S  L  R  K  R  E  H  L  -
b      M  K  *  K  K  L  R  K  I  L  K  N  L  *  G  N  E  S  I  *  -
c         *  S  E  K  S  S  E  R  S  *  K  I  S  K  E  T  R  A  F  R -
  6721 ------  --+----------+----------+----------+----------+---------- 6780
d      H  H  L  S  F  L  E  S  L  D  Q  F  I  E  L  S  V  L  A  N  -
e         S  S  T  F  F  A  *  F  S  R  S  F  D  R  L  F  R  S  C  K  -
f         I  F  H  F  F  S  L  F  I  K  F  F  R  *  P  F  S  L  M  *  -

T
                 s
                 p                                               B
                 5                      B U                      c
                 0                      AsMb                     e
                 9                      cowa                     8
                 I                      iFoJ                     3
                                        IIII                     I
                                         //
       GAGAAAGAAGTAGAGAAAAAATTGGAGAGCAAAAGCGGCAACAAAAATAAAATGGAAGCA
  6781 ------------+----------+----------+----------+----------+---------- 6840
       CTCTTTCTTCATCTCTTTTTTAACCTCTCGTTTTCGCCGTTGTTTTTATTTTACCTTCGT a      E  K  E  V  E  K  K  L  E  S  K  S  G  N  K  N  K  M  E  A  -
b      R  K  K  *  R  K  N  W  R  A  K  A  A  T  K  I  K  W  K  Q  -
c         E  R  S  R  E  K  I  G  E  Q  K  R  Q  Q  K  *  N  G  S  K  -
  6781 ------------+----------+----------+----------+----------+---------- 6840
d      L  S  L  L  L  S  F  I  P  S  C  F  R  C  C  F  Y  F  P  L  -
e         S  F  S  T  S  F  F  N  S  L  L  L  P  L  L  F  L  I  S  A  -
f            L  F  F  Y  L  F  F  Q  L  A  F  A  A  V  F  I  F  H  F  C  -

S
          C     C     C                               a              CBB
          Av    Av    v                              BuD  M          vss
          li    li    i                              c3p  n          imm
          uJ    uJ    J                              1An  1          JAB
          II    II    I                              III  I          III
            /     /    /                               /              /
       AAAGCTCAAGCTAACAGCCAAAAAGATGAGATTTTTGCGTTGATCAATAAAGAGGCTAAT
  6841 ------------+----------+----------+----------+----------+---------- 6900
       TTTCGAGTTCGATTGTCGGTTTTTCTACTCTAAAAACGCAACTAGTTATTTCTCCGATTA a      K  A  Q  A  N  S  Q  K  D  E  I  F  A  L  I  N  K  E  A  N  -
b      K  L  K  L  T  A  K  K  M  R  F  L  R  *  S  I  K  R  L  I  -
c         S  S  S  *  Q  P  K  R  D  F  C  V  D  Q  *  R  G  *  *  -
  6841 ------------+----------+----------+----------+----------+---------- 6900
d      L  L  E  L  *  C  G  F  L  H  S  K  Q  T  S  *  Y  L  P  *  -
e         F  A  *  A  L  L  W  F  S  S  I  K  A  N  I  L  L  S  A  L  -
f            F  S  L  S  V  A  L  F  I  L  N  K  R  Q  D  I  F  L  S  I  -

T
                                                                 s
                               H                        S        p
             H           D     iT     M                 f        5
             g           d     nf     s                 a        0
             a           e     fi     e                 N        9
             I           I     II     I                 I        I
                                /
       AGAGACGCAAGAGCAATCGCTTACGCTCAGAATCTTAAAGGCATCAAAAGGGAATTGTCT
  6901 ------------+----------+----------+----------+----------+---------- 6960
       TCTCTGCGTTCTCGTTAGCGAATGCGAGTCTTAGAATTTCCGTAGTTTTCCCTTAACAGA a      R  D  A  R  A  I  A  Y  A  Q  N  L  K  G  I  K  R  E  L  S  -
b      E  T  Q  E  Q  S  L  T  L  R  I  L  K  A  S  K  G  N  C  L  -
c         R  R  K  S  N  R  L  R  S  E  S  *  R  H  Q  K  G  I  V  *  -
```

FIG.2-SEQUENCE 1-PAGE 34

```
                6901 ----------+----------+----------+----------+----------+----------+ 6960
            d        Y  L  R  L  L  L  R  K  R  E  S  D  *  L  C  *  F  P  I  T     -
            e           L  S  A  L  A  I  A  *  A  *  F  R  L  P  M  L  L  S  N  D  -
            f              S  V  C  S  C  D  S  V  S  L  I  K  F  A  D  F  P  F  Q  R -

T                              T
                                    H      s                              s
                                    i      p                              Ep
                                    n      A5                             Ac5
                                    c      p0                             p0
                                    I      o9                             oR9
                                    I      11                             III
                                           /                              //
                     GATAAACTTGAAAATGTCAACAAGAATTTGAAAGACTTTGATATATCTTTTGATGAATTC
                6961 ----------+----------+----------+----------+----------+----------+ 7020
                     CTATTTGAACTTTTACAGTTGTTCTTAAACTTTCTGAAACTATTTAGAAAACTACTTAAG a        D  K  L  E  N  V  N  K  N  L  K  D  F  D  K  S  F  D  E  F     -
            b         I  N  L  K  M  S  T  R  I  *  K  T  L  I  N  L  L  M  N  S    -
            c           *  T  *  K  C  Q  Q  E  F  E  R  L  *  *  I  F  *  *  I  Q  -
                6961 ----------+----------+----------+----------+----------+----------+ 7020
            d        Q  Y  V  Q  F  H  *  C  S  N  S  L  S  Q  Y  I  K  Q  H  I     -
            e         S  L  S  S  F  T  L  L  F  K  F  S  K  S  L  D  K  S  S  N    -
            f           I  F  K  F  I  D  V  L  I  Q  F  V  K  I  F  R  K  I  F  E  -

M     C
                                                                b     v     M
                                                                o     i     s
                                                                I     J     e
                                                                I     I     I
                     AAAAATGGCAAAAATAAGGATTTCAGCAAGGCAGAAGAAACACTAAAAGCCCTTAAAGGT
                7021 ----------+----------+----------+----------+----------+----------+ 7080
                     TTTTTACCGTTTTTATTCCTAAAGTCGTTCCGTCTTCTTTGTGATTTTCGGGAATTTCCA a        K  N  G  K  N  K  D  F  S  K  A  E  E  T  L  K  A  L  K  G     -
            b         K  M  A  K  I  R  I  S  A  R  Q  K  K  H  *  K  P  L  K  V    -
            c           K  W  Q  K  *  G  F  Q  Q  G  R  R  N  T  K  S  P  *  R  F  -
                7021 ----------+----------+----------+----------+----------+----------+ 7080
            d        *  F  H  C  F  Y  P  N  *  C  P  L  L  F  V  L  L  G  *  L     -
            e         L  F  P  L  F  L  S  K  L  L  A  S  S  V  S  F  A  R  L  P    -
            f           F  I  A  F  I  L  I  E  A  L  C  F  F  C  *  F  G  K  F  T  -

CB
                            H                                         M     vsT
                            p                                         s     ios
                            h                                         e     RFe
                            I                                         I     III
                                                                            /
                     TCGGTGAAAGATTTAGGTATCAATCCAGAATGGATTTCAAAAGTTGAAAACCTTAATGCA
                7081 ----------+----------+----------+----------+----------+----------+ 7140
                     AGCCACTTTCTAAATCCATAGTTAGGTCTTACCTAAAGTTTTCAACTTTTGGAATTACGT a        S  V  K  D  L  G  I  N  P  E  W  I  S  K  V  E  N  L  N  A     -
            b         R  *  K  I  *  V  S  I  Q  N  G  F  Q  K  L  K  T  L  M  Q    -
            c           G  E  R  F  R  Y  Q  S  R  M  D  F  K  S  *  K  P  *  C  S  -
                7081 ----------+----------+----------+----------+----------+----------+ 7140
            d        N  P  S  L  N  L  Y  *  D  L  I  S  K  L  L  Q  F  G  *  H     -
            e         E  T  F  S  K  P  I  L  G  S  H  I  E  F  T  S  F  R  L  A    -
            f           R  H  F  I  *  T  D  I  W  F  P  N  *  F  N  F  V  K  I  C  -

T
                              s
                     C        Ep                                 M
                     Av       ABc5X                              a     C
                     li       pbo0m                              e     a
                     uJ       ovR9n                              I     c
                                                                 I     8
```

FIG.2-SEQUENCE1-PAGE35

FIG. 2-SEQUENCE 1-PAGE 36

```
c        S  V  S  R  S  Q  K  F  L  K  G  A  I  G  P  T  S  S  K  K  -
     7321 ---------+---------+---------+---------+---------+---------+ 7380
d        A  L  T  L  R  D  *  F  N  R  L  P  A  I  P  G  V  L  E  F  -
e        C  A  N  A  S  R  L  F  K  E  F  S  C  N  A  W  C  A  *  F  -
f           L  R  *  G  I  E  F  I  E  *  L  L  L  Q  G  L  L  S  L  F -

B
                    s              B
                    m              f                              M
                    A              a                              s
                    I              I                              e
                                                                  I
         AATGAAAGTCTCAATGCTAGAAAAAAATCTGAAATATATCAATCCGTTAAGAATGGTGTG
     7381 ---------+---------+---------+---------+---------+---------+ 7440
         TTACTTTCAGAGTTACGATCTTTTTTTAGACTTTATATAGTTAGGCAATTCTTACCACAC a        N  E  S  L  N  A  R  K  K  S  E  I  Y  Q  S  V  K  N  G  V  -
b        M  K  V  S  M  L  E  K  N  L  K  Y  I  N  P  L  R  M  V  *  -
c        *  K  S  Q  C  *  K  K  I  *  N  I  S  I  R  *  E  W  C  E  -
     7381 ---------+---------+---------+---------+---------+---------+ 7440
d        F  H  F  D  *  H  *  F  F  I  Q  F  I  D  I  R  *  S  H  H  -
e           F  S  L  R  L  A  L  F  F  D  S  I  Y  *  D  T  L  F  P  T -
f              I  F  T  E  I  S  S  F  F  R  F  Y  I  L  G  N  L  I  T H -

T
                                                                  t
              H  B                                                h
           N  g  c                                                l
           l  B  e                              C                 l
           a  f  E  8                           v                 l
           I  a  I  3                           i                 I
           V  I  I  I                           J                 I
         AATGGAACCCTAGTCGGTAATGGGTTATCTCAAGCAGAAGCCACAACTCTTTCTAAAAAC
     7441 ---------+---------+---------+---------+---------+---------+ 7500
         TTACCTTGGGATCAGCCATTACCCAATAGAGTTCGTCTTCGGTGTTGAGAAAGATTTTTG a        N  G  T  L  V  G  N  G  L  S  Q  A  E  A  T  T  L  S  K  N  -
b        M  E  P  *  S  V  M  G  Y  L  K  Q  K  P  Q  L  F  L  K  T  -
c        W  N  P  S  R  *  W  V  I  S  S  R  S  H  N  S  F  *  K  L  -
     7441 ---------+---------+---------+---------+---------+---------+ 7500
d        S  H  F  G  L  R  Y  H  T  I  E  L  L  L  W  L  E  K  *  F  -
e        F  P  V  R  T  P  L  P  N  D  *  A  S  A  V  V  R  E  L  F  -
f           I  S  G  *  D  T  I  P  *  R  L  C  F  G  C  S  K  R  F  V -

T
                                                   s
                                                   p
                          C                        A  5
                          v  B                     p  0                P
                          i  s                     o  9                l
                          R  m                     o  9                e
                          I  I                     I  I                I
         TTTTCGGACATCAAGAAAGAGTTGAATGCAAAACTTGGAAATTTCAATAACAATAACAAT
     7501 ---------+---------+---------+---------+---------+---------+ 7560
         AAAAGCCTGTAGTTCTTTCTCAACTTACGTTTTGAACCTTTAAAGTTATTGTTATTGTTA a        F  S  D  I  K  K  E  L  N  A  K  L  G  N  F  N  N  N  N  N  -
b        F  R  T  S  R  K  S  *  M  Q  N  L  E  I  S  I  T  I  T  I  -
c           F  G  H  Q  E  R  V  E  C  K  T  W  K  F  Q  *  Q  *  Q  * -
     7501 ---------+---------+---------+---------+---------+---------+ 7560
d        S  K  P  C  *  S  L  T  S  H  L  V  Q  F  N  *  Y  C  Y  C  -
e        K  E  S  M  L  F  S  N  F  A  F  S  P  F  K  L  L  L  L  L  -
f           K  R  V  D  L  F  L  Q  I  C  F  K  S  I  E  I  V  I  V  I -

H                                                C  B
           i                              M                 Ma sT
           n                              s                 wc os
```

FIG.2-SEQUENCE1-PAGE37

```
                  f                              e                    o8  Fe
                  I                              I                    II  II
                                                                       /
       AATGGACTCAAAAACGAACCCATTTATGCTAAAGTTAATAAAAAGAAAGCAGGGCAAGCA
7561   ----------+---------+---------+---------+---------+---------+ 7620
       TTACCTGAGTTTTTGCTTGGGTAAATACGATTTCAATTATTTTTCTTTCGTCCCGTTCGT a      N  G  L  K  N  E  P  I  Y  A  K  V  N  K  K  K  A  G  Q  A  -
b       M  D  S  K  T  N  P  F  M  L  K  L  I  K  R  K  Q  G  K  Q -
c        W  T  Q  K  R  T  H  L  C  *  S  *  *  K  E  S  R  A  S  S -
7561   ----------+---------+---------+---------+---------+---------+ 7620
d      Y  H  V  *  F  R  V  W  K  H  *  L  *  Y  F  S  L  L  A  L  -
e       L  P  S  L  F  S  G  M  *  A  L  T  L  L  F  F  A  P  C  A -
f        I  S  E  F  V  F  G  N  I  S  F  N  I  F  L  F  C  P  L  C -

T                                           T
                      t                                           s
                      Bh                                          p
          CCCC        cl         M              C          C      5
          ABajvvN     Bel        b         M    j          v      0    P
          lfceiih     b81        o         w    e          i      9    l
          ua8PJJe     v3I        I         o    P          R      I    e
          IIIIIII     III        I         I    I          I      I    I
            ////      /
       GCTAGCCTTGAAGAACCCATTTACGCTCAAGTTGCTAAAAAGGTAAATGCAAAAATTGAC
7621   ----------+---------+---------+---------+---------+---------+ 7680
       CGATCGGAACTTCTTGGGTAAATGCGAGTTCAACGATTTTTCCATTTACGTTTTTAACTG a      A  S  L  E  E  P  I  Y  A  Q  V  A  K  K  V  N  A  K  I  D  -
b       L  A  L  K  N  P  F  T  L  K  L  L  K  R  *  M  Q  K  L  T -
c        *  P  *  R  T  H  L  R  S  S  C  *  K  G  K  C  K  N  *  P -
7621   ----------+---------+---------+---------+---------+---------+ 7680
d      L  *  G  Q  L  V  W  K  R  E  L  Q  *  F  P  L  H  L  F  Q  -
e       A  L  R  S  S  G  M  *  A  *  T  A  L  F  T  F  A  F  I  S -
f        S  A  K  F  F  G  N  V  S  L  N  S  F  L  Y  I  C  F  N  V -

T
                                                              t
                                           M                  h
          H        T   T                 C    B   sC    C     l
          i        a   a         D       F    a   sTApa v     B1
          n        q   q         e       a    c   oscAc i     bl
          f        I   I         b       u    8   Feil8 J     vI
          I        I   I         I       I    I   IIIII I     II
                                                /  /
       CGACTCAATCAAATAGCAAGTGGTTTGGGTGTTGTAGGGCAAGCAGCGGGCTTCCCTTTG
7681   ----------+---------+---------+---------+---------+---------+ 7740
       GCTGAGTTAGTTTATCGTTCACCAAACCCACAACATCCCGTTCGTCGCCCGAAGGGAAAC a      R  L  N  Q  I  A  S  G  L  G  V  V  G  Q  A  A  G  F  P  L  -
b       D  S  I  K  *  Q  V  V  V  W  V  L  *  G  K  Q  R  A  S  L * -
c        T  Q  S  N  S  K  W  F  G  C  C  R  A  S  S  G  L  P  F  E -
7681   ----------+---------+---------+---------+---------+---------+ 7740
d      G  V  *  D  F  L  L  H  N  P  H  Q  L  A  L  L  P  S  G  K  -
e       R  S  L  *  I  A  L  P  K  P  T  T  P  C  A  A  P  K  G  K -
f        S  E  I  L  Y  C  T  T  Q  T  N  Y  P  L  C  R  A  E  R  Q -

T
                   N      S                                     s
                   l      a                                     p
                   a      u  D   D              C         H     5
                   I      3  p   d              v         iT    0
                   I      A  n   e              i         nf    9
                   I      I  I   I              J         fi    I
                   I      I  I   I              I         II    I
                                                                /
       AAAAGGCATGATAAAGTTGATGATCTCAGTAAGGTAGGGCTTTCAAGGAATCAAGAATTG
```

FIG.2-SEQUENCE1-PAGE38

```
        7741 ----------+----------+----------+----------+----------+----------+ 7800
             TTTTCCGTACTATTTCAACTACTAGAGTCATTCCATCCCGAAAGTTCCTTAGTTCTTAAC a        K  R  H  D  K  V  D  D  L  S  K  V  G  L  S  R  N  Q  E  L  -
    b         K  G  M  I  K  L  M  I  S  V  R  *  G  F  Q  G  I  K  N  W -
    c          K  A  *  *  S  *  *  S  Q  *  G  R  A  F  K  E  S  R  I  G -
        7741 ----------+----------+----------+----------+----------+----------+ 7800
    d        S  F  A  H  Y  L  Q  H  D  *  Y  P  L  A  K  L  S  D  L  I  -
    e         F  L  C  S  L  T  S  S  R  L  L  T  P  S  E  L  F  *  S  N -
    f          F  P  M  I  F  N  I  I  E  T  L  Y  P  K  *  P  I  L  F  Q -

T
                        s
            C           p                                B       C
            vD          5                                s       Av
            id          0                      A         p       li
            Je          9                      c         M       uJ
            II          I                      i         I       II
                                                 /
             GCTCAGAAAATTGACAATCTCAATCAAGCGGTATCAGAAGCTAAAGCAGGTTTTTTTGGC
        7801 ----------+----------+----------+----------+----------+----------+ 7860
             CGAGTCTTTTAACTGTTAGAGTTAGTTCGCCATAGTCTTCGATTTCGTCCAAAAAAACCG a        A  Q  K  I  D  N  L  N  Q  A  V  S  E  A  K  A  G  F  F  G  -
    b         L  R  K  L  T  I  S  I  K  R  Y  Q  K  L  K  Q  V  F  L  A -
    c          S  E  N  *  Q  S  Q  S  S  G  I  R  S  *  S  R  F  F  W  Q -
        7801 ----------+----------+----------+----------+----------+----------+ 7860
    d        P  E  S  F  Q  C  D  *  D  L  P  I  L  L  *  L  L  N  K  Q  -
    e         A  *  F  I  S  L  R  L  *  A  T  D  S  A  L  A  P  K  K  P -
    f          S  L  F  N  V  I  E  I  L  R  Y  *  F  S  F  C  T  K  K  A -

C         H                   N
                                            Av        iT                  Hl
            XB                              li        nf                  iaT
            bf                              aa        fi                  nIf
            aa                              uJ        fi                  fIi
            II                              II        II                  III
              /                              /                             //
             AATCTAGAGCAAACGATAGACAAGCTCAAAGATTCTACAAAACACAATCCCATGAATCTA
        7861 ----------+----------+----------+----------+----------+----------+ 7920
             TTAGATCTCGTTTGCTATCTGTTCGAGTTTCTAAGATGTTTTGTGTTAGGGTACTTAGAT a        N  L  E  Q  T  I  D  K  L  K  D  S  T  K  H  N  P  M  N  L  -
    b         I  *  S  K  R  *  T  S  S  K  I  L  Q  N  T  I  P  *  I  Y -
    c          S  R  A  N  D  R  Q  A  Q  R  F  Y  K  T  Q  S  H  E  S  M -
        7861 ----------+----------+----------+----------+----------+----------+ 7920
    d        C  D  L  A  F  S  L  C  A  *  L  N  *  L  V  C  D  W  S  D  -
    e         L  R  S  C  V  I  S  L  S  L  S  E  V  F  C  L  G  M  F  R -
    f          I  *  L  L  R  Y  V  L  E  F  I  R  C  F  V  I  G  H  I  * -

T
                                                                       s
                        C                                              p
                        v              R     B                    B    5
                        i              s     f                    f    0
                        R              a     a                    a    9
                        I              I     I                    I    I
             TGGGTTGAAAGTGCAAAAAAAGTACCTGCTAGTTTGTCAGCGAAACTAGACAATTACGCT
        7921 ----------+----------+----------+----------+----------+----------+ 7980
             ACCCAACTTTCACGTTTTTTTCATGGACGATCAAACAGTCGCTTTGATCTGTTAATGCGA a        W  V  E  S  A  K  K  V  P  A  S  L  S  A  K  L  D  N  Y  A  -
    b         G  L  K  V  Q  K  K  Y  L  L  V  C  Q  R  N  *  T  I  T  L -
    c          G  *  K  C  K  K  S  T  C  *  F  V  S  E  T  R  Q  L  R  Y -
        7921 ----------+----------+----------+----------+----------+----------+ 7980
    d        I  P  Q  F  H  L  F  L  V  Q  *  N  T  L  S  V  L  C  N  R  -
```

FIG.2-SEQUENCE1-PAGE39

```
e         H   T   S   L   A   F   F   F   T   G   A   L   K   D   A   F   S   S   L   *   A   -
f         P   N   F   T   C   F   F   Y   R   S   T   Q   *   R   F   *   V   I   V   S   -

C
              v           M           MV  M                                       B
              i           w           ss  w                                       c
              J           o           ep  o                                       g
              I           I           II  I                                       I
                                          /
          ACTAACAGCCACATACGCATTAATAGCAATATCAAAAATGGAGCAATCAATGAAAAAGCG
    7981  ----------+----------+----------+----------+----------+----------+   8040
          TGATTGTCGGTGTATGCGTAATTATCGTTATAGTTTTTACCTCGTTAGTTACTTTTTCGC a         T   N   S   H   I   R   I   N   S   N   I   K   N   G   A   I   N   E   K   A   -
b             L   T   A   T   Y   A   L   I   A   I   S   K   M   E   Q   S   M   K   K   R   -
c         *   Q   P   H   T   H   *   *   Q   Y   Q   K   W   S   N   Q   *   K   S   D   -
    7981  ----------+----------+----------+----------+----------+----------+   8040
d         *   *   C   G   C   V   C   *   Y   C   Y   *   F   H   L   L   *   H   F   L   -
e             V   L   L   W   M   R   M   L   L   L   I   L   F   P   A   I   L   S   F   A   -
f         S   V   A   V   Y   A   N   I   A   I   D   F   I   S   C   D   I   F   F   R   -

N           B
          BB      C   1           c                           C               C
          ssM     aCaNS            e   B       D              v               ABCv
          ris     cjIsp             8  c       d              i               lsji
          FEp     8eIph              3 g       e              J               uieJ
          III     IIIII               I I      I              I               IIII
           /       / //
          ACCGGCATGCTAACGCAAAAAAACCCTGAGTGGCTCAAGCTCGTGAATGATAAGATAGTT
    8041  ----------+----------+----------+----------+----------+----------+   8100
          TGGCCGTACGATTGCGTTTTTTTGGGACTCACCGAGTTCGAGCACTTACTATTCTATCAA a         T   G   M   L   T   Q   K   N   P   E   W   L   K   L   V   N   D   K   I   V   -
b         P   A   C   *   R   K   K   T   L   S   G   S   S   S   *   M   I   R   *   L   -
c         R   H   A   N   A   K   K   P   *   V   A   Q   A   R   E   *   *   D   S   C   -
    8041  ----------+----------+----------+----------+----------+----------+   8100
d         S   R   C   A   L   A   F   F   G   Q   T   A   *   A   R   S   H   Y   S   L   -
e         V   P   M   S   V   C   F   F   G   S   H   S   L   S   T   F   S   L   I   T   -
f             G   A   H   *   R   L   F   V   R   L   P   E   L   E   H   I   I   L   Y   N   -

T
                                              s
                                              p                   C
          FH                                  5                   v
          sh                                  0                   i
          pa                                  9                   J
          II                                  I                   I
          GCGCATAATGTAGGAAGCGTTCCTTTGTCAGAGTATGATAAAATTGGCTTCAACCAGAAG
    8101  ----------+----------+----------+----------+----------+----------+   8160
          CGCGTATTACATCCTTCGCAAGGAAACAGTCTCATACTATTTTAACCGAAGTTGGTCTTC a         A   H   N   V   G   S   V   P   L   S   E   Y   D   K   I   G   F   N   Q   K   -
b         R   I   M   *   E   A   F   L   C   Q   S   M   I   K   L   A   S   T   R   R   -
c         A   *   C   R   K   R   S   F   V   R   V   *   *   N   W   L   Q   P   E   E   -
    8101  ----------+----------+----------+----------+----------+----------+   8160
d         Q   A   Y   H   L   F   R   E   K   T   L   T   H   Y   F   Q   S   *   G   S   -
e         A   C   L   T   P   L   T   G   K   D   S   Y   S   L   I   P   K   L   W   F   -
f         R   M   I   Y   S   A   N   R   Q   *   L   I   I   F   N   A   E   V   L   L   -

M           H
                      b           iT
                      o           nf                                              C
                      I           fi                                              j
                      I           II                                              e
                                   /                                              I
          AATATGAAAGATTATTCTGATTCGTTCAAGTTTTCCACCAAGTTGAACAATGCTGTAAAA
```

FIG.2-SEQUENCE1-PAGE40

```
      8161 ----------+---------+---------+---------+---------+---------+ 8220
           TTATACTTTCTAATAAGACTAAGCAAGTTCAAAAGGTGGTTCAACTTGTTACGACATTTT a        N  M  K  D  Y  S  D  S  F  K  F  S  T  K  L  N  N  A  V  K  -
  b         I  *  K  I  I  L  I  R  S  S  F  P  P  S  *  T  M  L  *  K -
  c          Y  E  R  L  F  *  F  V  Q  V  F  H  Q  V  E  Q  C  C  K  R-
      8161 ----------+---------+---------+---------+---------+---------+ 8220
  d        S  Y  S  L  N  N  Q  N  T  *  T  K  W  W  T  S  C  H  Q  L  -
  e         F  I  F  S  *  E  S  E  N  L  N  E  V  L  N  F  L  A  T  F -
  f          I  H  F  I  I  R  I  R  E  L  K  G  G  L  Q  V  I  S  Y  F-

T
                     T                    T                     t
                     s                    s                     h
                     p              C     p             C       l       S
                     5              v     C5      M     v    N  l       f
                     0              i     j0      s     i    s  l       a
                     9              J     e9      e     R    f  I       N
                     I              I     II      I     II   I  I       I
           GACACTAATTCTGGCTTTACGCAATTTTTAACCAATGCATTTTCTACAGCATCTTATTAC
      8221 ----------+---------+---------+---------+---------+---------+ 8280
           CTGTGATTAAGACCGAAATGCGTTAAAAATTGGTTACGTAAAAGATGTCGTAGAATAATG a        D  T  N  S  G  F  T  Q  F  L  T  N  A  F  S  T  A  S  Y  Y  -
  b         T  L  I  L  A  L  R  N  F  *  P  M  H  F  L  Q  H  L  I  T -
  c          H  *  F  W  L  Y  A  I  F  N  Q  C  I  F  Y  S  I  L  L  L-
      8221 ----------+---------+---------+---------+---------+---------+ 8280
  d        L  C  *  N  Q  S  *  A  I  K  L  W  H  M  K  *  L  M  K  N  -
  e         S  V  L  E  P  K  V  C  N  K  V  L  A  N  E  V  A  D  *  * -
  f          V  S  I  R  A  K  R  L  K  *  G  I  C  K  R  C  C  R  I  V-

P
                                                    s
                                         N          p
                                         1H         M1
                            A            aiCT       a4     M
                            c            Injf       e0     s
                            i            Ifei       I6     e
                            I            IIII       II     I
                                         /          /
           TGCTTGGCGAGAGAAAATGCGGAGCATGGAATCAAGAACGTTAATACAAAAGGTGGTTTC
      8281 ----------+---------+---------+---------+---------+---------+ 8340
           ACGAACCGCTCTCTTTTACGCCTCGTACCTTAGTTCTTGCAATTATGTTTTCCACCAAAG a        C  L  A  R  E  N  A  E  H  G  I  K  N  V  N  T  K  G  G  F  -
  b         A  W  R  E  K  M  R  S  M  E  S  R  T  L  I  Q  K  V  V  S -
  c          L  G  E  R  K  C  G  A  W  N  Q  E  R  *  Y  K  R  W  F  P-
      8281 ----------+---------+---------+---------+---------+---------+ 8340
  d        S  S  P  S  L  F  H  P  A  H  F  *  S  R  *  Y  L  L  H  N  -
  e         Q  K  A  L  S  F  A  S  C  P  I  L  F  T  L  V  F  P  P  K -
  f          A  Q  R  S  F  I  R  L  M  S  D  L  V  N  I  C  F  T  T  E-

C            M            M                        M
                     j            s            s                        n
                     e            e            e                        l
                     I            I            I                        I
           CAAAAATCTTAAAGGATTAAGGAATACCAAAAACGCAAAAACCACCCCTTGCTAAAAGCG
      8341 ----------+---------+---------+---------+---------+---------+ 8400
           GTTTTTAGAATTTCCTAATTCCTTATGGTTTTTGCGTTTTTGGTGGGGAACGATTTTCGC a        Q  K  S  *  R  I  K  E  Y  Q  K  R  K  N  H  P  L  L  K  A  -
  b         K  N  L  K  G  L  R  N  T  K  N  A  K  T  T  P  C  *  K  R -
  c          K  I  L  K  D  *  G  I  P  K  T  Q  K  P  P  L  A  K  S  E-
      8341 ----------+---------+---------+---------+---------+---------+ 8400
  d        G  F  I  K  F  S  *  P  I  G  F  V  C  F  G  G  R  A  L  L  -
  e         W  F  D  *  L  I  L  S  Y  W  F  R  L  F  W  G  K  S  F  A -
```

FIG.2-SEQUENCE1-PAGE41

```
f           L  F  R  L  P  N  L  F  V  L  F  A  F  V  V  G  Q  *  F  R  -
                              B
                              p
                    M         uD
                    s         1d
                    e         0e
                    I         II
                       /
       AGGGGTTTTTTAATACTCCTTAGCAGAAATCCCAATCGTCTTTAGTATTTGGGATGAATG
 8401  ---------+---------+---------+---------+---------+---------+ 8460
       TCCCCAAAAAATTATGAGGAATCGTCTTTAGGGTTAGCAGAAATCATAAACCCTACTTAC a          R  G  F  L  I  L  L  S  R  N  P  N  R  L  *  Y  L  G  *  M  -
b           G  V  F  *  Y  S  L  A  E  I  P  I  V  F  S  I  W  D  E  C  -
c            G  F  F  N  T  P  *  Q  K  S  Q  S  S  L  V  F  G  M  N  A  -
 8401  ---------+---------+---------+---------+---------+---------+ 8460
d          S  P  N  K  L  V  G  *  C  F  D  W  D  D  K  T  N  P  I  F  -
e           L  P  K  K  I  S  R  L  L  F  G  L  R  R  *  Y  K  P  H  I  -
f            P  T  K  *  Y  E  K  A  S  I  G  I  T  K  L  I  Q  S  S  H  -

T
                 s
                 p            N
                 P            l                                    M
        B        F5     Bf    a                  B       B         C       a
        s        o0     sl    I                  a       f         v       e
        m        k9     1M    I                  e       a         i       I
        I        II     II    I                  I       I         R       I
               /       /                                                   I
       CTACCAATTCATGGTATCATATCCCCATACATTCGTATCTAGCGTAGGAAGTGTGCAAAG
 8461  ---------+---------+---------+---------+---------+---------+ 8520
       GATGGTTAAGTACCATAGTATAGGGGTATGTAAGCATAGATCGCATCCTTCACACGTTTC a          L  P  I  H  G  I  I  S  P  Y  I  R  I  *  R  R  K  C  A  K  -
b           Y  Q  F  M  V  S  Y  P  H  T  F  V  S  S  V  G  S  V  Q  S  -
c            T  N  S  W  Y  H  I  P  I  H  S  Y  L  A  *  E  V  C  K  V  -
 8461  ---------+---------+---------+---------+---------+---------+ 8520
d          A  V  L  E  H  Y  *  I  G  M  C  E  Y  R  A  Y  S  T  H  L  -
e           S  G  I  *  P  I  M  D  G  Y  M  R  I  *  R  L  F  H  A  F  -
f            *  W  N  M  T  D  Y  G  W  V  N  T  D  L  T  P  L  T  C  L  -

E
                                                                       s
                                                                    A  p
                       B                                            C1B1
                       Bs    M       S                    B         Avwa2S
                       sm    m       f                    s         1i2n8a
                       aA    e       c                    m         uJ1I6c
                       II    I       I                    I         IIIIII
                       /                                            / ///
       TTACGCCTTTGGAGATATGATGTGTGAGACCTGTAGGGAATGCGTTGGAGCTCAAACTCT
 8521  ---------+---------+---------+---------+---------+---------+ 8580
       AATGCGGAAACCTCTATACTACACACTCTGGACATCCCTTACGCAACCTCGAGTTTGAGA a          L  R  L  W  R  Y  D  V  *  D  L  *  G  M  R  W  S  S  N  S  -
b           Y  A  F  G  D  M  M  C  E  T  C  R  E  C  V  G  A  Q  T  L  -
c            T  P  L  E  I  *  C  V  R  P  V  G  N  A  L  E  L  K  L  C  -
 8521  ---------+---------+---------+---------+---------+---------+ 8580
d          T  V  G  K  S  I  H  H  T  L  G  T  P  F  A  N  S  S  L  S  -
e           N  R  R  Q  L  Y  S  T  H  S  R  Y  P  I  R  Q  L  E  F  E  -
f            *  A  K  P  S  I  I  H  S  V  Q  L  S  H  T  P  A  *  V  R  -

D
                    E        r      B  D                 B
                    c   B    a      s  r                 s         M
                    o   s    I      m  d                 c         w
```

FIG.2-SEQUENCE 1-PAGE 42

```
                    N 1           I    F I                   G    o
                    I I           I    I I                   I    I
             GTAAAATCCCTATTATAGGGACACAGAGTGAGAACCAAACTCTCCCTACGGGCAACATCA
      8581   ----------+---------+---------+---------+---------+---------+ 8640
             CATTTTAGGGATAATATCCCTGTGTCTCACTCTTGGTTTGAGAGGGATGCCCGTTGTAGT a              V  K  S  L  L  *  G  H  R  V  R  T  K  L  S  L  R  A  T  S  -
b              *  N  P  Y  Y  R  D  T  E  *  E  P  N  S  P  Y  G  Q  H  Q  -
c              K  I  P  I  I  G  T  Q  S  E  N  Q  T  L  P  T  G  N  I  S  -
      8581   ----------+---------+---------+---------+---------+---------+ 8640
d              Q  L  I  G  I  I  P  V  C  L  S  F  W  V  R  G  V  P  L  M  -
e              T  F  D  R  N  Y  P  C  L  T  L  V  L  S  E  R  R  A  V  D  -
f              Y  F  C  *  *  L  S  V  S  H  S  G  F  E  G  *  P  C  C  *

B
                                                    s
                                                    p
       CA  B        C                               1
       vvBsS M      v              A   H   B  2           M
       irfat w      i              c   p   m  8           s
       JIaJy o      J              i   h   g  6           e
       IIIII I      I              I   I   I  I           I
              //
             GCCTAGGAAGCCCAATCGTCTTTAGCGGTTGGGCACTTCACCTTAAAATATCCCGACAGA
      8641   ----------+---------+---------+---------+---------+---------+ 8700
             CGGATCCTTCGGGTTAGCAGAAATCGCCAACCCGTGAAGTGGAATTTTATAGGGCTGTCT a              A  *  E  A  Q  S  S  L  A  V  G  H  F  T  L  K  Y  P  D  R  -
b              P  R  K  P  N  R  L  *  R  L  G  T  S  P  *  N  I  P  T  D  -
c              L  G  S  P  I  V  F  S  G  W  A  L  H  L  K  I  S  R  Q  T  -
      8641   ----------+---------+---------+---------+---------+---------+ 8700
d              L  R  P  L  G  I  T  K  L  P  Q  A  S  *  R  L  I  D  R  C  -
e              A  *  S  A  W  D  D  K  A  T  P  C  K  V  K  F  Y  G  S  L  -
f              G  L  F  G  L  R  R  *  R  N  P  V  E  G  *  F  I  G  V  S  -

N
                      C                         l
                      v           MD            a                        M
                      i           sr            I                        s
                      J           ea    R       I                        e
                      I           II    I       I                        I
             CACTAACGAAAGGCTTTGTTCTTTAAAGTCTGCATGGATATTTCCTACCCCAAAAAGACT
      8701   ----------+---------+---------+---------+---------+---------+ 8760
             GTGATTGCTTTCCGAAACAAGAAATTTCAGACGTACCTATAAAGGATGGGGTTTTTCTGA a              H  *  R  K  A  L  F  F  K  V  C  M  D  I  S  Y  P  K  K  T  -
b              T  N  E  R  L  C  S  L  K  S  A  W  I  F  P  T  P  K  R  L  -
c              L  T  K  G  F  V  L  *  S  L  H  G  Y  F  L  P  Q  K  D  L  -
      8701   ----------+---------+---------+---------+---------+---------+ 8760
d              V  S  V  F  P  K  T  R  *  L  R  C  P  Y  K  R  G  W  F  S  -
e              C  *  R  F  A  K  N  K  L  T  Q  M  S  I  E  *  G  L  F  V  -
f              V  L  S  L  S  Q  E  K  F  D  A  H  I  N  G  V  G  F  L  S  -

T                                              T
                         s                                              s
                         p                                              p
                   M     5    M                B         S              5
                   s     0    s                f         f              0
                   e     9    e                a         c              9
                   I     I    I                I         I              I
             TAACCCTTTGCTTAAAATTAAGTTTGATTGTGCTAGTGGGTTCGTGCTATAGTGCGAAAA
      8761   ----------+---------+---------+---------+---------+---------+ 8820
             ATTGGGAAACGAATTTTAATTCAAACTAACACGATCACCCAAGCACGATATCACGCTTTT a              *  P  F  A  *  N  *  V  *  L  C  *  W  V  R  A  I  V  R  K  -
b              N  P  L  L  K  I  K  F  D  C  A  S  G  F  V  L  *  C  E  N  -
```

FIG.2-SEQUENCE1-PAGE43

```
c              T  L  C  L  K  L  S  L  I  V  L  V  G  S  C  Y  S  A  K  I  -
       8761 ---------+---------+---------+---------+---------+---------+ 8820
d              K  V  R  Q  K  F  N  L  K  I  T  S  T  P  E  H  *  L  A  F  -
e              *  G  K  A  *  F  *  T  Q  N  H  *  H  T  R  A  I  T  R  F  -
f              L  G  K  S  L  I  L  N  S  Q  A  L  P  N  T  S  Y  H  S  F  -

T
             s
             p                                                  C            S
             M5V   MP                                           Av           a
             s0s   sa                          B                li           u  D
             e9p   ec                          f                uJ           3  p
             III   II                          a                II           A. n
                 / /                           I               /             I  I
             TTAATTAAGGGTTATAAAGAGAGCATAAACTAGAAAAAACAAGTAGCTATAACAAAGATC
       8821 ---------+---------+---------+---------+---------+---------+ 8880
             AATTAATTCCCAATATTTCTCTCGTATTTGATCTTTTTTGTTCATCGATATTGTTTCTAG a              L  I  K  G  Y  K  E  S  I  N  *  K  K  Q  V  A  I  T  K  I  -
b              *  L  R  V  I  K  R  A  *  T  R  K  N  K  *  L  *  Q  R  S  -
c              N  *  G  L  *  R  E  H  K  L  E  K  T  S  S  Y  N  K  D  Q  -
       8821 ---------+---------+---------+---------+---------+---------+ 8880
d              I  L  *  P  N  Y  L  S  C  L  S  S  F  V  L  L  *  L  L  S  -
e              N  I  L  P  *  L  S  L  M  F  *. F  F  C  T  A  I  V  F  I  -
f              *  N  L  T  I  F  L  A  Y  V  L  F  F  L  Y  S  Y  C  L  D  -

T
                                    s      S
                              C     p      a
                        B  Av M     5      u  D  T  H  M         B
                        c  li w     0      3  p  h  h  s         c
                        g  uJ o     9      A  n  a  a  e         g
                        I  II I     I      I  I  I  I  I         I
                                   /
             AAGTTCAAAAAATCATAGAGCTTTTAGAGCAAATTGATCGCGCTCTTAACCAAAGAAAAA
       8881 ---------+---------+---------+---------+---------+---------+ 8940
             TTCAAGTTTTTTAGTATCTCGAAAATCTCGTTTAACTAGCGCGAGAATTGGTTTCTTTTT a              K  F  K  K  S  *  S  F  *  S  K  L  I  A  L  L  T  K  E  K  -
b              S  S  K  N  H  R  A  F  R  A  N  *  S  R  S  *  P  K  K  N  -
c              V  Q  K  I  I  E  L  L  E  Q  I  D  R  A  L  N  Q  R  K  I  -
       8881 ---------+---------+---------+---------+---------+---------+ 8940
d              *  T  *  F  I  M  S  S  K  S  C  I  S  R  A  R  L  W  L  F  -
e              L  N  L  F  D  Y  L  K  *  L  L  N  I  A  S  K  V  L  S  F  -
f              L  E  F  F  *  L  A  K  L  A  F  Q  D  R  E  *  G  F  F  F  -

T
             s
             p                                                     S
             5                             C            C           a
             0                             j            a           uHD
             9                             e            c           3gp
             I                             P            8           Aan
                                           I            I           I  III
             TCAGAAAAACCATAGGAATTATCACACCTTATAATGCCCAAAAAAGACGCTTGCGATCAG
       8941 ---------+---------+---------+---------+---------+---------+ 9000
             AGTCTTTTTGGTATCCTTAATAGTGTGGAATATTACGGGTTTTTCTGCGAACGCTAGTC a              S  E  K  P  *  E  L  S  H  L  I  M  P  K  K  D  A  C  D  Q  -
b              Q  K  N  H  R  N  Y  H  T  L  *  C  P  K  K  T  L  A  I  R  -
c              R  K  T  I  G  I  I  T  P  Y  N  A  Q  K  R  R  L  R  S  E  -
       8941 ---------+---------+---------+---------+---------+---------+ 9000
d              I  L  F  V  M  P  I  I  V  G  *  L  A  W  F  L  R  K  R  D  -
e              D  S  F  G  Y  S  N  D  C  R  I  I  G  L  F  S  A  Q  S  *  -
f              *  F  F  W  L  F  *  *  V  K  Y  H  G  F  F  V  S  A  I  L  -
```

B

FIG.2 -SEQUENCE 1 -PAGE 44

```
                              T                 s
                              s                 A  p
                    C    C    p         B       C1B1              S
                    j    v    A5        c       Avwa2S            f
                    e    i    p0        e       1i2n8a            a
                    P    J    o9        f       uJ1I6c            N
                    I    I    II        I       IIIIII            I
                                      /       /  ///
        AAGTGGAAAAATACGGCTTCAAGAATTTTGATGAGCTCAAAATAGACACTGTGGATGCCT
  9001  ----------+---------+---------+---------+---------+----------+  9060
        TTCACCTTTTTATGCCGAAGTTCTTAAAACTACTCGAGTTTTATCTGTGACACCTACGGA a     K  W  K  N  T  A  S  R  I  L  M  S  S  K  *  T  L  W  M  P  -
  b      S  G  K  I  R  L  Q  E  F  *  *  A  Q  N  L  H  C  G  C  L -
  c       V  E  K  Y  G  F  K  N  F  D  E  L  K  I  D  T  V  D  A  F -
  9001  ----------+---------+---------+---------+---------+----------+  9060
  d     S  T  S  F  Y  P  K  L  F  K  S  S  S  L  I  S  V  T  S  A  -
  e      F  H  F  F  V  A  E  L  I  K  I  L  E  F  Y  V  S  H  I  G -
  f       L  P  F  I  R  S  *  S  N  Q  H  A  *  F  L  C  Q  P  H  R -

M         C
                    EMF       b         j                           C
                    ano       o         e                           j
                    rlk       h         P                           e
                    III       I I       I                           P
        TTCAAGGTGAAGAGGCAGATATTATTATTTATTCCACCGTGAAAACTTGTGGTAATCTTT
  9061  ----------+---------+---------+---------+---------+----------+  9120
        AAGTTCCACTTCTCCGTCTATAATAATAAATAAGGTGGCACTTTTGAACACCATTAGAAA a     F  K  V  K  R  Q  I  L  L  F  I  P  P  *  K  L  V  V  I  F  -
  b      S  R  *  R  G  R  Y  Y  Y  L  F  H  R  E  N  L  W  *  S  F -
  c       Q  G  E  E  A  D  I  I  I  Y  S  T  V  K  T  C  G  N  L  S -
  9061  ----------+---------+---------+---------+---------+----------+  9120
  d     K  *  P  S  S  A  S  I  I  I  *  E  V  T  F  V  Q  P  L  R  -
  e      K  L  T  F  L  C  I  N  N  N  I  G  G  H  F  S  T  T  I  K -
  f       E  L  H  L  P  L  Y  *  *  K  N  W  R  S  F  K  H  Y  D  K -

H                   C                           R
                    B    iT             v         B                 1
                    f    nf             i         f                 e
                    a    fi             J         a                 A
                    I    II             I         I                 I
                     /
        CTTTCTTGCTAGATTCTAAACGCTTGAATGTGGCTATTTCTAGGGCAAAAGAAAATCTCA
  9121  ----------+---------+---------+---------+---------+----------+  9180
        GAAAGAACGATCTAAGATTTGCGAACTTACACCGATAAAGATCCCGTTTTCTTTTAGAGT a     L  S  C  *  I  L  N  A  *  M  W  L  F  L  G  Q  K  K  I  S  -
  b      F  L  A  R  F  *  T  L  E  C  G  Y  F  *  G  K  R  K  S  H -
  c       F  L  L  D  S  K  R  L  N  V  A  I  S  R  A  K  E  N  L  I -
  9121  ----------+---------+---------+---------+---------+----------+  9180
  d     E  K  K  S  S  E  L  R  K  F  T  A  I  E  L  A  F  S  F  R  -
  e      R  E  Q  *  I  R  F  A  Q  I  H  S  N  R  P  C  F  F  I  E -
  f       K  R  A  L  N  *  V  S  S  H  P  *  K  *  P  L  L  F  D  * -

T
                                        s
                                        p                           M
                    M                   A5                          b
                    s                   p0                          o
                    l                   o9                          I
                    I                   II                          I
                                      /
        TTTTTGTGGGTAAAAAGTCTTTCTTTGAGAATTTATGAAGCGATGAGAAGAATATCTTTA
  9181  ----------+---------+---------+---------+---------+----------+  9240
        AAAAACACCCATTTTTCAGAAAGAAACTCTTAAATACTTCGCTACTCTTCTTATAGAAAT
```

FIG.2-SEQUENCE 1-PAGE 45

```
a      F  L  W  V  K  S  L  S  L  R  I  Y  E  A  M  R  R  I  S  L  -
b      F  C  G  *  K  V  F  L  *  E  F  M  K  R  *  E  E  Y  L  *  -
c         F  V  G  K  K  S  F  F  E  N  L  *  S  D  E  K  N  I  F  S  -
  9181 ---------+---------+---------+---------+---------+---------+ 9240
d      M  K  T  P  L  F  D  K  K  S  F  K  H  L  S  S  F  F  I  K  -
e      N  K  H  T  F  L  R  E  K  L  I  *  S  A  I  L  L  I  D  K  -
f         K  Q  P  Y  F  T  K  R  Q  S  N  I  F  R  H  S  S  Y  R  *  -

E
                                        c
                                        o
          4                  H          4    H                  M    C
          7Ha                v          S    j    i             b    j
          Ihe                i          f    e    n             o    e
          IaI                R          c    P    4             I    P
          III                I          I    I    I             I    I
         GCGCTATTTTGCAAGTCTGTAGATAGGTAATCTTTTCCAAAGATAATCATTAGACATTCT
  9241 ---------+---------+---------+---------+---------+---------+ 9300
         CGCGATAAAACGTTCAGACATCTATCCATTAGAAAAGGTTTCTATTAGTAATCTGTAAGA a      A  L  F  C  K  S  V  D  R  *  S  F  P  K  I  I  I  R  H  S  -
b      R  Y  F  A  S  L  *  I  G  N  L  F  Q  R  *  S  L  D  I  L  -
c         A  I  L  Q  V  C  R  *  V  I  F  S  K  D  N  H  *  T  F  F  -
  9241 ---------+---------+---------+---------+---------+---------+ 9300
d      L  A  I  K  C  T  Q  L  Y  T  I  K  E  L  S  L  *  *  V  N  -
e      A  S  N  Q  L  D  T  S  L  Y  D  K  G  F  I  I  M  L  C  E  -
f         R  *  K  A  L  R  Y  I  P  L  R  K  W  L  Y  D  N  S  M  R  -

E
                                   c
                                   o
                                   4  H
                                   7Ha          B
                                   Ihe          s
                                   IaI          b
                                   III          I
         TCGCTTCAAAACGCTTTCATAAATCTCTCTAAAGCGCTTTATAATCAACACAATACCCTT
  9301 ---------+---------+---------+---------+---------+---------+ 9360
         AGCGAAGTTTTGCGAAAGTATTTAGAGAGATTTCGCGAAATATTAGTTGTGTTATGGGAA a      S  L  Q  N  A  F  I  N  L  S  K  A  L  Y  N  Q  H  N  T  L  -
b      R  F  K  T  L  S  *  I  S  L  K  R  F  I  I  N  T  I  P  L  -
c         A  S  K  R  F  H  K  S  L  *  S  A  L  *  S  T  Q  Y  P  Y  -
  9301 ---------+---------+---------+---------+---------+---------+ 9360
d      K  A  E  F  R  K  *  L  D  R  *  L  A  K  Y  D  V  C  Y  G  -
e      E  S  *  F  A  K  M  F  R  E  L  A  S  *  L  *  C  L  V  R  -
f         R  K  L  V  S  E  Y  I  E  R  F  R  K  I  I  L  V  I  G  K  -

T                      T
                                        s                      s
                C       C               p                      p
              AvS       v       BB      5              MDA5
              lif       i       ss      0              scp0
              uJc       J       11      9              eao9
              III       I       II      I              IIII
                //                                       /
         ATAGTGTGAGCTATAGCCCCTTTTTGGGAATTGAGTTATTTTGACTTTAAATTTTTATTA
  9361 ---------+---------+---------+---------+---------+---------+ 9420
         TATCACACTCGATATCGGGGAAAAACCCTTAACTCAATAAAACTGAAATTTAAAAATAAT a      I  V  *  A  I  A  P  F  W  E  L  S  Y  F  D  F  K  F  L  L  -
b      *  .C  E  L  *  P  L  F  G  N  *  V  I  L  T  L  N  F  Y  *  -
c         S  V  S  Y  S  P  F  L  G  I  E  L  F  *  L  *  I  F  I  S  -
  9361 ---------+---------+---------+---------+---------+---------+ 9420
d      *  L  T  L  *  L  G  K  K  P  I  S  N  N  Q  S  *  I  K  I  -
```

FIG.2-SEQUENCE1-PAGE46

```
e       I  T  H  A  I  A  G  K  Q  S  N  L  *  K  S  K  L  N  K  N  -
f       Y  H  S  S  Y  G  R  K  P  F  Q  T  I  K  V  K  F  K  *  *  -

T
        M     s
        a     p              C               CC              C     a                BBUC  C
        e     5              v               Ajv             B  v  u  D             Assba j
        I     0              i               lei             f  i  3  p             corac e
        I     9              J               uPJ             a  J  A  n             iFBJ8 P
        I     I              I               III             I  I  I  I             IIII  I
                                                              //                        //
        GCGTTACAATTTGAGCCATTCTTTAGCTTGTTTTTCTAGCCAGATCACATCGCCGCTCGC
  9421  ----------+----------+----------+----------+----------+----------+ 9480
        CGCAATGTTAAACTCGGTAAGAAATCGAACAAAAAGATCGGTCTAGTGTAGCGGCGAGCG a       A  L  Q  F  E  P  F  F  S  L  F  F  *  P  D  H  I  A  A  R  -
b       R  Y  N  L  S  H  S  L  A  C  F  S  S  Q  I  T  S  P  L  A  -
c          V  T  I  *  A  I  L  *  L  V  F  L  A  R  S  H  R  R  S  H  -
  9421  ----------+----------+----------+----------+----------+----------+ 9480
d       L  T  V  I  Q  A  M  R  *  S  T  K  R  A  L  D  C  R  R  E  -
e       A  N  C  N  S  G  N  K  L  K  N  K  *  G  S  *  M  A  A  R  -
f          R  *  L  K  L  W  E  K  A  Q  K  E  L  W  I  V  D  G  S  A  -

T
        N     s
        l     p                                    C
        aA    5              B               B     v              M  B              B  C
        Ip    0              s               s     i              s  b              sTv
        Io    9              l               m     R              e  v              osi
        II    I              I               I     I              I  I              FeR
                                                                                    III
                   /                                                                 /
        ATGAAATTCCACTTTAGGGAATGCGTGTGCATTTTTTTTAAGGGCGTATTTTTGCTGCAA
  9481  ----------+----------+----------+----------+----------+----------+ 9540
        TACTTTAAGGTGAAATCCCTTACGCACACGTAAAAAAAATTCCCGCATAAAAACGACGTT a       M  K  F  H  F  R  E  C  V  C  I  F  F  K  G  V  F  L  L  Q  -
b          *  N  S  T  L  G  N  A  C  A  F  F  L  R  A  Y  F  C  C  K  -
c       E  I  P  L  *  G  M  R  V  H  F  F  *  G  R  I  F  A  A  N  -
  9481  ----------+----------+----------+----------+----------+----------+ 9540
d       C  S  I  G  S  *  P  I  R  T  C  K  K  *  P  R  I  K  A  A  -
e       M  F  N  W  K  L  S  H  T  H  M  K  K  L  P  T  N  K  S  C  -
f       H  F  E  V  K  P  F  A  H  A  N  K  K  L  A  Y  K  Q  Q  L  -

S
                          f                                      F     B
                          a                                      o     s
                          N                                      k     b
                          I                                      I     I
        ATATCCTACAATAGCATCGCCCGAATGGATGAGTAGGGGGGGTGTTGAAAGGGCAAAATG
  9541  ----------+----------+----------+----------+----------+----------+ 9600
        TATAGGATGTTATCGTAGCGGGCTTACCTACTCATCCCCCCCACAACTTTCCCGTTTTAC a       I  S  Y  N  S  I  A  R  M  D  E  *  G  G  C  *  K  G  K  M  -
b       Y  P  T  I  A  S  P  E  W  M  S  R  G  G  V  E  R  A  K  C  -
c          I  L  Q  *  H  R  P  N  G  *  V  G  G  V  L  K  G  Q  N  A  -
  9541  ----------+----------+----------+----------+----------+----------+ 9600
d       F  I  R  C  Y  C  R  G  F  P  H  T  P  P  T  N  F  P  C  F  -
e       I  D  *  L  L  M  A  R  I  S  S  Y  P  P  H  Q  F  P  L  I  -
f       Y  G  V  I  A  D  G  S  H  I  L  L  P  P  T  S  L  A  F  H  -

T
                   s
              C    p                                              C  C
              v    5              M               M               a  v
              i    0              n               s               c  i
              J    9              l               e               8  R
```

FIG.2-SEQUENCE1-PAGE47

```
                      I   I        I    I           I I
              CTCCATAAAATAGCCCTCAATTTTTTGAGCGATTAAGGGAAAATGCGTGCAACCTAAAAT
        9601  ----------+---------+---------+---------+---------+---------+  9660
              GAGGTATTTTATCGGGAGTTAAAAAACTCGCTAATTCCCTTTTACGCACGTTGGATTTTA a            L  H  K  I  A  L  N  F  L  S  D  *  G  K  M  R  A  T  *  N  -
   b             S  I  K  *  P  S  I  F  *  A  I  K  G  K  C  V  Q  P  K  I -
   c              P  *  N  S  P  Q  F  F  E  R  L  R  E  N  A  C  N  L  K  * -
        9601  ----------+---------+---------+---------+---------+---------+  9660
   d            A  G  Y  F  L  G  *  N  K  S  R  N  L  S  F  A  H  L  R  F  -
   e             S  W  L  I  A  R  L  K  K  L  S  *  P  F  I  R  A  V  *  F -
   f              E  M  F  Y  G  E  I  K  Q  A  I  L  P  F  H  T  C  G  L  I -

T
                                                N                        s
                                             C  Cl                       p
                                  M          a  vaNS                     5
                                  s          c  iIsp                     0
                                  e          8  RIph                     9
                                  I          I  IIII                     I
                                                  ///
              AATCACTTCGGGAAAATCTTTAAGGGAGTGAAATAATAACGCATGCAAGTTTCTAACAAT
        9661  ----------+---------+---------+---------+---------+---------+  9720
              TTAGTGAAGCCCTTTTAGAAATTCCCTCACTTTATTATTGCGTACGTTCAAAGATTGTTA a            N  H  F  G  K  I  F  K  G  V  K  *  *  R  M  Q  V  S  N  N  -
   b             I  T  S  G  K  S  L  R  E  *  N  N  N  A  C  K  F  L  T  I -
   c              S  L  R  E  N  L  *  G  S  E  I  I  T  H  A  S  F  *  Q  F -
        9661  ----------+---------+---------+---------+---------+---------+  9720
   d            Y  D  S  R  S  F  R  *  P  L  S  I  I  V  C  A  L  K  *  C  -
   e             L  *  K  P  F  I  K  L  P  T  F  Y  Y  R  M  C  T  E  L  L -
   f              I  V  E  P  F  D  K  L  S  H  F  L  L  A  H  L  N  R  V  I -

M
                            b     M                                      C
                            o     n                                      v
                            I     l                                      i
                            I     I                                      J
                                                                         I
              TCGCCCTCTAAAATACTTTCTTCAATCAAAGGCACAAAAAGAGAAGTGGCTAAATGCGAA
        9721  ----------+---------+---------+---------+---------+---------+  9780
              AGCGGGAGATTTTATGAAAGAAGTTAGTTTCCGTGTTTTTCTCTTCACCGATTTACGCTT a            S  P  S  K  I  L  S  S  I  K  G  T  K  R  E  V  A  K  C  E  -
   b             R  P  L  K  Y  F  L  Q  S  K  A  Q  K  E  K  W  L  N  A  K -
   c              A  L  *  N  T  F  F  N  Q  R  H  K  K  R  S  G  *  M  R  N -
        9721  ----------+---------+---------+---------+---------+---------+  9780
   d            N  A  R  *  F  V  K  K  L  *  L  C  L  F  L  L  P  *  I  R  -
   e             E  G  E  L  I  S  E  E  I  L  P  V  F  L  S  T  A  L  H  S -
   f              R  G  R  F  Y  K  R  *  D  F  A  C  F  S  F  H  S  F  A  F -

S
                            C                            Ba
                            v           M                su  D        A
                            i           m                m3  p        l
                            J           e                FA  n        w
                            I           I                II  I        I
              ACATTCAAATAGCCTTGTTGTTTCAGGGCATTGTCATAAGCGTTGGATTGGATCGTCGCT
        9781  ----------+---------+---------+---------+---------+---------+  9840
              TGTAAGTTTATCGGAACAACAAAGTCCCGTAACAGTATTCGCAACCTAACCTAGCAGCGA a            T  F  K  *  P  C  C  F  R  A  L  S  *  A  L  D  W  I  V  A  -
   b             H  S  N  S  L  V  V  S  G  H  C  H  K  R  W  I  G  S  S  L -
   c              I  Q  I  A  L  L  F  Q  G  I  V  I  S  V  G  L  D  R  R  F -
        9781  ----------+---------+---------+---------+---------+---------+  9840
   d            F  M  *  I  A  K  N  N  *  P  M  T  M  L  T  P  N  S  R  R  -
   e             V  N  L  Y  G  Q  Q  K  L  A  N  D  Y  A  N  S  Q  I  T  A -
```

FIG.2-SEQUENCE 1-PAGE 48

```
f           C  E  F  L  R  T  T  E  P  C  Q  *  L  R  Q  I  P  D  D  S -
                                                            T
                                                            t
                                              S             h
                                              a             l
                         B                    u            Dl
                         f                    3            pl
                         a                    A            nI
                         I                    I            II
          TTTGTCCCTAGCACTAAAATAGGGGCGTTTTTATCTTTTACTTGTCGCTTGATCGCTAAA
     9841 -----------+----------+----------+----------+----------+----------+ 9900
          AAACAGGGATCGTGATTTTATCCCCGCAAAAATAGAAAATGAACAGCGAACTAGCGATTT a         F  V  P  S  T  K  I  G  A  F  L  S  F  T  C  R  L  I  A  K  -
b            L  S  L  A  L  K  *  G  R  F  Y  L  L  L  V  A  *  S  L  K -
c              C  P  *  H  *  N  R  G  V  F  I  F  Y  L  S  L  D  R  * N -
     9841 -----------+----------+----------+----------+----------+----------+ 9900
d         K  Q  G  *  C  *  F  L  P  T  K  I  K  *  K  D  S  S  R  *  -
e            K  T  G  L  V  L  I  P  A  N  K  D  K  V  Q  R  K  I  A L -
f              K  D  R  A  S  F  Y  P  R  K  *  R  K  S  T  A  Q  D  S F -

C                         R        M  C             S
             v                         l        Bb v             fE
             i              BB         e        so i             aa
             J              ss         A        mI R             Nr
             I              11         I        II I             II
                            II
          ATGCTTGGCTCAATCACGCCCACAATAGGGATTTTGGAATGCTTTTGCATCTCTTCTAAA
     9901 -----------+----------+----------+----------+----------+----------+ 9960
          TACGAACCGAGTTAGTGCGGGTGTTATCCCTAAAACCTTACGAAAACGTAGAGAAGATTT a         M  L  G  S  I  T  P  T  I  G  I  L  E  C  F  C  I  S  S  K  -
b            C  L  A  Q  S  R  P  Q  *  G  F  W  N  A  F  A  S  L  L K -
c              A  W  L  N  H  A  H  N  R  D  F  G  M  L  L  H  L  F  * S -
     9901 -----------+----------+----------+----------+----------+----------+ 9960
d         F  A  Q  S  L  *  A  W  L  L  S  K  P  I  S  K  C  R  K  *  -
e            I  S  P  E  I  V  G  V  I  P  I  K  S  H  K  Q  M  E  E L -
f              H  K  A  *  D  R  G  C  Y  P  N  Q  F  A  K  A  D  R  R F -

E
                   c
                   o                N                T
             C     4 HC             C  C  l          s
             ABv   7Haa     B  v  a aNS              p           A
             lfi   Ihec     s  i  c Isp              5           c
             uaJ   IaI8     b  R  8 Iph              0           i
             III   IIII     I  I  I III              9           I
                                                     I
          GCTAGAGCGCTCGCTGTGTTGCATGCCACAATCAATAATTCAATCTGGTGCGGTTTGAAA
     9961 -----------+----------+----------+----------+----------+----------+ 10020
          CGATCTCGCGAGCGACACAACGTACGGTGTTAGTTATTAAGTTAGACCACGCCAAACTTT a         A  R  A  L  A  V  L  H  A  T  I  N  N  S  I  W  C  G  L  K  -
b            L  E  R  S  L  C  C  M  P  Q  S  I  I  Q  S  G  A  V  * K -
c              *  S  A  R  C  V  A  C  H  N  Q  *  F  N  L  V  R  F  E K -
     9961 -----------+----------+----------+----------+----------+----------+ 10020
d         L  *  L  A  R  Q  T  A  H  W  L  *  Y  N  L  R  T  R  N  S  -
e            A  L  A  S  A  T  N  C  A  V  I  L  L  E  I  Q  H  P  K F -
f              S  S  R  E  S  H  Q  M  G  C  D  I  I  *  D  P  A  T  Q F -

T                       P
                   t         T             f
                   h         s       S     l
             C     l   C     p       a     l         B
             v     Dl  v     M5      u D   l         c
```

FIG.2-SEQUENCE1-PAGE49

FIG.2-SEQUENCE1-PAGE50

```
b         N  L  M  G  L  I  R  D  F  I  F  H  S  L  S  L  K  I  L  H  -
c            I  *  W  D  *  L  G  I  L  F  F  I  H  *  V  *  K  F  F  I -
    10201 ---------+---------+---------+---------+---------+---------+ 10260
d         K  I  *  H  S  *  N  P  I  K  N  K  M  *  *  T  *  F  N  K  -
e         *  N  L  P  I  L  *  P  N  *  K  E  N  M  L  N  L  F  E  E  -
f            L  K  I  P  N  I  L  S  K  I  K  *  E  N  L  K  F  I  R  * -

H
                                              i
                              C               n  C
                        D     v               d  Av
                        d     i               I  li
                        e     R               I  uJ
                        I     I               I  II
                                                 /
          TTGTCCTTAGTTTGTTGCATTTTAGAATAGACAAAGCTT
    10261 ---------+---------+---------+---------- 10299
          AACAGGAATCAAACAACGTAAAATCTTATCTGTTTCGAA a         L  S  L  V  C  C  I  L  E  *  T  K  L       -
b         C  P  *  F  V  A  F  *  N  R  Q  S          -
c            V  L  S  L  L  H  F  R  I  D  K  A       -
    10261 ---------+---------+---------+----------      10299
d         M  T  R  L  K  N  C  K  L  I  S  L  A       -
e         N  D  K  T  Q  Q  M  K  S  Y  V  F  S       -
f            Q  G  *  N  T  A  N  *  F  L  C  L  K    -
```

FIG.2-SEQUENCE1-PAGE51

```
                          S
               C          a                    C
               Av         u  D       A  Av                    D
               li         3  p       l  li                    d
               uJ         A  n       w  uJ                    e
               II         I  I       I  II                    I
                /                        /
       aaAAATcAAAGAGCTTATGGaTCATAGAGCTAAAGTTCTTTCAGACTTAGAAaacAAATA
    1  ----------+---------+---------+---------+---------+---------+  60
       ttTTTAgTTTCTCGAATACCtAGTATCTCGATTTCAAGAAAGTCTGAATCTTttgTTTAT K  N  Q  R  A  Y  G  S  *  S  *  S  S  F  R  L  R  K  Q  I  -
         K  I  K  E  L  M  D  H  R  A  K  V  L  S  D  L  E  N  K  Y -
          K  S  K  S  L  W  I  I  E  L  K  F  F  Q  T  *  K  T  N  T-
    1  ----------+---------+---------+---------+---------+---------+  60
       F  D  F  L  K  H  I  M  S  S  F  N  K  *  V  *  F  V  F      -
          F  *  L  A  *  P  D  Y  L  *  L  E  K  L  S  L  F  C  I   -
       F  I  L  S  S  I  S  *  L  A  L  T  R  E  S  K  S  F  L  Y   -

C     B
              M        v XB  s          M              H             D
              n        i bf  m          n              i             d
              1        J aa  A          1              n             e
              I        I II  I          I              4             I
                                                       I
       CAAAAAAGAAAAAGAGGCTCTAGAGAAAGAGACAAGAGGTAAAATCCTTACTGCTAAGTC
   61  ----------+---------+---------+---------+---------+---------+ 120
       GTTTTTTCTTTTTCTCCGAGATCTCTTTCTCTGTTCTCCATTTTAGGAATGACGATTCAG

Q  K  R  K  R  G  S  R  E  R  D  K  R  *  N  P  Y  C  *  V   -
         K  K  E  K  E  A  L  E  K  E  T  R  G  K  I  L  T  A  K  S -
          K  K  K  K  R  L  *  R  K  R  Q  E  V  K  S  L  L  L  S  Q-
   61  ----------+---------+---------+---------+---------+---------+ 120
       V  F  F  F  F  L  S  *  L  F  L  C  S  T  F  D  K  S  S  L   -
          C  F  L  F  L  P  E  L  S  L  S  L  L  Y  F  G  *  Q  *  T-
       L  F  S  F  S  A  R  S  F  S  V  L  P  L  I  R  V  A  L  D   -

S
              C        Ba            C  C
              v        suDXB   A     a  v     M                M
              i        t3pbf   l     c  i     s                bM
              J        YAnaa   w     8  J     e                on
              I        IIIII   I     I  I     I                II
                         /
       AAAGGCTTATGGGGATCTAGAGCAAGCCTTAAAAGATAACCCTCTCTATAAGAAACTTCT
  121  ----------+---------+---------+---------+---------+---------+ 180
       TTTCCGAATACCCCTAGATCTCGTTCGGAATTTTCTATTGGGAGAGATATTCTTTGAAGA K  G  L  W  G  S  R  A  S  L  K  R  *  P  S  L  *  E  T  S   -
         K  A  Y  G  D  L  E  Q  A  L  K  D  N  P  L  Y  K  K  L  L -
          R  L  M  G  I  *  S  K  P  *  K  I  T  L  S  I  R  N  F  -
  121  ----------+---------+---------+---------+---------+---------+ 180
       *  L  S  I  P  I  *  L  L  G  *  F  I  V  R  E  I  L  F  K   -
```

FIG.2-SEQUENCE2-PAGE 1

```
                    L  P  K  H  P  D  L  A  L  R  L  L  Y  G  E  R  Y  S  V  E  -
                 F  A  *  P  S  R  S  C  A  K  F  S  L  G  R  *  L  F  S  R  -
                                                                              M
                             MD          H                                    b
                             sr          p                                    o
                             ea          h                                    I
                             II          I                                    I
      TCCTAACCCTTATGCCTATGTTTTAAACCAAGAAACATTCACCAAAGAAGATAAGGAGCG
181   ---------+---------+---------+---------+---------+---------+ 240
      AGGATTGGGAATACGGATACAAAATTTGGTTCTTTGTAAGTGGTTTCTTCTATTCCTCGC

S  *  P  L  C  L  C  F  K  P  R  N  I  H  Q  R  R  *  G  A  -
            P  N  P  Y  A  Y  V  L  N  Q  E  T  F  T  K  E  D  K  E  R  -
               L  T  L  M  P  M  F  *  T  K  K  H  S  P  K  K  I  R  S  V  -
181   ---------+---------+---------+---------+---------+---------+ 240
         K  R  V  R  I  G  I  N  *  V  L  F  C  E  G  F  F  I  L  L  -
            E  *  G  K  H  R  H  K  L  G  L  F  M  *  W  L  L  Y  P  A  -
               G  L  G  *  A  *  T  K  F  W  S  V  N  V  L  S  S  L  S  R  -

E
                         BcS
                         soc                   H                    A
                         aRr                   p                    c
                         JIF                   h                    i
                         III                   I                    I
                           /
      TTTGAGTTATTACTACCCCCAGGTGAAAACGAGCAGtATTTTtgaaaAAACtACCGCtAC
241   ---------+---------+---------+---------+---------+---------+ 300
      AAACTCAATAATGATGGGGGTCCACTTTTGCTCGTCaTAAAActtttTTTGatGGCGaTG F  E  L  L  L  P  P  G  E  N  E  Q  Y  F  *  K  N  Y  R  Y  -
            L  S  Y  Y  Y  P  Q  V  K  T  S  S  I  F  E  K  T  T  A  T  -
               *  V  I  T  T  P  R  *  K  R  A  V  F  L  K  K  L  P  L  P  -
241   ---------+---------+---------+---------+---------+---------+ 300
         T  Q  T  I  V  V  G  L  H  F  R  A  T  N  K  F  F  S  G  S  -
            N  S  N  N  S  G  G  P  S  F  S  C  Y  K  Q  F  F  *  R  *  -
               K  L  *  *  *  G  W  T  F  V  L  L  I  K  S  F  V  V  A  V  -

B
                         Cp           C        T
                         vuD          v        a
                         ild          i        q
                         JOe          J        I
                         III          I        I
                           /
      CACTAAAGATAAGGCTCAGGCTTTGCtTCAAATGGGTGTGTTTTCTTTAGATGAAGAACA
301   ---------+---------+---------+---------+---------+---------+ 360
      GTGATTTCTATTCCGAGTCCGAAACGaAGTTTACCCACACAAAAGAAATCTACTTCTTGT H  *  R  *  G  S  G  F  A  S  N  G  C  V  F  F  R  *  R  T  -
            T  K  D  K  A  Q  A  L  L  Q  M  G  V  F  S  L  D  E  E  Q  -
               L  K  I  R  L  R  L  C  F  K  W  V  C  F  L  *  M  K  N  K  -
301   ---------+---------+---------+---------+---------+---------+ 360
         G  S  F  I  L  S  L  S  Q  K  L  H  T  H  K  R  *  I  F  F  -
            W  *  L  Y  P  E  P  K  A  E  F  P  H  T  K  K  L  H  L  V  -
               V  L  S  L  A  *  A  K  S  *  I  P  T  N  E  K  S  S  S  C  -

T
                                                            t
                                                            h
            M         C  C         C                 C      1          M
            b         a  v         Av                a      1    S     b
            o         c  i         li                c      1    s     o
            I         8  J         uJ                8      I    p     I
            I         I  I         II                I      I    I     I
```

FIG.2-SEQUENCE2-PAGE2

```
            AAACAAAAAAGCGAGCCGATTAGCTTTTATCTTACAAGCAAGCGATTGAAGAATATTCCAA
   361      ---------+---------+---------+---------+---------+---------+  420
            TTTGTTTTTTCGCTCGGCTAATCGAAATAGAATGTTCGTTCGCTAACTTCTTATAAGGTT

K  Q  K  S  E  P  I  S  F  I  L  Q  A  S  D  *  R  I  F  Q  -
             N  K  K  A  S  R  L  A  L  S  Y  K  Q  A  I  E  E  Y  S  N -
              T  K  K  R  A  D  *  L  Y  L  T  S  K  R  L  K  N  I  P  I -
   361      ---------+---------+---------+---------+---------+---------+  420
            L  V  F  F  R  A  S  *  S  *  R  V  L  L  R  N  F  F  I  G  -
             F  C  F  L  S  G  I  L  K  I  K  C  A  L  S  Q  L  I  N  W -
              F  L  F  A  L  R  N  A  K  D  *  L  C  A  I  S  S  Y  E  L -

T
                                    s
              C                     P                C                  C
              j                     5                j                  Av
              e                     0                e                  li
              P                     9                P                  uJ
              I                     I                I                  II
                                                                         /
            TAACATTTCTAATCTGTTGAGCAGAAAAGAATTGGATAATATAGATTATTACTTACAGCT
   421      ---------+---------+---------+---------+---------+---------+  480
            ATTGTAAAGATTAGACAACTCGTCTTTTCTTAACCTATTATATCTAATAATGAATGTCGA

*  H  F  *  S  V  E  Q  K  R  I  G  *  Y  R  L  L  L  T  A  -
             N  I  S  N  L  L  S  R  K  E  L  D  N  I  D  Y  Y  L  Q  L -
              T  F  L  I  C  *  A  E  K  N  W  I  I  *  I  I  T  Y  S  L -
   421      ---------+---------+---------+---------+---------+---------+  480
            I  V  N  R  I  Q  Q  A  S  F  F  Q  I  I  Y  I  I  V  *  L  -
             Y  C  K  *  D  T  S  C  F  L  I  P  Y  Y  L  N  N  S  V  A -
              L  M  E  L  R  N  L  L  F  S  N  S  L  I  S  *  *  K  C  S -

H
              P            i                          M        C
              l            n                          w        v
              e            f                          o        i
              I            I                          I        J
                                                              I
            TGAAAGAAACAAGTTTGACTCCAAAGCAAAAGATATTGCTCAAAAGGCTACTAACACGCT
   481      ---------+---------+---------+---------+---------+---------+  540
            ACTTTCTTTGTTCAAACTGAGGTTTCGTTTTCTATAACGAGTTTTCCGATGATTGTGCGA

*  K  K  Q  V  *  L  Q  S  K  R  Y  C  S  K  G  Y  *  H  A  -
             E  R  N  K  F  D  S  K  A  K  D  I  A  Q  K  A  T  N  T  L -
              K  E  T  S  L  T  P  K  Q  K  I  L  L  K  R  L  L  T  R  L -
   481      ---------+---------+---------+---------+---------+---------+  540
            K  F  S  V  L  K  V  G  F  C  F  I  N  S  L  L  S  S  V  R  -
             Q  F  F  C  T  Q  S  W  L  L  L  Y  Q  E  F  P  *  *  C  A -
              S  L  F  L  N  S  E  L  A  F  S  I  A  *  F  A  V  L  V  S -

N
                                           1
              M                            a                   MV
              s                            I                   ss
              e                            I                   ep
              I                            I                   II
                                                                /
            TATTTTTAACTCGGAACGCTTGGCGTTTAGCATGGCGATTGATAAGATTAATGAGAAATA
   541      ---------+---------+---------+---------+---------+---------+  600
            ATAAAAATTGAGCCTTGCGAACCGCAAATCGTACCGCTAACTATTCTAATTACTCTTTAT

Y  F  *  L  G  T  L  G  V  *  H  G  D  *  *  D  *  *  E  I  -
             I  F  N  S  E  R  L  A  F  S  M  A  I  D  K  I  N  E  K  Y -
              F  L  T  R  N  A  W  R  L  A  W  R  L  I  R  L  M  R  N  T -
   541      ---------+---------+---------+---------+---------+---------+  600
            K  N  K  V  R  F  A  Q  R  K  A  H  R  N  I  L  N  I  L  F  -
```

FIG.2-SEQUENCE2-PAGE3

```
                *  K  *  S  P  V  S  P  T  *  C  P  S  Q  Y  S  *  H  S  I  -
                  I  K  L  E  S  R  K  A  N  L  M  A  I  S  L  I  L  S  F  Y  -
                                                                              T
                                                                              s
              C              C                                                P
           M  v           M  v                                                5
           s  n           n  i                                                0
           e  l           l  J                                                9
           I  I           I  I                                                I
       CTTAAAGGGCTATGAGGCTTTTTCTAACTTGTTGAAAAATGTCAAAGATGATGTGGAATT
   601 ---------+---------+---------+---------+---------+---------+ 660
       GAATTTCCCGATACTCCGAAAAAGATTGAACAACTTTTTACAGTTTCTACTACACCTTAA
           L  K  G  L  *  G  F  F  *  L  V  E  K  C  Q  R  *  C  G  I  -
           L  K  G  Y  E  A  F  S  N  L  L  K  N  V  K  D  D  V  E  L  -
              *  R  A  M  R  L  F  L  T  C  *  K  M  S  K  M  M  W  N  *  -
   601 ---------+---------+---------+---------+---------+---------+ 660
           V  *  L  A  I  L  S  K  R  V  Q  Q  F  I  D  F  I  I  H  F  -
              S  L  P  S  H  P  K  K  *  S  T  S  F  H  *  L  H  H  P  I  -
                 K  F  P  *  S  A  K  E  L  K  N  F  F  T  L  S  S  T  S  N  -

T                    T        T
                                            s                    t        s
                                            p                    h        p
                                            5                    1        5
                                            0                    1        0
                                            9                    1        9
                                            I                    I        I
       GAATACTCTGACTAAAAACTTTACCAATCAAAAATTGAGTTTCGCACAAAAACAAAAATT
   661 ---------+---------+---------+---------+---------+---------+ 720
       CTTATGAGACTGATTTTTGAAATGGTTAGTTTTTAACTCAAAGCGTGTTTTTGTTTTTAA
           E  Y  S  D  *  K  L  Y  Q  S  K  I  E  F  R  T  K  T  K  I  -
           N  T  L  T  K  N  F  T  N  Q  K  L  S  F  A  Q  K  Q  K  L  -
              I  L  *  L  K  T  L  P  I  K  N  *  V  S  H  K  N  K  N  C  -
   661 ---------+---------+---------+---------+---------+---------+ 720
           Q  I  S  Q  S  F  V  K  G  I  L  F  Q  T  E  C  L  F  L  F  -
              S  Y  E  S  *  F  S  *  W  D  F  I  S  N  R  V  F  V  F  I  -
                 F  V  R  V  L  F  K  V  L  *  F  N  L  K  A  C  F  C  F  N  -

T
                          s
                 C        p                 H
                 Av       5                 i
                 li       0                 n                         M
                 uJ       9                 4                         s
                 II       I                 I                         e
                                                                      I
       GTGTTTGTTGGTTTTAGACAGCTTCAATTTTGATACCCAATCCAAAAAATCTATATTAAA
   721 ---------+---------+---------+---------+---------+---------+ 780
       CACAAACAACCAAAATCTGTCGAAGTTAAAACTATGGGTTAGGTTTTTAGATATAATTT
           V  F  V  G  F  R  Q  L  Q  F  *  Y  P  I  Q  K  I  Y  I  K  -
           C  L  L  V  L  D  S  F  N  F  D  T  Q  S  K  K  S  I  L  K  -
              V  C  W  F  *  T  A  S  I  L  I  P  N  P  K  N  L  Y  *  K  -
   721 ---------+---------+---------+---------+---------+---------+ 780
           Q  T  Q  Q  N  *  V  A  E  I  K  I  G  L  F  F  R  Y  *  -
              T  N  T  P  K  L  C  S  *  N  Q  Y  G  I  W  F  I  *  I  L  -
                 H  K  N  T  K  S  L  K  L  K  S  V  W  D  L  F  D  I  N  F  -
                          P
                          f
                          1                 S
                          1                 Ba
```

FIG.2-SEQUENCE2-PAGE4

```
                  S          1   A        su   D
                  s          0   1        a3   p
                  p          8   w        BA   n
                  I          I   I        II   I
       AAAGACTAATGAATACAATATTTTCGTAGATAGCGATCCTATGATGAGCGACAAAACAAC
781    ---------+---------+---------+---------+---------+---------+  840
       TTTCTGATTACTTATGTTATAAAAGCATCTATCGCTAGGATACTACTCGCTGTTTTGTTG

K D * * I Q Y F R R * R S Y D E R Q N N   -
        K T N E Y N I F V D S D P M M S D K T T  -
         R L M N T I F S * I A I L * * A T K Q L -
781    ---------+---------+---------+---------+---------+---------+  840
       F L S I F V I N E Y I A I R H H A V F C   -
        F S * H I C Y K R L Y R D * S S R C F L  -
         F V L S Y L I K T S L S G I I L S L V V -

T
                                s
         C                   M  p              C   C
         v                   b  M5             v   j
         i                   o  s0             i   e
         R                   I  e9             R   P
         I                   I  II             I   I
       TATGCAAAAAGAACACTACAAGATATTTAATTTCTTCAAAACAGTGGTTTCTGCATACCG
841    ---------+---------+---------+---------+---------+---------+  900
       ATACGTTTTTCTTGTGATGTTCTATAAATTAAAGAAGTTTTGTCACCAAAGACGTATGGC

Y A K R T L Q D I * F L Q N S G F C I P   -
        M Q K E H Y K I F N F F K T V V S A Y R  -
         C K K N T T R Y L I S S K Q W F L H T E -
841    ---------+---------+---------+---------+---------+---------+  900
       S H L F F V V L Y K I E E F C H N R C V   -
        * A F L V S C S I * N R * F L P K Q M G  -
         I C F S C * L I N L K K L V T T E A Y R -

C      B              M
                         j      s              b
                         e      m              o
                         P      A              I
                         I      I              I
       AAACAATGTTGCCAAGAATAATCCCTTTGAATAGGAAAGGAGACACTCTTGAAAAGCATC
901    ---------+---------+---------+---------+---------+---------+  960
       TTTGTTACAACGGTTCTTATTAGGGAAACTTATCCTTTCCTCTGTGAGAACTTTTCGTAG

K Q C C Q E * S L * I G K E T L L K S I   -
        N N V A K N N P F E * E R R H S * K A S  -
         T M L P R I I P L N R K G D T L E K H L -
901    ---------+---------+---------+---------+---------+---------+  960
       S V I N G L I I G K F L F P S V R S F C   -
        F C H Q W S Y D R Q I P F S V S K F L M  -
         F L T A L F L G K S Y S L L C E Q F A D -

S
         f     B                                C
         a     f                                v   M
         N     a                                i   s
         I     I                                J   e
                                                I   I
       TTCAAAAAACTAGGTTCTGTCGCTCTTTATTCTTTAGTTGTTTATGGGGGCTTAAACGCT
961    ---------+---------+---------+---------+---------+---------+ 1020
       AAGTTTTTTGATCCAAGACAGCGAGAAATAAGAAATCAACAAATACCCCCGAATTTGCGA

F K K L G S V A L Y S L V V Y G G L N A   -
        S K N * V L S L F I L * L F M G A * T L  -
         Q K T R F C R S L F F S C L W G L K R Y -
961    ---------+---------+---------+---------+---------+---------+ 1020
       R * F V L N Q R E K N K L Q K H P S L R   -
```

FIG.2-SEQUENCE2-PAGE5

```
              K L F S P E T A R  *  E K T T  *  P P K F A  -
                E F F  *  T R D S K I R  *  N N I P A  *  V S  -
                                    T
                                    s
                                    p
                                    5            C          C
                                    0            v          v    M D
                                    9            i          i    s r
                                    I            J          J    e a
                                                 I          I    I I
     ATCAATACAGCATTATTGCCGAGTGAATACAAAGAATTAGTGGCTTTGGGCTTTAAAAAA
1021 ---------+---------+---------+---------+---------+---------+ 1080
     TAGTTATGTCGTAATAACGGCTCACTTATGTTTCTTAATCACCGAAACCCGAAATTTTTT

I N T A L L P S E Y K E L V A L G F K K  -
        S I Q H Y C R V N T K N  *  W L W A L K K  -
         Q Y S I I A E  *  I Q R I S G F G L  *  K N  -
1021 ---------+---------+---------+---------+---------+---------+ 1080
      *  *  Y L M I A S H I C L I L P K P S  *  F  -
       I L V A N N G L S Y L S N T A K P K L F  -
        D I C C  *  Q R T F V F F  *  H S Q A K F F  -

T                        T
                             s                        s
              N              p.                       E p
              1              5          M             A c 5
              a              0          n             p o 0
              I              9          1             o R 9
              I              I          I.            I I I
                                                     / /
     ATCAAAACACTCTATCAAAGACATGATGACAAAGAATTACAAAAGAGGAAAAAGAATTC
1081 ---------+---------+---------+---------+---------+---------+ 1140
     TAGTTTTGTGAGATAGTTTCTGTACTACTGTTTCTTAATGTTTTCTCCTTTTTCTTAAG

I K T L Y Q R H D D K E I T K E E K E F  -
        S K H S I K D M M T K K L Q K R K K N S  -
         Q N T L S K T  *  *  Q R N Y K R G K R I R  -
1081 ---------+---------+---------+---------+---------+---------+ 1140
       F  *  F V R D F V H H C L F  *  L L P F L I  -
        I L V S  *  *  L C S S L S I V F S S F S N  -
         D F C E I L S M I V F F N C F L F F F E  -

T                              T
                       s                              s
                       P                              P
            M          5                              A 5
            w          0                              p 0
            o          9                              o 9
            I          I                              I I
                                                     /
     GCCACTAACGCTTTGAGAGAAAAATTACGAAATGATAGGGCGAGAGCAGAGCAAATTCAA
1141 ---------+---------+---------+---------+---------+---------+ 1200
     CGGTGATTGCGAAACTCTCTTTTTAATGCTTTACTATCCCGCTCTCGTCTCGTTTAAGTT

A T N A L R F K L R N D R A R A E Q I Q  -
        P L T L  *  E K N Y E M I G R E Q S K F K  -
          H  *  R F E R K I T K  *  *  G E S R A N S K  -
1141 ---------+---------+---------+---------+---------+---------+ 1200
      R W  *  R K S L F I V F H Y P S L L A F E  -
       A V L A K L S F N R F S L A L A S C I  *  -
          G S V S Q S F F  *  S I I P R S C L L N L  -

B
                                                      p
                                                      u
                       M                              B U C 1
```

FIG.2-SEQUENCE2-PAGE6

FIG.2-SEQUENCE2-PAGE7

```
            K   V   N   E   S   F   V   K   P   A   A   P   L   V   P   D   E   W   R   T   -
        R   *   M   N   L   L   *   N   L   L   L   R   L   C   L   M   S   G   E   R   -
            G   E   *   I   F   C   E   T   C   C   S   A   C   A   *   *   V   E   N   A   -
1381    ---------+---------+---------+---------+---------+---------+ 1440
            Y   P   S   H   I   K   Q   S   V   Q   Q   E   A   Q   A   Q   H   T   S   F   -
        L   T   F   S   D   K   T   F   G   A   A   G   S   T   G   S   S   H   L   V   -
            L   H   I   F   R   K   H   F   R   S   S   R   K   H   R   I   L   P   S   R   -

T   T
                                                                                t   t
                                                                                h   h
            T                                                                   1   1
            s                                                                   B1  1M
            P                                                                   cl  1s
            5                                                                   cI  Ie
            0                                                                   II  II
            9
            I                                                                    /
        CCTGAAATTGAAATCATTATCAATGAGTGTATTATTTCAAGCAACGATTATGATGGGTTA
1441    ---------+---------+---------+---------+---------+---------+ 1500
        GGACTTTAACTTTAGTAATAGTTACTCACATAATAAAGTTCGTTGCTAATACTACCCAAT

P   E   I   E   I   I   I   N   E   C   I   I   S   S   N   D   Y   D   G   L   -
        L   K   L   K   S   L   S   M   S   V   L   F   Q   A   T   I   M   M   G   *   -
            *   N   *   N   H   Y   Q   *   V   Y   Y   F   K   Q   R   L   *   W   V   K   -
1441    ---------+---------+---------+---------+---------+---------+ 1500
        A   Q   F   Q   F   *   *   *   H   T   Y   *   K   L   C   R   N   H   H   T   -
            G   S   I   S   I   M   I   L   S   H   I   I   E   L   L   S   *   S   P   N   -
        R   F   N   F   D   N   D   I   L   T   N   N   *   A   V   I   I   P   *   -

T                           T
            S                       S                       s                           s
            a                       a                       p                           p
            BuD                     u   D                   AA5                         A5
            c3p                     3   p                   1p0                         p0
            1An                     A   n                   wo9                         o9
            III                     I   I                   III                         II
            /                       //                                                  /
        AGAAAGTGTTTGATCAAAGACATCAAGGATCAAAAAATTCTTGCCCCCTTATTAGAAAAA
1501    ---------+---------+---------+---------+---------+---------+ 1560
        TCTTTCACAAACTAGTTTCTGTAGTTCCTAGTTTTTTAAGAACGGGGGAATAATCTTTTT

R   K   C   L   I   K   D   I   K   D   Q   K   I   L   A   P   L   L   E   K   -
        E   S   V   *   S   K   T   S   R   I   K   K   F   L   P   P   Y   *   K   K   -
            K   V   F   D   Q   R   H   Q   G   S   K   N   S   C   P   L   I   R   K   N   -
1501    ---------+---------+---------+---------+---------+---------+ 1560
        L   F   T   N   S   *   L   C   *   P   D   F   F   E   Q   G   R   I   L   F   -
            L   F   H   K   I   L   S   M   L   S   *   F   I   R   A   G   K   N   S   F   -
        S   L   T   Q   D   F   V   D   L   I   L   F   N   K   G   G   *   *   F   F   -

B
        X       s                                   XB      B       DM      MD
        m       m                                   bf      s       ds      sr
        n       A                                   aa      b       el      ea
        I       I                                   II      I       II      II
        /
        ATTCAAGAAATAGAGACAGAAAATAACAAGTTTTCTAGACAACACCTAAGTGGTTTAAAA
1561    ---------+---------+---------+---------+---------+---------+ 1620
        TAAGTTCTTTATCTCTGTCTTTTATTGTTCAAAAGATCTGTTGTGGATTCACCAAATTTT

I   Q   E   I   E   T   E   N   N   K   F   S   R   Q   H   L   S   G   L   K   -
        F   K   K   *   R   Q   K   I   T   S   F   L   D   N   T   *   V   V   *   N   -
            S   R   N   R   D   R   K   *   Q   V   F   *   T   T   P   K   W   F   K   T   -
1561    ---------+---------+---------+---------+---------+---------+ 1620
        F   E   L   F   L   S   L   F   Y   C   T   K   *   V   V   G   L   H   N   L   -
            I   *   S   I   S   V   S   F   L   L   N   E   L   C   C   R   L   P   K   F   -
        N   L   F   Y   L   C   F   I   V   L   K   R   S   L   V   *   T   T   *   F   -
```

FIG.2-SEQUENCE2-PAGE8

```
              M                          C
              s                          Av    M  H       E
              e                          li    w  h       a
              I                          uJ    o  a       r
                                         II    I  I       I
                                              /
      CTCACTCTTAATAACAGCAACAATAGAACCTTTCTTATAGCTTCGTGCGCTATTTGTGAG
1621  ---------+---------+---------+---------+---------+---------+ 1680
      GAGTGAGAATTATTGTCGTTGTTATCTTGGAAAGAATATCGAAGCACGCGATAAACACTC

L  T  L  N  N  S  N  N  R  T  F  L  I  A  S  C  A  I  C  E   -
        S  L  L  I  T  A  T  I  E  P  F  L  *  L  R  A  L  F  V  R  -
         H  S  *  *  Q  Q  Q  *  N  L  S  Y  S  F  V  R  Y  L  *  E -
1621  ---------+---------+---------+---------+---------+---------+ 1680
       V  *  E  *  Y  C  C  C  Y  F  R  E  *  L  K  T  R  *  K  H   -
        S  V  R  L  L  L  L  L  L  V  K  R  I  A  E  H  A  I  Q  S  -
         E  S  K  I  V  A  V  I  S  G  K  K  Y  S  R  A  S  N  T  L -

M                             E
              b                             c   S               C  C
              o                             o   c               v  a
              I                             R   r               i  c
              I                             I   F               R  8
                                            I   I               I  I
      AAGAGAAAAAAAGAAATGGAGCAAGAAAATAACTACCAGGATACTACAAATGCAAGCGAG
1681  ---------+---------+---------+---------+---------+---------+ 1740
      TTCTCTTTTTTTCTTTACCTCGTTCTTTTATTGATGGTCCTATGATGTTTACGTTCGCTC

K  R  K  K  E  M  E  Q  E  N  N  Y  Q  D  T  T  N  A  S  E   -
        R  E  K  K  K  W  S  K  K  I  T  T  R  I  L  Q  M  Q  A  S  -
         E  K  K  R  N  G  A  R  K  *  L  P  G  Y  Y  K  C  K  R  V -
1681  ---------+---------+---------+---------+---------+---------+ 1740
       S  S  F  F  L  F  P  A  L  F  Y  S  G  P  Y  *  L  H  L  R   -
        F  L  F  F  S  I  S  C  S  F  L  *  W  S  V  V  F  A  L  S  -
         L  S  F  F  F  H  L  L  F  I  V  V  L  I  S  C  I  A  L    -

M                                              B
              w                                              s
              o                                              m
              I                                              I
      TTTGGCACTACTGATACAAAAGAAAATGAAGCAAAAGATACAGCATTCTCAAACAATCGC
1741  ---------+---------+---------+---------+---------+---------+ 1800
      AAACCGTGATGACTATGTTTTCTTTTACTTCGTTTTCTATGTCGTAAGAGTTTGTTAGCG

F  G  T  T  D  T  K  E  N  E  A  K  D  T  A  F  S  N  N  R   -
        L  A  L  L  I  Q  K  K  M  K  Q  K  I  Q  H  S  Q  T  I  A  -
         W  H  Y  *  Y  K  R  K  *  S  K  R  Y  S  I  L  K  Q  S  L -
1741  ---------+---------+---------+---------+---------+---------+ 1800
       T  Q  C  *  Q  Y  L  L  F  H  L  L  L  Y  L  M  R  L  C  D   -
        N  P  V  V  S  V  F  S  F  S  A  F  S  V  A  N  E  F  L  R  -
         K  A  S  S  I  C  F  F  I  F  C  F  I  C  C  E  *  V  I  A -

T
              t
              h
              1                                                 N
              1         H              MV                   S    l
              1         g              ss                   f    a
              1         a              ep                   a    I
              I         I              II                   N    I
                                        /                   I
      TCTAAATCCGAACTGCCCAATAGCGTCATTAATCAAATAGAACAAAGCATCGCTCATGGA
1801  ---------+---------+---------+---------+---------+---------+ 1860
      AGATTTAGGCTTGACGGGTTATCGCAGTAATTAGTTTATCTTGTTTCGTAGCGAGTACCT
```

FIG.2-SEQUENCE2-PAGE9

```
              S   K   S   E   L   P   N   S   V   I   N   Q   I   E   Q   S   I   A   H   G   -
                L   N   P   N   C   P   I   A   S   L   I   K   *   N   K   A   S   L   M   E   -
                    *   I   R   T   A   Q   *   R   H   *   S   N   R   T   K   H   R   S   W   K -
     1801    ---------+---------+---------+---------+---------+---------+ 1860
              S   *   I   R   V   A   W   Y   R   *   *   D   F   L   V   F   C   R   E   H   -
                E   L   D   S   S   G   L   L   T   M   L   *   I   S   C   L   M   A   *   P   -
                  R   F   G   F   Q   G   I   A   D   N   I   L   Y   F   L   A   D   S   M   S   -

T
                       S      s
                       a      p         S
               A       u  D   5         a               B
               l       3  p   0         u  D           f
               w       A  n   9         3  p           a
               I       I  I   I         A  n           I
                                        I  I
              AAAAAATAGCGATCCAAATTATTAGATCAAAAAACAACTAGAGAAGCAAATCCCAAAGGT
     1861    ---------+---------+---------+---------+---------+---------+ 1920
              TTTTTTATCGCTAGGTTTAATAATCTAGTTTTTTGTTGATCTCTTCGTTTAGGGTTTCCA

K   K   *   R   S   K   L   L   D   Q   K   T   T   R   E   A   N   P   K   G   -
                K   N   S   D   P   N   Y   *   I   K   K   Q   L   E   K   Q   I   P   K   V   -
                  K   I   A   I   Q   I   I   R   S   K   N   N   *   R   S   K   S   Q   R   L   -
     1861    ---------+---------+---------+---------+---------+---------+ 1920
              F   F   I   A   I   W   I   I   L   D   F   F   L   *   L   L   L   D   W   L   -
                F   F   Y   R   D   L   N   N   S   *   F   V   V   L   S   A   F   G   L   P   -
                  F   F   L   S   G   F   *   *   I   L   F   C   S   S   F   C   I   G   F   T   -

S
                       C                                          a
                       v      D                 M                 u  D
                       i      d                 s                 3  p
                       J      e                 e                 A  n
                       I      I                 I                 I  I
              TAGAAATCATAGCCTATCATCTCAGAAAAATCATTTAACAATGATCTTACTTGATTGCCT
     1921    ---------+---------+---------+---------+---------+---------+ 1980
              ATCTTTAGTATCGGATAGTAGAGTCTTTTTAGTAAATTGTTACTAGAATGAACTAACGGA

*   K   S   *   P   I   I   S   E   K   S   F   N   N   D   L   T   *   L   P   -
                R   N   H   S   L   S   S   Q   K   N   H   L   T   M   I   L   L   D   C   L   -
                  E   I   I   A   Y   H   L   R   K   I   I   *   Q   *   S   Y   L   I   A   F   -
     1921    ---------+---------+---------+---------+---------+---------+ 1980
              N   S   I   M   A   *   *   R   L   F   I   M   *   C   H   D   *   K   I   A   -
                *   F   D   Y   G   I   M   E   S   F   D   N   L   L   S   R   V   Q   N   G   -
                  L   F   *   L   R   D   D   *   F   F   *   K   V   I   I   K   S   S   Q   R   -

S
                                              Ba
                              B               suDH           A    B
                              f               t3pg           l    s
                              a               YAna           w    e R
                              I               IIII           I    I
                                                / /
              TTCTTGTAGGTATTGTCGCTTACTTTGTTCTAGGGATCTTTCTAATGCGTCCAACTCCTC
     1981    ---------+---------+---------+---------+---------+---------+ 2040
              AAGAACATCCATAACAGCGAATGAAACAAGATCCCTAGAAAGATTACGCAGGTTGAGGAG

F   L   *   V   L   S   L   T   L   F   *   G   S   F   *   C   V   Q   L   L   -
                S   C   R   Y   C   R   L   L   C   S   R   D   L   S   N   A   S   N   S   S   -
                  L   V   G   I   V   A   Y   F   V   L   G   I   F   L   M   R   P   T   P   L   -
     1981    ---------+---------+---------+---------+---------+---------+ 2040
              K   R   T   P   I   T   A   *   K   T   R   P   I   K   R   I   R   G   V   G   -
                K   K   Y   T   N   D   S   V   K   N   *   P   D   K   *   H   T   W   S   R   -
                  E   Q   L   Y   Q   R   K   S   Q   E   L   S   R   E   L   A   D   L   E   E   -
              T                                 H                                       T
              s                                 i                                       s
```

FIG.2-SEQUENCE2-PAGE 10

```
                  p                          C             n   C           H                  p
                  5   M  MD        M         Av            d   Av          iT                 A5
                  0   n  sr        m         li            I   li          nf                 p0
                  9   l  ea        e         uJ            I   uJ          fi                 o9
                  I   I  II        I         II                II          II                 II
                  /                          /             /               /                  /
        TAAATAATTTAAAAAGACCTTGTTTTGAGCTAACATAAGCTTTCTGATTCCTTTGATGAA
  2041  ---------+---------+---------+---------+---------+---------+  2100
        ATTTATTAAATTTTTCTGGAACAAAACTCGATTGTATTCGAAAGACTAAGGAAACTACTT

*  I  I  *  K  D  L  V  L  S  *  H  K  L  S  D  S  F  D  E  -
          K  *  F  K  K  T  L  F  *  A  N  I  S  F  L  I  P  L  M  K  -
          N  N  L  K  R  P  C  F  E  L  T  *  A  F  *  F  L  *  *  N  -
  2041  ---------+---------+---------+---------+---------+---------+  2100
          R  F  L  K  F  L  G  Q  K  S  S  V  Y  A  K  Q  N  R  Q  H  -
          *  I  I  *  F  S  R  T  K  L  *  C  L  S  E  S  E  K  S  S  -
          L  Y  N  L  F  V  K  N  Q  A  L  M  L  K  R  I  G  K  I  F  -

C                                    C       C
                   vH                           M       j       Av      R
                   ig                           s       e       li      s
                   Ja                           e       P       uJ      a
                   II                           I       I       II      I
                   /                                                    /
        ATTTTTATTCTTTAGGCTTTCTACAAGCGTCTGTGAAGCAGTGATTAAAGAAGCTGTACC
  2101  ---------+---------+---------+---------+---------+---------+  2160
        TAAAAATAAGAAATCCGAAAGATGTTCGCAGACACTTCGTCACTAATTTCTTCGACATGG

I  F  I  L  *  A  F  Y  K  R  L  *  S  S  D  *  R  S  C  T  -
          F  L  F  F  R  L  S  T  S  V  C  E  A  V  I  K  E  A  V  P  -
          F  Y  S  L  G  F  L  Q  A  S  V  K  Q  *  L  K  K  L  Y  L  -
  2101  ---------+---------+---------+---------+---------+---------+  2160
          F  K  *  E  K  P  K  R  C  A  D  T  F  C  H  N  F  F  S  Y  -
          I  K  I  R  *  A  K  *  L  R  R  H  L  L  S  *  L  L  Q  V  -
          N  K  N  K  L  S  E  V  L  T  Q  S  A  T  I  L  S  A  T  G  -

C
                    M         j
                    n         e
                    l         P
                    I         I
        TCCAATGTTGCTCTGATACGCCTTTAGGGAAGTTTCTAAACGCTCTCTTATATTTTGTTT
  2161  ---------+---------+---------+---------+---------+---------+  2220
        AGGTTACAACGAGACTATGCGGAAATCCCTTCAAAGATTTGCGAGAGAATATAAAACAAA

S  N  V  A  L  I  R  L  *  G  S  F  *  T  L  S  Y  I  L  F  -
          P  M  L  L  *  Y  A  F  R  E  V  S  K  R  S  L  I  F  C  F  -
          Q  C  C  S  D  T  P  L  G  K  F  L  N  A  L  L  Y  F  V  F  -
  2161  ---------+---------+---------+---------+---------+---------+  2220
          R  W  H  Q  E  S  V  G  K  P  F  N  R  F  A  R  K  Y  K  T  -
          E  L  T  A  R  I  R  R  *  P  L  K  *  V  S  E  *  I  K  N  -
          G  I  N  S  Q  Y  A  K  L  S  T  E  L  R  E  R  I  N  Q  K  -

C
               T        Av                                      B       A
               a        li                                      b       c
               q        uJ                                      v       i
               I        II                                      I       I
                        /
        TTCTTGCTCGATTTTCAGCTTCCCTTCACAATAAAGAACTAAAACTTTATCGGATATTCC
  2221  ---------+---------+---------+---------+---------+---------+  2280
        AAGAACGAGCTAAAAGTCGAAGGGAAGTGTTATTTCTTGATTTTGAAATAGCCTATAAGG

F  L  L  D  F  Q  L  P  F  T  I  K  N  *  N  F  I  G  Y  S  -
          S  C  S  I  F  S  F  P  S  Q  *  R  T  K  T  L  S  D  I  P  -
          L  A  R  F  S  A  S  L  H  N  K  E  L  K  L  Y  R  I  F  R  -
```

FIG.2-SEQUENCE2-PAGE11

```
2221 ---------+---------+---------+---------+---------+---------+ 2280
      K  R  A  R  N  E  A  E  R  *  L  L  S  S  F  S  *  R  I  N  -
       K  K  S  S  K  *  S  G  K  V  I  F  F  *  F  K  I  P  Y  E  -
        E  Q  E  I  K  L  K  G  E  C  Y  L  V  L  V  K  D  S  I  G -

B
                    P
                    u
         B          l
      B  a T        1 D                D                    M
      a  a T        0 d                d                    s
      r  o s        2 e                e                    e
      D  F e                                                
      I  II II                         I                    I
              / /
         GCATTGCTGCTCAGCAGTATTTTGGTCTAAGGGATTGATTTTCATATAGGTTAATAAAAG
2281 ---------+---------+---------+---------+---------+---------+ 2340
         CGTAACGACGAGTCGTCATAAAACCAGATTCCCTAACTAAAAGTATATCCAATTATTTTC

A  L  L  L  S  S  I  L  V  *  G  I  D  F  H  I  G  *  *  K  -
       H  C  C  S  A  V  F  W  S  K  G  L  I  F  I  *  V  N  K  S  -
        I  A  A  Q  Q  Y  F  G  L  R  D  *  F  S  Y  R  L  I  K  V -
2281 ---------+---------+---------+---------+---------+---------+ 2340
      R  M  A  A  *  C  Y  K  P  R  L  S  Q  N  E  Y  L  N  I  F  -
       A  N  S  S  L  L  I  K  T  *  P  I  S  K  *  I  P  *  Y  F  -
        C  Q  Q  E  A  T  N  Q  D  L  P  N  I  K  M  Y  T  L  L  L -

C
              v B                      M
              i f         D            b                    D
              J a         r            o                    d
              II          d            I                    e
                          I            I                    I
         TTCAGGGCTAGACATATAAGTCTTGAAAATCACATCTTCTGAGATGAAAAATAACTCATT
2341 ---------+---------+---------+---------+---------+---------+ 2400
         AAGTCCCGATCTGTATATTCAGAACTTTTAGTGTAGAAGACTCTACTTTTTATTGAGTAA

F  R  A  R  H  I  S  L  E  N  H  I  F  *  D  E  K  *  L  I  -
       S  G  L  D  I  *  V  L  K  I  T  S  S  E  M  K  N  N  S  F  -
        Q  G  *  T  Y  K  S  *  K  S  H  L  L  R  *  K  I  T  H  S -
2341 ---------+---------+---------+---------+---------+---------+ 2400
      T  *  P  *  V  Y  L  D  Q  F  D  C  R  R  L  H  F  I  V  *  -
       N  L  A  L  C  I  L  R  S  F  *  M  K  Q  S  S  F  Y  S  M  -
        E  P  S  S  M  Y  T  K  F  I  V  D  E  S  I  F  F  L  E  N -

T
         s
         p      C                                          H
         5      v         B                          GC BBa U
         0      i         s                         M EdvAsseMb
         9      J         e                         n aiicorIwa
         I      I         R                         1 eIJiFDIoJ
                          I                         I IIIIIIII
                                                      / /////
         CGCTTCAAAATTGGCTTTCAATAACGCTAAATCTCCTCTCAAAGCAATGGCCGCTTTTTT
2401 ---------+---------+---------+---------+---------+---------+ 2460
         GCGAAGTTTTAACCGAAAGTTATTGCGATTTAGAGGAGAGTTTCGTTACCGGCGAAAAAA R  F  K  I  G  F  Q  *  R  *  I  S  S  Q  S  N  G  R  F  F  -
       A  S  K  L  A  F  N  N  A  K  S  P  L  K  A  M  A  A  F  L  -
        L  Q  N  W  L  S  I  T  L  N  L  L  S  K  Q  W  P  L  F  * -
2401 ---------+---------+---------+---------+---------+---------+ 2460
      E  S  *  F  Q  S  E  I  V  S  F  R  R  E  F  C  H  G  S  K  -
       R  K  L  I  P  K  *  Y  R  *  I  E  E  *  L  L  P  R  K  K  -
        A  E  F  N  A  K  L  L  A  L  D  G  R  L  A  I  A  A  K  K -

E
                                                     c
                                                     o
```

FIG.2-SEQUENCE2-PAGE 12

```
           M                 S                           4  H       C
           b                 f                           7HBa       vB
           o                 a                           Ihfe       if
           I                 N                           IaaI       Ja
           I                 I                           IIII       II
                                                           /
      GATGTTTAGAGCATCTTCTTGACCTATTTCATTATTAGCGCTAGGGCTAGTGGTTGAAAA
2461  ------------+---------+---------+---------+---------+---------+ 2520
      CTACAAATCTCGTAGAAGAACTGGATAAAGTAATAATCGCGATCCCGATCACCAACTTTT D  V  *  S  I  F  L  T  Y  F  I  I  S  A  R  A  S  G  *  K  -
        M  F  R  A  S  S  *  P  I  S  L  L  A  L  G  L  V  V  E  K -
         C  L  E  H  L  L  D  L  F  H  Y  *  R  *  G  *  W  L  K  K -
2461  ------------+---------+---------+---------+---------+---------+ 2520
       Q  H  K  S  C  R  R  S  R  N  *  *  *  R  *  P  *  H  N  F  -
        S  T  *  L  M  K  K  V  *  K  M  I  L  A  L  A  L  P  Q  F -
         I  N  L  A  D  E  Q  G  I  E  N  N  A  S  P  S  T  T  S  F -

B
              D              M                          Bs
              d              s                          sm
              e              e                          aA
              I              I                          II
                                                         /
      AATCTCATCTAAGTTTTTAAGCACTTGTTGGTTGGTCTCTTGGTAGGTGCTATCAAGTTG
2521  ------------+---------+---------+---------+---------+---------+ 2580
      TTAGAGTAGATTCAAAAATTCGTGAACAACCAACCAGAGAACCATCCACGATAGTTCAAC

N  L  I  *  V  F  K  H  L  L  V  G  L  L  V  G  A  I  K  L  -
        I  S  S  K  F  L  S  T  C  W  L  V  S  W  *  V  L  S  S  C -
         S  H  L  S  F  *  A  L  V  G  W  S  L  G  R  C  Y  Q  V  A -
2521  ------------+---------+---------+---------+---------+---------+ 2580
       F  D  *  R  L  K  *  A  S  T  P  Q  D  R  P  L  H  *  *  T  -
        F  R  M  *  T  K  L  C  K  N  T  P  R  K  T  P  A  I  L  N -
         I  E  D  L  N  K  L  V  Q  Q  N  T  E  Q  Y  T  S  D  L  Q -

M
           MD     A         b                     B
           sr     c         o                     c
           ea     i         I                     c
           II     I                               I
      CTTTAAACCGCTTGTTATATCTTCTCCCATCAAAACAGACAATAGCAAAAAAGAAGATAT
2581  ------------+---------+---------+---------+---------+---------+ 2640
      GAAATTTGGCGAACAATATAGAAGAGGGTAGTTTTGTCTGTTATCGTTTTTTCTTCTATA

L  *  T  A  C  Y  I  F  S  H  Q  N  R  Q  *  Q  K  R  R  Y  -
        F  K  P  L  V  I  S  S  P  I  K  T  D  N  S  K  K  E  D  M -
         L  N  R  L  L  Y  L  L  P  S  K  Q  T  I  A  K  K  K  I  W -
2581  ------------+---------+---------+---------+---------+---------+ 2640
       A  K  F  R  K  N  Y  R  R  G  D  F  C  V  I  A  F  F  F  I  -
        S  *  V  A  Q  *  I  K  E  W  *  F  L  C  Y  C  F  L  L  Y -
         K  L  G  S  T  I  D  E  G  M  L  V  S  L  L  L  F  S  S  I -

M                                      CC        B
              b       B                              ABavN     s
              o       s                              1fcih     r
              I       i                              ua8Je     D
              I       I                              IIIII     I
                                                        //
      GGTATTTTTCACGAGTGTTTTCATTTGACAATAACTTTAGAGCTAGCAATGTTTCTTGCT
2641  ------------+---------+---------+---------+---------+---------+ 2700
      CCATAAAAAGTGCTCACAAAAGTAAACTGTTATTGAAATCTCGATCGTTACAAAGAACGA G  I  F  H  E  C  F  H  L  T  I  T  L  E  L  A  M  F  L  A  -
        V  F  F  T  S  V  F  I  *  Q  *  L  *  S  *  Q  C  F  L  L -
         Y  F  S  R  V  F  S  F  D  N  N  F  R  A  S  N  V  S  C  C -
```

FIG.2-SEQUENCE2-PAGE 13

```
2641 ----------+----------+----------+----------+----------+----------+ 2700
      H  Y  K  E  R  T  N  E  N  S  L  L  K  L  A  L  L  T  E  Q    -
       P  I  K  *  S  H  K  *  K  V  I  V  K  S  S  A  I  N  R  A   -
        T  N  K  V  L  T  K  M  Q  C  Y  S  *  L  *  C  H  K  K  S  -

T
                s
                p           M                           C           H
                5           b                       B   v           iT
                0           o                       s   i           nf
                9           I                       l   J           fi
                I           I                       I   I           II
                                                                    /
     GTCGTTTCTCTTTCTAATTTCAGTTGTTCTTCCCAAAGGTCGGCTTTTTTTTCAAGATTC
2701 ----------+----------+----------+----------+----------+----------+ 2760
     CAGCAAAGAGAAAGATTAAAGTCAACAAGAAGGGTTTCCAGCCGAAAAAAAAGTTCTAAG .

V  V  S  L  S  N  F  S  C  S  S  Q  R  S  A  F  F  S  R  F    -
       S  F  L  F  L  I  S  V  V  L  P  K  G  R  L  F  F  Q  D  S   -
        R  F  S  F  *  F  Q  L  F  F  P  K  V  G  F  F  F  K  I  L  -
2701 ----------+----------+----------+----------+----------+----------+ 2760
      Q  R  K  E  K  *  N  *  N  N  K  G  F  T  P  K  K  K  L  I    -
       T  T  E  R  E  L  K  L  Q  E  E  W  L  D  A  K  K  E  L  N   -
        D  N  R  K  R  I  E  T  T  R  G  L  P  R  S  K  K  *  S  E  - s
                             a
         MD              M   u   D                       BH
         sr              s   3   p                       sh
         ea              e   A   n                       ma
         II              I   I   I                       II
                                                                    /
     TCTATATAGTTTAAATGATTTTCTGCGTTTAAGATCGCAACTTCTATGAGCGCATTCAAA
2761 ----------+----------+----------+----------+----------+----------+ 2820
     AGATATATCAAATTTACTAAAAGACGCAAATTCTAGCGTTGAAGATACTCGCGTAAGTTT

S  I  *  F  K  *  F  S  A  F  K  I  A  T  S  M  S  A  F  K    -
       L  Y  S  L  N  D  F  L  R  L  R  S  Q  L  L  *  A  H  S  N   -
        Y  I  V  *  M  I  F  C  V  *  D  R  N  F  Y  E  R  I  Q  I  -
2761 ----------+----------+----------+----------+----------+----------+ 2820
      R  *  I  T  *  I  I  K  Q  T  *  S  R  L  K  *  S  R  M  *    -
       E  I  Y  N  L  H  N  E  A  N  L  I  A  V  E  I  L  A  N  L   -
        R  Y  L  K  F  S  K  R  R  K  L  D  C  S  R  H  A  C  E  F  -

S                                       S
         a                                       a
     A   u   D           M                   A   u   D
     l   3   p           s                   l   3   p
     w   A   n           e                   w   A   n
     I   I   I           I                   I   I   I
     TCTACTGATCCTTTTAAGGTTTTGATTTCTCCATTGATCCCATTCAAATAAGCGATATTT
2821 ----------+----------+----------+----------+----------+----------+ 2880
     AGATGACTAGGAAAATTCCAAAACTAAAGAGGTAACTAGGGTAAGTTTATTCGCTATAAA

S  T  D  P  F  K  V  L  I  S  P  L  I  P  F  K  *  A  I  F    -
       L  L  I  L  L  R  F  *  F  L  H  *  S  H  S  N  K  R  Y  F   -
        Y  *  S  F  *  G  F  D  F  S  I  D  P  I  Q  I  S  D  I  L  -
2821 ----------+----------+----------+----------+----------+----------+ 2880
      I  *  Q  D  K  *  P  K  S  K  E  M  S  G  M  *  I  L  S  I    -
       D  V  S  G  K  L  T  K  I  E  G  N  I  G  N  L  Y  A  I  N   -
        R  S  I  R  K  L  N  Q  N  R  W  Q  D  W  E  F  L  R  Y  K  -

T
                                                                s
         C               S                       C              P
         v       D       f                       v              5
```

FIG.2-SEQUENCE2-PAGE 14

```
              i       d   a                          i                 0
              R       e   N                          J                 9
              I       I   I                          I                 I
        TGAAAATCTGCATCACTCAGTTTATTTTGAATAAGGGCTACAATCATTCTGTAATTCTGA
2881    ---------+---------+---------+---------+---------+---------+ 2940
        ACTTTTAGACGTAGTGAGTCAAATAAAACTTATTCCCGATGTTAGTAAGACATTAAGACT

*  K  S  A  S  L  S  L  F  *  I  R  A  T  I  I  L  *  F  *  -
          E  N  L  H  H  S  V  Y  F  E  *  G  L  Q  S  F  C  N  S  E -
           K  I  C  I  T  Q  F  I  L  N  K  G  Y  N  H  S  V  I  L  N-
2881    ---------+---------+---------+---------+---------+---------+ 2940
        K  F  I  Q  M  V  *  N  I  K  F  L  P  *  L  *  E  T  I  R   -
          Q  F  D  A  D  S  L  K  N  Q  I  L  A  V  I  M  R  Y  N  Q -
           S  F  R  C  *  E  T  *  K  S  Y  P  S  C  D  N  Q  L  E  S-

T
                      N  s
                   C  l  p                  C               R
                   a  aNS A5                v   B           l
                   c  Isp p0                i   c           e
                   8  Iph o9                J   c           A
                   I  III II                I   I           I
                     //  /
        ATAACCTGTTCCATAAGGCATGCTGAAATTTTTAGCCCATCAAGATAAGGGCATTTTGTG
2941    ---------+---------+---------+---------+---------+---------+ 3000
        TATTGGACAAGGTATTCCGTACGACTTTAAAAATCGGGTAGTTCTATTCCCGTAAAACAC

I  T  C  S  I  R  H  A  E  I  F  S  P  S  R  *  G  H  F  V   -
          *  P  V  P  *  G  M  L  K  F  L  A  H  Q  D  K  G  I  L  W -
           N  L  F  H  K  A  C  *  N  F  *  P  I  K  I  R  A  F  C  G-
2941    ---------+---------+---------+---------+---------+---------+ 3000
        F  L  R  N  W  L  A  H  Q  F  K  *  G  M  L  I  L  A  N  Q   -
          I  V  Q  E  M  L  C  A  S  I  K  L  G  D  L  Y  P  C  K  T -
           Y  G  T  G  Y  P  M  S  F  N  K  A  W  *  S  L  P  M  K  H-

T
                                     t
                                     h           N
                H   C          H     1      C  1
               HBa  j          iT    1      j  a          D
               hfe  e          nf    I      e  I          d
               aaI  P          fi    I      P  I          e
               III  I          II             I  I           I
               /              /
        GGCGCTAGAGTGAATGTTTCAATGATTCCAAATGGTCGCCCATGCTTGAAAAAAAACTAA
3001    ---------+---------+---------+---------+---------+---------+ 3060
        CCGCGATCTCACTTACAAAGTTACTAAGGTTTACCAGCGGGTACGAACTTTTTTTTGATT G  A  R  V  N  V  S  M  I  P  N  G  R  P  C  L  K  K  N  *   -
          A  L  E  *  M  F  Q  *  F  Q  M  V  A  H  A  *  K  K  T  K -
           R  *  S  E  C  F  N  D  S  K  W  S  P  M  L  E  K  K  L  R-
3001    ---------+---------+---------+---------+---------+---------+ 3060
        P  R  *  L  S  H  K  L  S  E  L  H  D  G  M  S  S  F  F  S   -
          P  A  L  T  F  T  E  I  I  G  F  P  R  G  H  K  F  F  F  * -
           A  S  S  H  I  N  *  H  N  W  I  T  A  W  A  Q  F  F  V  L-

T
                                                               s
               C                           C                   P
               a   H   MB                  v                   5
               c   h   wc                  i                   0
               8   a   oc                  J                   9
               I   I   II                  I                   I
        GAGCAGGCGCATAGATGGCACTTTGAAACAAAGCCTGACCTGTTAGGGAATTATAATCAA
3061    ---------+---------+---------+---------+---------+---------+ 3120
        CTCGTCCGCGTATCTACCGTGAAACTTTGTTTCGGACTGGACAATCCCTTAATATTAGTT
```

```
       E  Q  A  H  R  W  H  F  E  T  K  P  D  L  L  G  N  Y  N  Q  -
        S  R  R  I  D  G  T  L  K  Q  S  L  T  C  *  G  I  I  I  N  -
         A  G  A  *  M  A  L  *  N  K  A  *  P  V  R  E  L  *  S  I  -
3061   ---------+---------+---------+---------+---------+---------+  3120
       L  A  P  A  Y  I  A  S  Q  F  L  A  Q  G  T  L  S  N  Y  D  -
        S  C  A  C  L  H  C  K  S  V  F  G  S  R  N  P  F  *  L  *  -
         L  L  R  M  S  P  V  K  F  C  L  R  V  Q  *  P  I  I  I  L  -

C       C              N           H
                        v       Av             l     B     gM
                        i       li             a     s     ibM
                        R       uJ             I     m     Eos
                        I       II             I     A     IIe
                                               I     I     III
                                /                           //
       TAAGGGTCGCTTTTTGCATAGCTGTTTTCAACCATGTCTCAAAACCTTTTAAGGTTTCTT
3121   ---------+---------+---------+---------+---------+---------+  3180
       ATTCCCAGCGAAAAACGTATCGACAAAAGTTGGTACAGAGTTTTGGAAAATTCCAAAGAA

*  G  S  L  F  A  *  L  F  S  T  M  S  Q  N  L  L  R  F  L  -
        K  G  R  F  L  H  S  C  F  Q  P  C  L  K  T  F  *  G  F  F  -
         R  V  A  F  C  I  A  V  F  N  H  V  S  K  P  F  K  V  S  S  -
3121   ---------+---------+---------+---------+---------+---------+  3180
       I  L  T  A  K  Q  M  A  T  K  L  W  T  E  F  G  K  L  T  E  -
        Y  P  D  S  K  A  Y  S  N  E  V  M  D  *  F  R  K  L  N  R  -
         L  P  R  K  K  C  L  Q  K  *  G  H  R  L  V  K  *  P  K  K  -

B                                             X
                     s                                             m
                     a                                             n
                     B                                             I
                     I
       CAAACgCCTTGATACCAATCGTATTGTAAGCGATGTATTGAGCGTTGTCAGAAGAACTTC
3181   ---------+---------+---------+---------+---------+---------+  3240
       GTTTGcGGAACTATGGTTAGCATAACATTCGCTACATAACTCGCAACAGTCTTCTTGAAG

Q  T  P  *  Y  Q  S  Y  C  K  R  C  I  E  R  C  Q  K  N  F  -
        K  R  L  D  T  N  R  I  V  S  D  V  L  S  V  V  R  R  T  S  -
         N  A  L  I  P  I  V  L  *  A  M  Y  *  A  L  S  E  E  L  P  -
3181   ---------+---------+---------+---------+---------+---------+  3240
       E  F  A  K  I  G  I  T  N  Y  A  I  Y  Q  A  N  D  S  S  S  -
        *  V  G  Q  Y  W  D  Y  Q  L  R  H  I  S  R  Q  *  F  F  K  -
         L  R  R  S  V  L  R  I  T  L  S  T  N  L  T  T  L  L  V  E  -

T
                     s
            M    C   p                B         BM
       B  b Av   A5  p0               c         sa   B            C
       f  o li   p0  o9               e         te   s       M    Av
       a  I uJ   o9  II               8         EI   a       n    li
       I  I II   II                   3         II   J       l    uJ
                                      I         II   I       I    II
            /    /                    /                      /
       CTAGAGCTTGAGAAATTTCCATTTGTGTTTTTAGGGTAACCCTCGGTTCAAAGCTGTTTT
3241   ---------+---------+---------+---------+---------+---------+  3300
       GATCTCGAACTCTTTAAAGGTAAACACAAAAATCCCATTGGGAGCCAAGTTTCGACAAAA

L  E  L  E  K  F  P  F  V  F  L  G  *  P  S  V  Q  S  C  F  -
        *  S  L  R  N  F  H  L  C  F  *  G  N  P  R  F  K  A  V  F  -
         R  A  *  E  I  S  I  C  V  F  R  V  T  L  G  S  K  L  F  F  -
3241   ---------+---------+---------+---------+---------+---------+  3300
       G  L  A  Q  S  I  E  M  Q  T  K  L  T  V  R  P  E  F  S  N  -
        R  S  S  S  F  N  G  N  T  N  K  P  Y  G  E  T  *  L  Q  K  -
         *  L  K  L  F  K  W  K  H  K  *  P  L  G  R  N  L  A  T  K  -
                                                                  s
```

FIG.2-SEQUENCE2-PAGE 16

```
                              D              C  a
       M        D             r              Av BuD
       s        d             d              li c3p
       e        e             I              uJ 1An
       I        I             I              II III
                                              /  /
           TTAACGCTTCTAAGAGAGCGTTTTGCTGGTTCATTTTGAGCTTGATCATTTCGTTATTTT
      3301 ---------+---------+---------+---------+---------+---------+ 3360
           AATTGCGAAGATTCTCTCGCAAAACGACCAAGTAAAACTCGAACTAGTAAAGCAATAAAA

L  T  L  L  R  E  R  F  A  G  S  F  *  A  *  S  F  R  Y  F  -
            *  R  F  *  E  S  V  L  L  V  H  F  E  L  D  H  F  V  I  F -
             N  A  S  K  R  A  F  C  W  F  I  L  S  L  I  I  S  L  F  F -
      3301 ---------+---------+---------+---------+---------+---------+ 3360
           K  L  A  E  L  L  A  N  Q  Q  N  M  K  L  K  I  M  E  N  N   -
            K  V  S  R  L  S  R  K  A  P  E  N  Q  A  Q  D  N  R  *  K  -
             *  R  K  *  S  L  T  K  S  T  *  K  S  S  *  K  T  I  K   -

T
                           t
                      N    h                     T
                 C    l    l                     s
            HT   M    v    aN1                   P
            hh   w    i    Isl                   M5V
            aa   o    R    IpI                   s0s
            II   I    I    III                   e9p
             /        /                          III
                                                  /
           TTTGGAGCGCGATTTGCATGTTTTGGATTTCTGTTTGGGTATTAAtttttttgttttttCCA
      3361 ---------+---------+---------+---------+---------+---------+ 3420
           AAACCTCGCGCTAAACGTACAAAACCTAAAGACAAACCCATAATTaaaaaaacaaaaaGGT F  G  A  R  F  A  C  F  G  F  L  F  G  Y  *  F  F  V  F' P  -
            L  E  R  D  L  H  V  L  D  F  C  L  G  I  N  F  L  F  F  H -
             W  S  A  I  C  M  F  W  I  S  V  W  V  L  I  F  C  F  S  T -
      3361 ---------+---------+---------+---------+---------+---------+ 3420
           K  Q  L  A  I  Q  M  N  Q  I  E  T  Q  T  N  I  K  Q  K  E   -
            K  P  A  R  N  A  H  K  P  N  R  N  P  Y  *  N  K  T  K  G  -
             K  S  R  S  K  C  T  K  S  K  Q  K  P  I  L  K  K  N  K  W -

S
           a                         C           BHU              N
           u   D                     v   D   M   HAsab            1B
           3   P                     i   d   w   hcoea            as
           A   n                     R   e   o   aiFIJ            Ia
           I   I                     I   I   I   IIIII            IH
                                                  ///             II
           CGATCAttttGACATTCCCCCCCAATGCACTAAGCGCCGCTTGAATACCCTTCCATGACG
      3421 ---------+---------+---------+---------+---------+---------+ 3480
           GCTAGTaaaaCTGTAAGGGGGGGTTACGTGATTCGCGGCGAACTTATGGGAAGGTACTGC R  S  F  *  H  S  P  P  M  H  *  A  P  L  E  Y  P  S  M  T  -
            D  H  F  D  I  P  P  Q  C  T  K  R  R  L  N  T  L  P  *  R -
             I  I  L  T  F  P  P  N  A  L  S  A  A  *  I  P  F  H  D  A -
      3421 ---------+---------+---------+---------+---------+---------+ 3480
           V  I  M  K  V  N  G  G  L  A  S  L  A  A  Q  I  G  K  W  S   -
            R  D  N  Q  C  E  G  G  I  C  *  A  G  S  S  Y  G  E  M  V  -
             S  *  K  S  M  G  G  W  H  V  L  R  R  K  F  V  R  G  H  R -

T
                      t
                      h                        N
                      l    C    B              l
              H       l    v    s              a            MV
              g       l    i    p              I            ss
              a       I    R    M              I            ep
              I       I    I    I              I            II
```

FIG.2-SEQUENCE2-PAGE 17

```
       CCAAGCAAGATGTCTGAACCTGCaaaaaaccccccTGTCAtGccATTGACACCATTAATA
3481   ------------+---------+---------+---------+---------+---------+   3540
       GGTTCGTTCTACAGACTTGGACGttttttgggggggACAGTaCggTAACTGTGGTAATTAT P  S  K  M  S  E  P  A  K  N  P  P  V  M  P  L  T  P  L  I   -
        Q  A  R  C  L  N  L  Q  K  T  P  L  S  C  H  *  H  H  *  *  -
         K  Q  D  V  *  T  C  K  K  P  P  C  H  A  I  D  T  I  N  N -
3481   ------------+---------+---------+---------+---------+---------+   3540
       A  L  C  S  T  Q  V  Q  L  F  G  G  Q  *  A  M  S  V  M  L   -
        G  L  L  I  D  S  G  A  F  F  G  G  T  M  G  N  V  G  N  I  -
         W  A  L  H  R  F  R  C  F  V  G  R  D  H  W  Q  C  W  *  Y -
```

```
                                     E
                                     c
                                     o                        T
                                     4  H        N            s
               C                     7  H  a     1  C C  C H  p        
               v          M          I  h  a     a  v a AvDi  5P       M
               i          s          I  e  I     I  i c lidn  01       n
               J          e          I  a  I     I  R 8 uJef  9e       l
               I          I          I  I  I     I  I I IIII  II       I
```

```
       ACGCCATTAGCCCCTTTTAACATAGCGCTCATGGTTGCAAGCTGAGTCCTCAATTCTCCC
3541   ------------+---------+---------+---------+---------+---------+   3600
       TGCGGTAATCGGGGAAAATTGTATCGCGAGTACCAACGTTCGACTCAGGAGTTAAGAGGG

T  P  L  A  P  F  N  I  A  L  M  V  A  S  *  V  L  N  S  P   -
        R  H  *  P  L  L  T  *  R  S  W  L  Q  A  E  S  S  I  L  P  -
         A  I  S  P  F  *  H  S  A  H  G  C  K  L  S  P  Q  F  S  L -
3541   ------------+---------+---------+---------+---------+---------+   3600
       L  A  M  L  G  K  *  C  L  A  *  P  Q  L  S  L  G  *  N  E   -
        V  G  N  A  G  K  L  M  A  S  M  T  A  L  Q  T  R  L  E  G  -
         R  W  *  G  R  K  V  Y  R  E  H  N  C  A  S  D  E  I  R  G -
```

```
                                                              T
                                                              s
                  C           C                 C       C     p  C
       MH         M   v       j       B         Av      M  v  M5 j
       nh         w   i       e       f         l i     w  i  s0 e
       la         o   J       P       a         u J     o  J  e9 P
       II         I   I       I       I         I I     I  I  II I
```

```
       TCTATTTGCGCTTGAATGGCTTTTTCTTTGGCACTAGATTGAGCTTCTATGGCTTTTAAT
3601   ------------+---------+---------+---------+---------+---------+   3660
       AGATAAACGCGAACTTACCGAAAAAGAAACCGTGATCTAACTCGAAGATACCGAAAATTA

S  I  C  A  *  M  A  F  S  L  A  L  D  *  A  S  M  A  F  N   -
        L  F  A  L  E  W  L  F  L  W  H  *  I  E  L  L  W  L  L  I  -
         Y  L  R  L  N  G  F  F  F  G  T  R  L  S  F  Y  G  F  *  F -
3601   ------------+---------+---------+---------+---------+---------+   3660
       R  *  K  R  K  F  P  K  K  K  P  V  L  N  L  K  *  P  K  *   -
        E  I  Q  A  Q  I  A  K  E  K  A  S  S  Q  A  E  I  A  K  L  -
         R  N  A  S  S  H  S  K  R  Q  C  *  I  S  S  R  H  S  K  I -
```

```
       T
       t
       h
       1  B                                            BC
       1As              H        C                  BM sv       M  M
       1cr              g        v                  gw pi       s  w
       IiB              a        J                  lo MJ       e  o
       III              I        I                  II II       I  I
```

```
       TCggcgtGAGcggttttttGTTTGGCTTGTGCGTCTGCCTGAATGGCTTTTAAGGCAGGT
3661   ------------+---------+---------+---------+---------+---------+   3720
       AGccgcaCTCgccaaaaaaCAAACCGAACACGCAGACGGACTTACCGAAAATTCCGTCCA
```

FIG.2-SEQUENCE2-PAGE18

```
           S  A  *  A  V  F  C  L  A  C  A  S  A  *  M  A  F  K  A  G  -
            R  R  E  R  F  F  V  W  L  V  R  L  P  E  W  L  L  R  Q  V -
             G  V  S  G  F  L  F  G  L  C  V  C  L  N  G  F  *  G  R  F -
3661   ---------+---------+---------+---------+---------+---------+ 3720
            N  P  T  L  P  K  K  N  P  K  H  T  Q  R  F  P  K  *  P  L -
           E  A  H  A  T  K  Q  K  A  Q  A  D  A  Q  I  A  K  L  A  P -
          R  R  S  R  N  K  T  Q  S  T  R  R  G  S  H  S  K  L  C  T -

B
                              B  C    s                            C
                         B  R sCjM    p                            Cj
                         a  s mjen    2                            je
                         e  a AePl    4                            eP
                         I  I IIII    I                            II
                            ///                                    /
       TcaagCgTTATTACTACCTCTGTACCATTCAGAGACAAACCACAAAAAGTCAAGAAAGAA
3721   ---------+---------+---------+---------+---------+---------+ 3780
       AgttcGcAATAATGATGGAGACATGGTAAGTCTCTGTTTGGTGTTTTTCAGTTCTTTCTT
            S  S  V  I  T  T  S  V  P  F  R  D  K  P  Q  K  V  K  K  E -
           Q  A  L  L  L  P  L  Y  H  S  E  T  N  H  K  K  S  R  K  K -
            K  R  Y  Y  Y  L  C  T  I  Q  R  Q  T  T  K  S  Q  E  R  K -
3721   ---------+---------+---------+---------+---------+---------+ 3780
            N  L  R  *  *  *  R  Q  V  M  *  L  C  V  V  F  L  *  S  L -
           E  L  T  I  V  V  E  T  G  N  L  S  L  G  C  F  T  L  F  S -
         *  A  N  N  S  G  R  Y  W  E  S  V  F  W  L  F  D  L  F  F -

B
       s
       P                  M
       2                  s                                 M
       4                  e                                 n              C
       I                  I                                 l              v
                                                            I              i
                                                                           R
                                                                           I
       AATATGCTTAAAAAACATTTCACATCTCTTTCCTCACTTCACGATTATTTTAGTTTGCAC
3781   ---------+---------+---------+---------+---------+---------+ 3840
       TTATACGAATTTTTTGTAAAGTGTAGAGAAAGGAGTGAAGTGCTAATAAAATCAAACGTG
           N  M  L  K  K  H  F  T  S  L  S  S  L  H  D  Y  F  S  L  H -
            I  C  L  K  N  I  S  H  L  F  P  H  F  T  I  L  V  C  T -
             Y  A  *  K  T  F  H  I  S  F  L  T  S  R  L  F  *  F  A  P -
3781   ---------+---------+---------+---------+---------+---------+ 3840
            F  Y  A  *  F  V  N  *  M  E  K  R  V  E  R  N  N  *  N  A -
           F  I  S  L  F  C  K  V  D  R  E  E  S  *  S  *  K  L  K  C -
            I  H  K  F  F  M  E  C  R  K  G  *  K  V  I  I  K  T  Q  V -

H
                                                 i
                              C                  A  n        C
                    M        Av                 fMMd        Av
                    s        li                 lswI        li
                    e        uJ                 IeoI        uJ
                    I        II                 IIII        II
                              /                                /
       CCTTTCTGTTAAGTAGCTATCTTTTTGCCCCTTAAGCTTGTCTTTGATGTAATCAAGGTA
3841   ---------+---------+---------+---------+---------+---------+ 3900
       GGAAAGACAATTCATCGATAGAAAAACGGGGAATTCGAACAGAAACTACATTAGTTCCAT
            P  F  C  *  V  A  I  F  L  P  L  K  L  V  F  D  V  I  K  V -
           L  S  V  K  *  L  S  F  C  P  L  S  L  S  L  M  *  S  R  * -
             F  L  L  S  S  Y  L  F  A  P  *  A  C  L  *  C  N  Q  G  K -
3841   ---------+---------+---------+---------+---------+---------+ 3900
            G  K  R  N  L  L  *  R  K  A  G  *  A  Q  R  Q  H  L  *  P -
           G  K  Q  *  T  A  I  K  K  G  R  L  S  T  K  S  T  I  L  T -
            R  E  T  L  Y  S  D  K  Q  G  K  L  K  D  K  I  Y  D  L  Y -
```

FIG.2-SEQUENCE2-PAGE 19

```
                                   T
                                   s
                                   p
                                   5
                                   0
                                   9
                                   I
       AGTCAAATGCGATTTCAAAAAAGATTTATTCGCTACTATATTGTAATTATATAGCGAACT
3901   ---------+---------+---------+---------+---------+---------+ 3960
       TCAGTTTACGCTAAAGTTTTTTCTAAATAAGCGATGATATAACATTAATATATCGCTTGA

S  Q  M  R  F  Q  K  R  F  I  R  Y  Y  I  V  I  I  *  R  T  -
         V  K  C  D  F  K  K  D  L  F  A  T  I  L  *  L  Y  S  E  L  -
          S  N  A  I  S  K  K  I  Y  S  L  L  Y  C  N  Y  I  A  N  L -
3901   ---------+---------+---------+---------+---------+---------+ 3960
        L  D  F  A  I  E  F  F  I  *  E  S  S  Y  Q  L  *  I  A  F  -
         L  *  I  R  N  *  F  L  N  I  R  *  *  I  T  I  I  Y  R  V  -
          T  L  H  S  K  L  F  S  K  N  A  V  I  N  Y  N  Y  L  S  S -

B
                              c    C
                          B   e   Av                      M  i
                          f   8   li                      s  n
                          a   3   uJ                      e  4
                          I   I   II                      I  I
                                      /
       TATGTTAGAAATCGCTTGAGTGTCATAGGTGCTAGTAGCTAATCCTGATTGATTAAGTAT
3961   ---------+---------+---------+---------+---------+---------+ 4020
       ATACAATCTTTAGCGAACTCACAGTATCCACGATCATCGATTAGGACTAACTAATTCATA

Y  V  R  N  R  L  S  V  I  G  A  S  S  *  S  *  L  I  K  Y  -
         M  L  E  I  A  *  V  S  *  V  L  V  A  N  P  D  *  L  S  I  -
          C  *  K  S  L  E  C  H  R  C  *  *  L  I  L  I  D  *  V  S -
3961   ---------+---------+---------+---------+---------+---------+ 4020
        K  H  *  F  D  S  S  H  *  L  H  *  Y  S  I  R  I  S  *  T  -
         *  T  L  F  R  K  L  T  M  P  A  L  L  *  D  Q  N  I  L  Y  -
          I  N  S  I  A  Q  T  D  Y  T  S  T  A  L  G  S  Q  N  L  I -

T                         T
                              s                         s
                 C            p                         p
                 v            5                         A5
                 i            0                         p0
                 R            9                         o9
                 I            I                         II
                                                         /
       CATTTGAGAAGCGTTCTGCAACAAATTGGTAttattttCACAAATTCTATATAGTATTC
4021   ---------+---------+---------+---------+---------+---------+ 4080
       GTAAACTCTTCGCAAGACGTTGTTTAACCATaataaaaaGTGTTTAAGATATATCATAAG H  L  R  S  V  L  Q  Q  I  G  I  I  F  H  K  F  Y  I  V  F  -
         I  *  E  A  F  C  N  K  L  V  L  F  F  T  N  S  I  *  Y  S  -
          F  E  K  R  S  A  T  N  W  Y  Y  F  S  Q  I  L  Y  S  I  L -
4021   ---------+---------+---------+---------+---------+---------+ 4080
        D  N  S  F  R  E  A  V  F  Q  Y  *  K  E  C  I  R  Y  L  I  -
         *  K  L  L  T  R  C  C  I  P  I  I  K  *  L  N  *  I  T  N  -
          M  Q  S  A  N  Q  L  L  N  T  N  N  K  V  F  E  I  Y  Y  E -

T
           s
           p
           A5
           p0                        B
           o9                        s                       B
           II                        m                       s
             /                       F                       l
                                     I                       I
```

FIG.2-SEQUENCE2-PAGE20

```
         TCTCAAAATTTCTGCTACTTTTTCAGCATAGCAATAAACAGCAAGAACCTTGTCCCCAAT
   4081  ----------+---------+---------+---------+---------+---------+ 4140
         AGAGTTTTAAAGACGATGAAAAAGTCGTATCGTTATTTGTCGTTCTTGGAACAGGGGTTA

S  Q  N  F  C  Y  F  F  S  I  A  I  N  S  K  N  L  V  P  N  -
          L  K  I  S  A  T  F  S  A  *  Q  *  T  A  R  T  L  S  P  I -
           S  K  F  L  L  L  F  Q  H  S  N  K  Q  Q  E  P  C  P  Q  * -
   4081  ----------+---------+---------+---------+---------+---------+ 4140
         R  E  F  N  R  S  S  K  *  C  L  L  L  C  C  S  G  Q  G  W  -
          E  *  F  K  Q  *  K  K  L  M  A  I  F  L  L  F  R  T  G  L -
           R  L  I  E  A  V  K  E  A  Y  C  Y  V  A  L  V  K  D  G  I -

N                                      ME
                     C   Cl                                      ac
                     a   vaNS          M                         eo
                     c   iIsp          s                         I5
                     8   RIph          e                         I7
                     I   IIII          I                         II
                         ///
         AGGGCATGCAGGAGTGGttATAGGATTAACGCCTGAAGTTAGGGCATTAGTgcgtAACGC
   4141  ----------+---------+---------+---------+---------+---------+ 4200
         TCCCGTACGTCCTCACCaaTATCCTAATTGCGGACTTCAATCCCGTAATCAcgcaTTGCG R  A  C  R  S  G  Y  R  I  N  A  *  S  *  G  I  S  A  *  R  -
          G  H  A  G  V  V  I  G  L  T  P  E  V  R  A  L  V  R  N  A -
           G  M  Q  E  W  L  *  D  *  R  L  K  L  G  H  *  C  V  T  L -
   4141  ----------+---------+---------+---------+---------+---------+ 4200
         Y  P  M  C  S  H  N  Y  S  *  R  R  F  N  P  C  *  H  T  V  -
          L  A  H  L  L  P  *  L  I  L  A  Q  L  *  P  M  L  A  Y  R -
           P  C  A  P  T  T  I  P  N  V  G  S  T  L  A  N  T  R  L  A -

T
                                       N               s
                                       1  B            p      C  C
                                   H   Ma s             A5     v  a
                                   g   wI  a            p0    i  c
                                   a   oI  H            o9    R  8
                                   I   II  I            II    I  I
                                       /                /
         TTGGTATTTAGCATAAACAGTGGGCATAGAAACGCTCATGGGcGTCATAGAAATTTGCA
   4201  ----------+---------+---------+---------+---------+---------+ 4260
         AACCATAAATCGTATTTGTCACCCGTATCTTTGCGAGTACCCCgCAGTATCTTTAAACGT

L  V  F  S  I  N  S  G  H  R  N  A  H  G  A  S  *  K  F  A  -
          W  Y  L  A  *  T  V  G  I  E  T  L  M  G  R  H  R  N  L  H -
           G  I  *  H  K  Q  W  A  *  K  R  S  W  G  V  I  E  I  C  M -
   4201  ----------+---------+---------+---------+---------+---------+ 4260
         S  P  I  *  C  L  C  H  A  Y  F  R  E  H  P  T  M  S  I  Q  -
          K  T  N  L  M  F  L  P  C  L  F  A  *  P  A  D  Y  F  N  A -
           Q  Y  K  A  Y  V  T  P  M  S  V  S  M  P  R  *  L  F  K  C -

N                                  H
              Cl                                 g
              vaNS           C             Mi A      R     C
              iIsp           v        H    wE  c     s     Av
              RIph           i        h    oI  i     a     li
              IIII           J        a    II  I     I     uJ
                             I        I                    II
              ///                                                 /
         TGCAACTGAAAAACACTTTTGATGAGCCAACAAGCGCACCTAAAGCGGTACAGCTATCAA
   4261  ----------+---------+---------+---------+---------+---------+ 4320
         ACGTTGACTTTTTGTGAAAACTACTCGGTTGTTCGCGTGGATTTCGCCATGTCGATAGTT

C  N  *  K  T  L  L  M  S  Q  Q  A  H  L  K  R  Y  S  Y  Q  -
          A  T  E  K  H  F  *  *  A  N  K  R  T  *  S  G  T  A  I  K -
           Q  L  K  N  T  F  D  E  P  T  S  A  P  K  A  V  Q  L  S  R -
   4261  ----------+---------+---------+---------+---------+---------+ 4320
```

FIG.2-SEQUENCE2-PAGE21

```
              M   C   S   F   F   V   K   S   S   G   V   L   A   G   L   A   I   C   S   D   -
                H   L   Q   F   V   S   K   I   L   W   C   A   C   R   F   R   Y   L   *   *   -
                  A   V   S   F   C   K   Q   H   A   L   L   R   V   *   L   P   V   A   I   L  -

T       T
                                    t       t
                            A       h       h                                               B
              H             c       l       l   C       C               C                   c
              iT            e       l       1Av         a               M   vB              e
              nf            I       l       1li         c               w   is              8
              fi            I       I       IuJ         8               o   Jr              3
              II            I       I       III         I               I   II              I
                  /                     /
         GGAATCGGTGTATCATTCATTGAGCTGTTGCTTGCTTGAGAAGCCAGTTGCTCTTGTAGA
    4321 ----------+---------+---------+---------+---------+---------+ 4380
         CCTTAGCCACATAGTAAGTAACTCGACAACGAACGAACTCTTCGGTCAACGAGAACATCT

G   I   G   V   S   F   I   E   L   L   L   A   *   E   A   S   C   S   C   R   -
                E   S   V   Y   H   S   L   S   C   C   L   L   E   K   P   V   A   L   V   E   -
                  N   R   C   I   I   H   *   A   V   A   C   L   R   S   Q   L   L   *   S   -
    4321 ----------+---------+---------+---------+---------+---------+ 4380
              L   F   R   H   I   M   *   Q   A   T   A   Q   K   L   L   W   N   S   K   Y   -
                P   I   P   T   D   N   M   S   S   N   S   A   Q   S   A   L   Q   E   Q   L   -
                  S   D   T   Y   *   E   N   L   Q   Q   K   S   S   F   G   T   A   R   T   S   -

C                           B   C
              ABv     BB                          sTv
              lfi     ab                          osi               S                   C
              uaJ     gv                          FeR               s                   j
              III     II                          III               P                   e
                  /                                   /             I                   I
         GCTAGGGCGTATTTTGGTGCTGCACTTGTAATATTGCCTAATATACCGTCATCATTTCAA
    4381 ----------+---------+---------+---------+---------+---------+ 4440
         CGATCCCGCATAAAACCACGACGTGAACATTATAACGGATTATATGGCAGTAGTAAAGTT A   R   A   Y   F   G   A   A   L   V   I   L   P   N   I   P   S   S   F   Q   -
                L   G   R   I   L   V   L   H   L   *   Y   C   L   I   Y   R   H   H   F   N   -
                  *   G   V   F   W   C   C   T   C   N   I   A   *   Y   T   V   I   I   S   T   -
    4381 ----------+---------+---------+---------+---------+---------+ 4440
              L   *   P   T   N   Q   H   Q   V   Q   L   I   A   *   Y   V   T   M   M   E   -
                A   L   A   Y   K   P   A   A   S   T   I   N   G   L   I   G   D   D   N   *   -
                  S   P   R   I   K   T   S   C   K   Y   Y   Q   R   I   Y   R   *   *   K   L   -

H
                                                            i
                      C                                     n       C
                      a       B       C                     d   Av          M
                      c       f       j                     I   li          w
                      8       a       e                     I   uJ          o
                      I       I       I                     I   II          I
                  /                                             /
         CCGTTGTTGGCACGCTAGGAACAGCGATTTGATTTGTCGCATAAGCTTCAATAGCACTGG
    4441 ----------+---------+---------+---------+---------+---------+ 4500
         GGCAACAACCGTGCGATCCTTGTCGCTAAACTAAACAGCGTATTCGAAGTTATCGTGACC

P   L   L   A   R   *   E   Q   R   F   D   L   S   H   K   L   Q   *   H   W   -
                R   C   W   H   A   R   N   S   D   L   I   C   R   I   S   F   N   S   T   G   -
                  V   V   G   T   L   G   T   A   I   *   F   V   A   *   A   S   I   A   L   G   -
    4441 ----------+---------+---------+---------+---------+---------+ 4500
              V   T   T   P   V   S   P   V   A   I   Q   N   T   A   Y   A   E   I   A   S   -
                G   N   N   A   R   *   S   C   R   N   S   K   D   C   L   S   *   Y   C   Q   -
                  R   Q   Q   C   A   L   F   L   S   K   I   Q   R   M   L   K   L   L   V   P   -

T
                                      t                                                     T
                      M               h                                                     s
```

FIG.2-SEQUENCE2-PAGE22

```
                        a         l          C C                          P
            B           e         l          a v            M             5
            s           I         l          c i            s             0
            r           I         I          8 R            e             9
            I           I         I          I I            I             I
            GATTTTTAGGGGTGGTGTTACTCGCTAAAATGCTTGCAATCTGACTATTAACAGCACCAA
    4501    ---------+---------+---------+---------+---------+---------+  4560
            CTAAAAATCCCCACCACAATGAGCGATTTTACGAACGTTAGACTGATAATTGTCGTGGTT

D F * G W C Y S L K C L Q S D Y * Q H Q     -
              I F R G G V T R * N A C N L T I N S T N   -
               F L G V V L L A K M L A I * L L T A P I -
    4501    ---------+---------+---------+---------+---------+---------+  4560
             P N K P T T N S A L I S A I Q S N V A G     -
              S K * P H H * E S F H K C D S * * C C W   -
               I K L P P T V R * F A Q L R V I L L V L -

T                T
                B                             s                B s
                s C   B         C             p                c p
                s aHHsST        v             M A5             eM5            S   M
                H chhath        i             s p0             8s0            s   s
                I 8aaJya        J             e o9             3e9            p   e
                I IIIIII        I             I II             III            I   I
                  /  //                       /                //
            TTTGCGCGCCTTggcTGTTGCCTTGAGCGTTAAATTCCCCTGTTAATTTGCTAATATTTA
    4561    ---------+---------+---------+---------+---------+---------+  4620
            AAACGCGCGGAAccgACAACGGAACTCGCAATTTAAGGGGACAATTAAACGATTATAAAT F A R L G C C L E R * I P L L I C * Y L     -
              L R A L A V A L S V K F P C * F A N I *   -
               C A P W L L P * A L N S P V N L L I F K -
    4561    ---------+---------+---------+---------+---------+---------+  4620
             I Q A G Q S N G Q A N F E G T L K S I N     -
              N A R R P Q Q R S R * I G R N I Q * Y K   -
               K R A K A T A K L T L N G Q * N A L I * -

T
                        N       S                              s
                   C    l       a    R                         p
                   vM   a       u    Dl      M                 M5
                   is   I       3    pe      s                 u0
                   J1   I       A    nA      e                 n9
                   II   I       I    II      I                 II
                   /                 /                         /
            AGATATTGTTCCCCACAGCCATGCTTTGATCGTTAAAACCTTGATACAATTGGTTGTATT
    4621    ---------+---------+---------+---------+---------+---------+  4680
            TCTATAACAAGGGGTGTCGGTACGAAACTAGCAATTTTGGAACTATGTTAACCAACATAA

R Y C S P Q P C F D R * N L D T I G C I     -
              D I V P H S H A L I V K T L I Q L V V L   -
               I L F P T A M L * S L K P * Y N W L Y C -
    4621    ---------+---------+---------+---------+---------+---------+  4680
             L I N N G V A M S Q D N F G Q Y L Q N Y     -
              L Y Q E G C G H K S R * F R S V I P O I   -
               S I T G W L W A K I T L V K I C N T T N -

E       N
                BUC         c       C l       S C            B
                Asbv        o   M   a aNS     f v            c
                coai        5   s   c Isp     a i            e
                iFJJ        7   1   8 Iph     N J            f
                IIII        I   I   I III     I I            I
                                    /         //
            GTTGGTTAGCGGCTTTCATAGGCATGCTTACGGCTTCAGCGATGCTTTGATTGTATTGGG
    4681    ---------+---------+---------+---------+---------+---------+  4740
```

FIG.2-SEQUENCE2-PAGE23

```
                CAACCAATCGCCGAAAGTATCCGTACGAATGCCGAAGTCGCTACGAAACTAACATAACCC
           V  G  *  R  L  S  *  A  C  L  R  L  Q  R  C  F  D  C  I  G   -
            L  V  S  G  F  H  R  H  A  Y  G  F  S  D  A  L  I  V  L  G  -
             W  L  A  A  F  I  G  M  L  T  A  S  A  M  L  *  L  Y  W  V -
       4681 ---------+---------+---------+---------+---------+---------+ 4740
             Q  Q  N  A  A  K  M  P  M  S  V  A  E  A  I  S  Q  N  Y  Q -
              T  P  *  R  S  E  Y  A  H  K  R  S  *  R  H  K  S  Q  I  P -
               N  T  L  P  K  *  L  C  A  *  P  K  L  S  A  K  I  T  N  P -

N
                   l                                                B
               R   a     A           A                    B         sT
               c   I     c           c                    b         os
               a   I     i           i                    v         Fe
               I   I     I           I                    I         II
                                                                    /
                TCATGATAGCGGTCATTTGCGGATTAGTAAACCCAACAATAATAGGAATAATCGCTGCTG
       4741 ---------+---------+---------+---------+---------+---------+ 4800
                AGTACTATCGCCAGTAAACGCCTAATCATTTGGGTTGTTATTATCCTTATTAGCGACGAC

S  *  *  R  S  F  A  D  *  *  T  Q  Q  *  *  E  *  S  L  L   -
            H  D  S  G  H  L  R  I  S  K  P  N  N  N  R  N  N  R  C  C  -
             M  I  A  V  I  C  G  L  V  N  P  T  I  I  G  I  I  A  A  V -
       4741 ---------+---------+---------+---------+---------+---------+ 4800
             T  M  I  A  T  M  Q  P  N  T  F  G  V  I  I  P  I  I  A  A -
              D  H  Y  R  D  N  A  S  *  Y  V  W  C  Y  Y  S  Y  D  S  S -
               *  S  L  P  *  K  R  I  L  L  G  L  L  L  F  L  R  Q  Q  -

S
                              C          Aa
               M     A    F   v   B      vu                         B    M
               w     c    a   i   s      a9                         s    n
               o     i    u   R   l      16                         b    l
               I     I    I   I   I      II                         I    I
                                         /
                TCATAGCACCCGCTACTATTCCTGCAAATGGTCCTGCGACACCACTTGTGTTGAGATGAT
       4801 ---------+---------+---------+---------+---------+---------+ 4860
                AGTATCGTGGGCGATGATAAGGACGTTTACCAGGACGCTGTGGTGAACACAACTCTACTA

S  *  H  P  L  L  F  L  Q  M  V  L  R  H  H  L  C  *  D  D   -
            H  S  T  R  Y  Y  S  C  K  W  S  C  D  T  T  C  V  E  M  I  -
             I  A  P  A  T  I  P  A  N  G  P  A  T  P  L  V  L  R  *  L -
       4801 ---------+---------+---------+---------+---------+---------+ 4860
             T  M  A  G  A  V  I  G  A  F  P  G  A  V  G  S  T  N  L  H -
              D  Y  C  G  S  S  N  R  C  I  T  R  R  C  W  K  H  Q  S  S -
               *  L  V  R  *  *  E  Q  L  H  D  Q  S  V  V  Q  T  S  I  I -

C C C           H     M      C
                                 v aSv  P        iT    b      Av     R
                                 i cfi  s        nf    o      li     s
                                 J 8cR  t        fi    I      uJ     a
                                 I III  I        II    I      II     I
                                   /              /            /
                TGAGGAAACTTCCGATAAGAAGCCTGCAGAAGATGATTcATATATAGCTTGTGtACCTgc
       4861 ---------+---------+---------+---------+---------+---------+ 4920
                ACTCCTTTGAAGGCTATTCTTCGGACGTCTTCTACTAAgTATATATCGAACACaTGGAcg

*  G  N  F  R  *  E  A  C  R  R  *  F  I  Y  S  L  C  T  C   -
            E  E  T  S  D  K  K  P  A  E  D  D  S  Y  I  A  C  V  P  A  -
             R  K  L  P  I  R  S  L  Q  K  M  I  H  I  *  L  V  Y  L  P -
       4861 ---------+---------+---------+---------+---------+---------+ 4920
             N  L  F  S  G  I  L  L  R  C  F  I  I  *  I  Y  S  T  Y  R -
              Q  P  F  K  R  Y  S  A  Q  L  L  H  N  M  Y  L  K  H  V  Q -
               S  S  V  E  S  L  F  G  A  S  S  S  E  Y  I  A  Q  T  G  A -
```

FIG.2-SEQUENCE2-PAGE24

```
       H N
       B i l
       sMnHa      B    M            B                     H
       pscpI      f    s            s                    iT    D
       MeIaI      a    e            l                    nf    d
       IIIII      I    I            I                    fi    e
                                                         II    I
           //                                              /
          CATGTTAACACCCCCTAGTTAATACCCTAATATCGGTGGTAAAAACGATGAATCTGAGTA
    4921  ---------+---------+---------+---------+---------+---------+  4980
          GTACAATTGTGGGGGATCAATTATGGGATTATAGCCACCATTTTTGCTACTTAGACTCAT H  V  N  T  P  *  L  I  P  *  Y  R  W  *  K  R  *  I  *  V  -
           M  L  T  P  P  S  *  Y  P  N  I  G  G  K  N  D  E  S  E  Y  -
             C  *  H  P  L  V  N  T  L  I  S  V  V  K  T  M  N  L  S  M  -
    4921  ---------+---------+---------+---------+---------+---------+  4980
           G  H  *  C  G  R  T  L  V  R  I  D  T  T  F  V  I  F  R  L  -
            W  T  L  V  G  *  N  I  G  *  Y  R  H  Y  F  R  H  I  Q  T  -
              M  N  V  G  G  L  *  Y  G  L  I  P  P  L  F  S  S  D  S  Y  -

T
                          t
                          h   N                    S
              C           l   l                   Aa                    P     C
              v           l   a                   vu        B           Bf    v R
              i           I   I                   a9        c           sl    i c
              R           I   I                   I6        c           1M    J a
              I           I   I                   II        I           II    I I
                                                   /
          TGTTGGTGCATAACCATACATGAAAGGATTGTTTGGACCGTAATCGCCCATCATTTGGCT
    4981  ---------+---------+---------+---------+---------+---------+  5040
          ACAACCACGTATTGGTATGTACTTTCCTAACAAACCTGGCATTAGCGGGTAGTAAACCGA

C  W  C  I  T  I  H  E  R  I  V  W  T  V  I  A  H  H  L  A  -
           V  G  A  *  P  Y  M  K  G  L  F  G  P  *  S  P  I  I  W  L  -
             L  V  H  N  H  T  *  K  D  C  L  D  R  N  R  P  S  F  G  S  -
    4981  ---------+---------+---------+---------+---------+---------+  5040
           I  N  T  C  L  W  V  H  F  S  Q  K  S  R  L  R  G  D  N  P  -
            H  Q  H  M  V  M  C  S  L  I  T  Q  V  T  I  A  W  *  K  A  -
              T  P  A  Y  G  Y  M  F  P  N  N  P  G  Y  D  G  M  M  Q  S  -

N
              l
              a               M                    R
              I           b   B                    1B
              I           o   s                    ef
              I           I   m                    Aa
              I           I   I                    II
          CATGAGAAGATTTTGAATGCCCCACATCGCATTGATACCTAGATTATCATTAGGTTGAAA
    5041  ---------+---------+---------+---------+---------+---------+  5100
          GTACTCTTCTAAAACTTACGGGGTGTAGCGTAACTATGGATCTAATAGTAATCCAACTTT

H  E  K  I  L  N  A  P  H  R  I  D  T  *  I  I  I  R  L  K  -
           M  R  R  F  *  M  P  H  I  A  L  I  P  R  L  S  L  G  *  K  -
             *  E  D  F  E  C  P  T  S  H  *  Y  L  D  Y  H  *  V  E  N  -
    5041  ---------+---------+---------+---------+---------+---------+  5100
           E  H  S  S  K  S  H  G  V  D  C  Q  Y  R  S  *  *  T  S  -
            *  S  F  I  K  F  A  G  C  R  M  S  V  *  I  I  M  L  N  F  -
              M  L  L  N  Q  I  G  W  M  A  N  I  G  L  N  D  N  P  Q  F  -

T
                              s
                              p
                              A5
                              p0        M
                              o9        s
                              II        e
                                        I
                               /
```

FIG.2-SEQUENCE2-PAGE25

```
         ACTCCCTAAACTTATGTCGTCAAATTTGATATTAACATTTTTATCATTATAGTCATTGAG
5101     ------------+---------+---------+---------+---------+---------+ 5160
         TGAGGGATTTGAATACAGCAGTTTAAACTATAATTGTAAAAATAGTAATATCAGTAACTC

T  P  *  T  Y  V  V  K  F  D  I  N  I  F  I  I  I  V  I  E  -
          L  P  K  L  M  S  S  N  L  I  L  T  F  L  S  L  *  S  L  S  -
           S  L  N  L  C  R  Q  I  *  Y  *  H  F  Y  H  Y  S  H  *  V -
5101     ------------+---------+---------+---------+---------+---------+ 5160
         F  E  R  F  K  H  R  *  I  Q  Y  *  C  K  *  *  *  L  *  Q  -
          V  G  *  V  *  T  T  L  N  S  I  L  M  K  I  M  I  T  M  S  -
           S  G  L  S  I  D  D  F  K  I  N  V  N  K  D  N  Y  D  N  L -

H                                  S               S
                  C  a                               B a             a
                  E  vHaM            B               suD      A      u  D    XB
                  a  iaIs            f               t3p      l      3  p    bf
                  e  JeIc            a               YAn      w      A  n    aa
                  I  IIII            I               III      I      I  I    II
                     ///             /
         TATGGCCACTTTTTGCTCTAGGGTTTCTTTAGGGATCTCTATTTTTAGTTGATCTCTAGA
5161     ------------+---------+---------+---------+---------+---------+ 5220
         ATACCGGTGAAAAACGAGATCCCAAAGAAATCCCTAGAGATAAAAATCAACTAGAGATCT

Y  G  H  F  L  L  *  G  F  F  R  D  L  Y  F  *  L  I  S  R  -
          M  A  T  F  C  S  R  V  S  L  G  I  S  I  F  S  *  S  L  E  -
           W  P  L  F  A  L  G  F  L  *  G  S  L  F  L  V  D  L  *  K -
5161     ------------+---------+---------+---------+---------+---------+ 5220
         T  H  G  S  K  A  R  P  N  R  *  P  D  R  N  K  T  S  R  *  -
          Y  P  W  K  K  S  *  P  K  K  L  S  R  *  K  *  N  I  E  L  -
           I  A  V  K  Q  E  L  T  E  K  P  I  E  I  K  L  Q  D  R  S -

E
                  C       c
                  v       o       M
                  i       5       b
                  J       7       o
                  I       I       I
                                  I
         AACAAGCCCCACGCTATTTAGTGCCATATCTTCAGGACTAATATCTTTTATATCAGTGTT
5221     ------------+---------+---------+---------+---------+---------+ 5280
         TTGTTCGGGGTGCGATAAATCACGGTATAGAAGTCCTGATTATAGAAAATATAGTCACAA

N  K  P  H  A  I  *  C  H  I  F  R  T  N  I  F  Y  I  S  V  -
          T  S  P  T  L  F  S  A  I  S  S  G  L  I  S  F  I  S  V  F  -
           Q  A  P  R  Y  L  V  P  Y  L  Q  D  *  Y  L  L  Y  Q  C  F -
5221     ------------+---------+---------+---------+---------+---------+ 5280
         F  C  A  G  R  *  K  T  G  Y  R  *  S  *  Y  R  K  Y  *  H  -
          F  L  G  W  A  I  *  H  W  I  K  L  V  L  I  K  *  I  L  T  -
           V  L  G  V  S  N  L  A  M  D  E  P  S  I  D  K  I  D  T  N -

T
                  H                          N                         s
                  i                          l                         p
                  MnH                        aMN                       5       M
                  scp                        Iss                       0       s
                  eIa                        Ilp                       9       e
                  III                        III                       I       I
                   /                          /
         TTGGTCAGCGTTAAcGGACTGTAAACATGCCAATGATAAGACACCAAGCAAATAGTAATT
5281     ------------+---------+---------+---------+---------+---------+ 5340
         AACCAGTCGCAATTgCCTGACATTTGTACGGTTACTATTCTGTGGTTCGTTTATCATTAA L  V  S  V  N  G  L  *  T  C  Q  *  *  D  T  K  Q  I  V  I  -
          W  S  A  L  T  D  C  K  H  A  N  D  K  T  P  S  K  *  *  F  -
           G  Q  R  *  R  T  V  N  M  P  M  I  R  H  Q  A  N  S  N  L -
5281     ------------+---------+---------+---------+---------+---------+ 5340
         K  P  *  R  *  R  V  T  F  M  G  I  I  L  C  W  A  F  L  L  -
```

FIG.2-SEQUENCE2-PAGE26

```
         K  T  L  T  L  P  S  Y  V  H  W  H  Y  S  V  L  C  I  T  I -
            Q  D  A  N  V  S  Q  L  C  A  L  S  L  V  G  L  L  Y  Y  N -
       T
       T t
       s h
       p 1                                        H
       p 1                                        i
       5 1                           P            n
       0 1                           l            f
       9 I                           e            I
       I I                           I
       /
       TAATTTTATAAAAATCcGTTTTCATACTTTTGACTCCTTTATTCTTATTTTTAGCACTAT
5341   ---------+---------+---------+---------+---------+---------+ 5400
       ATTAAAATATTTTTAGgCAAAAGTATGAAAACTGAGGAAATAAGAATAAAAATCGTGATA

*  F  Y  K  N  P  F  S  Y  F  *  L  L  Y  S  Y  F  *  H  Y  -
        N  F  I  K  I  R  F  H  T  F  D  S  F  I  L  I  F  S  T  I  -
         I  L  *  K  S  V  F  I  L  L  T  P  L  F  L  F  A  L  F  -
5341   ---------+---------+---------+---------+---------+---------+ 5400
         K  I  K  Y  F  D  T  K  M  S  K  V  G  K  N  K  N  K  A  S -
        *  N  *  L  F  G  N  E  Y  K  Q  S  R  *  E  *  K  *  C  *  -
         L  K  I  F  I  R  K  *  V  K  S  E  K  I  R  I  K  L  V  I -

T
                                                        t
                                               S        h
                                               a        l
       B      H   M                            u   D T l
       f      h   s                            3   p a l
       a      a   e                            A   n q I
       I      I   I                            I   I I I
                                                 /
       TCTAGCGCATTAACGCCACTCAATCGTTATTTTTGTTTTGATTTTTTTGATCGAGCATTT
5401   ---------+---------+---------+---------+---------+---------+ 5460
       AGATCGCGTAATTGCGGTGAGTTAGCAATAAAAACAAAACTAAAAAAACTAGCTCGTAAA

S  S  A  L  T  P  L  N  R  Y  F  C  F  D  F  F  D  R  A  F  -
         L  A  H  *  R  H  S  I  V  I  F  V  L  I  F  L  I  E  H  F -
       *  R  I  N  A  T  Q  S  L  F  L  F  *  F  F  *  S  S  I  L   -
5401   ---------+---------+---------+---------+---------+---------+ 5460
         N  *  R  M  L  A  V  *  D  N  N  K  N  Q  N  K  Q  D  L  M -
        E  L  A  N  V  G  S  L  R  *  K  Q  K  S  K  K  S  R  A  N  -
         R  A  C  *  R  W  E  I  T  I  K  T  K  I  K  K  I  S  C  K -

M
                   a
                   e                                 C           C
                   I                    S            Av          Av
                   I                    s            li          li
                   I                    p            uJ          uJ
                                        I            II          II
                                                      /           /
       TGTTTGTTACTTCATCAATGTTTTGAAAATATTTTTCAAAAAGCTCTTTCTTTTTAGCTT
5461   ---------+---------+---------+---------+---------+---------+ 5520
       ACAAACAATGAAGTAGTTACAAAACTTTTATAAAAAGTTTTTCGAGAAAGAAAAATCGAA

C  L  L  L  H  Q  C  F  E  N  I  F  Q  K  A  L  S  F  *  L  -
         V  C  Y  F  I  N  V  L  K  I  F  F  K  K  L  F  L  F  S  F -
          F  V  T  S  S  M  F  *  K  Y  F  S  K  S  S  F  F  L  A  S -
5461   ---------+---------+---------+---------+---------+---------+ 5520
          K  N  T  V  E  D  I  N  Q  F  Y  K  E  F  L  E  K  K  K  A -
         Q  K  N  S  *  *  H  K  S  F  I  K  *  F  A  R  E  K  *  S  -
          T  Q  *  K  M  L  T  K  F  I  N  K  L  F  S  K  R  K  L  K -

T
                   a                                      N            N
```

FIG.2-SEQUENCE2-PAGE27

```
                                H         p              H         l            C    l
                                iT        5              i         aPM          v N  a
                                nf        0              n         Ils          i s  I
                                fi        9              f         Iee          R i  I
                                II        I              I         III          I I  I
                                 /                        /         /
         CAACGCTCATATCAATCTGAATCCAATTAGGAATAATGGAGTCCATGATTAAATGCATGA
    5521 ---------+---------+---------+---------+---------+---------+ 5580
         GTTGCGAGTATAGTTAGACTTAGGTTAATCCTTATTACCTCAGGTACTAATTTACGTACT

Q   R   S   Y   Q   S   E   S   N   *   E   *   W   S   P   *   L   N   A   *    -
           N   A   H   I   N   L   N   P   I   R   N   N   G   V   H   D   *   M   H   E  -
             T   L   I   S   I   *   I   Q   L   G   I   M   E   S   M   I   K   C   M   K -
    5521 ---------+---------+---------+---------+---------+---------+ 5580
         E   V   S   M   D   I   Q   I   W   N   P   I   I   S   D   M   I   L   H   M    -
           *   R   E   Y   *   D   S   D   L   *   S   Y   H   L   G   H   N   F   A   H  -
             L   A   *   I   L   R   F   G   I   L   F   L   P   T   W   S   *   I   C   S -

N
                                  l
                          M       a
                          s       I
                          l       I
                          I       I
         AGTCATAGGCATGATTTTT
    5581 ---------+--------- 5599
         TCAGTATCCGTACTAAAAA

S   H   R   H   D   F    -
           V   I   G   M   I   F  -
             S   *   A   *   F    -
    5581 ---------+--------- 5599
         F   D   Y   A   H   N K  -
           L   *   L   C   S   K  -
             T   M   P   M   I   K -
```

FIG.2-SEQUENCE2-PAGE28

```
                          T
                          s
              N           p              B    C
              l           A5             s    v    M
              a           p0             r    i    n
              I           o9             D    R    l
              I           II             I    I    I
              /
     AGGCAAAAAACATGAAAACATCACTAAATTCACTTGTCCTCATTGCAATATCACACACCA
  1  ------------+---------+---------+---------+---------+---------+ 60
     TCCGTTTTTTGTACTTTTGTAGTGATTTAAGTGAACAGGAGTAACGTTATAGTGTGTGGT a    R  Q  K  T  *  K  H  H  *  I  H  L  S  S  L  Q  Y  H  T  P  -
b     G  K  K  H  E  N  I  T  K  F  T  C  P  H  C  N  I  T  H  H  -
c      A  K  N  M  K  T  S  L  N  S  L  V  L  I  A  I  S  H  T  T  -
  1  ------------+---------+---------+---------+---------+---------+ 60
d    A  F  F  M  F  V  D  S  F  E  S  T  R  M  A  I  D  C  V        -
e      C  F  V  H  F  C  *  *  I  *  K  D  E  N  C  Y  *  V  G     -
f       P  L  F  C  S  F  M  V  L  N  V  Q  G  *  Q  L  I  V  C  W -

C                          N
              H      a         S              C l
              g      c         s              a aBNS
              a      8         p              c Ifsp
              I      I         I              8 Iaph
                                              I IIII
                                                //
     CAGAGATTACAATGCGAGCGTCAATATTAGAAACTACGCTTTAGGCATGCTAGATGACAG
 61  ------------+---------+---------+---------+---------+---------+ 120
     GTCTCTAATGTTACGCTCGCAGTTATAATCTTTGATGCGAAATCCGTACGATCTACTGTC a    Q  R  L  Q  C  E  R  Q  Y  *  K  L  R  F  R  H  A  R  *  Q  -
b     R  D  Y  N  A  S  V  N  I  R  N  Y  A  L  G  M  L  D  D  R  -
c      E  I  T  M  R  A  S  I  L  E  T  T  L  *  A  C  *  M  T  G  -
 61  ------------+---------+---------+---------+---------+---------+ 120
d    V  S  I  V  I  R  A  D  I  N  S  V  V  S  *  A  H  *  I  V    -
e      C  L  N  C  H  S  R  *  Y  *  F  S  R  K  L  C  A  L  H  C  -
f       L  S  *  L  A  L  T  L  I  L  F  *  A  K  P  M  S  S  S  L -

GCATAAAATAAAGATAGATAAAAGTAGGGTAGGGATTATCCGAACTGATTACGCTCATTA
121  ------------+---------+---------+---------+---------+---------+ 180
     CGTATTTTATTTCTATCTATTTTCATCCCATCCCTAATAGGCTTGACTAATGCGAGTAAT a    A  *  N  K  D  R  *  K  *  G  R  D  Y  P  N  *  L  R  S  L  -
b     H  K  I  K  I  D  K  S  R  V  G  I  I  R  T  D  Y  A  H  Y  -
c      I  K  *  R  *  I  K  V  G  *  G  L  S  E  L  I  T  L  I  T  -
121  ------------+---------+---------+---------+---------+---------+ 180
d    P  M  F  Y  L  Y  I  F  T  P  Y  P  N  D  S  S  I  V  S  M    -
e      A  Y  F  L  S  L  Y  F  Y  P  L  S  *  G  F  Q  N  R  E  N  -
f       C  L  I  F  I  S  L  L  L  T  P  I  I  R  V  S  *  A  *  * -
                                    H
```

FIG.2-SEQUENCE3-PAGE 1

```
                         i
                         n   CS              C
                     H   d   Avf   M    Av              B    M
                     h   I   lia   w    li              s    n
                     a   I   uJN   o    uJ              l    l
                     I   I   III   I    II              I    I
                             //         /
        CACTGATGAGCGCATCAAAGCTTGTGGAGCTTCCTCTAATGGGGTTATTTCTAAATATGG
    181 ----------+---------+---------+---------+---------+---------+ 240
        GTGACTACTCGCGTAGTTTCGAACACCTCGAAGGAGATTACCCCAATAAAGATTTATACC a       H  *  *  A  H  Q  S  L  W  S  F  L  *  W  G  Y  F  *  I  W  -
b          T  D  E  R  I  K  A  C  G  A  S  S  N  G  V  I  S  K  Y  G  -
c             L  M  S  A  S  K  L  V  E  L  P  L  M  G  L  F  L  N  M  A -
    181 ----------+---------+---------+---------+---------+---------+ 240
d       V  S  I  L  A  D  F  S  T  S  S  G  R  I  P  N  N  R  F  I  -
e          C  Q  H  A  C  *  L  K  H  L  K  R  *  H  P  *  K  *  I  H  -
f             V  S  S  R  M  L  A  Q  P  A  E  E  L  P  T  I  E  L  Y  P  -

S
                    Ba                 C
                    suD    B    AABv
                    t3p    f    llfi
                    YAn    a    uwaJ
                    III    I    IIII
                    /           //
        CAACATATTGGATCTAGCTAGTTATGGAGCGATGAAGCAAGAAAAAGCCCAATCGCTTTA
    241 ----------+---------+---------+---------+---------+---------+ 300
        GTTGTATAACCTAGATCGATCAATACCTCGCTACTTCGTTCTTTTTCGGGTTAGCGAAAT a       Q  H  I  G  S  S  *  L  W  S  D  E  A  R  K  S  P  I  A  L  -
b          N  I  L  D  L  A  S  Y  G  A  M  K  Q  E  K  A  Q  S  L  *  -
c             T  Y  W  I  *  L  V  M  E  R  *  S  K  K  K  P  N  R  F  S -
    241 ----------+---------+---------+---------+---------+---------+ 300
d       A  V  Y  Q  I  *  S  T  I  S  R  H  L  L  F  F  G  L  R  K  -
e          C  C  I  P  D  L  *  N  H  L  S  S  A  L  F  L  G  I  A  K  -
f             L  M  N  S  R  A  L  *  P  A  I  F  C  S  F  A  W  D  S  *  -

T
              s                   S                        M
              p                   a                        a
              5                   u    D                   e
              0                   3    p                   I
              9                   A    n                   I
              I                   I    I                   I
        GCGTTGGTAATTCACAAAAAGCAAGATCGGTTGTAAAAATGCGTTACAACTAAAATAAAG
    301 ----------+---------+---------+---------+---------+---------+ 360
        CGCAACCATTAAGTGTTTTTCGTTCTAGCCAACATTTTTACGCAATGTTGATTTTATTTC a       A  L  V  I  H  K  K  Q  D  R  L  *  K  C  V  T  T  K  I  K  -
b          R  W  *  F  T  K  S  K  I  G  C  K  N  A  L  Q  L  K  *  R  -
c             V  G  N  S  Q  K  A  R  S  V  V  K  M  R  Y  N  *  N  K  G -
    301 ----------+---------+---------+---------+---------+---------+ 360
d       L  T  P  L  E  C  F  A  L  D  T  T  F  I  R  *  L  *  F  L  -
e          A  N  T  I  *  L  F  C  S  R  N  Y  F  H  T  V  V  L  I  F  -
f             R  Q  Y  N  V  F  L  L  I  P  Q  L  F  A  N  C  S  F  Y  L -

H    A                                C
                         i    fM    P                          ABv
                         n    ls    l                          lfi
                         f    Ie    e                          uaJ
                         I    II    I                          III
                                                               /
        GGTCAAGATAACTCATTTTCAAAAAGGAGTCTTAAGTAATAAAATCATAATGTTCAGCTA
    361 ----------+---------+---------+---------+---------+---------+ 420
        CCAGTTCTATTGAGTAAAAGTTTTTCCTCAGAATTCATTATTTTAGTATTACAAGTCGAT
```

FIG.2-SEQUENCE3-PAGE2

```
a      G  Q  D  N  S  F  S  K  R  S  L  K  *  *  N  H  N  V  Q  L  -
b       V  K  I  T  H  F  Q  K  G  V  L  S  N  K  I  I  M  F  S  * -
c        S  R  *  L  I  F  K  K  E  S  *  V  I  K  S  *  C  S  A  S -
     361 ---------+---------+---------+---------+---------+---------+ 420
d      P  D  L  Y  S  M  K  L  F  S  D  *  T  I  F  D  Y  H  E  A  -
e       P  *  S  L  E  N  E  F  L  L  R  L  Y  Y  F  *  L  T  *  S -
f        T  L  I  V  *  K  *  F  P  T  K  L  L  I  M  I  N  L  *  -

T
                              t                    T
                 S            h                    s
                 a      C     l                    p
                 BuD M  Av    l           H    A5
                 c3p n  1i    l           p    p0
                 1An 1  uJ    I           h    o9
                 III I  II    I           I    II
                   /      /                  /
         GTAATCTATTGCCTCGTTGATCAAACAAAGCTCTGCGTGAAAGATGAAAAAATTTCACCT
     421 ---------+---------+---------+---------+---------+---------+ 480
         CATTAGATAACGGAGCAACTAGTTTGTTTCGAGACGCACTTTCTACTTTTTTAAAGTGGA a      V  I  Y  C  L  V  D  Q  T  K  L  C  V  K  D  E  K  I  S  P  -
b       *  S  I  A  S  L  I  K  Q  S  S  A  *  K  M  K  K  F  H  L -
c        N  L  L  P  R  *  S  N  K  A  L  R  E  R  *  K  N  F  T  F -
     421 ---------+---------+---------+---------+---------+---------+ 480
d      L  L  R  N  G  R  Q  D  F  L  A  R  R  S  L  H  F  F  K  V  -
e       T  I  *  Q  R  T  S  *  V  F  S  Q  T  F  S  S  F  I  E  G -
f        Y  D  I  A  E  N  I  L  C  L  E  A  H  F  I  F  F  N  *  R -

B        H              B
              M         S         s        i              c
              s         f         m        n              e  A    B
              e         c         A        4              8  c    b
              I         I         I        I              3  i    v
                                                          I  I    I
         TTAGATAGTTAATACACCACTACAGTCTTACTTGAGAGACACTCATTTTATTAGCGGTTT
     481 ---------+---------+---------+---------+---------+---------+ 540
         AATCTATCAATTATGTGGTGATGTCAGAATGAACTCTCTGTGAGTAAAATAATCGCCAAA a      L  D  S  *  Y  T  T  T  V  L  L  E  R  H  S  F  Y  *  R  F  -
b       *  I  V  N  T  P  L  Q  S  Y  L  R  D  T  H  F  I  S  G  F -
c        R  *  L  I  H  H  Y  S  L  T  *  E  T  L  I  L  L  A  V  L -
     481 ---------+---------+---------+---------+---------+---------+ 540
d      K  L  Y  N  I  C  W  *  L  R  V  Q  S  V  S  M  K  N  A  T  -
e       K  S  L  *  Y  V  V  V  T  K  S  S  L  C  E  N  *  *  R  N -
f        *  I  T  L  V  G  S  C  D  *  K  L  S  V  *  K  I  L  P  K -

S       N            E
              B          C                Ba      1   C        c
              sT         j           A    suD     a   j        o
              os         e           l    t3p     I   e        5
              Fe         P           w    YAn     I   P        7
              II         I           I    III     I   I        I
                /                          /
         TGTCTGATTTGCTGCTACCAAAACCATTACCAACCAAAGCAGATCCCATGTTTTTGATAC
     541 ---------+---------+---------+---------+---------+---------+ 600
         ACAGACTAAACGACGATGGTTTTGGTAATGGTTGGTTTCGTCTAGGGTACAAAAACTATG a      C  L  I  C  C  Y  Q  N  H  Y  Q  P  K  Q  I  P  C  F  *  Y  -
b       V  *  F  A  A  T  K  T  I  T  N  Q  S  R  S  H  V  F  D  T -
c        S  D  L  L  L  P  K  P  L  P  T  K  A  D  P  M  F  L  I  L -
     541 ---------+---------+---------+---------+---------+---------+ 600
d      K  D  S  K  S  S  G  F  G  N  G  V  L  A  S  G  M  N  K  I  -
e       Q  R  I  Q  Q  *  W  F  W  *  W  G  F  C  I  G  H  K  Q  Y -
f        T  Q  N  A  A  V  L  V  M  V  L  W  L  L  D  W  T  K  S  V -
```

FIG.2-SEQUENCE3-PAGE3

```
                                T
                                s
           H M                  p
        T  i b T  X             A 5                                       M
        a  n o f  m             p 0                                       s
        q  f I i  n             o 9                                       e
        I  I I I  I             I I                                       I
         //                     /
      TATCGAATCCATTCTTCAGCACTTCTGCCATAAAATTCTTGATATTGTCCATAGGCAAGT
  601 ----------+----------+----------+----------+----------+----------+ 660
      ATAGCTTAGGTAAGAAGTCGTGAAGACGGTATTTTAAGAACTATAACAGGTATCCGTTCA a       Y  R  I  H  S  S  A  L  L  P  *  N  S  *  Y  C  P  *  A  S  -
b        I  E  S  I  L  Q  H  F  C  H  K  I  L  D  I  V  H  R  Q  V  -
c         S  N  P  F  F  S  T  S  A  I  K  F  L  I  L  S  I  G  K  L  -
  601 ----------+----------+----------+----------+----------+----------+ 660
d       S  D  F  G  N  K  L  V  E  A  M  F  N  K  I  N  D  M  P  L  -
e        *  R  I  W  E  E  A  S  R  G  Y  F  E  Q  Y  Q  G  Y  A  L  -
f         I  S  D  M  R  *  C  K  Q  W  L  I  R  S  I  T  W  L  C  T  -

T
        s
        p                B
        A 5              s              M           B     M
        p 0              m              s           c     s
        o 9              F              e           c     e
        I I              I              I           I     I
         /
      TAAATTTTTTCCCTAATGCTTCATTAAGTCCCATCATTAACATCAGAAAGAACAAAAAAT
  661 ----------+----------+----------+----------+----------+----------+ 720
      ATTTAAAAAAGGGATTACGAAGTAATTCAGGGTAGTAATTGTAGTCTTTCTTGTTTTTTA a       *  I  F  S  L  M  L  H  *  V  P  S  L  T  S  E  R  T  K  N  -
b        K  F  F  P  *  C  F  I  K  S  H  H  *  H  Q  K  E  Q  K  I  -
c         N  F  F  P  N  A  S  L  S  P  I  I  N  I  R  K  N  K  K  F  -
  661 ----------+----------+----------+----------+----------+----------+ 720
d       N  F  K  K  G  L  A  E  N  L  G  M  M  L  M  L  F  F  L  F  -
e        *  I  K  E  R  I  S  *  *  T  G  D  N  V  D  S  L  V  F  F  -
f         L  N  K  G  *  H  K  M  L  D  W  *  *  C  *  F  S  C  F  I  -

M                                         B
              s                                         s
              e                                         r
              I                                         I
      TTAATATCATAGAAAACAAATCACTGGATAAACCTGTAAAAAGATTTGTTCCCCCACCCA
  721 ----------+----------+----------+----------+----------+----------+ 780
      AATTATAGTATCTTTTGTTTAGTGACCTATTTGGACATTTTCTAAACAAGGGGGTGGGT a       L  I  S  *  K  T  N  H  W  I  N  L  *  K  D  L  F  P  H  P  -
b        *  Y  H  R  K  Q  I  T  G  *  T  C  K  K  I  C  S  P  T  Q  -
c         N  I  I  E  N  K  S  L  D  K  P  V  K  R  F  V  P  P  N  -
  721 ----------+----------+----------+----------+----------+----------+ 780
d       N  L  I  M  S  F  L  D  S  S  L  G  T  F  L  N  T  G  G  -
e        K  I  D  Y  F  V  F  *  Q  I  F  R  Y  F  S  K  N  G  W  G  -
f         *  Y  *  L  F  C  I  V  P  Y  V  Q  L  F  I  Q  E  G  V  W  -

T
          T                                             t
          B s              N  S                  B      h
        C C T  sp          l  a              C   s      l
        C A j  vaAp5       Ba Du             C j  p     2
        j l e  iqp20       cI p3             j e  2     1
        e u P  JIo49       lI nA             e P  4     I
        I I I  IIIIII      II II             I I  >I    I
         / / /    /          /    /           /
```

FIG.2-SEQUENCE3-PAGE4

```
            ACAAAGAAGCTAAAATTTTTCCCATGATCAGTCCTTTTATTTTTGGTTGTGTAAGTTCTT
        781 ----------+---------+---------+---------+---------+---------+ 840
            TGTTTCTTCGATTTTAAAAAGGGTACTAGTCAGGAAAATAAAAACCAACACATTCAAGAA a         T  K  K  L  K  F  F  P  *  S  V  L  L  F  L  V  V  *  V  L   -
  b          Q  R  S  *  N  F  S  H  D  Q  S  F  Y  F  W  L  C  K  F  L  -
  c           K  E  A  K  I  F  P  M  I  S  P  F  I  F  G  C  V  S  S  C -
        781 ----------+---------+---------+---------+---------+---------+ 840
  d         L  L  S  A  L  I  K  G  M  I  L  G  K  I  K  P  Q  T  L  E   -
  e          V  F  F  S  F  N  K  G  H  D  T  R  K  N  K  T  T  Y  T  R  -
  f           C  L  L  *  F  K  E  W  S  *  D  K  *  K  Q  N  H  L  N  K -

X
                                              m
                                              n
                                              I
            GCTTGTTCTTATCTCTAATGCGTGTTTTAGTAGGAAGCATTTCACAATAGCATACCTAAA
        841 ----------+---------+---------+---------+---------+---------+ 900
            CGAACAAGAATAGAGATTACGCACAAAATCATCCTTCGTAAAGTGTTATCGTATGGATTT a         A  C  S  Y  L  *  C  V  F  *  *  E  A  F  H  N  S  I  P  K   -
  b          L  V  L  I  S  N  A  C  F  S  R  K  H  F  T  I  A  Y  L  K  -
  c           L  F  L  S  L  M  R  V  L  V  G  S  I  S  Q  *  H  T  *  S -
        841 ----------+---------+---------+---------+---------+---------+ 900
  d         Q  K  N  K  D  R  I  R  T  K  T  P  L  M  E  C  Y  C  V  *   -
  e          A  Q  E  *  R  *  H  T  N  *  Y  S  A  N  *  L  L  M  G  L  -
  f           S  T  R  I  E  L  A  H  K  L  L  F  C  K  V  I  A  Y  R  F -

T
                        s
            C           p           H                       N
            Av    D     A5          iT                      l
            li    d     p0          nf          R           a
            uJ    e     o9          fi          c           I
            II    I     II          II          a           I
                                                I           I
             /     /     /
            GCTACTAAGAAAATTCTTGAATCTATTGGTAAGATTACTCATGAAATCAAGCGATAAGTA
        901 ----------+---------+---------+---------+---------+---------+ 960
            CGATGATTCTTTTAAGAACTTAGATAACCATTCTAATGAGTACTTTAGTTCGCTATTCAT a         A  T  K  K  I  L  E  S  I  G  K  I  T  H  E  I  K  R  *  V   -
  b          L  L  R  K  F  L  N  L  L  V  R  L  L  M  K  S  S  D  K  *  -
  c           Y  *  E  N  S  *  I  Y  W  *  D  Y  S  *  N  Q  A  I  S  S -
        901 ----------+---------+---------+---------+---------+---------+ 960
  d         L  *  *  S  F  E  Q  I  *  Q  Y  S  *  E  H  F  *  A  I  L   -
  e          A  V  L  F  I  R  S  D  I  P  L  I  V  *  S  I  L  R  Y  T  -
  f           S  S  L  F  N  K  F  R  N  T  L  N  S  M  F  D  L  S  L  Y -

T                             T
                              t                             t
                              h                             h
            C                 1             C               1
            v                 1             v               1
            i           S     1             i               1
            J           s     I             J               I
            I           p     I             I               I
                        I
            GCCACCAATCGCAAACAAATCAAATATTTTGCCACCAAACAAGCCATATCCTTTTTGTTT
        961 ----------+---------+---------+---------+---------+---------+ 1020
            CGGTGGTTAGCGTTTGTTTAGTTTATAAAACGGTGGTTTGTTCGGTATAGGAAAAACAAA a         A  T  N  R  K  Q  I  K  Y  F  A  T  K  Q  A  I  S  F  L  F   -
  b          P  P  I  A  N  K  S  N  I  L  P  P  N  K  P  Y  P  F  C  F  -
  c           H  Q  S  Q  T  N  Q  I  F  C  H  Q  T  S  H  I  L  F  V  F -
        961 ----------+---------+---------+---------+---------+---------+ 1020
  d         L  W  W  D  C  V  F  *  I  N  Q  W  W  V  L  W  I  R  K  T   -
  e          A  V  L  R  L  C  I  L  Y  K  A  V  L  C  A  M  D  K  K  N  -
```

FIG.2-SEQUENCE3-PAGE5

```
f            G  G  I  A  F  L  D  F  I  K  G  G  F  L  G  Y  G  K  Q  K -
                      T           T              T
                      s           s              s
                      p           p              p
                      5           A5             5   M5V
                      0           p0           S s0s
                      9           o9           s p e9p
                      I           II             I III
                                    /                   /
         TTATCTCCTAATTATAGCAAATTTTTATCAATATTAATTTGGAAAACCACCACCATATCA
    1021 ----------+---------+---------+---------+---------+---------+ 1080
         AATAGAGGATTAATATCGTTTAAAAATAGTTATAATTAAACCTTTTGGTGGTGGTATAGT a       L  S  P  N  Y  S  K  F  L  S  I  L  I  W  K  T  T  T  I  S  -
b        Y  L  L  I  I  A  N  F  Y  Q  Y  *  F  G  K  P  P  P  Y  Q -
c          I  S  *  L  *  Q  I  F  I  N  I  N  L  E  N  H  H  H  I  K -
    1021 ----------+---------+---------+---------+---------+---------+ 1080
d       K  I  E  *  N  Y  C  I  K  I  L  I  L  K  S  F  W  W  W  I  -
e        K  D  G  L  *  L  L  N  K  D  I  N  I  Q  F  V  V  V  M  D -
f          *  R  R  I  I  A  F  K  *  *  Y  *  N  P  F  G  G  G  Y  * -

T                        T                      T
                  s                        s                      s
                  p         S          C   p                      p
                  5         f     B    v   5      MD    T H   M  A5   MD
                  0         a     f    i   0      sr    h h   s  p0   sr
                  9         N     a    R   9      ea    a a   e  o9   ea
                  I         I     I    I   I      II    I I   I  II   II
                             /
         AAAACAAATTACTAACACACTAGATGCAGAATTATTTTTTAAAAACGCGCACTTAAATTT
    1081 ----------+---------+---------+---------+---------+---------+ 1140
         TTTTGTTTAATGATTGTGTGATCTACGTCTTAATAAAAAATTTTTGCGCGTGAATTTAAA a       K  T  N  Y  *  H  T  R  C  R  I  I  F  *  K  R  A  L  K  F  -
b        K  Q  I  T  N  T  L  D  A  E  L  F  F  K  N  A  H  L  N  L -
c          N  K  L  L  T  H  *  M  Q  N  Y  F  L  K  T  R  T  *  I  * -
    1081 ----------+---------+---------+---------+---------+---------+ 1140
d       L  F  L  N  S  V  C  *  I  C  F  *  K  K  F  V  R  V  *  I  -
e        F  V  F  *  *  C  V  L  H  L  I  I  K  *  F  R  A  S  L  N -
f          F  C  I  V  L  V  S  S  A  S  N  N  K  L  F  A  C  K  F  K -

N                                                     CC
              l                                                     ABav
              a                             X                       1fci
              i                             c                       ua8J
              I                             m                       IIII
              I                             I                         /
         AAAATCATGGGGTTTTAGGATTTGAATACCAAAAATAGATTGGTTTTTTCAAATAAGCTA
    1141 ----------+---------+---------+---------+---------+---------+ 1200
         TTTTAGTACCCCAAAATCCTAAACTTATGGTTTTTATCTAACCAAAAAAGTTTATTCGAT a       K  I  M  G  F  *  D  L  N  T  K  N  R  L  V  F  S  N  K  L  -
b        K  S  W  G  F  R  I  *  I  P  K  I  D  W  F  F  Q  I  S  * -
c          N  H  G  V  L  G  F  E  Y  Q  K  *  I  G  F  F  K  *  A  S -
    1141 ----------+---------+---------+---------+---------+---------+ 1200
d       *  F  *  P  T  K  P  N  S  Y  W  F  Y  I  P  K  K  L  Y  A  -
e        L  I  M  P  N  *  S  K  F  V  L  F  L  N  T  K  E  F  L  S -
f          F  D  H  P  K  L  I  Q  I  G  F  I  S  Q  N  K  *  I  L  * -

T
                                                                    t
                                                                    h
           C                                                        1
           AvN              H M                                     1
```

FIG.2-SEQUENCE3-PAGE6

```
         lih        h s                              l
         uJe        a e                              I
         III        I I                              I
                   //
          GCTTTGTGTATGCGCTTAAAAAGATTTTGGTTTTTAGTCAGTAAGGTTTTATGCTAATGT
     1201 ---------+---------+---------+---------+---------+---------+ 1260
          CGAAACACATACGCGAATTTTTCTAAAACCAAAAATCAGTCATTCCAAAATACGATTACA a        A  L  C  M  R  L  K  R  F  W  F  L  V  S  K  V  L  C  *  C  -
  b        L  C  V  C  A  *  K  D  F  G  F  *  S  V  R  F  Y  A  N  V  -
  c          F  V  Y  A  L  K  K  I  L  V  F  S  Q  *  G  F  M  L  M  F -
     1201 ---------+---------+---------+---------+---------+---------+ 1260
  d        L  K  T  Y  A  S  L  F  I  K  T  K  L  *  Y  P  K  I  S  I  -
  e        A  K  H  I  R  K  F  L  N  Q  N  K  T  L  L  T  K  H  *  H  -
  f          S  Q  T  H  A  *  F  S  K  P  K  *  D  T  L  N  *  A  L  T -

T                      T
                           s                      s                   B
                           p                      p               H   c
                           A5                     A5              iT  e
                           p0                     p0              nf  8
                           o9                     o9              fi  3
                           II                     II              II  I
                           /                      /               /
          TTGGAAATAAAGAAATTTCTCTAAATCAAGTCTTGAGAAATTTTTGAACGAATCATAAGA
     1261 ---------+---------+---------+---------+---------+---------+ 1320
          AACCTTTATTTCTTTAAAGAGATTTAGTTCAGAACTCTTTAAAAACTTGCTTAGTATTCT a        L  E  I  K  K  F  L  *  I  K  S  *  E  I  F  E  R  I  R   -
  b         W  K  *  R  N  F  S  K  S  S  L  E  K  F  L  N  E  S  *  E -
  c            G  N  K  E  I  S  L  N  Q  V  L  R  N  F  *  T  N  H  K N-
     1261 ---------+---------+---------+---------+---------+---------+ 1320
  d        N  P  F  L  S  I  E  R  F  *  T  K  L  F  K  Q  V  F  *  L  -
  e         K  S  I  F  F  N  R  *  I  L  D  Q  S  I  K  S  R  I  M  L -
  f            Q  F  Y  L  F  K  E  L  D  L  R  S  F  N  K  F  S  D  Y S-

T                                  T
                  s                                  s
          D  p           H                    C      p           CA
          r  5           i        MP          Av     A5          vfM
          d  0           n        sl          li     p0          ils
          I  9           f        le          uJ     o9          JIe
          I  I           I        II          II     II          III
                 /              /                           /
          ACCAATTTTGCCATTGAGTCATAAGTATGATTAGCTTCATTGTGAATTTTGCGTGGCTTA
     1321 ---------+---------+---------+---------+---------+---------+ 1380
          TGGTTAAAACGGTAACTCAGTATTCATACTAATCGAAGTAACACTTAAAACGCACCGAAT a        T  N  F  A  I  E  S  *  V  *  L  A  S  L  *  I  L  R  G  L  -
  b         P  I  L  P  L  S  H  K  Y  D  *  L  H  C  E  F  C  V  A  * -
  c            Q  F  C  H  *  V  I  S  M  I  S  F  I  V  N  F  A  W  L K-
     1321 ---------+---------+---------+---------+---------+---------+ 1380
  d        F  W  N  Q  W  Q  T  M  L  I  I  L  K  M  T  F  K  A  H  S  -
  e         V  L  K  A  M  S  D  Y  T  H  N  A  E  N  H  I  K  R  P  K -
  f            G  I  K  G  N  L  *  L  Y  S  *  S  *  Q  S  N  Q  T  A *-

M  D
                                   w  d
                                   o  e
                                   I  I
          AGAGATAGTATTTGCTTATTATGCTGAGAGAAACGAGTAGTAAAAGATAAGTAGTGTAAT
     1381 ---------+---------+---------+---------+---------+---------+ 1440
          TCTCTATCATAAACGAATAATACGACTCTCTTTGCTCATCATTTTCTATTCATCACATTA a        R  D  S  I  C  L  L  C  *  E  K  R  V  V  K  D  R  *  C  N  -
  b         E  I  V  F  A  Y  Y  A  E  R  N  E  *  *  K  I  S  S  V  I -
```

FIG.2-SEQUENCE3-PAGE7

```
c         R * Y L L I M L R E T S S K R * V V * * -
    1381 ----------+----------+----------+----------+----------+----------+ 1440
d         L L Y Y K S I I S L S V L L L L Y T T Y  -
e           L S L I Q K N H Q S F R T T F S L Y H L -
f             S I T N A * * A S L F S Y Y F I L L T I -

C           C                           C
                    ABv         j                    S      H j
                    lfi         e                    s      p e
                    uaJ         P                    p      h P
                    III         I                    I      I I
                     /
         AAAAAAAGCTAGGTTTTATTATAAGAGCGAATAAGAATAATATTGGATAAACTAAAATCA
    1441 ----------+----------+----------+----------+----------+----------+ 1500
         TTTTTTTCGATCCAAAATAATATTCTCGCTTATTCTTATTATAACCTATTTGATTTTAGT a         K K S * V L L * E R I R I I L D K L K S  -
b           K K A R F Y Y K S E * E * Y W I N * N H  -
c             K K L G F I I R A N K N N I G * T K I T -
    1441 ----------+----------+----------+----------+----------+----------+ 1500
d         Y F F S P K I I L A F L F L I P Y V L I  -
e           L F L * T K N Y S R I L I I N S L S F D -
f             F F A L N * * L L S Y S Y Y Q I F * F * -

C
                             v
                             i
                             J
                             I
         CCCCTGCCCCATAAGAAAAAAGCCCTATT
    1501 ----------+----------+---------- 1529
         GGGGACGGGGTATTCTTTTTTCGGGATAA a         P L P H K K K A L    -
b           P C P I R K K P Y  -
c             P A P * E K S P I -
    1501 ----------+----------+---------- 1529
d         V G A G Y S F L G I  -
e           G R G W L F F A R N -
f             G Q G M L F F G *  -
```

FIG.2-SEQUENCE3-PAGE8

| | | | | |
|---|---|---|---|---|
| 1 | GGATATATTG | AACCATTAAG | TGCAAATGAT | CTATATCGCT | TCCATCGCAA |
| 51 | TGATAATGAA | ATGACTTTGG | GTGGCTATCT | CATCTATAAC | AGACTTAATA |
| 101 | AAGTTATTCA | AATCCCCTTG | CAACAACTTT | TTTCTATACT | TACACACTAA |
| 151 | AATCAAATGG | GCTTTTAGAT | TATGCTTGCT | TCGGTTGGTT | GAAATATACC |
| 201 | CCCTTAATGG | GTAATGGTTT | TTTCTCATTC | CTCTATCCTT | ATTCATTATT |
| 251 | TATAAAAACA | TTGTATAATA | ATACAAGATA | AAGATAAGGA | GTTATTTTTc |
| 301 | TTAACGCTAT | CAAGTTTAGA | ATTTATCCTA | ACGCTCAACA | AAAAGAGCTT |
| 351 | ATTTCTAAAC | ATTTTGGCTG | TTCTAGGGTC | GTGTATAACT | ACTTTTTAGA |
| 401 | TTACCGACAA | AAGCAATACG | CAAAAGGCTT | AAAGAAACTT | ACTTCACCAT |
| 451 | GCAAAAAGTC | TTAACCCAAA | TCAAGCACCA | AGAAAAATAC | CATTACCTCA |
| 501 | ATGAATGCAA | TTCTCAAAGC | TTGCAAATGG | CGTTAAGACA | GCTTGTGAGT |
| 551 | GCTTATGATA | ATTTCTTTAG | CAAAAGAGCG | AGATACCCTA | AATTCAAATC |
| 601 | TAAAAAAAAa | gcTAAACAAT | CTTTTGCAAT | CCCCAAAAC | ATAGAAATCA |
| 651 | AAACAGAGAC | TCAAACCATC | GCTCTCCCTA | AATTCAAAGA | GGGCATTAAG |
| 701 | GCTAAATTAC | ACAGAGAATT | GCCTAAAGAT | AGCGTTATCA | AACAGGCTTT |
| 751 | TATTTCTTGC | ATAGcCGgTC | AATATTTTTG | TTCTATATCC | TATGAAACCA |
| 801 | AAGAGCCTAT | CCCTAAACCT | ACCATCATTA | AAAAGCGGT | AGGTTTAGAC |
| 851 | ATGGGCTTAA | GaACGCTCAT | TGTTACAAGC | gaTAAAATAG | AATACCCACA |
| 901 | CATCCGTTTT | TATCAAAAAT | TAGAAAAGAA | ACTCACTAAA | GcGgAAAGGA |
| 951 | GGTTAAGTAA | AAAAGTAAAA | GGCTCCAACA | ACAGGAAAAA | ACAAGCTAAA |
| 1001 | AAGGTAGCTA | GATTGCATCT | AGCTTGTTCA | AACACTAGAG | ATGACTACTT |

FIG.3A

```
1051  GCATAAAATC AGTAATGAGA TAACCAATCA ATACGATTTG ATAGGGGTAG
1101  AAACTTTGAA TGTTAAGGGG CTTATGAGAA CCTATCATTC TAAAAGCCTT
1151  GCTAATGCGA GTTGGGGgAA ATTCCTTACT ATGCTAAAAT ACAAAGCCCA
1201  AAGAAAAGCT AAAACCCTAT TAGGCATAGA CAGATTTTTC CCTAGCTCTc
1251  aATTGTGTTC TTATTGTGGG TTCAATACAG GCAAAAAACA TGAAAACATC
1301  ACTAAATTCA CTTGTCCTCA TTGCAATATC ACACACCACA GAGATTACAA
1351  TGCGAGCGTC AATATTAGAA ACTACGCTTT AGGCATGCTA GATGACAGGC
1401  ATAAAATAAA GATAGATAAA AGTAGGGTAG GGATTATCCG AACTGATTAC
1451  GCTCATTACA CTGATGAGCG CATCAAAGCT TGTGGAGCTT CCTCTAATGG
1501  GGTTATTTCT AAATATGGCA ACATATTGGA TCTAGCTAGT TATGGAGCGA
1551  TGAAGCAAGA AAAAGCCCAA TCGCTTTAGC GTTGGTAATT CACAAAAAGC
1601  AAGATCGGTT GTAAAAATGC GTTACAACTA AAATAAAGGG TCAAGATAAC
1651  TCATTTTCAA AAAGGAGTCT TAAGTAATAA AATCATAATG TTCAGCTAGT
1701  AATCTATTGC CTCGTTGATC AAACAAAGCT CTGCGTGAAA GATGAAAAAA
1751  TTTCACCTTT AGATAGTTAA TACACCACTA CAGTCTTACT TGAGAGACAC
1801  TCATTTTATT AGCGGTTTTG TCTGATTTGC TGCTACCAAA ACCATTACCA
1851  ACCAAAGCAG ATCCCATGTT TTTGATACTA TCGAATCCAT TCTTCAGCAC
1901  TTCTGCCATA AAATTCTTGA TATTGTCCAT AGGCAAGTTA AATTTTTTCC
1951  CTAATGCTTC ATTAAGTCCC ATCATTAACA TCAGAAAGAA CAAAAAATTT
2001  AATATCATAG AAAACAAATC ACTGGATAAA CCTGTAAAAA GATTTGTTCC
2051  CCCACCCAAC AAAGAAGCTA AAATTTTTCC CATGATCAGT CCTTTTATTT
2101  TTGGTTGTGT AAGTTCTTGC TTGTTCTTAT CTCTAATGCG TGTTTAGTA
2151  GGAAGCATTT CACAATAGCA TACCTAAAGC TACTAAGAAA ATTCTTGAAT
```

FIG.3B

```
2201  CTATTGGTAA GATTACTCAT GAAATCAAGC GATAAGTAGC CACCAATCGC
2251  AAACAAATCA AATATTTTGC CACCAAACAA GCCATATCCT TTTTGTTTTT
2301  ATCTCCTAAT TATAGCAAAT TTTTATCAAT ATTAATTTGG AAAACCACCA
2351  CCATATCAAA AACAAATTAC TAACACACTA GATGCAGAAT TATTTTTTAA
2401  AAACGCGCAC TTAAATTTAA AATCATGGGG TTTTAGGATT TGAATACCAA
2451  AAATAGATTG GTTTTTTCAA ATAAGCTAGC TTTGTGTATG CGCTTAAAAA
2501  GATTTTGGTT TTTAGTCAGT AAGGTTTTAT GCTAATGTTT GGAAATAAAG
2551  AAATTTCTCT AAATCAAGTC TTGAGAAATT TTTGAACGAA TCATAAGAAC
2601  CAATTTTGCC ATTGAGTCAT AAGTATGATT AGCTTCATTG TGAATTTTGC
2651  GTGGCTTAAG AGATAGTATT TGCTTATTAT GCTGAGAGAA ACGAGTAGTA
2701  AAAGATAAGT AGTGTAATAA AAAAGCTAG GTTTTATTAT AAGAGCGAAT
2751  AAGAATAATA TTGGATAAAC TAAAATCACC CCTGCCCCAT AAGAAAAAAG
2801  CCCTATTAAA AAACCTATAA CGATAGAGCT GATATTGAAC AGCCTATAAT
2851  AAAGGCTGTA CTTATCTAAA TGTTTGTTGA AAGAATATTT GAATTGTAAG
2901  AaGTTTTGTT TTAATTTGCT AATTTGGTTG GTTCCATTTT GGTTTTAAa
2951  GAAATaGTTC AGGGCGGTGA aCTTATAAAG GAGCATAAAA TAATAAATAT
3001  TTTaCAAAAC CACCCTAATC TAACTCCAAA TCTCAAaGAA TACCCCACTT
3051  GCTGATACTA GCATGTGGTA TAGCACAAAC CAACGATTTG TTTGTTTATG
3101  CCAAACAAAG AACAGAAAAC ATCTGTTAAA GAATAAAGGA GTTTTCCATC
3151  TAAAAAACAC AAATCTATTA TATAGAAATA ATCTTAAGAG AAACTTAAAA
3201  AATACCAACA AGCCGCATAC AAGCAAGAAA AACATAACAC TATAAGACCT
3251  GGATTTTATT TACCTTTTGG ATATGGAAAA ATCTTGATTC ATAGTTTTGT
3301  AAAAATTGTG GTAAAATGCA TTGATATTCT TTGAAATTTT AAGGTTACAA
```

FIG.3C

```
3351  AAACTATAAG ATGCTTGCaA AAATTGTTTT TAGCTCATTG GTTgcgTTTG
3401  GAGTTTTGTC GGCTAATGTG GAGCAGTTTG GTTCATTTTT CAACGAGATA
3451  AAAAAAGAAC AAGAAGAAGT GGCTGCAAAA GAAGACGCTC TTAAGGctcg
3501  CAAGAAGCTC TTAAACAATA CGCATGATTT CTTAGAAGAC TTGATTTTTA
3551  GAAAACAAAA AATCAAAGAG CTTATGGATC ATAGAGCTAA AGTTCTTTCA
3601  GACTTAGAAA ACAAATACAA AAAAGAAAAA GAGGCTCTAG AGAAAGAGAC
3651  AAGAGGTAAA ATCCTTACTG CTAAGTCAAA GGCTTATGGG GATCTAGAGC
3701  AAGCCTTAAA AGATAACCCT CTCTATAAGA AACTTCTTCC TAACCCTTAT
3751  GCCTATGTTT TAAACCAAGA AACATTCACC AAAGAAGATA AGGAGCGTTT
3801  GAGTTATTAC TACCCCCAGG TGAAAACGAG CAGtATTTTt gaaaAAActA
3851  CCGCtACCAC TAAAGATAAG GCTCAGGCTT TGCttCAAAT GGGTGTGTTT
3901  TCTTTAGATG AAGAACAAAA CAAAAAAGCG AGCCGATTAG CTTTATCTTA
3951  CAAGCAAGCG ATTGAAGAAT ATTCCAATAA CATTTCTAAT CTGTTGAGCA
4001  GAAAGAATT GGATAATATA GATTATTACT TACAGCTTGA AAGAAACAAG
4051  TTTGACTCCA AAGCAAAAGA TATTGCTCAA AAGGCTACTA ACACGCTTAT
4101  TTTTAACTCG GAACGCTTGG CGTTTAGCAT GGCGATTGAT AAGATTAATG
4151  AGAAATACTT AAAGGGCTAT GAGGCTTTTT CTAACTTGTT GAAAAATGTC
4201  AAAGATGATG TGGAATTGAA TACTCTGACT AAAAACTTTA CCAATCAAAA
4251  ATTGAGTTTC GCACAAAAAC AAAAATTGTG TTTGTTGGTT TTAGACAGCT
4301  TCAATTTTGA TACCCAATCC AAAAAATCTA TATTAAAAAA GACTAATGAA
4351  TACAATATTT TCGTAGATAG CGATCCTATG ATGAGCGACA AAACAACTAT
4401  GCAAAAAGAA CACTACAAGA TATTTAATTT CTTCAAAACA GTGGTTTCTG
4451  CATACCGAAA CAATGTTGCC AAGAATAATC CCTTTGAATA GGAAAGGAGA
```

FIG.3D

| | | | | |
|---|---|---|---|---|
| 4501 | CACTCTTGAA | AAGCATCTTC | AAAAAACTAG | GTTCTGTCGC | TCTTTATTCT |
| 4551 | TTAGTTGTTT | ATGGGGGCTT | AAACGCTATC | AATACAGCAT | TATTGCCGAG |
| 4601 | TGAATACAAA | GAATTAGTGG | CTTTGGGCTT | TAAAAAAATC | AAAACACTCT |
| 4651 | ATCAAAGACA | TGATGACAAA | GAAATTACAA | AAGAGGAAAA | AGAATTCGCC |
| 4701 | ACTAACGCTT | TGAGAGAAAA | ATTACGAAAT | GATAGGGCGA | GAGCAGAGCA |
| 4751 | AATTCAAAAG | AATATTGAAG | CGTTTGAAAA | AAAGAACAAC | TCTTCTGTTC |
| 4801 | AAAAAAAAGC | GGCTAAGCAC | AAAGGATTAC | AAGAATTAAA | CGAAATTAAC |
| 4851 | GCTAACCCTT | TGAATGACAA | CCCTAATGGC | AATTCTTCCA | CTGAAACCAA |
| 4901 | ATCTAATAAA | GATGATAACT | TTGATGAGAT | GATCAATAAG | GTGAATGAAT |
| 4951 | CTTTTGTGAA | ACCTGCTGCT | CCGCTTGTCC | CTGATGAGTG | GAGAACGCCT |
| 5001 | GAAATTGAAA | TCATTATCAA | TGAGTGTATT | ATTTCAAGCA | ACGATTATGA |
| 5051 | TGGGTTAAGA | AAGTGTTTGA | TCAAAGACAT | CAAGGATCAA | AAAATTCTTG |
| 5101 | CCCCCTTATT | AGAAAAAATT | CAAGAAATAG | AGACAGAAAA | TAACAAGTTT |
| 5151 | TCTAGACAAC | ACCTAAGTGG | TTTAAAACTC | ACTCTTAATA | ACAGCAACAA |
| 5201 | TAGAACCTTT | CTTATAGCTT | CGTGCGCTAT | TTGTGAGAAG | AGAAAAAAAG |
| 5251 | AAATGGAGCA | AGAAAATAAC | TACCAGGATA | CTACAAATGC | AAGCGAGTTT |
| 5301 | GGCACTACTG | ATACAAAAGA | AAATGAAGCA | AAAGATACAG | CATTCTCAAA |
| 5351 | CAATCGCTCT | AAATCCGAAC | TGCCCAATAG | CGTCATTAAT | CAAATAGAAC |
| 5401 | AAAGCATCGC | TCATGGAAAA | AAATAGCGAT | CCAAATTATT | AGATCAAAAA |
| 5451 | ACAACTAGAG | AAGCAAATCC | CAAAGGTTAG | AAATCATAGC | CTATCATCTC |
| 5501 | AGAAAAATCA | TTTAACAATG | ATCTTACTTG | ATTGCCTTTC | TTGTAGGTAT |
| 5551 | TGTCGCTTAC | TTTGTTCTAG | GGATCTTTCT | AATGCGTCCA | ACTCCTCTAA |
| 5601 | ATAATTTAAA | AAGACCTTGT | TTTGAGCTAA | CATAAGCTTT | CTGATTCCTT |

FIG.3E

```
5651  TGATGAAATT TTTATTCTTT AGGCTTTCTA CAAGCGTCTG TGAAGCAGTG
5701  ATTAAAGAAG CTGTACCTCC AATGTTGCTC TGATACGCCT TTAGGGAAGT
5751  TTCTAAACGC TCTCTTATAT TTTGTTTTTC TTGCTCGATT TTCAGCTTCC
5801  CTTCACAATA AAGAACTAAA ACTTTATCGG ATATTCCGCA TTGCTGCTCA
5851  GCAGTATTTT GGTCTAAGGG ATTGATTTTC ATATAGGTTA ATAAAAGTTC
5901  AGGGCTAGAC ATATAAGTCT TGAAAATCAC ATCTTCTGAG ATGAAAAATA
5951  ACTCATTCGC TTCAAAATTG GCTTTCAATA ACGCTAAATC TCCTCTCAAA
6001  GCAATGGCCG CTTTTTTGAT GTTTAGAGCA TCTTCTTGAC CTATTTCATT
6051  ATTAGCGCTA GGGCTAGTGG TTGAAAAAAT CTCATCTAAG TTTTTAAGCA
6101  CTTGTTGGTT GGTCTCTTGG TAGGTGCTAT CAAGTTGCTT TAAACCGCTT
6151  GTTATATCTT CTCCCATCAA AACAGACAAT AGCAAAAAAG AAGATATGGT
6201  ATTTTCACG AGTGTTTTCA TTTGACAATA ACTTTAGAGC TAGCAATGTT
6251  TCTTGCTGTC GTTTCTCTTT CTAATTTCAG TTGTTCTTCC CAAAGGTCGG
6301  CTTTTTTTTC AAGATTCTCT ATATAGTTTA AATGATTTTC TGCGTTTAAG
6351  ATCGCAACTT CTATGAGCGC ATTCAAATCT ACTGATCCTT TTAAGGTTTT
6401  GATTTCTCCA TTGATCCCAT TCAAATAAGC GATATTTGA AAATCTGCAT
6451  CACTCAGTTT ATTTTGAATA AGGGCTACAA TCATTCTGTA ATTCTGAATA
6501  ACCTGTTCCA TAAGGCATGC TGAAATTTTT AGCCCATCAA GATAAGGGCA
6551  TTTTGTGGGC GCTAGAGTGA ATGTTTCAAT GATTCCAAAT GGTCGCCCAT
6601  GCTTGAAAAA AAACTAAGAG CAGGCGCATA GATGGCACTT TGAAACAAAG
6651  CCTGACCTGT TAGGGAATTA TAATCAATAA GGGTCGCTTT TTGCATAGCT
6701  GTTTTCAACC ATGTCTCAAA ACCTTTTAAG GTTTCTTCAA ACgCCTTGAT
6751  ACCAATCGTA TTGTAAGCGA TGTATTGAGC GTTGTCAGAA GAACTTCCTA
```

FIG.3F

6801 GAGCTTGAGA AATTTCCATT TGTGTTTTTA GGGTAACCCT CGGTTCAAAG

6851 CTGTTTTTTA ACGCTTCTAA GAGAGCGTTT TGCTGGTTCA TTTTGAGCTT

6901 GATCATTTCG TTATTTTTTT GGAGCGCGAT TTGCATGTTT TGGATTTCTG

6951 TTTGGGTATT AAttttttgt ttttCCACGA TCAttttGAC ATTCCCCCCC

7001 AATGCACTAA GCGCCGCTTG AATACCCTTC CATGACGCCA AGCAAGATGT

7051 CTGAACCTGC aaaaaacccc ccTGTCAtGc cATTGACACC ATTAATAACG

7101 CCATTAGCCC CTTTTAACAT AGCGCTCATG GTTGCAAGCT GAGTCCTCAA

7151 TTCTCCCTCT ATTTGCGCTT GAATGGCTTT TTCTTTGGCA CTAGATTGAG

7201 CTTCTATGGC TTTTAATTCg gcgtGAGcgg ttttttGTTT GGCTTGTGCG

7251 TCTGCCTGAA TGGCTTTTAA GGCAGGTTca agCgTTATTA CTACCTCTGT

7301 ACCATTCAGA GACAAACCAC AAAAAGTCAA GAAAGAAAAT ATGCTTAAAA

7351 AACATTTCAC ATCTCTTTCC TCACTTCACG ATTATTTTAG TTTGCACCCT

7401 TTCTGTTAAG TAGCTATCTT TTTGCCCCTT AAGCTTGTCT TTGATGTAAT

7451 CAAGGTAAGT CAAATGCGAT TTCAAAAAAG ATTTATTCGC TACTATATTG

7501 TAATTATATA GCGAACTTAT GTTAGAAATC GCTTGAGTGT CATAGGTGCT

7551 AGTAGCTAAT CCTGATTGAT TAAGTATCAT TTGAGAAGCG TTCTGCAACA

7601 AATTGGTAtt atttttCACA AATTCTATAT AGTATTCTCT CAAAATTTCT

7651 GCTACTTTTT CAGCATAGCA ATAAACAGCA AGAACCTTGT CCCCAATAGG

7701 GCATGCAGGA GTGGttATAG GATTAACGCC TGAAGTTAGG GCATTAGTgc 7751 gtAACGCTTG GTATTTAGCA TAAACAGTGG GCATAGAAAC GCTCATGGGG 7801 cGTCATAGAA ATTTGCATGC AACTGAAAAA CACTTTTGAT GAGCCAACAA

7851 GCGCACCTAA AGCGGTACAG CTATCAAGGA ATCGGTGTAT CATTCATTGA

7901 GCTGTTGCTT GCTTGAGAAG CCAGTTGCTC TTGTAGAGCT AGGGCGTATT

FIG.3G

```
7951  TTGGTGCTGC ACTTGTAATA TTGCCTAATA TACCGTCATC ATTTCAACCG
8001  TTGTTGGCAC GCTAGGAACA GCGATTTGAT TTGTCGCATA AGCTTCAATA
8051  GCACTGGGAT TTTTAGGGGT GGTGTTACTC GCTAAAATGC TTGCAATCTG
8101  ACTATTAACA GCACCAATTT GCGCGCCTTg gcTGTTGCCT TGAGCGTTAA
8151  ATTCCCTGT  TAATTTGCTA ATATTTAAGA TATTGTTCCC CACAGCCATG
8201  CTTTGATCGT TAAAACCTTG ATACAATTGG TTGTATTGTT GGTTAGCGGC
8251  TTTCATAGGC ATGCTTACGG CTTCAGCGAT GCTTTGATTG TATTGGGTCA
8301  TGATAGCGGT CATTTGCGGA TTAGTAAACC CAACAATAAT AGGAATAATC
8351  GCTGCTGTCA TAGCACCCGC TACTATTCCT GCAAATGGTC CTGCGACACC
8401  ACTTGTGTTG AGATGATTGA GGAAACTTCC GATAAGAAGC CTGCAGAAGA
8451  TGATTcATAT ATAGCTTGTG tACCTgccAT GTTAACACCC CCTAGTTAAT
8501  ACCCTAATAT CGGTGGTAAA AACGATGAAT CTGAGTATGT TGGTGCATAA
8551  CCATACATGA AAGGATTGTT TGGACCGTAA TCGCCCATCA TTTGGCTCAT
8601  GAGAAGATTT TGAATGCCCC ACATCGCATT GATACCTAGA TTATCATTAG
8651  GTTGAAAACT CCCTAAACTT ATGTCGTCAA ATTTGATATT AACATTTTTA
8701  TCATTATAGT CATTGAGTAT GGCCACTTTT TGCTCTAGGG TTTCTTTAGG
8751  GATCTCTATT TTTAGTTGAT CTCTAGAAAC AAGCCCCACG CTATTTAGTG
8801  CCATATCTTC AGGACTAATA TCTTTTATAT CAGTGTTTTG GTCAGCGTTA
8851  AcGGACTGTA AACATGCCAA TGATAAGACA CCAAGCAAAT AGTAATTTAA
8901  TTTTATAAAA ATCcGTTTTC ATACTTTTGA CTCCTTTATT CTTATTTTTA
8951  GCACTATTCT AGCGCATTAA CGCCACTCAA TCGTTATTTT TGTTTTGATT
9001  TTTTTGATCG AGCATTTGT  TTGTTACTTC ATCAATGTTT TGAAAATATT
9051  TTTCAAAAAG CTCTTTCTTT TTAGCTTCAA CGCTCATATC AATCTGAATC
```

FIG.3H

9101 CAATTAGGAA TAATGGAGTC CATGATTAAA TGCATGAAGT CATAGGCATG

9151 ATTTTTTGGG TATATTTTGT TCTGAACATA GTATTCTAAA AAATTCGCTT

9201 GAACAAAAAA AATCTCTATA TCGCTCTGCA TATCCTCGCT TATGTTGTTA

9251 TTGATAGGTT TTTCTAGTAA TCTGAGAATC CTATACGACT GCATGATAGT

9301 TTCTAGCATG AAGTAAGCAT AAACATAAAC TAATGAGACA AAGAATTGT

9351 TTGCTTTAAA CGAGCTTGCG TCATTTTCC CACTTTGAAG AGGAATTAAT

9401 CTTGATAATG TTTTTTGGGG ATCTTGCCCA TCGTTTATTT CTTTAAAAAA

9451 GCGGAAATCT AAATCCTGAT TACTGAGAAA TGACTTGACA AAGTGAAGAT

9501 TAGCATTGAG ACTATCTATG AGACCTGAAT AAAGGTGCTC TGTTTTGACA

9551 TCATCTATAT TTAAAACATT CTCATAAAAC ACATTGACAT GGTCTTCTAA

9601 GAAATTAGAA AAGTCATAAA GAGTGGTAAG GTTTTGTTCA GTGATTTCGC

9651 CTTCCATTTC TTCTTCTATG AAGTCCAATT CTTCTTTCAG TTCAAAAAGA

9701 TAATTAGAAA AACTATCCAA AATCGTCAAG ACATCATTTT CAAAATTTCC

9751 AATAATTTTT GTTCACGCAA ATTTTGTTTC ATTTTAATAC TCCTCTATTT

9801 GTTGATACAT TTGTCTCAAG GCCTGATATT TATCTATGAT ACTATGGTTT

9851 TGGATAATCT TATCAATTTC TTTGACAAAT ACAGTATCTG TGGATAAAAT

9901 TTTCAAATAT TCTTTAGGAA TGCCTCTCAA ATTAAAActa gcgataaCGC

9951 TAGGGCTTCC ATCCTGTTTG TAGAGGATTT TCCTATCTAG TCCCTTAGTG

10001 ATGATTTCAA ATTCTTTTTC TGTAACATTA GCCAATCTTT GGTAATCAGA

10051 AAGATTGCCC CCATCGTTTC TCAAAAAAAT CTTTGTAGGG CATTGTTCTC

10101 TAATCGTATC AGCAATAGGG CAAGCCAAAA GATCAGTGAT GCTTTGAGTC

10151 GCAAGTCTGA CAATAGCGTT TCTTTTCCTT GCAGTTTTTA GCATGTCTCT

10201 TACAAAATAA GCGACCTTTG GATCGCCTAA ATATTTCCAG GCTTCATCAA

FIG.31

```
10251  TATCTAAGAC AAATCTACGC CCATCCATTG CCTCTTGGAT ACGAGCGAAA
10301  AGGTAAAAAC AAATAAAggg CGAAACATCA TTATTGtctA AGAAACTTGA
10351  CCCATCAACG CCAATAATCG TTTTTGAAAA ATCTAAGCGA tctGTTGCTT
10401  TATTATCAAA AAGCCATTGA AATTCACCAT TGGTTGATTT GCAAAAGGC
10451  GCTAATCGCg CGACAAgccc ATTAGGATCA TTGTGGTCTT TCCCGAAAGC
10501  ATTAATAAGT TGAGTGATGG GATAATCTAG ATTCATATTT CCTGTGATAA
10551  GGTTGGTTAC TGCGCTGCAA GCGTATTAGA ATCTGCTAGG CTAAAAGAGA
10601  TGCTGTTGCC ATTTTCATCT TTTTCATCGC TTTTAGTTGC TAAGTTTTTC
10651  ACAAGCTCTT TGACAACAGA AATAGCTGTT TGTTTTTGCT CCATTGTTGC
10701  ATTTGTTTTT TGCACACAAG CCGCCCAAGC AAAAGGATTT AATCCTGTAT
10751  CTGTCCCTAG CTCAATCTTG ACATACTCCC CACCCATTGC GACAATATTC
10801  CCATAAGCGC CATAATCTTT ATCCATATAA ACCATAGTGA GCTTTTGCTT
10851  GTCTTTGCTG ACATTAGCAG GAAAATTATA GGCAAATTGT CCCATAGCGT
10901  TCAAGGTCAT TGACATAAAC ACTGTCTTAC CTGAACCGGT TGAGCCAAGT
10951  ATCAAAGTGT GTCCTGCTGA AGCTGAACCA AAATCAGTGG GCATGTGGAA
11001  GTTCAGATAA AAAGGCGAAT TGATCTCGCT TTTTAgcgTC ATCACACTAT
11051  TGCCCCAAGC GTTATTCTCT TGATTGCCAT CAAAACTCAT AGCCCTCATA
11101  GCGATGAAAT CAGCAAAATT ATTAGAAGTT ACATCAAAAA TAAAAGGAAG
11151  CGTGATAAAA GAGCAATGTT TGGCAAAAAA GTAATTTTCC ATAGAGAAAG
11201  TCGCTGCGTT GGCTAAAAAA CCTTTAGCGT TAAGACTAGA GACGCATTCC
11251  TTAACGCTTT GTTTCATTTT TTCAAAGCTA TCAGCAAACA GCACTAAAGA
11301  ATTACCATAA CTGCCTAGCG TAATATCACC ATTACCCACT AATTCGCTCA
11351  AGCAACCTAA AGTCATGCCC TGTTCTTTAG AGCCTCCACT AATAATAATT
```

FIG.3J

| | |
|---|---|
| 11401 | CTTCTAGAGG TGAAAGCCAG TTTGTCCTTT AAAACCTGTG AGTTTTTAGG |
| 11451 | CGAATAAGCA TGCATGAAAA TAAATTCGCT GTCTAGGGCG TTGATTTTAT |
| 11501 | CAAACAAATC GCTTTGTGAT TTAGGGGCGT ATTCACTAAT CTCAATAGCG |
| 11551 | CTAAATATT TTTCACTCAA ATCGTCATTT AAGATTTTTC CATGCTTATT |
| 11601 | GGCAAAATAA ACTTCTTTCA CCCCACCATG CATTTTTCC TTGAGATACA |
| 11651 | AGTCTTTTCG GTTGCAAATA AAGGGGCTT CATTCATTCC CACAAGAAAA |
| 11701 | TTGTAAAATT CGCATTGTTT GGAGTAAATA ACGCCATCTT TAGTGTATTC |
| 11751 | TTTTAATCTA GTGGGGTGGT ATTTGCTCAA CAGCTCTTCT ATGAGCTCTA |
| 11801 | TCCTATCCTT GAAGTTTTCA AGCTTGGCTC TAATAATCCT TTGAAACTCT |
| 11851 | TCAAAATTAT TGTCTGCAAA ATGCTTTTTA TTCATAACGG GTTCATTGAG |
| 11901 | AGTGTCTAAT AAATCTTGCT CTATGGTCAG AAAAAAACTA ATATCATAAA |
| 11951 | AACTTTCTCT CTTTTGCTTC TCATTATAGG CTCGCATGAA ATCATTAGAA |
| 12001 | AAAATAAGAC CATAGTCCCT ATTGGTTTCA TCAATAACGA TTTTCTTTTT |
| 12051 | AATAGTGTGA AAATAGAATT TGAATTCAGG GGTAACAAAA TTCCTAAAAA |
| 12101 | CGCTATAAAT AGAAGCGTGT AACTCTATGA GATCTTTTTT GGAAGTGGTT |
| 12151 | AAAAAATCAA TGCCCCCCAA TTTGATTGTG CCTAAAAGAG AATAGTTGTT |
| 12201 | AGTAAGGATC ACCCCATCAT CTAAAAAACA TTCATAGTTA TTTGCTAGAT |
| 12251 | AGGAGTTTGC AGCGCTCACA AGTCTGTCTT CTCTGTTTGG ATTTAAGTGG |
| 12301 | ATGTCATTAG CCATTTCTTT ACTAGGCTTC ATGGAAAAAA TGCTCATGAA |
| 12351 | CGCTTTGTTT TTCACGCCCT TAAACAAAAA AGGTTTTTTA AATTTCATCG |
| 12401 | CTCGCTCCAT TCTTTGATAA AGCCTATAAT CTTTCTTGAA TCCAAGAGCT |
| 12451 | ACAAGCACAA TAACAATCGC TACAATCAAA ACAGGTTCAT AGGCTTGAAA |
| 12501 | AAGAATAACA GATAATACAA TGGTTACAAA CAATATAAAT ATAGAGGAAT |

FIG.3K

```
12551  AAATAAAAGT TTCAGGGAAA CCAAACAACC TATTCCCCCC ATCAAACAAG
12601  ACTTTAAAAA AGGGATTGAC ACCCTTTTGC ATGTCTGCTT TAAGTTCTTC
12651  TATTTTTTGA AACTGCCGCT TTTGAACCTC TTGCTCTATA ATTAGCTTTT
12701  TTTGTTCATC AGCCTGCTTG CTTGCCACAA ACACCTCTCT CTTTATAGAT
12751  ATACCGCTTC ACATGTAATC GTATAAAAGA TTTTTTTGAG AGACTCTACG
12801  GTGCTAATAT GTTTCAAAAG ATCATTAGGA TCATAAGAAT TGAATACGGC
12851  CAATAAAACA TTATATAACT TATCATCGCA TAGAATTTCT CTTGTTTCTC
12901  CGCGCAATGA CAGAAAGCAG CGTTGTTTGT TGGTCGTGCT GATGCTTTTG
12951  AAAGTAAAAA AGTCTTTCAC TTCAGGATTG ATCTGTAATT CTACATTCAA
13001  TCCCATTTCC TTACCCTTTT CATCAAAGAT TTTTTCAATA ACTGGATCGT
13051  AATGCTTCAA ATCCTTTATT TTTTTAAGGA CTCTATTGAC AATCACGAAG
13101  TCAAAAACTT CATCTTTGAT AATATCGGGA TTGACTTCTT TGAAAGTTAC
13151  TTTCTTGTCT TTCAAATTTT TGATAGTCGC TTTGAAACTA TCAAAATCTA
13201  AATTTGTATA AACAAGCCCA TTGGGAGTGT TTTTTTCTTT TTCTTGTGCT
13251  TCTTTTTTGG CTTCTTTGTC ATCATTTGCT AACCCATACG AACTGAAAAC
13301  AACGAGACTT AAGAGAACTT TCAAAAAAAA GCCTCTTAGT TTCTTATTGC
13351  TATTATTATT ATTGTTGATC AACTTAGCTA GCTCCTCCAC CCTCGCCAAT
13401  ATTGAAGCCA AACTTAGTGC TCAAATAGAT AATACCGCCT GCCACCGCTA
13451  ACATAGCTAT GGGTTGCGCG TAACGAAAAA CAGTCGCCTG ACCTCTTTTA
13501  ATGTCATCAG AGATTTTCCA AATATCCGCT ATGCCTTTGA CCCCTAAAGC
13551  GCAACCACCT ACGATCGCTA GAACAGAAAT GATCTGAATA ACCAAACCTT
13601  TAGTTGCAGT GACGCCTTCT GTAGGACTGG CGACCGCATT TAAAGGATTG
13651  GTTGTTACCA CTAGCCCTAA AGTTACTACA ACTTTCTTGT AGCTGTCAGT
```

FIG.3L

```
13701  GATTCTTGTA AAAAATTTCA TGCGTTTCCT TTCAAATTGA AATCAATCGC
13751  TTGAGTATAT CAAAAAAAAA AGTATTTTTA TACTATTCAT ACAAGCGCTA
13801  CTTTATAATT TAAATCAAAA CCGACGCTTT TGCTCGGCAA CTGACATCAT
13851  TCAGGAATAG TAAACCTACT TGTCCCAACC ATTTTTCTTT CTCAAGTCGT
13901  TGTAGAATTG TAGATCTTTA GGATCTTTGA TGTATTTTTT AATCGTCTCA
13951  GGTTGAAACC TAAAAACAAG CAAAAACAAA CCCAAGCTGA TCAGAGTGAG
14001  AATAAAGCTC CATTTTAAGC AACTCCATAG ACCACTAAAG AAACTTTTTT
14051  TGAGGCTATC TTTGAAAATC TGTCCTATTG ATTTGTTTTC CATTTTGTTT
14101  CCCATGTGGA TCTTGTGGAT CACAAACGCT TAATTATACA TGCTATAGTA
14151  AGCATGACAC ACAAACCAAA CTATTTTTAG AACGCTTCAT GTGCTCACCT
14201  TGACTAACCA TTTCTCCAAC CATACTTTAG CGTTGCATTT GATTTCTTCA
14251  AAAAGATTCA TTTCTTATTT CTTGTTCTTA TTAAAGTTCT TTCATTTTAG
14301  CAAATTTTTG TTAATTGTGG GTAAAAATGT GAATCGTCCT AGCCTTTAGA
14351  CGCCTGCAAC GATCGGGCTT TTTTCAATAT TAATAATGAT TAATGAAAAA
14401  AAAAAAAAAT GCTTGATATT GTTGTATAAT GAGAATGTTC AAAGACATGA
14451  ATTGACTACT CAAGCGTGTA GCGATTTTTA GCAGTCTTTG ACACTAACAA
14501  GATACCGATA GGTATGAAAC TAGGTATAGT AAGGAGAAAC AATGACTAAC
14551  GAAACCATTG ACCAACAACC ACAAACCGAA GCGGCTTTTA ACCCGCAGCA
14601  ATTTATCAAT AATCTTCAAG TAGCTTTTCT TAAAGTTGAT AACGCTGTCG
14651  CTTCATACGA TCCTGATCAA AAACCAATCG TTGATAAGAA CGATAGGGAT
14701  AACAGGCAAG CTTTTGAAGG AATCTCGCAA TTAAGGGAAG AATACTCCAA
14751  TAAAGCGATC AAAAATCCTA CCAAAAAGAA TCAGTATTTT TCAGACTTTA
14801  TCAATAAGAG CAATGATTTA ATCAACAAAG ACAATCTCAT TGATGTAGAA
```

FIG.3M

| | |
|---|---|
| 14851 | TCTTCCACAA AGAGCTTTCA GAAATTTGGG GATCAGCGTT ACCGAATTTT |
| 14901 | CACAAGTTGG GTGTCCCATC AAAACGATCC GTCTAAAATC AACACCCGAT |
| 14951 | CGATCCGAAA TTTTATGGAA AATATCATAC AACCCCCTAT CCTTGATGAT |
| 15001 | AAAGAGAAAG CGGAGTTTTT GAAATCTGCC AAACAATCTT TTGCAGGAAT |
| 15051 | CATTATAGGG AATCAAATCC GAACGGATCA AAAGTTCATG GGCGTGTTTG |
| 15101 | ATGAGTCCTT GAAAGAAAGG CAAGAAGCAG AAAAAAATGG AGAGCCTACT |
| 15151 | GGTGGGGATT GGTTGGATAT TTTTCTCTCA TTTATATTTG ACAAAAAACA |
| 15201 | ATCTTCTGAT GTCAAAGAAG CAATCAATCA AGAACCAGTT CCCCATGTCC |
| 15251 | AACCAGATAT AGCCACTACC ACCACCGACA TACAAGGCTT ACCGCCTGAA |
| 15301 | GCTAGAGATT TACTTGATGA AAGGGGTAAT TTTTCTAAAT TCACTCTTGG |
| 15351 | CGATATGGAA ATGTTAGATG TTGAGGGAGT CGCTGACATT GATCCCAATT |
| 15401 | ACAAGTTCAA TCAATTATTG ATTCACAATA ACGCTCTGTC TTCTGTGTTA |
| 15451 | ATGGGGAGTC ATAATGGCAT AGAACCTGAA AAAGTTTCAT TGTTGTATGG |
| 15501 | GGGCAATGGT GGTCCTGGAG CTAGGCATGA TTGGAACGCC ACCGTTGGTT |
| 15551 | ATAAAGACCA ACAAGGCAAC AATGTGGCTA CAATAATTAA TGTGCATATG |
| 15601 | AAAAACGGCA GTGGCTTAGT CATAGCAGGT GGTGAGAAAG GGATTAACAA |
| 15651 | CCCTAGTTTT TATCTCTACA AAGAAGACCA ACTCACAGGC TCACAACGAG |
| 15701 | CATTAAGTCA AGAAGAGATC CAAAACAAAA TAGATTTCAT GGAATTTCTT |
| 15751 | GCACAAAATA ATGCTAAATT AGACAACTTG AGCGAGAAAG AGAAGGAAAA |
| 15801 | ATTCCGAACT GAGATTAAAG ATTTCCAAAA AGACTCTAAG GCTTATTTAG |
| 15851 | ACGCCCTAGG GAATGATCGT ATTGCTTTTG TTTCTAAAAA AGACACAAAA |
| 15901 | CATTCAGCTT TAATTACTGA GTTTGGTAAT GGGGATTTGA GCTACACTCT |
| 15951 | CAAAGATTAT GGGAAAAAAG CAGATAAAGC TTTAGATAGG GAGAAAAATG |

FIG.3N

```
16001  TTACTCTTCA  AGGTAGCCTA  AAACATGATG  GCGTGATGTT  TGTTGATTAT
16051  TCTAATTTCA  AATACACCAA  CGCCTCCAAG  AATCCCAATA  AGGGTGTAGG
16101  CGTTACGAAT  GGCGTTTCCC  ATTTAGAAGT  AGGCTTTAAC  AAGGTAGCTA
16151  TCTTTAATTT  GCCTGATTTA  AATAATCTCG  CTATCACTAG  TTTCGTAAGG
16201  CGGAATTTAG  AGGATAAACT  AACCACTAAA  GGATTGTCCC  CACAAGAAGC
16251  TAATAAGCTT  ATCAAAGATT  TTTTGAGCAG  CAACAAAGAA  TTGGTTGGAA
16301  AAACTTTAAA  CTTCAATAAA  GCTGTAGCTG  ACGCTAAAAA  CACAGGCAAT
16351  TATGATGAAG  TGAAAAAAGC  TCAGAAAGAT  CTTGAAAAAT  CTCTAAGGAA
16401  ACGAGAGCAT  TTAGAGAAAG  AAGTAGAGAA  AAAATTGGAG  AGCAAAAGCG
16451  GCAACAAAAA  TAAAATGGAA  GCAAAAGCTC  AAGCTAACAG  CCAAAAAGAT
16501  GAGATTTTTG  CGTTGATCAA  TAAAGAGGCT  AATAGAGACG  CAAGAGCAAT
16551  CGCTTACGCT  CAGAATCTTA  AAGGCATCAA  AAGGGAATTG  TCTGATAAAC
16601  TTGAAAATGT  CAACAAGAAT  TTGAAAGACT  TTGATAAATC  TTTTGATGAA
16651  TTCAAAAATG  GCAAAAATAA  GGATTTCAGC  AAGGCAGAAG  AAACACTAAA
16701  AGCCCTTAAA  GGTTCGGTGA  AGATTTAGG   TATCAATCCA  GAATGGATTT
16751  CAAAAGTTGA  AAACCTTAAT  GCAGCTTTGA  ATGAATTCAA  AAATGGCAAA
16801  AATAAGGATT  TCAGCAAGGT  AACGCAAGCA  AAAAGCGACC  TTGAAAATTC
16851  CGTTAAAGAT  GTGATCATCA  ATCAAAAGGT  AACGGATAAA  GTTGATAATC
16901  TCAATCAAGC  GGTATCAGTG  CTAAAGCAA   CGGGTGATTT  CAGTAGGGTA
16951  GAGCAAGCGT  TAGCCGATCT  CAAAAATTTC  TCAAAGGAGC  AATTGGCCCA
17001  ACAAGCTCAA  AAAATGAAA   GTCTCAATGC  TAGAAAAAAA  TCTGAAATAT
17051  ATCAATCCGT  TAAGAATGGT  GTGAATGGAA  CCCTAGTCGG  TAATGGGTTA
17101  TCTCAAGCAG  AAGCCACAAC  TCTTTCTAAA  AACTTTTCGG  ACATCAAGAA
```

FIG.30

```
17151  AGAGTTGAAT GCAAAACTTG GAAATTTCAA TAACAATAAC AATAATGGAC
17201  TCAAAAACGA ACCCATTTAT GCTAAAGTTA ATAAAAAGAA AGCAGGGCAA
17251  GCAGCTAGCC TTGAAGAACC CATTTACGCT CAAGTTGCTA AAAAGGTAAA
17301  TGCAAAAATT GACCGACTCA ATCAAATAGC AAGTGGTTTG GGTGTTGTAG
17351  GGCAAGCAGC GGGCTTCCCT TTGAAAAGGC ATGATAAAGT TGATGATCTC
17401  AGTAAGGTAG GGCTTTCAAG GAATCAAGAA TTGGCTCAGA AAATTGACAA
17451  TCTCAATCAA GCGGTATCAG AAGCTAAAGC AGGTTTTTTT GGCAATCTAG
17501  AGCAAACGAT AGACAAGCTC AAAGATTCTA CAAAACACAA TCCCATGAAT
17551  CTATGGGTTG AAAGTGCAAA AAAAGTACCT GCTAGTTTGT CAGCGAAACT
17601  AGACAATTAC GCTACTAACA GCCACATACG CATTAATAGC AATATCAAAA
17651  ATGGAGCAAT CAATGAAAAA GCGACCGGCA TGCTAACGCA AAAAAACCCT
17701  GAGTGGCTCA AGCTCGTGAA TGATAAGATA GTTGCGCATA ATGTAGGAAG
17751  CGTTCCTTTG TCAGAGTATG ATAAAATTGG CTTCAACCAG AAGAATATGA
17801  AAGATTATTC TGATTCGTTC AAGTTTTCCA CCAAGTTGAA CAATGCTGTA
17851  AAAGACACTA ATTCTGGCTT TACGCAATTT TTAACCAATG CATTTTCTAC
17901  AGCATCTTAT TACTGCTTGG CGAGAGAAAA TGCGGAGCAT GGAATCAAGA
17951  ACGTTAATAC AAAAGGTGGT TTCCAAAAAT CTTAAAGGAT TAAGGAATAC
18001  CAAAAACGCA AAACCACCC CTTGCTAAAA GCGAGGGGTT TTTTAATACT
18051  CCTTAGCAGA AATCCCAATC GTCTTTAGTA TTTGGGATGA ATGCTACCAA
18101  TTCATGGTAT CATATCCCCA TACATTCGTA TCTAGCGTAG GAAGTGTGCA
18151  AAGTTACGCC TTTGGAGATA TGATGTGTGA GACCTGTAGG GAATGCGTTG
18201  GAGCTCAAAC TCTGTAAAAT CCCTATTATA GGGACACAGA GTGAGAACCA
18251  AACTCTCCCT ACGGGCAACA TCAGCCTAGG AAGCCCAATC GTCTTTAGCG
```

FIG.3P

```
18301  GTTGGGCACT TCACCTTAAA ATATCCCGAC AGACACTAAC GAAAGGCTTT
18351  GTTCTTTAAA GTCTGCATGG ATATTTCCTA CCCCAAAAAG ACTTAACCCT
18401  TTGCTTAAAA TTAAGTTTGA TTGTGCTAGT GGGTTCGTGC TATAGTGCGA
18451  AAATTAATTA AGGGTTATAA AGAGAGCATA AACTAGAAAA AACAAGTAGC
18501  TATAACAAAG ATCAAGTTCA AAAATCATA GAGCTTTTAG AGCAAATTGA
18551  TCGCGCTCTT AACCAAGAA AAATCAGAAA AACCATAGGA ATTATCACAC
18601  CTTATAATGC CAAAAAAGA CGCTTGCGAT CAGAAGTGGA AAAATACGGC
18651  TTCAAGAATT TTGATGAGCT CAAAATAGAC ACTGTGGATG CCTTTCAAGG
18701  TGAAGAGGCA GATATTATTA TTTATTCCAC CGTGAAAACT TGTGGTAATC
18751  TTTCTTTCTT GCTAGATTCT AAACGCTTGA ATGTGGCTAT TTCTAGGGCA
18801  AAAGAAAATC TCATTTTTGT GGGTAAAAAG TCTTTCTTTG AGAATTTATG
18851  AAGCGATGAG AAGAATATCT TTAGCGCTAT TTTGCAAGTC TGTAGATAGG
18901  TAATCTTTTC CAAAGATAAT CATTAGACAT TCTTCGCTTC AAAACGCTTT
18951  CATAAATCTC TCTAAAGCGC TTTATAATCA ACACAATACC CTTATAGTGT
19001  GAGCTATAGC CCCTTTTGG GAATTGAGTT ATTTTGACTT TAAATTTTTA
19051  TTAGCGTTAC AATTTGAGCC ATTCTTTAGC TTGTTTTTCT AGCCAGATCA
19101  CATCGCCGCT CGCATGAAAT TCCACTTTAG GGAATGCGTG TGCATTTTTT
19151  TTAAGGGCGT ATTTTTGCTG CAAATATCCT ACAATAGCAT CGCCCGAATG
19201  GATGAGTAGG GGGGGTGTTG AAAGGGCAAA ATGCTCCATA AAATAGCCCT
19251  CAATTTTTTG AGCGATTAAG GGAAAATGCG TGCAACCTAA AATAATCACT
19301  TCGGGAAAAT CTTTAAGGGA GTGAAATAAT AACGCATGCA AGTTTCTAAC
19351  AATTCGCCCT CTAAAATACT TTCTTCAATC AAAGGCACAA AAAGAGAAGT
19401  GGCTAAATGC GAAACATTCA AATAGCCTTG TTGTTTCAGG GCATTGTCAT
```

FIG.3Q

| | | | | |
|---|---|---|---|---|
| 19451 | AAGCGTTGGA | TTGGATCGTC | GCTTTTGTCC | CTAGCACTAA | AATAGGGGCG |
| 19501 | TTTTTATCTT | TTACTTGTCG | CTTGATCGCT | AAAATGCTTG | GCTCAATCAC |
| 19551 | GCCCACAATA | GGGATTTTGG | AATGCTTTTG | CATCTCTTCT | AAAGCTAGAG |
| 19601 | CGCTCGCTGT | GTTGCATGCC | ACAATCAATA | ATTCAATCTG | GTGCGGTTTG |
| 19651 | AAAAAATCCA | AAGCCTCTAA | GCCAAATTGC | TTGATCGTAG | TGGGGTCTTT |
| 19701 | AGTGCCATAA | GGCACTCTAG | CCGTATCGCC | ATAATAGATG | ATTTCATCAA |
| 19751 | ATAATTGCGC | TTTTAAAAGG | CTTTTTAAAA | CGCTAAACCC | TCCCACACCG |
| 19801 | CTATCAAAAA | CGCCTATTTT | CATGACACTT | TTTTAATTTA | ATGGGATTAA |
| 19851 | TTAGGGATTT | TATTTTTCAT | TCATTAAGTT | TAAAAATTCT | TCATTGTCCT |
| 19901 | TAGTTTGTTG | CATTTTAGAA | TAGACAAAGC | TT | |

FIG.3R

*CagI* Search History code name: JF coordinates and amino acid sequence:1-927
```
  1   LLFRLPTKAI RKRLKETYFT MQKVLTQIKH QEKYHYLNEC NSQSLQMALR
 51   QLVSAYDNFF SKRARYPKFK SKKKAKQSFA IPQNIEIKTE TQTIALPKFK
101   EGIKAKLHRE LPKDSVIKQA FISCIAGQYF CSISYETKEP IPKPTIIKKA
151   VGLDMGLRTL IVTSDKIEYP HIRFYQKLEK KLTKAERRLS KKVKGSNNRK
201   KQAKKVARLH LACSNTRDDY LHKISNEITN QYDLIGVETL NVKGLMRTYH
251   SKSLANASWG KFLTMLKYKA QRKAKTLLGI DRFFPSSQLC SYCGFNTGKK
301   HENITKFTCP HCNITHHRDY NASVNIRNYA LGMLDDRHKI KIDKSRVGII
351   RTDYAHYTDE RIKACGASSN GVISKYGNIL DLASYGAMKQ EKAQSL
```
number of residues:396
GenMark (matrices for *Helicobacter pylori*)
Motifs:not significant findings (nsf)
Pepplot:na
Profilesegment(IRIS database):nsf
Blastp (pdb, swissprot, SPupdate, pir, genpept,GPupdate):nsf
Blitz ( swissprot ):
117/117   (5.23e-06/top score)
Virulence protein   VSDF_SALDU; 119AA.
82/117   (4.64e+00/5.23e-06)
Toxin corregulated pilus biosynthesis protein F precursor (TCP pilus biosynthesis protein TCPF)_VIBCH; 338 AA.
Shuffle:na
Bestfit:na code name: KF coordinates and amino acid sequence:1145-1516
```
  1   ETLILLAVLS DLLLPKPLPT KADPMFLILS NPFFSTSAIK FLILSIGKLN
 51   FFPNASLSPI INIRKNKKFN IIENKSLDKP VKRFVPPPNK EAKIFPMISP
101   FIFGCVSSCL FLSLMRVLVG SISQ
```
number of residues:124
GenMark (matrices for *Helicobacter pylori*)
Motifs:nsf
Pepplot:na
Profilesegment(IRIS database):nsf
Blastp (pdb, swissprot, SPupdate, pir, genpept,GPupdate):nsf
Blitz ( swissprot ):
85/85  (4.54e-01/top score)

FIG.4A

Polysialic acid transport protein KPSM_ECOLI; 258 AA.)
Shuffle:na
Bestfit:na code name: LF1 coordinates and amino acid sequence:2694-3839

```
  1 GYKNYKMLAK IVFSSLVAFG VLSANVEQFG SFFNEIKKEQ EEVAAKEDAL
 51 KARKKLLNNT HDFLEDLIFR KQKIKELMDH RAKVLSDLEN KYKKEKEALE
101 KETRGKILTA KSKAYGDLEQ ALKDNPLYKK LLPNPYAYVL NQETFTKEDK
151 ERLSYYYPQV KTSSIFEKTT ATTKDKAQAL LQMGVFSLDE EQNKKASRLA
201 LSYKQAIEEY SNNISNLLSR KELDNIDYYL QLERNKFDSK AKDIAQKATN
251 TLIFNSERLA FSMAIDKINE KYLKGYEAFS NLLKNVKDDV ELNTLTKNFT
301 NQKLSFAQKQ KLCLLVLDSF NFDTQSKKSI LKKTNEYNIF VDSDPMMSDK
351 TTMQKEHYKI FNFFKTVVSA YRNNVAKNNP FE
``` number of residues:382
GenMark (matrices for *Helicobacter pylori*)
Motifs:nsf
Pepplot:no
Profilesegment(IRIS database):nsf
Blastp ( pdb, swissprot, SPupdate, pir, genpept,GPupdate):
71/71 (Identities=29%, positives 45%)
Merozoite surface antigen 1 gene_PFMEZSA1A; 651AA.
Merozoite surface protein 1, 42 kDa C-terminal region; 372 AA.
47/71 (Identities=20%, positives 58%)
Hook-associated protein type 3_VPU; 397AA.
Blitz ( swissprot ):
122/122 (1.43e-04/top score)
Glycogen phosphorilase, liver form_Human; 847 AA.
95/122 (8.57e-01/1.43e-04)
TRK system potassium uptake protein TRKA_ECOLI; 458AA.
91/122 (2.72e+00/1.43e-04)
Merozoite surface antigen precursor; 1631 AA.
Shuffle:na
Bestfit: na code name LF2 coordinates and amino acid sequence:3839-4774

```
  1 IGKETLLKSI FKKLGSVALY SLVVYGGLNA INTALLPSEY KELVALGFKK
 51 IKTLYQRHDD KEITKEEKEF ATNALREKLR NDRARAEQIQ KNIEAFEKKN
101 NSSVQKKAAK EKGLQELNEI NANPLNDNPN GNSSTETKSN KDDNFDEMIN
```

FIG.4B

```
151  KVNESFVKPA APLVPDEWRT PEIEIIINEC IISSNDYDGL RKCLIKDIKD
201  QKILAPLLEK IQEIETENNK FSRQHLSGLK LTLNNSNNRT FLIASCAICE
251  KRKKEMEQEN NYQDTTNASE FGTTDTKENE AKDTAFSNNR SKSELPNSVI
301  NQIEQSIAHG KK
``` number of residues:312
GenMark (matrices for *Helicobacter pylori* )
Motifs:nsf
Pepplot:na
Profilesegment(IRIS database):nsf
Blastp ( pdb, swissprot, SPupdate, pir, genpept,GPupdate):nsf
Blitz ( swissprot ):
104/115 (2.09e-02/4.93e-04)
Protein phosphatase PP2A-1 catalytic subunit_Yeast; 369AA.
89/115 (2.32e+00/4.93e-04)
Replicating protein A. tumefaciens_AGRTU; 250 AA.
88/115 (3.11e+00/4.93e-04)
Major outer membrane protein P.IB precursor (protein IB) (PIB) (porin)_NEILA; 337AA.
Shuffle:na
Bestfit:na code name: IR coordinates and amino acid sequence:1524-1132
```
  1  VCYCEMLPTK TRIRDKNKQE LTQPKIKGLI MGKILASLLG GGTNLFTGLS
 51  SDLFSMILNF LFFLMLMMGL NEALGKKFNL PMDNIKNFMA EVLKNGFDSI
101  KNMGSALVGN GFGSSKSDKT ANKMSVSQVR L
```
number of residues:131
GenMark (matrices for *Helicobacter pylori* )
Motifs:nsf
Pepplot:na
Profilesegment(IRIS database):
Hypotetical protein C2 Vc02_SFVKA; 92 AA.
Protein transport protein SEC22 (protein SLY)_Yeast; 214 AA.
Hypotetical 18.3 kDa protein in HLYB 3' region_VIBCH; 171 AA.
Blastp ( pdb, swissprot, SPupdate, pir, genpept,GPupdate):nsf
Blitz ( swissprot ):
109/109 (3.21e-04/top score)
Sodium/neutral amino acid cotransporter (system A transporter)_PIG; 660 AA.
Shuffle:na
Bestfit:na

FIG.4C code name: HR2 coordinates and amino acid sequence: 2352-1945
```
  1   NIYYFMLLYK FTALNYFFKN QNGTNQISKL KQNFLQFKYS FNKHLDKYSL
 51   YYRLFNISSI VIGFLIGLFS YGAGVILVYP ILFLFALIIK PSFFYYTTYL
101   LLLVSLSIIS KYYLLSHAKF TMKLIILMTQ WQNWFL
```
number of residues: 136
GenMark (matrices for *Helicobacter pylori*)
Motifs: na
Pepplot: na
Profilesegment(IRIS database):
Fimbrial assembly protein (serogroups C1 and C2) Fmbc_BACNO; 131 AA.
Fimbrial assembly protein (serogroup I) Fmbi_BACNO; 257 AA.
Fimbrial assembly protein (serogroup E1) FmbX_BACNO; 257 AA.
Virulence protein PGP4-D (ORF4)(Protein P-8) GP4D_CHLTR; 102AA.
Preprotein translocase SECY subunit_BACST; 99AA.
Blastp ( pdb, swissprot, SPupdate, pir, genpept,GPupdate):nsf
Blitz ( swissprot ):
103/103 (4.91e-02/top score)
Stage 2 sporulation protein E_BACSU; 827 AA.
88/103 (3.01e+00/4.91e-02)
Type 4 prepilin-like protein specific leader peptidase_BACSU; 248 AA.
85/103 (6.51e+00/4.91e-02)
Protein I5 VI05_VARV; 79AA.
Cyclolysin secretion ATP-binding protein CYAB_BORPE; 712AA.
Shuffle: na
Bestfit: na code name: HR1 coordinates and amino acid sequence: 2610-2374
```
 1   IKSRSYSVMF FLLVCGLLVF FKFLLRLFLY NRFVFFRWKT PLFFNRCFLF
51   FVWHKQTNRW FVLYHMLVSA SGVFFEIWS
```
number of residues: 79
GenMark (matrices for *Helicobacter pylori*)
Motifs: nsf
Pepplot: na

FIG.4D

Profilesegment(IRIS database):
General secretory pathway protein g precursor_ERWCH; 153AA.
General secretory pathway protein g precursor (pullulanase secretion)_KLEPN; 140 AA.
Blastp ( pdb, swissprot, SPupdate, pir, genpept,GPupdate):nsf
Blitz ( swissprot ):
100/100 (9.41e-03/top score)
NADH- Ubiquinone oxidoreductase chain 5 (also chain 1,2)_ASCSU; 547AA.
Shuffle:na
Bestfit:na code name: GR2 coordinates and amino acid sequence:5584-4862

```
1    SYCQMKTLVK NTISSFLLLS VLMGEDITSG LKQLDSTYQE TNQQVLKNLD
51   EIFSTTSPSA NNEIGQEDAL NIKKAAIALR GDLALLKANF EANELFFISE
101  DVIFKTYMSS PELLLTYMKI NPLDQNTAEQ QCGISDKVLV LYCEGKLKIE
151  QEKQNIRERL ETSLKAYQSN IGGTASLITA SQTLVESLKN KNFIKGIRKL
201  MLAQNKVFLN YLEELDALER SLEQSKRQYL QERQSSKIIV K
``` number of residues:241
GenMark (matrices for *Helicobacter pylori* )
Motifs:nsf
Pepplot:none
Profilesegment(IRIS database):
Exotoxin A regulatory protein_PSEAE; 259 AA.
27.5 kDa virulence protein VRP3_SALCHE; 240 AA.
Virulence protein MKFA  VRP4_SALTY; 236 AA.
Virulence factor vsdD _SALDU;
Blastp ( pdb, swissprot, SPupdate, pir, genpept,GPupdate):nsf
Blitz ( swissprot ):
90/95 (1.12e+00/2.33e-1)
D-Xylose transporter ATP-binding protein XYLG_ECOLI; 513 AA.
85/95 (5.00e+00/2.33e-1)
Olygopeptide transport system permease protein OPPC_SALTY; 302 AA.
83/95 (8.90e+00/2.33e-1)
Sporulation kinase A (stage II sporulation protein J)_BACSU; 606 AA.
Shuffle:na

FIG.4E

Bestfit:na code name: GR1 coordinates and amino acid sequence:5964-5572
```
  1   FFFKBGRPFG IIETFTLAPT KCPYLDGLKI SACLMEQVIQ NYRMIVALIQ
 51   NKLSDADFQN IAYLNGINGE IKTLKGSVDL NALIEVAILN AENBLNYIEN
101   LEKKADLWEE QLKLERETTA RNIASSKVIV K
```
number of residues:131
GenMark (matrices for *Helicobacter pylori*)
Motifs:nsf
Pepplot:na
Profilesegment(IRIS database):
SinR protein_BACLI_BACSU; 111AA.
Blastp ( pdb, swissprot, SPupdate, pir, genpept,GPupdate):nsf
Blitz ( swissprot ):
95/96 (4.96e-02/3.53e-02)
Chemotaxis CHEV protein_BACSU; 303 AA.
83/96 (2.38e+00/3.53e-02)
Outer membrane protein YOPM_YERPE; 367 AA.
82/96 (3.22e+00/3.53e-02)
Phosphoglicerate transport system sensor protein PGTB_SALTY; 593AA.
Shuffle:na
Bestfit:na code name: FR3 coordinates and amino acid sequence:6425-5916
```
  1   QGGFLQVQTS CLASWKGIQA ALSALGGNVK MIVEKQKINT QTEIQNMQIA
 51   LQKNNEMIKL KMNQQNALLE ALKNSFEPRV TLKTQMEISQ ALGSSSDNAQ
101   YIAYNTIGIK AFEETLKGFE TWLKTAMQKA TLIDYNSLTG QALFQSAIYA
151   PALSFFSSMG DBLESLKHSL
```
number of residues:170
GenMark (matrices for *Helicobacter pylori*)
Motifs:nsf
Pepplot:na
Profilesegment(IRIS database):
Sporulation protein SPO16_Yeast; 198 AA.
Probable transporter protein MBPX_MARPO; 370 AA.
Hypotetical 16.0 kDa protein in ENVA-SECA intergienic region

FIG.4F (ORFX); 147 AA.
Blastp ( pdb, swissprot, SPupdate, pir, genpept,GPupdate):na
Blitz ( swissprot ):
91/93 (9.91e-01/5.54e-01)
Probable ATP-dependent DNA-Helicase RECG_ECOLI; 693AA.
Shuffle:na
Bestfit:na code name: FR2 coordinates and amino acid sequence:6726-6361
1    SEERDVKCFL SIFSFLTFCG LSLNGTEVVI TLEPALKAIQ ADAQAKQKTA
51   HAELKAIEAQ SSAKEKAIQA QIEGELRTQL ATMSAMLKGA NGVINGVNGM
101  TGGFFAGSDI LLGVMEGYSS GA
number of residues:122
GenMark (matrices for *Helicobacter pylori* )
Motifs:nsf
Pepplot:na
Profilesegment(IRIS database):nsf
Blastp ( pdb, swissprot, SPupdate, pir, genpept,GPupdate):
62/62 (identities=30%; positives=46%)
Flagellin A_PSEPU; 688 AA.
61/62 (identities=33%; positives=49%)
Flagellin B_PSEPU; 479 AA.
Blitz ( swissprot ):
89/90 (4.13e-01/3.02e-01)
Methyl-accepting chemotaxis protein II (MCP-II)(Aspartate chemoreceptor protein)_ECOLI; 553AA.
83/90 (2.55e+00/3.02e-02)
Methyl-accepting chemotaxis protein II (MCP-II)(Aspartate chemoreceptor protein)_SALTY; 552AA.
82/90 (3.22e+00/3.02e-02)
Hemolysin secretion protein precursor HLYB_VIBCH; 548 AA.
82/90 (3.42e+00/3.02e-02)
Methyl-accepting chemotaxis citrate transducer (Citrate chemoreceptor protein)_SALTY; 547AA.
81/90 (4.57e+00/3.02e-02)
Chemotaxis protein CHEA_SALTY; 671 AA.
81/90 (4.57e+00/3.02e-02)
Flagellar hook-associated protein 2 (HAP2) (Filament cap protein)_VIBPA; 445 AA.

FIG.4G

Shuffle:na
Bestfit:na code name: FR1 coordinates and amino acid sequence:7153-6725
```
  1    RPMSVSMPTV YAKYQALRTN ALTSGVNPIT TPACPIGDKV LAVYCYAEKV
 51    AEILREYYIE FVKNNTNLLQ NASQMILNQS GLATSTYDTQ AISNISSLYN
101    YNIVANKSFL KSHLTYLDYI KDKLKGQKDS YLTERVQTKI IVK
```
number of residues:143
GenMark (matrices for *Helicobacter pylori*)
Motifs:nsf
Pepplot:na
Profilesegment(IRIS database):
Maltodextrin transport system permease protein MALD_STRPN; 277 AA.
Oligopeptide transport system permease protein OPPB_LACLA; 319 AA.
Hemolysin C, chromosomal_ECOLI; 174 AA.
Blastp ( pdb, swissprot, SPupdate, pir, genpept,GPupdate):
64/64 (Identities=28%; positives 38%)
YBR291C yeast putative mitochondrial carrier; 299AA.
64/64 (Identities=28%; positives 39%)
Mitochondrial citrate transport protein_Yeast; 299 AA.
48/64 (Identities=27%; positives 46%)
Surface array protein SAP_CAMFE; 960AA.
Blitz ( swissprot ):
116/116 (7.29e-06/Top score)
PAC protein precursor_STRMU;1565 AA.
82/116 (1.94e+00/7.29e-06)
Outer membrane protein F precursor OMPF_ECOLI; 362 AA.
Shuffle:na
Bestfit:na code name: ER2 coordinates and amino acid sequence:7805-7329
```
  1    IIFCRLLIGS FLNHLNTSGV AGPFAGIVAG AMTAAIIPII VGFTNPQMTA
 51    IMTQYNQSIA EAVSMPMKAA NQQYNQLYQG FNDQSMAVGN NILNISKLTG
101    EFNAQGNSQG AQIGAVNSQI ASILASNTTP KNPSAIEAYA TNQIAVPSVP
151    TTVEMMTVY
```

FIG.4H number of residues: 159
GenMark (matrices for *Helicobacter pylori*)
Motifs:nsf
Pepplot:na
Profilesegment(IRIS database):
General secretion pathway protein I precursor_PSEAE 129AA.
Blastp ( pdb, swissprot, SPupdate, pir, genpept,GPupdate):
42/62 (identities=29%; positives=54%)
PILC pilin biogenesis protein_PSEAE; 406 AA.
Blitz ( swissprot ):nsf
Shuffle:na
Bestfit:na code name: ER1 coordinates and amino acid sequence:8269-7850
1    KRIFIKLNYY LLGVLSLACL QSVNADQNTD IKDISPEDMA LNSVGLVSRD
51   QLKIEIPKET LEQKVAILND YNDKNVNIKF DDISLGSFQP NDNLGINAMW
101  GIQNLLMSQM MGDYGPNNPF MYGYAPTYSD SSFLPPILGY
number of residues: 140
GenMark (matrices for *Helicobacter pylori*)
Motifs:na
Pepplot:na
Profilesegment(IRIS database):
Minor fimbrial protein PAPF_ECOLI;167 AA.
Fimbrial protein Q precursor (beta pilin)(Q pilin)_MORBO; 157 AA.
Wound responsive GWIN3 protein precursor_POPSP; 200AA.
Blastp ( pdb, swissprot, SPupdate, pir, genpept,GPupdate):nsf
Blitz ( swissprot ):
86/96 (1.45e+00/6.02e-02)
Toxin corregulated pilus biosynthesis protein D (TCP pilus biosynthesis protein TCPD)_VIBCH; 273 AA.
82/96 (2.38e+00/6.02e-02)
Flagellar motor switch protein FLIM_CAUCR; 373 AA.
Shuffle:na
Bestfit:na code name: DR coordinates and amino acid sequence:9113-8331
1    TKIIGNFEND VLTILDSFSN YLFELKEELD FIEEEMEGEI TEQNLTTLYD

FIG.41

```
 51   FSNFLEDHVN VFYENVLNID DVKTEHLYSG LIDSLNANLH FVKSFLSNQD
101   LDFRFFKEIN DGQDPQKTLS RLIPLQSGKN DASSFKANNS FVSLVYVYAY
151   FMLETIMQSY RILRLLEKPI NNNISEDMQS DIEIFFVQAN FLEYYVQNKI
201   YPKNHAYDFM HLIMDSIIPN WIQIDMSVEA KKKELFEKYF QNIDEVTNKM
251   LDQKNQNKNN D
``` number of residues: 261
GenMark (matrices for *Helicobacter pylori*)
Motifs:nsf
Pepplot:na
Profilesegment(IRIS database):
RFBI protein_SHIFL; 124 AA.
NIFY protein_KLEPN; 229 AA.
Hypothetical 20.1 kDa protein in HTGA 5' region (ORF5)_ECOLI; 188 AA.
Blastp ( pdb, swissprot, SPupdate, pir, genpept,GPupdate):nsf
Blitz ( swissprot ):
93/95 (1.40e+00/7.89e-01)
Outer membrane protein alpha precursor_THEMA; 400 AA.
Shuffle:na
Bestfit:na code name: CR2 coordinates and amino acid sequence: 9926-9138
```
  1   YACSAVTNLI TGNMNLDYPI TQLINAFGKD HNDPNGLVAR LAPFCKSTNG
 51   EFQWLFDNKA TDRLDFSKTI IGVDGSSFLD NNDVSPFICF YLFARIQEAM
101   DGRRFVLDID EAWKYLGDPK VAYFVRDMLK TARKRNAIVR LATQSITDLL
151   ACPIADTIRE QCPTKIFLRN DGGNLSDYQR LANVTEKEFE IITKGLDRKI
201   LYKQDGSPSV IASFNLRGIP KEYLKILSTD TVFVKEIDKI IQNHSIIDKY
251   QALRQMYQQI EEY
```
number of residues: 263
GenMark (matrices for *Helicobacter pylori*)
Motifs:nsf
Pepplot:na
Profilesegment(IRIS database):nsf
Blastp ( pdb, swissprot, SPupdate, pir, genpept,GPupdate):
251/251 (3.8e-27)( Identities=38%; positives 55%)
VirB4 homolog_BPERT; 824 AA.
189/251 (2.1e-18)( Identities=35%; positives 50%)
VirB4 homolog (plasmid pTi15955)_ATVIRB10; 751 AA.
189/251 (2.1e-18)( Identities=35%; positives 50%)
VirB4 homolog (plasmid pTiA6)_AGRT9; 789 AA.
186/251 (5.8e-18)( Identities=35%; positives 49%)

FIG.4J

VirB4 homolog (plasmid pTi58)_AGRT5; 789 AA.
Blitz ( swissprot ):
362/362 (0.00e+00/top score)
virB4 protein precursor_AGRT9; 789 AA.
359/362 (0.00e+00/top score)
virB4 protein precursor_AGRT5; 789 AA.
83/96 (2.38e+00/3.53e-02)
Shuffle:OK
Bestfit:OK code name: CR1 coordinates and amino acid sequence:12109-9911
```
  1   SGISIKREVF VASKQADEQK KLIIEQEVQK RQFQKIEELK ADMQKGVNPF
 51   FKVLFDGGNR LFGFPETFIY SSIFILFVTI VLSVILFQAY EPVLIVAIVI
101   VLVALGFKKD YRLYQRMERA MKFKKPFLFK GVKNKAFMSI FSMKPSKEMA
151   NDIHLNPNRE DRLVSAANSY LANNYECFLD DGVILTNNYS LLGTIKLGGI
201   DFLTTSKKDL IELHASIYSV FRNFVTPEFK FYFHTIKKKI VIDETNRDYG
251   LIFSNDFMRA YNEKQKRESF YDISFFLTIE QDLLDTLNEP VMNKKHFADN
301   NFEEFQRIIR AKLENFKDRI ELIEELLSKY HPTRLKEYTK DGVIYSKQCE
351   FYNFLVGMNE APFICNRKDL YLKEKMHGGV KEVYFANKHG KILNDDLSEK
401   YFSAIEISEY APKSQSDLFD KINALDSEFI FMHAYSPKNS QVLKDKLAFT
451   SRRIIISGGS KEQGMTLGCL SELVGNGDIT LGSYGNSLVL FADSFEKMKQ
501   SVKECVSSLN AKGFLANAAT FSMENYFFAK HCSFITLPFI FDVTSNNFAD
551   FIAMRAMSFD GNQENNAWGN SVMTLKSEIN SPFYLNFHMP TDFGSASAGH
601   TLILGSTGSG KTVFMSMTLN AMGQFAYNFP ANVSKDKQKL TMVYMDKDYG
651   AYGNIVAMGG EYVKIELGTD TGLNPFAWAA CVQKTNATME QKQTAISVVK
701   ELVKNLATKS DEKDENGNSI SFSLADSNTL AAQ
```
number of residues:733
GenMark (matrices for *Helicobacter pylori* )
Motifs:nsf
Pepplot:na
Profilesegment(IRIS database):nsf
Blastp ( pdb, swissprot, SPupdate, pir, genpept,GPupdate):nsf
Blitz ( swissprot ):
125/125(6.28e-05/top score)
virB4 protein precursor_AGRT5; 789 AA.
124/125(9.08e-05/6.28e-05)
virB4 protein precursor_AGRT9; 789 AA.
Shuffle:OK
Bestfit:OK

FIG.4K code name: BR2 coordinates and amino acid sequence: 12771-12097

```
1    ALSLASILAR VEELAKLINN NNNSNKKLRG FFLKVLLSLV VFSSYGLAND
51   DKEAKKEAQE KEKNTPNGLV YTNLDFDSFK ATIKNLKDKK VTFKEVNPDI
101  IKDEVFDFVI VNRVLKKIKD LKHYDPVIEK IFDEKGKEMG LNVELQINPE
151  VKDFFTFKSI STTNKQRCFL SLRGETREIL CDDKLYNVLL AVFNSYDPND
201  LLKEISTVES LKKIFYTITC EAVYL
``` number of residues: 225
GenMark (matrices for *Helicobacter pylori*)
Motifs: nsf
Pepplot: na
Profilesegment(IRIS database):
FliI protein (FLAA locus ORF 10)_BACSU; 140 AA.
Blastp ( pdb, swissprot, SPupdate, pir, genpept,GPupdate):nsf
Blitz ( swissprot ):
80/95 (1.25e+01/1.18e-01)
General secretion pathway GSPJ_ERWCH; 206 AA.
Shuffle: na
Bestfit: na code name: BR1 coordinates and amino acid sequence: 13093-12728

```
1    FQFERKRMKF FTRITDSYKK VVVTLGLVVT TNPLNAVASP TEGVTATKGL
51   VIQIISVLAI VGGCALGVKG IADIWKISDD IKRGQATVFR YAQPIAMLAV
101  AGGIIYLSTK FGFNIGEGGG AS
``` number of residues: 122
GenMark (matrices for *Helicobacter pylori*)
Motifs: Lipoprotein binding domain
Pepplot: na
Profilesegment(IRIS database):
General secretion pathway protein I precursor_XANCP; 138 AA.
ISTA protein (insertion sequence IS640)_SHISO; 315 AA.
Blastp ( pdb, swissprot, SPupdate, pir, genpept,GPupdate):nsf
Blitz ( swissprot ):
94/94 (1.07e-02/top score)
Sensor protein ENVZ_SALTY; 450 AA.
94/94 (1.07e-02/top score)
Sensor protein ENVZ_ECOLI; 450 AA
87/94 (1.41e-02/1.07e-02)
TRAH PROTEIN PRECURSOR_ECOLI; 458 AA

FIG.4L

76/94 (5.94e+00/1.07e-02)
Pathogenicity-related ORF2_XANCG; 214 AA
Shuffle:na
Bestfit:na code name: XR coordinates and amino acid sequence:13480-13220
1    AFVIBKIBMG  NKMENKSIGQ  IFKDSLKKSF  FSGLWSCLKW  SFILTLISLG
51   LFLLVFRFQP  ETIKKYIKDP  KDLQFYNDLR  KKNGWDK
number of residues:87
GenMark (matrices for *Helicobacter pylori*)
Motifs:nsf
Pepplot:na
Profilesegment(IRIS database):
FLIL protein_ECOLI; 154 AA.
Tail completion protein R (GPR)_BPP2; 155 AA.
Blastp ( pdb, swissprot, SPupdate, pir, genpept,GPupdate):nsf
38/48 (identities=47%; positives=68%)
BACN17G_7 hypotetical protein_BACSU; 98 AA.
Blitz ( swissprot ):
88/88 (2.26e-01/top score)
Transport system permease protein p69_MYCHR; 580 AA.
82/88 (1.51e+00/2.26e-02)
Sensor protein UHPB_ECOLI; 500 AA.
80/88 (2.79e+00/2.26e-02)
Sensor protein UHPB_SALTY; 500 AA.
74/88 (1.63e+01/2.26e-02)
Hypotetical 16.6 kDa protein outside the virF region (ORF3)_AGRT9; 150AA.
Shuffle:none
Bestfit:none code name: GLU coordinates and amino acid sequence:19185-18648
1    KSVMKIGVFD  SGVGGFSVLK  SLLKAQLFDE  IIYYGDTARV  PYGTKDPTTI
51   KQFGLEALDF  FKPHQIELLI  VACNTASALA  LEEMQKHSKI  PIVGVIEPSI
101  LAIKRQVKDK  NAPILVLGTK  ATIQSNAYDN  ALKQQGYLNV  SBLATSLFVP
151  LIEESILEGE  LLETCMRYYF  TPLKIFPK
number of residues:178

FIG.4M

GenMark (matrices for *Helicobacter pylori*)
Motifs:nsf
Pepplot:na
Profilesegment(IRIS database):nsf
Blastp ( pdb, swissprot, SPupdate, pir, genpept,GPupdate):
176-75 (1.1e-25><1.4e-10)
G l u t a m a t e
racemasi_SHU_LACFI_PEDIOCOCCUS_LEPRAE_BREVIS_COLI;
266 AA.
Blitz ( swissprot ):nt
Shuffle:na
Bestfit:na

FIG.4N

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
      (A) LENGTH: 10299 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
TTTGTTCAGT GATTTCGCCT TCCATTTCTT CTTCTATGAA GTCCAATTCT TCTTTCAGTT      60

CAAAAAGATA ATTAGAAAAA CTATCCAAAA TCGTCAAGAC ATCATTTTCA AAATTTCCAA     120

TAATTTTTGT TCACGCAAAT TTTGTTTCAT TTTAATACTC CTCTATTTGT TGATACATTT     180

GTCTCAAGGC CTGATATTTA TCTATGATAC TATGGTTTTG GATAATCTTA TCAATTTCTT     240

TGACAAATAC AGTATCTGTG GATAAAATTT TCAAATATTC TTTAGGAATG CCTCTCAAAT     300

TAAAACTAGC GATAACGCTA GGGCTTCCAT CCTGTTTGTA GAGGATTTTC CTATCTAGTC     360

CCTTAGTGAT GATTTCAAAT TCTTTTTCTG TAACATTAGC CAATCTTTGG TAATCAGAAA     420

GATTGCCCCC ATCGTTTCTC AAAAAAATCT TTGTAGGGCA TTGTTCTCTA ATCGTATCAG     480

CAATAGGGCA AGCCAAAAGA TCAGTGATGC TTTGAGTCGC AAGTCTGACA ATAGCGTTTC     540

TTTTCCTTGC AGTTTTTAGC ATGTCTCTTA CAAAATAAGC GACCTTTGGA TCGCTAAATA     600

TTTCCAGGCT TCATCAATAT CTAAGACAAA TCTACGCCCA TCCATTGCCT CTTGGATACG     660

AGCGAAAAGG TAAAAACAAA TAAAGGGCGA AACATCATTA TTGTCTAAGA AACTTGACCC     720

ATCAACGCCA ATAATCGTTT TTGAAAAATC TAAGCGATCT GTTGCTTTAT TATCAAAAAG     780

CCATTGAAAT TCACCATTGG TTGATTTGCA AAAAGGCGCT AATCGCGCGA CAAGCCCATT     840

AGGATCATTG TGGTCTTTCC CGAAAGCATT AATAAGTTGA GTGATGGGAT AATCTAGATT     900
```

-continued

| | | | | | |
|---|---|---|---|---|---|
| CATATTTCCT | GTGATAAGGT | TGGTTACTGC | GCTGCAAGCG | TATTAGAATC | TGCTAGGCTA | 960 |
| AAAGAGATGC | TGTTGCCATT | TTCATCTTTT | TCATCGCTTT | TAGTTGCTAA | GTTTTTCACA | 1020 |
| AGCTCTTTGA | CAACAGAAAT | AGCTGTTTGT | TTTTGCTCCA | TTGTTGCATT | TGTTTTTTGC | 1080 |
| ACACAAGCCG | CCCAAGCAAA | AGGATTTAAT | CCTGTATCTG | TCCCTAGCTC | AATCTTGACA | 1140 |
| TACTCCCCAC | CCATTGCGAC | AATATTCCCA | TAAGCGCCAT | AATCTTTATC | CATATAAACC | 1200 |
| ATAGTGAGCT | TTTGCTTGTC | TTTGCTGACA | TTAGCAGGAA | AATTATAGGC | AAATTGTCCC | 1260 |
| ATAGCGTTCA | AGGTCATTGA | CATAAACACT | GTCTTACCTG | AACCGGTTGA | GCCAAGTATC | 1320 |
| AAAGTGTGTC | CTGCTGAAGC | TGAACCAAAA | TCAGTGGGCA | TGTGGAAGTT | CAGATAAAAA | 1380 |
| GGCGAATTGA | TCTCGCTTTT | TAGCGTCATC | ACACTATTGC | CCAAGCGTT | ATTCTCTTGA | 1440 |
| TTGCCATCAA | AACTCATAGC | CCTCATAGCG | ATGAAATCAG | CAAAATTATT | AGAAGTTACA | 1500 |
| TCAAAAATAA | AAGGAAGCGT | GATAAAGAG | CAATGTTTGG | CAAAAAAGTA | ATTTTCCATA | 1560 |
| GAGAAAGTCG | CTGCGTTGGC | TAAAAAACCT | TTAGCGTTAA | GACTAGAGAC | GCATTCCTTA | 1620 |
| ACGCTTTGTT | TCATTTTTTC | AAAGCTATCA | GCAAACAGCA | CTAAAGAATT | ACCATAACTG | 1680 |
| CCTAGCGTAA | TATCACCATT | ACCCACTAAT | TCGCTCAAGC | AACCTAAAGT | CATGCCCTGT | 1740 |
| TCTTTAGAGC | CTCCACTAAT | AATAATTCTT | CTAGAGGTGA | AAGCCAGTTT | GTCCTTTAAA | 1800 |
| ACCTGTGAGT | TTTTAGGCGA | ATAAGCATGC | ATGAAAATAA | ATTCGCTGTC | TAGGGCGTTG | 1860 |
| ATTTTATCAA | ACAAATCGCT | TTGTGATTTA | GGGGCGTATT | CACTAATCTC | AATAGCGCTA | 1920 |
| AAATATTTTT | CACTCAAATC | GTCATTTAAG | ATTTTTCCAT | GCTTATTGGC | AAAATAAACT | 1980 |
| TCTTTCACCC | CACCATGCAT | TTTTTCCTTG | AGATACAAGT | CTTTTCGGTT | GCAAATAAAA | 2040 |
| GGGGCTTCAT | TCATTCCCAA | AAGAAAATTG | TAAAATTCGC | ATTGTTTGGA | GTAAATAACG | 2100 |
| CCATCTTTAG | TGTATTCTTT | TAATCTAGTG | GGGTGGTATT | TGCTCAACAG | CTCTTCTATG | 2160 |
| AGCTCTATCC | TATCCTTGAA | GTTTTCAAGC | TTGGCTCTAA | TAATCCTTTG | AAACTCTTCA | 2220 |
| AAATTATTGT | CTGCAAAATG | CTTTTTATTC | ATAACGGGTT | CATTGAGAGT | GTCTAATAAA | 2280 |
| TCTTGCTCTA | TGGTCAGAAA | AAAACTAATA | TCATAAAAAC | TTTCTCTCTT | TTGCTTCTCA | 2340 |
| TTATAGGCTC | GCATGAAATC | ATTAGAAAAA | ATAAGACCAT | AGTCCCTATT | GGTTTCATCA | 2400 |
| ATAACGATTT | TCTTTTTAAT | AGTGTGAAAA | TAGAATTTGA | ATTCAGGGGT | AACAAAATTC | 2460 |
| CTAAAAACGC | TATAAATAGA | AGCGTGTAAC | TCTATGAGAT | CTTTTTTGGA | AGTGGTTAAA | 2520 |
| AAATCAATGC | CCCCCAATTT | GATTGTGCCT | AAAAGAGAAT | AGTTGTTAGT | AAGGATCACC | 2580 |
| CCATCATCTA | AAAAACATTC | ATAGTTATTT | GCTAGATAGG | AGTTTGCAGC | GCTCACAAGT | 2640 |
| CTGTCTTCTC | TGTTTGGATT | TAAGTGGATG | TCATTAGCCA | TTTCTTTACT | AGGCTTCATG | 2700 |
| GAAAAAATGC | TCATGAACGC | TTTGTTTTTC | ACGCCCTTAA | ACAAAAAAGG | TTTTTAAAT | 2760 |
| TTCATCGCTC | GCTCCATTCT | TTGATAAAGC | CTATAATCTT | TCTTGAATCC | AAGAGCTACA | 2820 |
| AGCACAATAA | CAATCGCTAC | AATCAAAACA | GGTTCATAGG | CTTGAAAAAG | AATAACAGAT | 2880 |
| AATACAATGG | TTACAAACAA | TATAAATATA | GAGGAATAAA | TAAAAGTTTC | AGGGAAACCA | 2940 |
| AACAACCTAT | TCCCCCCATC | AAACAAGACT | TTAAAAAAGG | GATTGACACC | CTTTTGCATG | 3000 |
| TCTGCTTTAA | GTTCTTCTAT | TTTTTGAAAC | TGCCGCTTTT | GAACCTCTTG | CTCTATAATT | 3060 |
| AGCTTTTTTT | GTTCATCAGC | CTGCTTGCTT | GCCACAAACA | CCTCTCTCTT | TATAGATATA | 3120 |
| CCGCTTCACA | TGTAATCGTA | TAAAAGATTT | TTTTGAGAGA | CTCTACGGTG | CTAATATGTT | 3180 |
| TCAAAGATC | ATTAGGATCA | TAAGAATTGA | ATACGGCCAA | TAAAACATTA | TATAACTTAT | 3240 |
| CATCGCATAG | AATTTCTCTT | GTTTCTCCGC | GCAATGACAG | AAAGCAGCGT | TGTTTGTTGG | 3300 |

```
TCGTGCTGAT GCTTTTGAAA GTAAAAAAGT CTTTCACTTC AGGATTGATC TGTAATTCTA      3360

CATTCAATCC CATTTCCTTA CCCTTTTCAT CAAAGATTTT TTCAATAACT GGATCGTAAT      3420

GCTTCAAATC CTTTATTTTT TTAAGGACTC TATTGACAAT CACGAAGTCA AAAACTTCAT      3480

CTTTGATAAT ATCGGGATTG ACTTCTTTGA AAGTTACTTT CTTGTCTTTC AAATTTTTGA      3540

TAGTCGCTTT GAAACTATCA AAATCTAAAT TTGTATAAAC AAGCCCATTG GGAGTGTTTT      3600

TTTCTTTTTC TTGTGCTTCT TTTTTGGCTT CTTTGTCATC ATTTGCTAAC CCATACGAAC      3660

TGAAAACAAC GAGACTTAAG AGAACTTTCA AAAAAAGCC TCTTAGTTTC TTATTGCTAT       3720

TATTATTATT GTTGATCAAC TTAGCTAGCT CCTCCACCCT CGCCAATATT GAAGCCAAAC      3780

TTAGTGCTCA AATAGATAAT ACCGCCTGCC ACCGCTAACA TAGCTATGGG TTGCGCGTAA      3840

GCAAAAACAG TCGCCTGACC TCTTTTAATG TCATCAGAGA TTTTCCAAAT ATCCGCTATG      3900

CCTTTGACCC CTAAAGCGCA ACCACCTACG ATCGCTAGAA CAGAAATGAT CTGAATAACC      3960

AAACCTTTAG TTGCAGTGAC GCCTTCTGTA GGACTGGCGA CCGCCATTAA AGGATTGGTT      4020

GTTACCACTA GCCCTAAAGT TACTACAACT TTCTTGTAGC TGTCAGTGAT TCTTGTAAAA      4080

AATTTCATGC GTTTCCTTTC AAATTGAAAT CAATCGCTTG AGTATATCAA AAAAAAAAGT     4140

ATTTTTATAC TATTCATACA AGCGCTACTT TATAATTTAA ATCAAAACCG ACGCTTTTGC      4200

TCGGCAACTG ACATCATTCA GGAATAGTAA ACCTACTTGT CCCAACCATT TTTCTTTCTC     4260

AAGTCGTTGT AGAATTGTAG ATCTTTAGGA TCTTTGATGT ATTTTTTAAT CGTCTCAGGT     4320

TGAAACCTAA AAACAAGCAA AAACAAACCC AAGCTGATCA GAGTGAGAAT AAAGCTCCAT      4380

TTTAAGCAAC TCCATAGACC ACTAAAGAAA CTTTTTTTGA GGCTATCTTT GAAAATCTGT     4440

CCTATTGATT TGTTTTCCAT TTTGTTTCCC ATGTGGATCT TGTGGATCAC AAACGCTTAA     4500

TTATACATGC TATAGTAAGC ATGACACACA AACCAAACTA TTTTTAGAAC GCTTCATGTG     4560

CTCACCTTGA CTAACCATTT CTCCAACCAT ACTTTAGCGT TGCATTTGAT TCTTCAAAA      4620

AGATTCATTT CTTATTTCTT GTTCTTATTA AAGTTCTTTC ATTTTAGCAA ATTTTTGTTA    4680

ATTGTGGGTA AAAATGTGAA TCGTCCTAGC CTTTAGACGC CTGCAACGAT CGGGCTTTTT    4740

TCAATATTAA TAATGATTAA TGAAAAAAAA AAAAAATGCT TGATATTGTT GTATAATGAG    4800

AATGTTCAAA GACATGAATT GACTACTCAA GCGTGTAGCG ATTTTTAGCA GTCTTTGACA     4860

CTAACAAGAT ACCGATAGGT ATGAAACTAG GTATAGTAAG GAGAAACAAT GACTAACGAA     4920

ACCATTGACC AACAACCACA AACCGAAGCG GCTTTTAACC CGCAGCAATT TATCAATAAT    4980

CTTCAAGTAG CTTTTCTTAA AGTTGATAAC GCTGTCGCTT CATACGATCC TGATCAAAAA   5040

CCAATCGTTG ATAAGAACGA TAGGGATAAC AGGCAAGCTT TTGAAGGAAT CTCGCAATTA   5100

AGGGAAGAAT ACTCCAATAA AGCGATCAAA AATCCTACCA AAAAGAATCA GTATTTTTCA   5160

GACTTTATCA ATAAGAGCAA TGATTTAATC AACAAAGACA ATCTCATTGA TGTAGAATCT   5220

TCCACAAAGA GCTTTCAGAA ATTTGGGGAT CAGCGTTACC GAATTTTCAC AAGTTGGGTG   5280

TCCCATCAAA ACGATCCGTC TAAAATCAAC ACCCGATCGA TCCGAAATTT TATGGAAAAT   5340

ATCATACAAC CCCCTATCCT TGATGATAAA GAGAAAGCGG AGTTTTTGAA ATCTGCCAAA   5400

CAATCTTTTG CAGGAATCAT TATAGGGAAT CAAATCCGAA CGGATCAAAA GTTCATGGGC   5460

GTGTTTGATG AGTCCTTGAA AGAAAGGCAA GAAGCAGAAA AAAATGGAGA GCCTACTGGT   5520

GGGGATTGGT TGGATATTTT TCTCTCATTT ATATTTGACA AAAACAATC TTCTGATGTC    5580

AAAGAAGCAA TCAATCAAGA ACCAGTTCCC CATGTCCAAC CAGATATAGC CACTACCACC   5640

ACCGACATAC AAGGCTTACC GCCTGAAGCT AGAGATTTAC TTGATGAAAG GGGTAATTTT   5700
```

```
TCTAAATTCA CTCTTGGCGA TATGGAAATG TTAGATGTTG AGGGAGTCGC TGACATTGAT    5760

CCCAATTACA AGTTCAATCA ATTATTGATT CACAATAACG CTCTGTCTTC TGTGTTAATG    5820

GGGAGTCATA ATGGCATAGA ACCTGAAAAA GTTTCATTGT TGTATGGGGG CAATGGTGGT    5880

CCTGGAGCTA GGCATGATTG GAACGCCACC GTTGGTTATA AAGACCAACA AGGCAACAAT    5940

GTGGCTACAA TAATTAATGT GCATATGAAA AACGGCAGTG GCTTAGTCAT AGCAGGTGGT    6000

GAGAAAGGGA TTAACAACCC TAGTTTTTAT CTCTACAAAG AAGACCAACT CACAGGCTCA    6060

CAACGAGCAT TAAGTCAAGA AGAGATCCAA AACAAAATAG ATTTCATGGA ATTTCTTGCA    6120

CAAAATAATG CTAAATTAGA CAACTTGAGC GAGAAAGAGA AGGAAAAATT CCGAACTGAG    6180

ATTAAAGATT TCCAAAAAGA CTCTAAGGCT TATTTAGACG CCCTAGGGAA TGATCGTATT    6240

GCTTTTGTTT CTAAAAAGA CACAAAACAT TCAGCTTTAA TTACTGAGTT TGGTAATGGG    6300

GATTTGAGCT ACACTCTCAA AGATTATGGG AAAAAGCAG ATAAAGCTTT AGATAGGGAG    6360

AAAAATGTTA CTCTTCAAGG TAGCCTAAAA CATGATGGCG TGATGTTTGT TGATTATTCT    6420

AATTTCAAAT ACACCAACGC CTCCAAGAAT CCCAATAAGG GTGTAGGCGT TACGAATGGC    6480

GTTTCCCATT TAGAAGTAGG CTTTAACAAG GTAGCTATCT TTAATTTGCC TGATTTAAAT    6540

AATCTCGCTA TCACTAGTTT CGTAAGGCGG AATTTAGAGG ATAAACTAAC CACTAAAGGA    6600

TTGTCCCCAC AAGAAGCTAA TAAGCTTATC AAAGATTTTT TGAGCAGCAA CAAAGAATTG    6660

GTTGGAAAAA CTTTAAACTT CAATAAAGCT GTAGCTGACG CTAAAAACAC AGGCAATTAT    6720

GATGAAGTGA AAAAAGCTCA GAAAGATCTT GAAAAATCTC TAAGGAAACG AGAGCATTTA    6780

GAGAAAGAAG TAGAGAAAAA ATTGGAGAGC AAAAGCGGCA ACAAAAATAA AATGGAAGCA    6840

AAAGCTCAAG CTAACAGCCA AAAAGATGAG ATTTTTGCGT TGATCAATAA AGAGGCTAAT    6900

AGAGACGCAA GAGCAATCGC TTACGCTCAG AATCTTAAAG GCATCAAAAG GGAATTGTCT    6960

GATAAACTTG AAAATGTCAA CAAGAATTTG AAAGACTTTG ATAAATCTTT TGATGAATTC    7020

AAAAATGGCA AAAATAAGGA TTTCAGCAAG GCAGAAGAAA CACTAAAAGC CCTTAAAGGT    7080

TCGGTGAAAG ATTTAGGTAT CAATCCAGAA TGGATTTCAA AAGTTGAAAA CCTTAATGCA    7140

GCTTTGAATG AATTCAAAAA TGGCAAAAAT AAGGATTTCA GCAAGGTAAC GCAAGCAAAA    7200

AGCGACCTTG AAAATTCCGT TAAAGATGTG ATCATCAATC AAAAGGTAAC GGATAAAGTT    7260

GATAATCTCA ATCAAGCGGT ATCAGTGGCT AAAGCAACGG GTGATTTCAG TAGGGTAGAG    7320

CAAGCGTTAG CCGATCTCAA AAATTTCTCA AAGGAGCAAT TGGCCCAACA AGCTCAAAAA    7380

AATGAAAGTC TCAATGCTAG AAAAAAATCT GAAATATATC AATCCGTTAA GAATGGTGTG    7440

AATGGAACCC TAGTCGGTAA TGGGTTATCT CAAGCAGAAG CCACAACTCT TTCTAAAAAC    7500

TTTTCGGACA TCAAGAAAGA GTTGAATGCA AAACTTGGAA ATTTCAATAA CAATAACAAT    7560

AATGGACTCA AAAACGAACC CATTTATGCT AAAGTTAATA AAAAGAAAGC AGGGCAAGCA    7620

GCTAGCCTTG AAGAACCCAT TTACGCTCAA GTTGCTAAAA AGGTAAATGC AAAAATTGAC    7680

CGACTCAATC AAATAGCAAG TGGTTTGGGT GTTGTAGGGC AAGCAGCGGG CTTCCCTTTG    7740

AAAAGGCATG ATAAAGTTGA TGATCTCAGT AAGGTAGGGC TTTCAAGGAA TCAAGAATTG    7800

GCTCAGAAAA TTGACAATCT CAATCAAGCG GTATCAGAAG CTAAAGCAGG TTTTTTTGGC    7860

AATCTAGAGC AAACGATAGA CAAGCTCAAA GATTCTACAA AACACAATCC CATGAATCTA    7920

TGGGTTGAAA GTGCAAAAAA AGTACCTGCT AGTTTGTCAG CGAAACTAGA CAATTACGCT    7980

ACTAACAGCC ACATACGCAT TAATAGCAAT ATCAAAAATG GAGCAATCAA TGAAAAAGCG    8040

ACCGGCATGC TAACGCAAAA AAACCCTGAG TGGCTCAAGC TCGTGAATGA TAAGATAGTT    8100
```

```
GCGCATAATG TAGGAAGCGT TCCTTTGTCA GAGTATGATA AAATTGGCTT CAACCAGAAG    8160
AATATGAAAG ATTATTCTGA TTCGTTCAAG TTTTCCACCA AGTTGAACAA TGCTGTAAAA    8220
GACACTAATT CTGGCTTTAC GCAATTTTTA ACCAATGCAT TTTCTACAGC ATCTTATTAC    8280
TGCTTGGCGA GAGAAAATGC GGAGCATGGA ATCAAGAACG TTAATACAAA AGGTGGTTTC    8340
CAAAAATCTT AAAGGATTAA GGAATACCAA AAACGCAAAA ACCACCCCTT GCTAAAAGCG    8400
AGGGGTTTTT TAATACTCCT TAGCAGAAAT CCCAATCGTC TTTAGTATTT GGGATGAATG    8460
CTACCAATTC ATGGTATCAT ATCCCCATAC ATTCGTATCT AGCGTAGGAA GTGTGCAAAG    8520
TTACGCCTTT GGAGATATGA TGTGTGAGAC CTGTAGGGAA TGCGTTGGAG CTCAAACTCT    8580
GTAAAATCCC TATTATAGGG ACACAGAGTG AGAACCAAAC TCTCCCTACG GGCAACATCA    8640
GCCTAGGAAG CCCAATCGTC TTTAGCGGTT GGGCACTTCA CCTTAAAATA TCCCGACAGA    8700
CACTAACGAA AGGCTTTGTT CTTTAAAGTC TGCATGGATA TTTCCTACCC CAAAAAGACT    8760
TAACCCTTTG CTTAAAATTA AGTTTGATTG TGCTAGTGGG TTCGTGCTAT AGTGCGAAAA    8820
TTAATTAAGG GTTATAAAGA GAGCATAAAC TAGAAAAAAC AAGTAGCTAT AACAAAGATC    8880
AAGTTCAAAA AATCATAGAG CTTTTAGAGC AAATTGATCG CGCTCTTAAC CAAGAAAAA    8940
TCAGAAAAAC CATAGGAATT ATCACACCTT ATAATGCCCA AAAAAGACGC TTGCGATCAG    9000
AAGTGGAAAA ATACGGCTTC AAGAATTTTG ATGAGCTCAA AATAGACACT GTGGATGCCT    9060
TTCAAGGTGA AGAGGCAGAT ATTATTATTT ATTCCACCGT GAAAACTTGT GGTAATCTTT    9120
CTTTCTTGCT AGATTCTAAA CGCTTGAATG TGGCTATTTC TAGGGCAAAA GAAAATCTCA    9180
TTTTTGTGGG TAAAAAGTCT TTCTTTGAGA ATTTACGAAG CGATGAGAAG AATATCTTTA    9240
GCGCTATTTT GCAAGTCTGT AGATAGGTAA TCTTTTCCAA AGATAATCAT TAGACATTCT    9300
TCGCTTCAAA ACGCTTTCAT AAATCTCTCT AAAGCGCTTT ATAATCAACA CAATACCCTT    9360
ATAGTGTGAG CTATAGCCCC TTTTTGGGAA TTGAGTTATT TTGACTTTAA ATTTTTATTA    9420
GCGTTACAAT TTGAGCCATT CTTTAGCTTG TTTTTCTAGC CAGATCACAT CGCCGCTCGC    9480
ATGAAATTCC ACTTTAGGGA ATGCGTGTGC ATTTTTTTTA AGGGCGTATT TTTGCTGCAA    9540
ATATCCTACA ATAGCATCGC CCGAATGGAT GAGTAGGGGG GGTGTTGAAA GGGCAAAATG    9600
CTCCATAAAA TAGCCCTCAA TTTTTTGAGC GATTAAGGGA AAATGCGTGC AACCTAAAAT    9660
AATCACTTCG GGAAAATCTT TAAGGGAGTG AAATAATAAC GCATGCAAGT TTCTAACAAT    9720
TCGCCCTCTA AAATACTTTC TTCAATCAAA GGCACAAAAA GAGAAGTGGC TAAATGCGAA    9780
ACATTCAAAT AGCCTTGTTG TTTCAGGGCA TTGTCATAAG CGTTGGATTG GATCGTCGCT    9840
TTTGTCCCTA GCACTAAAAT AGGGGCGTTT TTATCTTTTA CTTGTCGCTT GATCGCTAAA    9900
ATGCTTGGCT CAATCACGCC CACAATAGGG ATTTTGGAAT GCTTTTGCAT CTCTTCTAAA    9960
GCTAGAGCGC TCGCTGTGTT GCATGCCACA ATCAATAATT CAATCTGGTG CGGTTTGAAA   10020
AAATCCAAAG CCTCTAAGCC AAATTGCTTG ATCGTAGTGG GGTCTTTAGT GCCATAAGGC   10080
ACTCTAGCCG TATCGCCATA ATAGATGATT TCATCAAATA ATTGCGCTTT TAAAAGGCTT   10140
TTTAAAACGC TAAACCCTCC CACACCGCTA TCAAAAACGC CTATTTTCAT GACACTTTTT   10200
TAATTTAATG GGATTAATTA GGGATTTTAT TTTTCATTCA TTAAGTTTAA AAATTCTTCA   10260
TTGTCCTTAG TTTGTTGCAT TTTAGAATAG ACAAAGCTT                          10299
```

(2) INFORMATION FOR SEQ ID NO:2:

(i) SEQUENCE CHARACTERISTICS:
        (A) LENGTH: 3289 amino acids
        (B) TYPE: amino acid (C) STRANDEDNESS: single
(D) TOPOLOGY: linear (ii) MOLECULE TYPE: protein (xi) SEQUENCE DESCRIPTION: SEQ ID NO:2:

```
Phe Val Gln Phe Arg Leu Pro Phe Leu Leu Ser Pro Ile Leu Leu
1               5                   10                  15

Ser Val Gln Lys Asp Asn Lys Asn Tyr Pro Lys Ser Ser Arg His His
                20                  25                  30

Phe Gln Asn Phe Gln Phe Leu Phe Thr Gln Ile Leu Phe His Phe Asn
            35                  40                  45

Thr Pro Leu Phe Val Asp Thr Phe Val Ser Arg Pro Asp Ile Tyr Leu
        50                  55                  60

Tyr Tyr Gly Phe Gly Ser Tyr Gln Phe Leu Gln Ile Gln Tyr Leu Trp
65                  70                  75                  80

Ile Lys Phe Ser Asn Ile Leu Glu Cys Leu Ser Asn Asn Arg Arg Gly
                85                  90                  95

Phe His Pro Val Cys Arg Gly Phe Ser Tyr Leu Val Pro Phe Gln Ile
            100                 105                 110

Leu Phe Leu His Pro Ile Phe Gly Asn Gln Lys Asp Cys Pro His Arg
        115                 120                 125

Phe Ser Lys Lys Ser Leu Gly Ile Val Leu Ser Tyr Gln Gln Gly Lys
    130                 135                 140

Pro Lys Asp Gln Cys Phe Glu Ser Gln Val Gln Arg Phe Phe Ser Leu
145                 150                 155                 160

Gln Phe Leu Ala Cys Leu Leu Gln Asn Lys Arg Pro Leu Asp Arg Ile
                165                 170                 175

Phe Pro Gly Phe Ile Asn Ile Asp Lys Ser Thr Pro Ile His Cys Leu
            180                 185                 190

Leu Asp Thr Ser Glu Lys Val Lys Thr Asn Lys Gly Arg Asn Ile Ile
        195                 200                 205

Ile Val Glu Thr Pro Ile Asn Ala Asn Asn Arg Phe Lys Ile Ala Ile
    210                 215                 220

Cys Cys Phe Ile Ile Lys Lys Pro Leu Lys Phe Thr Ile Gly Phe Ala
225                 230                 235                 240

Lys Arg Arg Ser Arg Asp Lys Pro Ile Arg Ile Val Val Phe Pro
                245                 250                 255

Glu Ser Ile Asn Lys Leu Ser Asp Gly Ile Ile His Ile Ser Cys
            260                 265                 270

Asp Lys Val Gly Tyr Cys Ala Ala Ser Val Leu Glu Ser Ala Arg Leu
        275                 280                 285

Lys Glu Met Leu Leu Pro Phe Ser Ser Phe Ser Ser Leu Leu Val Ala
    290                 295                 300

Lys Phe Thr Ser Ser Leu Thr Thr Glu Ile Ala Val Cys Phe Cys
305                 310                 315                 320

Ser Ile Val Ala Phe Val Phe Cys Thr Gln Ala Ala Gln Ala Lys Gly
                325                 330                 335

Phe Asn Pro Val Ser Val Pro Ser Ser Ile Leu Thr Tyr Ser Pro Pro
            340                 345                 350

Ile Ala Thr Ile Phe Pro Ala Pro Ser Leu Ser Ile Thr Ile Val Ser
        355                 360                 365

Phe Cys Leu Ser Leu Leu Thr Leu Ala Gly Lys Leu Ala Asn Cys Pro
    370                 375                 380

Ile Ala Phe Lys Val Ile Asp Ile Asn Thr Val Leu Pro Glu Pro Val
```

-continued

```
               385                 390                 395                 400

Glu Pro Ser Ile Lys Val Cys Pro Ala Glu Ala Pro Lys Ser Val
                         405                 410                 415

Gly Met Trp Lys Phe Arg Lys Gly Glu Leu Ile Ser Leu Phe Ser Val
                     420                 425                 430

Ile Thr Leu Leu Pro Gln Ala Leu Phe Ser Leu Pro Ser Lys Leu Ile
                     435                 440                 445

Ala Leu Ile Ala Met Lys Ser Ala Lys Leu Leu Glu Val Thr Ser Lys
                     450                 455                 460

Ile Lys Gly Ser Val Ile Lys Glu Gln Cys Leu Ala Lys Lys Phe Ser
         465                 470                 475                 480

Ile Glu Lys Val Ala Ala Leu Ala Lys Lys Pro Leu Ala Leu Arg Leu
                         485                 490                 495

Glu Thr His Ser Leu Thr Leu Cys Phe Ile Phe Ser Lys Leu Ser Ala
                         500                 505                 510

Asn Ser Thr Lys Glu Leu Pro Leu Pro Ser Val Ile Ser Pro Leu Pro
                         515                 520                 525

Thr Asn Ser Leu Lys Gln Pro Lys Val Met Pro Cys Ser Leu Glu Pro
                         530                 535                 540

Pro Leu Ile Ile Leu Leu Glu Val Lys Ala Ser Leu Ser Phe Lys
         545                 550                 555                 560

Thr Cys Glu Phe Leu Gly Glu Ala Cys Met Lys Ile Asn Ser Leu Ser
                         565                 570                 575

Arg Ala Leu Ile Leu Ser Asn Lys Ser Leu Cys Asp Leu Gly Ala Tyr
                         580                 585                 590

Ser Leu Ile Ser Ile Ala Leu Lys Tyr Phe Ser Leu Lys Ser Ser Phe
                         595                 600                 605

Lys Ile Phe Pro Cys Leu Leu Ala Lys Thr Ser Phe Thr Pro Pro Cys
                         610                 615                 620

Ile Phe Ser Leu Arg Tyr Lys Ser Phe Arg Leu Gln Ile Lys Gly Ala
         625                 630                 635                 640

Ser Phe Ile Pro Lys Arg Lys Leu Asn Ser His Cys Leu Glu Ile Thr
                         645                 650                 655

Pro Ser Leu Val Tyr Ser Phe Asn Leu Val Gly Trp Tyr Leu Leu Asn
                         660                 665                 670

Ser Ser Ser Met Ser Ser Ile Leu Ser Leu Lys Phe Ser Ser Leu Ala
                         675                 680                 685

Leu Ile Ile Leu Asn Ser Ser Lys Leu Leu Ser Ala Lys Cys Phe Leu
                         690                 695                 700

Phe Ile Thr Gly Ser Leu Arg Val Ser Asn Lys Ser Cys Ser Met Val
         705                 710                 715                 720

Arg Lys Lys Leu Ile Ser Lys Leu Ser Leu Phe Cys Phe Ser Leu Ala
                         725                 730                 735

Arg Met Lys Ser Leu Glu Lys Ile Arg Pro Ser Leu Leu Val Ser Ser
                         740                 745                 750

Ile Thr Ile Phe Phe Leu Ile Val Lys Asn Leu Asn Ser Gly Val Thr
                         755                 760                 765

Lys Phe Leu Lys Thr Leu Ile Glu Ala Cys Asn Ser Met Arg Ser Phe
                         770                 775                 780

Leu Glu Val Val Lys Lys Ser Met Pro Pro Asn Leu Ile Val Pro Lys
         785                 790                 795                 800

Arg Glu Leu Leu Val Arg Ile Thr Pro Ser Ser Lys Lys His Ser Leu
                         805                 810                 815
```

```
Phe Ala Arg Glu Phe Ala Ala Leu Thr Ser Leu Ser Ser Leu Phe Gly
            820                 825                 830

Phe Lys Trp Met Ser Leu Ala Ile Ser Leu Leu Gly Phe Met Glu Lys
        835                 840                 845

Met Leu Met Asn Ala Leu Phe Phe Thr Pro Leu Asn Lys Lys Gly Phe
    850                 855                 860

Leu Asn Phe Ile Ala Arg Ser Ile Leu Ser Leu Ser Phe Leu Asn Pro
865                 870                 875                 880

Arg Ala Thr Ser Thr Ile Thr Ile Ala Thr Ile Lys Thr Gly Ser Ala
                885                 890                 895

Lys Arg Ile Thr Asp Asn Thr Met Val Thr Asn Asn Ile Asn Ile Glu
                900                 905                 910

Glu Ile Lys Val Ser Gly Lys Pro Asn Asn Leu Phe Pro Pro Ser Asn
            915                 920                 925

Lys Thr Leu Lys Lys Gly Leu Thr Pro Phe Cys Met Ser Ala Leu Ser
        930                 935                 940

Ser Ser Ile Phe Asn Cys Arg Phe Thr Ser Cys Ser Ile Ile Ser Phe
945                 950                 955                 960

Phe Cys Ser Ser Ala Cys Leu Leu Ala Thr Asn Thr Ser Leu Phe Ile
                965                 970                 975

Asp Ile Pro Leu His Met Ser Tyr Lys Arg Phe Phe Glu Thr Leu Arg
            980                 985                 990

Cys Tyr Val Ser Lys Asp His Asp His Lys Asn Ile Arg Pro Ile Lys
        995                 1000                1005

His Tyr Ile Thr Tyr His Arg Ile Glu Phe Leu Leu Phe Leu Arg Ala
    1010                1015                1020

Met Thr Glu Ser Ser Val Val Cys Trp Ser Cys Cys Phe Lys Lys Ser
1025                1030                1035                1040

Leu Ser Leu Gln Asp Ser Val Ile Leu His Ser Ile Pro Phe Pro Tyr
                1045                1050                1055

Pro Phe His Gln Arg Phe Phe Gln Leu Asp Arg Asn Ala Ser Asn Pro
            1060                1065                1070

Leu Phe Phe Gly Leu Tyr Gln Ser Arg Ser Gln Lys Leu His Leu Tyr
        1075                1080                1085

Arg Asp Leu Leu Lys Leu Leu Ser Cys Leu Ser Asn Phe Ser Leu Asn
1090                1095                1100

Tyr Gln Asn Leu Asn Leu Tyr Lys Gln Ala His Trp Glu Cys Phe Phe
1105                1110                1115                1120

Leu Phe Leu Val Leu Leu Phe Trp Leu Leu Cys His His Leu Leu Thr
                1125                1130                1135

His Thr Asn Lys Gln Arg Asp Leu Arg Glu Leu Ser Lys Ser Leu
            1140                1145                1150

Leu Val Ser Tyr Cys Tyr Tyr Tyr Cys Ser Thr Leu Ala Pro Pro
        1155                1160                1165

Pro Ser Pro Ile Leu Lys Pro Asn Leu Val Leu Lys Ile Ile Pro Pro
    1170                1175                1180

Ala Thr Ala Asn Ile Ala Met Gly Cys Ala Ala Lys Thr Val Ala Pro
1185                1190                1195                1200

Leu Leu Met Ser Ser Glu Ile Phe Gln Ile Ser Ala Met Pro Leu Thr
                1205                1210                1215

Pro Lys Ala Gln Pro Pro Thr Ile Ala Arg Thr Glu Met Ile Ile Thr
            1220                1225                1230

Lys Pro Leu Val Ala Val Thr Pro Ser Val Gly Leu Ala Thr Ala Ile
        1235                1240                1245
```

```
Lys Gly Leu Val Val Thr Thr Ser Pro Lys Val Thr Thr Thr Phe Leu
    1250                1255                1260

Leu Ser Val Ile Leu Val Lys Asn Phe Met Arg Phe Leu Ser Asn Asn
1265                1270                1275                1280

Gln Ser Leu Glu Tyr Ile Lys Lys Ser Ile Phe Ile Leu Phe Ile
                1285                1290                1295

Gln Ala Leu Leu Tyr Asn Leu Asn Gln Asn Arg Arg Phe Cys Ser Ala
        1300                1305                1310

Thr Asp Ile Ile Gln Glu Thr Tyr Leu Ser Gln Pro Phe Phe Phe Leu
        1315                1320                1325

Lys Ser Leu Asn Cys Arg Ser Leu Gly Ser Leu Met Tyr Phe Leu Ile
        1330                1335                1340

Val Ser Gly Asn Leu Lys Thr Ser Lys Asn Lys Pro Lys Leu Ile Arg
1345                1350                1355                1360

Val Arg Ile Lys Leu His Phe Lys Gln Leu His Arg Pro Leu Lys Lys
                1365                1370                1375

Leu Phe Leu Arg Leu Ser Leu Lys Ile Cys Pro Ile Asp Leu Phe Ser
        1380                1385                1390

Ile Leu Phe Pro Met Trp Ile Leu Trp Ile Thr Asn Ala Leu Tyr Met
        1395                1400                1405

Leu Ala His Thr Asn Gln Thr Ile Phe Arg Thr Leu His Val Leu Thr
        1410                1415                1420

Leu Thr Asn His Phe Ser Asn His Thr Leu Ala Leu His Leu Ile Ser
1425                1430                1435                1440

Ser Lys Arg Phe Ile Ser Tyr Phe Leu Phe Leu Leu Lys Phe Phe His
                1445                1450                1455

Phe Ser Lys Phe Leu Leu Ile Val Gly Lys Asn Val Asn Arg Pro Ser
        1460                1465                1470

Leu Thr Pro Ala Thr Ile Gly Leu Phe Ser Ile Leu Ile Met Ile Asn
        1475                1480                1485

Glu Lys Lys Lys Lys Cys Leu Ile Leu Leu Tyr Asn Glu Asn Val Gln
        1490                1495                1500

Arg His Glu Leu Thr Thr Gln Ala Cys Ser Asp Phe Gln Ser Leu Thr
1505                1510                1515                1520

Leu Thr Arg Tyr Arg Val Asn Val Gly Glu Thr Met Thr Asn Glu Thr
                1525                1530                1535

Ile Asp Gln Gln Pro Gln Thr Glu Ala Ala Phe Asn Pro Gln Gln Phe
        1540                1545                1550

Ile Asn Asn Leu Gln Val Ala Phe Leu Lys Val Asp Asn Ala Val Ala
        1555                1560                1565

Ser Tyr Asp Pro Asp Gln Lys Pro Ile Val Asp Lys Asn Asp Arg Asp
        1570                1575                1580

Asn Arg Gln Ala Phe Glu Gly Ile Ser Gln Leu Arg Glu Glu Tyr Ser
1585                1590                1595                1600

Asn Lys Ala Ile Lys Asn Pro Thr Lys Lys Asn Gln Tyr Phe Ser Asp
                1605                1610                1615

Phe Ile Asn Lys Ser Asn Asp Leu Ile Asn Lys Asp Asn Leu Ile Asp
        1620                1625                1630

Val Glu Ser Ser Thr Lys Ser Phe Gln Lys Phe Gly Asp Gln Arg Tyr
        1635                1640                1645

Arg Ile Phe Thr Ser Trp Val Ser His Gln Asn Asp Pro Ser Lys Ile
        1650                1655                1660

Asn Thr Arg Ser Ile Arg Asn Phe Met Glu Asn Ile Ile Gln Pro Pro
```

-continued

```
             1665                1670                1675                1680
   Ile Leu Asp Asp Lys Glu Lys Ala Glu Phe Leu Lys Ser Ala Lys Gln
                    1685                1690                1695

Ser Phe Ala Gly Ile Ile Ile Gly Asn Gln Ile Arg Thr Asp Gln Lys
                    1700                1705                1710

Phe Met Gly Val Phe Asp Glu Ser Leu Lys Glu Arg Gln Glu Ala Glu
                    1715                1720                1725

Lys Asn Gly Glu Pro Thr Gly Gly Asp Trp Leu Asp Ile Phe Leu Ser
                    1730                1735                1740

Phe Ile Phe Asp Lys Lys Gln Ser Ser Asp Val Lys Glu Ala Ile Asn
   1745                1750                1755                1760

Gln Glu Pro Val Pro His Val Gln Pro Asp Ile Ala Thr Thr Thr Thr
                    1765                1770                1775

Asp Ile Gln Gly Leu Pro Pro Glu Ala Arg Asp Leu Leu Asp Glu Arg
                    1780                1785                1790

Gly Asn Phe Ser Lys Phe Thr Leu Gly Asp Met Glu Met Leu Asp Val
                    1795                1800                1805

Glu Gly Val Ala Asp Ile Asp Pro Asn Tyr Lys Phe Asn Gln Leu Leu
                    1810                1815                1820

Ile His Asn Asn Ala Leu Ser Ser Val Leu Met Gly Ser His Asn Gly
   1825                1830                1835                1840

Ile Glu Pro Glu Lys Val Ser Leu Leu Tyr Gly Gly Asn Gly Gly Pro
                    1845                1850                1855

Gly Ala Arg His Asp Trp Asn Ala Thr Val Gly Tyr Lys Asp Gln Gln
                    1860                1865                1870

Gly Asn Asn Val Ala Thr Ile Ile Asn Val His Met Lys Asn Gly Ser
                    1875                1880                1885

Gly Leu Val Ile Ala Gly Gly Glu Lys Gly Ile Asn Asn Pro Ser Phe
                    1890                1895                1900

Tyr Leu Tyr Lys Glu Asp Gln Leu Thr Gly Ser Gln Arg Ala Leu Ser
   1905                1910                1915                1920

Gln Glu Glu Ile Gln Asn Lys Ile Asp Phe Met Glu Phe Leu Ala Gln
                    1925                1930                1935

Asn Asn Ala Lys Leu Asp Asn Leu Ser Glu Lys Glu Lys Glu Lys Phe
                    1940                1945                1950

Arg Thr Glu Ile Lys Asp Phe Gln Lys Asp Ser Lys Ala Tyr Leu Asp
                    1955                1960                1965

Ala Leu Gly Asn Asp Arg Ile Ala Phe Val Ser Lys Lys Asp Thr Lys
                    1970                1975                1980

His Ser Ala Leu Ile Thr Glu Phe Gly Asn Gly Asp Leu Ser Tyr Thr
   1985                1990                1995                2000

Leu Lys Asp Tyr Gly Lys Lys Ala Asp Lys Ala Leu Asp Arg Glu Lys
                    2005                2010                2015

Asn Val Thr Leu Gln Gly Ser Leu Lys His Asp Gly Val Met Phe Val
                    2020                2025                2030

Asp Tyr Ser Asn Phe Lys Tyr Thr Asn Ala Ser Lys Asn Pro Asn Lys
                    2035                2040                2045

Gly Val Gly Val Thr Asn Gly Val Ser His Leu Glu Val Gly Phe Asn
                    2050                2055                2060

Lys Val Ala Ile Phe Asn Leu Pro Asp Leu Asn Asn Leu Ala Ile Thr
   2065                2070                2075                2080

Ser Phe Val Arg Arg Asn Leu Glu Asp Lys Leu Thr Thr Lys Gly Leu
                    2085                2090                2095
```

-continued

```
Ser Pro Gln Glu Ala Asn Lys Leu Ile Lys Asp Phe Leu Ser Ser Asn
            2100                2105                2110
Lys Glu Leu Val Gly Lys Thr Leu Asn Phe Asn Lys Ala Val Ala Asp
            2115                2120                2125
Ala Lys Asn Thr Gly Asn Tyr Asp Glu Val Lys Lys Ala Gln Lys Asp
            2130                2135                2140
Leu Glu Lys Ser Leu Arg Lys Arg Glu His Leu Glu Lys Glu Val Glu
2145                2150                2155                2160
Lys Lys Leu Glu Ser Lys Ser Gly Asn Lys Asn Lys Met Glu Ala Lys
            2165                2170                2175
Ala Gln Ala Asn Ser Gln Lys Asp Glu Ile Phe Ala Leu Ile Asn Lys
            2180                2185                2190
Glu Ala Asn Arg Asp Ala Arg Ala Ile Ala Tyr Ala Gln Asn Leu Lys
            2195                2200                2205
Gly Ile Lys Arg Glu Leu Ser Asp Lys Leu Glu Asn Val Asn Lys Asn
            2210                2215                2220
Leu Lys Asp Phe Asp Lys Ser Phe Asp Glu Phe Lys Asn Gly Lys Asn
2225                2230                2235                2240
Lys Asp Phe Ser Lys Ala Glu Glu Thr Leu Lys Ala Leu Lys Gly Ser
            2245                2250                2255
Val Lys Asp Leu Gly Ile Asn Pro Glu Trp Ile Ser Val Glu Asn
            2260                2265                2270
Leu Asn Ala Ala Leu Asn Glu Phe Lys Asn Gly Lys Asn Lys Asp Phe
            2275                2280                2285
Ser Lys Val Thr Gln Ala Lys Ser Asp Leu Glu Asn Ser Val Lys Asp
            2290                2295                2300
Val Ile Ile Asn Gln Lys Val Thr Asp Lys Val Asp Asn Leu Asn Gln
2305                2310                2315                2320
Ala Val Ser Val Ala Lys Ala Thr Gly Asp Phe Ser Arg Val Glu Gln
            2325                2330                2335
Ala Leu Ala Asp Leu Lys Asn Phe Ser Lys Glu Gln Leu Ala Gln Gln
            2340                2345                2350
Ala Gln Lys Asn Glu Ser Leu Asn Ala Arg Lys Lys Ser Glu Ile Tyr
            2355                2360                2365
Gln Ser Val Lys Asn Gly Val Asn Gly Thr Leu Val Gly Asn Gly Leu
            2370                2375                2380
Ser Gln Ala Glu Ala Thr Thr Leu Ser Lys Asn Phe Ser Asp Ile Lys
2385                2390                2395                2400
Lys Glu Leu Asn Ala Lys Leu Gly Asn Phe Asn Asn Asn Asn Asn
            2405                2410                2415
Gly Leu Lys Asn Glu Pro Ile Tyr Ala Lys Val Asn Lys Lys Ala
            2420                2425                2430
Gly Gln Ala Ala Ser Leu Glu Glu Pro Ile Tyr Ala Gln Val Ala Lys
            2435                2440                2445
Lys Val Asn Ala Lys Ile Asp Arg Leu Asn Gln Ile Ala Ser Gly Leu
            2450                2455                2460
Gly Val Val Gly Gln Ala Ala Gly Phe Pro Leu Lys Arg His Asp Lys
2465                2470                2475                2480
Val Asp Asp Leu Ser Lys Val Gly Leu Ser Arg Asn Gln Glu Leu Ala
            2485                2490                2495
Gln Lys Ile Asp Asn Leu Asn Gln Ala Val Ser Glu Ala Lys Ala Gly
            2500                2505                2510
Phe Phe Gly Asn Leu Glu Gln Thr Ile Asp Lys Leu Lys Asp Ser Thr
            2515                2520                2525
```

```
Lys His Asn Pro Met Asn Leu Trp Val Glu Ser Ala Lys Lys Val Pro
                2530                2535                2540
Ala Ser Leu Ser Ala Lys Leu Asp Asn Tyr Ala Thr Asn Ser His Ile
2545                2550                2555                2560
Arg Ile Asn Ser Asn Ile Lys Asn Gly Ala Ile Asn Glu Lys Ala Thr
                2565                2570                2575
Gly Met Leu Thr Gln Lys Asn Pro Glu Trp Leu Lys Leu Val Asn Asp
                2580                2585                2590
Lys Ile Val Ala His Asn Val Gly Ser Val Pro Leu Ser Glu Tyr Asp
                2595                2600                2605
Lys Ile Gly Phe Asn Gln Lys Asn Met Lys Asp Tyr Ser Asp Ser Phe
                2610                2615                2620
Lys Phe Ser Thr Lys Leu Asn Asn Ala Val Lys Asp Thr Asn Ser Gly
2625                2630                2635                2640
Phe Thr Gln Phe Leu Thr Asn Ala Phe Ser Thr Ala Ser Tyr Tyr Cys
                2645                2650                2655
Leu Ala Arg Glu Asn Ala Glu His Gly Ile Lys Asn Val Asn Thr Lys
                2660                2665                2670
Gly Gly Phe Gln Lys Ser Arg Ile Lys Glu Tyr Gln Lys Arg Lys Asn
                2675                2680                2685
His Pro Leu Leu Lys Ala Arg Gly Phe Leu Ile Leu Leu Ser Arg Asn
                2690                2695                2700
Pro Asn Arg Leu Tyr Leu Gly Met Leu Pro Ile His Gly Ile Ile Ser
2705                2710                2715                2720
Pro Tyr Ile Arg Ile Arg Arg Lys Cys Ala Lys Leu Arg Leu Trp Arg
                2725                2730                2735
Tyr Asp Val Asp Leu Gly Met Arg Trp Ser Ser Asn Ser Val Lys Ser
                2740                2745                2750
Leu Leu Gly His Arg Val Arg Thr Lys Leu Ser Leu Arg Ala Thr Ser
                2755                2760                2765
Ala Glu Ala Gln Ser Ser Leu Ala Val Gly His Phe Thr Leu Lys Tyr
                2770                2775                2780
Pro Asp Arg His Arg Lys Ala Leu Phe Phe Lys Val Cys Met Asp Ile
2785                2790                2795                2800
Ser Tyr Pro Lys Lys Thr Pro Phe Ala Asn Val Leu Cys Trp Val Arg
                2805                2810                2815
Ala Ile Val Arg Lys Leu Ile Lys Gly Tyr Lys Glu Ser Ile Asn Lys
                2820                2825                2830
Lys Gln Val Ala Ile Thr Lys Ile Lys Phe Lys Ser Ser Phe Ser
                2835                2840                2845
Lys Leu Ile Ala Leu Leu Thr Lys Glu Lys Ser Glu Lys Pro Glu Leu
2850                2855                2860
Ser His Leu Ile Met Pro Lys Lys Asp Ala Cys Asp Gln Lys Trp Lys
2865                2870                2875                2880
Asn Thr Ala Ser Arg Ile Leu Met Ser Ser Lys Thr Leu Trp Met Pro
                2885                2890                2895
Phe Lys Val Lys Arg Gln Ile Leu Leu Phe Ile Pro Pro Lys Leu Val
                2900                2905                2910
Val Ile Phe Leu Ser Cys Ile Leu Asn Ala Met Trp Leu Phe Leu Gly
                2915                2920                2925
Gln Lys Lys Ile Ser Phe Leu Trp Val Lys Ser Leu Ser Leu Arg Ile
                2930                2935                2940
Tyr Glu Ala Met Arg Arg Ile Ser Leu Ala Leu Phe Cys Lys Ser Val
```

-continued

```
                2945                2950                2955                2960
    Asp Arg Ser Phe Pro Lys Ile Ile Arg His Ser Ser Leu Gln Asn
                    2965                2970                2975
    Ala Phe Ile Asn Leu Ser Lys Ala Leu Tyr Asn Gln His Asn Thr Leu
                    2980                2985                2990
    Ile Val Ala Ile Ala Pro Phe Trp Glu Leu Ser Tyr Phe Asp Phe Lys
                    2995                3000                3005
    Phe Leu Leu Ala Leu Gln Phe Glu Pro Phe Phe Ser Leu Phe Phe Pro
                    3010                3015                3020
    Asp His Ile Ala Ala Arg Met Lys Phe His Phe Arg Glu Cys Val Cys
    3025                3030                3035                3040
    Ile Phe Phe Lys Gly Val Phe Leu Leu Gln Ile Ser Tyr Asn Ser Ile
                    3045                3050                3055
    Ala Arg Met Asp Glu Gly Gly Cys Lys Gly Lys Met Leu His Lys Ile
                    3060                3065                3070
    Ala Leu Asn Phe Leu Ser Asp Gly Lys Met Arg Ala Thr Asn Asn His
                    3075                3080                3085
    Phe Gly Lys Ile Phe Lys Gly Val Lys Arg Met Gln Val Ser Asn Asn
                    3090                3095                3100
    Ser Pro Ser Lys Ile Leu Ser Ser Ile Lys Gly Thr Lys Arg Glu Val
    3105                3110                3115                3120
    Ala Lys Cys Glu Thr Phe Lys Pro Cys Cys Phe Arg Ala Leu Ser Ala
                    3125                3130                3135
    Leu Asp Trp Ile Val Ala Phe Val Pro Ser Thr Lys Ile Gly Ala Phe
                    3140                3145                3150
    Leu Ser Phe Thr Cys Arg Leu Ile Ala Lys Met Leu Gly Ser Ile Thr
                    3155                3160                3165
    Pro Thr Ile Gly Ile Leu Glu Cys Phe Cys Ile Ser Ser Lys Ala Arg
                    3170                3175                3180
    Ala Leu Ala Val Leu His Ala Thr Ile Asn Asn Ser Ile Trp Cys Gly
    3185                3190                3195                3200
    Leu Lys Lys Ser Lys Ala Ser Lys Pro Asn Cys Leu Ile Val Val Gly
                    3205                3210                3215
    Ser Leu Val Pro Gly Thr Leu Ala Val Ser Pro Met Ile Ser Ser Asn
                    3220                3225                3230
    Asn Cys Ala Phe Lys Arg Leu Phe Lys Thr Leu Asn Pro Pro Thr Pro
                    3235                3240                3245
    Leu Ser Lys Thr Pro Ile Phe Met Thr Leu Phe Phe Asn Gly Ile Asn
                    3250                3255                3260
    Gly Phe Tyr Phe Ser Phe Ile Leu Phe Lys Asn Ser Ser Leu Ser Leu
    3265                3270                3275                3280
    Val Cys Cys Ile Leu Glu Thr Lys Leu
                    3285
```

(2) INFORMATION FOR SEQ ID NO:3:

(i) SEQUENCE CHARACTERISTICS:
        (A) LENGTH: 3174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
    Leu Phe Ser Asp Phe Ala Phe His Phe Phe Tyr Glu Val Gln Phe
    1                   5                   10                  15
```

```
Phe Phe Gln Phe Lys Lys Ile Ile Arg Lys Thr Ile Gln Asn Arg Gln
            20                  25                  30

Asp Ile Ile Phe Lys Ile Ser Asn Asn Phe Cys Ser Arg Lys Phe Cys
        35                  40                  45

Phe Ile Leu Ile Leu Leu Tyr Leu Leu Ile His Leu Ser Gln Gly Leu
    50                  55                  60

Ile Phe Ile Tyr Asp Thr Met Val Leu Asp Asn Leu Ile Asn Phe Phe
65                  70                  75                  80

Asp Lys Tyr Ser Ile Cys Gly Asn Phe Gln Ile Phe Phe Arg Asn Ala
                85                  90                  95

Ser Gln Ile Lys Thr Ser Asp Asn Ala Arg Ala Ser Ile Leu Phe Val
            100                 105                 110

Glu Asp Phe Pro Ile Ser Leu Ser Asp Asp Phe Lys Phe Phe Cys
        115                 120                 125

Asn Ile Ser Gln Ser Leu Val Ile Arg Lys Ile Ala Pro Ile Val Ser
    130                 135                 140

Gln Lys Asn Leu Cys Arg Ala Leu Phe Ser Asn Arg Ile Ser Asn Arg
145                 150                 155                 160

Ala Ser Gln Lys Ile Ser Asp Ala Leu Ser Arg Lys Ser Asp Asn Ser
                165                 170                 175

Val Ser Phe Pro Cys Ser Phe His Val Ser Tyr Lys Ile Ser Asp Leu
            180                 185                 190

Trp Ile Ala Lys Tyr Phe Gln Ala Ser Ser Ile Ser Lys Thr Asn Leu
        195                 200                 205

Arg Pro Ser Ile Ala Ser Trp Ile Arg Ala Lys Arg Lys Gln Ile Lys
    210                 215                 220

Gly Glu Thr Ser Leu Leu Ser Lys Lys Leu Asp Pro Ser Thr Pro Ile
225                 230                 235                 240

Ile Val Phe Glu Lys Ser Lys Arg Ser Val Ala Leu Leu Ser Lys Ser
                245                 250                 255

His Asn Ser Pro Leu Val Asp Leu Gln Lys Gly Ala Asn Arg Ala Thr
            260                 265                 270

Ser Pro Leu Gly Ser Leu Trp Ser Phe Pro Lys Ala Leu Ile Ser Val
        275                 280                 285

Met Gly Ser Arg Phe Ile Phe Pro Val Ile Arg Leu Val Thr Ala Leu
    290                 295                 300

Gln Ala Tyr Asn Leu Leu Gly Lys Arg Cys Cys Cys His Phe His Leu
305                 310                 315                 320

Phe His Arg Phe Leu Leu Ser Phe Ser Gln Ala Leu Gln Gln Lys Leu
                325                 330                 335

Phe Val Phe Ala Pro Leu Leu His Leu Phe Phe Ala His Lys Pro Pro
            340                 345                 350

Lys Gln Lys Asp Leu Ile Leu Tyr Leu Ser Leu Ala Gln Ser His Thr
        355                 360                 365

Pro His Pro Leu Arg Gln Tyr Ser His Lys Arg His Asn Leu Tyr Pro
    370                 375                 380

Tyr Lys Pro Ala Phe Ala Cys Leu Cys His Gln Glu Asn Tyr Arg Gln
385                 390                 395                 400

Ile Val Pro Arg Ser Arg Ser Leu Thr Thr Leu Ser Tyr Leu Asn Arg
                405                 410                 415

Leu Ser Gln Val Ser Lys Cys Val Leu Leu Lys Leu Asn Gln Asn Gln
            420                 425                 430

Trp Ala Cys Gly Ser Ser Asp Lys Lys Ala Asn Ser Arg Phe Leu Ala
```

```
                      435                 440                 445
    Ser Ser His Tyr Cys Pro Lys Arg Tyr Ser Leu Asp Cys His Gln Asn
        450                 455                 460
    Ser Pro Ser Arg Asn Gln Gln Asn Tyr Lys Leu His Gln Lys Lys Glu
    465                 470                 475                 480
    Ala Lys Ser Asn Val Trp Gln Lys Ser Asn Phe Pro Arg Lys Ser Leu
                    485                 490                 495
    Arg Trp Leu Lys Asn Leu Arg Asp Arg Ile Pro Arg Phe Val Ser
                500                 505                 510
    Phe Phe Gln Ser Tyr Gln Thr Ala Leu Lys Asn Tyr His Asn Cys
            515                 520                 525
    Leu Ala Tyr His His Tyr Pro Leu Ile Arg Ser Ser Asn Leu Lys Ser
        530                 535                 540
    Cys Pro Val Leu Ser Leu His Phe Phe Arg Lys Pro Val Cys Pro Leu
    545                 550                 555                 560
    Lys Pro Val Ser Phe Ala Asn Lys His Ala Lys Ile Arg Cys Leu Gly
                    565                 570                 575
    Arg Phe Tyr Gln Thr Asn Arg Phe Val Ile Gly Arg Ile His Ser Gln
                580                 585                 590
    Arg Asn Ile Phe His Ser Asn Arg His Leu Arg Phe Phe His Ala Tyr
            595                 600                 605
    Trp Gln Asn Lys Leu Leu Ser Pro His His Ala Phe Phe Pro Asp Thr
        610                 615                 620
    Ser Leu Phe Gly Cys Lys Lys Gly Leu His Ser Phe Pro Lys Glu Asn
    625                 630                 635                 640
    Cys Lys Ile Arg Ile Val Trp Ser Lys Arg His Leu Cys Ile Leu Leu
                    645                 650                 655
    Ile Trp Gly Gly Ile Cys Ser Thr Ala Leu Leu Ala Leu Ser Tyr Pro
                660                 665                 670
    Ser Phe Gln Ala Trp Leu Ser Phe Glu Thr Leu Gln Asn Tyr Cys Leu
            675                 680                 685
    Gln Asn Ala Phe Tyr Ser Arg Val His Glu Cys Leu Ile Asn Leu Ala
        690                 695                 700
    Leu Trp Ser Glu Lys Asn Tyr His Lys Asn Phe Leu Ser Phe Ala Ser
    705                 710                 715                 720
    His Tyr Arg Leu Ala Asn His Lys Lys Asp His Ser Pro Tyr Trp Phe
                    725                 730                 735
    His Gln Arg Phe Ser Phe Cys Glu Asn Arg Ile Ile Gln Gly Gln Asn
                740                 745                 750
    Ser Lys Arg Tyr Lys Lys Arg Val Thr Leu Asp Leu Phe Trp Lys Trp
            755                 760                 765
    Leu Lys Asn Gln Cys Pro Pro Ile Leu Cys Leu Lys Glu Asn Ser Cys
        770                 775                 780
    Gly Ser Pro His His Leu Lys Asn Ile His Ser Tyr Leu Leu Asp Arg
    785                 790                 795                 800
    Ser Leu Gln Arg Ser Gln Val Cys Leu Leu Cys Leu Asp Leu Ser Gly
                    805                 810                 815
    Cys His Pro Phe Leu Tyr Ala Ser Trp Lys Lys Cys Ser Thr Leu Cys
                820                 825                 830
    Phe Ser Arg Pro Thr Lys Lys Val Phe Ile Ser Ser Leu Ala Pro Phe
            835                 840                 845
    Phe Asp Lys Ala Tyr Asn Leu Ser Ile Gln Glu Leu Gln Ala Gln Gln
        850                 855                 860
```

```
Ser Leu Gln Ser Lys Gln Val His Arg Leu Glu Lys Glu Gln Ile Ile
865                 870                 875                 880

Gln Trp Leu Gln Thr Ile Ile Arg Asn Lys Lys Phe Gln Gly Asn Gln
                885                 890                 895

Thr Thr Tyr Ser Pro His Gln Thr Arg Leu Lys Arg Asp His Pro Phe
            900                 905                 910

Ala Cys Leu Leu Val Leu Leu Phe Glu Thr Ala Ala Phe Glu Pro
        915                 920                 925

Leu Ala Leu Leu Ala Phe Phe Val His Gln Pro Ala Cys Leu Pro Gln
    930                 935                 940

Thr Pro Leu Ser Leu Ile Tyr Arg Phe Thr Cys Asn Arg Ile Lys Asp
945                 950                 955                 960

Phe Phe Glu Arg Leu Tyr Gly Ala Asn Met Phe Gln Lys Ile Ile Arg
                965                 970                 975

Ile Ile Arg Ile Glu Tyr Gly Gln Asn Ile Ile Leu Ile Ile Ala Asn
            980                 985                 990

Phe Ser Cys Phe Ser Ala Gln Gln Lys Ala Ala Leu Phe Val Gly Arg
        995                 1000                1005

Ala Asp Ala Phe Glu Ser Lys Lys Val Phe His Phe Arg Ile Asp Leu
    1010                1015                1020

Phe Tyr Ile Gln Ser His Phe Leu Thr Leu Phe Ile Lys Asp Phe Phe
1025                1030                1035                1040

Asn Asn Trp Ile Val Met Leu Gln Ile Leu Tyr Phe Phe Lys Asp Ser
                1045                1050                1055

Ile Asp Asn His Glu Val Lys Asn Phe Ile Phe Asp Asn Ile Gly Ile
            1060                1065                1070

Asp Phe Phe Glu Ser Tyr Phe Leu Val Phe Gln Ile Phe Asp Ser Arg
        1075                1080                1085

Phe Glu Thr Ile Lys Ile Ile Cys Ile Asn Lys Pro Ile Gly Ser Val
    1090                1095                1100

Phe Phe Phe Phe Leu Cys Phe Phe Gly Phe Phe Val Ile Ile Cys
1105                1110                1115                1120

Pro Ile Arg Thr Glu Asn Asn Glu Thr Glu Asn Phe Gln Lys Lys Ala
                1125                1130                1135

Ser Phe Leu Ile Ala Ile Ile Ile Val Asp Gln Leu Ser Leu Leu
            1140                1145                1150

His Pro Arg Gln Tyr Ser Gln Thr Cys Ser Asn Arg Tyr Arg Leu Pro
        1155                1160                1165

Pro Leu Thr Leu Trp Val Ala Arg Lys Gln Lys Gln Ser Pro Asp Leu
    1170                1175                1180

Phe Cys His Gln Arg Phe Ser Lys Tyr Pro Leu Cys Leu Pro Leu Lys
1185                1190                1195                1200

Arg Asn His Leu Arg Ser Leu Glu Gln Lys Ser Glu Pro Asn Leu Leu
                1205                1210                1215

Gln Arg Leu Leu Asp Trp Arg Pro Leu Lys Asp Trp Leu Leu Pro
            1220                1225                1230

Leu Ala Leu Lys Leu Leu Gln Leu Ser Cys Ser Cys Gln Phe Leu Lys
        1235                1240                1245

Ile Ser Cys Val Ser Phe Gln Ile Glu Ile Asn Arg Leu Ser Ile Ser
    1250                1255                1260

Lys Lys Lys Val Phe Leu Tyr Tyr Ser Tyr Lys Arg Tyr Phe Ile Ile
1265                1270                1275                1280

Ile Lys Thr Asp Ala Phe Ala Arg Gln Leu Thr Ser Phe Arg Asn Ser
                1285                1290                1295
```

```
Lys Pro Thr Cys Pro Asn His Phe Ser Phe Ser Ser Arg Cys Arg Ile
            1300                1305                1310

Val Asp Leu Asp Leu Cys Ile Phe Ser Ser Gln Val Glu Thr Lys Gln
        1315                1320                1325

Ala Lys Thr Asn Pro Ser Ser Glu Glu Ser Ser Ile Leu Ser Asn Ser
        1330                1335                1340

Ile Asp His Arg Asn Phe Phe Gly Tyr Leu Lys Ser Val Leu Leu Ile
1345                1350                1355                1360

Cys Phe Pro Phe Cys Phe Pro Cys Gly Ser Cys Gly Ser Gln Thr Leu
            1365                1370                1375

Asn Tyr Thr Cys Tyr Ser Lys His Asp Thr Gln Thr Lys Leu Phe Leu
        1380                1385                1390

Glu Arg Phe Met Cys Ser Pro Leu Thr Ile Ser Pro Thr Ile Leu Arg
        1395                1400                1405

Cys Ile Phe Leu Gln Lys Asp Ser Phe Leu Ile Ser Cys Ser Tyr Ser
        1410                1415                1420

Ser Phe Ile Leu Ala Asn Phe Cys Leu Trp Val Lys Met Ile Val Leu
1425                1430                1435                1440

Ala Phe Arg Arg Leu Gln Arg Ser Gly Phe Phe Gln Tyr Leu Met Lys
            1445                1450                1455

Lys Lys Lys Asn Ala Tyr Cys Cys Ile Met Arg Met Phe Lys Asp Met
        1460                1465                1470

Asn Leu Leu Lys Arg Val Ala Ile Phe Ser Ser Leu His Gln Asp Thr
        1475                1480                1485

Asp Arg Tyr Glu Thr Arg Tyr Ser Lys Glu Lys Gln Leu Thr Lys Pro
        1490                1495                1500

Leu Thr Asn Asn His Lys Pro Lys Arg Leu Leu Thr Arg Ser Asn Leu
1505                1510                1515                1520

Ser Ile Ile Phe Lys Leu Phe Leu Lys Leu Ile Thr Leu Ser Leu His
            1525                1530                1535

Thr Ile Leu Ile Lys Asn Gln Ser Leu Ile Arg Thr Ile Gly Ile Thr
            1540                1545                1550

Gly Lys Leu Leu Lys Glu Ser Arg Asn Gly Lys Asn Thr Pro Ile Lys
        1555                1560                1565

Arg Ser Lys Ile Leu Pro Lys Arg Ile Ser Ile Phe Gln Thr Leu Ser
        1570                1575                1580

Ile Arg Ala Met Ile Ser Thr Lys Thr Ile Ser Leu Met Asn Leu Pro
1585                1590                1595                1600

Gln Arg Ala Phe Arg Asn Leu Gly Ile Ser Val Thr Glu Phe Ser Gln
            1605                1610                1615

Val Gly Cys Pro Ile Lys Thr Ile Arg Leu Lys Ser Thr Pro Asp Arg
        1620                1625                1630

Ser Glu Ile Leu Trp Lys Ile Ser Tyr Asn Pro Leu Ser Leu Met Ile
        1635                1640                1645

Lys Arg Lys Arg Ser Phe Asn Leu Pro Asn Asn Leu Leu Gln Glu Ser
        1650                1655                1660

Leu Gly Ile Lys Ser Glu Arg Ile Lys Ser Ser Trp Ala Cys Leu Met
1665                1670                1675                1680

Ser Pro Lys Lys Gly Lys Lys Gln Lys Met Glu Ser Leu Leu Val
            1685                1690                1695

Gly Ile Gly Trp Ile Phe Phe Ser His Leu Tyr Leu Thr Lys Asn Asn
        1700                1705                1710

Leu Leu Met Ser Lys Lys Gln Ser Ile Lys Asn Gln Phe Pro Met Ser
```

```
                    1715                1720                1725
    Asn Gln Ile Pro Leu Pro Pro Pro Thr Tyr Lys Ala Tyr Arg Leu Lys
        1730                1735                1740

Leu Glu Ile Tyr Leu Met Lys Gly Val Ile Phe Leu Asn Ser Leu Leu
    1745                1750                1755                1760

Ala Ile Trp Lys Cys Met Leu Arg Glu Ser Leu Thr Leu Ile Pro Ile
                    1765                1770                1775

Thr Ser Ser Ile Asn Tyr Phe Thr Ile Thr Leu Cys Leu Leu Cys Trp
                    1780                1785                1790

Gly Val Ile Met Ala Asn Leu Lys Lys Phe His Cys Cys Met Gly Ala
                1795                1800                1805

Met Val Val Leu Glu Leu Gly Met Ile Gly Thr Pro Pro Leu Val Ile
        1810                1815                1820

Lys Thr Asn Lys Ala Thr Met Trp Leu Gln Leu Met Cys Ile Lys Thr
    1825                1830                1835                1840

Ala Val Ala Ser Gln Val Val Arg Lys Gly Leu Thr Thr Leu Val Phe
                    1845                1850                1855

Ile Ser Thr Lys Lys Thr Asn Ser Gln Ala His Asn Glu His Val Lys
                    1860                1865                1870

Lys Arg Ser Lys Thr Lys Ile Ser Trp Asn Phe Leu His Lys Ile Met
                1875                1880                1885

Leu Asn Thr Thr Ala Arg Lys Arg Lys Asn Ser Glu Leu Arg Leu
        1890                1895                1900

Lys Ile Ser Lys Lys Thr Leu Arg Leu Ile Thr Pro Gly Met Ile Val
    1905                1910                1915                1920

Leu Leu Leu Phe Leu Lys Lys Thr Gln Asn Ile Gln Leu Leu Leu Ser
                    1925                1930                1935

Leu Val Met Gly Ile Ala Thr Leu Ser Lys Ile Met Gly Lys Lys Gln
                1940                1945                1950

Ile Lys Leu Ile Gly Arg Lys Met Leu Leu Phe Lys Val Ala Asn Met
                1955                1960                1965

Met Ala Cys Leu Leu Ile Ile Leu Ile Ser Asn Thr Pro Thr Pro Pro
        1970                1975                1980

Arg Ile Pro Ile Arg Val Ala Leu Arg Met Ala Phe Pro Ile Lys Ala
    1985                1990                1995                2000

Leu Thr Arg Leu Ser Leu Ile Cys Leu Ile Ile Ile Ser Leu Ser Leu
                    2005                2010                2015

Val Ser Gly Gly Ile Arg Ile Asn Pro Leu Lys Asp Cys Pro His Lys
                    2020                2025                2030

Lys Leu Ile Ser Leu Ser Lys Ile Phe Ala Ala Thr Lys Asn Trp Leu
                2035                2040                2045

Glu Lys Leu Thr Ser Ile Lys Leu Leu Thr Leu Lys Thr Gln Ala Ile
        2050                2055                2060

Met Met Lys Lys Lys Leu Arg Lys Ile Leu Lys Asn Leu Gly Asn Glu
    2065                2070                2075                2080

Ser Ile Arg Lys Lys Arg Lys Asn Trp Arg Ala Lys Ala Ala Thr Lys
                    2085                2090                2095

Ile Lys Trp Lys Gln Lys Leu Leu Leu Thr Ala Lys Met Arg Phe
                2100                2105                2110

Leu Arg Ser Ile Lys Arg Leu Ile Glu Thr Gln Glu Gln Ser Leu Thr
                    2115                2120                2125

Leu Arg Ile Leu Lys Ala Ser Lys Gly Asn Cys Leu Ile Asn Leu Lys
                2130                2135                2140
```

```
Met Ser Thr Arg Ile Lys Thr Leu Ile Asn Leu Leu Met Asn Ser Lys
2145                2150                2155                2160

Met Ala Lys Ile Arg Ile Ser Ala Arg Gln Lys Lys His Lys Pro Leu
            2165                2170                2175

Lys Val Arg Lys Ile Val Ser Ile Gln Asn Gly Phe Gln Lys Leu Lys
        2180                2185                2190

Thr Leu Met Gln Leu Met Asn Ser Lys Met Ala Lys Ile Arg Ile Ser
    2195                2200                2205

Ala Arg Arg Lys Gln Lys Ala Thr Leu Lys Ile Pro Leu Lys Met Ser
2210                2215                2220

Ser Ile Lys Arg Arg Ile Lys Leu Ile Ile Ser Ile Lys Arg Tyr Gln
2225                2230                2235                2240

Trp Leu Lys Gln Arg Val Ile Ser Val Gly Ser Lys Arg Pro Ile Ser
            2245                2250                2255

Lys Ile Ser Gln Arg Ser Asn Trp Pro Asn Lys Leu Lys Met Lys
        2260                2265                2270

Val Ser Met Leu Glu Lys Asn Leu Lys Tyr Ile Asn Pro Leu Arg Met
    2275                2280                2285

Val Met Glu Pro Ser Val Met Gly Tyr Leu Lys Gln Lys Pro Gln Leu
    2290                2295                2300

Phe Leu Lys Thr Phe Arg Thr Ser Arg Lys Ser Met Gln Asn Leu Glu
2305                2310                2315                2320

Ile Ser Ile Thr Ile Thr Ile Met Asp Ser Lys Thr Asn Pro Phe Met
            2325                2330                2335

Leu Lys Leu Ile Lys Arg Lys Gly Lys Gln Leu Ala Leu Lys Asn
        2340                2345                2350

Pro Phe Thr Leu Lys Leu Leu Lys Arg Met Gln Lys Leu Thr Asp Ser
    2355                2360                2365

Ile Lys Gln Val Val Trp Val Leu Gly Lys Gln Arg Ala Ser Leu Lys
2370                2375                2380

Gly Met Ile Lys Leu Met Ile Ser Val Arg Gly Phe Gln Gly Ile Lys
2385                2390                2395                2400

Asn Trp Leu Arg Lys Leu Thr Ile Ser Ile Lys Arg Tyr Gln Lys Leu
            2405                2410                2415

Lys Gln Val Phe Leu Ala Ile Ser Lys Arg Thr Ser Ser Lys Ile Leu
        2420                2425                2430

Gln Asn Thr Ile Pro Ile Tyr Gly Leu Lys Val Gln Lys Lys Tyr Leu
    2435                2440                2445

Leu Val Cys Gln Arg Asn Thr Ile Thr Leu Leu Thr Ala Thr Tyr Ala
    2450                2455                2460

Leu Ile Ala Ile Ser Lys Met Glu Gln Ser Met Lys Lys Arg Pro Ala
2465                2470                2475                2480

Cys Arg Lys Lys Thr Leu Ser Gly Ser Ser Met Ile Arg Leu Arg
            2485                2490                2495

Ile Met Glu Ala Phe Leu Cys Gln Ser Met Ile Lys Leu Ala Ser Thr
        2500                2505                2510

Arg Arg Ile Lys Ile Ile Leu Ile Arg Ser Ser Phe Pro Ser Thr
    2515                2520                2525

Met Leu Lys Thr Leu Ile Leu Ala Leu Arg Asn Phe Pro Met His Phe
    2530                2535                2540

Leu Gln His Leu Ile Thr Ala Trp Arg Glu Lys Met Arg Ser Met Glu
2545                2550                2555                2560

Ser Arg Thr Leu Ile Gln Lys Val Val Ser Lys Asn Leu Lys Gly Leu
            2565                2570                2575
```

-continued

```
Arg Asn Thr Lys Asn Ala Lys Thr Thr Pro Cys Lys Arg Gly Val Phe
            2580                2585                2590

Tyr Ser Leu Ala Glu Ile Pro Ile Val Phe Ser Ile Trp Asp Glu Cys
            2595                2600                2605

Tyr Gln Phe Met Val Ser Tyr Pro His Thr Phe Val Ser Ser Val Gly
            2610                2615                2620

Ser Val Gln Ser Tyr Ala Phe Gly Asp Met Met Cys Glu Thr Cys Arg
2625                2630                2635                2640

Glu Cys Val Gly Ala Gln Thr Leu Asn Pro Tyr Tyr Arg Asp Thr Glu
            2645                2650                2655

Glu Pro Asn Ser Pro Tyr Gly Gln His Gln Pro Arg Lys Pro Asn Arg
            2660                2665                2670

Leu Arg Leu Gly Thr Ser Pro Asn Ile Pro Thr Asp Thr Asn Glu Arg
            2675                2680                2685

Leu Cys Ser Leu Lys Ser Ala Trp Ile Phe Pro Thr Pro Lys Arg Leu
            2690                2695                2700

Asn Pro Leu Leu Lys Ile Lys Phe Asp Cys Ala Ser Gly Phe Val Leu
2705                2710                2715                2720

Cys Glu Asn Leu Arg Val Ile Lys Arg Ala Thr Arg Lys Asn Lys Leu
            2725                2730                2735

Gln Arg Ser Ser Ser Lys Asn His Arg Ala Phe Arg Ala Asn Ser Arg
            2740                2745                2750

Ser Pro Lys Lys Asn Gln Lys Asn His Arg Asn Tyr His Thr Leu Cys
            2755                2760                2765

Pro Lys Lys Thr Leu Ala Ile Arg Ser Gly Lys Ile Arg Leu Gln Glu
            2770                2775                2780

Phe Ala Gln Asn Arg His Cys Gly Cys Leu Ser Arg Arg Gly Arg Tyr
2785                2790                2795                2800

Tyr Tyr Leu Phe His Arg Glu Asn Leu Trp Ser Phe Phe Leu Ala Arg
            2805                2810                2815

Phe Thr Leu Glu Cys Gly Tyr Phe Gly Lys Arg Lys Ser His Phe Cys
            2820                2825                2830

Gly Lys Val Phe Leu Glu Phe Thr Lys Arg Glu Glu Tyr Leu Arg Tyr
            2835                2840                2845

Phe Ala Ser Leu Ile Gly Asn Leu Phe Gln Arg Ser Leu Asp Ile Leu
2850                2855                2860

Arg Phe Lys Thr Leu Ser Ile Ser Leu Lys Arg Phe Ile Ile Asn Thr
2865                2870                2875                2880

Ile Pro Leu Cys Glu Leu Pro Leu Phe Gly Asn Val Ile Leu Thr Leu
            2885                2890                2895

Asn Phe Tyr Arg Tyr Asn Leu Ser His Ser Leu Ala Cys Phe Ser Ser
            2900                2905                2910

Gln Ile Thr Ser Pro Leu Ala Asn Ser Thr Leu Gly Asn Ala Cys Ala
            2915                2920                2925

Phe Phe Leu Arg Ala Tyr Phe Cys Cys Lys Tyr Pro Thr Ile Ala Ser
            2930                2935                2940

Pro Glu Trp Met Ser Arg Gly Gly Val Glu Arg Ala Lys Cys Ser Ile
2945                2950                2955                2960

Lys Pro Ser Ile Phe Ala Ile Lys Gly Lys Cys Val Gln Pro Lys Ile
            2965                2970                2975

Ile Thr Ser Gly Lys Ser Leu Arg Glu Asn Asn Asn Ala Cys Lys Phe
            2980                2985                2990

Leu Thr Ile Arg Pro Leu Lys Tyr Phe Leu Gln Ser Lys Ala Gln Lys
```

```
                    2995                3000                3005

Glu Lys Trp Leu Asn Ala Lys His Ser Asn Ser Leu Val Ser Gly
        3010                3015                3020

His Cys His Lys Arg Trp Ile Gly Ser Ser Leu Leu Ser Leu Ala Leu
    3025                3030                3035                3040

Lys Gly Arg Phe Tyr Leu Leu Val Ala Ser Leu Lys Cys Leu Ala
                    3045                3050                3055

Gln Ser Arg Pro Gln Gly Phe Trp Asn Ala Phe Ala Ser Leu Leu Lys
                    3060                3065                3070

Leu Glu Arg Ser Leu Cys Cys Met Pro Gln Ser Ile Ile Gln Ser Gly
                3075                3080                3085

Ala Val Lys Asn Pro Lys Pro Leu Ser Gln Ile Ala Ser Trp Gly Leu
                3090                3095                3100

Cys His Lys Ala Leu Pro Tyr Arg His Asn Arg Phe His Gln Ile Ile
    3105                3110                3115                3120

Ala Leu Leu Lys Gly Phe Leu Lys Arg Thr Leu Pro His Arg Tyr Gln
                3125                3130                3135

Lys Arg Leu Phe Ser His Phe Asn Leu Met Gly Leu Ile Arg Asp
                3140                3145                3150

Phe Ile Phe His Ser Leu Ser Leu Lys Ile Leu His Cys Pro Phe Val
                3155                3160                3165

Ala Phe Asn Arg Gln Ser
                3170

(2) INFORMATION FOR SEQ ID NO:4:

(i) SEQUENCE CHARACTERISTICS:
        (A) LENGTH: 3177 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Cys Ser Val Ile Ser Pro Ser Ile Ser Ser Ser Met Lys Ser Asn Ser
    1               5                   10                  15

Ser Phe Ser Ser Lys Arg Leu Glu Lys Leu Ser Lys Ile Val Lys Thr
                20                  25                  30

Ser Phe Ser Lys Phe Pro Ile Ile Phe Val His Ala Asn Phe Val Ser
                35                  40                  45

Phe Tyr Ser Ser Ile Cys Tyr Ile Cys Leu Lys Ala Tyr Leu Ser Met
            50                  55                  60

Ile Leu Trp Phe Trp Ile Ile Leu Ser Ile Leu Thr Asn Thr Val
    65                  70                  75                  80

Ser Val Asp Lys Ile Phe Lys Tyr Ser Leu Gly Met Pro Leu Lys Leu
                    85                  90                  95

Lys Leu Ala Ile Thr Leu Gly Leu Pro Ser Cys Leu Arg Ile Phe Leu
                100                 105                 110

Ser Ser Pro Leu Val Met Ile Ser Asn Ser Phe Ser Val Thr Leu Ala
                115                 120                 125

Asn Leu Trp Ser Glu Arg Leu Pro Pro Ser Phe Leu Lys Lys Ile Phe
                130                 135                 140

Val Gly His Cys Ser Leu Ile Val Ser Ala Ile Gly Gln Ala Lys Arg
    145                 150                 155                 160

Ser Val Met Leu Val Ala Ser Leu Thr Ile Ala Phe Leu Phe Leu Ala
                    165                 170                 175
```

```
Val Phe Ser Met Ser Leu Thr Lys Ala Thr Phe Gly Ser Leu Asn Ile
            180                 185                 190

Ser Arg Leu His Gln Tyr Leu Arg Gln Ile Tyr Ala His Pro Leu Pro
        195                 200                 205

Leu Gly Tyr Glu Arg Lys Gly Lys Asn Lys Arg Ala Lys His His Tyr
    210                 215                 220

Cys Leu Arg Asn Leu Thr His Gln Arg Gln Ser Phe Leu Lys Asn Leu
225                 230                 235                 240

Ser Asp Leu Leu Tyr Tyr Gln Lys Ala Ile Glu Ile His His Trp
                245                 250                 255

Leu Ile Cys Lys Lys Ala Leu Ile Ala Arg Gln Ala His Asp His Cys
            260                 265                 270

Gly Leu Ser Arg Lys His Val Glu Trp Asp Asn Leu Asp Ser Tyr Phe
        275                 280                 285

Leu Gly Trp Leu Leu Arg Cys Lys Arg Ile Arg Ile Cys Ala Lys Arg
    290                 295                 300

Asp Ala Val Ala Ile Phe Ile Phe Ile Ala Phe Ser Cys Val Phe
305                 310                 315                 320

His Lys Leu Phe Asp Asn Arg Asn Ser Cys Leu Phe Leu Leu His Cys
                325                 330                 335

Cys Ile Cys Phe Leu His Thr Ser Arg Pro Ser Lys Arg Ile Ser Cys
            340                 345                 350

Ile Cys Pro Leu Asn Leu Asp Ile Leu Pro Thr His Cys Asp Asn Ile
        355                 360                 365

Pro Ile Ser Ala Ile Ile Phe Ile His Ile Asn His Ser Glu Leu Leu
    370                 375                 380

Leu Val Phe Ala Asp Ile Ser Arg Lys Ile Ile Gly Lys Leu Ser His
385                 390                 395                 400

Ser Val Gln Gly His His Lys His Cys Leu Thr Thr Gly Ala Lys Tyr
                405                 410                 415

Gln Ser Val Ser Cys Ser Thr Lys Ile Ser Gly His Val Glu Val Gln
            420                 425                 430

Ile Lys Arg Arg Ile Asp Leu Ala Phe Arg His His Thr Ile Ala Pro
        435                 440                 445

Ser Val Ile Leu Leu Ile Ala Ile Lys Thr His Ser Pro His Ser Asp
    450                 455                 460

Glu Ile Ser Lys Ile Ile Arg Ser Tyr Ile Lys Asn Lys Arg Lys Arg
465                 470                 475                 480

Asp Lys Arg Ala Met Phe Gly Lys Lys Val Ile Phe His Arg Glu Ser
                485                 490                 495

Arg Cys Val Gly Lys Thr Phe Ser Val Lys Thr Arg Asp Ala Phe Leu
            500                 505                 510

Asn Ala Leu Phe His Phe Lys Ala Ile Ser Lys Gln His Arg Ile
        515                 520                 525

Thr Ile Thr Ala Arg Asn Ile Thr Ile Thr His Phe Ala Gln Ala Thr
    530                 535                 540

Ser His Ala Leu Phe Phe Arg Ala Ser Thr Asn Asn Ser Ser Arg
545                 550                 555                 560

Gly Glu Ser Gln Phe Val Leu Asn Leu Val Phe Arg Arg Ile Ser Met
                565                 570                 575

His Glu Asn Lys Phe Ala Val Gly Val Asp Phe Ile Lys Gln Ile Ala
            580                 585                 590

Leu Phe Arg Gly Val Phe Thr Asn Leu Asn Ser Ala Lys Ile Phe Phe
```

-continued

```
                595                 600                 605
    Thr Gln Ile Val Ile Asp Phe Ser Met Leu Ile Gly Lys Ile Asn Phe
        610                 615                 620
    Phe His Pro Thr Met His Phe Leu Glu Ile Gln Val Phe Ser Val
    625                 630                 635                 640
    Ala Asn Lys Arg Gly Phe Ile His Ser Gln Lys Ile Val Lys Phe
                    645                 650                 655
    Ala Leu Phe Gly Val Asn Asn Ala Ile Phe Ser Val Phe Ser Ser
                660                 665                 670
    Gly Val Val Phe Ala Gln Gln Leu Phe Tyr Glu Leu Tyr Pro Ile Leu
            675                 680                 685
    Glu Val Phe Lys Leu Gly Ser Asn Asn Pro Leu Lys Leu Phe Lys Ile
        690                 695                 700
    Ile Val Cys Lys Met Leu Phe Ile His Asn Gly Phe Ile Glu Ser Val
    705                 710                 715                 720
    Ile Leu Leu Tyr Gly Gln Lys Lys Thr Asn Ile Ile Lys Thr Phe Ser
                    725                 730                 735
    Leu Leu Leu Leu Ile Ile Gly Ser His Glu Ile Arg Lys Asn Lys
                740                 745                 750
    Thr Ile Val Pro Ile Gly Phe Ile Asn Asn Asp Phe Leu Phe Asn Ser
            755                 760                 765
    Val Lys Ile Glu Phe Glu Phe Arg Gly Asn Lys Ile Pro Lys Asn Ala
        770                 775                 780
    Ile Asn Arg Ser Val Leu Tyr Glu Ile Phe Phe Gly Ser Gly Lys Ile
    785                 790                 795                 800
    Asn Ala Pro Gln Phe Asp Cys Ala Lys Arg Ile Val Val Ser Lys Asp
                    805                 810                 815
    His Pro Ile Ile Lys Thr Phe Ile Val Ile Cys Ile Gly Val Cys Ser
                820                 825                 830
    Ala His Lys Ser Val Phe Ser Val Trp Ile Val Asp Val Ile Ser His
            835                 840                 845
    Phe Phe Thr Arg Leu His Gly Lys Asn Ala His Glu Arg Phe Val Phe
        850                 855                 860
    His Ala Leu Lys Gln Lys Arg Phe Phe Lys Phe His Arg Ser Leu His
    865                 870                 875                 880
    Ser Leu Ile Lys Pro Ile Ile Phe Leu Glu Ser Lys Ser Tyr Lys His
                    885                 890                 895
    Asn Asn Asn Arg Tyr Asn Gln Asn Arg Phe Ile Gly Leu Lys Lys Asn
                900                 905                 910
    Asn Arg Tyr Asn Gly Tyr Lys Gln Tyr Lys Tyr Arg Gly Ile Asn Lys
            915                 920                 925
    Ser Phe Arg Glu Thr Lys Gln Pro Ile Pro Pro Ile Lys Gln Asp Phe
        930                 935                 940
    Lys Lys Gly Ile Asp Thr Leu Leu His Val Cys Phe Lys Phe Tyr
    945                 950                 955                 960
    Phe Leu Lys Leu Pro Leu Leu Asn Leu Leu Tyr Asn Leu Phe Leu
                    965                 970                 975
    Phe Ile Ser Leu Leu Ala Cys His Lys His Leu Ser Leu Tyr Arg Tyr
                980                 985                 990
    Thr Ala Ser His Val Ile Val Lys Ile Phe Leu Arg Asp Ser Thr Val
            995                 1000                1005
    Leu Ile Cys Phe Lys Arg Ser Leu Gly Ser Glu Leu Asn Thr Ala Asn
        1010                1015                1020
```

```
Lys Thr Leu Tyr Asn Leu Ser Ser His Arg Ile Ser Leu Val Ser Pro
1025                1030                1035                1040

Arg Asn Asp Arg Lys Gln Arg Cys Leu Leu Val Val Leu Met Leu Leu
            1045                1050                1055

Lys Val Lys Lys Ser Phe Thr Ser Gly Leu Ile Cys Asn Ser Thr Phe
    1060                1065                1070

Asn Pro Ile Ser Leu Pro Phe Ser Lys Ile Phe Ser Ile Thr Gly
        1075                1080                1085

Ser Cys Phe Lys Ser Phe Ile Phe Leu Arg Thr Leu Leu Thr Ile Thr
    1090                1095                1100

Lys Ser Lys Thr Ser Ser Leu Ile Ile Ser Gly Leu Thr Ser Leu Lys
1105                1110                1115                1120

Val Thr Phe Leu Ser Phe Lys Phe Leu Ile Val Ala Leu Lys Leu Ser
            1125                1130                1135

Lys Ser Lys Phe Val Thr Ser Pro Leu Gly Val Phe Ser Phe Ser
        1140                1145                1150

Cys Ala Ser Phe Leu Ala Ser Leu Ser Ser Phe Ala Asn Pro Tyr Glu
            1155                1160                1165

Leu Lys Thr Thr Arg Leu Lys Arg Thr Phe Lys Lys Pro Leu Ser
        1170                1175                1180

Phe Leu Leu Leu Leu Leu Leu Leu Ile Asn Leu Ala Ser Ser Ser
1185                1190                1195                1200

Thr Leu Ala Asn Ile Glu Ala Lys Leu Ser Ala Gln Ile Asp Asn Thr
            1205                1210                1215

Ala Cys His Arg His Ser Tyr Gly Leu Arg Val Ser Lys Asn Ser Arg
            1220                1225                1230

Leu Thr Ser Phe Asn Val Ile Arg Asp Phe Pro Asn Ile Arg Tyr Ala
        1235                1240                1245

Phe Asp Pro Ser Ala Thr Thr Tyr Asp Arg Asn Arg Asn Asp Leu Asn
        1250                1255                1260

Asn Gln Thr Phe Ser Cys Ser Asp Ala Phe Cys Arg Thr Gly Asp Arg
1265                1270                1275                1280

His Arg Ile Gly Cys Tyr His Pro Ser Tyr Tyr Asn Phe Leu Val Ala
            1285                1290                1295

Val Ser Asp Ser Cys Lys Lys Phe His Ala Phe Pro Phe Lys Leu Lys
            1300                1305                1310

Ser Ile Ala Val Tyr Gln Lys Lys Lys Tyr Phe Tyr Thr Ile His Thr
        1315                1320                1325

Ser Ala Thr Leu Phe Lys Ser Lys Pro Thr Leu Leu Leu Gly Asn His
        1330                1335                1340

His Ser Gly Ile Val Asn Leu Leu Val Pro Thr Ile Phe Leu Ser Gln
1345                1350                1355                1360

Val Val Val Glu Leu Ile Phe Arg Ile Phe Asp Val Phe Phe Asn Arg
            1365                1370                1375

Leu Arg Leu Lys Pro Lys Asn Lys Gln Lys Gln Thr Gln Ala Asp Gln
        1380                1385                1390

Ser Glu Asn Lys Ala Pro Phe Ala Thr Pro Thr Thr Lys Glu Thr Phe
        1395                1400                1405

Phe Glu Ala Ile Phe Glu Asn Leu Ser Tyr Phe Val Phe His Phe Val
        1410                1415                1420

Ser His Val Asp Leu Val Asp His Lys Arg Leu Ile Ile His Ala Ile
1425                1430                1435                1440

Val Ser Met Thr His Lys Pro Asn Tyr Phe Asn Ala Ser Cys Ala His
            1445                1450                1455
```

```
Leu Asp Pro Phe Leu Gln Pro Tyr Phe Ser Val Ala Phe Asp Phe Phe
            1460                1465                1470

Lys Lys Ile His Phe Leu Phe Leu Val Leu Ile Lys Val Leu Ser Phe
        1475                1480                1485

Gln Ile Phe Val Asn Cys Gly Lys Cys Glu Ser Ser Pro Leu Asp Ala
    1490                1495                1500

Cys Asn Asp Arg Ala Phe Phe Asn Ile Asn Asn Asp Lys Lys Lys Lys
1505                1510                1515                1520

Met Leu Asp Ile Val Val Glu Cys Ser Lys Thr Ile Asp Tyr Ser Ser
                1525                1530                1535

Val Arg Phe Leu Ala Val Phe Asp Thr Asn Lys Ile Pro Ile Gly Met
            1540                1545                1550

Lys Leu Gly Ile Val Arg Arg Asn Asn Asp Arg Asn His Pro Thr Thr
        1555                1560                1565

Thr Asn Arg Ser Gly Phe Pro Ala Ala Ile Tyr Gln Ser Ser Ser Ser
    1570                1575                1580

Phe Ser Ser Arg Cys Arg Phe Ile Arg Ser Ser Lys Thr Asn Arg Glu
1585                1590                1595                1600

Arg Gly Gln Ala Ser Phe Arg Asn Leu Ala Ile Lys Gly Arg Ile Leu
                1605                1610                1615

Gln Ser Asp Gln Lys Ser Tyr Gln Lys Glu Ser Val Phe Phe Arg Leu
            1620                1625                1630

Tyr Gln Glu Gln Phe Asn Gln Gln Arg Gln Ser His Cys Arg Ile Phe
        1635                1640                1645

His Lys Glu Leu Ser Glu Ile Trp Gly Ser Ala Leu Pro Asn Phe His
    1650                1655                1660

Lys Leu Gly Val Pro Ser Lys Arg Ser Val Asn Gln His Pro Ile Asp
1665                1670                1675                1680

Pro Lys Phe Tyr Gly Lys Tyr His Thr Thr Pro Tyr Pro Arg Glu Ser
                1685                1690                1695

Gly Val Phe Glu Ile Cys Gln Thr Ile Phe Cys Arg Asn His Tyr Arg
            1700                1705                1710

Glu Ser Asn Pro Asn Gly Ser Lys Val His Gly Arg Val Val Leu Glu
        1715                1720                1725

Arg Lys Ala Arg Ser Arg Lys Lys Trp Arg Ala Tyr Trp Trp Gly Leu
    1730                1735                1740

Val Gly Tyr Phe Ser Leu Ile Tyr Ile Gln Lys Thr Ile Phe Cys Gln
1745                1750                1755                1760

Arg Ser Asn Gln Ser Arg Thr Ser Ser Pro Cys Pro Thr Arg Tyr Ser
                1765                1770                1775

His Tyr His His Arg His Thr Arg Leu Thr Ala Ser Arg Phe Thr Lys
            1780                1785                1790

Gly Phe Phe Ile His Ser Trp Arg Tyr Gly Asn Val Arg Cys Gly Ser
        1795                1800                1805

Arg His Ser Gln Leu Gln Val Gln Ser Ile Ile Asp Ser Gln Arg Ser
    1810                1815                1820

Val Phe Cys Val Asn Gly Glu Ser Trp His Arg Thr Lys Ser Phe Ile
1825                1830                1835                1840

Val Val Trp Gly Gln Trp Trp Ser Trp Ser Ala Leu Glu Arg His Arg
                1845                1850                1855

Trp Leu Arg Pro Thr Arg Gln Gln Cys Gly Tyr Asn Asn Cys Ala Tyr
            1860                1865                1870

Glu Lys Arg Gln Trp Leu Ser His Ser Arg Trp Glu Arg Asp Gln Pro
```

```
                        1875                1880                1885
        Phe Leu Ser Leu Gln Arg Arg Pro Thr His Arg Leu Thr Thr Ser Ile
            1890                1895                1900

Lys Ser Arg Arg Asp Pro Lys Gln Asn Arg Phe His Gly Ile Ser Cys
        1905                1910                1915                1920

Thr Lys Cys Ile Arg Gln Leu Glu Arg Glu Arg Glu Gly Lys Ile Pro
                    1925                1930                1935

Asn Asp Arg Phe Pro Lys Arg Leu Gly Leu Phe Arg Arg Pro Arg Glu
                        1940                1945                1950

Ser Tyr Cys Phe Cys Phe Lys Arg His Lys Thr Phe Ser Phe Asn Tyr
                    1955                1960                1965

Val Trp Trp Gly Phe Glu Leu His Ser Gln Arg Leu Trp Glu Lys Ser
            1970                1975                1980

Arg Ser Phe Arg Gly Glu Lys Cys Tyr Ser Ser Arg Pro Lys Thr Trp
        1985                1990                1995                2000

Arg Asp Val Cys Leu Phe Phe Gln Ile His Gln Arg Leu Gln Glu Ser
                        2005                2010                2015

Gln Gly Cys Arg Arg Tyr Glu Trp Arg Phe Pro Phe Arg Ser Arg Leu
                    2020                2025                2030

Gln Gly Ser Tyr Leu Phe Ala Phe Lys Ser Arg Tyr His Phe Arg Lys
                    2035                2040                2045

Ala Glu Phe Arg Gly Thr Asn His Arg Ile Val Pro Thr Arg Ser Ala
        2050                2055                2060

Tyr Gln Arg Phe Phe Glu Gln Gln Gln Arg Ile Gly Trp Lys Asn Phe
        2065                2070                2075                2080

Lys Leu Gln Ser Cys Ser Arg Lys His Arg Gln Leu Ser Glu Lys Ser
                    2085                2090                2095

Ser Glu Arg Ser Lys Ile Ser Lys Glu Thr Arg Ala Phe Arg Glu Arg
                2100                2105                2110

Ser Arg Glu Lys Ile Gly Glu Gln Lys Arg Gln Gln Lys Asn Gly Ser
                    2115                2120                2125

Lys Ser Ser Ser Gln Pro Lys Arg Asp Phe Cys Val Asp Gln Arg Gly
                    2130                2135                2140

Arg Arg Lys Ser Asn Arg Leu Arg Ser Glu Ser Arg His Gln Lys Gly
        2145                2150                2155                2160

Ile Val Thr Lys Cys Gln Gln Glu Phe Glu Arg Leu Ile Phe Ile Gln
                    2165                2170                2175

Lys Trp Gln Lys Gly Phe Gln Gln Gly Arg Arg Asn Thr Lys Ser Pro
                    2180                2185                2190

Arg Phe Gly Glu Arg Phe Arg Tyr Gln Ser Arg Met Asp Phe Lys Ser
                    2195                2200                2205

Lys Pro Cys Ser Phe Glu Ile Gln Lys Trp Gln Lys Gly Phe Gln Gln
                    2210                2215                2220

Gly Asn Ala Ser Lys Lys Arg Pro Lys Phe Arg Arg Cys Asp His Gln
        2225                2230                2235                2240

Ser Lys Gly Asn Gly Ser Ser Gln Ser Ser Gly Ile Ser Gly Ser Asn
                        2245                2250                2255

Gly Phe Gln Gly Arg Ala Ser Val Ser Arg Ser Gln Lys Phe Leu Lys
                    2260                2265                2270

Gly Ala Ile Gly Pro Thr Ser Ser Lys Lys Lys Ser Gln Cys Lys Lys
                    2275                2280                2285

Ile Asn Ile Ser Ile Arg Glu Trp Cys Glu Trp Asn Pro Ser Arg Trp
                    2290                2295                2300
```

-continued

```
Val Ile Ser Ser Arg Ser His Asn Ser Phe Lys Leu Phe Gly His Gln
2305                2310                2315                2320

Glu Arg Val Glu Cys Lys Thr Trp Lys Phe Gln Gln Gln Trp Thr Gln
            2325                2330                2335

Lys Arg Thr His Leu Cys Ser Lys Glu Ser Arg Ala Ser Ser Pro Arg
        2340                2345                2350

Thr His Leu Arg Ser Ser Cys Lys Gly Lys Cys Lys Asn Pro Thr Gln
    2355                2360                2365

Ser Asn Ser Lys Trp Phe Gly Cys Cys Arg Ala Ser Ser Gly Leu Pro
2370                2375                2380

Phe Glu Lys Ala Ser Ser Gln Gly Arg Ala Phe Lys Glu Ser Arg Ile
2385                2390                2395                2400

Gly Ser Glu Asn Gln Ser Gln Ser Gly Ile Arg Ser Ser Arg Phe
            2405                2410                2415

Phe Trp Gln Ser Arg Ala Asn Asp Arg Gln Ala Gln Arg Phe Tyr Lys
        2420                2425                2430

Thr Gln Ser His Glu Ser Met Gly Lys Cys Lys Lys Ser Thr Cys Phe
    2435                2440                2445

Val Ser Glu Thr Arg Gln Leu Arg Tyr Gln Pro His Thr His Gln Tyr
2450                2455                2460

Gln Lys Trp Ser Asn Gln Lys Ser Asp Arg His Ala Asn Ala Lys Lys
2465                2470                2475                2480

Pro Val Ala Gln Ala Arg Glu Asp Ser Cys Ala Cys Arg Lys Arg Ser
            2485                2490                2495

Phe Val Arg Val Asn Trp Leu Gln Pro Glu Glu Tyr Glu Arg Leu Phe
        2500                2505                2510

Phe Val Gln Val Phe His Gln Val Glu Gln Cys Cys Lys Arg His Phe
    2515                2520                2525

Trp Leu Tyr Ala Ile Phe Asn Gln Cys Ile Phe Tyr Ser Ile Leu Leu
2530                2535                2540

Leu Leu Gly Glu Arg Lys Cys Gly Ala Trp Asn Gln Glu Arg Tyr Lys
2545                2550                2555                2560

Arg Trp Phe Pro Lys Ile Leu Lys Asp Gly Ile Pro Lys Thr Gln Lys
            2565                2570                2575

Pro Pro Leu Ala Lys Ser Glu Gly Phe Phe Asn Thr Pro Gln Lys Ser
        2580                2585                2590

Gln Ser Ser Leu Val Phe Gly Met Asn Ala Thr Asn Ser Trp Tyr His
    2595                2600                2605

Ile Pro Ile His Ser Tyr Leu Ala Glu Val Cys Lys Val Thr Pro Leu
2610                2615                2620

Glu Ile Cys Val Arg Pro Val Gly Asn Ala Leu Glu Leu Lys Leu Cys
2625                2630                2635                2640

Lys Ile Pro Ile Ile Gly Thr Gln Ser Glu Asn Gln Thr Leu Pro Thr
            2645                2650                2655

Gly Asn Ile Ser Leu Gly Ser Pro Ile Val Phe Ser Gly Trp Ala Leu
        2660                2665                2670

His Leu Lys Ile Ser Arg Gln Thr Leu Thr Lys Gly Phe Val Leu Ser
    2675                2680                2685

Leu His Gly Tyr Phe Leu Pro Gln Lys Asp Leu Thr Leu Cys Leu Lys
2690                2695                2700

Leu Ser Leu Ile Val Leu Val Gly Ser Cys Tyr Ser Ala Lys Ile Asn
2705                2710                2715                2720

Gly Leu Arg Glu His Lys Leu Glu Lys Thr Ser Ser Tyr Asn Lys Asp
            2725                2730                2735
```

```
Gln Val Gln Lys Ile Ile Glu Leu Leu Glu Gln Ile Asp Arg Ala Leu
            2740                2745                2750

Asn Gln Arg Lys Ile Arg Lys Thr Ile Gly Ile Ile Thr Pro Tyr Asn
            2755                2760                2765

Ala Gln Lys Arg Arg Leu Arg Ser Glu Val Glu Lys Tyr Gly Phe Lys
            2770                2775                2780

Asn Phe Asp Glu Leu Lys Ile Asp Thr Val Asp Ala Phe Gln Gly Glu
2785                2790                2795                2800

Glu Ala Asp Ile Ile Ile Tyr Ser Thr Val Lys Thr Cys Gly Asn Leu
            2805                2810                2815

Ser Phe Leu Leu Asp Ser Lys Arg Leu Asn Val Ala Ile Ser Arg Ala
            2820                2825                2830

Lys Glu Asn Leu Ile Phe Val Gly Lys Lys Ser Phe Glu Asn Leu
            2835                2840                2845

Arg Ser Asp Glu Lys Asn Ile Phe Ser Ala Ile Leu Gln Val Cys Arg
            2850                2855                2860

Val Ile Phe Ser Lys Asp Asn His Thr Phe Phe Ala Ser Lys Arg Phe
2865                2870                2875                2880

His Lys Ser Leu Ser Ala Leu Ser Thr Gln Tyr Pro Tyr Ser Val Ser
            2885                2890                2895

Tyr Ser Pro Phe Leu Gly Ile Glu Leu Phe Leu Ile Phe Ile Ser Val
            2900                2905                2910

Thr Ile Ala Ile Leu Leu Val Phe Leu Ala Arg Ser His Arg Arg Ser
            2915                2920                2925

His Glu Ile Pro Leu Gly Met Arg Val His Phe Phe Gly Arg Ile Phe
            2930                2935                2940

Ala Ala Asn Ile Leu Gln His Arg Pro Asn Gly Val Gly Val Leu
2945                2950                2955                2960

Lys Gly Gln Asn Ala Pro Asn Ser Pro Gln Phe Glu Arg Leu Arg
            2965                2970                2975

Glu Asn Ala Cys Asn Leu Lys Ser Leu Arg Glu Asn Leu Gly Ser Glu
            2980                2985                2990

Ile Ile Thr His Ala Ser Phe Gln Phe Ala Leu Asn Thr Phe Phe Asn
            2995                3000                3005

Gln Arg His Lys Lys Arg Ser Gly Met Arg Asn Ile Gln Ile Ala Leu
            3010                3015                3020

Leu Phe Gln Gly Ile Val Ile Ser Val Gly Leu Asp Arg Arg Phe Cys
3025                3030                3035                3040

Pro His Asn Arg Gly Val Phe Ile Phe Tyr Leu Ser Leu Asp Arg Asn
            3045                3050                3055

Ala Trp Leu Asn His Ala His Asn Arg Asp Phe Gly Met Leu Leu His
            3060                3065                3070

Leu Phe Ser Ser Ala Arg Cys Val Ala Cys His Asn Gln Phe Asn Leu
            3075                3080                3085

Val Arg Phe Glu Lys Ile Gln Ser Leu Ala Lys Leu Leu Asp Arg Ser
            3090                3095                3100

Gly Val Phe Ser Ala Ile Arg His Ser Ser Arg Ile Ala Ile Ile Asp
3105                3110                3115                3120

Asp Phe Ile Lys Leu Arg Phe Lys Ala Phe Asn Ala Lys Pro Ser His
            3125                3130                3135

Thr Ala Ile Lys Asn Ala Tyr Phe His Asp Thr Phe Leu Ile Trp Asp
            3140                3145                3150

Leu Gly Ile Leu Phe Phe Ile His Val Lys Phe Phe Ile Val Leu Ser
```

```
              3155           3160           3165
     Leu Leu His Phe Arg Ile Asp Lys Ala
        3170           3175
```

(2) INFORMATION FOR SEQ ID NO:5:

(i) SEQUENCE CHARACTERISTICS:
       (A) LENGTH: 10299 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:5:

```
AAGCTTTGTC TATTCTAAAA TGCAACAAAC TAAGGACAAT GAAGAATTTT TAAACTTAAT     60

GAATGAAAAA TAAAATCCCT AATTAATCCC ATTAAATTAA AAAAGTGTCA TGAAAATAGG    120

CGTTTTTGAT AGCGGTGTGG GAGGGTTTAG CGTTTTAAAA AGCCTTTTAA AAGCGCAATT    180

ATTTGATGAA ATCATCTATT ATGGCGATAG CGCTAGAGTG CCTTATGGCA CTAAAGACCC    240

CACTACGATC AAGCAATTTG GCTTAGAGGC TTTGGATTTT TTCAAACCGC ACCAGATTGA    300

ATTATTGATT GTGGCATGCA ACACAGCGAG CGCTCTAGCT TTAGAAGAGA TGCAAAAGCA    360

TTCCAAAATC CCTATTGTGG GCGTGATTGA GCCAAGCATT TTAGCGATCA AGCGACAAGT    420

AAAAGATAAA AACGCCCCTA TTTTAGTGCT AGGGACAAAA GCGACGATCC AATCCAACGC    480

TTATGACAAT GCCCTGAAAC AACAAGGCTA TTTGAATGTT TCGCATTTAG CCACTTCTCT    540

TTTTGTGCCT TTGATTGAAG AAAGTATTTT AGAGGGCGAA TTGTTAGAAA CTTGCATGCG    600

TTATTATTTC ACTCCCTTAA AGATTTTCCC GAAGTGATTA TTTTAGGTTG CACGCATTTT    660

CCCTTAATCG CTCAAAAAAT TGAGGGCTAT TTTATGGAGC ATTTTGCCCT TTCAACACCC    720

CCCCTACTCA TCCATTCGGG CGATGCTATT GTAGGATATT TGCAGCAAAA ATACGCCCTT    780

AAAAAAAATG CACACGCATT CCCTAAAGTG GAATTTCATG CGAGCGGCGA TGTGATCTGG    840

CTAGAAAAAC AAGCTAAAGA ATGGCTCAAA TTGTAACGCT AATAAAAATT TAAAGTCAAA    900

ATAACTCAAT TCCCAAAAAG GGGCTATAGC TCACACTATA AGGGTATTGT GTTGATTATA    960

AAGCGCTTTA GAGAGATTTA TGAAAGCGTT TTGAAGCGAA GAATGTCTAA TGATTATCTT   1020

TGGAAAAGAT TACCTATCTA CAGACTTGCA AAATAGCGCT AAAGATATTC TTCTCATCGC   1080

TTCGTAAATT CTCAAAGAAA GACTTTTTAC CCACAAAAAT GAGATTTTCT TTTGCCCTAG   1140

AAATAGCCAC ATTCAAGCGT TTAGAATCTA GCAAGAAAGA AAGATTACCA CAAGTTTTCA   1200

CGGTGGAATA AATAATAATA TCTGCCTCTT CACCTTGAAA GGCATCCACA GTGTCTATTT   1260

TGAGCTCATC AAAATTCTTG AAGCCGTATT TTTCCACTTC TGATCGCAAG CGTCTTTTTT   1320

GGGCATTATA AGGTGTGATA ATTCCTATGG TTTTTCTGAT TTTTCTTTGG TTAAGAGCGC   1380

GATCAATTTG CTCTAAAAGC TCTATGATTT TTTGAACTTG ATCTTTGTTA TAGCTACTTG   1440

TTTTTTCTAG TTTATGCTCT CTTTATAACC CTTAATTAAT TTTCGCACTA TAGCACGAAC   1500

CCACTAGCAC AATCAAACTT AATTTTAAGC AAAGGGTTAA GTCTTTTTGG GGTAGGAAAT   1560

ATCCATGCAG ACTTTAAAGA ACAAAGCCTT TCGTTAGTGT CTGTCGGGAT ATTTTAAGGT   1620

GAAGTGCCCA ACCGCTAAAG ACGATTGGGC TTCCTAGGCT GATGTTGCCC GTAGGGAGAG   1680

TTTGGTTCTC ACTCTGTGTC CCTATAATAG GGATTTTACA GAGTTTGAGC TCCAACGCAT   1740

TCCCTACAGG TCTCACACAT CATATCTCCA AAGGCGTAAC TTTGCACACT TCCTACGCTA   1800

GATACGAATG TATGGGGATA TGATACCATG AATTGGTAGC ATTCATCCCA AATACTAAAG   1860
```

```
ACGATTGGGA TTTCTGCTAA GGAGTATTAA AAAACCCCTC GCTTTTAGCA AGGGGTGGTT    1920
TTTGCGTTTT TGGTATTCCT TAATCCTTTA AGATTTTTGG AAACCACCTT TTGTATTAAC    1980
GTTCTTGATT CCATGCTCCG CATTTTCTCT CGCCAAGCAG TAATAAGATG CTGTAGAAAA    2040
TGCATTGGTT AAAAATTGCG TAAAGCCAGA ATTAGTGTCT TTTACAGCAT TGTTCAACTT    2100
GGTGGAAAAC TTGAACGAAT CAGAATAATC TTTCATATTC TTCTGGTTGA AGCCAATTTT    2160
ATCATACTCT GACAAAGGAA CGCTTCCTAC ATTATGCGCA ACTATCTTAT CATTCACGAG    2220
CTTGAGCCAC TCAGGGTTTT TTTGCGTTAG CATGCCGGTC GCTTTTTCAT TGATTGCTCC    2280
ATTTTTGATA TTGCTATTAA TGCGTATGTG GCTGTTAGTA GCGTAATTGT CTAGTTTCGC    2340
TGACAAACTA GCAGGTACTT TTTTTGCACT TTCAACCCAT AGATTCATGG GATTGTGTTT    2400
TGTAGAATCT TTGAGCTTGT CTATCGTTTG CTCTAGATTG CCAAAAAAAC CTGCTTTAGC    2460
TTCTGATACC GCTTGATTGA GATTGTCAAT TTTCTGAGCC AATTCTTGAT TCCTTGAAAG    2520
CCCTACCTTA CTGAGATCAT CAACTTTATC ATGCCTTTTC AAAGGGAAGC CCGCTGCTTG    2580
CCCTACAACA CCCAAACCAC TTGCTATTTG ATTGAGTCGG TCAATTTTTG CATTTACCTT    2640
TTTAGCAACT TGAGCGTAAA TGGGTTCTTC AAGGCTAGCT GCTTGCCCTG CTTTCTTTTT    2700
ATTAACTTTA GCATAAATGG GTTCGTTTTT GAGTCCATTA TTGTTATTGT TATTGAAATT    2760
TCCAAGTTTT GCATTCAACT CTTTCTTGAT GTCCGAAAAG TTTTTAGAAA GAGTTGTGGC    2820
TTCTGCTTGA GATAACCCAT TACCGACTAG GGTTCCATTC ACACCATTCT TAACGGATTG    2880
ATATATTTCA GATTTTTTTC TAGCATTGAG ACTTTCATTT TTTTGAGCTT GTTGGGCCAA    2940
TTGCTCCTTT GAGAAATTTT TGAGATCGGC TAACGCTTGC TCTACCCTAC TGAAATCACC    3000
CGTTGCTTTA GCCACTGATA CCGCTTGATT GAGATTATCA ACTTTATCCG TTACCTTTTG    3060
ATTGATGATC ACATCTTTAA CGGAATTTTC AAGGTCGCTT TTTGCTTGCG TTACCTTGCT    3120
GAAATCCTTA TTTTTGCCAT TTTTGAATTC ATTCAAAGCT GCATTAAGGT TTCAACTTT     3180
TGAAATCCAT TCTGGATTGA TACCTAAATC TTTCACCGAA CCTTTAAGGG CTTTTAGTGT    3240
TTCTTCTGCC TTGCTGAAAT CCTTATTTTT GCCATTTTTG AATTCATCAA AAGATTTATC    3300
AAAGTCTTTC AAATTCTTGT TGACATTTTC AAGTTTATCA GACAATTCCC TTTTGATGCC    3360
TTTAAGATTC TGAGCGTAAG CGATTGCTCT TGCGTCTCTA TTAGCCTCTT TATTGATCAA    3420
CGCAAAAATC TCATCTTTTT GGCTGTTAGC TTGAGCTTTT GCTTCCATTT TATTTTGTT     3480
GCCGCTTTTG CTCTCCAATT TTTTCTCTAC TTCTTTCTCT AAATGCTCTC GTTTCCTTAG    3540
AGATTTTTCA AGATCTTTCT GAGCTTTTTT CACTTCATCA TAATTGCCTG TGTTTTTAGC    3600
GTCAGCTACA GCTTTATTGA AGTTTAAAGT TTTTCCAACC AATTCTTTGT TGCTGCTCAA    3660
AAAATCTTTG ATAAGCTTAT TAGCTTCTTG TGGGGACAAT CCTTTAGTGG TTAGTTTATC    3720
CTCTAAATTC CGCCTTACGA AACTAGTGAT AGCGAGATTA TTTAAATCAG GCAAATTAAA    3780
GATAGCTACC TTGTTAAAGC CTACTTCTAA ATGGGAAACG CCATTCGTAA CGCCTACACC    3840
CTTATTGGGA TTCTTGGAGG CGTTGGTGTA TTTGAAATTA GAATAATCAA CAAACATCAC    3900
GCCATCATGT TTTAGGCTAC CTTGAAGAGT AACATTTTTC TCCCTATCTA AGCTTTATC     3960
TGCTTTTTTC CCATAATCTT TGAGAGTGTA GCTCAAATCC CCATTACCAA ACTCAGTAAT    4020
TAAAGCTGAA TGTTTTGTGT CTTTTTTAGA AACAAAAGCA ATACGATCAT TCCCTAGGGC    4080
GTCTAAATAA GCCTTAGAGT CTTTTTGGAA ATCTTTAATC TCAGTTCGGA ATTTTTCCTT    4140
CTCTTTCTCG CTCAAGTTGT CTAATTTAGC ATTATTTTGT GCAAGAAATT CCATGAAATC    4200
TATTTTGTTT TGGATCTCTT CTTGACTTAA TGCTCGTTGT GAGCCTGTGA GTTGGTCTTC    4260
```

```
TTTGTAGAGA TAAAAACTAG GGTTGTTAAT CCCTTTCTCA CCACCTGCTA TGACTAAGCC   4320

ACTGCCGTTT TTCATATGCA CATTAATTAT TGTAGCCACA TTGTTGCCTT GTTGGTCTTT   4380

ATAACCAACG GTGGCGTTCC AATCATGCCT AGCTCCAGGA CCACCATTGC CCCCATACAA   4440

CAATGAAACT TTTTCAGGTT CTATGCCATT ATGACTCCCC ATTAACACAG AAGACAGAGC   4500

GTTATTGTGA ATCAATAATT GATTGAACTT GTAATTGGGA TCAATGTCAG CGACTCCCTC   4560

AACATCTAAC ATTTCCATAT CGCCAAGAGT GAATTTAGAA AAATTACCCC TTTCATCAAG   4620

TAAATCTCTA GCTTCAGGCG GTAAGCCTTG TATGTCGGTG GTGGTAGTGG CTATATCTGG   4680

TTGGACATGG GGAACTGGTT CTTGATTGAT TGCTTCTTTG ACATCAGAAG ATTGTTTTTT   4740

GTCAAATATA AATGAGAGAA AAATATCCAA CCAATCCCCA CCAGTAGGCT CTCCATTTTT   4800

TTCTGCTTCT TGCCTTTCTT TCAAGGACTC ATCAAACACG CCCATGAACT TTTGATCCGT   4860

TCGGATTTGA TTCCCTATAA TGATTCCTGC AAAAGATTGT TTGGCAGATT TCAAAAACTC   4920

CGCTTTCTCT TTATCATCAA GGATAGGGGG TTGTATGATA TTTTCCATAA AATTTCGGAT   4980

CGATCGGGTG TTGATTTTAG ACGGATCGTT TTGATGGGAC ACCCAACTTG TGAAAATTCG   5040

GTAACGCTGA TCCCCAAATT TCTGAAAGCT CTTTGTGGAA GATTCTACAT CAATGAGATT   5100

GTCTTTGTTG ATTAAATCAT TGCTCTTATT GATAAAGTCT GAAAAATACT GATTCTTTTT   5160

GGTAGGATTT TTGATCGCTT TATTGGAGTA TTCTTCCCTT AATTGCGAGA TTCCTTCAAA   5220

AGCTTGCCTG TTATCCCTAT CGTTCTTATC AACGATTGGT TTTTGATCAG GATCGTATGA   5280

AGCGACAGCG TTATCAACTT TAAGAAAAGC TACTTGAAGA TTATTGATAA ATTGCTGCGG   5340

GTTAAAAGCC GCTTCGGTTT GTGGTTGTTG GTCAATGGTT TCGTTAGTCA TTGTTTCTCC   5400

TTACTATACC TAGTTTCATA CCTATCGGTA TCTTGTTAGT GTCAAAGACT GCTAAAAATC   5460

GCTACACGCT TGAGTAGTCA ATTCATGTCT TTGAACATTC TCATTATACA ACAATATCAA   5520

GCATTTTTTT TTTTTTTCAT TAATCATTAT TAATATTGAA AAAAGCCCGA TCGTTGCAGG   5580

CGTCTAAAGG CTAGGACGAT TCACATTTTT ACCCACAATT AACAAAAATT TGCTAAAATG   5640

AAAGAACTTT AATAAGAACA AGAAATAAGA AATGAATCTT TTTGAAGAAA TCAAATGCAA   5700

CGCTAAAGTA TGGTTGGAGA AATGGTTAGT CAAGGTGAGC ACATGAAGCG TTCTAAAAAT   5760

AGTTTGGTTT GTGTGTCATG CTTACTATAG CATGTATAAT TAAGCGTTTG TGATCCACAA   5820

GATCCACATG GGAAACAAAA TGGAAAACAA ATCAATAGGA CAGATTTTCA AAGATAGCCT   5880

CAAAAAAGT TTCTTTAGTG GTCTATGGAG TTGCTTAAAA TGGAGCTTTA TTCTCACTCT   5940

GATCAGCTTG GGTTTGTTTT TGCTTGTTTT TAGGTTTCAA CCTGAGACGA TTAAAAAATA   6000

CATCAAAGAT CCTAAAGATC TACAATTCTA CAACGACTTG AGAAAGAAAA ATGGTTGGGA   6060

CAAGTAGGTT TACTATTCCT GAATGATGTC AGTTGCCGAG CAAAAGCGTC GGTTTTGATT   6120

TAAATTATAA AGTAGCGCTT GTATGAATAG TATAAAAATA CTTTTTTTTT TGATATACTC   6180

AAGCGATTGA TTTCAATTTG AAAGGAAACG CATGAAATTT TTTACAAGAA TCACTGACAG   6240

CTACAAGAAA GTTGTAGTAA CTTTAGGGCT AGTGGTAACA ACCAATCCTT TAATGGCGGT   6300

CGCCAGTCCT ACAGAAGGCG TCACTGCAAC TAAAGGTTTG GTTATTCAGA TCATTTCTGT   6360

TCTAGCGATC GTAGGTGGTT GCGCTTAGG GGTCAAAGGC ATAGCGGATA TTTGGAAAAT   6420

CTCTGATGAC ATTAAAAGAG GTCAGGCGAC TGTTTTTGCT TACGCGCAAC CCATAGCTAT   6480

GTTAGCGGTG GCAGGCGGTA TTATCTATTT GAGCACTAAG TTTGGCTTCA ATATTGGCGA   6540

GGGTGGAGGA GCTAGCTAAG TTGATCAACA ATAATAATAA TAGCAATAAG AAACTAAGAG   6600

GCTTTTTTTT GAAAGTTCTC TTAAGTCTCG TTGTTTTCAG TTCGTATGGG TTAGCAAATG   6660
```

```
ATGACAAAGA AGCCAAAAAA GAAGCACAAG AAAAAGAAAA AAACACTCCC AATGGGCTTG      6720

TTTATACAAA TTTAGATTTT GATAGTTTCA AAGCGACTAT CAAAAATTTG AAAGACAAGA      6780

AAGTAACTTT CAAAGAAGTC AATCCCGATA TTATCAAAGA TGAAGTTTTT GACTTCGTGA      6840

TTGTCAATAG AGTCCTTAAA AAAATAAAGG ATTTGAAGCA TTACGATCCA GTTATTGAAA      6900

AAATCTTTGA TGAAAAGGGT AAGGAAATGG GATTGAATGT AGAATTACAG ATCAATCCTG      6960

AAGTGAAAGA CTTTTTTACT TTCAAAAGCA TCAGCACGAC CAACAAACAA CGCTGCTTTC      7020

TGTCATTGCG CGGAGAAACA AGAGAAATTC TATGCGATGA TAAGTTATAT AATGTTTTAT      7080

TGGCCGTATT CAATTCTTAT GATCCTAATG ATCTTTTGAA ACATATTAGC ACCGTAGAGT      7140

CTCTCAAAAA AATCTTTTAT ACGATTACAT GTGAAGCGGT ATATCTATAA AGAGAGAGGT      7200

GTTTGTGGCA AGCAAGCAGG CTGATGAACA AAAAAAGCTA ATTATAGAGC AAGAGGTTCA      7260

AAAGCGGCAG TTTCAAAAAA TAGAAGAACT TAAAGCAGAC ATGCAAAAGG GTGTCAATCC      7320

CTTTTTTAAA GTCTTGTTTG ATGGGGGGAA TAGGTTGTTT GGTTTCCCTG AAACTTTTAT      7380

TTATTCCTCT ATATTTATAT TGTTTGTAAC CATTGTATTA TCTGTTATTC TTTTTCAAGC      7440

CTATGAACCT GTTTTGATTG TAGCGATTGT TATTGTGCTT GTAGCTCTTG GATTCAAGAA      7500

AGATTATAGG CTTTATCAAA GAATGGAGCG AGCGATGAAA TTTAAAAAAC CTTTTTTGTT      7560

TAAGGGCGTG AAAAACAAAG CGTTCATGAG CATTTTTTCC ATGAAGCCTA GTAAAGAAAT      7620

GGCTAATGAC ATCCACTTAA ATCCAAACAG AGAAGACAGA CTTGTGAGCG CTGCAAACTC      7680

CTATCTAGCA ATAACTATG AATGTTTTTT AGATGATGGG GTGATCCTTA CTAACAACTA      7740

TTCTCTTTTA GGCACAATCA AATTGGGGGG CATTGATTTT TTAACCACTT CCAAAAAAGA      7800

TCTCATAGAG TTACACGCTT CTATTTATAG CGTTTTTAGG AATTTTGTTA CCCCTGAATT      7860

CAAATTCTAT TTTCACACTA TTAAAAAGAA AATCGTTATT GATGAAACCA ATAGGGACTA      7920

TGGTCTTATT TTTTCTAATG ATTTCATGCG AGCCTATAAT GAGAAGCAAA AGAGAGAAAG      7980

TTTTTATGAT ATTAGTTTTT TTCTGACCAT AGAGCAAGAT TTATTAGACA CTCTCAATGA      8040

ACCCGTTATG AATAAAAAGC ATTTTGCAGA CAATAATTTT GAAGAGTTTC AAAGGATTAT      8100

TAGAGCCAAG CTTGAAAACT TCAAGGATAG GATAGAGCTC ATAGAAGAGC TGTTGAGCAA      8160

ATACCACCCC ACTAGATTAA AAGAATACAC TAAAGATGGC GTTATTTACT CCAAACAATG      8220

CGAATTTTAC AATTTTCTTG TGGGAATGAA TGAAGCCCCT TTTATTTGCA ACCGAAAAGA      8280

CTTGTATCTC AAGGAAAAAA TGCATGGTGG GGTGAAAGAA GTTTATTTTG CCAATAAGCA      8340

TGGAAAAATC TTAAATGACG ATTTGAGTGA AAAATATTTT AGCGCTATTG AGATTAGTGA      8400

ATACGCCCCT AAATCACAAA GCGATTTGTT TGATAAAATC AACGCCCTAG ACAGCGAATT      8460

TATTTTCATG CATGCTTATT CGCCTAAAAA CTCACAGGTT TTAAAGGACA AACTGGCTTT      8520

CACCTCTAGA AGAATTATTA TTAGTGGAGG CTCTAAAGAA CAGGGCATGA CTTTAGGTTG      8580

CTTGAGCGAA TTAGTGGGTA ATGGTGATAT TACGCTAGGC AGTTATGGTA ATTCTTTAGT      8640

GCTGTTTGCT GATAGCTTTG AAAAAATGAA ACAAAGCGTT AAGGAATGCG TCTCTAGTCT      8700

TAACGCTAAA GGTTTTTTAG CCAACGCAGC GACTTTCTCT ATGGAAAATT ACTTTTTTGC      8760

CAAACATTGC TCTTTTATCA CGCTTCCTTT TATTTTTGAT GTAACTTCTA ATAATTTTGC      8820

TGATTTCATC GCTATGAGGG CTATGAGTTT TGATGGCAAT CAAGAGAATA ACGCTTGGGG      8880

CAATAGTGTG ATGACGCTAA AAAGCGAGAT CAATTCGCCT TTTTATCTGA ACTTCCACAT      8940

GCCCACTGAT TTTGGTTCAG CTTCAGCAGG ACACACTTTG ATACTTGGCT CAACCGGTTC      9000

AGGTAAGACA GTGTTTATGT CAATGACCTT GAACGCTATG GGACAATTTG CCTATAATTT      9060
```

```
TCCTGCTAAT GTCAGCAAAG ACAAGCAAAA GCTCACTATG GTTTATATGG ATAAAGATTA    9120

TGGCGCTTAT GGGAATATTG TCGCAATGGG TGGGGAGTAT GTCAAGATTG AGCTAGGGAC    9180

AGATACAGGA TTAAATCCTT TTGCTTGGGC GGCTTGTGTG CAAAAAACAA ATGCAACAAT    9240

GGAGCAAAAA CAAACAGCTA TTTCTGTTGT CAAAGAGCTT GTGAAAAACT TAGCAACTAA    9300

AAGCGATGAA AAAGATGAAA ATGGCAACAG CATCTCTTTT AGCCTAGCAG ATTCTAATAC    9360

GCTTGCAGCG CAGTAACCAA CCTTATCACA GGAAATATGA ATCTAGATTA TCCCATCACT    9420

CAACTTATTA ATGCTTTCGG GAAAGACCAC AATGATCCTA ATGGGCTTGT CGCGCGATTA    9480

GCGCCTTTTT GCAAATCAAC CAATGGTGAA TTTCAATGGC TTTTTGATAA TAAAGCAACA    9540

GATCGCTTAG ATTTTTCAAA AACGATTATT GGCGTTGATG GGTCAAGTTT CTTAGACAAT    9600

AATGATGTTT CGCCCTTTAT TTGTTTTTAC CTTTTCGCTC GTATCCAAGA GGCAATGGAT    9660

GGGCGTAGAT TTGTCTTAGA TATTGATGAA GCCTGGAAAT ATTTAGCGAT CCAAAGGTCG    9720

CTTATTTTGT AAGAGACATG CTAAAAACTG CAAGGAAAAG AAACGCTATT GTCAGACTTG    9780

CGACTCAAAG CATCACTGAT CTTTTGGCTT GCCCTATTGC TGATACGATT AGAGAACAAT    9840

GCCCTACAAA GATTTTTTTG AGAAACGATG GGGGCAATCT TTCTGATTAC CAAAGATTGG    9900

CTAATGTTAC AGAAAAAGAA TTTGAAATCA TCACTAAGGG ACTAGATAGG AAAATCCTCT    9960

ACAAACAGGA TGGAAGCCCT AGCGTTATCG CTAGTTTTAA TTTGAGAGGC ATTCCTAAAG   10020

AATATTTGAA AATTTTATCC ACAGATACTG TATTTGTCAA AGAAATTGAT AAGATTATCC   10080

AAAACCATAG TATCATAGAT AAATATCAGG CCTTGAGACA AATGTATCAA CAAATAGAGG   10140

AGTATTAAAA TGAAACAAAA TTTGCGTGAA CAAAAATTAT GGAAATTTTA GAAAATGATG   10200

TCTTGACGAT TTTGGATAGT TTTTCTAATT ATCTTTTTGA ACTGAAAGAA GAATTGGACT   10260

TCATAGAAGA AGAAATGGAA GGCGAAATCA CTGAACAAA                         10299
```

(2) INFORMATION FOR SEQ ID NO:6:

(i) SEQUENCE CHARACTERISTICS:
        (A) LENGTH: 3169 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Ala Leu Ser Ile Leu Lys Cys Asn Lys Leu Arg Thr Met Lys Asn Phe
 1               5                  10                  15

Thr Met Lys Asn Lys Ile Pro Asn Ser His Ile Lys Lys Val Ser Lys
                20                  25                  30

Ala Phe Leu Ile Ala Val Trp Glu Gly Leu Ala Phe Lys Ala Phe Lys
            35                  40                  45

Arg Asn Tyr Leu Met Lys Ser Ser Ile Met Ala Ile Ala Leu Glu Cys
        50                  55                  60

Leu Met Ala Leu Lys Thr Pro Leu Arg Ser Ser Asn Leu Ala Arg Leu
65                  70                  75                  80

Trp Ile Phe Ser Asn Arg Thr Arg Leu Asn Tyr Leu Trp His Ala Thr
                85                  90                  95

Gln Arg Ala Leu Leu Lys Arg Cys Lys Ser Ile Pro Lys Ser Leu Leu
            100                 105                 110

Trp Ala Leu Ser Gln Ala Phe Arg Ser Asp Lys Lys Ile Lys Thr
            115                 120                 125

Pro Leu Phe Cys Gly Gln Lys Arg Arg Ser Asn Pro Thr Leu Met Thr
```

```
                130                 135                 140
Met Pro Asn Asn Lys Ala Ile Met Phe Arg Ile Pro Leu Leu Phe Leu
145                 150                 155                 160

Cys Leu Leu Lys Lys Val Phe Arg Ala Asn Cys Lys Leu Ala Cys Val
                165                 170                 175

Ile Ile Ser Leu Pro Arg Phe Ser Arg Ser Asp Tyr Phe Arg Leu His
                180                 185                 190

Ala Phe Ser Leu Asn Arg Ser Lys Asn Gly Leu Phe Tyr Gly Ala Phe
                195                 200                 205

Cys Pro Phe Asn Thr Pro Thr His Pro Phe Gly Arg Cys Tyr Cys
210                 215                 220

Arg Ile Phe Ala Ala Lys Ile Arg Pro Lys Cys Thr Arg Ile Pro
225                 230                 235                 240

Ser Gly Ile Ser Cys Glu Arg Arg Cys Asp Leu Ala Arg Lys Thr Ser
                245                 250                 255

Arg Met Ala Gln Ile Val Thr Leu Ile Lys Ile Ser Gln Asn Asn Ser
                260                 265                 270

Ile Pro Lys Lys Gly Leu Leu Thr Leu Gly Tyr Cys Val Asp Tyr Lys
                275                 280                 285

Ala Leu Arg Asp Leu Lys Arg Phe Glu Ala Lys Asn Val Leu Ser Leu
                290                 295                 300

Glu Lys Ile Thr Tyr Leu Gln Thr Cys Lys Ile Ala Leu Lys Ile Phe
305                 310                 315                 320

Phe Ser Ser Leu Arg Lys Phe Ser Lys Lys Asp Phe Leu Pro Thr Lys
                325                 330                 335

Met Arg Phe Ser Phe Ala Leu Glu Ile Ala Thr Phe Lys Arg Leu Glu
                340                 345                 350

Ser Ser Lys Lys Glu Arg Leu Pro Gln Val Phe Thr Val Glu Ile Ile
                355                 360                 365

Ile Ser Ala Ser Ser Pro Lys Ala Ser Thr Val Ser Ile Leu Ser Ser
                370                 375                 380

Ser Lys Phe Leu Lys Pro Tyr Phe Ser Thr Ser Asp Arg Lys Arg Leu
385                 390                 395                 400

Phe Trp Ala Leu Gly Val Ile Ile Pro Met Val Phe Leu Ile Phe Leu
                405                 410                 415

Trp Leu Arg Ala Arg Ser Ile Cys Ser Lys Ser Ser Met Ile Phe Thr
                420                 425                 430

Ser Leu Leu Leu Val Phe Ser Leu Cys Ser Leu Tyr Asn Pro
                435                 440                 445

Leu Ile Phe Ala Leu His Glu Pro Thr Ser Thr Ile Lys Leu Asn Phe
450                 455                 460

Lys Gln Arg Val Lys Ser Phe Trp Gly Arg Lys Tyr Pro Cys Arg Leu
465                 470                 475                 480

Arg Thr Lys Pro Phe Val Ser Val Cys Arg Asp Ile Leu Arg Ser Ala
                485                 490                 495

Gln Pro Leu Lys Thr Ile Gly Leu Pro Arg Leu Met Leu Pro Val Gly
                500                 505                 510

Arg Val Trp Phe Ser Leu Cys Val Pro Ile Ile Gly Ile Leu Gln Ser
                515                 520                 525

Leu Ser Ser Asn Ala Phe Pro Thr Gly Leu Thr His His Ile Ser Lys
                530                 535                 540

Gly Val Thr Leu His Thr Ser Tyr Ala Arg Tyr Glu Cys Met Gly Ile
545                 550                 555                 560
```

```
Tyr His Glu Leu Val Ala Phe Ile Pro Asn Thr Lys Asp Asp Trp Asp
            565                 570                 575
Phe Cys Gly Val Leu Lys Asn Pro Ser Leu Leu Ala Arg Gly Gly Phe
            580                 585                 590
Cys Val Phe Gly Ile Pro Ser Phe Lys Ile Phe Gly Asn His Leu Leu
            595                 600                 605
Tyr Arg Ser Phe His Ala Pro His Phe Leu Ser Pro Ser Ser Asn Lys
            610                 615                 620
Met Leu Lys Met His Trp Leu Lys Ile Ala Ser Gln Asn Cys Leu Leu
625                 630                 635                 640
Gln His Cys Ser Thr Trp Trp Lys Thr Thr Asn Gln Asn Asn Leu Ser
                645                 650                 655
Tyr Ser Ser Gly Ser Gln Phe Tyr His Thr Leu Thr Lys Glu Arg Phe
            660                 665                 670
Leu His Tyr Ala Gln Leu Ser Tyr His Ser Arg Ala Ala Thr Gln Gly
            675                 680                 685
Phe Phe Ala Leu Ala Cys Arg Ser Leu Phe His Leu Leu His Phe Tyr
            690                 695                 700
Cys Tyr Cys Val Cys Gly Cys Arg Asn Cys Leu Val Ser Leu Thr Asn
705                 710                 715                 720
Gln Val Leu Phe Leu His Phe Gln Pro Ile Asp Ser Trp Asp Cys Val
                725                 730                 735
Leu Asn Leu Ala Cys Leu Ser Phe Ala Leu Asp Cys Gln Lys Asn Leu
            740                 745                 750
Leu Leu Leu Ile Pro Leu Asp Asp Cys Gln Phe Ser Glu Pro Ile Leu
            755                 760                 765
Asp Ser Leu Lys Ala Leu Pro Tyr Asp His Gln Leu Tyr His Ala Phe
770                 775                 780
Ser Lys Gly Ser Pro Leu Leu Ala Leu Gln His Pro Asn His Leu Leu
785                 790                 795                 800
Phe Asp Val Gly Gln Phe Leu His Leu Pro Phe Gln Leu Glu Arg Lys
                805                 810                 815
Trp Val Leu Gln Gly Leu Leu Ala Leu Leu Ser Phe Tyr Leu His Lys
                820                 825                 830
Trp Val Arg Phe Val His Tyr Cys Tyr Cys Tyr Asn Phe Gln Val Leu
            835                 840                 845
His Ser Thr Leu Ser Cys Pro Lys Ser Phe Lys Glu Leu Trp Leu Leu
850                 855                 860
Leu Glu Ile Thr His Tyr Arg Leu Gly Phe His Ser His Ser Arg
865                 870                 875                 880
Ile Asp Ile Phe Gln Ile Phe Phe His Asp Phe His Phe Glu Leu
                885                 890                 895
Val Gly Pro Ile Ala Pro Leu Arg Asn Phe Asp Arg Leu Thr Leu Ala
            900                 905                 910
Leu Pro Tyr Asn His Pro Leu Pro Leu Ile Pro Leu Asp Asp Tyr
            915                 920                 925
Gln Leu Tyr Pro Leu Pro Phe Asp Ser His Leu Arg Asn Phe Gln Gly
            930                 935                 940
Arg Phe Leu Leu Ala Leu Pro Cys Asn Pro Tyr Phe Cys His Phe Ile
945                 950                 955                 960
His Ser Lys Leu His Gly Phe Gln Leu Leu Lys Ser Ile Leu Asp Tyr
                965                 970                 975
Leu Asn Leu Ser Pro Asn Leu Gly Leu Leu Val Phe Leu Leu Pro Cys
            980                 985                 990
```

```
Asn Pro Tyr Phe Cys His Phe Ile His Gln Lys Ile Tyr Gln Ser Leu
        995                 1000                1005

Ser Asn Ser Cys His Phe Gln Val Tyr Gln Thr Ile Pro Phe Cys Leu
    1010                1015                1020

Asp Ser Glu Arg Lys Arg Leu Leu Arg Leu Tyr Pro Leu Tyr Ser
1025            1030                1035            1040

Thr Gln Lys Ser His Leu Phe Gly Cys Leu Glu Leu Leu Pro Phe
            1045                1050                1055

Tyr Phe Cys Cys Arg Phe Cys Ser Pro Ile Phe Ser Leu Leu Ser
            1060                1065            1070

Leu Asn Ala Leu Val Ser Leu Glu Ile Phe Gln Asp Leu Ser Glu Leu
        1075                1080                1085

Phe Ser Leu His His Asn Cys Leu Cys Phe Arg Gln Leu Gln Leu Tyr
        1090                1095                1100

Ser Leu Lys Phe Phe Gln Pro Ile Leu Cys Cys Ser Lys Asn Leu
1105            1110                1115            1120

Ala Tyr Leu Leu Val Gly Thr Ile Leu Trp Leu Val Tyr Pro Leu Asn
            1125                1130                1135

Ser Ala Leu Arg Asn Arg Asp Tyr Leu Asn Gln Ala Asn Arg Leu Pro
        1140                1145                1150

Cys Ser Leu Leu Leu Asn Gly Lys Arg His Ser Arg Leu His Pro Tyr
        1155                1160                1165

Trp Asp Ser Trp Arg Arg Trp Cys Ile Asn Asn Asn Gln Gln Thr Ser
        1170                1175                1180

Arg His His Val Leu Gly Tyr Leu Glu Glu His Phe Ser Pro Tyr Leu
1185            1190                1195                1200

Lys Leu Tyr Leu Leu Phe Ser His Asn Leu Glu Cys Ser Ser Asn Pro
            1205                1210                1215

His Tyr Gln Thr Gln Leu Lys Leu Asn Val Leu Cys Leu Phe Lys Gln
            1220                1225                1230

Lys Gln Tyr Asp His Ser Leu Gly Arg Leu Asn Lys Pro Ser Leu Phe
            1235                1240                1245

Gly Asn Leu Ser Gln Phe Gly Ile Phe Pro Ser Leu Ser Arg Ser Ser
        1250                1255                1260

Cys Leu Ile His Tyr Phe Val Gln Glu Ile Pro Asn Leu Phe Cys Phe
1265            1270                1275                1280

Gly Ser Leu Leu Asp Leu Met Leu Val Val Ser Leu Val Gly Leu Leu
            1285                1290                1295

Cys Arg Asp Lys Asn Gly Cys Ser Leu Ser His His Leu Leu Leu Ser
            1300                1305                1310

His Cys Arg Phe Ser Tyr Ala His Leu Leu Pro His Cys Cys Leu Val
            1315                1320                1325

Gly Leu Tyr Asn Gln Arg Trp Arg Ser Asn His Ala Leu Gln Asp His
        1330                1335                1340

His Cys Pro His Thr Thr Met Lys Leu Phe Gln Val Leu Cys His Tyr
1345            1350                1355                1360

Asp Ser Pro Leu Thr Gln Lys Thr Glu Arg Tyr Cys Glu Ser Ile Ile
            1365                1370                1375

Asp Thr Cys Asn Trp Asp Gln Cys Gln Arg Leu Pro Gln His Leu Thr
            1380                1385                1390

Phe Pro Tyr Arg Gln Glu Ile Lys Asn Tyr Pro Phe His Gln Val Asn
            1395                1400                1405

Leu Leu Gln Ala Val Ser Leu Val Cys Arg Trp Trp Trp Leu Tyr Leu
```

```
            1410                1415                1420

Val Gly His Gly Glu Leu Val Leu Asp Leu Leu His Gln Lys Ile
1425                1430                1435                1440

Val Phe Cys Gln Ile Met Arg Glu Lys Tyr Pro Thr Asn Pro His Gln
                1445                1450                1455

Ala Leu His Phe Phe Leu Leu Leu Ala Phe Leu Ser Arg Thr His Gln
                1460                1465                1470

Thr Arg Pro Thr Phe Asp Pro Phe Gly Phe Asp Ser Leu Phe Leu Gln
                1475                1480                1485

Lys Ile Val Trp Gln Ile Ser Lys Thr Pro Leu Ser Leu Tyr His Gln
                1490                1495                1500

Gly Gly Val Val Tyr Phe Pro Asn Phe Gly Ser Ile Gly Cys Phe Thr
1505                1510                1515                1520

Asp Arg Phe Asp Gly Thr Pro Asn Leu Lys Phe Gly Asn Ala Asp Pro
                1525                1530                1535

Gln Ile Ser Glu Ser Ser Leu Trp Lys Ile Leu His Gln Asp Cys Leu
                1540                1545                1550

Cys Leu Asn His Cys Ser Tyr Ser Leu Lys Asn Thr Asp Ser Phe Trp
                1555                1560                1565

Asp Phe Ser Leu Tyr Trp Ser Ile Leu Pro Leu Ile Ala Arg Phe Leu
                1570                1575                1580

Gln Lys Leu Ala Cys Tyr Pro Tyr Arg Ser Tyr Gln Arg Leu Val Phe
1585                1590                1595                1600

Asp Gln Asp Arg Met Lys Arg Gln Arg Tyr Gln Leu Glu Lys Leu Leu
                1605                1610                1615

Glu Asp Tyr Ile Ala Ala Gly Lys Pro Leu Arg Phe Val Val Gly
                1620                1625                1630

Gln Trp Phe Arg Ser Leu Phe Leu Leu Thr Ile Pro Ser Phe Ile Pro
                1635                1640                1645

Ile Gly Ile Leu Leu Val Ser Lys Thr Ala Lys Asn Arg Tyr Thr Leu
                1650                1655                1660

Glu Ser Ile His Val Phe Glu His Ser His Tyr Thr Thr Ile Ser Ser
1665                1670                1675                1680

Ile Phe Phe Phe Phe His Ser Leu Leu Ile Leu Lys Lys Ala Arg Ser
                1685                1690                1695

Leu Gln Ala Ser Lys Gly Asp Asp Ser His Phe Tyr Pro Gln Leu Thr
                1700                1705                1710

Lys Ile Cys Asn Glu Arg Thr Leu Ile Arg Thr Arg Asn Lys Lys Ile
                1715                1720                1725

Phe Leu Lys Lys Ser Asn Ala Thr Leu Lys Tyr Gly Trp Arg Asn Gly
                1730                1735                1740

Ser Arg Ala His Glu Ala Phe Lys Phe Gly Leu Cys Val Met Leu Thr
1745                1750                1755                1760

Ile Ala Cys Ile Ile Lys Arg Leu Ser Thr Arg Ser Thr Trp Glu Thr
                1765                1770                1775

Lys Trp Lys Thr Asn Gln Asp Arg Phe Ser Lys Ile Ala Ser Lys Lys
                1780                1785                1790

Val Ser Leu Val Val Tyr Gly Val Ala Asn Gly Ala Leu Phe Ser Leu
                1795                1800                1805

Ser Ala Trp Val Cys Phe Cys Leu Phe Leu Gly Phe Asn Leu Arg Arg
                1810                1815                1820

Leu Lys Asn Thr Ser Lys Ile Leu Lys Ile Tyr Asn Ser Thr Thr Thr
1825                1830                1835                1840
```

```
Glu Arg Lys Met Val Gly Thr Ser Arg Phe Thr Ile Pro Glu Cys Gln
            1845                1850                1855
Leu Pro Ser Lys Ser Val Gly Phe Asp Leu Asn Tyr Lys Val Ala Leu
            1860                1865                1870
Val Ile Val Lys Tyr Phe Phe Tyr Thr Gln Ala Ile Asp Phe Asn
            1875                1880                1885
Leu Lys Gly Asn Ala Asn Phe Leu Gln Glu Ser Leu Thr Ala Thr Arg
            1890                1895                1900
Lys Leu Leu Gly Trp Gln Pro Ile Leu Trp Arg Ser Pro Val Leu Gln
1905                1910                1915                1920
Lys Ala Ser Leu Gln Leu Lys Val Trp Leu Phe Arg Ser Phe Leu Phe
            1925                1930                1935
Arg Ser Val Val Ala Leu Gly Ser Lys Ala Arg Ile Phe Gly Lys Ser
            1940                1945                1950
Leu Met Thr Leu Lys Glu Val Arg Arg Leu Phe Leu Leu Thr Arg Asn
            1955                1960                1965
Pro Leu Cys Arg Trp Gln Ala Val Leu Ser Ile Ala Leu Ser Leu Ala
            1970                1975                1980
Ser Ile Leu Ala Arg Val Glu Glu Leu Ala Lys Leu Ile Asn Asn Asn
1985                1990                1995                2000
Asn Asn Ser Asn Lys Lys Leu Arg Gly Phe Phe Leu Lys Val Leu Leu
            2005                2010                2015
Ser Leu Val Val Phe Ser Ser Tyr Gly Leu Ala Asn Asp Asp Lys Glu
            2020                2025                2030
Ala Lys Lys Glu Ala Gln Glu Lys Glu Lys Asn Thr Pro Asn Gly Leu
            2035                2040                2045
Val Tyr Thr Asn Leu Asp Phe Asp Ser Phe Lys Ala Thr Ile Lys Asn
            2050                2055                2060
Leu Lys Asp Lys Lys Val Thr Phe Lys Glu Val Asn Pro Asp Ile Ile
2065                2070                2075                2080
Lys Asp Glu Val Phe Asp Phe Val Ile Val Asn Arg Val Leu Lys Lys
            2085                2090                2095
Ile Lys Asp Leu Lys His Tyr Asp Pro Val Ile Glu Lys Ile Phe Asp
            2100                2105                2110
Glu Lys Gly Lys Glu Met Gly Leu Asn Val Glu Leu Gln Ile Asn Pro
            2115                2120                2125
Glu Val Lys Asp Phe Phe Thr Phe Lys Ser Ile Ser Thr Thr Asn Lys
            2130                2135                2140
Gln Arg Cys Phe Leu Ser Leu Arg Gly Glu Thr Arg Glu Ile Leu Cys
2145                2150                2155                2160
Asp Asp Lys Leu Tyr Asn Val Leu Leu Ala Val Phe Asn Ser Tyr Asp
            2165                2170                2175
Pro Asn Asp Leu Leu Lys His Ile Ser Thr Val Glu Ser Leu Lys Lys
            2180                2185                2190
Ile Phe Tyr Thr Ile Thr Cys Glu Ala Val Tyr Leu Arg Glu Arg Cys
            2195                2200                2205
Leu Trp Gln Ala Ser Arg Leu Met Asn Lys Ser Leu Ser Lys Arg
            2210                2215                2220
Phe Lys Ser Gly Ser Phe Lys Lys Asn Leu Lys Gln Thr Cys Lys
2225                2230                2235                2240
Arg Val Ser Ile Pro Phe Leu Lys Ser Cys Leu Met Gly Gly Ile Gly
            2245                2250                2255
Cys Leu Val Ser Leu Lys Leu Leu Phe Ile Pro Leu Tyr Leu Tyr Cys
            2260                2265                2270
```

-continued

```
Leu Pro Leu Tyr Tyr Leu Leu Phe Phe Lys Pro Met Asn Leu Phe
    2275                2280            2285

Leu Arg Leu Leu Leu Cys Leu Leu Asp Ser Arg Lys Ile Ile Gly
    2290                2295            2300

Phe Ile Lys Glu Trp Ser Glu Arg Asn Leu Lys Asn Leu Phe Cys Leu
2305            2310            2315            2320

Arg Ala Lys Thr Lys Arg Ser Ala Phe Phe Pro Ser Leu Val Lys Lys
                2325            2330            2335

Trp Leu Met Thr Ser Thr Ile Gln Thr Glu Lys Thr Asp Leu Ala Leu
                2340            2345            2350

Gln Thr Pro Ile Gln Ile Thr Met Asn Val Phe Met Met Gly Ser Leu
                2355            2360            2365

Leu Thr Thr Ile Leu Phe Ala Gln Ser Asn Trp Gly Ala Leu Ile Phe
    2370            2375            2380

Pro Leu Pro Lys Lys Ile Ser Ser Tyr Thr Leu Leu Phe Ile Ala Phe
2385            2390            2395            2400

Leu Gly Ile Leu Leu Pro Leu Asn Ser Asn Ser Ile Phe Thr Leu Leu
                2405            2410            2415

Lys Arg Lys Ser Leu Leu Met Lys Pro Ile Gly Thr Met Val Leu Phe
                2420            2425            2430

Phe Leu Met Ile Ser Cys Glu Pro Ile Met Arg Ser Lys Arg Glu Lys
                2435            2440            2445

Val Phe Met Ile Leu Val Phe Phe Pro Ser Lys Ile Tyr Thr Leu Ser
                2450            2455            2460

Met Asn Pro Leu Ile Lys Ser Ile Leu Gln Thr Ile Ile Leu Lys Ser
2465            2470            2475            2480

Phe Lys Gly Leu Leu Glu Pro Ser Leu Lys Thr Ser Arg Ile Gly Ser
                2485            2490            2495

Ser Lys Ser Cys Ala Asn Thr Thr Pro Leu Asp Lys Asn Thr Leu Lys
                2500            2505            2510

Met Ala Leu Phe Thr Pro Asn Asn Ala Asn Phe Thr Ile Phe Leu Trp
                2515            2520            2525

Glu Met Lys Pro Leu Leu Phe Ala Thr Glu Lys Thr Cys Ile Ser Arg
                2530            2535            2540

Lys Lys Cys Met Val Gly Lys Lys Phe Ile Leu Pro Ile Ser Met Glu
2545            2550            2555            2560

Lys Ser Met Thr Ile Val Lys Asn Ile Leu Ala Leu Leu Arg Leu Val
                2565            2570            2575

Asn Thr Pro Leu Asn His Lys Ala Ile Cys Leu Ile Lys Ser Thr Pro
                2580            2585            2590

Thr Ala Asn Leu Phe Ser Cys Met Leu Ile Arg Leu Lys Thr His Arg
                2595            2600            2605

Phe Arg Thr Asn Trp Leu Ser Pro Leu Glu Glu Leu Leu Leu Val Glu
                2610            2615            2620

Ala Leu Lys Asn Arg Ala Leu Val Ala Ala Asn Trp Val Met Val Ile
2625            2630            2635            2640

Leu Arg Ala Val Met Val Ile Leu Cys Cys Leu Leu Ile Ala Leu Lys
                2645            2650            2655

Lys Asn Lys Ala Leu Arg Asn Ala Ser Leu Val Leu Thr Leu Lys Val
                2660            2665            2670

Phe Pro Thr Gln Arg Leu Ser Leu Trp Lys Ile Thr Phe Leu Pro Asn
                2675            2680            2685

Ile Ala Leu Leu Ser Arg Phe Leu Leu Phe Leu Met Leu Leu Ile Ile
```

```
                2690                2695                2700
Leu Leu Ile Ser Ser Leu Gly Leu Val Leu Met Ala Ile Lys Arg Ile
2705                2710                2715                2720

Thr Leu Gly Ala Ile Val Arg Lys Ala Arg Ser Ile Arg Leu Phe Ile
                2725                2730                2735

Thr Ser Thr Cys Pro Leu Ile Leu Val Gln Leu Gln Gln Asp Thr Leu
                2740                2745                2750

Tyr Leu Ala Gln Pro Val Gln Val Arg Gln Cys Leu Cys Gln Pro Thr
                2755                2760                2765

Leu Trp Asp Asn Leu Pro Ile Ile Phe Leu Leu Met Ser Ala Lys Thr
                2770                2775                2780

Ser Lys Ser Ser Leu Trp Phe Ile Trp Ile Lys Ile Met Ala Leu Met
2785                2790                2795                2800

Gly Ile Leu Ser Gln Trp Val Gly Ser Met Ser Arg Leu Ser Gly Gln
                2805                2810                2815

Ile Gln Asp Ile Leu Leu Leu Gly Arg Leu Val Cys Lys Lys Gln Met
                2820                2825                2830

Gln Gln Trp Ser Lys Asn Lys Gln Leu Phe Leu Leu Ser Lys Ser Leu
                2835                2840                2845

Lys Thr Gln Leu Lys Ala Met Lys Lys Met Lys Met Ala Thr Ala Ser
2850                2855                2860

Leu Leu Ala Gln Ile Leu Ile Arg Leu Gln Arg Ser Asn Gln Pro Tyr
2865                2870                2875                2880

His Arg Lys Tyr Glu Ser Arg Leu Ser His His Ser Thr Tyr Cys Phe
                2885                2890                2895

Arg Glu Arg Pro Gln Ser Trp Ala Cys Arg Ala Ile Ser Ala Phe Leu
                2900                2905                2910

Gln Ile Asn Gln Trp Ile Ser Met Ala Phe Ser Asn Arg Ser Leu Arg
                2915                2920                2925

Phe Phe Lys Asn Asp Tyr Trp Arg Trp Val Lys Phe Leu Arg Gln Cys
                2930                2935                2940

Phe Ala Leu Tyr Leu Phe Leu Pro Phe Arg Ser Tyr Pro Arg Gly Asn
2945                2950                2955                2960

Gly Trp Ala Ile Cys Leu Arg Tyr Ser Leu Glu Ile Phe Ser Asp Pro
                2965                2970                2975

Lys Val Ala Tyr Phe Val Arg Asp Met Leu Lys Thr Ala Arg Lys Arg
                2980                2985                2990

Asn Ala Ile Val Arg Leu Ala Thr Gln Ser Ile Thr Asp Leu Leu Ala
                2995                3000                3005

Cys Pro Ile Ala Asp Thr Ile Arg Glu Gln Cys Pro Thr Lys Ile Phe
                3010                3015                3020

Leu Arg Asn Asp Gly Gly Asn Leu Ser Asp Tyr Gln Arg Leu Ala Asn
3025                3030                3035                3040

Val Thr Glu Lys Glu Phe Glu Ile Ile Thr Lys Gly Leu Asp Arg Lys
                3045                3050                3055

Ile Leu Tyr Lys Gln Asp Gly Ser Pro Ser Val Ile Ala Ser Phe Asn
                3060                3065                3070

Leu Arg Gly Ile Pro Lys Glu Tyr Leu Lys Ile Leu Ser Thr Asp Thr
                3075                3080                3085

Val Phe Val Lys Glu Ile Asp Lys Ile Ile Gln Asn His Ser Ile Ile
                3090                3095                3100

Asp Lys Tyr Gln Ala Leu Arg Gln Met Tyr Gln Gln Ile Glu Glu Tyr
3105                3110                3115                3120
```

-continued

```
Asn Glu Thr Lys Phe Ala Thr Lys Ile Met Glu Ile Leu Glu Asn Asp
            3125                3130                3135

Val Leu Thr Ile Leu Asp Ser Phe Ser Asn Tyr Leu Phe Glu Leu Lys
        3140                3145                3150

Glu Glu Leu Asp Phe Ile Glu Glu Met Glu Gly Glu Ile Thr Glu
    3155                3160                3165

Gln
```

(2) INFORMATION FOR SEQ ID NO:7:

(i) SEQUENCE CHARACTERISTICS:
        (A) LENGTH: 3287 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Ser Phe Val Tyr Ser Lys Met Gln Gln Thr Lys Asp Asn Glu Glu Phe
1               5                   10                  15

Leu Asn Leu Met Asn Glu Lys Asn Pro Leu Ile Pro Leu Asn Lys Ser
            20                  25                  30

Val Met Lys Ile Gly Val Phe Asp Ser Val Gly Gly Phe Ser Val
        35                  40                  45

Leu Lys Ser Leu Leu Lys Ala Gln Leu Phe Asp Glu Ile Ile Tyr Tyr
50                  55                  60

Gly Asp Ser Ala Arg Val Pro Tyr Gly Thr Lys Asp Pro Thr Thr Ile
65              70                  75                  80

Lys Gln Phe Gly Leu Glu Ala Leu Asp Phe Phe Lys Pro His Gln Ile
                85                  90                  95

Glu Leu Leu Ile Val Ala Cys Asn Thr Ala Ser Ala Leu Ala Leu Glu
            100                 105                 110

Glu Met Gln Lys His Ser Lys Ile Pro Ile Val Gly Val Ile Glu Pro
        115                 120                 125

Ser Ile Leu Ala Ile Lys Arg Gln Val Lys Asp Lys Asn Ala Pro Ile
130                 135                 140

Leu Val Leu Gly Thr Lys Ala Thr Ile Gln Ser Asn Ala Tyr Asp Asn
145                 150                 155                 160

Ala Leu Lys Gln Gln Gly Tyr Leu Asn Val Ser His Leu Ala Thr Ser
                165                 170                 175

Leu Phe Val Pro Leu Ile Glu Glu Ser Ile Leu Glu Gly Glu Leu Leu
            180                 185                 190

Glu Thr Cys Met Arg Tyr Tyr Phe Thr Pro Leu Lys Ile Phe Pro Lys
        195                 200                 205

Leu Phe Val Ala Arg Ile Phe Pro Ser Leu Lys Lys Leu Arg Ala Ile
210                 215                 220

Leu Trp Ser Ile Leu Pro Phe Gln His Pro Pro Tyr Ser Ser Ile Arg
225                 230                 235                 240

Ala Met Leu Leu Asp Ile Cys Ser Lys Asn Thr Pro Leu Lys Lys Met
                245                 250                 255

His Thr His Ser Leu Lys Trp Asn Phe Met Arg Ala Ala Met Ser Gly
            260                 265                 270

Lys Asn Lys Leu Lys Asn Gly Ser Asn Cys Asn Ala Asn Lys Asn Leu
        275                 280                 285

Lys Ser Lys Leu Asn Ser Gln Lys Gly Ala Ile Ala His Thr Ile Arg
290                 295                 300
```

```
Val Leu Cys Leu Ser Ala Leu Glu Arg Phe Met Lys Ala Phe Ser Glu
305                 310                 315                 320

Glu Cys Leu Met Ile Ile Phe Gly Lys Asp Tyr Leu Ser Thr Asp Leu
                325                 330                 335

Gln Asn Ser Ala Lys Asp Ile Leu Leu Ile Ala Ser Ile Leu Lys Glu
                340                 345                 350

Arg Leu Phe Thr His Lys Asn Glu Ile Phe Phe Cys Pro Arg Asn Ser
            355                 360                 365

His Ile Gln Ala Phe Arg Ile Gln Glu Arg Lys Ile Thr Thr Ser Phe
        370                 375                 380

His Gly Gly Ile Asn Asn Asn Ile Cys Leu Phe Thr Leu Lys Gly Ile
385                 390                 395                 400

His Ser Val Tyr Phe Glu Leu Ile Lys Ile Leu Glu Ala Val Phe Phe
                405                 410                 415

His Phe Ser Gln Ala Ser Phe Leu Gly Ile Ile Arg Cys Asp Asn Ser
                420                 425                 430

Tyr Gly Phe Ser Asp Phe Ser Leu Val Lys Ser Ala Ile Asn Leu Leu
            435                 440                 445

Lys Leu Tyr Asp Phe Leu Asn Leu Ile Phe Val Ile Ala Thr Cys Phe
                450                 455                 460

Phe Phe Met Leu Ser Leu Pro Leu Ile Asn Phe Arg Thr Ile Ala Arg
465                 470                 475                 480

Thr His His Asn Gln Thr Phe Ala Lys Gly Val Phe Leu Gly Glu Ile
                485                 490                 495

Ser Met Gln Thr Leu Lys Asn Lys Ala Phe Arg Cys Leu Ser Gly Tyr
                500                 505                 510

Phe Lys Val Lys Cys Pro Thr Ala Lys Asp Asp Trp Ala Ser Ala Asp
            515                 520                 525

Val Ala Arg Arg Glu Ser Leu Val Leu Thr Leu Cys Pro Tyr Asn Arg
                530                 535                 540

Asp Phe Thr Glu Phe Glu Leu Gln Arg Ile Pro Tyr Arg Ser His Thr
545                 550                 555                 560

Ser Tyr Leu Gln Arg Arg Asn Phe Ala His Phe Leu Arg Ile Arg Met
                565                 570                 575

Tyr Gly Asp Met Ile Pro Ile Gly Ser Ile His Pro Lys Tyr Arg Arg
                580                 585                 590

Leu Gly Phe Leu Leu Arg Ser Ile Lys Lys Pro Leu Ala Phe Ser Lys
            595                 600                 605

Gly Trp Phe Leu Arg Phe Trp Tyr Ser Leu Ile Leu Asp Phe Trp Lys
            610                 615                 620

Pro Pro Phe Val Leu Thr Phe Leu Ile Pro Cys Ser Ala Phe Ser Leu
625                 630                 635                 640

Ala Lys Gln Asp Ala Val Glu Asn Ala Leu Val Lys Asn Cys Val Lys
                645                 650                 655

Pro Glu Leu Val Ser Phe Thr Ala Leu Phe Asn Leu Val Glu Asn Leu
                660                 665                 670

Asn Glu Ser Glu Ser Phe Ile Phe Phe Trp Leu Lys Pro Ile Leu Ser
                675                 680                 685

Tyr Ser Asp Lys Gly Thr Leu Pro Thr Leu Cys Ala Thr Ile Leu Ser
                690                 695                 700

Phe Thr Ser Leu Ser His Ser Gly Phe Phe Cys Val Ser Met Pro Val
705                 710                 715                 720

Ala Phe Ser Leu Ile Ala Pro Phe Leu Ile Leu Leu Leu Met Arg Met
```

-continued

```
                725                 730                 735
Trp Leu Leu Val Ala Leu Ser Ser Phe Ala Asp Lys Leu Ala Gly Thr
            740                 745                 750
Phe Phe Ala Leu Ser Thr His Arg Phe Met Gly Leu Cys Phe Val Glu
        755                 760                 765
Ser Leu Ser Leu Ser Ile Val Cys Ser Arg Leu Pro Lys Lys Pro Ala
    770                 775                 780
Leu Ala Ser Asp Thr Ala Leu Arg Leu Ser Ile Phe Ala Asn Ser Phe
785                 790                 795                 800
Leu Glu Ser Pro Thr Leu Leu Arg Ser Ser Thr Leu Ser Cys Leu Phe
                805                 810                 815
Lys Gly Lys Pro Ala Ala Cys Pro Thr Thr Pro Lys Pro Leu Ala Ile
            820                 825                 830
Leu Ser Arg Ser Ile Phe Ala Phe Thr Phe Leu Ala Thr Ala Met Gly
        835                 840                 845
Ser Ser Arg Leu Ala Ala Cys Pro Ala Phe Phe Leu Leu Thr Leu Ala
    850                 855                 860
Met Gly Ser Phe Leu Ser Pro Leu Leu Leu Leu Leu Lys Phe Pro
865                 870                 875                 880
Ser Phe Ala Phe Asn Ser Phe Leu Met Ser Glu Lys Phe Leu Glu Arg
                885                 890                 895
Val Val Ala Ser Ala Asp Asn Pro Leu Pro Thr Arg Val Pro Phe Thr
            900                 905                 910
Pro Phe Leu Thr Asp Tyr Ile Ser Asp Phe Phe Leu Ala Leu Arg Leu
        915                 920                 925
Ser Phe Phe Ala Cys Trp Ala Asn Cys Ser Phe Glu Lys Phe Leu Arg
    930                 935                 940
Ser Ala Asn Ala Cys Ser Thr Leu Leu Lys Ser Pro Val Ala Leu Ala
945                 950                 955                 960
Thr Asp Thr Ala Leu Arg Leu Ser Thr Leu Ser Val Thr Phe Leu Met
                965                 970                 975
Ile Thr Ser Leu Thr Glu Phe Ser Arg Ser Leu Phe Ala Cys Val Thr
            980                 985                 990
Leu Leu Lys Ser Leu Phe Leu Pro Phe Leu Asn Ser Phe Lys Ala Ala
        995                 1000                1005
Leu Arg Phe Ser Thr Phe Glu Ile His Ser Gly Leu Ile Pro Lys Ser
    1010                1015                1020
Phe Thr Glu Pro Leu Arg Ala Phe Ser Val Ser Ala Leu Leu Lys
1025                1030                1035                1040
Ser Leu Phe Leu Pro Phe Leu Asn Ser Ser Lys Asp Leu Ser Lys Ser
                1045                1050                1055
Phe Lys Phe Leu Leu Thr Phe Ser Ser Leu Ser Asp Asn Ser Leu Leu
            1060                1065                1070
Met Pro Leu Arg Phe Ala Ala Ile Ala Leu Ala Ser Leu Leu Ala Ser
        1075                1080                1085
Leu Leu Ile Asn Ala Lys Ile Ser Ser Phe Trp Leu Leu Ala Ala Phe
    1090                1095                1100
Ala Ser Ile Leu Phe Leu Leu Pro Leu Leu Ser Asn Phe Ser
1105                1110                1115                1120
Thr Ser Phe Ser Lys Cys Ser Arg Phe Leu Arg Asp Phe Ser Arg Ser
                1125                1130                1135
Phe Ala Phe Phe Thr Ser Ser Leu Pro Val Phe Leu Ala Ser Ala Thr
            1140                1145                1150
```

-continued

```
Ala Leu Leu Lys Phe Lys Val Phe Pro Thr Asn Ser Leu Leu Leu Leu
        1155                1160                1165

Lys Lys Ser Leu Ile Ser Leu Leu Ala Ser Cys Gly Asp Asn Pro Leu
        1170                1175                1180

Val Val Ser Leu Ser Ser Lys Phe Arg Leu Thr Lys Leu Val Ile Ala
1185                1190                1195                1200

Arg Leu Phe Lys Ser Gly Lys Leu Lys Ile Ala Thr Leu Leu Lys Pro
                1205                1210                1215

Thr Ser Lys Trp Glu Thr Pro Phe Val Thr Pro Thr Pro Leu Leu Gly
                1220                1225                1230

Phe Leu Glu Ala Leu Val Tyr Leu Lys Leu Glu Ser Thr Asn Ile Thr
                1235                1240                1245

Pro Ser Cys Phe Arg Leu Pro Arg Val Thr Phe Ser Leu Ser Lys
                1250                1255                1260

Ala Leu Ser Ala Phe Phe Pro Ser Leu Arg Val Leu Lys Ser Pro Leu
1265                1270                1275                1280

Pro Asn Ser Val Ile Lys Ala Glu Cys Phe Val Ser Phe Leu Glu Thr
                1285                1290                1295

Lys Ala Ile Arg Ser Phe Pro Arg Ala Ser Lys Ala Leu Glu Ser Phe
                1300                1305                1310

Trp Lys Ser Leu Ile Ser Val Arg Asn Phe Ser Phe Ser Phe Ser Leu
                1315                1320                1325

Lys Leu Ser Asn Leu Ala Leu Phe Cys Ala Arg Asn Ser Met Lys Ser
                1330                1335                1340

Ile Leu Phe Trp Ile Ser Ser Leu Asn Ala Arg Cys Glu Pro Val Ser
1345                1350                1355                1360

Trp Ser Ser Leu Arg Lys Leu Gly Leu Leu Ile Pro Phe Ser Pro Pro
                1365                1370                1375

Ala Met Thr Lys Pro Leu Pro Phe Phe Ile Cys Thr Leu Ile Ile Val
                1380                1385                1390

Ala Thr Leu Leu Pro Cys Trp Ser Leu Pro Thr Val Ala Phe Gln Ser
                1395                1400                1405

Cys Leu Ala Pro Gly Pro Pro Leu Pro Pro Tyr Asn Asn Glu Thr Phe
        1410                1415                1420

Ser Gly Ser Met Pro Leu Leu Pro Ile Asn Thr Glu Asp Arg Ala Leu
1425                1430                1435                1440

Leu Ile Asn Asn Leu Asn Leu Leu Gly Ser Met Ser Ala Thr Pro Ser
                1445                1450                1455

Thr Ser Asn Ile Ser Ile Ser Pro Arg Val Asn Leu Glu Lys Leu Pro
                1460                1465                1470

Leu Ser Ser Ser Lys Ser Leu Ala Ser Gly Gly Lys Pro Cys Met Ser
                1475                1480                1485

Val Val Val Val Ala Ile Ser Gly Trp Thr Trp Gly Thr Gly Ser Leu
        1490                1495                1500

Ile Ala Ser Leu Thr Ser Glu Asp Cys Phe Leu Ser Asn Ile Asn Glu
1505                1510                1515                1520

Arg Lys Ile Ser Asn Gln Ser Pro Val Gly Ser Pro Phe Phe Ser
                1525                1530                1535

Ala Ser Cys Leu Ser Phe Lys Asp Ser Ser Asn Thr Pro Met Asn Phe
        1540                1545                1550

Ser Val Arg Ile Phe Pro Ile Met Ile Pro Ala Lys Asp Cys Leu Ala
        1555                1560                1565

Asp Phe Lys Asn Ser Ala Phe Ser Leu Ser Ser Arg Ile Gly Gly Cys
        1570                1575                1580
```

```
Met Ile Phe Ser Ile Lys Phe Arg Ile Asp Arg Val Leu Ile Leu Asp
1585                1590                1595                1600

Gly Ser Phe Trp Asp Thr Gln Leu Val Lys Ile Arg Arg Ser Pro Asn
            1605                1610                1615

Phe Lys Leu Phe Val Glu Asp Ser Thr Ser Met Arg Leu Ser Leu Leu
            1620                1625                1630

Ile Lys Ser Leu Leu Leu Leu Ile Lys Ser Glu Lys Tyr Phe Phe Leu
            1635                1640                1645

Val Gly Phe Leu Ile Ala Leu Leu Glu Tyr Ser Ser Leu Asn Cys Glu
            1650                1655                1660

Ile Pro Ser Lys Ala Cys Leu Leu Ser Leu Ser Phe Leu Ser Thr Ile
1665                1670                1675                1680

Gly Phe Ser Gly Ser Tyr Glu Ala Thr Ala Leu Ser Thr Leu Arg Lys
            1685                1690                1695

Ala Thr Arg Leu Leu Ile Asn Cys Cys Gly Leu Lys Ala Ala Ser Val
            1700                1705                1710

Cys Gly Cys Trp Ser Met Val Ser Leu Val Ile Val Ser Pro Tyr Tyr
            1715                1720                1725

Thr Phe His Thr Tyr Arg Tyr Leu Val Ser Val Lys Asp Cys Lys Ser
            1730                1735                1740

Leu His Ala Val Val Asn Ser Cys Leu Thr Phe Ser Leu Tyr Asn Asn
1745                1750                1755                1760

Ile Lys His Phe Phe Phe Ser Leu Ile Ile Asn Ile Glu Lys
            1765                1770                1775

Ser Pro Ile Val Ala Gly Val Arg Leu Gly Arg Phe Thr Phe Leu Pro
            1780                1785                1790

Thr Ile Asn Lys Asn Leu Leu Lys Lys Asn Phe Asn Lys Asn Lys Lys
            1795                1800                1805

Glu Met Asn Leu Phe Glu Glu Ile Lys Cys Asn Ala Lys Val Trp Leu
            1810                1815                1820

Glu Lys Trp Leu Val Lys Val Ser Thr Ser Val Leu Lys Ile Val Trp
1825                1830                1835                1840

Phe Val Cys His Ala Tyr Tyr Ser Met Tyr Asn Ala Phe Val Ile His
            1845                1850                1855

Lys Ile His Met Gly Asn Lys Met Glu Asn Lys Ser Ile Gly Gln Ile
            1860                1865                1870

Phe Lys Asp Ser Leu Lys Lys Ser Phe Phe Ser Gly Leu Trp Ser Cys
            1875                1880                1885

Leu Lys Trp Ser Phe Ile Leu Thr Leu Ile Ser Leu Gly Leu Phe Leu
            1890                1895                1900

Leu Val Phe Arg Phe Gln Pro Glu Thr Ile Lys Lys Tyr Ile Lys Asp
1905                1910                1915                1920

Pro Lys Asp Leu Gln Phe Tyr Asn Asp Leu Arg Lys Lys Asn Gly Trp
            1925                1930                1935

Asp Lys Val Tyr Tyr Ser Met Met Ser Val Ala Glu Gln Lys Arg Arg
            1940                1945                1950

Phe Phe Lys Leu Ser Ser Ala Cys Met Asn Ser Ile Lys Ile Leu Phe
            1955                1960                1965

Phe Leu Ile Tyr Ser Ser Asp Phe Gln Phe Glu Arg Lys Arg Met Lys
            1970                1975                1980

Phe Phe Thr Arg Ile Thr Asp Ser Tyr Lys Lys Val Val Val Thr Leu
1985                1990                1995                2000

Gly Leu Val Val Thr Thr Asn Pro Leu Met Ala Val Ala Ser Pro Thr
```

```
                    2005                 2010                 2015
    Glu Gly Val Thr Ala Thr Lys Gly Leu Val Ile Gln Ile Ile Ser Val
                         2020                 2025                 2030

Leu Ala Ile Val Gly Gly Cys Ala Leu Gly Val Lys Gly Ile Ala Asp
                         2035                 2040                 2045

Ile Trp Lys Ile Ser Asp Asp Ile Lys Arg Gly Gln Ala Thr Val Phe
                         2050                 2055                 2060

Ala Tyr Ala Gln Pro Ile Ala Met Leu Ala Val Ala Gly Gly Ile Ile
    2065                 2070                 2075                 2080

Tyr Leu Ser Thr Lys Phe Gly Phe Asn Ile Gly Glu Gly Gly Gly Ala
                         2085                 2090                 2095

Ser Val Asp Gln Gln Gln Glu Thr Lys Arg Leu Phe Phe Glu Ser Ser
                         2100                 2105                 2110

Leu Lys Ser Arg Cys Phe Gln Phe Val Trp Val Ser Lys Gln Arg Ser
                         2115                 2120                 2125

Gln Lys Arg Ser Thr Arg Lys Arg Lys Lys His Ser Gln Trp Ala Cys
                         2130                 2135                 2140

Leu Tyr Lys Phe Arg Phe Phe Gln Ser Asp Tyr Gln Lys Phe Glu Arg
    2145                 2150                 2155                 2160

Gln Glu Ser Asn Phe Gln Arg Ser Gln Ser Arg Tyr Tyr Gln Arg Ser
                         2165                 2170                 2175

Phe Leu Arg Asp Cys Gln Ser Pro Lys Asn Lys Gly Phe Glu Ala Leu
                         2180                 2185                 2190

Arg Ser Ser Tyr Lys Asn Leu Lys Gly Gly Asn Gly Ile Glu Cys Arg
                         2195                 2200                 2205

Ile Thr Asp Gln Ser Ser Glu Arg Leu Phe Tyr Phe Gln Lys His Gln
                         2210                 2215                 2220

His Asp Gln Gln Thr Thr Leu Leu Ser Val Ile Ala Arg Arg Asn Lys
    2225                 2230                 2235                 2240

Arg Asn Ser Met Arg Val Ile Cys Phe Ile Gly Arg Ile Gln Phe Leu
                         2245                 2250                 2255

Ser Ser Phe Glu Thr Tyr His Arg Arg Val Ser Gln Lys Asn Leu Leu
                         2260                 2265                 2270

Tyr Asp Tyr Met Ser Gly Ile Ser Ile Lys Arg Glu Val Phe Val Ala
                         2275                 2280                 2285

Ser Lys Gln Ala Asp Glu Gln Lys Lys Leu Ile Ile Glu Gln Glu Val
                         2290                 2295                 2300

Gln Lys Arg Gln Phe Gln Lys Ile Glu Glu Leu Lys Ala Asp Met Gln
    2305                 2310                 2315                 2320

Lys Gly Val Asn Pro Phe Phe Lys Val Leu Phe Asp Gly Gly Asn Arg
                         2325                 2330                 2335

Leu Phe Gly Phe Pro Glu Thr Phe Ile Tyr Ser Ser Ile Phe Ile Leu
                         2340                 2345                 2350

Phe Val Thr Ile Val Leu Ser Val Ile Leu Phe Gln Ala Tyr Glu Pro
                         2355                 2360                 2365

Val Leu Ile Val Ala Ile Val Ile Val Leu Val Ala Leu Gly Phe Lys
                         2370                 2375                 2380

Lys Asp Tyr Arg Leu Tyr Gln Arg Met Glu Arg Ala Met Lys Phe Lys
    2385                 2390                 2395                 2400

Lys Pro Phe Leu Phe Lys Gly Val Lys Asn Lys Ala Phe Met Ser Ile
                         2405                 2410                 2415

Phe Ser Met Lys Pro Ser Lys Glu Met Ala Asn Asp Ile His Leu Asn
                         2420                 2425                 2430
```

```
Pro Asn Arg Glu Asp Arg Leu Val Ser Ala Ala Asn Ser Tyr Leu Ala
        2435                2440                2445

Asn Asn Tyr Glu Cys Phe Leu Asp Asp Gly Val Ile Leu Thr Asn Asn
        2450                2455                2460

Tyr Ser Leu Leu Gly Thr Ile Lys Leu Gly Ile Asp Phe Leu Thr
2465                2470                2475                2480

Thr Ser Lys Lys Asp Leu Ile Glu Leu His Ala Ser Ile Tyr Ser Val
        2485                2490                2495

Phe Arg Asn Phe Val Thr Pro Glu Phe Lys Phe Tyr Phe His Thr Ile
        2500                2505                2510

Lys Lys Lys Ile Val Ile Asp Glu Thr Asn Arg Asp Tyr Gly Leu Ile
        2515                2520                2525

Phe Ser Asn Asp Phe Met Arg Ala Tyr Asn Gly Lys Gln Lys Arg Glu
        2530                2535                2540

Ser Phe Tyr Asp Ile Ser Phe Phe Leu Thr Ile Glu Gln Asp Leu Leu
2545                2550                2555                2560

Asp Thr Leu Asn Glu Pro Val Met Asn Lys Lys His Phe Ala Asp Asn
        2565                2570                2575

Asn Phe Glu Glu Phe Gln Arg Ile Ile Arg Ala Lys Leu Glu Asn Phe
        2580                2585                2590

Lys Asp Arg Ile Glu Leu Ile Glu Glu Leu Leu Ser Lys Tyr His Pro
        2595                2600                2605

Thr Arg Leu Lys Glu Tyr Thr Lys Asp Gly Val Ile Tyr Ser Lys Gln
        2610                2615                2620

Cys Glu Phe Tyr Asn Phe Leu Val Gly Met Asn Glu Ala Pro Phe Ile
2625                2630                2635                2640

Cys Asn Arg Lys Asp Leu Tyr Leu Lys Glu Lys Met His Gly Gly Val
        2645                2650                2655

Lys Glu Val Tyr Phe Ala Asn Lys His Gly Lys Ile Leu Asn Asp Asp
        2660                2665                2670

Leu Ser Glu Lys Tyr Phe Ser Ala Ile Glu Ile Ser Glu Tyr Ala Pro
        2675                2680                2685

Lys Ser Gln Ser Asp Leu Phe Asp Lys Ile Asn Ala Leu Asp Ser Glu
        2690                2695                2700

Phe Ile Phe Met His Ala Tyr Ser Pro Lys Asn Ser Gln Val Leu Lys
2705                2710                2715                2720

Asp Lys Leu Ala Phe Thr Ser Arg Arg Ile Ile Ile Ser Gly Gly Ser
        2725                2730                2735

Lys Glu Gln Gly Met Thr Leu Gly Cys Leu Ser Glu Leu Val Gly Asn
        2740                2745                2750

Gly Asp Ile Thr Leu Gly Ser Tyr Gly Asn Ser Leu Val Leu Phe Ala
        2755                2760                2765

Asp Ser Phe Glu Lys Met Lys Gln Ser Val Lys Glu Cys Val Ser Ser
        2770                2775                2780

Leu Asn Ala Lys Gly Phe Leu Ala Asn Ala Ala Thr Phe Ser Met Glu
2785                2790                2795                2800

Asn Tyr Phe Phe Ala Lys His Cys Ser Phe Ile Thr Leu Pro Phe Ile
        2805                2810                2815

Phe Asp Val Thr Ser Asn Asn Phe Ala Asp Phe Ile Ala Met Arg Ala
        2820                2825                2830

Met Ser Phe Asp Gly Asn Gln Glu Asn Asn Ala Trp Gly Asn Ser Val
        2835                2840                2845

Met Thr Leu Lys Ser Glu Ile Asn Ser Pro Phe Tyr Leu Asn Phe His
        2850                2855                2860
```

-continued

```
Met Pro Thr Asp Phe Gly Ser Ala Ser Ala Gly His Thr Leu Ile Leu
2865                 2870                2875                2880

Gly Ser Thr Gly Ser Gly Lys Thr Val Phe Met Ser Met Thr Leu Asn
            2885                2890                2895

Ala Met Gly Gln Phe Ala Tyr Asn Phe Pro Ala Asn Val Ser Lys Asp
            2900                2905                2910

Lys Gln Lys Leu Thr Met Val Tyr Met Asp Lys Asp Tyr Gly Ala Tyr
            2915                2920                2925

Gly Asn Ile Val Ala Met Gly Gly Glu Tyr Val Lys Ile Glu Leu Gly
            2930                2935                2940

Thr Asp Thr Gly Leu Asn Pro Phe Ala Trp Ala Ala Cys Val Gln Lys
2945                2950                2955                2960

Thr Asn Ala Thr Met Glu Gln Lys Gln Thr Ala Ile Ser Val Val Lys
                2965                2970                2975

Glu Leu Val Lys Asn Leu Ala Thr Lys Ser Asp Glu Lys Asp Glu Asn
                2980                2985                2990

Gly Asn Ser Ile Ser Phe Ser Leu Ala Asp Ser Asn Thr Leu Ala Ala
            2995                3000                3005

Gln Pro Thr Leu Ser Gln Glu Ile Ile Ile Pro Ser Leu Asn Leu
            3010                3015                3020

Leu Met Leu Ser Gly Lys Thr Thr Met Ile Leu Met Gly Leu Ser Arg
3025                3030                3035                3040

Asp Arg Leu Phe Ala Asn Gln Pro Met Val Asn Phe Asn Gly Phe Leu
                3045                3050                3055

Ile Ile Lys Gln Gln Ile Ala Ile Phe Gln Lys Arg Leu Leu Ala Leu
                3060                3065                3070

Met Gly Gln Val Ser Thr Ile Met Met Phe Arg Pro Leu Phe Val Phe
            3075                3080                3085

Thr Phe Ser Leu Val Ser Lys Arg Gln Trp Met Gly Val Asp Leu Ser
            3090                3095                3100

Ile Leu Met Lys Pro Gly Asn Ile Arg Ser Lys Gly Arg Leu Phe Cys
3105                3110                3115                3120

Lys Arg His Ala Lys Asn Cys Lys Glu Lys Lys Arg Tyr Cys Gln Thr
                3125                3130                3135

Cys Asp Ser Lys His His Ser Phe Gly Leu Pro Tyr Cys Tyr Asp Arg
            3140                3145                3150

Thr Met Pro Tyr Lys Asp Phe Phe Glu Lys Arg Trp Gly Gln Ser Phe
            3155                3160                3165

Leu Pro Lys Ile Gly Cys Tyr Arg Lys Arg Ile Asn His His Gly Thr
            3170                3175                3180

Arg Glu Asn Pro Leu Gln Thr Gly Trp Lys Pro Arg Tyr Arg Phe Phe
3185                3190                3195                3200

Glu Arg His Ser Arg Ile Phe Glu Asn Phe Ile His Arg Tyr Cys Ile
                3205                3210                3215

Cys Gln Arg Asn Asp Tyr Pro Lys Pro Tyr His Arg Ile Ser Gly Leu
            3220                3225                3230

Glu Thr Asn Val Ser Thr Asn Arg Gly Val Leu Lys Asn Lys Ile Cys
            3235                3240                3245

Val Asn Lys Asn Tyr Gly Asn Phe Arg Lys Cys Leu Asp Asp Phe Gly
            3250                3255                3260

Phe Phe Leu Ser Phe Thr Glu Arg Ile Gly Leu His Arg Arg Arg
3265                3270                3275                3280

Asn Gly Arg Arg Asn His Thr
```

3285

(2) INFORMATION FOR SEQ ID NO:8:

(i) SEQUENCE CHARACTERISTICS:
        (A) LENGTH: 3200 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Lys Leu Cys Leu Phe Asn Ala Thr Asn Gly Gln Arg Ile Phe Lys Leu
 1               5                  10                  15

Asn Glu Lys Ile Lys Ser Leu Ile Asn Pro Ile Lys Leu Lys Lys Cys
            20                  25                  30

His Glu Asn Arg Arg Phe Arg Cys Gly Arg Val Arg Phe Lys Lys Pro
        35                  40                  45

Phe Lys Ser Ala Ile Ile Asn His Leu Leu Trp Arg Arg Ser Ala Leu
    50                  55                  60

Trp His Arg Pro His Tyr Asp Gln Ala Ile Trp Leu Arg Gly Phe Gly
65                  70                  75                  80

Phe Phe Gln Thr Ala Pro Asp Ile Ile Asp Cys Gly Met Gln His Ser
                85                  90                  95

Glu Arg Ser Ser Phe Arg Arg Asp Ala Lys Ala Phe Gln Asn Pro Tyr
            100                 105                 110

Cys Gly Arg Asp Ala Lys His Phe Ser Asp Gln Ala Thr Ser Lys Arg
        115                 120                 125

Lys Arg Pro Tyr Phe Ser Ala Arg Asp Lys Ser Asp Pro Ile Gln
    130                 135                 140

Arg Leu Gln Cys Pro Glu Thr Thr Arg Leu Phe Glu Cys Phe Ala Phe
145                 150                 155                 160

Ser His Phe Ser Phe Cys Ala Phe Asp Arg Lys Tyr Phe Arg Gly Arg
                165                 170                 175

Ile Val Arg Asn Leu His Ala Leu Leu Phe His Ser Leu Lys Asp Phe
            180                 185                 190

Pro Glu Val Ile Ile Leu Gly Cys Thr His Phe Pro Leu Ile Ala Gln
        195                 200                 205

Lys Ile Glu Gly Tyr Phe Met Glu His Phe Ala Leu Ser Thr Pro Pro
    210                 215                 220

Leu Leu Ile His Ser Gly Asp Ala Ile Val Gly Tyr Leu Gln Gln Lys
225                 230                 235                 240

Tyr Ala Leu Lys Lys Asn Ala His Ala Phe Pro Lys Val Glu Phe His
                245                 250                 255

Ala Ser Gly Asp Val Ile Trp Leu Glu Lys Gln Ala Lys Glu Trp Leu
            260                 265                 270

Lys Leu Arg Lys Phe Lys Val Lys Ile Thr Gln Phe Pro Lys Arg Gly
        275                 280                 285

Tyr Ser Ser His Tyr Lys Gly Ile Val Leu Ile Ile Lys Arg Phe Arg
    290                 295                 300

Glu Ile Tyr Glu Ser Val Leu Lys Arg Met Ser Asn Asp Tyr Leu
305                 310                 315                 320

Trp Lys Arg Leu Pro Ile Tyr Arg Leu Ala Lys Arg Arg Tyr Ser Ser
                325                 330                 335

His Arg Phe Val Asn Ser Gln Arg Lys Thr Phe Tyr Pro Gln Lys Asp
            340                 345                 350
```

```
Phe Leu Leu Pro Lys Pro His Ser Ser Val Asn Leu Ala Arg Lys Lys
            355                 360                 365

Asp Tyr His Lys Phe Ser Arg Trp Asn Lys Tyr Leu Pro Leu His Leu
        370                 375                 380

Glu Arg His Pro Gln Cys Leu Phe Ala His Gln Asn Ser Ser Arg Ile
385                 390                 395                 400

Phe Pro Leu Leu Ile Ala Ser Val Phe Phe Gly His Tyr Lys Val Phe
                405                 410                 415

Leu Trp Phe Phe Phe Phe Phe Gly Glu Arg Asp Gln Phe Ala Leu Lys
            420                 425                 430

Ala Leu Phe Phe Glu Leu Asp Leu Cys Tyr Ser Tyr Leu Phe Phe Leu
            435                 440                 445

Val Tyr Ala Leu Phe Ile Thr Leu Asn Phe Ser His Tyr Ser Thr Asn
        450                 455                 460

Pro Leu Ala Gln Ser Asn Leu Ile Leu Ser Lys Gly Leu Ser Leu Phe
465                 470                 475                 480

Gly Val Gly Asn Ile His Ala Asp Phe Lys Glu Gln Ser Leu Ser Leu
                485                 490                 495

Val Ser Val Gly Ile Phe Gly Glu Val Pro Asn Arg Arg Leu Gly
            500                 505                 510

Phe Leu Gly Cys Cys Pro Gly Glu Phe Gly Ser His Ser Val Ser Leu
            515                 520                 525

Gly Phe Tyr Arg Val Ala Pro Thr His Ser Leu Gln Val Ser His Ile
        530                 535                 540

Ile Ser Pro Lys Ala Leu Cys Thr Leu Pro Thr Leu Asp Thr Asn Val
545                 550                 555                 560

Trp Gly Tyr Asp Thr Met Asn Trp His Ser Ser Gln Ile Leu Lys Thr
                565                 570                 575

Ile Gly Ile Ser Ala Lys Glu Tyr Lys Thr Pro Arg Phe Gln Gly Val
            580                 585                 590

Val Phe Ala Phe Leu Val Phe Leu Asn Pro Leu Arg Phe Leu Glu Thr
        595                 600                 605

Thr Phe Cys Ile Asn Val Leu Asp Ser Met Leu Arg Ile Phe Ser Arg
610                 615                 620

Gln Ala Val Ile Arg Cys Cys Arg Lys Cys Ile Gly Lys Leu Arg Lys
625                 630                 635                 640

Ala Arg Ile Ser Val Phe Tyr Ser Ile Val Gln Leu Gly Gly Lys Leu
                645                 650                 655

Glu Arg Ile Arg Ile Ile Phe His Ile Leu Leu Val Glu Ala Asn Phe
            660                 665                 670

Ile Ile Leu Gln Arg Asn Ala Ser Tyr Ile Met Arg Asn Tyr Leu Ile
        675                 680                 685

Ile His Glu Leu Glu Pro Leu Arg Val Phe Leu Arg His Ala Gly Arg
        690                 695                 700

Phe Phe Ile Asp Cys Ser Ile Phe Asp Ile Ala Ile Asn Ala Tyr Val
705                 710                 715                 720

Ala Val Ser Ser Val Ile Val Phe Arg Gln Thr Ser Arg Tyr Phe Phe
                725                 730                 735

Cys Thr Phe Asn Pro Ile His Gly Ile Val Phe Cys Arg Ile Phe Glu
            740                 745                 750

Leu Val Tyr Arg Leu Leu Ile Ala Lys Lys Thr Cys Phe Ser Phe Tyr
        755                 760                 765

Arg Leu Ile Glu Ile Val Asn Phe Leu Ser Gln Phe Leu Ile Pro Lys
```

-continued

```
            770                 775                 780
Pro Tyr Leu Thr Glu Ile Ile Asn Phe Ile Met Pro Phe Gln Arg Glu
785                 790                 795                 800

Ala Arg Cys Leu Pro Tyr Asn Thr Gln Thr Thr Cys Tyr Leu Ile Glu
                805                 810                 815

Ser Val Asn Phe Cys Ile Tyr Leu Phe Ser Asn Leu Ser Val Asn Gly
                820                 825                 830

Phe Phe Lys Ala Ser Cys Leu Pro Cys Phe Leu Phe Ile Asn Phe Ser
                835                 840                 845

Ile Asn Gly Phe Val Phe Glu Ser Ile Ile Val Ile Val Ile Glu Ile
                850                 855                 860

Ser Lys Phe Cys Ile Gln Leu Phe Leu Asp Val Arg Lys Val Phe Arg
865                 870                 875                 880

Lys Ser Cys Gly Phe Cys Leu Arg Pro Ile Thr Asp Gly Ser Ile His
                885                 890                 895

Thr Ile Leu Asn Gly Leu Ile Tyr Phe Arg Phe Ser Ser Ile Glu
                900                 905                 910

Thr Phe Ile Phe Leu Ser Leu Leu Gly Gln Leu Leu Leu Glu Ile Phe
                915                 920                 925

Glu Ile Gly Arg Leu Leu Tyr Pro Thr Glu Ile Thr Arg Cys Phe Ser
930                 935                 940

His Tyr Arg Leu Ile Glu Ile Ile Asn Phe Ile Arg Tyr Leu Leu Ile
945                 950                 955                 960

Asp Asp His Ile Phe Asn Gly Ile Phe Lys Val Ala Phe Cys Leu Arg
                965                 970                 975

Tyr Leu Ala Glu Ile Leu Ile Phe Ala Ile Phe Glu Phe Ile Gln Ser
                980                 985                 990

Cys Ile Lys Val Phe Asn Phe Asn Pro Phe Trp Ile Asp Thr Ile Phe
                995                 1000                1005

His Arg Thr Phe Lys Gly Phe Cys Phe Phe Cys Leu Ala Glu Ile Leu
                1010                1015                1020

Ile Phe Ala Ile Phe Glu Phe Ile Lys Arg Phe Ile Lys Val Phe Gln
1025                1030                1035                1040

Ile Leu Val Asp Ile Phe Lys Phe Ile Arg Gln Phe Pro Phe Asp Ala
                1045                1050                1055

Phe Lys Ile Leu Ser Val Ser Asp Cys Ser Cys Val Ser Ile Ser Leu
                1060                1065                1070

Phe Ile Asp Gln Arg Lys Asn Leu Ile Phe Leu Ala Val Ser Leu Ser
                1075                1080                1085

Phe Cys Phe His Phe Ile Phe Val Ala Ala Phe Ala Leu Gln Phe Phe
                1090                1095                1100

Leu Tyr Phe Phe Leu Met Leu Ser Phe Pro Arg Phe Phe Lys Ile Phe
1105                1110                1115                1120

Leu Ser Phe Phe His Phe Ile Ile Ala Cys Val Phe Ser Val Ser
                1125                1130                1135

Tyr Ser Phe Ile Glu Val Ser Phe Ser Asn Gln Phe Val Ala Ala
                1140                1145                1150

Gln Lys Ile Phe Asp Lys Leu Ile Ser Phe Leu Trp Gly Gln Ser Phe
                1155                1160                1165

Ser Gly Phe Ile Leu Ile Pro Pro Tyr Glu Thr Ser Asp Ser Glu Ile
                1170                1175                1180

Ile Ile Arg Gln Ile Lys Asp Ser Tyr Leu Val Lys Ala Tyr Phe Met
1185                1190                1195                1200
```

-continued

Gly Asn Ala Ile Arg Asn Ala Tyr Thr Leu Ile Gly Ile Leu Gly Gly
            1205                1210                1215

Val Gly Val Phe Glu Ile Arg Ile Ile Asn Lys His His Ala Ile Met
        1220                1225                1230

Phe Ala Thr Leu Lys Ser Asn Ile Phe Leu Pro Ile Ser Phe Ile Cys
        1235                1240                1245

Phe Phe Pro Ile Ile Phe Glu Ser Val Ala Gln Ile Pro Ile Thr Lys
        1250                1255                1260

Leu Ser Asn Ser Met Phe Cys Val Phe Phe Arg Asn Lys Ser Asn Thr
1265                1270                1275                1280

Ile Ile Pro Gly Val Ile Ser Leu Arg Val Phe Leu Glu Ile Phe Asn
            1285                1290                1295

Leu Ser Ser Glu Phe Phe Leu Leu Phe Leu Ala Gln Val Val Phe Ser
            1300                1305                1310

Ile Ile Leu Cys Lys Lys Phe His Glu Ile Tyr Phe Val Leu Asp Leu
            1315                1320                1325

Phe Leu Thr Cys Ser Leu Ala Cys Glu Leu Val Phe Phe Val Glu Ile
            1330                1335                1340

Lys Thr Arg Val Val Asn Pro Phe Leu Thr Thr Cys Tyr Asp Ala Thr
1345                1350                1355                1360

Ala Val Phe His Met His Ile Asn Tyr Cys Ser His Ile Val Ala Leu
            1365                1370                1375

Leu Val Phe Ile Thr Asn Gly Gly Val Pro Ile Met Pro Ser Ser Arg
            1380                1385                1390

Thr Thr Ile Ala Pro Ile Gln Gln Asn Phe Phe Arg Phe Tyr Ala Ile
            1395                1400                1405

Met Thr Pro His His Arg Arg Gln Ser Val Ile Val Asn Gln Leu Ile
        1410                1415                1420

Glu Leu Val Ile Gly Ile Asn Val Ser Asp Ser Leu Asn Ile His Phe
1425                1430                1435                1440

His Ile Ala Lys Ser Glu Phe Arg Lys Ile Thr Pro Phe Ile Lys Ile
            1445                1450                1455

Ser Ser Phe Arg Arg Ala Leu Tyr Val Gly Gly Ser Gly Tyr Ile
            1460                1465                1470

Trp Leu Asp Met Gly Asn Trp Phe Leu Ile Asp Cys Phe Phe Asp Ile
        1475                1480                1485

Arg Arg Leu Phe Phe Val Lys Tyr Lys Glu Lys Asn Ile Gln Pro Ile
1490                1495                1500

Pro Thr Ser Arg Leu Ser Ile Phe Cys Phe Leu Pro Phe Phe Gln
1505                1510                1515                1520

Gly Leu Ile Lys His Ala His Glu Leu Leu Ile Arg Ser Asp Leu Ile
            1525                1530                1535

Pro Tyr Asn Asp Ser Cys Lys Arg Leu Phe Gly Arg Phe Gln Lys Leu
        1540                1545                1550

Arg Phe Leu Phe Ile Ile Lys Asp Arg Gly Leu Tyr Asp Ile Phe His
        1555                1560                1565

Lys Ile Ser Asp Arg Ser Gly Val Asp Phe Arg Ile Val Leu Met
        1570                1575                1580

Gly His Pro Thr Cys Glu Asn Ser Val Thr Leu Ile Pro Lys Phe Leu
1585                1590                1595                1600

Lys Ala Leu Cys Gly Arg Phe Tyr Ile Asn Glu Ile Val Phe Val Asp
                1605                1610                1615

Ile Ile Ala Leu Ile Asp Lys Val Lys Ile Leu Ile Leu Phe Gly Arg
            1620                1625                1630

-continued

```
Ile Phe Asp Arg Phe Ile Gly Val Phe Pro Leu Arg Asp Ser Phe
    1635                1640                1645

Lys Ser Leu Pro Val Ile Pro Ile Val Leu Ile Asn Asp Trp Phe Leu
        1650                1655                1660

Ile Arg Ile Val Ser Asp Ser Val Ile Asn Phe Lys Lys Ser Tyr Leu
1665            1670                1675                1680

Lys Ile Ile Asp Lys Leu Leu Arg Val Lys Ser Arg Phe Gly Leu Trp
            1685                1690                1695

Leu Leu Val Asn Gly Phe Val Ser His Cys Phe Ser Leu Leu Tyr Leu
                1700                1705                1710

Val Ser Tyr Leu Ser Val Ser Cys Cys Gln Arg Leu Leu Lys Ile Ala
            1715                1720                1725

Thr Arg Leu Ser Ser Gln Phe Met Ser Leu Asn Ile Leu Ile Ile Gln
            1730                1735                1740

Gln Tyr Gln Ala Phe Phe Phe Phe Ile Asn His Tyr Tyr Lys Lys
1745                1750                1755                1760

Pro Asp Arg Cys Arg Arg Leu Lys Ala Arg Thr Ile His Ile Phe Thr
                1765                1770                1775

His Asn Gln Lys Phe Ala Lys Met Lys Glu Leu Glu Gln Glu Ile Arg
            1780                1785                1790

Asn Glu Ser Phe Arg Asn Gln Met Gln Arg Ser Met Val Gly Glu Met
            1795                1800                1805

Val Ser Gln Gly Glu His Met Lys Arg Ser Lys Asn Ser Leu Val Cys
            1810                1815                1820

Val Ser Cys Leu Leu His Val Leu Ser Val Cys Asp Pro Gln Asp Pro
1825                1830                1835                1840

His Gly Lys Gln Asn Gly Lys Gln Ile Asn Arg Thr Asp Phe Gln Arg
                1845                1850                1855

Pro Gln Lys Lys Phe Leu Trp Ser Met Glu Leu Leu Lys Met Glu Leu
            1860                1865                1870

Tyr Ser His Ser Asp Gln Leu Gly Phe Val Phe Ala Cys Phe Val Ser
            1875                1880                1885

Thr Asp Asp Lys Ile His Gln Arg Ser Arg Ser Thr Ile Leu Gln Arg
            1890                1895                1900

Leu Glu Lys Glu Lys Trp Leu Gly Gln Val Gly Leu Leu Phe Leu Asn
1905                1910                1915                1920

Asp Val Ser Cys Arg Ala Lys Ala Ser Val Leu Ile Ile Ile Lys Arg
                1925                1930                1935

Leu Tyr Glu Tyr Lys Asn Thr Phe Phe Phe Asp Ile Leu Lys Arg Leu
            1940                1945                1950

Ile Ser Ile Lys Glu Thr His Glu Ile Phe Tyr Lys Asn His Gln Leu
        1955                1960                1965

Gln Glu Ser Cys Ser Asn Phe Arg Ala Ser Gly Asn Asn Gln Ser Phe
    1970                1975                1980

Asn Gly Gly Arg Gln Ser Tyr Arg Arg Arg His Cys Asn Arg Phe Gly
1985                1990                1995                2000

Tyr Ser Asp His Phe Cys Ser Ser Asp Arg Arg Trp Leu Arg Phe Arg
                2005                2010                2015

Gly Gln Arg His Ser Gly Tyr Leu Glu Asn Leu His Lys Arg Ser Gly
            2020                2025                2030

Asp Cys Phe Cys Leu Arg Ala Thr His Ser Tyr Val Ser Gly Gly Arg
            2035                2040                2045

Arg Tyr Tyr Leu Phe Glu His Val Trp Leu Gln Tyr Trp Arg Gly Trp
```

-continued

```
                2050                2055                2060
Arg Ser Leu Ser Ser Thr Ile Ile Ile Ala Ile Arg Asn Glu Ala
2065                2070                2075                2080

Phe Phe Lys Phe Ser Val Ser Leu Phe Ser Val Arg Met Gly Gln Met
                    2085                2090                2095

Met Thr Lys Lys Pro Lys Lys Lys His Lys Lys Lys Lys Thr Leu
                2100                2105                2110

Pro Met Gly Leu Phe Ile Gln Ile Ile Leu Ile Val Ser Lys Arg Leu
                2115                2120                2125

Ser Lys Ile Lys Thr Arg Lys Leu Ser Lys Lys Ser Ile Pro Ile Leu
            2130                2135                2140

Ser Lys Met Lys Phe Leu Thr Ser Leu Ser Ile Glu Ser Leu Lys Lys
2145                2150                2155                2160

Arg Ile Ser Ile Thr Ile Gln Leu Leu Lys Lys Ser Leu Met Lys Arg
                2165                2170                2175

Val Arg Lys Trp Asp Met Asn Tyr Arg Ser Ile Leu Lys Lys Thr Phe
                    2180                2185                2190

Leu Leu Ser Lys Ala Ser Ala Arg Pro Thr Asn Asn Ala Ala Phe Cys
                2195                2200                2205

His Cys Ala Glu Lys Gln Glu Lys Phe Tyr Ala Met Ile Ser Tyr Ile
                2210                2215                2220

Met Phe Tyr Trp Pro Tyr Ser Ile Leu Met Ile Leu Met Ile Phe Asn
2225                2230                2235                2240

Ile Leu Ala Pro Ser Leu Ser Lys Lys Ser Phe Ile Arg Leu His Val
                2245                2250                2255

Lys Arg Tyr Ile Tyr Lys Glu Arg Gly Val Cys Gly Lys Gln Ala Gly
                2260                2265                2270

Thr Lys Lys Ala Asn Tyr Arg Ala Arg Gly Ser Lys Ala Ala Val Ser
                2275                2280                2285

Lys Asn Arg Arg Thr Ser Arg His Ala Lys Gly Cys Gln Ser Leu Phe
                2290                2295                2300

Ser Leu Val Trp Gly Glu Val Val Trp Phe Pro Asn Phe Tyr Leu Phe
2305                2310                2315                2320

Leu Tyr Ile Tyr Ile Val Cys Asn His Cys Ile Ile Cys Tyr Ser Phe
                2325                2330                2335

Ser Ser Leu Thr Cys Phe Asp Cys Ser Asp Cys Tyr Cys Ala Cys Ser
                2340                2345                2350

Ser Trp Ile Gln Glu Arg Leu Ala Leu Ser Lys Asn Gly Ala Ser Asp
                2355                2360                2365

Glu Ile Lys Thr Phe Phe Val Gly Arg Glu Lys Gln Ser Val His Glu
                2370                2375                2380

His Phe Phe His Glu Ala Arg Asn Gly His Pro Leu Lys Ser Lys Gln
2385                2390                2395                2400

Arg Arg Gln Thr Cys Glu Arg Cys Lys Leu Leu Ser Ser Lys Leu Met
                    2405                2410                2415

Phe Phe Arg Trp Gly Asp Pro Tyr Gln Leu Phe Ser Phe Arg His Asn
                2420                2425                2430

Gln Ile Gly Gly His Phe Phe Asn His Phe Gln Lys Arg Ser His Arg
                2435                2440                2445

Val Thr Arg Phe Tyr Leu Arg Phe Glu Phe Cys Tyr Pro Ile Gln Ile
                2450                2455                2460

Leu Phe Ser His Tyr Lys Glu Asn Arg Tyr Asn Gln Gly Leu Trp Ser
2465                2470                2475                2480
```

```
Tyr Phe Phe His Ala Ser Leu Glu Ala Lys Glu Arg Lys Phe Leu
            2485                2490                2495

Tyr Phe Phe Ser Asp His Arg Ala Arg Phe Ile Arg His Ser Gln Thr
                2500                2505                2510

Arg Tyr Glu Lys Ala Phe Cys Arg Gln Phe Arg Val Ser Lys Asp Tyr
        2515                2520                2525

Ser Gln Ala Lys Leu Gln Gly Asp Arg Ala His Arg Arg Ala Val Glu
        2530                2535                2540

Gln Ile Pro Pro His Ile Lys Arg Ile His Arg Trp Arg Tyr Leu Leu
2545                2550                2555                2560

Gln Thr Met Arg Ile Leu Gln Phe Ser Cys Gly Asn Glu Ser Pro Phe
                2565                2570                2575

Tyr Leu Gln Pro Lys Arg Leu Val Ser Gln Gly Lys Asn Ala Trp Trp
                2580                2585                2590

Gly Glu Arg Ser Leu Phe Cys Gln Ala Trp Lys Asn Leu Lys Arg Phe
                2595                2600                2605

Glu Lys Ile Phe Arg Tyr Asp Ile Arg Pro Ile Thr Lys Arg Phe Val
        2610                2615                2620

Asn Gln Arg Pro Arg Gln Arg Ile Tyr Phe His Ala Cys Leu Phe Ala
2625                2630                2635                2640

Lys Leu Thr Gly Phe Lys Gly Gln Thr Gly Phe His Leu Lys Asn Tyr
                2645                2650                2655

Tyr Trp Arg Leu Arg Thr Gly His Asp Phe Arg Leu Leu Glu Arg Ile
                2660                2665                2670

Ser Gly Trp Tyr Tyr Ala Arg Gln Leu Trp Phe Phe Ser Ala Val Cys
                2675                2680                2685

Leu Lys Asn Glu Thr Lys Arg Gly Met Arg Leu Ser Arg Arg Phe Phe
        2690                2695                2700

Ser Gln Arg Ser Asp Phe Leu Tyr Gly Lys Leu Leu Phe Cys Gln Thr
2705                2710                2715                2720

Leu Leu Phe Tyr His Ala Ser Phe Tyr Phe Cys Asn Phe Phe Cys Phe
                2725                2730                2735

His Arg Tyr Glu Gly Tyr Glu Phe Trp Gln Ser Arg Glu Arg Leu Gly
                2740                2745                2750

Gln Cys Asp Asp Ala Lys Lys Arg Asp Gln Phe Ala Phe Leu Ser Glu
        2755                2760                2765

Leu Pro His Ala His Phe Trp Phe Ser Phe Ser Arg Thr His Phe Asp
        2770                2775                2780

Thr Trp Leu Asn Arg Phe Arg Asp Ser Val Tyr Val Asn Asp Leu Glu
2785                2790                2795                2800

Arg Tyr Gly Thr Ile Cys Leu Phe Ser Cys Cys Gln Gln Arg Gln Ala
                2805                2810                2815

Lys Ala His Tyr Gly Leu Tyr Gly Arg Leu Trp Arg Leu Trp Glu Tyr
                2820                2825                2830

Cys Arg Asn Gly Trp Gly Val Cys Gln Asp Ala Arg Asp Arg Tyr Arg
                2835                2840                2845

Ile Lys Ser Phe Cys Leu Gly Gly Leu Cys Ala Lys Asn Lys Cys Asn
                2850                2855                2860

Asn Gly Ala Lys Thr Asn Ser Tyr Phe Cys Cys Gln Arg Ala Cys Glu
2865                2870                2875                2880

Lys Leu Ser Asn Lys Arg Lys Arg Lys Trp Gln Gln His Leu Phe Pro
                2885                2890                2895

Ser Arg Phe Tyr Ala Cys Ser Ala Val Thr Asn Leu Ile Thr Gly Asn
                2900                2905                2910
```

```
Met Asn Leu Asp Tyr Pro Ile Thr Gln Leu Ile Asn Ala Phe Gly Lys
            2915                2920                2925
Asp His Asn Asp Pro Asn Gly Leu Val Ala Arg Leu Ala Pro Phe Cys
        2930                2935                2940
Lys Ser Thr Asn Gly Glu Phe Gln Trp Leu Phe Asp Asn Lys Ala Thr
2945                2950                2955                2960
Asp Arg Leu Asp Phe Ser Lys Thr Ile Ile Gly Val Asp Gly Ser Ser
            2965                2970                2975
Phe Leu Asp Asn Asn Asp Val Ser Pro Phe Ile Cys Phe Tyr Leu Phe
        2980                2985                2990
Ala Arg Ile Gln Glu Ala Met Asp Gly Arg Arg Phe Val Leu Asp Ile
            2995                3000                3005
Asp Glu Ala Trp Lys Tyr Leu Ala Ile Gln Arg Ser Leu Ile Leu Glu
        3010                3015                3020
Thr Cys Lys Leu Gln Gly Lys Glu Thr Leu Leu Ser Asp Leu Arg Leu
3025                3030                3035                3040
Lys Ala Ser Leu Ile Phe Trp Leu Ala Leu Leu Leu Ile Arg Leu Glu
            3045                3050                3055
Asn Asn Ala Leu Gln Arg Phe Phe Glu Thr Met Gly Ala Ile Phe Leu
        3060                3065                3070
Ile Thr Lys Asp Trp Leu Met Leu Gln Lys Lys Asn Leu Lys Ser Ser
            3075                3080                3085
Leu Arg Asp Ile Gly Lys Ser Ser Thr Asn Arg Met Glu Ala Leu Ala
        3090                3095                3100
Leu Ser Leu Val Leu Ile Glu Ala Phe Leu Lys Asn Ile Lys Phe Tyr
3105                3110                3115                3120
Pro Gln Ile Leu Tyr Leu Ser Lys Lys Leu Ile Arg Leu Ser Lys Thr
            3125                3130                3135
Ile Val Ser Ile Asn Ile Arg Pro Asp Lys Cys Ile Asn Lys Arg Ser
        3140                3145                3150
Ile Lys Met Lys Gln Asn Leu Arg Glu Gln Lys Leu Trp Lys Phe Lys
            3155                3160                3165
Met Met Ser Arg Phe Trp Ile Val Phe Leu Ile Ile Phe Leu Asn Lys
        3170                3175                3180
Lys Asn Trp Thr Ser Lys Lys Lys Trp Lys Ala Lys Ser Leu Asn Lys
3185                3190                3195                3200
```

(2) INFORMATION FOR SEQ ID NO:9:

(i) SEQUENCE CHARACTERISTICS:
        (A) LENGTH: 5599 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
AAAAATCAAA GAGCTTATGG ATCATAGAGC TAAAGTTCTT TCAGACTTAG AAAACAAATA    60

CAAAAAGAA AAAGAGGCTC TAGAGAAAGA GACAAGAGGT AAAATCCTTA CTGCTAAGTC    120

AAAGGCTTAT GGGGATCTAG AGCAAGCCTT AAAAGATAAC CCTCTCTATA AGAAACTTCT    180

TCCTAACCCT TATGCCTATG TTTTAAACCA AGAAACATTC ACCAAAGAAG ATAAGGAGCG    240

TTTGAGTTAT TACTACCCCC AGGTGAAAAC GAGCAGTATT TTTAAAAAAA CTACCGCTAC    300

CACTAAAGAT AAGGCTCAGG CTTTGCTTCA AATGGGTGTG TTTTCTTTAG ATGAAGAACA    360
```

```
AAACAAAAAA GCGAGCCGAT TAGCTTTATC TTACAAGCAA GCGATTGAAG AATATTCCAA   420

TAACATTTCT AATCTGTTGA GCAGAAAAGA ATTGGATAAT ATAGATTATT ACTTACAGCT   480

TGAAAGAAAC AAGTTTGACT CCAAAGCAAA AGATATTGCT CAAAAGGCTA CTAACACGCT   540

TATTTTTAAC TCGGAACGCT TGGCGTTTAG CATGGCGATT GATAAGATTA ATGAGAAATA   600

CTTAAAGGGC TATGAGGCTT TTTCTAACTT GTTGAAAAAT GTCAAGATG ATGTGGAATT    660

GAATACTCTG ACTAAAAACT TTACCAATCA AAAATTGAGT TTCGCACAAA AACAAAAATT   720

GTGTTTGTTG GTTTTAGACA GCTTCAATTT TGATACCCAA TCCAAAAAAT CTATATTAAA   780

AAAGACTAAT GAATACAATA TTTTCGTAGA TAGCGATCCT ATGATGAGCG ACAAAACAAC   840

TATGCAAAAA GAACACTACA AGATATTTAA TTTCTTCAAA ACAGTGGTTT CTGCATACCG   900

AAACAATGTT GCCAAGAATA ATCCCTTTGA ATAGGAAAGG AGACACTCTT GAAAAGCATC   960

TTCAAAAAAC TAGGTTCTGT CGCTCTTTAT TCTTTAGTTG TTTATGGGGG CTTAAACGCT  1020

ATCAATACAG CATTATTGCC GAGTAATAC AAAGAATTAG TGGCTTTGGG CTTTAAAAAA   1080

ATCAAAACAC TCTATCAAAG ACATGATGAC AAAGAAATTA CAAAGAGGA AAAAGAATTC   1140

GCCACTAACG CTTTGAGAGA AAAATTACGA ATGATAGGG CGAGAGCAGA GCAAATTCAA   1200

AAGAATATTG AAGCGTTTGA AAAAAAGAAC AACTCTTCTG TTCAAAAAAA AGCGGCTAAG   1260

CACAAAGGAT TACAAGAATT AAACGAAATT AACGCTAACC CTTTGAATGA CAACCCTAAT   1320

GGCAATTCTT CCACTGAAAC CAAATCTAAT AAAGATGATA ACTTTGATGA GATGATCAAT   1380

AAGGTGAATG AATCTTTTGT GAAACCTGCT GCTCCGCTTG TGCCTGATGA GTGGAGAACG   1440

CCTGAAATTG AAATCATTAT CAATGAGTGT ATTATTTCAA GCAACGATTA TGATGGGTTA   1500

AGAAAGTGTT TGATCAAAGA CATCAAGGAT CAAAAAATTC TTGCCCCCTT ATTAGAAAAA   1560

ATTCAAGAAA TAGAGACAGA AAATAACAAG TTTTCTAGAC AACACCTAAG TGGTTTAAAA   1620

CTCACTCTTA ATAACAGCAA CAATAGAACC TTTCTTATAG CTTCGTGCGC TATTTGTGAG   1680

AAGAGAAAAA AAGAAATGGA GCAAGAAAAT AACTACCAGG ATACTACAAA TGCAAGCGAG   1740

TTTGGCACTA CTGATACAAA AGAAAATGAA GCAAAAGATA CAGCATTCTC AAACAATCGC   1800

TCTAAATCCG AACTGCCCAA TAGCGTCATT AATCAAATAG AACAAAGCAT CGCTCATGGA   1860

AAAAAATAGC GATCCAAATT ATTAGATCAA AAAACAACTA GAGAAGCAAA TCCCAAAGGT   1920

TAGAAATCAT AGCCTATCGT CTCAGAAAAA TCATTTAACA ATGATCTTAC TTGATTGCCT   1980

TTCTTGTAGG TATTGTCGCT TACTTTGTTC TAGGGATCTT TCTAATGCGT CCAACTCCTC   2040

TAAATAATTT AAAAAGACCT TGTTTTGAGC TAACATAAGC TTTCTGATTC CTTTGATGAA   2100

ATTTTTATTC TTTAGGCTTT CTACAAGCGT CTGTGAAGCA GTGATTAAAG AAGCTGTACC   2160

TCCAATGTTG CTCTGATACG CCTTTAGGGA AGTTTCTAAA CGCTCTCTTA TATTTTGTTT   2220

TTCTTGCTCG ATTTTCAGCT TCCCTTCACA ATAAAGAACT AAAACTTTAT CGGATATTCC   2280

GCATTGCTGC TCAGCAGTAT TTTGGTCTAA GGGATTGATT TCATATAGG TTAATAAAAG    2340

TTCAGGGCTA GACATATAAG TCTTGAAAAT CACATCTTCT GAGATGAAAA ATAACTCATT   2400

CGCTTCAAAA TTGGCTTTCA ATAACGCTAA ATCTCCTCTC AAAGCAATGG CCGCTTTTTT   2460

GATGTTTAGA GCATCTTCTT GACCTATTTC ATTATTAGCG CTAGGGCTAG TGGTTGAAAA   2520

AATCTCATCT AAGTTTTTAA GCACTTGTTG GTTGGTCTCT TGGTAGGTGC TATCAAGTTG   2580

CTTTAAACCG CTTGTTATAT CTTCTGCCAT CAAAACAGAC AATAGCAAAA AGAAGATAT    2640

GGTATTTTTC ACGAGTGTTT TCATTTGACA ATAACTTTAG AGCTAGCAAT GTTTCTTGCT   2700

GTCGTTTCTC TTTCTAATTT CAGTTGTTCT TCCCAAAGGT CGGCTTTTTT TTCAAGATTC   2760
```

| | |
|---|---|
| TCTATATAGT TTAAATGATT TTCTGCGTTT AAGATCGCAA CTTCTATGAG CGCATTCAAA | 2820 |
| TCTACTGATC CTTTTAAGGT TTTGATTTCT CCATTGATCC CATTCAAATA AGCGATATTT | 2880 |
| TGAAAATCTG CATCACTCAG TTTATTTTGA ATAAGGGCTA CAATCATTCT GTAATTCTGA | 2940 |
| ATAACCTGTT CCATAAGGCA TGCTGAAATT TTTAGCCCAT CAAGATAAGG GCATTTGTG | 3000 |
| GGCGCTAGAG TGAATGTTTC AATGATTCCA AATGGTCGCC CATGCTTGAA AAAAAACTAA | 3060 |
| GAGCAGGCGC ATAGATGGCA CTTTGAAACA AAGCCTGACC TGTTAGGGAA TTATAATCAA | 3120 |
| TAAGGGTCGC TTTTTGCATA GCTGTTTTCA ACCATGTCTC AAAACCTTTT AAGGTTTCTT | 3180 |
| CAAACGCCTT GATACCAATC GTATTGTAAG CGATGTATTG AGCGTTGTCA GAAGAACTTC | 3240 |
| CTAGAGCTTG AGAAATTTCC ATTTGTGTTT TTAGGGTAAC CCTCGGTTCA AAGCTGTTTT | 3300 |
| TTAACGCTTC TAAGAGAGCG TTTTGCTGGT TCATTTTGAG CTTGATCATT TCGTTATTTT | 3360 |
| TTTGGAGCGC GATTTGCATG TTTTGGATTT CTGTTTGGGT ATTAATTTTT TGTTTTTCCA | 3420 |
| CGATCATTTT GACATTCCCC CCCAATGCAC TAAGCGCCGC TTGAATACCC TTCCATGACG | 3480 |
| CCAAGCAAGA TGTCTGAACC TGCAAAAAAC CCCCCTGTCA TGCCATTGAC ACCATTAATA | 3540 |
| ACGCCATTAG CCCCTTTTAA CATAGCGCTC ATGGTTGCAA GCTGAGTCCT CAATTCTCCC | 3600 |
| TCTATTTGCG CTTGAATGGC TTTTTCTTTG GCACTAGATT GAGCTTCTAT GGCTTTTAAT | 3660 |
| TCGGCTTGAG CGGTTTTTTG TTTGGCTTGT GCGTCTGCCT GAATGGCTTT TAAGGCAGGT | 3720 |
| TCAAGCGTTA TTACTACCTC TGTACCATTC AGAGACAAAC CACAAAAAGT CAAGAAAGAA | 3780 |
| AATATGCTTA AAAAACATTT CACATCTCTT TCCTCACTTC ACGATTATTT TAGTTTGCAC | 3840 |
| CCTTTCTGTT AAGTAGCTAT CTTTTTGCCC CTTAAGCTTG TCTTTGATGT AATCAAGGTA | 3900 |
| AGTCAAATGC GATTTCAAAA AAGATTTATT CGCTACTATA TTGTAATTAT ATAGCGAACT | 3960 |
| TATGTTAGAA ATCGCTTGAG TGTCATAGGT GCTAGTAGCT AATCCTGATT GATTAAGTAT | 4020 |
| CATTTGAGAA GCGTTCTGCA ACAAATTGGT ATTATTTTTC ACAAATTCTA TATAGTATTC | 4080 |
| TCTCAAAATT TCTGCTACTT TTTCAGCATA GCAATAAACA GCAAGAACCT TGTCCCCAAT | 4140 |
| AGGGCATGCA GGAGTGGTCA TAGGATTAAC GCCTGAAGTT AGGGCATTAG TGGCTAACGC | 4200 |
| TTGGTATTTA GCATAAACAG TGGGCATAGA AACGCTCATG GGGCGTCATA GAAATTTGCA | 4260 |
| TGCAACTGAA AAACACTTTT GATGAGCCAA CAAGCGCACC TAAAGCGGTA CAGCTATCAA | 4320 |
| GGAATCGGTG TATCATTCAT TGAGCTGTTG CTTGCTTGAG AACGCAGTTG CTCTTGTAGA | 4380 |
| GCTAGGGCGT ATTTTGGTGC TGCACTTGTA ATATTGCCTA ATATACCGTC ATCATTTCAA | 4440 |
| CCGTTGTTGG CACGCTAGGA ACAGCGATTT GATTTGTCGC ATAAGCTTCA ATAGCACTGG | 4500 |
| GATTTTTAGG GGTGGTGTTA CTCGCTAAAA TGCTTGCAAT CTGACTATTA ACAGCACCAA | 4560 |
| TTTGCGCGCC TTGCGTGTTG CCTTGTGCGT TAAATTCCCC TGTTAATTTG CTAATATTTA | 4620 |
| AGATATTGTT CCCCACAGCC ATGCTTTGAT CGTTAAAACC TTGAAACAAT TGGTTGTATT | 4680 |
| GTTGGTTAGC GGCTTTCATA GGCATGCTTA CGGCTTCAGC GATGCTTTGA TTGTATTGGG | 4740 |
| TCATGATAGC GGTCATTTGC GGATTAGTAA ACCCAACAAT AATAGGAATA ATCGCTGCTG | 4800 |
| TCATAGCACC CGCTACTATT CCTGCAAATG GTCCTGCGAC ACCACTTGTG TTGAGATGAT | 4860 |
| TGAGGAAACT TCCGATAAGA AGCCTGCAGA AGATGATTCA TATATAGCTT GTGTACCTGC | 4920 |
| CATGTTAACA CCCCCTAGTT AATACCCTAA TATCGGTGGT AAAAACGATG AATCTGAGTA | 4980 |
| TGTTGGTGCA TAACCATACA TGAAAGGATT GTTTGGACCG TAATCGCCCA TCATTTGGCT | 5040 |
| CATGAGAAGA TTTTGAATGC CCCACATCGC ATTGATACCT AGATTATCAT TAGGTTGAAA | 5100 |
| ACTCCCTAAA CTTATGTCGT CAAATTTGAT ATTAACATTT TTATCATTAT AGTCATTGAG | 5160 |

```
TATGGCCACT TTTTGCTCTA GGGTTTCTTT AGGGATCTCT ATTTTTAGTT GATCTCTAGA      5220

AACAAGCCCC ACGCTATTTA GTGCCATATC TTCAGGACTA ATATCTTTTA TATCAGTGTT      5280

TTGGTCAGCG TTAACGGACT GTAAACATGC CAATGATAAG ACACCAAGCA AATAGTAATT      5340

TAATTTTATA AAAATCCGTT TTCATACTTT TGACTCCTTT ATTCTTATTT TTAGCACTAT      5400

TCTAGCGCAT TAACGCCACT CAATCGTTAT TTTTGTTTTG ATTTTTTTGA TCGAGCATTT      5460

TGTTTGTTAC TTCATCAATG TTTTGAAAAT ATTTTTCAAA AAGCTCTTTC TTTTTAGCTT      5520

CAACGCTCAT ATCAATCTGA ATCCAATTAG GAATAATGGA GTCCATGATT AAATGCATGA      5580

AGTCATAGGC ATGATTTTT                                                  5599
```

(2) INFORMATION FOR SEQ ID NO:10:

(i) SEQUENCE CHARACTERISTICS:
        (A) LENGTH: 1727 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Lys Asn Gln Arg Ala Tyr Gly Ser Ser Ser Phe Arg Leu Arg Lys
 1               5                  10                  15

Gln Ile Gln Lys Arg Lys Arg Gly Ser Arg Glu Arg Asp Lys Arg Asn
             20                  25                  30

Pro Tyr Cys Val Lys Gly Leu Trp Gly Ser Arg Ala Ser Leu Lys Arg
             35                  40                  45

Pro Ser Leu Glu Thr Ser Ser Pro Leu Cys Leu Cys Phe Lys Pro Arg
 50                  55                  60

Asn Ile His Gln Arg Arg Gly Ala Phe Glu Leu Leu Pro Pro Gly
 65                  70                  75              80

Glu Asn Glu Gln Tyr Phe Lys Asn Tyr Arg Tyr His Arg Gly Ser Gly
                 85                  90                  95

Phe Ala Ser Asn Gly Cys Val Phe Phe Arg Arg Thr Lys Gln Lys Ser
                100                 105                 110

Glu Pro Ile Ser Phe Ile Leu Gln Ala Ser Asp Arg Ile Phe Gln His
            115                 120                 125

Phe Ser Val Glu Gln Lys Arg Ile Gly Tyr Arg Leu Leu Leu Thr Ala
130                 135                 140

Lys Lys Gln Val Leu Gln Ser Lys Arg Tyr Cys Ser Lys Gly Tyr His
145                 150                 155                 160

Ala Tyr Phe Leu Gly Thr Leu Gly Val His Gly Asp Asp Glu Ile Leu
                165                 170                 175

Lys Gly Leu Gly Phe Phe Leu Val Glu Lys Cys Gln Arg Cys Gly Ile
            180                 185                 190

Glu Tyr Ser Asp Lys Leu Tyr Gln Ser Lys Ile Glu Phe Arg Thr Lys
            195                 200                 205

Thr Lys Ile Val Phe Val Gly Phe Arg Gln Leu Gln Phe Tyr Pro Ile
            210                 215                 220

Gln Lys Ile Tyr Ile Lys Lys Asp Ile Gln Tyr Phe Arg Arg Ser
225                 230                 235                 240

Tyr Asp Glu Arg Gln Asn Asn Tyr Ala Lys Arg Thr Leu Gln Asp Ile
                245                 250                 255

Phe Leu Gln Asn Ser Gly Phe Cys Ile Pro Lys Gln Cys Cys Gln Glu
            260                 265                 270
```

```
Ser Leu Ile Gly Lys Glu Thr Leu Lys Ser Ile Phe Lys Lys Leu
        275                 280                 285

Gly Ser Val Ala Leu Tyr Ser Leu Val Val Tyr Gly Leu Asn Ala
        290                 295                 300

Ile Asn Thr Ala Leu Leu Pro Ser Glu Tyr Lys Glu Leu Val Ala Leu
305                     310                 315                 320

Gly Phe Lys Lys Ile Lys Thr Leu Tyr Gln Arg His Asp Asp Lys Glu
                325                 330                 335

Ile Thr Lys Glu Glu Lys Glu Phe Ala Thr Asn Ala Leu Arg Glu Lys
                340                 345                 350

Leu Arg Asn Asp Arg Ala Arg Ala Glu Gln Ile Gln Lys Asn Ile Glu
        355                 360                 365

Ala Phe Glu Lys Lys Asn Asn Ser Ser Val Gln Lys Ala Ala Lys
370                 375                 380

His Lys Gly Leu Gln Glu Leu Asn Glu Ile Asn Ala Asn Pro Leu Asn
385                 390                 395                 400

Asp Asn Pro Asn Gly Asn Ser Ser Thr Glu Thr Lys Ser Asn Lys Asp
                405                 410                 415

Asp Asn Phe Asp Glu Met Ile Asn Lys Val Asn Glu Ser Phe Val Lys
        420                 425                 430

Pro Ala Ala Pro Leu Val Pro Asp Glu Trp Arg Thr Pro Glu Ile Glu
        435                 440                 445

Ile Ile Ile Asn Glu Cys Ile Ile Ser Ser Asn Asp Tyr Asp Gly Leu
450                 455                 460

Arg Lys Cys Leu Ile Lys Asp Ile Lys Asp Gln Lys Ile Leu Ala Pro
465                 470                 475                 480

Leu Leu Glu Lys Ile Gln Glu Ile Glu Thr Glu Asn Asn Lys Phe Ser
                485                 490                 495

Arg Gln His Leu Ser Gly Leu Lys Leu Thr Leu Asn Asn Ser Asn Asn
        500                 505                 510

Arg Thr Phe Leu Ile Ala Ser Cys Ala Ile Cys Glu Lys Arg Lys Lys
        515                 520                 525

Glu Met Glu Gln Glu Asn Asn Tyr Gln Asp Thr Thr Asn Ala Ser Glu
        530                 535                 540

Phe Gly Thr Thr Asp Thr Lys Glu Asn Glu Ala Lys Asp Thr Ala Phe
545                 550                 555                 560

Ser Asn Asn Arg Ser Lys Ser Glu Leu Pro Asn Ser Val Ile Asn Gln
                565                 570                 575

Ile Glu Gln Ser Ile Ala His Gly Lys Lys Arg Ser Lys Leu Leu Asp
                580                 585                 590

Gln Lys Thr Thr Arg Glu Ala Asn Pro Lys Gly Lys Ser Pro Ile Val
        595                 600                 605

Ser Glu Lys Ser Phe Asn Asn Asp Leu Thr Leu Pro Phe Leu Val Leu
610                 615                 620

Ser Leu Thr Leu Phe Gly Ser Phe Cys Val Gln Leu Leu Ile Ile Lys
625                 630                 635                 640

Asp Leu Val Leu Ser His Lys Leu Ser Asp Ser Phe Asp Glu Ile Phe
                645                 650                 655

Ile Leu Ala Phe Tyr Lys Arg Leu Ser Ser Asp Arg Ser Cys Thr Ser
                660                 665                 670

Asn Val Ala Leu Ile Arg Leu Gly Ser Phe Thr Leu Ser Tyr Ile Leu
                675                 680                 685

Phe Phe Leu Leu Asp Phe Gln Leu Pro Phe Thr Ile Lys Asn Asn Phe
690                 695                 700
```

```
Ile Gly Tyr Ser Ala Leu Leu Leu Ser Ser Ile Leu Val Gly Ile Asp
705                 710                 715                 720

Phe His Ile Gly Lys Phe Arg Ala Arg His Ile Ser Leu Glu Asn His
            725                 730                 735

Ile Phe Asp Glu Lys Leu Ile Arg Phe Lys Ile Gly Phe Gln Arg Ile
                740                 745                 750

Ser Ser Gln Ser Asn Gly Arg Phe Phe Asp Val Ser Ile Phe Leu Thr
            755                 760                 765

Tyr Phe Ile Ile Ser Ala Arg Ala Ser Gly Lys Asn Leu Ile Val Phe
        770                 775                 780

Lys His Leu Leu Val Gly Leu Val Gly Ala Ile Lys Leu Leu Thr
785                 790                 795                 800

Ala Cys Tyr Ile Phe Cys His Gln Asn Arg Gln Lys Arg Arg Tyr
                805                 810                 815

Gly Ile Phe His Glu Cys Phe His Leu Thr Ile Thr Leu Glu Leu Ala
            820                 825                 830

Met Phe Leu Ala Val Val Ser Leu Ser Asn Phe Ser Cys Ser Ser Gln
        835                 840                 845

Arg Ser Ala Phe Phe Ser Arg Phe Ser Ile Phe Lys Phe Ser Ala Phe
850                 855                 860

Lys Ile Ala Thr Ser Met Ser Ala Phe Lys Ser Thr Asp Pro Phe Lys
865                 870                 875                 880

Val Leu Ile Ser Pro Leu Ile Pro Phe Lys Ala Ile Phe Lys Ser Ala
            885                 890                 895

Ser Leu Ser Leu Phe Ile Arg Ala Thr Ile Ile Leu Phe Ile Thr Cys
        900                 905                 910

Ser Ile Arg His Ala Glu Ile Phe Ser Pro Ser Arg Gly His Phe Val
        915                 920                 925

Gly Ala Arg Val Asn Val Ser Met Ile Pro Asn Gly Arg Pro Cys Leu
        930                 935                 940

Lys Lys Asn Glu Gln Ala His Arg Trp His Phe Glu Thr Lys Pro Asp
945                 950                 955                 960

Leu Leu Gly Asn Tyr Asn Gln Gly Ser Leu Phe Ala Leu Phe Ser Thr
            965                 970                 975

Met Ser Gln Asn Leu Leu Arg Phe Leu Gln Thr Pro Tyr Gln Ser Tyr
            980                 985                 990

Cys Lys Arg Cys Ile Glu Arg Cys Gln Lys Asn Phe Leu Glu Leu Glu
            995                 1000                1005

Lys Phe Pro Phe Val Phe Leu Gly Pro Ser Val Gln Ser Cys Phe Leu
    1010                1015                1020

Thr Leu Leu Arg Glu Arg Phe Ala Gly Ser Phe Ala Ser Phe Arg Tyr
1025                1030                1035                1040

Phe Phe Gly Ala Arg Phe Ala Cys Phe Gly Phe Leu Gly Tyr Phe
                1045                1050                1055

Phe Val Phe Pro Arg Ser Phe His Ser Pro Met His Ala Pro Leu
            1060                1065                1070

Glu Tyr Pro Ser Met Thr Pro Ser Lys Met Ser Glu Pro Ala Lys Asn
        1075                1080                1085

Pro Pro Val Met Pro Leu Thr Pro Leu Ile Thr Pro Leu Ala Pro Phe
            1090                1095                1100

Asn Ile Ala Leu Met Val Ala Ser Val Leu Asn Ser Pro Ser Ile Cys
1105                1110                1115                1120

Ala Met Ala Phe Ser Leu Ala Leu Asp Ala Ser Met Ala Phe Asn Ser
```

-continued

```
                    1125                1130                1135
Ala Ala Val Phe Cys Leu Ala Cys Ala Ser Ala Met Ala Phe Lys Ala
                1140                1145                1150
Gly Ser Ser Val Ile Thr Thr Ser Val Pro Phe Arg Asp Lys Pro Gln
            1155                1160                1165
Lys Val Lys Lys Glu Asn Met Leu Lys Lys His Phe Thr Ser Leu Ser
        1170                1175                1180
Ser Leu His Asp Tyr Phe Ser Leu His Pro Phe Cys Val Ala Ile Phe
1185                1190                1195                1200
Leu Pro Leu Lys Leu Val Phe Asp Val Ile Lys Val Ser Gln Met Arg
                1205                1210                1215
Phe Gln Lys Arg Phe Ile Arg Tyr Tyr Ile Val Ile Arg Thr Tyr
            1220                1225                1230
Val Arg Asn Arg Leu Ser Val Ile Gly Ala Ser Ser Ser Leu Ile Lys
        1235                1240                1245
Tyr His Leu Arg Ser Val Leu Gln Gln Ile Gly Ile Phe His Lys
    1250                1255                1260
Phe Tyr Ile Val Phe Ser Gln Asn Phe Cys Tyr Phe Ser Ile Ala
1265                1270                1275                1280
Ile Asn Ser Lys Asn Leu Val Pro Asn Arg Ala Cys Arg Ser Gly His
                1285                1290                1295
Arg Ile Asn Ala Ser Gly Ile Ser Gly Arg Leu Val Phe Ser Ile Asn
            1300                1305                1310
Ser Gly His Arg Asn Ala His Gly Ala Ser Lys Phe Ala Cys Asn Lys
        1315                1320                1325
Thr Leu Leu Met Ser Gln Gln Ala His Leu Lys Arg Tyr Ser Tyr Gln
    1330                1335                1340
Gly Ile Gly Val Ser Phe Ile Glu Leu Leu Leu Ala Glu Arg Ser Cys
1345                1350                1355                1360
Ser Cys Arg Ala Arg Ala Tyr Phe Gly Ala Ala Leu Val Ile Leu Pro
                1365                1370                1375
Asn Ile Pro Ser Ser Phe Gln Pro Leu Leu Ala Arg Glu Gln Arg Phe
            1380                1385                1390
Asp Leu Ser His Lys Leu Gln His Trp Asp Phe Gly Trp Cys Tyr Ser
        1395                1400                1405
Leu Lys Cys Leu Gln Ser Asp Tyr Gln His Gln Phe Ala Arg Leu Ala
    1410                1415                1420
Cys Cys Leu Val Arg Ile Pro Leu Ile Cys Tyr Leu Arg Tyr Cys
1425                1430                1435                1440
Ser Pro Gln Pro Cys Phe Asp Arg Asn Leu Glu Thr Ile Gly Cys Ile
                1445                1450                1455
Val Gly Arg Leu Ser Ala Cys Leu Arg Leu Gln Arg Cys Phe Asp Cys
            1460                1465                1470
Ile Gly Ser Arg Ser Phe Ala Asp Thr Gln Gln Glu Ser Leu Leu Ser
        1475                1480                1485
His Pro Leu Leu Phe Leu Gln Met Val Leu Arg His His Leu Cys Asp
    1490                1495                1500
Asp Gly Asn Phe Arg Glu Ala Cys Arg Arg Phe Ile Tyr Ser Leu Cys
1505                1510                1515                1520
Thr Cys His Val Asn Thr Pro Leu Ile Pro Tyr Arg Trp Lys Arg Ile
                1525                1530                1535
Val Cys Trp Cys Ile Thr Ile His Glu Arg Ile Val Trp Thr Val Ile
            1540                1545                1550
```

```
Ala His His Leu Ala His Glu Lys Ile Leu Asn Ala Pro His Arg Ile
            1555                1560                1565

Asp Thr Ile Ile Ile Arg Leu Lys Thr Pro Thr Tyr Val Val Lys Phe
        1570                1575                1580

Asp Ile Asn Ile Phe Ile Ile Val Ile Glu Tyr Gly His Phe Leu
1585                1590                1595                1600

Leu Gly Phe Phe Arg Asp Leu Tyr Phe Leu Ile Ser Arg Asn Lys Pro
                1605                1610                1615

His Ala Ile Cys His Ile Phe Arg Thr Asn Ile Phe Tyr Ile Ser Val
            1620                1625                1630

Leu Val Ser Val Asn Gly Leu Thr Cys Gln Asp Thr Lys Gln Ile Val
            1635                1640                1645

Ile Phe Tyr Lys Asn Pro Phe Ser Tyr Phe Leu Leu Tyr Ser Tyr Phe
            1650                1655                1660

His Tyr Ser Ser Ala Leu Thr Pro Leu Asn Arg Tyr Phe Cys Phe Asp
1665                1670                1675                1680

Phe Phe Asp Arg Ala Phe Cys Leu Leu His Gln Cys Phe Glu Asn
                1685                1690                1695

Ile Phe Gln Lys Ala Leu Ser Phe Leu Gln Arg Ser Tyr Gln Ser Glu
                1700                1705                1710

Ser Asn Glu Trp Ser Pro Leu Asn Ala Ser His Arg His Asp Phe
            1715                1720                1725

(2) INFORMATION FOR SEQ ID NO:11:

(i) SEQUENCE CHARACTERISTICS:
        (A) LENGTH: 1781 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Lys Ile Lys Glu Leu Met Asp His Arg Ala Lys Val Leu Ser Asp Leu
    1               5                   10                  15

Glu Asn Lys Tyr Lys Lys Glu Lys Glu Ala Leu Glu Lys Glu Thr Arg
                    20                  25                  30

Gly Lys Ile Leu Thr Ala Lys Ser Lys Ala Tyr Gly Asp Leu Glu Gln
                35                  40                  45

Ala Leu Lys Asp Asn Pro Leu Tyr Lys Leu Leu Pro Asn Pro Tyr
    50                  55                  60

Ala Tyr Val Leu Asn Gln Glu Thr Phe Thr Lys Glu Asp Lys Glu Arg
    65                  70                  75                  80

Leu Ser Tyr Tyr Tyr Pro Gln Val Lys Thr Ser Ser Ile Phe Lys Lys
                    85                  90                  95

Thr Thr Ala Thr Thr Lys Asp Lys Ala Gln Ala Leu Leu Gln Met Gly
                    100                 105                 110

Val Phe Ser Leu Asp Glu Glu Gln Asn Lys Lys Ala Ser Arg Leu Ala
                115                 120                 125

Leu Ser Tyr Lys Gln Ala Ile Glu Glu Tyr Ser Asn Asn Ile Ser Asn
    130                 135                 140

Leu Leu Ser Arg Lys Glu Leu Asp Asn Ile Asp Tyr Tyr Leu Gln Leu
    145                 150                 155                 160

Glu Arg Asn Lys Phe Asp Ser Lys Ala Lys Asp Ile Ala Gln Lys Ala
                    165                 170                 175

Thr Asn Thr Leu Ile Phe Asn Ser Glu Arg Leu Ala Phe Ser Met Ala
```

```
            180             185             190
Ile Asp Lys Ile Asn Glu Lys Tyr Leu Lys Gly Tyr Glu Ala Phe Ser
        195                 200                 205
Asn Leu Leu Lys Asn Val Lys Asp Asp Val Glu Leu Asn Thr Leu Thr
    210                 215                 220
Lys Asn Phe Thr Asn Gln Lys Leu Ser Phe Ala Gln Lys Gln Lys Leu
225                 230                 235                 240
Cys Leu Leu Val Leu Asp Ser Phe Asn Phe Asp Thr Gln Ser Lys Lys
                245                 250                 255
Ser Ile Leu Lys Lys Thr Asn Glu Tyr Asn Ile Phe Val Asp Ser Asp
        260                 265                 270
Pro Met Met Ser Asp Lys Thr Thr Met Gln Lys Glu His Tyr Lys Ile
        275                 280                 285
Phe Asn Phe Phe Lys Thr Val Val Ser Ala Tyr Arg Asn Asn Val Ala
    290                 295                 300
Lys Asn Asn Pro Phe Glu Glu Arg Arg His Ser Lys Ala Ser Ser Lys
305                 310                 315                 320
Asn Val Leu Ser Leu Phe Ile Leu Leu Phe Met Gly Ala Thr Leu Ser
                325                 330                 335
Ile Gln His Tyr Cys Arg Val Asn Thr Lys Asn Trp Leu Trp Ala Leu
            340                 345                 350
Lys Lys Ser Lys His Ser Ile Lys Asp Met Met Thr Lys Lys Leu Gln
        355                 360                 365
Lys Arg Lys Lys Asn Ser Pro Leu Thr Leu Glu Lys Asn Tyr Glu Met
        370                 375                 380
Ile Gly Arg Glu Gln Ser Lys Phe Lys Arg Ile Leu Lys Arg Leu Lys
385                 390                 395                 400
Lys Arg Thr Thr Leu Leu Phe Lys Lys Arg Leu Ser Thr Lys Asp
                405                 410                 415
Tyr Lys Asn Thr Lys Leu Thr Leu Thr Leu Met Thr Thr Leu Met Ala
            420                 425                 430
Ile Leu Pro Leu Lys Pro Asn Leu Ile Lys Met Ile Thr Leu Met Arg
            435                 440                 445
Ser Ile Arg Met Asn Leu Leu Asn Leu Leu Arg Leu Cys Leu Met
    450                 455                 460
Ser Gly Glu Arg Leu Lys Leu Lys Ser Leu Ser Met Ser Val Leu Phe
465                 470                 475                 480
Gln Ala Thr Ile Met Met Gly Glu Ser Val Ser Lys Thr Ser Arg Ile
                485                 490                 495
Lys Lys Phe Leu Pro Pro Tyr Lys Lys Phe Lys Lys Arg Gln Lys Ile
            500                 505                 510
Thr Ser Phe Leu Asp Asn Thr Val Val Asn Ser Leu Leu Ile Thr Ala
        515                 520                 525
Thr Ile Glu Pro Phe Leu Leu Arg Ala Leu Phe Val Arg Arg Glu Lys
    530                 535                 540
Lys Lys Trp Ser Lys Lys Ile Thr Thr Arg Ile Leu Gln Met Gln Ala
545                 550                 555                 560
Ser Leu Ala Leu Leu Ile Gln Lys Lys Met Lys Gln Lys Ile Gln His
                565                 570                 575
Ser Gln Thr Ile Ala Leu Asn Pro Asn Cys Pro Ile Ala Ser Leu Ile
        580                 585                 590
Lys Asn Lys Ala Ser Leu Met Glu Lys Asn Ser Asp Pro Asn Tyr Ile
        595                 600                 605
```

-continued

```
Lys Lys Gln Leu Glu Lys Gln Ile Pro Lys Val Arg Asn His Ser Leu
    610             615                 620
Ser Ser Gln Lys Asn His Leu Thr Met Ile Leu Leu Asp Cys Leu Ser
625             630                 635                 640
Cys Arg Tyr Cys Arg Leu Leu Cys Ser Arg Asp Leu Ser Asn Ala Ser
                645                 650                 655
Asn Ser Ser Lys Phe Lys Lys Thr Leu Phe Ala Asn Ile Ser Phe Leu
                660                 665                 670
Ile Pro Leu Met Lys Phe Leu Phe Phe Arg Leu Ser Thr Ser Val Cys
            675                 680                 685
Glu Ala Val Ile Lys Glu Ala Val Pro Pro Met Leu Leu Tyr Ala Phe
690             695                 700
Arg Glu Val Ser Lys Arg Ser Leu Ile Phe Cys Phe Ser Cys Ser Ile
705             710                 715                 720
Phe Ser Phe Pro Ser Gln Arg Thr Lys Thr Leu Ser Asp Ile Pro His
                725                 730                 735
Cys Cys Ser Ala Val Phe Trp Ser Lys Gly Leu Ile Phe Ile Val Asn
            740                 745                 750
Lys Ser Ser Gly Leu Asp Ile Val Leu Lys Ile Thr Ser Ser Glu Met
            755                 760                 765
Lys Asn Asn Ser Phe Ala Ser Lys Leu Ala Phe Asn Asn Ala Lys Ser
770                 775                 780
Pro Leu Lys Ala Met Ala Ala Phe Leu Met Phe Arg Ala Ser Ser Pro
785             790                 795                 800
Ile Ser Leu Leu Ala Leu Gly Leu Val Val Glu Lys Ile Ser Ser Lys
                805                 810                 815
Phe Leu Ser Thr Cys Trp Leu Val Ser Trp Val Leu Ser Ser Cys Phe
            820                 825                 830
Lys Pro Leu Val Ile Ser Ser Ala Ile Lys Thr Asp Asn Ser Lys Lys
            835                 840                 845
Glu Asp Met Val Phe Phe Thr Ser Val Phe Ile Gln Leu Ser Gln Cys
850                 855                 860
Phe Leu Leu Ser Phe Leu Phe Leu Ile Ser Val Val Leu Pro Lys Gly
865                 870                 875                 880
Arg Leu Phe Phe Gln Asp Ser Leu Tyr Ser Leu Asn Asp Phe Leu Arg
                885                 890                 895
Leu Arg Ser Gln Leu Leu Ala His Ser Asn Leu Leu Ile Leu Leu Arg
                900                 905                 910
Phe Phe Leu His Ser His Ser Asn Lys Arg Tyr Phe Glu Asn Leu His
            915                 920                 925
His Ser Val Tyr Phe Glu Gly Leu Gln Ser Phe Cys Asn Ser Glu Pro
            930                 935                 940
Val Pro Gly Met Leu Lys Phe Leu Ala His Gln Asp Lys Gly Ile Leu
945                 950                 955                 960
Trp Ala Leu Glu Met Phe Gln Phe Gln Met Val Ala His Ala Lys Lys
                965                 970                 975
Thr Lys Ser Arg Arg Ile Asp Gly Thr Leu Lys Gln Ser Leu Thr Cys
                980                 985                 990
Gly Ile Ile Ile Asn Lys Gly Arg Phe Leu His Ser Cys Phe Gln Pro
            995                 1000                1005
Cys Leu Lys Thr Phe Gly Phe Phe Lys Arg Leu Asp Thr Asn Arg Ile
        1010                1015                1020
Val Ser Asp Val Leu Ser Val Arg Arg Thr Ser Ser Leu Arg Asn
1025                1030                1035                1040
```

```
Phe His Leu Cys Phe Gly Asn Pro Arg Phe Lys Ala Val Phe Arg Phe
                1045                1050                1055

Glu Ser Val Leu Leu Val His Phe Glu Leu Asp His Phe Val Ile Phe
                1060                1065                1070

Leu Glu Arg Asp Leu His Val Leu Asp Phe Cys Leu Gly Ile Asn Phe
                1075                1080                1085

Leu Phe Phe His Asp His Phe Asp Ile Pro Pro Gln Cys Thr Lys Arg
                1090                1095                1100

Arg Leu Asn Thr Leu Pro Arg Gln Ala Arg Cys Leu Asn Leu Gln Lys
1105                1110                1115                1120

Thr Pro Leu Ser Cys His His Arg His Pro Leu Leu Thr Arg Ser
                1125                1130                1135

Trp Leu Gln Ala Glu Ser Ser Ile Leu Pro Leu Phe Ala Leu Glu Trp
                1140                1145                1150

Leu Phe Leu Trp His Ile Glu Leu Leu Trp Leu Leu Ile Arg Leu Glu
                1155                1160                1165

Arg Phe Phe Val Trp Leu Val Arg Leu Pro Glu Trp Leu Leu Arg Gln
                1170                1175                1180

Val Gln Ala Leu Leu Leu Pro Leu Tyr His Ser Glu Thr Asn His Lys
1185                1190                1195                1200

Lys Ser Arg Lys Lys Ile Cys Leu Lys Asn Ile Ser His Leu Phe Pro
                1205                1210                1215

His Phe Thr Ile Ile Leu Val Cys Thr Leu Ser Val Lys Leu Ser Phe
                1220                1225                1230

Cys Pro Leu Ser Leu Ser Leu Met Ser Arg Val Lys Cys Asp Phe Lys
                1235                1240                1245

Lys Asp Leu Phe Ala Thr Ile Leu Leu Tyr Ser Glu Leu Met Leu Glu
1250                1255                1260

Ile Ala Val Ser Val Leu Val Ala Asn Pro Asp Leu Ser Ile Ile Glu
1265                1270                1275                1280

Ala Phe Cys Asn Lys Leu Val Leu Phe Phe Thr Asn Ser Ile Tyr Ser
                1285                1290                1295

Leu Lys Ile Ser Ala Thr Phe Ser Ala Gln Thr Ala Arg Thr Leu Ser
                1300                1305                1310

Pro Ile Gly His Ala Gly Val Val Ile Gly Leu Thr Pro Glu Val Arg
                1315                1320                1325

Ala Leu Val Ala Asn Ala Trp Tyr Leu Ala Thr Val Gly Ile Glu Thr
                1330                1335                1340

Leu Met Gly Arg His Arg Asn Leu His Ala Thr Glu Lys His Phe Ala
1345                1350                1355                1360

Asn Lys Arg Thr Ser Gly Thr Ala Ile Lys Glu Ser Val Tyr His Ser
                1365                1370                1375

Leu Ser Cys Cys Leu Leu Glu Asn Ala Val Ala Leu Val Glu Leu Gly
                1380                1385                1390

Arg Ile Leu Val Leu His Leu Tyr Cys Leu Ile Tyr Arg His His Phe
                1395                1400                1405

Asn Arg Cys Trp His Ala Arg Asn Ser Asp Leu Ile Cys Arg Ile Ser
                1410                1415                1420

Phe Asn Ser Thr Gly Ile Phe Arg Gly Gly Val Thr Arg Asn Ala Cys
1425                1430                1435                1440

Asn Leu Thr Ile Asn Ser Thr Asn Leu Arg Ala Leu Arg Val Ala Leu
                1445                1450                1455

Cys Val Lys Phe Pro Cys Phe Ala Asn Ile Asp Ile Val Pro His Ser
```

|   |   | 1460 |   |   | 1465 |   |   | 1470 |   |   |   |
|---|---|---|---|---|---|---|---|---|---|---|---|

His Ala Leu Ile Val Lys Thr Leu Lys Gln Leu Val Leu Leu Val
                1475            1480            1485

Ser Gly Phe His Arg His Ala Tyr Gly Phe Ser Asp Ala Leu Ile Val
                1490            1495            1500

Leu Gly His Asp Ser Gly His Leu Arg Ile Ser Lys Pro Asn Asn Asn
1505            1510            1515            1520

Arg Asn Asn Arg Cys Cys His Ser Thr Arg Tyr Tyr Ser Cys Lys Trp
                1525            1530            1535

Ser Cys Asp Thr Thr Cys Val Glu Met Ile Glu Glu Thr Ser Asp Lys
                1540            1545            1550

Lys Pro Ala Glu Asp Asp Ser Tyr Ile Ala Cys Val Pro Ala Met Leu
                1555            1560            1565

Thr Pro Pro Ser Tyr Pro Asn Ile Gly Gly Lys Asn Asp Glu Ser Glu
                1570            1575            1580

Tyr Val Gly Ala Pro Tyr Met Lys Gly Leu Phe Gly Pro Ser Pro Ile
1585            1590            1595            1600

Ile Trp Leu Met Arg Arg Phe Met Pro His Ile Ala Leu Ile Pro Arg
                1605            1610            1615

Leu Ser Leu Gly Lys Leu Pro Lys Leu Met Ser Ser Asn Leu Ile Leu
                1620            1625            1630

Thr Phe Leu Ser Leu Ser Leu Ser Met Ala Thr Phe Cys Ser Arg Val
                1635            1640            1645

Ser Leu Gly Ile Ser Ile Phe Ser Ser Leu Glu Thr Ser Pro Thr Leu
                1650            1655            1660

Phe Ser Ala Ile Ser Ser Gly Leu Ile Ser Phe Ile Ser Val Phe Trp
1665            1670            1675            1680

Ser Ala Leu Thr Asp Cys Lys His Ala Asn Asp Lys Thr Pro Ser Lys
                1685            1690            1695

Phe Asn Phe Ile Lys Ile Arg Phe His Thr Phe Asp Ser Phe Ile Leu
                1700            1705            1710

Ile Phe Ser Thr Ile Leu Ala His Arg His Ser Ile Val Ile Phe Val
                1715            1720            1725

Leu Ile Phe Leu Ile Glu His Phe Val Cys Tyr Phe Ile Asn Val Leu
                1730            1735            1740

Lys Ile Phe Phe Lys Lys Leu Phe Leu Phe Ser Phe Asn Ala His Ile
1745            1750            1755            1760

Asn Leu Asn Pro Ile Arg Asn Asn Gly Val His Asp Met His Glu Val
                1765            1770            1775

Ile Gly Met Ile Phe
                1780

(2) INFORMATION FOR SEQ ID NO:12:

(i) SEQUENCE CHARACTERISTICS:
        (A) LENGTH: 1720 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Lys Ser Lys Ser Leu Trp Ile Ile Glu Leu Lys Phe Phe Gln Thr Lys
1               5               10              15

Thr Asn Thr Lys Lys Lys Lys Arg Leu Arg Lys Arg Gln Glu Val Lys
                20              25              30

```
Ser Leu Leu Leu Ser Gln Arg Leu Met Gly Ile Ser Lys Pro Lys Ile
         35                  40                  45

Thr Leu Ser Ile Arg Asn Phe Phe Leu Thr Leu Met Pro Met Phe Thr
     50                  55                  60

Lys Lys His Ser Pro Lys Lys Ile Arg Ser Val Val Ile Thr Thr Pro
 65                  70                  75                  80

Arg Lys Arg Ala Val Phe Leu Lys Lys Leu Pro Leu Pro Leu Lys Ile
                 85                  90                  95

Arg Leu Arg Leu Cys Phe Lys Trp Val Cys Phe Leu Met Lys Asn Lys
                100                 105                 110

Thr Lys Lys Arg Ala Asp Leu Tyr Leu Thr Ser Lys Arg Leu Lys Asn
         115                 120                 125

Ile Pro Ile Thr Phe Leu Ile Cys Ala Glu Lys Asn Trp Ile Ile Ile
         130                 135                 140

Ile Thr Tyr Ser Leu Lys Glu Thr Ser Leu Thr Pro Lys Gln Lys Ile
145                 150                 155                 160

Leu Leu Lys Arg Leu Leu Thr Arg Leu Phe Leu Thr Arg Asn Ala Trp
                165                 170                 175

Arg Leu Ala Trp Arg Leu Ile Arg Leu Met Arg Asn Thr Arg Ala Met
                180                 185                 190

Arg Leu Phe Leu Thr Cys Lys Met Ser Lys Met Met Trp Asn Ile Leu
                195                 200                 205

Leu Lys Thr Leu Pro Ile Lys Asn Val Ser His Lys Asn Lys Asn Cys
    210                 215                 220

Val Cys Trp Phe Thr Ala Ser Ile Leu Ile Pro Asn Pro Lys Asn Leu
225                 230                 235                 240

Tyr Lys Arg Leu Met Asn Thr Ile Phe Ser Ile Ala Ile Leu Ala Thr
                245                 250                 255

Lys Gln Leu Cys Lys Lys Asn Thr Thr Arg Tyr Leu Ile Ser Ser Lys
                260                 265                 270

Gln Trp Phe Leu His Thr Glu Thr Met Leu Pro Arg Ile Ile Pro Leu
                275                 280                 285

Asn Arg Lys Gly Asp Thr Leu Glu Lys His Leu Gln Lys Thr Arg Phe
    290                 295                 300

Cys Arg Ser Leu Phe Phe Ser Cys Leu Trp Gly Leu Lys Arg Tyr Gln
305                 310                 315                 320

Tyr Ser Ile Ile Ala Glu Ile Gln Arg Ile Ser Gly Phe Gly Leu Lys
                325                 330                 335

Asn Gln Asn Thr Leu Ser Lys Thr Gln Arg Asn Tyr Lys Arg Gly Lys
                340                 345                 350

Arg Ile Arg His Arg Phe Glu Arg Lys Ile Thr Lys Gly Glu Ser Arg
                355                 360                 365

Ala Asn Ser Lys Glu Tyr Ser Val Lys Lys Glu Gln Leu Phe Cys Ser
    370                 375                 380

Lys Lys Ser Gly Ala Gln Arg Ile Thr Arg Ile Lys Arg Asn Arg Pro
385                 390                 395                 400

Phe Glu Gln Pro Trp Gln Phe Phe His Asn Gln Ile Arg Leu Asp Asp
                405                 410                 415

Gln Gly Glu Ile Phe Cys Glu Thr Cys Ser Ala Cys Ala Val Glu
                420                 425                 430

Asn Ala Asn Asn His Tyr Gln Val Tyr Tyr Phe Lys Gln Arg Leu Trp
    435                 440                 445

Val Lys Lys Val Phe Asp Gln Arg His Gln Gly Ser Lys Asn Ser Cys
```

```
            450             455             460
Pro Leu Ile Arg Lys Asn Ser Arg Asn Arg Asp Arg Lys Gln Val Phe
465                 470                 475                 480

Thr Thr Pro Lys Trp Phe Lys Thr His Ser Gln Gln Gln Asn Leu Ser
                485                 490                 495

Tyr Ser Phe Val Arg Tyr Leu Glu Glu Lys Lys Arg Asn Gly Ala Arg
            500                 505                 510

Lys Leu Pro Gly Tyr Tyr Lys Cys Lys Arg Val Trp His Tyr Tyr Lys
            515                 520                 525

Arg Lys Ser Lys Arg Tyr Ser Ile Leu Lys Gln Ser Leu Ile Arg Thr
530                 535                 540

Ala Gln Arg His Ser Asn Arg Thr Lys His Arg Ser Trp Lys Lys Ile
545                 550                 555                 560

Ala Ile Gln Ile Ile Arg Ser Lys Asn Asn Arg Ser Lys Ser Gln Arg
                565                 570                 575

Leu Glu Ile Ile Ala Tyr Arg Leu Arg Lys Ile Ile Gln Ser Tyr Leu
            580                 585                 590

Ile Ala Phe Leu Val Gly Ile Val Ala Tyr Phe Val Leu Gly Ile Phe
            595                 600                 605

Leu Met Arg Pro Thr Pro Leu Asn Asn Leu Lys Arg Pro Cys Phe Glu
610                 615                 620

Leu Thr Ala Phe Phe Leu Asn Phe Tyr Ser Leu Gly Phe Leu Gln Ala
625                 630                 635                 640

Ser Val Lys Gln Leu Lys Lys Leu Tyr Leu Gln Cys Cys Ser Asp Thr
                645                 650                 655

Pro Leu Gly Lys Phe Leu Asn Ala Leu Leu Tyr Phe Val Phe Leu Ala
            660                 665                 670

Arg Phe Ser Ala Ser Leu His Asn Lys Glu Leu Lys Leu Tyr Arg Ile
            675                 680                 685

Phe Arg Ile Ala Ala Gln Gln Tyr Phe Gly Leu Arg Asp Phe Ser Tyr
690                 695                 700

Arg Leu Ile Lys Val Gln Gly Thr Tyr Lys Ser Lys Ser His Leu Leu
705                 710                 715                 720

Arg Lys Ile Thr His Ser Leu Gln Asn Trp Leu Ser Ile Thr Leu Asn
                725                 730                 735

Leu Leu Ser Lys Gln Trp Pro Leu Phe Cys Leu Glu His Leu Leu Asp
            740                 745                 750

Leu Phe His Tyr Arg Gly Trp Leu Lys Ser His Leu Ser Phe Ala
            755                 760                 765

Leu Val Gly Trp Ser Leu Gly Arg Cys Tyr Gln Val Ala Leu Asn Arg
770                 775                 780

Leu Leu Tyr Leu Leu Pro Ser Lys Gln Thr Ile Ala Lys Lys Ile
785                 790                 795                 800

Trp Tyr Phe Ser Arg Val Phe Ser Phe Asp Asn Asn Phe Arg Ala Ser
                805                 810                 815

Asn Val Ser Cys Cys Arg Phe Ser Phe Gln Leu Phe Pro Lys
            820                 825                 830

Val Gly Phe Phe Phe Lys Ile Leu Tyr Ile Val Met Ile Phe Cys Val
            835                 840                 845

Asp Arg Asn Phe Tyr Glu Arg Ile Gln Ile Tyr Ser Phe Gly Phe Asp
850                 855                 860

Phe Ser Ile Asp Pro Ile Gln Ile Ser Asp Ile Leu Lys Ile Cys Ile
865                 870                 875                 880
```

```
Thr Gln Phe Ile Leu Asn Lys Gly Tyr Asn His Ser Val Ile Leu Asn
            885                 890                 895

Asn Leu Phe His Lys Ala Cys Asn Phe Pro Ile Lys Ile Arg Ala Phe
            900                 905                 910

Cys Gly Arg Ser Glu Cys Phe Asn Asp Ser Lys Trp Ser Pro Met Leu
            915                 920                 925

Glu Lys Lys Leu Arg Ala Gly Ala Met Ala Leu Asn Lys Ala Pro Val
            930                 935                 940

Arg Glu Leu Ser Ile Arg Val Ala Phe Cys Ile Ala Val Phe Asn His
945                 950                 955                 960

Val Ser Lys Pro Phe Lys Val Ser Ser Asn Ala Leu Ile Pro Ile Val
            965                 970                 975

Leu Ala Met Tyr Ala Leu Ser Glu Glu Leu Pro Arg Ala Glu Ile Ser
            980                 985                 990

Ile Cys Val Phe Arg Val Thr Leu Gly Ser Lys Leu Phe Phe Asn Ala
            995                 1000                1005

Ser Lys Arg Ala Phe Cys Trp Phe Ile Leu Ser Leu Ile Ile Ser Leu
            1010                1015                1020

Phe Phe Trp Ser Ala Ile Cys Met Phe Trp Ile Ser Val Trp Val Leu
1025                1030                1035                1040

Ile Phe Cys Phe Ser Thr Ile Ile Leu Thr Phe Pro Pro Asn Ala Leu
            1045                1050                1055

Ser Ala Ala Ile Pro Phe His Asp Ala Lys Gln Asp Val Thr Cys Lys
            1060                1065                1070

Lys Pro Pro Cys His Ala Ile Asp Thr Ile Asn Asn Ala Ile Ser Pro
            1075                1080                1085

Phe His Ser Ala His Gly Cys Lys Leu Ser Pro Gln Phe Ser Leu Tyr
            1090                1095                1100

Leu Arg Leu Asn Gly Phe Phe Gly Thr Arg Leu Ser Phe Tyr Gly
1105                1110                1115                1120

Phe Phe Gly Leu Ser Gly Phe Leu Phe Gly Leu Cys Val Cys Leu Asn
            1125                1130                1135

Gly Phe Gly Arg Phe Lys Arg Tyr Tyr Tyr Leu Cys Thr Ile Gln Arg
            1140                1145                1150

Gln Thr Thr Lys Ser Gln Glu Arg Lys Tyr Ala Lys Thr Phe His Ile
            1155                1160                1165

Ser Phe Leu Thr Ser Arg Leu Phe Phe Ala Pro Phe Leu Leu Ser Ser
            1170                1175                1180

Tyr Leu Phe Ala Pro Ala Cys Leu Cys Asn Gln Gly Lys Ser Asn Ala
1185                1190                1195                1200

Ile Ser Lys Lys Ile Tyr Ser Leu Leu Tyr Cys Asn Tyr Ile Ala Asn
            1205                1210                1215

Leu Cys Lys Ser Leu Glu Cys His Arg Cys Leu Ile Leu Ile Asp Val
            1220                1225                1230

Ser Phe Glu Lys Arg Ser Ala Thr Asn Trp Tyr Tyr Phe Ser Gln Ile
            1235                1240                1245

Leu Tyr Ser Ile Leu Ser Lys Phe Leu Leu Leu Phe Gln His Ser Asn
            1250                1255                1260

Lys Gln Gln Glu Pro Cys Pro Gln Gly Met Gly Glu Trp Ser Asp Arg
1265                1270                1275                1280

Leu Lys Leu Gly His Trp Leu Thr Leu Gly Ile His Lys Gln Trp Ala
            1285                1290                1295

Lys Arg Ser Trp Gly Val Ile Glu Ile Cys Met Gln Leu Lys Asn Thr
            1300                1305                1310
```

```
Phe Asp Glu Pro Thr Ser Ala Pro Lys Ala Val Gln Leu Ser Arg Asn
        1315                1320                1325

Arg Cys Ile Ile His Ala Val Ala Cys Leu Arg Thr Gln Leu Leu Leu
        1330                1335                1340

Ser Gly Val Phe Trp Cys Cys Thr Cys Asn Ile Ala Tyr Thr Val Ile
1345                1350                1355                1360

Ile Ser Thr Val Val Gly Thr Leu Gly Thr Ala Ile Phe Val Ala Ala
        1365                1370                1375

Ser Ile Ala Leu Gly Phe Leu Gly Val Val Leu Leu Ala Lys Met Leu
        1380                1385                1390

Ala Ile Leu Leu Thr Ala Pro Ile Cys Ala Pro Cys Val Leu Pro Cys
        1395                1400                1405

Ala Leu Asn Ser Pro Val Asn Leu Leu Ile Phe Lys Ile Leu Phe Pro
        1410                1415                1420

Thr Ala Met Leu Ser Leu Lys Pro Asn Asn Trp Leu Tyr Cys Trp Leu
1425                1430                1435                1440

Ala Ala Phe Ile Gly Met Leu Thr Ala Ser Ala Met Leu Leu Tyr Trp
        1445                1450                1455

Val Met Ile Ala Val Ile Cys Gly Leu Val Asn Pro Thr Ile Ile Gly
        1460                1465                1470

Ile Ile Ala Ala Val Ile Ala Pro Ala Thr Ile Pro Ala Asn Gly Pro
        1475                1480                1485

Ala Thr Pro Leu Val Leu Arg Leu Arg Lys Leu Pro Ile Arg Ser Leu
        1490                1495                1500

Gln Lys Met Ile His Ile Leu Val Tyr Leu Pro Cys His Pro Leu Val
1505                1510                1515                1520

Asn Thr Leu Ile Ser Val Val Lys Thr Met Asn Leu Ser Met Leu Val
        1525                1530                1535

His Asn His Thr Lys Asp Cys Leu Asp Arg Asn Arg Pro Ser Phe Gly
        1540                1545                1550

Ser Glu Asp Phe Glu Cys Pro Thr Ser His Tyr Leu Asp Tyr His Val
        1555                1560                1565

Glu Asn Ser Leu Asn Leu Cys Arg Gln Ile Tyr His Phe Tyr His Tyr
        1570                1575                1580

Ser His Val Trp Pro Leu Phe Ala Leu Gly Phe Leu Gly Ser Leu Phe
1585                1590                1595                1600

Leu Val Asp Leu Lys Gln Ala Pro Arg Tyr Leu Val Pro Tyr Leu Gln
        1605                1610                1615

Asp Tyr Leu Leu Tyr Gln Cys Phe Gly Gln Arg Arg Thr Val Asn Met
        1620                1625                1630

Pro Met Ile Arg His Gln Ala Asn Ser Asn Leu Ile Leu Lys Ser Val
        1635                1640                1645

Phe Ile Leu Leu Thr Pro Leu Phe Leu Phe Leu Ala Leu Phe Arg Ile
        1650                1655                1660

Asn Ala Thr Gln Ser Leu Phe Leu Phe Phe Ser Ser Ile Leu Phe
1665                1670                1675                1680

Val Thr Ser Ser Met Phe Lys Tyr Phe Ser Lys Ser Ser Phe Leu
        1685                1690                1695

Ala Ser Thr Leu Ile Ser Ile Ile Gln Leu Gly Ile Met Glu Ser Met
        1700                1705                1710

Ile Lys Cys Met Lys Ser Ala Phe
        1715                1720
```

(2) INFORMATION FOR SEQ ID NO:13:

(i) SEQUENCE CHARACTERISTICS:
        (A) LENGTH: 5599 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
AAAAATCATG CCTATGACTT CATGCATTTA ATCATGGACT CCATTATTCC TAATTGGATT      60
CAGATTGATA TGAGCGTTGA AGCTAAAAAG AAAGAGCTTT TTGAAAAATA TTTTCAAAAC     120
ATTGATGAAG TAACAAACAA AATGCTCGAT CAAAAAAATC AAAACAAAAA TAACGATTGA     180
GTGGCGTTAA TGCGCTAGAA TAGTGCTAAA AATAAGAATA AAGGAGTCAA AAGTATGAAA     240
ACGGATTTTT ATAAAATTAA ATTACTATTT GCTTGGTGTC TTATCATTGG CATGTTTACA     300
GTCCGTTAAC GCTGACCAAA ACACTGATAT AAAAGATATT AGTCCTGAAG ATATGGCACT     360
AAATAGCGTG GGGCTTGTTT CTAGAGATCA ACTAAAAATA GAGATCCCTA AGAAACCCT     420
AGAGCAAAAA GTGGCCATAC TCAATGACTA TAATGATAAA AATGTTAATA TCAAATTTGA     480
CGACATAAGT TTAGGGAGTT TTCAACCTAA TGATAATCTA GGTATCAATG CGATGTGGGG     540
CATTCAAAAT CTTCTCATGA GCCAAATGAT GGGCGATTAC GGTCCAAACA ATCCTTTCAT     600
GTATGGTTAT GCACCAACAT ACTCAGATTC ATCGTTTTTA CCACCGATAT TAGGGTATTA     660
ACTAGGGGGT GTTAACATGG CAGGTACACA AGCTATATAT GAATCATCTT CTGCAGGCTT     720
CTTATCGGAA GTTTCCTCAA TCATCTCAAC ACAAGTGGTG TCGCAGGACC ATTTGCAGGA     780
ATAGTAGCGG GTGCTATGAC AGCAGCGATT ATTCCTATTA TTGTTGGGTT TACTAATCCG     840
CAAATGACCG CTATCATGAC CCAATACAAT CAAAGCATCG CTGAAGCCGT AAGCATGCCT     900
ATGAAAGCCG CTAACCAACA ATACAACCAA TTGTTTCAAG GTTTTAACGA TCAAAGCATG     960
GCTGTGGGGA ACAATATCTT AAATATTAGC AAATTAACAG GGGAATTTAA CGCACAAGGC    1020
AACACGCAAG GCGCGCAAAT TGGTGCTGTT AATAGTCAGA TTGCAAGCAT TTTAGCGAGT    1080
AACACCACCC CTAAAAATCC CAGTGCTATT GAAGCTTATG CGACAAATCA AATCGCTGTT    1140
CCTAGCGTGC CAACAACGGT TGAAATGATG ACGGTATATT AGGCAATATT ACAAGTGCAG    1200
CACCAAAATA CGCCCTAGCT CTACAAGAGC AACTGCGTTC TCAAGCAAGC AACAGCTCAA    1260
TGAATGATAC ACCGATTCCT TGATAGCTGT ACCGCTTTAG GTGCGCTTGT TGGCTCATCA    1320
AAAGTGTTTT TCAGTTGCAT GCAAATTTCT ATGACGCCCC ATGAGCGTTT CTATGCCCAC    1380
TGTTTATGCT AAATACCAAG CGTTAGCCAC TAATGCCCTA ACTTCAGGCG TTAATCCTAT    1440
GACCACTCCT GCATGCCCTA TTGGGGACAA GGTTCTTGCT GTTTATTGCT ATGCTGAAAA    1500
AGTAGCAGAA ATTTTGAGAG AATACTATAT AGAATTTGTG AAAAATAATA CCAATTTGTT    1560
GCAGAACGCT TCTCAAATGA TACTTAATCA ATCAGGATTA GCTACTAGCA CCTATGACAC    1620
TCAAGCGATT TCTAACATAA GTTCGCTATA TAATTACAAT ATAGTAGCGA ATAAATCTTT    1680
TTTGAAATCG CATTTGACTT ACCTTGATTA CATCAAAGAC AAGCTTAAGG GGCAAAAAGA    1740
TAGCTACTTA ACAGAAAGGG TGCAAACTAA AATAATCGTG AAGTGAGGAA AGAGATGTGA    1800
AATGTTTTTT AAGCATATTT TCTTTCTTGA CTTTTTGTGG TTTGTCTCTG AATGGTACAG    1860
AGGTAGTAAT AACGCTTGAA CCTGCCTTAA AAGCCATTCA GGCAGACGCA CAAGCCAAAC    1920
AAAAAACCGC TCAAGCCGAA TTAAAAGCCA TAGAAGCTCA ATCTAGTGCC AAAGAAAAAG    1980
CCATTCAAGC GCAAATAGAG GGAGAATTGA GGACTCAGCT TGCAACCATG AGCGCTATGT    2040
```

```
TAAAAGGGGC TAATGGCGTT ATTAATGGTG TCAATGGCAT GACAGGGGGG TTTTTTGCAG    2100

GTTCAGACAT CTTGCTTGGC GTCATGGAAG GGTATTCAAG CGGCGCTTAG TGCATTGGGG    2160

GGGAATGTCA AAATGATCGT GGAAAAACAA AAAATTAATA CCCAAACAGA AATCCAAAAC    2220

ATGCAAATCG CGCTCCAAAA AAATAACGAA ATGATCAAGC TCAAATGAA CCAGCAAAAC     2280

GCTCTCTTAG AAGCGTTAAA AAACAGCTTT GAACCGAGGG TTACCCTAAA ACACAAATG    2340

GAAATTTCTC AAGCTCTAGG AAGTTCTTCT GACAACGCTC AATACATCGC TTACAATACG    2400

ATTGGTATCA AGGCGTTTGA AGAAACCTTA AAAGGTTTTG AGACATGGTT GAAAACAGCT    2460

ATGCAAAAAG CGACCCTTAT TGATTATAAT TCCCTAACAG GTCAGGCTTT GTTTCAAAGT    2520

GCCATCTATG CGCCTGCTCT TAGTTTTTTT TCAAGCATGG GCGACCATTT GGAATCATTG    2580

AAACATTCAC TCTAGCGCCC ACAAAATGCC CTTATCTTGA TGGGCTAAAA ATTTCAGCAT    2640

GCCTTATGGA ACAGGTTATT CAGAATTACA GAATGATTGT AGCCCTTATT CAAAATAAAC    2700

TGAGTGATGC AGATTTTCAA AATATCGCTT ATTTGAATGG GATCAATGGA GAAATCAAAA    2760

CCTTAAAAGG ATCAGTAGAT TTGAATGCGC TCATAGAAGT TGCGATCTTA AACGCAGAAA    2820

ATCATTTAAA CTATATAGAG AATCTTGAAA AAAAGCCGA CCTTTGGGAA GAACAACTGA     2880

AATTAGAAAG AGAAACGACA GCAAGAAACA TTGCTAGCTC TAAAGTTATT GTCAAATGAA    2940

AACACTCGTG AAAAATACCA TATCTTCTTT TTTGCTATTG TCTGTTTTGA TGGCAGAAGA    3000

TATAACAAGC GGTTTAAAGC AACTTGATAG CACCTACCAA GAGACCAACC AACAAGTGCT    3060

TAAAAACTTA GATGAGATTT TTTCAACCAC TAGCCCTAGC GCTAATAATG AAATAGGTCA    3120

AGAAGATGCT CTAAACATCA AAAAGCGGC CATTGCTTTG AGAGGAGATT TAGCGTTATT     3180

GAAAGCCAAT TTTGAAGCGA ATGAGTTATT TTTCATCTCA GAAGATGTGA TTTTCAAGAC    3240

TTATATGTCT AGCCCTGAAC TTTTATTAAC CTATATGAAA ATCAATCCCT TAGACCAAAA    3300

TACTGCTGAG CAGCAATGCG GAATATCCGA TAAAGTTTTA GTTCTTTATT GTGAAGGGAA    3360

GCTGAAAATC GAGCAAGAAA AACAAAATAT AAGAGAGCGT TTAGAAACTT CCCTAAAGGC    3420

GTATCAGAGC AACATTGGAG GTACAGCTTC TTTAATCACT GCTTCACAGA CGCTTGTAGA    3480

AAGCCTAAAG AATAAAAATT TCATCAAAGG AATCAGAAAG CTTATGTTAG CTCAAAACAA    3540

GGTCTTTTTA AATTATTTAG AGGAGTTGGA CGCATTAGAA AGATCCCTAG AACAAAGTAA    3600

GCGACAATAC CTACAAGAAA GGCAATCAAG TAAGATCATT GTTAAATGAT TTTTCTGAGA    3660

CGATAGGCTA TGATTTCTAA CCTTTGGGAT TTGCTTCTCT AGTTGTTTTT TGATCTAATA    3720

ATTTGGATCG CTATTTTTTT CCATGAGCGA TGCTTTGTTC TATTTGATTA ATGACGCTAT    3780

TGGGCAGTTC GGATTAGAG CGATTGTTTG AGAATGCTGT ATCTTTTGCT TCATTTTCTT     3840

TTGTATCAGT AGTGCCAAAC TCGCTTGCAT TTGTAGTATC CTGGTAGTTA TTTTCTTGCT    3900

CCATTTCTTT TTTTCTCTTC TCACAAATAG CGCACGAAGC TATAAGAAAG GTTCTATTGT    3960

TGCTGTTATT AAGAGTGAGT TTTAAACCAC TTAGGTGTTG TCTAGAAAAC TTGTTATTTT    4020

CTGTCTCTAT TTCTTGAATT TTTTCTAATA AGGGGCAAG AATTTTTTGA TCCTTGATGT     4080

CTTTGATCAA ACACTTTCTT AACCCATCAT AATCGTTGCT TGAAATAATA CACTCATTGA    4140

TAATGATTTC AATTTCAGGC GTTCTCCACT CATCAGGCAC AAGCGGAGCA GCAGGTTTCA    4200

CAAAAGATTC ATTCACCTTA TTGATCATCT CATCAAAGTT ATCATCTTTA TTAGATTTGG    4260

TTTCAGTGGA AGAATTGCCA TTAGGGTTGT CATTCAAAGG GTTAGCGTTA ATTTCGTTTA    4320

ATTCTTGTAA TCCTTTGTGC TTAGCCGCTT TTTTTTGAAC AGAAGAGTTG TTCTTTTTTT    4380

CAAACGCTTC AATATTCTTT TGAATTTGCT CTGCTCTCGC CCTATCATTT CGTAATTTTT    4440
```

-continued

```
CTCTCAAAGC GTTAGTGGCG AATTCTTTTT CCTCTTTTGT AATTTCTTTG TCATCATGTC      4500

TTTGATAGAG TGTTTTGATT TTTTTAAAGC CCAAAGCCAC TAATTCTTTG TATTCACTCG      4560

GCAATAATGC TGTATTGATA GCGTTTAAGC CCCCATAAAC AACTAAAGAA TAAAGAGCGA      4620

CAGAACCTAG TTTTTTGAAG ATGCTTTTCA AGAGTGTCTC CTTTCCTATT CAAAGGGATT      4680

ATTCTTGGCA ACATTGTTTC GGTATGCAGA ACCACTGTT TTGAAGAAAT TAAATATCTT      4740

GTAGTGTTCT TTTTGCATAG TTGTTTTGTC GCTCATCATA GGATCGCTAT CTACGAAAAT      4800

ATTGTATTCA TTAGTCTTTT TTAATATAGA TTTTTTGGAT TGGGTATCAA AATTGAAGCT      4860

GTCTAAAACC AACAAACACA ATTTTTGTTT TTGTGCGAAA CTCAATTTTT GATTGGTAAA      4920

GTTTTTAGTC AGAGTATTCA ATTCCACATC ATCTTTGACA TTTTTCAACA AGTTAGAAAA      4980

AGCCTCATAG CCCTTTAAGT ATTTCTCATT AATCTTATCA ATCGCCATGC TAAACGCCAA      5040

GCGTTCCGAG TTAAAAATAA GCGTGTTAGT AGCCTTTTGA GCAATATCTT TTGCTTTGGA      5100

GTCAAACTTG TTTCTTTCAA GCTGTAAGTA ATAATCTATA TTATCCAATT CTTTTCTGCT      5160

CAACAGATTA GAAATGTTAT TGGAATATTC TTCAATCGCT TGCTTGTAAG ATAAAGCTAA      5220

TCGGCTCGCT TTTTGTTTT GTTCTTCATC TAAAGAAAAC ACACCCATTT GAAGCAAAGC      5280

CTGAGCCTTA TCTTTAGTGG TAGCGGTAGT TTTTTTAAAA ATACTGCTCG TTTTCACCTG      5340

GGGGTAGTAA TAACTCAAAC GCTCCTTATC TTCTTTGGTG AATGTTTCTT GGTTTAAAAC      5400

ATAGGCATAA GGGTTAGGAA GAAGTTTCTT ATAGAGAGGG TTATCTTTTA AGGCTTGCTC      5460

TAGATCCCCA TAAGCCTTTG ACTTAGCAGT AAGGATTTTA CCTCTTGTCT CTTTCTCTAG      5520

AGCCTCTTTT TCTTTTTTGT ATTTGTTTTC TAAGTCTGAA AGAACTTTAG CTCTATGATC      5580

CATAAGCTCT TTGATTTTT                                                  5599
```

(2) INFORMATION FOR SEQ ID NO:14:

(i) SEQUENCE CHARACTERISTICS:
        (A) LENGTH: 1732 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Lys Asn His Ala Tyr Asp Phe Met His Leu Ile Met Asp Ser Ile Ile
 1               5                  10                  15

Pro Asn Trp Ile Gln Ile Asp Met Ser Val Glu Ala Lys Lys Lys Glu
            20                  25                  30

Leu Phe Glu Lys Tyr Phe Gln Asn Ile Asp Glu Val Thr Asn Lys Met
        35                  40                  45

Leu Asp Gln Lys Asn Gln Asn Lys Asn Asn Asp Val Ala Leu Met Arg
    50                  55                  60

Asn Ser Ala Lys Asn Lys Asn Lys Gly Val Lys Ser Met Lys Thr Asp
65                  70                  75                  80

Phe Tyr Lys Ile Lys Leu Leu Phe Ala Trp Cys Leu Ile Ile Gly Met
                85                  90                  95

Phe Thr Val Arg Arg Pro Lys His Tyr Lys Arg Tyr Ser Arg Tyr Gly
            100                 105                 110

Thr Lys Arg Gly Ala Cys Phe Arg Ser Thr Lys Asn Arg Asp Pro Arg
        115                 120                 125

Asn Pro Arg Ala Lys Ser Gly His Thr Gln Leu Lys Cys Tyr Gln Ile
    130                 135                 140
```

-continued

```
Arg His Lys Phe Arg Glu Phe Ser Thr Ser Arg Tyr Gln Cys Asp Val
145                 150                 155                 160

Gly His Ser Lys Ser Ser His Glu Pro Asn Asp Gly Arg Leu Arg Ser
                165                 170                 175

Lys Gln Ser Phe His Val Trp Leu Cys Thr Asn Ile Leu Arg Phe Ile
            180                 185                 190

Val Phe Thr Thr Asp Ile Arg Val Leu Thr Arg Gly Cys His Gly Arg
        195                 200                 205

Tyr Thr Ser Tyr Ile Ile Ile Phe Cys Arg Leu Leu Ile Gly Ser Phe
    210                 215                 220

Leu Asn His Leu Asn Thr Ser Gly Val Ala Gly Pro Phe Ala Gly Ile
225                 230                 235                 240

Val Ala Gly Ala Met Thr Ala Ala Ile Ile Pro Ile Ile Val Gly Phe
                245                 250                 255

Thr Asn Pro Gln Met Thr Ala Ile Met Thr Gln Tyr Asn Gln Ser Ile
                260                 265                 270

Ala Glu Ala Val Ser Met Pro Met Lys Ala Ala Asn Gln Gln Tyr Asn
            275                 280                 285

Gln Leu Phe Gln Gly Phe Asn Asp Gln Ser Met Ala Val Gly Asn Asn
        290                 295                 300

Ile Leu Asn Ile Ser Lys Leu Thr Gly Glu Phe Asn Ala Gln Gly Asn
305                 310                 315                 320

Thr Gln Gly Ala Gln Ile Gly Ala Val Asn Ser Gln Ile Ala Ser Ile
                325                 330                 335

Leu Ala Ser Asn Thr Thr Pro Lys Asn Pro Ser Ala Ile Glu Ala Tyr
                340                 345                 350

Ala Thr Asn Gln Ile Ala Val Pro Ser Val Pro Thr Thr Val Glu Met
            355                 360                 365

Met Thr Val Tyr Ala Ile Leu Gln Val Gln His Gln Asn Thr Pro Leu
        370                 375                 380

Tyr Lys Ser Asn Cys Val Leu Lys Gln Ala Thr Ala Gln Met Ile His
385                 390                 395                 400

Arg Phe Leu Asp Ser Cys Thr Ala Leu Gly Ala Leu Val Gly Ser Ser
                405                 410                 415

Lys Val Phe Phe Ser Cys Met Gln Ile Ser Met Thr Pro His Glu Arg
            420                 425                 430

Phe Tyr Ala His Cys Leu Cys Ile Pro Ser Val Ser His Cys Pro Asn
        435                 440                 445

Phe Arg Arg Ser Tyr Asp His Ser Cys Met Pro Tyr Trp Gly Gln Gly
    450                 455                 460

Ser Cys Cys Leu Leu Leu Cys Lys Ser Ser Arg Asn Phe Glu Arg Ile
465                 470                 475                 480

Leu Tyr Arg Ile Cys Glu Lys Tyr Gln Phe Val Ala Glu Arg Phe Ser
                485                 490                 495

Asn Asp Thr Ser Ile Arg Ile Ser Tyr His Leu His Ser Ser Asp Phe
            500                 505                 510

His Lys Phe Ala Ile Leu Gln Tyr Ser Ser Glu Ile Phe Phe Glu Ile
        515                 520                 525

Ala Phe Asp Leu Pro Leu His Gln Arg Gln Ala Gly Ala Lys Arg Leu
    530                 535                 540

Leu Asn Arg Lys Gly Ala Asn Asn Arg Glu Val Arg Lys Glu Met
545                 550                 555                 560

Asn Val Phe Ala Tyr Phe Leu Ser Leu Phe Val Val Cys Leu Met Val
                565                 570                 575
```

```
Gln Arg Arg Leu Asn Leu Pro Lys Pro Phe Arg Gln Thr His Lys Pro
            580                 585                 590

Asn Lys Lys Pro Leu Lys Pro Asn Lys Pro Lys Leu Asn Leu Val Pro
            595                 600                 605

Lys Lys Lys Pro Phe Lys Arg Lys Arg Glu Asn Gly Leu Ser Leu Gln
            610                 615                 620

Pro Ala Leu Cys Lys Gly Leu Met Ala Leu Leu Met Val Ser Met Ala
625                 630                 635                 640

Gln Gly Gly Phe Leu Gln Val Gln Thr Ser Cys Leu Ala Ser Trp Lys
                    645                 650                 655

Gly Ile Gln Ala Ala Leu Ser Ala Leu Gly Gly Asn Val Lys Met Ile
            660                 665                 670

Val Glu Lys Gln Lys Ile Asn Thr Gln Thr Glu Ile Gln Asn Met Gln
            675                 680                 685

Ile Ala Leu Gln Lys Asn Asn Glu Met Ile Lys Leu Lys Met Asn Gln
            690                 695                 700

Gln Asn Ala Leu Leu Glu Ala Leu Lys Asn Ser Phe Glu Pro Arg Val
705                 710                 715                 720

Thr Leu Lys Thr Gln Met Glu Ile Ser Gln Ala Leu Gly Ser Ser Ser
                    725                 730                 735

Asp Asn Ala Gln Tyr Ile Ala Tyr Asn Thr Ile Gly Ile Lys Ala Phe
                    740                 745                 750

Glu Glu Thr Leu Lys Gly Phe Glu Thr Trp Leu Lys Thr Ala Met Gln
            755                 760                 765

Lys Ala Thr Leu Ile Asp Tyr Asn Ser Leu Thr Gly Gln Ala Leu Phe
            770                 775                 780

Gln Ser Ala Ile Tyr Ala Pro Ala Leu Ser Phe Phe Ser Ser Met Gly
785                 790                 795                 800

Asp His Leu Glu Ser Leu Lys His Ser Leu Arg Pro Gln Asn Ala Leu
                    805                 810                 815

Ile Leu Met Gly Lys Phe Gln His Ala Leu Trp Asn Arg Leu Phe Arg
                    820                 825                 830

Ile Thr Glu Leu Pro Leu Phe Lys Ile Asn Val Met Gln Ile Phe Lys
            835                 840                 845

Ile Ser Leu Ile Met Gly Ser Met Glu Lys Ser Lys Pro Lys Asp Gln
            850                 855                 860

Ile Met Arg Ser Lys Leu Arg Ser Thr Gln Lys Ile Ile Thr Ile Arg
865                 870                 875                 880

Ile Leu Lys Lys Lys Pro Thr Phe Gly Lys Asn Asn Asn Lys Glu Lys
                    885                 890                 895

Arg Gln Gln Glu Thr Leu Leu Ala Leu Lys Leu Leu Ser Asn Glu Asn
            900                 905                 910

Thr Arg Glu Lys Tyr His Ile Phe Phe Ala Ile Val Cys Phe Asp
            915                 920                 925

Gly Arg Arg Tyr Asn Lys Arg Phe Lys Ala Thr His Leu Pro Arg Asp
930                 935                 940

Gln Pro Thr Ser Ala Lys Leu Arg Asp Phe Asn His Pro Arg Asn
945                 950                 955                 960

Arg Ser Arg Arg Cys Ser Lys His Gln Lys Ser Gly His Cys Phe Glu
                    965                 970                 975

Arg Arg Phe Ser Val Ile Glu Ser Gln Phe Ser Glu Val Ile Phe His
                    980                 985                 990

Leu Arg Arg Cys Asp Phe Gln Asp Leu Tyr Val Pro Thr Phe Ile Asn
```

-continued

```
              995                  1000                 1005
Leu Tyr Glu Asn Gln Ser Leu Arg Pro Lys Tyr Cys Ala Ala Met Arg
    1010                1015                1020
Asn Ile Arg Ser Phe Ser Ser Leu Leu Arg Glu Ala Glu Asn Arg Ala
1025                1030                1035                1040
Arg Lys Thr Lys Tyr Lys Arg Ala Phe Arg Asn Phe Pro Lys Gly Val
            1045                1050                1055
Ser Glu Gln His Trp Arg Tyr Ser Phe Phe Asn His Cys Phe Thr Asp
            1060                1065                1070
Ala Cys Arg Lys Pro Lys Glu Lys Phe His Gln Arg Asn Gln Lys Ala
        1075                1080                1085
Tyr Val Ser Ser Lys Gln Gly Leu Phe Lys Leu Phe Arg Gly Val Gly
        1090                1095                1100
Arg Ile Arg Lys Ile Pro Arg Thr Lys Ala Thr Ile Pro Thr Arg Lys
1105                1110                1115                1120
Ala Ile Lys Asp His Cys Met Ile Phe Leu Arg Arg Ala Met Ile Ser
            1125                1130                1135
Asn Leu Trp Asp Leu Leu Leu Phe Phe Asp Leu Ile Ile Trp Ile
            1140                1145                1150
Ala Ile Phe Phe His Glu Arg Cys Phe Val Leu Phe Asp Arg Tyr Trp
            1155                1160                1165
Ala Val Arg Ile Ser Asp Cys Leu Arg Met Leu Tyr Leu Leu Leu His
        1170                1175                1180
Phe Leu Leu Tyr Gln Cys Gln Thr Arg Leu His Leu Tyr Pro Gly Ser
1185                1190                1195                1200
Tyr Phe Leu Ala Pro Phe Leu Phe Phe Ser Ser His Lys Arg Thr Lys
            1205                1210                1215
Leu Glu Arg Phe Tyr Cys Cys Cys Tyr Glu Val Leu Asn His Leu Gly
            1220                1225                1230
Val Val Lys Thr Cys Tyr Phe Leu Ser Leu Phe Leu Glu Phe Phe Leu
            1235                1240                1245
Ile Arg Gly Gln Glu Phe Phe Asp Pro Cys Leu Ser Asn Thr Phe Leu
        1250                1255                1260
Thr His His Asn Arg Cys Leu Lys Tyr Thr His Phe Gln Phe Gln Ala
1265                1270                1275                1280
Phe Ser Thr His Gln Ala Gln Ala Glu Gln Gln Val Ser Gln Lys Ile
            1285                1290                1295
His Ser Pro Tyr Ser Ser His Gln Ser Tyr His Leu Tyr Ile Trp Phe
        1300                1305                1310
Gln Trp Lys Asn Cys His Gly Cys His Ser Lys Gly Arg Phe Arg Leu
        1315                1320                1325
Ile Leu Val Ile Leu Cys Ala Pro Leu Phe Phe Glu Gln Lys Ser Cys
    1330                1335                1340
Ser Phe Phe Gln Thr Leu Gln Tyr Ser Phe Glu Phe Ala Leu Leu Ser
1345                1350                1355                1360
Pro Tyr His Phe Val Ile Phe Leu Ser Lys Arg Trp Arg Ile Leu Phe
            1365                1370                1375
Pro Leu Leu Phe Leu Cys His Val Phe Asp Arg Val Phe Phe Phe
            1380                1385                1390
Ser Pro Lys Pro Leu Ile Leu Cys Ile His Ser Ala Ile Met Leu Tyr
        1395                1400                1405
Arg Leu Ser Pro His Lys Gln Leu Lys Asn Lys Glu Arg Gln Asn Leu
    1410                1415                1420
```

```
Val Phe Arg Cys Phe Ser Arg Val Ser Pro Phe Leu Phe Lys Gly Ile
1425                1430                1435                1440

Ile Leu Gly Asn Ile Val Ser Val Cys Arg Asn His Cys Phe Glu Glu
                1445                1450                1455

Ile Lys Tyr Leu Val Val Phe Phe Leu His Ser Cys Phe Val Ala His
            1460                1465                1470

His Arg Ile Ala Ile Tyr Glu Asn Ile Val Phe Ile Ser Leu Phe Tyr
        1475                1480                1485

Arg Phe Phe Gly Leu Gly Ile Lys Ile Glu Ala Val Asn Gln Gln Thr
    1490                1495                1500

Gln Phe Leu Phe Leu Cys Glu Thr Gln Phe Leu Ile Gly Lys Val Phe
1505                1510                1515                1520

Ser Gln Ser Ile Gln Phe His Ile Ile Phe Asp Ile Phe Gln Gln Val
                1525                1530                1535

Arg Lys Ser Leu Ile Ala Leu Val Phe Leu Ile Asn Leu Ile Asn Arg
            1540                1545                1550

His Ala Lys Arg Gln Ala Phe Arg Val Lys Asn Lys Arg Val Ser Ser
        1555                1560                1565

Leu Leu Ser Asn Ile Phe Cys Phe Gly Val Lys Leu Val Ser Phe Lys
    1570                1575                1580

Leu Val Ile Ile Tyr Ile Ile Gln Phe Phe Ser Ala Gln Gln Ile Arg
1585                1590                1595                1600

Asn Val Ile Gly Ile Phe Phe Asn Arg Leu Leu Val Arg Ser Ser Ala
                1605                1610                1615

Arg Phe Phe Val Leu Phe Phe Ile Arg Lys His Thr His Leu Lys Gln
            1620                1625                1630

Ser Leu Ser Leu Ile Phe Ser Gly Ser Gly Ser Phe Phe Lys Asn Thr
        1635                1640                1645

Ala Arg Phe His Leu Gly Val Val Ile Thr Gln Thr Leu Leu Ile Phe
    1650                1655                1660

Phe Gly Glu Cys Phe Leu Val Asn Ile Gly Ile Arg Val Arg Lys Lys
1665                1670                1675                1680

Phe Leu Ile Glu Arg Val Ile Phe Gly Leu Leu Ile Pro Ile Ser Leu
                1685                1690                1695

Leu Ser Ser Lys Asp Phe Thr Ser Cys Leu Phe Leu Ser Leu Phe Phe
            1700                1705                1710

Phe Phe Val Phe Val Phe Val Lys Asn Phe Ser Ser Met Ile His Lys
        1715                1720                1725

Leu Phe Asp Phe
    1730

(2) INFORMATION FOR SEQ ID NO:15:

(i) SEQUENCE CHARACTERISTICS:
        (A) LENGTH: 1724 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Lys Ser Cys Leu Leu His Ala Phe Asn His Gly Leu His Tyr Ser Leu
1               5                   10                  15

Asp Ser Asp Tyr Glu Arg Ser Lys Glu Arg Ala Phe Lys Ile Phe Ser
            20                  25                  30

Lys His Ser Asn Lys Gln Asn Ala Arg Ser Lys Lys Ser Lys Gln Lys
```

-continued

```
                 35                  40                  45
Arg Leu Ser Gly Val Asn Ala Leu Glu Cys Lys Glu Arg Ser Gln Lys
        50                  55                  60
Tyr Glu Asn Gly Phe Leu Asn Ile Thr Ile Cys Leu Val Ser Tyr His
 65                  70                  75                  80
Trp His Val Tyr Ser Pro Leu Thr Leu Thr Lys Thr Leu Ile Lys Ile
                85                  90                  95
Leu Val Leu Lys Ile Trp His Ile Ala Trp Gly Leu Phe Leu Glu Ile
               100                 105                 110
Asn Lys Arg Ser Leu Lys Lys Pro Ser Lys Lys Trp Pro Tyr Ser Met
           115                 120                 125
Thr Ile Met Ile Lys Met Leu Ile Ser Asn Leu Thr Thr Val Gly Val
130                 135                 140
Phe Asn Leu Met Ile Ile Val Ser Met Arg Cys Gly Ala Phe Lys Ile
145                 150                 155                 160
Phe Ser Ala Lys Trp Ala Ile Thr Val Gln Thr Ile Leu Ser Cys Met
               165                 170                 175
Val Met His Gln His Thr Gln Ile His Arg Phe Tyr Arg Tyr Gly
               180                 185                 190
Ile Asn Gly Val Leu Thr Trp Gln Val His Lys Leu Tyr Met Asn His
           195                 200                 205
Leu Leu Gln Ala Ser Tyr Arg Lys Phe Pro Gln Ser Ser Gln His Lys
210                 215                 220
Trp Cys Arg Arg Thr Ile Cys Arg Asn Ser Ser Gly Cys Tyr Asp Ser
225                 230                 235                 240
Ser Asp Tyr Ser Tyr Tyr Cys Trp Val Tyr Ser Ala Asn Asp Arg Tyr
               245                 250                 255
His Asp Pro Ile Gln Ser Lys His Arg Ser Arg Lys His Ala Tyr Glu
           260                 265                 270
Ser Arg Pro Thr Ile Gln Pro Ile Val Ser Arg Phe Arg Ser Lys His
       275                 280                 285
Gly Cys Gly Glu Gln Tyr Leu Lys Tyr Gln Ile Asn Arg Gly Ile Arg
290                 295                 300
Thr Arg Gln His Ala Arg Arg Ala Asn Trp Cys Cys Ser Asp Cys Lys
305                 310                 315                 320
His Phe Ser Glu His His Pro Lys Ser Gln Cys Tyr Ser Leu Cys Asp
               325                 330                 335
Lys Ser Asn Arg Cys Ser Arg Ala Asn Asn Gly Asn Asp Asp Gly Ile
           340                 345                 350
Leu Gly Asn Ile Thr Ser Ala Ala Pro Lys Tyr Ala Leu Ala Leu Gln
       355                 360                 365
Glu Gln Leu Arg Ser Gln Ala Ser Asn Ser Ser Met Asn Asp Thr Pro
370                 375                 380
Ile Pro Leu Tyr Arg Phe Arg Cys Ala Cys Trp Leu Ile Lys Ser Val
385                 390                 395                 400
Phe Gln Leu His Ala Asn Phe Tyr Asp Ala Pro Ala Phe Leu Cys Pro
               405                 410                 415
Leu Phe Met Leu Asn Thr Lys Arg Pro Leu Met Pro Leu Gln Ala Leu
           420                 425                 430
Ile Leu Pro Leu Leu His Ala Leu Leu Gly Thr Arg Phe Leu Leu Phe
       435                 440                 445
Ile Ala Met Leu Lys Lys Gln Lys Phe Glu Asn Thr Ile Asn Leu Lys
450                 455                 460
```

```
Ile Ile Pro Ile Cys Cys Arg Thr Leu Leu Lys Tyr Leu Ile Asn Gln
465                 470                 475                 480

Asp Leu Leu Ala Pro Met Thr Leu Lys Arg Phe Leu Thr Val Arg Tyr
                485                 490                 495

Ile Ile Thr Ile Arg Ile Asn Leu Phe Asn Arg Ile Leu Thr Leu Ile
            500                 505                 510

Thr Ser Lys Thr Ser Leu Arg Gly Lys Lys Ile Ala Thr Gln Lys Gly
        515                 520                 525

Cys Lys Leu Lys Ser Ser Glu Glu Arg Asp Val Lys Cys Phe Leu Ser
    530                 535                 540

Ile Phe Ser Phe Leu Thr Phe Cys Gly Leu Ser Leu Asn Gly Thr Glu
545                 550                 555                 560

Val Val Ile Thr Leu Glu Pro Ala Leu Lys Ala Ile Gln Ala Asp Ala
                565                 570                 575

Gln Ala Lys Gln Lys Thr Ala Gln Ala Glu Leu Lys Ala Ile Glu Ala
            580                 585                 590

Gln Ser Ser Ala Lys Glu Lys Ala Ile Gln Ala Gln Ile Glu Gly Glu
        595                 600                 605

Leu Arg Thr Gln Leu Ala Thr Met Ser Ala Met Leu Lys Gly Ala Asn
    610                 615                 620

Gly Val Ile Asn Gly Val Asn Gly Met Thr Gly Gly Phe Phe Ala Gly
625                 630                 635                 640

Ser Asp Ile Leu Leu Gly Val Met Glu Gly Tyr Ser Ser Gly Ala Cys
                645                 650                 655

Ile Gly Gly Glu Cys Gln Asn Asp Arg Gly Lys Thr Lys Asn Tyr Pro
            660                 665                 670

Asn Arg Asn Pro Lys His Ala Asn Arg Ala Pro Lys Lys Arg Asn Asp
        675                 680                 685

Gln Ala Gln Asn Glu Pro Ala Lys Arg Ser Leu Arg Ser Val Lys Lys
    690                 695                 700

Gln Leu Thr Glu Gly Tyr Pro Lys Asn Thr Asn Gly Asn Phe Ser Ser
705                 710                 715                 720

Ser Arg Lys Phe Phe Gln Arg Ser Ile His Arg Leu Gln Tyr Asp Trp
                725                 730                 735

Tyr Gln Gly Val Arg Asn Leu Lys Arg Phe Asp Met Val Glu Asn Ser
            740                 745                 750

Tyr Ala Lys Ser Asp Pro Tyr Leu Phe Pro Asn Arg Ser Gly Phe Val
        755                 760                 765

Ser Lys Cys His Leu Cys Ala Cys Ser Phe Phe Lys His Gly Arg
    770                 775                 780

Pro Phe Gly Ile Ile Glu Thr Phe Thr Leu Ala Pro Thr Lys Cys Pro
785                 790                 795                 800

Tyr Leu Asp Gly Leu Lys Ile Ser Ala Cys Leu Met Glu Gln Val Ile
                805                 810                 815

Gln Asn Tyr Arg Met Ile Val Ala Leu Ile Gln Asn Lys Leu Ser Asp
            820                 825                 830

Ala Asp Phe Gln Asn Ile Ala Tyr Leu Asn Gly Ile Asn Gly Glu Ile
        835                 840                 845

Lys Thr Leu Lys Gly Ser Val Asp Leu Asn Ala Leu Ile Glu Val Ala
    850                 855                 860

Ile Leu Asn Ala Glu Asn His Leu Asn Tyr Ile Glu Asn Leu Glu Lys
865                 870                 875                 880

Lys Ala Asp Leu Trp Glu Glu Gln Leu Lys Leu Glu Arg Glu Thr Thr
                885                 890                 895
```

```
Ala Arg Asn Ile Ala Ser Ser Lys Val Ile Val Lys Lys His Ser Lys
            900                 905                 910

Ile Pro Tyr Leu Leu Phe Cys Tyr Cys Leu Phe Trp Gln Lys Ile Gln
            915                 920                 925

Ala Val Ser Asn Leu Ile Ala Pro Thr Lys Arg Pro Thr Asn Lys Cys
            930                 935                 940

Leu Lys Thr Met Arg Phe Phe Gln Pro Leu Ala Leu Ala Leu Ile Met
945                 950                 955                 960

Lys Val Lys Lys Met Leu Thr Ser Lys Lys Arg Pro Leu Leu Glu Glu
                965                 970                 975

Ile Arg Tyr Lys Pro Ile Leu Lys Arg Met Ser Tyr Phe Ser Ser Gln
            980                 985                 990

Lys Met Phe Ser Arg Leu Ile Cys Leu Ala Leu Asn Phe Tyr Pro Ile
            995                 1000                1005

Lys Ser Ile Pro Thr Lys Ile Leu Leu Ser Ser Asn Ala Glu Tyr Pro
            1010                1015                1020

Ile Lys Phe Phe Phe Ile Val Lys Gly Ser Lys Ser Ser Lys Lys Asn
1025                1030                1035                1040

Lys Ile Glu Ser Val Lys Leu Pro Arg Arg Ile Arg Ala Thr Leu Glu
                1045                1050                1055

Val Gln Leu Leu Ser Leu Leu His Arg Arg Leu Lys Ala Arg Ile Lys
            1060                1065                1070

Ile Ser Ser Lys Glu Ser Glu Ser Leu Cys Leu Lys Thr Arg Ser Phe
            1075                1080                1085

Ile Ile Arg Ser Trp Thr His Lys Asp Pro Asn Lys Val Ser Asp Asn
            1090                1095                1100

Thr Tyr Lys Lys Gly Asn Gln Val Arg Ser Leu Leu Asn Asp Phe Ser
1105                1110                1115                1120

Glu Thr Ile Gly Tyr Asp Phe Pro Leu Gly Phe Ala Ser Leu Val Val
            1125                1130                1135

Phe Ser Asn Asn Leu Asp Arg Tyr Phe Phe Pro Ala Met Leu Cys Ser
            1140                1145                1150

Ile Leu Met Thr Leu Leu Gly Ser Ser Asp Leu Glu Arg Leu Phe Glu
            1155                1160                1165

Asn Ala Val Ser Phe Ala Ser Phe Ser Phe Val Ser Val Val Pro Asn
            1170                1175                1180

Ser Leu Ala Phe Val Val Ser Trp Leu Phe Ser Cys Ser Ile Ser Phe
1185                1190                1195                1200

Phe Leu Phe Ser Gln Ile Ala His Glu Ala Ile Arg Lys Val Leu Leu
            1205                1210                1215

Leu Leu Leu Leu Arg Val Ser Phe Lys Pro Leu Arg Cys Cys Leu Glu
            1220                1225                1230

Asn Leu Leu Phe Ser Val Ser Ile Ser Ile Phe Ser Asn Lys Gly Ala
            1235                1240                1245

Arg Ile Phe Ser Leu Met Ser Leu Ile Lys His Phe Leu Asn Pro Ser
            1250                1255                1260

Ser Leu Leu Glu Ile Ile His Ser Leu Met Ile Ser Ile Ser Gly
1265                1270                1275                1280

Val Leu His Ser Ser Gly Thr Ser Gly Ala Ala Gly Phe Thr Lys Asp
                1285                1290                1295

Ser Phe Thr Leu Leu Ile Ile Ser Ser Lys Leu Ser Ser Leu Leu Asp
            1300                1305                1310

Leu Val Ser Val Glu Glu Leu Pro Leu Gly Leu Ser Phe Lys Gly Leu
```

```
                  1315                1320                1325
    Ala Leu Ile Ser Phe Asn Ser Cys Asn Pro Leu Cys Leu Ala Ala Phe
        1330                1335                1340
    Phe Thr Glu Glu Leu Phe Phe Phe Ser Asn Ala Ser Ile Phe Phe Ile
    1345                1350                1355                1360
    Cys Ser Ala Leu Ala Leu Ser Phe Arg Asn Phe Ser Leu Lys Ala Leu
                    1365                1370                1375
    Val Ala Asn Ser Phe Ser Ser Phe Val Ile Ser Leu Ser Ser Cys Leu
                1380                1385                1390
    Ser Val Leu Ile Phe Leu Lys Pro Lys Ala Thr Asn Ser Leu Tyr Ser
                1395                1400                1405
    Leu Gly Asn Asn Ala Val Leu Ile Ala Phe Lys Pro Pro Thr Thr Lys
        1410                1415                1420
    Glu Arg Ala Thr Glu Pro Ser Phe Leu Lys Met Leu Phe Lys Ser Val
    1425                1430                1435                1440
    Ser Phe Pro Ile Gln Arg Asp Tyr Ser Trp Gln His Cys Phe Gly Met
                    1445                1450                1455
    Gln Lys Pro Leu Phe Arg Asn Ile Ser Cys Ser Val Leu Phe Ala Leu
                    1460                1465                1470
    Phe Cys Arg Ser Ser Asp Arg Tyr Leu Arg Lys Tyr Cys Ile His Ser
                    1475                1480                1485
    Phe Leu Ile Ile Phe Trp Ile Gly Tyr Gln Asn Ser Cys Leu Lys Pro
        1490                1495                1500
    Thr Asn Thr Ile Phe Val Phe Val Arg Asn Ser Ile Phe Asp Trp Ser
    1505                1510                1515                1520
    Phe Ser Glu Tyr Ser Ile Pro His His Leu His Phe Ser Thr Ser Lys
                    1525                1530                1535
    Lys Pro His Ser Pro Leu Ser Ile Ser His Ser Tyr Gln Ser Pro Cys
                    1540                1545                1550
    Thr Pro Ser Val Pro Ser Lys Ala Cys Pro Phe Glu Gln Tyr Leu Leu
                1555                1560                1565
    Leu Trp Ser Gln Thr Cys Phe Phe Gln Ala Val Ser Asn Asn Leu Tyr
                1570                1575                1580
    Tyr Pro Ile Leu Phe Cys Ser Thr Asp Lys Cys Tyr Trp Asn Ile Leu
    1585                1590                1595                1600
    Gln Ser Leu Ala Cys Lys Ile Lys Leu Ile Gly Ser Leu Phe Cys Phe
                    1605                1610                1615
    Val Leu His Leu Lys Lys Thr His Pro Phe Glu Ala Lys Pro Glu Pro
                1620                1625                1630
    Tyr Leu Trp Arg Phe Phe Lys Tyr Cys Ser Phe Ser Pro Gly Gly Ser
                1635                1640                1645
    Asn Asn Ser Asn Ala Pro Tyr Leu Leu Trp Met Phe Leu Gly Leu Lys
                1650                1655                1660
    His Arg His Lys Gly Glu Glu Val Ser Tyr Arg Glu Gly Tyr Leu Leu
    1665                1670                1675                1680
    Arg Leu Ala Leu Asp Pro His Lys Pro Leu Thr Gln Gly Phe Tyr Leu
                    1685                1690                1695
    Leu Ser Leu Ser Leu Glu Pro Leu Phe Leu Phe Cys Ile Cys Phe Leu
                    1700                1705                1710
    Ser Leu Lys Glu Leu Leu Tyr Asp Pro Ala Leu Phe
                    1715                1720
```

(2) INFORMATION FOR SEQ ID NO:16:

(i) SEQUENCE CHARACTERISTICS:
    (A) LENGTH: 1786 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:16:

Lys Ile Met Pro Met Thr Ser Cys Ile Ser Trp Thr Pro Leu Phe Leu
1               5                   10                  15

Ile Gly Phe Arg Leu Ile Ala Leu Lys Leu Lys Arg Lys Ser Phe Leu
            20                  25                  30

Lys Asn Ile Phe Lys Thr Leu Met Lys Gln Thr Lys Cys Ser Ile Lys
            35                  40                  45

Lys Ile Lys Thr Lys Ile Thr Ile Glu Trp Arg Cys Ala Arg Ile Val
50                  55                  60

Leu Lys Ile Arg Ile Lys Glu Ser Lys Val Lys Arg Ile Phe Ile Lys
65                  70                  75                  80

Leu Asn Tyr Tyr Leu Leu Gly Val Leu Ser Leu Ala Cys Leu Gln Ser
                85                  90                  95

Val Asn Ala Asp Gln Asn Thr Asp Ile Lys Asp Ile Ser Pro Glu Asp
            100                 105                 110

Met Ala Leu Asn Ser Val Gly Leu Val Ser Arg Asp Gln Leu Lys Ile
            115                 120                 125

Glu Ile Pro Lys Glu Thr Leu Glu Gln Lys Val Ala Ile Leu Asn Asp
130                 135                 140

Tyr Asn Asp Lys Asn Val Asn Ile Lys Phe Asp Asp Ile Ser Leu Gly
145                 150                 155                 160

Ser Phe Gln Pro Asn Asp Asn Leu Gly Ile Asn Ala Met Trp Gly Ile
                165                 170                 175

Gln Asn Leu Leu Met Ser Gln Met Met Gly Asp Tyr Gly Pro Asn Asn
            180                 185                 190

Pro Phe Met Tyr Gly Tyr Ala Pro Thr Tyr Ser Asp Ser Ser Phe Leu
            195                 200                 205

Pro Pro Ile Leu Gly Tyr Leu Gly Gly Val Asn Met Ala Gly Thr Gln
210                 215                 220

Ala Ile Tyr Glu Ser Ser Ser Ala Gly Phe Leu Ser Glu Val Ser Ser
225                 230                 235                 240

Ile Ile Ser Thr Gln Val Val Ser Gln Asp His Leu Gln Glu Arg Val
                245                 250                 255

Leu Gln Gln Arg Leu Phe Leu Leu Leu Gly Leu Leu Ile Arg Lys
            260                 265                 270

Pro Leu Ser Pro Asn Thr Ile Lys Ala Ser Leu Lys Pro Ala Cys Leu
            275                 280                 285

Lys Pro Leu Thr Asn Asn Thr Asn Cys Phe Lys Val Leu Thr Ile
290                 295                 300

Lys Ala Trp Leu Trp Gly Thr Ile Ser Ile Leu Ala Asn Gln Gly Asn
305                 310                 315                 320

Leu Thr His Lys Ala Thr Arg Lys Ala Arg Lys Leu Val Leu Leu Ile
                325                 330                 335

Val Arg Leu Gln Ala Phe Arg Val Thr Pro Pro Leu Lys Ile Pro Val
            340                 345                 350

Leu Leu Lys Leu Met Arg Gln Ile Lys Ser Leu Phe Leu Ala Cys Gln
            355                 360                 365

Gln Arg Leu Lys Arg Tyr Ile Arg Gln Tyr Tyr Lys Cys Ser Thr Lys

```
              370             375             380
    Ile Arg Pro Ser Ser Thr Arg Ala Thr Ala Phe Ser Ser Lys Gln Gln
    385                 390                 395                 400

Leu Asn Glu Tyr Thr Asp Ser Leu Ile Ala Val Pro Leu Val Arg Leu
                        405                 410                 415

Leu Ala His Gln Lys Cys Phe Ser Val Ala Cys Lys Phe Leu Arg Pro
                420                 425                 430

Met Ser Val Ser Met Pro Thr Val Tyr Ala Lys Tyr Gln Ala Leu Ala
                435                 440                 445

Thr Asn Ala Leu Thr Ser Gly Val Asn Pro Met Thr Thr Pro Ala Cys
                450                 455                 460

Pro Ile Gly Asp Lys Val Leu Ala Val Tyr Cys Tyr Ala Glu Lys Val
    465                 470                 475                 480

Ala Glu Ile Leu Arg Glu Tyr Tyr Ile Glu Phe Val Lys Asn Asn Thr
                        485                 490                 495

Asn Leu Leu Gln Asn Ala Ser Gln Met Ile Leu Asn Gln Ser Gly Leu
                        500                 505                 510

Ala Thr Ser Thr Tyr Asp Thr Gln Ala Ile Ser Asn Ile Ser Ser Leu
                    515                 520                 525

Tyr Asn Tyr Asn Ile Val Ala Asn Lys Ser Phe Leu Lys Ser His Leu
                    530                 535                 540

Thr Tyr Leu Asp Tyr Ile Lys Asp Lys Leu Lys Gly Gln Lys Asp Ser
    545                 550                 555                 560

Tyr Leu Thr Glu Arg Val Gln Thr Lys Ile Ile Val Lys Gly Lys Arg
                        565                 570                 575

Cys Glu Met Phe Phe Lys His Ile Phe Phe Leu Asp Phe Leu Trp Phe
                    580                 585                 590

Val Ser Glu Trp Tyr Arg Gly Ser Asn Asn Ala Thr Cys Leu Lys Ser
                    595                 600                 605

His Ser Gly Arg Arg Thr Ser Gln Thr Lys Asn Arg Ser Ser Arg Ile
                    610                 615                 620

Lys Ser His Arg Ser Ser Ile Cys Gln Arg Lys Ser His Ser Ser Ala
    625                 630                 635                 640

Asn Arg Gly Arg Ile Glu Asp Ser Ala Cys Asn His Glu Arg Tyr Val
                        645                 650                 655

Lys Arg Gly Trp Arg Tyr Trp Cys Gln Trp His Asp Arg Gly Val Phe
                    660                 665                 670

Cys Arg Phe Arg His Leu Ala Trp Arg His Gly Arg Val Phe Lys Arg
                    675                 680                 685

Arg Leu Val His Trp Gly Gly Met Ser Lys Ser Trp Lys Asn Lys Lys
                    690                 695                 700

Leu Ile Pro Lys Gln Lys Ser Lys Thr Cys Lys Ser Arg Ser Lys Lys
    705                 710                 715                 720

Ile Thr Lys Ser Ser Ser Lys Thr Ser Lys Thr Leu Ser Lys Arg Lys
                        725                 730                 735

Thr Ala Leu Asn Arg Gly Leu Pro Lys His Lys Trp Lys Phe Leu Lys
                    740                 745                 750

Leu Glu Val Leu Leu Thr Thr Leu Asn Thr Ser Leu Thr Ile Arg Leu
                    755                 760                 765

Val Ser Arg Arg Leu Lys Lys Pro Lys Val Leu Arg His Gly Lys Gln
                    770                 775                 780

Leu Cys Lys Lys Arg Pro Leu Leu Ile Ile Pro Gln Val Arg Leu
    785                 790                 795                 800
```

```
Cys Phe Lys Val Pro Ser Met Arg Leu Leu Leu Val Phe Phe Gln Ala
                805                 810                 815

Trp Ala Thr Ile Trp Asn His Asn Ile His Ser Ser Ala His Lys Met
                820                 825                 830

Pro Leu Ser Trp Ala Lys Asn Phe Ser Met Pro Tyr Gly Thr Gly Tyr
                835                 840                 845

Ser Glu Leu Gln Asn Asp Cys Ser Pro Tyr Ser Lys Thr Glu Cys Arg
    850                 855                 860

Phe Ser Lys Tyr Arg Leu Phe Glu Trp Asp Gln Trp Arg Asn Gln Asn
865                 870                 875                 880

Leu Lys Arg Ile Ser Arg Phe Glu Cys Ala His Arg Ser Cys Asp Leu
                885                 890                 895

Lys Arg Arg Lys Ser Phe Lys Leu Tyr Arg Glu Ser Lys Lys Ser Arg
                900                 905                 910

Pro Leu Gly Arg Thr Thr Glu Ile Arg Lys Arg Asn Asp Ser Lys Lys
                915                 920                 925

His Cys Leu Ser Tyr Cys Gln Met Lys Thr Leu Val Lys Asn Thr Ile
    930                 935                 940

Ser Ser Phe Leu Leu Leu Ser Val Leu Met Ala Glu Asp Ile Thr Ser
945                 950                 955                 960

Gly Leu Lys Gln Leu Asp Ser Thr Tyr Gln Glu Thr Asn Gln Gln Val
                965                 970                 975

Leu Lys Asn Leu Asp Glu Ile Phe Ser Thr Thr Ser Pro Ser Ala Asn
                980                 985                 990

Asn Glu Ile Gly Gln Glu Asp Ala Leu Asn Ile Lys Lys Ala Ala Ile
    995                 1000                1005

Ala Leu Arg Gly Asp Leu Ala Leu Leu Lys Ala Asn Phe Glu Ala Asn
    1010                1015                1020

Glu Leu Phe Phe Ile Ser Glu Asp Val Ile Phe Lys Thr Tyr Met Ser
1025                1030                1035                1040

Ser Pro Glu Leu Leu Leu Thr Tyr Met Lys Ile Asn Pro Leu Asp Gln
                1045                1050                1055

Asn Thr Ala Glu Gln Gln Cys Gly Ile Ser Asp Lys Val Leu Val Leu
                1060                1065                1070

Tyr Cys Glu Gly Lys Leu Lys Ile Glu Gln Glu Lys Gln Asn Ile Arg
    1075                1080                1085

Glu Arg Leu Glu Thr Ser Leu Lys Ala Tyr Gln Ser Asn Ile Gly Gly
    1090                1095                1100

Thr Ala Ser Leu Ile Thr Ala Ser Gln Thr Leu Val Glu Ser Leu Lys
1105                1110                1115                1120

Asn Lys Asn Phe Ile Lys Gly Ile Arg Lys Leu Met Leu Ala Gln Asn
                1125                1130                1135

Lys Val Phe Leu Asn Tyr Leu Glu Glu Leu Asp Ala Leu Glu Arg Ser
                1140                1145                1150

Leu Glu Gln Ser Lys Arg Gln Tyr Leu Gln Glu Arg Gln Ser Ser Lys
                1155                1160                1165

Ile Ile Val Lys Phe Phe Asp Asp Arg Leu Phe Leu Thr Phe Gly Ile
                1170                1175                1180

Cys Phe Ser Ser Cys Phe Leu Ile Phe Gly Ser Leu Phe Phe Ser Met
1185                1190                1195                1200

Ser Asp Ala Leu Phe Tyr Leu Ile Asn Asp Ala Ile Gly Gln Phe Gly
                1205                1210                1215

Phe Arg Ala Ile Val Glu Cys Cys Ile Phe Cys Phe Ile Phe Phe Cys
                1220                1225                1230
```

```
Ile Ser Ser Ala Lys Leu Ala Cys Ile Cys Ser Ile Leu Val Val Ile
        1235                1240                1245

Phe Leu Leu His Phe Phe Ser Leu Leu Thr Asn Ser Ala Arg Ser
        1250                1255                1260

Tyr Lys Lys Gly Ser Ile Val Ala Val Ile Lys Ser Glu Phe Thr Thr
1265                1270                1275                1280

Val Leu Ser Arg Lys Leu Val Ile Phe Cys Leu Tyr Phe Leu Asn Phe
                1285                1290                1295

Phe Gly Gly Lys Asn Phe Leu Ile Leu Asp Val Phe Asp Gln Thr Leu
            1300                1305                1310

Ser Pro Ile Ile Ile Val Ala Asn Asn Thr Leu Ile Asp Asn Asp Phe
            1315                1320                1325

Asn Phe Arg Arg Ser Pro Leu Ile Arg His Lys Arg Ser Arg Phe
            1330                1335                1340

His Lys Arg Phe Ile His Leu Ile Asp His Leu Ile Lys Val Ile Ile
1345                1350                1355                1360

Phe Ile Arg Phe Gly Phe Ser Gly Arg Ile Ala Ile Arg Val Val Ile
                1365                1370                1375

Gln Arg Val Ser Val Asn Phe Val Phe Leu Ser Phe Val Leu Ser Arg
            1380                1385                1390

Phe Phe Leu Asn Arg Arg Val Val Leu Phe Phe Lys Arg Phe Asn Ile
        1395                1400                1405

Leu Leu Asn Leu Leu Cys Ser Arg Pro Ile Ile Ser Phe Phe Ser Gln
        1410                1415                1420

Ser Val Ser Gly Glu Phe Phe Phe Leu Phe Cys Asn Phe Phe Val Ile
1425                1430                1435                1440

Met Ser Leu Ile Glu Cys Phe Asp Phe Phe Lys Ala Gln Ser His Phe
            1445                1450                1455

Phe Val Phe Thr Arg Gln Cys Cys Ile Asp Ser Val Ala Pro Ile Asn
            1460                1465                1470

Asn Arg Ile Lys Ser Asp Arg Thr Phe Phe Glu Asp Ala Phe Gln Glu
        1475                1480                1485

Cys Leu Leu Ser Tyr Ser Lys Gly Leu Phe Leu Ala Thr Leu Phe Arg
        1490                1495                1500

Tyr Ala Glu Thr Thr Val Leu Lys Lys Leu Asn Ile Leu Cys Ser Phe
1505                1510                1515                1520

Cys Ile Val Val Leu Ser Leu Ile Ile Gly Ser Leu Ser Thr Lys Ile
                1525                1530                1535

Leu Tyr Ser Leu Val Phe Phe Asn Ile Asp Phe Leu Asp Trp Val Ser
            1540                1545                1550

Lys Leu Lys Leu Ser Lys Thr Asn Lys His Asn Phe Cys Phe Cys Ala
        1555                1560                1565

Lys Leu Asn Phe Leu Val Lys Phe Leu Val Arg Val Phe Asn Ser Thr
        1570                1575                1580

Ser Ser Leu Thr Phe Phe Asn Lys Leu Glu Lys Ala Ser Pro Phe Lys
1585                1590                1595                1600

Tyr Phe Ser Leu Ile Leu Ser Ile Ala Met Leu Asn Ala Lys Arg Ser
                1605                1610                1615

Glu Leu Lys Ile Ser Val Leu Val Ala Phe Ala Ile Ser Phe Ala Leu
            1620                1625                1630

Glu Ser Asn Leu Phe Leu Ser Ser Cys Lys Ser Ile Leu Ser Asn Ser
            1635                1640                1645

Phe Leu Leu Asn Arg Leu Glu Met Leu Leu Glu Tyr Ser Ser Ile Ala
```

|      | 1650 |      |      |      | 1655 |      |      |      | 1660 |      |      |
|------|------|------|------|------|------|------|------|------|------|------|------|

Cys Leu Asp Lys Ala Asn Arg Leu Ala Phe Leu Phe Cys Ser Ser Ser
1665             1670            1675            1680

Lys Glu Asn Thr Pro Ile Ser Lys Ala Ala Leu Ser Leu Val Val Ala
         1685            1690            1695

Val Val Phe Leu Lys Ile Leu Leu Val Phe Thr Trp Gly Leu Lys Arg
        1700            1705            1710

Ser Leu Ser Ser Leu Val Asn Val Ser Trp Phe Lys Thr Ala Gly Leu
         1715           1720            1725

Gly Arg Ser Phe Leu Arg Gly Leu Ser Phe Lys Ala Cys Ser Arg Ser
        1730            1735            1740

Pro Ala Phe Asp Leu Ala Val Arg Ile Leu Pro Leu Val Ser Phe Ser
1745            1750            1755            1760

Arg Ala Ser Phe Ser Phe Leu Tyr Leu Phe Ser Lys Ser Glu Arg Thr
        1765            1770            1775

Leu Ala Leu Ser Ile Ser Ser Leu Ile Phe
        1780            1785

(2) INFORMATION FOR SEQ ID NO:17:

(i) SEQUENCE CHARACTERISTICS:
        (A) LENGTH: 1529 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
AGGCAAAAAA CATGAAAACA TCACTAAATT CACTTGTCCT CATTGCAATA TCACACACCA      60

CAGAGATTAC AATGCGAGCG TCAATATTAG AAACTACGCT TTAGGCATGC TAGATGACAG     120

GCATAAAATA AAGATAGATA AAAGTAGGGT AGGGATTATC CGAACTGATT ACGCTCATTA     180

CACTGATGAG CGCATCAAAG CTTGTGGAGC TTCCTCTAAT GGGGTTATTT CTAAATATGG     240

CAACATATTG GATCTAGCTA GTTATGGAGC GATGAAGCAA GAAAAAGCCC AATCGCTTTA     300

GCGTTGGTAA TTCACAAAAA GCAAGATCGG TTGTAAAAAT GCGTTACAAC TAAAATAAAG     360

GGTCAAGATA ACTCATTTTC AAAAAGGAGT CTTAAGTAAT AAAATCATAA TGTTCAGCTA     420

GTAATCTATT GCCTCGTTGA TCAAACAAAG CTCTGCGTGA AGATGAAAA AATTTCACCT      480

TTAGATAGTT AATACACCAC TACAGTCTTA CTTGAGAGAC ACTCATTTTA TTAGCGGTTT     540

TGTCTGATTT GCTGCTACCA AAACCATTAC CAACCAAAGC AGATCCCATG TTTTTGATAC     600

TATCGAATCC ATTCTTCAGC ACTTCTGCCA TAAAATTCTT GATATTGTCC ATAGGCAAGT     660

TAAATTTTTT CCCTAATGCT TCATTAAGTC CCATCATTAA CATCAGAAAG AACAAAAAAT     720

TTAATATCAT AGAAAACAAA TCACTGGATA AACCTGTAAA AAGATTTGTT CCGCCACCCA     780

ACAAAGAAGC TAAAATTTTT CCCATGATCA GTCCTTTTAT TTTTGGTTGT GTAAGTTCTT     840

GCTTGTTCGG ATCTCTAATG CGTGTTTTAG TAGGAAGCAT TTCACAATAG CATACCTAAA     900

GCTACTAAGA AAATTCTTGA ATCTATTGGT AAGATTACTC ATGAAATCAA GCGATAAGTA     960

GCCACCAATC GCAAACAAAT CAAATATTTT GCCACCAAAC AAGCCATATC CTTTTTGTTT    1020

TTATCTCCTA ATTATAGCAA ATTTTTATCA ATATTAATTT GGAAAACCAC CACCATATCA    1080

AAAACAAATT ACTAACACAC TAGATGCAGA ATTATTTTTA AAAACGCTC ACTTAAATTT     1140

AAAATCATGG GGTTTTAGGA TTTGAATACC AAAAATAGAT TGGTTTTTTC AAATAAGCTA    1200

GCTTTGTGTA TGCGCTTAAA AAGATTTTAG TTTTTAGTCA GTAAGGTTTT ATGCTAATGT    1260
```

-continued

```
TTGGAAATAA AGAAATTTCT CTAAATCAAG TCTTGAGAAA TTTTTGAACG AATCATAAGA    1320

ACCAATTTTG CCATTGAGTC ATAAGTATGA TTAGCTTCAT TGTGAATTTT GCGTGGCTTA    1380

AGAGATAGTA TTTGCTTATT ATGCTGAGAG AAACGAGTAG TAAAAGATAA GTAGTGTAAT    1440

AAAAAAAGCT AGGTTTTATT ATAAGAGCGA ATAAGAATAA TATTGGATAA ACTAAAATCA    1500

CCCCTGCCCC ATAAGAAAAA AGCCCTATT                                      1529
```

(2) INFORMATION FOR SEQ ID NO:18:

(i) SEQUENCE CHARACTERISTICS:
        (A) LENGTH: 464 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
Arg Gln Lys Thr Lys His His Ile His Leu Ser Ser Leu Gln Tyr His
 1               5                  10                  15

Thr Pro Gln Arg Leu Gln Cys Glu Arg Gln Tyr Lys Leu Arg Phe Arg
            20                  25                  30

His Ala Arg Gln Ala Asn Lys Asp Arg Lys Gly Arg Asp Tyr Pro Asn
        35                  40                  45

Leu Arg Ser Leu His Ala His Gln Ser Leu Trp Ser Phe Leu Trp Gly
    50                  55                  60

Tyr Phe Ile Trp Gln His Ile Gly Ser Ser Leu Trp Ser Asp Glu Ala
65                  70                  75                  80

Arg Lys Ser Pro Ile Ala Leu Ala Leu Val Ile His Lys Lys Gln Asp
                85                  90                  95

Arg Leu Lys Cys Val Thr Thr Lys Ile Lys Gly Gln Asp Asn Ser Phe
            100                 105                 110

Ser Lys Arg Ser Leu Lys Asn His Asn Val Gln Leu Val Ile Tyr Cys
        115                 120                 125

Leu Val Asp Gln Thr Lys Leu Cys Val Lys Asp Glu Lys Ile Ser Pro
    130                 135                 140

Leu Asp Ser Tyr Thr Thr Thr Val Leu Leu Glu Arg His Ser Phe Tyr
145                 150                 155                 160

Arg Phe Cys Leu Ile Cys Cys Tyr Gln Asn His Tyr Gln Pro Lys Gln
                165                 170                 175

Ile Pro Cys Phe Tyr Tyr Arg Ile His Ser Ser Ala Leu Leu Pro Asn
            180                 185                 190

Ser Tyr Cys Pro Ala Ser Ile Phe Ser Leu Met Leu His Val Pro Ser
        195                 200                 205

Leu Thr Ser Glu Arg Thr Lys Asn Leu Ile Ser Lys Thr Asn His Trp
    210                 215                 220

Ile Asn Leu Lys Asp Leu Phe Arg His Pro Thr Lys Leu Lys Phe
225                 230                 235                 240

Phe Pro Ser Val Leu Leu Phe Leu Val Val Val Leu Ala Cys Ser Asp
                245                 250                 255

Leu Cys Val Phe Glu Ala Phe His Asn Ser Ile Pro Lys Ala Thr Lys
            260                 265                 270

Lys Ile Leu Glu Ser Ile Gly Lys Ile Thr His Glu Ile Lys Arg Val
        275                 280                 285

Ala Thr Asn Arg Lys Gln Ile Lys Tyr Phe Ala Thr Lys Gln Ala Ile
    290                 295                 300
```

```
Ser Phe Leu Phe Leu Ser Pro Asn Tyr Ser Lys Phe Leu Ser Ile Leu
305                 310                 315                 320

Ile Trp Lys Thr Thr Thr Ile Ser Lys Thr Asn Tyr His Thr Arg Cys
            325                 330                 335

Arg Ile Ile Phe Lys Lys Arg Ser Leu Lys Phe Lys Ile Met Gly Phe
                340                 345                 350

Asp Leu Asn Thr Lys Asn Arg Leu Val Phe Ser Asn Lys Leu Ala Leu
            355                 360                 365

Cys Met Arg Leu Lys Arg Phe Phe Leu Val Ser Lys Val Leu Cys Cys
        370                 375                 380

Leu Glu Ile Lys Lys Phe Leu Ile Lys Ser Glu Ile Phe Glu Arg Ile
385                 390                 395                 400

Ile Arg Thr Asn Phe Ala Ile Glu Ser Val Leu Ala Ser Leu Ile Leu
                405                 410                 415

Arg Gly Leu Arg Asp Ser Ile Cys Leu Leu Cys Glu Lys Arg Val Val
            420                 425                 430

Lys Asp Lys Cys Asn Lys Lys Ser Val Leu Leu Glu Arg Ile Arg Ile
            435                 440                 445

Ile Leu Asp Lys Leu Lys Ser Pro Leu Pro His Lys Lys Lys Ala Leu
450                 455                 460
```

(2) INFORMATION FOR SEQ ID NO:19:

(i) SEQUENCE CHARACTERISTICS:
        (A) LENGTH: 481 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Gly Lys Lys His Glu Asn Ile Thr Lys Phe Thr Cys Pro His Cys Asn
1               5                   10                  15

Ile Thr His His Arg Asp Tyr Asn Ala Ser Val Asn Ile Arg Asn Tyr
            20                  25                  30

Ala Leu Gly Met Leu Asp Asp Arg His Lys Ile Lys Ile Asp Lys Ser
        35                  40                  45

Arg Val Gly Ile Ile Arg Thr Asp Tyr Ala His Tyr Thr Asp Glu Arg
    50                  55                  60

Ile Lys Ala Cys Gly Ala Ser Ser Asn Gly Val Ile Ser Lys Tyr Gly
65                  70                  75                  80

Asn Ile Leu Asp Leu Ala Ser Tyr Gly Ala Met Lys Gln Glu Lys Ala
            85                  90                  95

Gln Ser Leu Arg Trp Phe Thr Lys Ser Lys Ile Gly Cys Lys Asn Ala
        100                 105                 110

Leu Gln Leu Lys Arg Val Lys Ile Thr His Phe Gln Lys Gly Val Leu
    115                 120                 125

Ser Asn Lys Ile Ile Met Phe Ser Ser Ile Ala Ser Leu Ile Lys Gln
130                 135                 140

Ser Ser Ala Lys Met Lys Lys Phe His Leu Ile Val Asn Thr Pro Leu
145                 150                 155                 160

Gln Ser Tyr Leu Arg Asp Thr His Phe Ile Ser Gly Phe Val Phe Ala
            165                 170                 175

Ala Thr Lys Thr Ile Thr Asn Gln Ser Arg Ser His Val Phe Asp Thr
        180                 185                 190
```

```
Ile Glu Ser Ile Leu Gln His Phe Cys His Lys Ile Leu Asp Ile Val
            195                 200                 205

His Arg Gln Val Lys Phe Phe Pro Cys Phe Ile Lys Ser His His His
210                 215                 220

Gln Lys Glu Gln Lys Ile Tyr His Arg Lys Gln Ile Thr Gly Thr Cys
225                 230                 235                 240

Lys Lys Ile Cys Ser Ala Thr Gln Gln Arg Ser Asn Phe Ser His Asp
            245                 250                 255

Gln Ser Phe Tyr Phe Trp Leu Cys Lys Phe Leu Val Arg Ile Ser
            260                 265                 270

Asn Ala Cys Phe Ser Arg Lys His Phe Thr Ile Ala Tyr Leu Lys Leu
            275                 280                 285

Leu Arg Lys Phe Leu Asn Leu Leu Val Arg Leu Leu Met Lys Ser Ser
            290                 295                 300

Asp Lys Pro Pro Ile Ala Asn Lys Ser Asn Ile Leu Pro Pro Asn Lys
305                 310                 315                 320

Pro Tyr Pro Phe Cys Phe Tyr Leu Leu Ile Ile Ala Asn Phe Tyr Gln
            325                 330                 335

Tyr Phe Gly Lys Pro Pro Tyr Gln Lys Gln Ile Thr Asn Thr Leu
            340                 345                 350

Asp Ala Glu Leu Phe Leu Lys Asn Ala His Leu Asn Leu Lys Ser Trp
            355                 360                 365

Gly Phe Arg Ile Ile Pro Lys Ile Asp Trp Phe Phe Gln Ile Ser Leu
370                 375                 380

Cys Val Cys Ala Lys Asp Phe Ser Phe Ser Val Arg Phe Tyr Ala Asn
385                 390                 395                 400

Val Trp Lys Arg Asn Phe Ser Lys Ser Ser Leu Glu Lys Phe Leu Asn
            405                 410                 415

Glu Ser Glu Pro Ile Leu Pro Leu Ser His Lys Tyr Asp Leu His Cys
            420                 425                 430

Glu Phe Cys Val Ala Glu Ile Val Phe Ala Tyr Tyr Ala Glu Arg Asn
            435                 440                 445

Glu Lys Ile Ser Ser Val Ile Lys Lys Ala Arg Phe Tyr Tyr Lys Ser
            450                 455                 460

Glu Glu Tyr Trp Ile Asn Asn His Pro Cys Pro Ile Arg Lys Lys Pro
465                 470                 475                 480

Tyr (2) INFORMATION FOR SEQ ID NO:20:

(i) SEQUENCE CHARACTERISTICS:
        (A) LENGTH: 471 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

Ala Lys Asn Met Lys Thr Ser Leu Asn Ser Leu Val Leu Ile Ala Ile
1               5                  10                  15

Ser His Thr Thr Glu Ile Thr Met Arg Ala Ser Ile Leu Glu Thr Thr
            20                  25                  30

Leu Ala Cys Met Thr Gly Ile Lys Arg Ile Lys Val Gly Gly Leu Ser
            35                  40                  45

Glu Leu Ile Thr Leu Ile Thr Leu Met Ser Ala Ser Lys Leu Val Glu
50                  55                  60
```

```
Leu Pro Leu Met Gly Leu Phe Leu Asn Met Ala Thr Tyr Trp Ile Leu
 65                  70                  75                  80

Val Met Glu Arg Ser Lys Lys Pro Asn Arg Phe Ser Val Gly Asn
                 85                  90                  95

Ser Gln Lys Ala Arg Ser Val Val Lys Met Arg Tyr Asn Asn Lys Gly
                100                 105                 110

Ser Arg Leu Ile Phe Lys Lys Glu Ser Val Ile Lys Ser Cys Ser Ala
                115                 120                 125

Ser Asn Leu Leu Pro Arg Ser Asn Lys Ala Leu Arg Glu Arg Lys Asn
            130                 135                 140

Phe Thr Phe Arg Leu Ile His His Tyr Ser Leu Thr Glu Thr Leu Ile
145                 150                 155                 160

Leu Leu Ala Val Leu Ser Asp Leu Leu Leu Pro Lys Pro Leu Pro Thr
                165                 170                 175

Lys Ala Asp Pro Met Phe Leu Ile Leu Ser Asn Pro Phe Phe Ser Thr
                180                 185                 190

Ser Ala Ile Lys Phe Leu Ile Leu Ser Ile Gly Lys Leu Asn Phe Phe
                195                 200                 205

Pro Asn Ala Ser Leu Ser Pro Ile Ile Asn Ile Arg Lys Asn Lys Lys
            210                 215                 220

Phe Asn Ile Ile Glu Asn Lys Ser Leu Asp Pro Val Lys Arg Phe
225                 230                 235                 240

Val Pro Pro Asn Lys Glu Ala Lys Ile Phe Pro Met Ile Ser Pro
                245                 250                 255

Phe Ile Phe Gly Cys Val Ser Ser Cys Leu Phe Gly Ser Leu Met Arg
                260                 265                 270

Val Leu Val Gly Ser Ile Ser Gln His Thr Ser Tyr Glu Asn Ser Ile
                275                 280                 285

Tyr Trp Asp Tyr Ser Asn Gln Ala Ile Ser Ser His Gln Ser Gln Thr
            290                 295                 300

Asn Gln Ile Phe Cys His Gln Thr Ser His Ile Leu Phe Val Phe Ile
305                 310                 315                 320

Ser Leu Gln Ile Phe Ile Asn Ile Asn Leu Glu Asn His His His Ile
                325                 330                 335

Lys Asn Lys Leu Leu Thr His Met Gln Asn Tyr Phe Lys Thr Leu Thr
                340                 345                 350

Ile Asn His Gly Val Leu Gly Phe Glu Tyr Gln Lys Ile Gly Phe Phe
                355                 360                 365

Lys Ala Ser Phe Val Tyr Ala Leu Lys Lys Ile Leu Val Phe Ser Gln
                370                 375                 380

Gly Phe Met Leu Met Phe Gly Asn Lys Glu Ile Ser Leu Asn Gln Val
385                 390                 395                 400

Leu Arg Asn Phe Thr Asn His Lys Asn Gln Phe Cys His Val Ile Ser
                405                 410                 415

Met Ile Ser Phe Ile Val Asn Phe Ala Trp Leu Lys Arg Tyr Leu Leu
                420                 425                 430

Ile Met Leu Arg Glu Thr Ser Ser Lys Arg Val Val Lys Lys Leu Gly
                435                 440                 445

Phe Ile Ile Arg Ala Asn Lys Asn Asn Ile Gly Thr Lys Ile Thr Pro
                450                 455                 460

Ala Pro Glu Lys Ser Pro Ile
465                 470
```

(2) INFORMATION FOR SEQ ID NO:21:

(i) SEQUENCE CHARACTERISTICS:
        (A) LENGTH: 1529 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
AATAGGGCTT TTTTCTTATG GGGCAGGGGT GATTTTAGTT TATCCAATAT TATTCTTATT      60
CGCTCTTATA ATAAAACCTA GCTTTTTTTA TTACACTACT TATCTTTTAC TACTCGTTTC     120
TCTCAGCATA ATAAGCAAAT ACTATCTCTT AAGCCACGCA AAATTCACAA TGAAGCTAAT     180
CATACTTATG ACTCAATGGC AAAATTGGTT CTTATGATTC GTTCAAAAAT TTCTCAAGAC     240
TTGATTTAGA GAAATTTCTT TATTTCCAAA CATTAGCATA AAACCTTACT GACTAAAAAC     300
TAAAATCTTT TTAAGCGCAT ACACAAAGCT AGCTTATTTG AAAAAACCAA TCTATTTTTG     360
GTATTCAAAT CCTAAAACCC CATGATTTTA AATTTAAGTG AGCGTTTTTT AAAAATAATT     420
CTGCATCTAG TGTGTTAGTA ATTTGTTTTT GATATGGTGG TGGTTTTCCA AATTAATATT     480
GATAAAAATT TGCTATAATT AGGAGATAAA AACAAAAAGG ATATGGCTTG TTTGGTGGCA     540
AAATATTTGA TTTGTTTGCG ATTGGTGGCT ACTTATCGCT TGATTTCATG AGTAATCTTA     600
CCAATAGATT CAAGAATTTT CTTAGTAGCT TTAGGTATGC TATTGTGAAA TGCTTCCTAC     660
TAAAACACGC ATTAGAGATC CGAACAAGCA AGAACTTACA CAACCAAAAA TAAAAGGACT     720
GATCATGGGA AAAATTTTAG CTTCTTTGTT GGGTGGCGGA ACAAATCTTT TTACAGGTTT     780
ATCCAGTGAT TTGTTTTCTA TGATATTAAA TTTTTTGTTC TTTCTGATGT TAATGATGGG     840
ACTTAATGAA GCATTAGGGA AAAAATTTAA CTTGCCTATG GACAATATCA AGAATTTTAT     900
GGCAGAAGTG CTGAAGAATG GATTCGATAG TATCAAAAAC ATGGGATCTG CTTTGGTTGG     960
TAATGGTTTT GGTAGCAGCA AATCAGACAA AACCGCTAAT AAAATGAGTG TCTCTCAAGT    1020
AAGACTGTAG TGGTGTATTA ACTATCTAAA GGTGAAATTT TTTCATCTTT CACGCAGAGC    1080
TTTGTTTGAT CAACGAGGCA ATAGATTACT AGCTGAACAT TATGATTTTA TTACTTAAGA    1140
CTCCTTTTTG AAAATGAGTT ATCTTGACCC TTTATTTTAG TTGTAACGCA TTTTTACAAC    1200
CGATCTTGCT TTTTGTGAAT TACCAACGCT AAAGCGATTG GGCTTTTTCT TGCTTCATCG    1260
CTCCATAACT AGCTAGATCC AATATGTTGC CATATTTAGA AATAACCCCA TTAGAGGAAG    1320
CTCCACAAGC TTTGATGCGC TCATCAGTGT AATGAGCGTA ATCAGTTCGG ATAATCCCTA    1380
CCCTACTTTT ATCTATCTTT ATTTTATGCC TGTCATCTAG CATGCCTAAA GCGTAGTTTC    1440
TAATATTGAC GCTCGCATTG TAATCTCTGT GGTGTGTGAT ATTGCAATGA GGACAAGTGA    1500
ATTTAGTGAT GTTTTCATGT TTTTTGCCT                                      1529
```

(2) INFORMATION FOR SEQ ID NO:22:

(i) SEQUENCE CHARACTERISTICS:
        (A) LENGTH: 485 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

```
Ile Gly Leu Phe Ser Tyr Gly Ala Gly Val Ile Leu Val Tyr Pro Ile
 1               5                  10                  15
```

```
Leu Phe Leu Phe Ala Leu Ile Ile Lys Pro Ser Phe Phe Tyr Tyr Thr
                20                  25                  30

Thr Tyr Leu Leu Leu Leu Val Ser Leu Ser Ile Ile Ser Lys Tyr Tyr
            35                  40                  45

Leu Leu Ser His Ala Lys Phe Thr Met Lys Leu Ile Ile Leu Met Thr
        50                  55                  60

Gln Trp Gln Asn Trp Phe Leu Phe Val Gln Lys Phe Leu Lys Thr Phe
 65                  70                  75                  80

Arg Glu Ile Ser Leu Phe Pro Asn Ile Ser Ile Lys Pro Tyr Leu Lys
                85                  90                  95

Thr Lys Ile Phe Leu Ser Ala Tyr Thr Lys Leu Ala Tyr Leu Lys Lys
            100                 105                 110

Pro Ile Tyr Phe Trp Tyr Ser Asn Pro Lys Thr Pro Phe Ile Val Ser
        115                 120                 125

Val Phe Lys Phe Cys Ile Cys Val Ser Asn Leu Phe Leu Ile Trp Trp
130                 135                 140

Trp Phe Ser Lys Leu Ile Leu Ile Lys Ile Cys Tyr Asn Glu Ile Lys
145                 150                 155                 160

Thr Lys Arg Ile Trp Leu Val Trp Gln Asn Ile Phe Val Cys Asp
                165                 170                 175

Trp Trp Leu Leu Ile Ala Phe His Glu Ser Tyr Gln Ile Gln Glu Phe
            180                 185                 190

Ser Leu Val Cys Tyr Cys Glu Met Leu Pro Thr Lys Thr Arg Ile Arg
        195                 200                 205

Asp Pro Asn Lys Gln Glu Leu Thr Gln Pro Lys Ile Lys Gly Leu Ile
        210                 215                 220

Met Gly Lys Ile Leu Ala Ser Leu Leu Gly Gly Gly Thr Asn Leu Phe
225                 230                 235                 240

Thr Gly Leu Ser Ser Asp Leu Phe Ser Met Ile Leu Asn Phe Leu Phe
                245                 250                 255

Phe Leu Met Leu Met Met Gly Leu Asn Glu Ala Leu Gly Lys Lys Phe
            260                 265                 270

Asn Leu Pro Met Asp Asn Ile Lys Asn Phe Met Ala Glu Val Leu Lys
        275                 280                 285

Asn Gly Phe Asp Ser Ile Lys Asn Met Gly Ser Ala Leu Val Gly Asn
    290                 295                 300

Gly Phe Gly Ser Ser Lys Ser Asp Lys Thr Ala Asn Lys Met Ser Val
305                 310                 315                 320

Ser Gln Val Arg Leu Trp Cys Ile Asn Tyr Leu Lys Val Lys Phe Phe
                325                 330                 335

His Leu Ser Arg Arg Ala Leu Phe Asp Gln Arg Gly Asn Arg Leu Leu
            340                 345                 350

Ala Glu His Tyr Asp Phe Ile Thr Asp Ser Phe Leu Lys Met Ser Tyr
        355                 360                 365

Leu Asp Pro Leu Phe Leu Arg Ile Phe Thr Thr Asp Leu Ala Phe Cys
370                 375                 380

Glu Leu Pro Thr Leu Lys Arg Leu Gly Phe Phe Leu Leu His Arg Ser
385                 390                 395                 400

Ile Thr Ser Ile Gln Tyr Val Ala Ile Phe Arg Asn Asn Pro Ile Arg
                405                 410                 415

Gly Ser Ser Thr Ser Phe Asp Ala Leu Ile Ser Val Met Ser Val Ile
            420                 425                 430

Ser Ser Asp Asn Pro Tyr Pro Thr Phe Ile Tyr Leu Tyr Phe Met Pro
        435                 440                 445
```

Val Ile His Ala Ser Val Val Ser Asn Ile Asp Ala Arg Ile Val Ile
450                 455                 460

Ser Val Val Cys Asp Ile Ala Met Arg Thr Ser Glu Phe Ser Asp Val
465                 470                 475                 480

Phe Met Phe Phe Ala
                485

(2) INFORMATION FOR SEQ ID NO:23:

(i) SEQUENCE CHARACTERISTICS:
      (A) LENGTH: 469 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:23:

Asn Arg Ala Phe Phe Leu Trp Gly Arg Gly Asp Phe Ser Leu Ser Asn
1               5                   10                  15

Ile Ile Leu Ile Arg Ser Tyr Asn Lys Thr Leu Phe Leu Leu His Tyr
                20                  25                  30

Leu Ser Phe Thr Thr Arg Phe Ser Gln His Asn Lys Gln Ile Leu Ser
            35                  40                  45

Leu Lys Pro Arg Lys Ile His Asn Glu Ala Asn His Thr Tyr Asp Ser
50                  55                  60

Met Ala Lys Leu Val Leu Met Ile Arg Ser Lys Ile Ser Gln Asp Leu
65                  70                  75                  80

Ile Arg Asn Phe Phe Ile Ser Lys His His Lys Thr Leu Leu Thr Lys
                85                  90                  95

Asn Asn Leu Phe Lys Arg Ile His Lys Ala Ser Leu Phe Glu Lys Thr
            100                 105                 110

Asn Leu Phe Leu Val Phe Lys Ser Asn Pro Met Ile Leu Asn Leu Ser
            115                 120                 125

Glu Arg Phe Leu Lys Ile Ile Leu His Leu Val Cys Phe Val Phe Asp
130                 135                 140

Met Val Val Phe Gln Ile Asn Ile Asp Lys Asn Leu Leu Leu Gly
145                 150                 155                 160

Asp Lys Asn Lys Lys Asp Met Ala Cys Leu Val Ala Lys Tyr Leu Ile
                165                 170                 175

Cys Leu Arg Leu Val Ala Thr Tyr Arg Leu Ile Ser Val Ile Leu Pro
            180                 185                 190

Ile Asp Ser Arg Ile Phe Leu Val Ala Leu Gly Met Leu Leu Asn Ala
            195                 200                 205

Ser Tyr Asn Thr His Arg Ser Glu Gln Ala Arg Thr Tyr Thr Thr Lys
210                 215                 220

Asn Lys Arg Thr Asp His Gly Lys Asn Phe Ser Phe Val Gly Trp
225                 230                 235                 240

Arg Asn Lys Ser Phe Tyr Arg Phe Ile Gln Phe Val Tyr Asp Ile
                245                 250                 255

Lys Phe Phe Val Leu Ser Asp Val Asn Asp Gly Thr Ser Ile Arg Glu
            260                 265                 270

Lys Ile Leu Ala Tyr Gly Gln Tyr Gln Glu Phe Tyr Gly Arg Ser Ala
            275                 280                 285

Glu Glu Trp Ile Arg Tyr Gln Lys His Gly Ile Cys Phe Gly Trp Trp
290                 295                 300

```
Phe Trp Gln Gln Ile Arg Gln Asn Arg Asn Glu Cys Leu Ser Ser Lys
305                 310                 315                 320

Thr Val Val Tyr Leu Ser Lys Gly Glu Ile Phe Ser Ser Phe Thr
            325                 330                 335

Gln Ser Phe Val Ser Thr Arg Gln Ile Thr Ser Thr Leu Phe Tyr Tyr
            340                 345                 350

Leu Arg Leu Leu Phe Glu Asn Glu Leu Ser Pro Phe Ile Leu Val Val
            355                 360                 365

Thr His Phe Tyr Asn Arg Ser Cys Phe Leu Ile Thr Asn Ala Lys Ala
            370                 375                 380

Ile Gly Leu Phe Leu Ala Ser Ser Leu His Asn Leu Asp Pro Ile Cys
385                 390                 395                 400

Cys His Ile Lys Pro His Arg Lys Leu His Lys Leu Cys Ala His Gln
            405                 410                 415

Cys Asn Glu Arg Asn Gln Phe Gly Ser Leu Pro Tyr Phe Tyr Leu Ser
            420                 425                 430

Leu Phe Tyr Ala Cys His Leu Ala Cys Leu Lys Arg Ser Phe Tyr Arg
            435                 440                 445

Ser His Cys Asn Leu Cys Gly Val Tyr Cys Asn Glu Asp Lys Ile Cys
            450                 455                 460

Phe His Val Phe Cys
465
```

(2) INFORMATION FOR SEQ ID NO:24:

(i) SEQUENCE CHARACTERISTICS:
        (A) LENGTH: 462 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

```
Gly Phe Phe Leu Met Gly Gln Gly Phe Phe Ile Gln Tyr Tyr Ser Tyr
1               5                   10                  15

Ser Leu Leu Asn Leu Ala Phe Phe Ile Thr Leu Leu Ile Phe Tyr Tyr
            20                  25                  30

Ser Phe Leu Ser Ala Ala Asn Thr Ile Ser Ala Thr Gln Asn Ser Gln
            35                  40                  45

Ser Ser Tyr Leu Leu Asn Gly Lys Ile Gly Ser Tyr Asp Ser Phe Lys
50                  55                  60

Asn Phe Ser Arg Leu Asp Leu Glu Lys Phe Leu Tyr Phe Gln Thr Leu
65                  70                  75                  80

Ala Asn Leu Thr Asp Lys Leu Lys Ser Phe Ala His Thr Gln Ser Leu
            85                  90                  95

Ile Lys Asn Gln Ser Ile Phe Gly Ile Gln Ile Leu Lys Pro His Asp
            100                 105                 110

Phe Lys Phe Lys Ala Phe Phe Lys Asn Asn Ser Ala Ser Ser Val Leu
            115                 120                 125

Val Ile Cys Phe Tyr Gly Gly Gly Phe Pro Asn Tyr Lys Phe Ala Ile
            130                 135                 140

Ile Arg Arg Lys Gln Lys Gly Tyr Gly Leu Phe Gly Gly Lys Ile Phe
145                 150                 155                 160

Asp Leu Phe Ala Ile Gly Gly Tyr Leu Ser Leu Asp Phe Met Ser Asn
            165                 170                 175

Leu Thr Asn Arg Phe Lys Asn Phe Leu Ser Ser Phe Arg Tyr Ala Ile
```

```
                    180                 185                 190
    Val Lys Cys Phe Leu Lys His Ala Leu Glu Ile Arg Thr Ser Lys
                195                 200                 205

Asn Leu His Asn Gln Lys Lys Asp Ser Trp Glu Lys Phe Leu Leu Cys
            210                 215                 220

Trp Val Ala Glu Gln Ile Phe Leu Gln Val Tyr Pro Val Ile Cys Phe
    225                 230                 235                 240

Leu Tyr Ile Phe Cys Ser Phe Cys Trp Asp Leu Met Lys His Gly Lys
                        245                 250                 255

Asn Leu Thr Cys Leu Trp Thr Ile Ser Arg Ile Leu Trp Gln Lys Cys
                260                 265                 270

Arg Met Asp Ser Ile Val Ser Lys Thr Trp Asp Leu Leu Trp Leu Val
                275                 280                 285

Met Val Leu Val Ala Ala Asn Gln Thr Lys Pro Leu Ile Lys Val Ser
                290                 295                 300

Leu Lys Asp Cys Ser Gly Val Leu Thr Ile Arg Asn Phe Phe Ile Phe
    305                 310                 315                 320

His Ala Glu Leu Cys Leu Ile Asn Glu Ala Ile Asp Tyr Leu Asn Ile
                        325                 330                 335

Met Ile Leu Leu Lys Thr Pro Phe Lys Val Ile Leu Thr Leu Tyr
                340                 345                 350

Phe Ser Cys Asn Ala Phe Leu Gln Pro Ile Leu Leu Phe Val Asn Tyr
                355                 360                 365

Gln Arg Ser Asp Trp Ala Phe Ser Cys Phe Ile Ala Pro Leu Ala Arg
                370                 375                 380

Ser Asn Met Leu Pro Tyr Leu Glu Ile Thr Pro Leu Glu Glu Ala Pro
    385                 390                 395                 400

Gln Ala Leu Met Arg Ser Ser Val Ala Ser Val Arg Ile Ile Pro Thr
                        405                 410                 415

Leu Leu Leu Ser Ile Phe Ile Leu Cys Leu Ser Ser Met Pro Lys
                420                 425                 430

Ala Phe Leu Ile Leu Thr Leu Ala Leu Ser Leu Trp Cys Val Ile Leu
                435                 440                 445

Gln Gly Gln Val Asn Leu Val Met Phe Ser Cys Phe Leu Pro
    450                 455                 460
```

(2) INFORMATION FOR SEQ ID NO:25:

(i) SEQUENCE CHARACTERISTICS:
        (A) LENGTH: 19932 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
GGATATATTG AACCATTAAG TGCAAATGAT CTATATCGCT TCCATCGCAA TGATAATGAA      60

ATGACTTTGG GTGGCTATCT CATCTATAAC AGACTTAATA AAGTTATTCA AATCCCCTTG     120

CAACAACTTT TTTCTATACT TACACACTAA AATCAAATGG GCTTTTAGAT TATGCTTGCT     180

TCGGTTGGTT GAAATATACC CCCTTAATGG GTAATGGTTT TTTCTCATTC CTCTATCCTT     240

ATTCATTATT TATAAAAACA TTGTATAATA ATACAAGATA AAGATAAGGA GTTATTTTTC     300

TTAACGCTAT CAAGTTTAGA ATTTATCCTA ACGCTCAACA AAAAGAGCTT ATTTCTAAAC     360

ATTTTGGCTG TTCTAGGGTC GTGTATAACT ACTTTTTAGA TTACCGACAA AAGCAATACG     420
```

```
CAAAAGGCTT AAAGAAACTT ACTTCACCAT GCAAAAAGTC TTAACCCAAA TCAAGCACCA      480

AGAAAAATAC CATTACCTCA ATGAATGCAA TTCTCAAAGC TTGCAAATGG CGTTAAGACA      540

GCTTGTGAGT GCTTATGATA ATTTCTTTAG CAAAAGAGCG AGATACCCTA AATTCAAATC      600

TAAAAAAAAA GCTAAACAAT CTTTTGCAAT CCCCCAAAAC ATAGAAATCA AAACAGAGAC      660

TCAAACCATC GCTCTCCCTA AATTCAAAGA GGGCATTAAG GCTAAATTAC ACAGAGAATT      720

GCCTAAAGAT AGCGTTATCA AACAGGCTTT TATTTCTTGC ATAGCCGGTC AATATTTTTG      780

TTCTATATCC TATGAAACCA AAGAGCCTAT CCCTAAACCT ACCATCATTA AAAAAGCGGT      840

AGGTTTAGAC ATGGGCTTAA GAACGCTCAT TGTTACAAGC GATAAAATAG AATACCCACA      900

CATCCGTTTT TATCAAAAAT TAGAAAAGAA ACTCACTAAA GCGGAAAGGA GGTTAAGTAA      960

AAAAGTAAAA GGCTCCAACA ACAGGAAAAA ACAAGCTAAA AAGGTAGCTA GATTGCATCT     1020

AGCTTGTTCA AACACTAGAG ATGACTACTT GCATAAAATC AGTAATGAGA TAACCAATCA     1080

ATACGATTTG ATAGGGGTAG AAACTTTGAA TGTTAAGGGG CTTATGAGAA CCTATCATTC     1140

TAAAAGCCTT GCTAATGCGA GTTGGGGGAA ATTCCTTACT ATGCTAAAAT ACAAAGCCCA     1200

AAGAAAAGCT AAAACCCTAT TAGGCATAGA CAGATTTTTC CCTAGCTCTC AATTGTGTTC     1260

TTATTGTGGG TTCAATACAG GCAAAAAACA TGAAAACATC ACTAAATTCA CTTGTCCTCA     1320

TTGCAATATC ACACACCACA GAGATTACAA TGCGAGCGTC AATATTAGAA ACTACGCTTT     1380

AGGCATGCTA GATGACAGGC ATAAAATAAA GATAGATAAA AGTAGGGTAG GGATTATCCG     1440

AACTGATTAC GCTCATTACA CTGATGAGCG CATCAAAGCT TGTGGAGCTT CCTCTAATGG     1500

GGTTATTTCT AAATATGGCA ACATATTGGA TCTAGCTAGT TATGGAGCGA TGAAGCAAGA     1560

AAAAGCCCAA TCGCTTTAGC GTTGGTAATT CACAAAAAGC AAGATCGGTT GTAAAAATGC     1620

GTTACAACTA AAATAAAGGG TCAAGATAAC TCATTTTCAA AAAGGAGTCT TAAGTAATAA     1680

AATCATAATG TTCAGCTAGT AATCTATTGC CTCGTTGATC AAACAAAGCT CTGCGTGAAA     1740

GATGAAAAAA TTTCACCTTT AGATAGTTAA TACACCACTA CAGTCTTACT TGAGAGACAC     1800

TCATTTTATT AGCGGTTTTG TCTGATTTGC TGCTACCAAA ACCATTACCA ACCAAAGCAG     1860

ATCCCATGTT TTTGATACTA TCGAATCCAT TCTTCAGCAC TTCTGCCATA AAATTCTTGA     1920

TATTGTCCAT AGGCAAGTTA AATTTTTTCC CTAATGCTTC ATTAAGTCCC ATCATTAACA     1980

TCAGAAAGAA CAAAAAATTT AATATCATAG AAAACAAATC ACTGGATAAA CCTGTAAAAA     2040

GATTTGTTCC CCCACCCAAC AAAGAAGCTA AAATTTTTCC CATGATCAGT CCTTTTATTT     2100

TTGGTTGTGT AAGTTCTTGC TTGTTCTTAT CTCTAATGCG TGTTTTAGTA GGAAGCATTT     2160

CACAATAGCA TACCTAAAGC TACTAAGAAA ATTCTTGAAT CTATTGGTAA GATTACTCAT     2220

GAAATCAAGC GATAAGTAGC CACCAATCGC AAACAAATCA AATATTTTGC CACCAAACAA     2280

GCCATATCCT TTTTGTTTTT ATCTCCTAAT TATAGCAAAT TTTTATCAAT ATTAATTTGG     2340

AAAACCACCA CCATATCAAA AACAAATTAC TAACACACTA GATGCAGAAT TATTTTTTAA     2400

AAACGCGCAC TTAAATTTAA AATCATGGGG TTTTAGGATT TGAATACCAA AAATAGATTG     2460

GTTTTTTCAA ATAAGCTAGC TTTGTGTATG CGCTTAAAAA GATTTTGGTT TTTAGTCAGT     2520

AAGGTTTTAT GCTAATGTTT GGAAATAAAG AAATTTCTCT AAATCAAGTC TTGAGAAATT     2580

TTTGAACGAA TCATAAGAAC CAATTTTGCC ATTGAGTCAT AAGTATGATT AGCTTCATTG     2640

TGAATTTTGC GTGGCTTAAG AGATAGTATT TGCTTATTAT GCTGAGAGAA ACGAGTAGTA     2700

AAAGATAAGT AGTGTAATAA AAAAAGCTAG GTTTTATTAT AAGAGCGAAT AAGAATAATA     2760

TTGGATAAAC TAAAATCACC CCTGCCCCAT AAGAAAAAAG CCCTATTAAA AAACCTATAA     2820
```

```
CGATAGAGCT GATATTGAAC AGCCTATAAT AAAGGCTGTA CTTATCTAAA TGTTTGTTGA    2880

AAGAATATTT GAATTGTAAG AAGTTTTGTT TTAATTTGCT AATTTGGTTG GTTCCATTTT    2940

GGTTTTTAAA GAAATAGTTC AGGGCGGTGA ACTTATAAAG GAGCATAAAA TAATAAATAT    3000

TTTACAAAAC CACCCTAATC TAACTCCAAA TCTCAAAGAA TACCCCACTT GCTGATACTA    3060

GCATGTGGTA TAGCACAAAC CAACGATTTG TTTGTTTATG CCAAACAAAG AACAGAAAAC    3120

ATCTGTTAAA GAATAAAGGA GTTTTCCATC TAAAAAACAC AAATCTATTA TATAGAAATA    3180

ATCTTAAGAG AAACTTAAAA AATACCAACA AGCCGCATAC AAGCAAGAAA AACATAACAC    3240

TATAAGACCT GGATTTTATT TACCTTTTGG ATATGGAAAA ATCTTGATTC ATAGTTTTGT    3300

AAAAATTGTG GTAAAATGCA TTGATATTCT TTGAAATTTT AAGGTTACAA AAACTATAAG    3360

ATGCTTGCAA AAATTGTTTT TAGCTCATTG GTTGCGTTTG GAGTTTTGTC GGCTAATGTG    3420

GAGCAGTTTG GTTCATTTTT CAACGAGATA AAAAAGAAC AAGAAGAAGT GGCTGCAAAA     3480

GAAGACGCTC TTAAGGCTCG CAAGAAGCTC TTAAACAATA CGCATGATTT CTTAGAAGAC    3540

TTGATTTTTA GAAAACAAAA AATCAAAGAG CTTATGGATC ATAGAGCTAA AGTTCTTTCA    3600

GACTTAGAAA ACAAATACAA AAAAGAAAAA GAGGCTCTAG AGAAAGAGAC AAGAGGTAAA    3660

ATCCTTACTG CTAAGTCAAA GGCTTATGGG GATCTAGAGC AAGCCTTAAA AGATAACCCT    3720

CTCTATAAGA AACTTCTTCC TAACCCTTAT GCCTATGTTT TAAACCAAGA AACATTCACC    3780

AAAGAAGATA AGGAGCGTTT GAGTTATTAC TACCCCCAGG TGAAAACGAG CAGTATTTTT    3840

GAAAAAACTA CCGCTACCAC TAAAGATAAG GCTCAGGCTT TGCTTCAAAT GGGTGTGTTT    3900

TCTTTAGATG AAGAACAAAA CAAAAAAGCG AGCCGATTAG CTTTATCTTA CAAGCAAGCG    3960

ATTGAAGAAT ATTCCAATAA CATTTCTAAT CTGTTGAGCA GAAAAGAATT GGATAATATA    4020

GATTATTACT TACAGCTTGA AAGAAACAAG TTTGACTCCA AAGCAAAAGA TATTGCTCAA    4080

AAGGCTACTA CACACGCTTAT TTTTAACTCG GAACGCTTGG CGTTTAGCAT GGCGATTGAT    4140

AAGATTAATG AGAAATACTT AAAGGGCTAT GAGGCTTTTT CTAACTTGTT GAAAAATGTC    4200

AAAGATGATG TGGAATTGAA TACTCTGACT AAAAAACTTTA CCAATCAAAA ATTGAGTTTC    4260

GCACAAAAAC AAAAATTGTG TTTGTTGGTT TTAGACAGCT TCAATTTTGA TACCCAATCC    4320

AAAAAATCTA TATTAAAAAA GACTAATGAA TACAATATTT TCGTAGATAG CGATCCTATG    4380

ATGAGCGACA AAACAACTAT GCAAAAAGAA CACTACAAGA TATTTAATTT CTTCAAAACA    4440

GTGGTTTCTG CATACCGAAA CAATGTTGCC AAGAATAATC CCTTTGAATA GGAAAGGAGA    4500

CACTCTTGAA AAGCATCTTC AAAAAACTAG GTTCTGTCGC TCTTTATTCT TTAGTTGTTT    4560

ATGGGGCTT AAACGCTATC AATACAGCAT TATTGCCGAG TGAATACAAA GAATTAGTGG     4620

CTTTGGGCTT TAAAAAAATC AAAACACTCT ATCAAAGACA TGATGACAAA GAAATTACAA    4680

AAGAGGAAAA AGAATTCGCC ACTAACGCTT TGAGAGAAAA ATTACGAAAT GATAGGGCGA    4740

GAGCAGAGCA AATTCAAAAG AATATTGAAG CGTTTGAAAA AAAGAACAAC TCTTCTGTTC    4800

AAAAAAAAGC GGCTAAGCAC AAAGGATTAC AAGAATTAAA CGAAATTAAC GCTAACCCTT    4860

TGAATGACAA CCCTAATGGC AATTCTTCCA CTGAAACCAA ATCTAATAAA GATGATAACT    4920

TTGATGAGAT GATCAATAAG GTGAATGAAT CTTTTGTGAA ACCTGCTGCT CCGCTTGTGC    4980

CTGATGAGTG GAGAACGCCT GAAATTGAAA TCATTATCAA TGAGTGTATT ATTTCAAGCA    5040

ACGATTATGA TGGGTTAAGA AAGTGTTTGA TCAAAGACAT CAAGGATCAA AAAATTCTTG    5100

CCCCCTTATT AGAAAAAATT CAAGAAATAG AGACAGAAAA TAACAAGTTT TCTAGACAAC    5160

ACCTAAGTGG TTTAAAACTC ACTCTTAATA ACAGCAACAA TAGAACCTTT CTTATAGCTT    5220
```

```
CGTGCGCTAT TTGTGAGAAG AGAAAAAAAG AAATGGAGCA AGAAAATAAC TACCAGGATA    5280

CTACAAATGC AAGCGAGTTT GGCACTACTG ATACAAAAGA AAATGAAGCA AAAGATACAG    5340

CATTCTCAAA CAATCGCTCT AAATCCGAAC TGCCCAATAG CGTCATTAAT CAAATAGAAC    5400

AAAGCATCGC TCATGGAAAA AAATAGCGAT CCAAATTATT AGATCAAAAA ACAACTAGAG    5460

AAGCAAATCC CAAAGGTTAG AAATCATAGC CTATCATCTC AGAAAAATCA TTTAACAATG    5520

ATCTTACTTG ATTGCCTTTC TTGTAGGTAT TGTCGCTTAC TTTGTTCTAG GGATCTTTCT    5580

AATGCGTCCA ACTCCTCTAA ATAATTTAAA AAGACCTTGT TTTGAGCTAA CATAAGCTTT    5640

CTGATTCCTT TGATGAAATT TTTATTCTTT AGGCTTTCTA CAAGCGTCTG TGAAGCAGTG    5700

ATTAAAGAAG CTGTACCTCC AATGTTGCTC TGATACGCCT TTAGGGAAGT TTCTAAACGC    5760

TCTCTTATAT TTTGTTTTTC TTGCTCGATT TTCAGCTTCC CTTCACAATA AAGAACTAAA    5820

ACTTATCGG ATATTCCGCA TTGCTGCTCA GCAGTATTTT GGTCTAAGGG ATTGATTTTC     5880

ATATAGGTTA ATAAAAGTTC AGGGCTAGAC ATATAAGTCT TGAAAATCAC ATCTTCTGAG    5940

ATGAAAAATA ACTCATTCGC TTCAAAATTG GCTTTCAATA ACGCTAAATC TCCTCTCAAA    6000

GCAATGGCCG CTTTTTTGAT GTTTAGAGCA TCTTCTTGAC CTATTTCATT ATTAGCGCTA    6060

GGGCTAGTGG TTGAAAAAAT CTCATCTAAG TTTTTAAGCA CTTGTTGGTT GGTCTCTTGG    6120

TAGGTGCTAT CAAGTTGCTT TAAACCGCTT GTTATATCTT CTCCCATCAA AACAGACAAT    6180

AGCAAAAAAG AAGATATGGT ATTTTTCACG AGTGTTTTCA TTTGACAATA ACTTTAGAGC    6240

TAGCAATGTT TCTTGCTGTC GTTTCTCTTT CTAATTTCAG TTGTTCTTCC CAAAGGTCGG    6300

CTTTTTTTTC AAGATTCTCT ATATAGTTTA AATGATTTTC TGCGTTTAAG ATCGCAACTT    6360

CTATGAGCGC ATTCAAATCT ACTGATCCTT TTAAGGTTTT GATTTCTCCA TTGATCCCAT    6420

TCAAATAAGC GATATTTTGA AAATCTGCAT CACTCAGTTT ATTTTGAATA AGGGCTACAA    6480

TCATTCTGTA ATTCTGAATA ACCTGTTCCA TAAGCATGC TGAAATTTTT AGCCCATCAA     6540

GATAAGGGCA TTTTGTGGGC GCTAGAGTGA ATGTTTCAAT GATTCCAAAT GGTCGCCCAT    6600

GCTTGAAAAA AAACTAAGAG CAGGCGCATA GATGGCACTT TGAAACAAAG CCTGACCTGT    6660

TAGGGAATTA TAATCAATAA GGGTCGCTTT TTGCATAGCT GTTTTCAACC ATGTCTCAAA    6720

ACCTTTTAAG GTTTCTTCAA ACGCCTTGAT ACCAATCGTA TTGTAAGCGA TGTATTGAGC    6780

GTTGTCAGAA GAACTTCCTA GAGCTTGAGA AATTTCCATT TGTGTTTTTA GGGTAACCCT    6840

CGGTTCAAAG CTGTTTTTTA ACGCTTCTAA GAGAGCGTTT TGCTGGTTCA TTTTGAGCTT    6900

GATCATTTCG TTATTTTTTT GGAGCGCGAT TTGCATGTTT TGGATTTCTG TTTGGGTATT    6960

AATTTTTGT TTTTCCACGA TCATTTTGAC ATTCCCCCCC AATGCACTAA GCGCCGCTTG     7020

AATACCCTTC CATGACGCCA AGCAAGATGT CTGAACCTGC AAAAAACCCC CCTGTCATGC    7080

CATTGACACC ATTAATAACG CCATTAGCCC CTTTTAACAT AGCGCTCATG GTTGCAAGCT    7140

GAGTCCTCAA TTCTCCCTCT ATTTGCGCTT GAATGGCTTT TTCTTTGGCA CTAGATTGAG    7200

CTTCTATGGC TTTTAATTCG GCGTGAGCGG TTTTTTGTTT GGCTTGTGCG TCTGCCTGAA    7260

TGGCTTTTAA GGCAGGTTCA AGCGTTATTA CTACCTCTGT ACCATTCAGA GACAAACCAC    7320

AAAAAGTCAA GAAAGAAAAT ATGCTTAAAA AACATTTCAC ATCTCTTTCC TCACTTCACG    7380

ATTATTTTAG TTTGCACCCT TTCTGTTAAG TAGCTATCTT TTTGCCCCTT AAGCTTGTCT    7440

TTGATGTAAT CAAGGTAAGT CAAATGCGAT TTCAAAAAAG ATTTATTCGC TACTATATTG    7500

TAATTATATA GCGAACTTAT GTTAGAAATC GCTTGAGTGT CATAGGTGCT AGTAGCTAAT    7560

CCTGATTGAT TAAGTATCAT TTGAGAAGCG TTCTGCAACA AATTGGTATT ATTTTTCACA    7620
```

```
AATTCTATAT AGTATTCTCT CAAAATTTCT GCTACTTTTT CAGCATAGCA ATAAACAGCA    7680

AGAACCTTGT CCCCAATAGG GCATGCAGGA GTGGTTATAG GATTAACGCC TGAAGTTAGG    7740

GCATTAGTGC GTAACGCTTG GTATTTAGCA TAAACAGTGG GCATAGAAAC GCTCATGGGG    7800

CGTCATAGAA ATTTGCATGC AACTGAAAAA CACTTTTGAT GAGCCAACAA GCGCACCTAA    7860

AGCGGTACAG CTATCAAGGA ATCGGTGTAT CATTCATTGA GCTGTTGCTT GCTTGAGAAG    7920

CCAGTTGCTC TTGTAGAGCT AGGGCGTATT TTGGTGCTGC ACTTGTAATA TTGCCTAATA    7980

TACCGTCATC ATTTCAACCG TTGTTGGCAC GCTAGGAACA GCGATTTGAT TTGTCGCATA    8040

AGCTTCAATA GCACTGGGAT TTTTAGGGGT GGTGTTACTC GCTAAAATGC TTGCAATCTG    8100

ACTATTAACA GCACCAATTT GCGCGCCTTG GCTGTTGCCT TGAGCGTTAA ATTCCCCTGT    8160

TAATTTGCTA ATATTTAAGA TATTGTTCCC CACAGCCATG CTTTGATCGT TAAAACCTTG    8220

ATACAATTGG TTGTATTGTT GGTTAGCGGC TTTCATAGGC ATGCTTACGG CTTCAGCGAT    8280

GCTTTGATTG TATTGGGTCA TGATAGCGGT CATTTGCGGA TTAGTAAACC CAACAATAAT    8340

AGGAATAATC GCTGCTGTCA TAGCACCCGC TACTATTCCT GCAAATGGTC CTGCGACACC    8400

ACTTGTGTTG AGATGATTGA GGAAACTTCC GATAAGAAGC CTGCAGAAGA TGATTCATAT    8460

ATAGCTTGTG TACCTGCCAT GTTAACACCC CCTAGTTAAT ACCCTAATAT CGGTGGTAAA    8520

AACGATGAAT CTGAGTATGT TGGTGCATAA CCATACATGA AAGGATTGTT TGGACCGTAA    8580

TCGCCCATCA TTTGGCTCAT GAGAAGATTT TGAATGCCCC ACATCGCATT GATACCTAGA    8640

TTATCATTAG GTTGAAAACT CCCTAAACTT ATGTCGTCAA ATTTGATATT AACATTTTA    8700

TCATTATAGT CATTGAGTAT GGCCACTTTT TGCTCTAGGG TTTCTTTAGG GATCTCTATT    8760

TTTAGTTGAT CTCTAGAAAC AAGCCCCACG CTATTTAGTG CCATATCTTC AGGACTAATA    8820

TCTTTTATAT CAGTGTTTTG GTCAGCGTTA ACGGACTGTA AACATGCCAA TGATAAGACA    8880

CCAAGCAAAT AGTAATTTAA TTTTATAAAA ATCCGTTTTC ATACTTTTGA CTCCTTTATT    8940

CTTATTTTTA GCACTATTCT AGCGCATTAA CGCCACTCAA TCGTTATTTT TGTTTTGATT    9000

TTTTTGATCG AGCATTTTGT TTGTTACTTC ATCAATGTTT TGAAAATATT TTTCAAAAAG    9060

CTCTTTCTTT TTAGCTTCAA CGCTCATATC AATCTGAATC CAATTAGGAA TAATGGAGTC    9120

CATGATTAAA TGCATGAAGT CATAGGCATG ATTTTTTGGG TATATTTTGT TCTGAACATA    9180

GTATTCTAAA AAATTCGCTT GAACAAAAAA AATCTCTATA TCGCTCTGCA TATCCTCGCT    9240

TATGTTGTTA TTGATAGGTT TTTCTAGTAA TCTGAGAATC CTATACGACT GCATGATAGT    9300

TTCTAGCATG AAGTAAGCAT AAACATAAAC TAATGAGACA AAAGAATTGT TTGCTTTAAA    9360

CGAGCTTGCG TCATTTTTCC CACTTTGAAG AGGAATTAAT CTTGATAATG TTTTTTGGGG    9420

ATCTTGCCCA TCGTTTATTT CTTTAAAAAA GCGGAAATCT AAATCCTGAT TACTGAGAAA    9480

TGACTTGACA AAGTGAAGAT TAGCATTGAG ACTATCTATG AGACCTGAAT AAAGGTGCTC    9540

TGTTTTGACA TCATCTATAT TTAAAACATT CTCATAAAAC ACATTGACAT GGTCTTCTAA    9600

GAAATTAGAA AAGTCATAAA GAGTGGTAAG GTTTTGTTCA GTGATTTCGC CTTCCATTTC    9660

TTCTTCTATG AAGTCCAATT CTTCTTTCAG TTCAAAAGA TAATTAGAAA AACTATCCAA    9720

AATCGTCAAG ACATCATTTT CAAAATTTCC AATAATTTTT GTTCACGCAA ATTTTGTTTC    9780

ATTTTAATAC TCCTCTATTT GTTGATACAT TTGTCTCAAG GCCTGATATT TATCTATGAT    9840

ACTATGGTTT TGGATAATCT TATCAATTTC TTTGACAAAT ACAGTATCTG TGGATAAAAT    9900

TTTCAAATAT TCTTTAGGAA TGCCTCTCAA ATTAAAACTA GCGATAACGC TAGGGCTTCC    9960

ATCCTGTTTG TAGAGGATTT TCCTATCTAG TCCCTTAGTG ATGATTTCAA ATTCTTTTTC    10020
```

```
TGTAACATTA GCCAATCTTT GGTAATCAGA AAGATTGCCC CCATCGTTTC TCAAAAAAAT    10080

CTTTGTAGGG CATTGTTCTC TAATCGTATC AGCAATAGGG CAAGCCAAAA GATCAGTGAT    10140

GCTTTGAGTC GCAAGTCTGA CAATAGCGTT TCTTTTCCTT GCAGTTTTTA GCATGTCTCT    10200

TACAAAATAA GCGACCTTTG GATCGCCTAA ATATTTCCAG GCTTCATCAA TATCTAAGAC    10260

AAATCTACGC CCATCCATTG CCTCTTGGAT ACGAGCGAAA AGGTAAAAAC AAATAAAGGG    10320

CGAAACATCA TTATTGTCTA AGAAACTTGA CCCATCAACG CCAATAATCG TTTTTGAAAA    10380

ATCTAAGCGA TCTGTTGCTT TATTATCAAA AAGCCATTGA AATTCACCAT GGTTGATTT    10440

GCAAAAGGC GCTAATCGCG CGACAAGCCC ATTAGGATCA TTGTGGTCTT TCCCGAAAGC    10500

ATTAATAAGT TGAGTGATGG GATAATCTAG ATTCATATTT CCTGTGATAA GGTTGGTTAC    10560

TGCGCTGCAA GCGTATTAGA ATCTGCTAGG CTAAAAGAGA TGCTGTTGCC ATTTTCATCT    10620

TTTTCATCGC TTTTAGTTGC TAAGTTTTTC ACAAGCTCTT TGACAACAGA AATAGCTGTT    10680

TGTTTTTGCT CCATTGTTGC ATTTGTTTTT TGCACACAAG CCGCCCAAGC AAAAGGATTT    10740

AATCCTGTAT CTGTCCCTAG CTCAATCTTG ACATACTCCC CACCCATTGC GACAATATTC    10800

CCATAAGCGC CATAATCTTT ATCCATATAA ACCATAGTGA GCTTTTGCTT GTCTTTGCTG    10860

ACATTAGCAG GAAAATTATA GGCAAATTGT CCCATAGCGT TCAAGGTCAT TGACATAAAC    10920

ACTGTCTTAC CTGAACCGGT TGAGCCAAGT ATCAAAGTGT GTCCTGCTGA AGCTGAACCA    10980

AAATCAGTGG GCATGTGGAA GTTCAGATAA AAAGGCGAAT TGATCTCGCT TTTTAGCGTC    11040

ATCACACTAT TGCCCCAAGC GTTATTCTCT TGATTGCCAT CAAAACTCAT AGCCCTCATA    11100

GCGATGAAAT CAGCAAAATT ATTAGAAGTT ACATCAAAAA TAAAAGGAAG CGTGATAAAA    11160

GAGCAATGTT TGGCAAAAAA GTAATTTTCC ATAGAGAAAG TCGCTGCGTT GGCTAAAAAA    11220

CCTTTAGCGT TAAGACTAGA GACGCATTCC TTAACGCTTT GTTTCATTTT TTCAAAGCTA    11280

TCAGCAAACA GCACTAAAGA ATTACCATAA CTGCCTAGCG TAATATCACC ATTACCCACT    11340

AATTCGCTCA AGCAACCTAA AGTCATGCCC TGTTCTTTAG AGCCTCCACT AATAATAATT    11400

CTTCTAGAGG TGAAAGCCAG TTTGTCCTTT AAAACCTGTG AGTTTTTAGG CGAATAAGCA    11460

TGCATGAAAA TAAATTCGCT GTCTAGGGCG TTGATTTTAT CAAACAAATC GCTTTGTGAT    11520

TTAGGGGCGT ATTCACTAAT CTCAATAGCG CTAAAATATT TTTCACTCAA ATCGTCATTT    11580

AAGATTTTTC CATGCTTATT GGCAAAATAA ACTTCTTTCA CCCCACCATG CATTTTTTCC    11640

TTGAGATACA AGTCTTTTCG GTTGCAAATA AAAGGGGCTT CATTCATTCC CACAAGAAAA    11700

TTGTAAAATT CGCATTGTTT GGAGTAAATA ACGCCATCTT TAGTGTATTC TTTTAATCTA    11760

GTGGGGTGGT ATTTGCTCAA CAGCTCTTCT ATGAGCTCTA TCCTATCCTT GAAGTTTTCA    11820

AGCTTGGCTC TAATAATCCT TTGAAACTCT TCAAAATTAT TGTCTGCAAA ATGCTTTTTA    11880

TTCATAACGG GTTCATTGAG AGTGTCTAAT AAATCTTGCT CTATGGTCAG AAAAAAACTA    11940

ATATCATAAA AACTTTCTCT CTTTTGCTTC TCATTATAGG CTCGCATGAA ATCATTAGAA    12000

AAAATAAGAC CATAGTCCCT ATTGGTTTCA TCAATAACGA TTTTCTTTTT AATAGTGTGA    12060

AAATAGAATT TGAATTCAGG GGTAACAAAA TTCCTAAAAA CGCTATAAAT AGAAGCGTGT    12120

AACTCTATGA GATCTTTTTT GGAAGTGGTT AAAAAATCAA TGCCCCCCAA TTTGATTGTG    12180

CCTAAAAGAG AATAGTTGTT AGTAAGGATC ACCCCATCAT CTAAAAAACA TTCATAGTTA    12240

TTTGCTAGAT AGGAGTTTGC AGCGCTCACA AGTCTGTCTT CTCTGTTTGG ATTTAAGTGG    12300

ATGTCATTAG CCATTTCTTT ACTAGGCTTC ATGGAAAAAA TGCTCATGAA CGCTTTGTTT    12360

TTCACGCCCT TAAACAAAAA AGGTTTTTTA AATTTCATCG CTCGCTCCAT TCTTTGATAA    12420
```

```
AGCCTATAAT CTTTCTTGAA TCCAAGAGCT ACAAGCACAA TAACAATCGC TACAATCAAA    12480

ACAGGTTCAT AGGCTTGAAA AAGAATAACA GATAATACAA TGGTTACAAA CAATATAAAT    12540

ATAGAGGAAT AAATAAAAGT TTCAGGGAAA CCAAACAACC TATTCCCCCC ATCAAACAAG    12600

ACTTTAAAAA AGGGATTGAC ACCCTTTTGC ATGTCTGCTT TAAGTTCTTC TATTTTTTGA    12660

AACTGCCGCT TTTGAACCTC TTGCTCTATA ATTAGCTTTT TTTGTTCATC AGCCTGCTTG    12720

CTTGCCACAA ACACCTCTCT CTTTATAGAT ATACCGCTTC ACATGTAATC GTATAAAAGA    12780

TTTTTTTGAG AGACTCTACG GTGCTAATAT GTTTCAAAAG ATCATTAGGA TCATAAGAAT    12840

TGAATACGGC CAATAAAACA TTATATAACT TATCATCGCA TAGAATTTCT CTTGTTTCTC    12900

CGCGCAATGA CAGAAAGCAG CGTTGTTTGT TGGTCGTGCT GATGCTTTTG AAAGTAAAAA    12960

AGTCTTTCAC TTCAGGATTG ATCTGTAATT CTACATTCAA TCCCATTTCC TTACCCTTTT    13020

CATCAAAGAT TTTTTCAATA ACTGGATCGT AATGCTTCAA ATCCTTTATT TTTTTAAGGA    13080

CTCTATTGAC AATCACGAAG TCAAAAACTT CATCTTTGAT AATATCGGGA TTGACTTCTT    13140

TGAAAGTTAC TTTCTTGTCT TTCAAATTTT TGATAGTCGC TTTGAAACTA TCAAAATCTA    13200

AATTTGTATA AACAAGCCCA TTGGGAGTGT TTTTTTCTTT TTCTTGTGCT TCTTTTTTGG    13260

CTTCTTTGTC ATCATTTGCT AACCCATACG AACTGAAAAC AACGAGACTT AAGAGAACTT    13320

TCAAAAAAAA GCCTCTTAGT TTCTTATTGC TATTATTATT ATTGTTGATC AACTTAGCTA    13380

GCTCCTCCAC CCTCGCCAAT ATTGAAGCCA AACTTAGTGC TCAAATAGAT AATACCGCCT    13440

GCCACCGCTA ACATAGCTAT GGGTTGCGCG TAACGAAAAA CAGTCGCCTG ACCTCTTTTA    13500

ATGTCATCAG AGATTTTCCA AATATCCGCT ATGCCTTTGA CCCCTAAAGC GCAACCACCT    13560

ACGATCGCTA GAACAGAAAT GATCTGAATA ACCAAACCTT TAGTTGCAGT GACGCCTTCT    13620

GTAGGACTGG CGACCGCATT TAAAGGATTG GTTGTTACCA CTAGCCCTAA AGTTACTACA    13680

ACTTTCTTGT AGCTGTCAGT GATTCTTGTA AAAAATTTCA TGCGTTTCCT TTCAAATTGA    13740

AATCAATCGC TTGAGTATAT CAAAAAAAAA AGTATTTTTA TACTATTCAT ACAAGCGCTA    13800

CTTTATAATT TAAATCAAAA CCGACGCTTT TGCTCGGCAA CTGACATCAT TCAGGAATAG    13860

TAAACCTACT TGTCCCAACC ATTTTTCTTT CTCAAGTCGT TGTAGAATTG TAGATCTTTA    13920

GGATCTTTGA TGTATTTTTT AATCGTCTCA GGTTGAAACC TAAAAACAAG CAAAAACAAA    13980

CCCAAGCTGA TCAGAGTGAG AATAAAGCTC CATTTTAAGC AACTCCATAG ACCACTAAAG    14040

AAACTTTTTT TGAGGCTATC TTTGAAAATC TGTCCTATTG ATTTGTTTTC CATTTTGTTT    14100

CCCATGTGGA TCTTGTGGAT CACAAACGCT TAATTATACA TGCTATAGTA AGCATGACAC    14160

ACAAACCAAA CTATTTTTAG AACGCTTCAT GTGCTCACCT TGACTAACCA TTTCTCCAAC    14220

CATACTTTAG CGTTGCATTT GATTTCTTCA AAAAGATTCA TTTCTTATTT CTTGTTCTTA    14280

TTAAAGTTCT TTCATTTTAG CAAATTTTTG TTAATTGTGG GTAAAAATGT GAATCGTCCT    14340

AGCCTTTAGA CGCCTGCAAC GATCGGGCTT TTTTCAATAT TAATAATGAT TAATGAAAAA    14400

AAAAAAAAAT GCTTGATATT GTTGTATAAT GAGAATGTTC AAAGACATGA ATTGACTACT    14460

CAAGCGTGTA GCGATTTTTA GCAGTCTTTG ACACTAACAA GATACCGATA GGTATGAAAC    14520

TAGGTATAGT AAGGAGAAAC AATGACTAAC GAAACCATTG ACCAACAACC ACAAACCGAA    14580

GCGGCTTTTA ACCCGCAGCA ATTTATCAAT AATCTTCAAG TAGCTTTTCT TAAAGTTGAT    14640

AACGCTGTCG CTTCATACGA TCCTGATCAA AAACCAATCG TTGATAAGAA CGATAGGGAT    14700

AACAGGCAAG CTTTTGAAGG AATCTCGCAA TTAAGGAAG AATACTCCAA TAAAGCGATC    14760

AAAAATCCTA CCAAAAAGAA TCAGTATTTT TCAGACTTTA TCAATAAGAG CAATGATTTA    14820
```

-continued

```
ATCAACAAAG ACAATCTCAT TGATGTAGAA TCTTCCACAA AGAGCTTTCA GAAATTTGGG   14880

GATCAGCGTT ACCGAATTTT CACAAGTTGG GTGTCCCATC AAAACGATCC GTCTAAAATC   14940

AACACCCGAT CGATCCGAAA TTTTATGGAA AATATCATAC AACCCCCTAT CCTTGATGAT   15000

AAAGAGAAAG CGGAGTTTTT GAAATCTGCC AAACAATCTT TTGCAGGAAT CATTATAGGG   15060

AATCAAATCC GAACGGATCA AAAGTTCATG GGCGTGTTTG ATGAGTCCTT GAAAGAAAGG   15120

CAAGAAGCAG AAAAAAATGG AGAGCCTACT GGTGGGGATT GGTTGGATAT TTTTCTCTCA   15180

TTTATATTTG ACAAAAAACA ATCTTCTGAT GTCAAAGAAG CAATCAATCA AGAACCAGTT   15240

CCCCATGTCC AACCAGATAT AGCCACTACC ACCACCGACA TACAAGGCTT ACCGCCTGAA   15300

GCTAGAGATT TACTTGATGA AAGGGGTAAT TTTTCTAAAT TCACTCTTGG CGATATGGAA   15360

ATGTTAGATG TTGAGGGAGT CGCTGACATT GATCCCAATT ACAAGTTCAA TCAATTATTG   15420

ATTCACAATA ACGCTCTGTC TTCTGTGTTA ATGGGGAGTC ATAATGGCAT AGAACCTGAA   15480

AAAGTTTCAT TGTTGTATGG GGGCAATGGT GGTCCTGGAG CTAGGCATGA TTGGAACGCC   15540

ACCGTTGGTT ATAAAGACCA ACAAGGCAAC AATGTGGCTA CAATAATTAA TGTGCATATG   15600

AAAAACGGCA GTGGCTTAGT CATAGCAGGT GGTGAGAAAG GGATTAACAA CCCTAGTTTT   15660

TATCTCTACA AAGAAGACCA ACTCACAGGC TCACAACGAG CATTAAGTCA AGAAGAGATC   15720

CAAAACAAAA TAGATTTCAT GGAATTTCTT GCACAAAATA ATGCTAAATT AGACAACTTG   15780

AGCGAGAAAG AGAAGGAAAA ATTCCGAACT GAGATTAAAG ATTTCCAAAA AGACTCTAAG   15840

GCTTATTTAG ACGCCCTAGG GAATGATCGT ATTGCTTTTG TTTCTAAAAA AGACACAAAA   15900

CATTCAGCTT TAATTACTGA GTTTGGTAAT GGGGATTTGA GCTACACTCT CAAAGATTAT   15960

GGGAAAAAAG CAGATAAAGC TTTAGATAGG GAGAAAAATG TTACTCTTCA AGGTAGCCTA   16020

AAACATGATG GCGTGATGTT TGTTGATTAT TCTAATTTCA ATACACCAA CGCCTCCAAG    16080

AATCCCAATA AGGGTGTAGG CGTTACGAAT GGCGTTTCCC ATTTAGAAGT AGGCTTTAAC   16140

AAGGTAGCTA TCTTTAATTT GCCTGATTTA AATAATCTCG CTATCACTAG TTTCGTAAGG   16200

CGGAATTTAG AGGATAAACT AACCACTAAA GGATTGTCCC CACAAGAAGC TAATAAGCTT   16260

ATCAAAGATT TTTTGAGCAG CAACAAAGAA TTGGTTGGAA AAACTTTAAA CTTCAATAAA   16320

GCTGTAGCTG ACGCTAAAAA CACAGGCAAT TATGATGAAG TGAAAAAAGC TCAGAAAGAT   16380

CTTGAAAAAT CTCTAAGGAA ACGAGAGCAT TTAGAGAAAG AAGTAGAGAA AAAATTGGAG   16440

AGCAAAAGCG GCAACAAAAA TAAAATGGAA GCAAAAGCTC AAGCTAACAG CCAAAAAGAT   16500

GAGATTTTTG CGTTGATCAA TAAAGAGGCT AATAGAGACG CAAGAGCAAT CGCTTACGCT   16560

CAGAATCTTA AAGGCATCAA AAGGGAATTG TCTGATAAAC TTGAAAATGT CAACAAGAAT   16620

TTGAAAGACT TTGATAAATC TTTTGATGAA TTCAAAAATG GCAAAAATAA GGATTTCAGC   16680

AAGGCAGAAG AAACACTAAA AGCCCTTAAA GGTTCGGTGA AAGATTTAGG TATCAATCCA   16740

GAATGGATTT CAAAAGTTGA AAACCTTAAT GCAGCTTTGA ATGAATTCAA AAATGGCAAA   16800

AATAAGGATT TCAGCAAGGT AACGCAAGCA AAAAGCGACC TTGAAAATTC CGTTAAAGAT   16860

GTGATCATCA ATCAAAAGGT AACGGATAAA GTTGATAATC TCAATCAAGC GGTATCAGTG   16920

GCTAAAGCAA CGGGTGATTT CAGTAGGGTA GAGCAAGCGT TAGCCGATCT CAAAAATTTC   16980

TCAAGGAGC AATTGGCCCA ACAAGCTCAA AAAATGAAA GTCTCAATGC TAGAAAAAAA    17040

TCTGAAATAT ATCAATCCGT TAAGAATGGT GTGAATGGAA CCCTAGTCGG TAATGGGTTA   17100

TCTCAAGCAG AAGCCACAAC TCTTTCTAAA AACTTTCGG ACATCAAGAA AGAGTTGAAT    17160

GCAAAACTTG GAAATTTCAA TAACAATAAC AATAATGGAC TCAAAAACGA ACCCATTTAT   17220
```

```
GCTAAAGTTA ATAAAAAGAA AGCAGGGCAA GCAGCTAGCC TTGAAGAACC CATTTACGCT    17280

CAAGTTGCTA AAAAGGTAAA TGCAAAAATT GACCGACTCA ATCAAATAGC AAGTGGTTTG    17340

GGTGTTGTAG GGCAAGCAGC GGGCTTCCCT TTGAAAAGGC ATGATAAAGT TGATGATCTC    17400

AGTAAGGTAG GGCTTTCAAG GAATCAAGAA TTGGCTCAGA AAATTGACAA TCTCAATCAA    17460

GCGGTATCAG AAGCTAAAGC AGGTTTTTTT GGCAATCTAG AGCAAACGAT AGACAAGCTC    17520

AAAGATTCTA CAAAACACAA TCCCATGAAT CTATGGGTTG AAAGTGCAAA AAAAGTACCT    17580

GCTAGTTTGT CAGCGAAACT AGACAATTAC GCTACTAACA GCCACATACG CATTAATAGC    17640

AATATCAAAA ATGGAGCAAT CAATGAAAAA GCGACCGGCA TGCTAACGCA AAAAAACCCT    17700

GAGTGGCTCA AGCTCGTGAA TGATAAGATA GTTGCGCATA ATGTAGGAAG CGTTCCTTTG    17760

TCAGAGTATG ATAAAATTGG CTTCAACCAG AAGAATATGA AAGATTATTC TGATTCGTTC    17820

AAGTTTTCCA CCAAGTTGAA CAATGCTGTA AAAGACACTA ATTCTGGCTT TACGCAATTT    17880

TTAACCAATG CATTTTCTAC AGCATCTTAT TACTGCTTGG CGAGAGAAAA TGCGGAGCAT    17940

GGAATCAAGA ACGTTAATAC AAAAGGTGGT TTCCAAAAAT CTTAAAGGAT TAAGGAATAC    18000

CAAAAACGCA AAAACCACCC CTTGCTAAAA GCGAGGGGTT TTTTAATACT CCTTAGCAGA    18060

AATCCCAATC GTCTTTAGTA TTTGGGATGA ATGCTACCAA TTCATGGTAT CATATCCCCA    18120

TACATTCGTA TCTAGCGTAG GAAGTGTGCA AAGTTACGCC TTTGGAGATA TGATGTGTGA    18180

GACCTGTAGG GAATGCGTTG GAGCTCAAAC TCTGTAAAAT CCCTATTATA GGGACACAGA    18240

GTGAGAACCA AACTCTCCCT ACGGGCAACA TCAGCCTAGG AAGCCCAATC GTCTTTAGCG    18300

GTTGGGCACT TCACCTTAAA ATATCCCGAC AGACACTAAC GAAAGGCTTT GTTCTTTAAA    18360

GTCTGCATGG ATATTTCCTA CCCCAAAAAG ACTTAACCCT TTGCTTAAAA TTAAGTTTGA    18420

TTGTGCTAGT GGGTTCGTGC TATAGTGCGA AAATTAATTA AGGGTTATAA AGAGAGCATA    18480

AACTAGAAAA AACAAGTAGC TATAACAAAG ATCAAGTTCA AAAAATCATA GAGCTTTTAG    18540

AGCAAATTGA TCGCGCTCTT AACCAAAGAA AAATCAGAAA AACCATAGGA ATTATCACAC    18600

CTTATAATGC CCAAAAAAGA CGCTTGCGAT CAGAAGTGGA AAAATACGGC TTCAAGAATT    18660

TTGATGAGCT CAAAATAGAC ACTGTGGATG CCTTTCAAGG TGAAGAGGCA GATATTATTA    18720

TTTATTCCAC CGTGAAAACT TGTGGTAATC TTTCTTTCTT GCTAGATTCT AAACGCTTGA    18780

ATGTGGCTAT TTCTAGGGCA AAAGAAAATC TCATTTTTGT GGGTAAAAAG TCTTTCTTTG    18840

AGAATTTATG AAGCGATGAG AAGAATATCT TTAGCGCTAT TTTGCAAGTC TGTAGATAGG    18900

TAATCTTTTC CAAAGATAAT CATTAGACAT TCTTCGCTTC AAAACGCTTT CATAAATCTC    18960

TCTAAAGCGC TTTATAATCA ACACAATACC CTTATAGTGT GAGCTATAGC CCCTTTTTGG    19020

GAATTGAGTT ATTTTGACTT TAAATTTTTA TTAGCGTTAC AATTTGAGCC ATTCTTTAGC    19080

TTGTTTTTCT AGCCAGATCA CATCGCCGCT CGCATGAAAT TCCACTTTAG GGAATGCGTG    19140

TGCATTTTTT TTAAGGGCGT ATTTTTGCTG CAAATATCCT ACAATAGCAT CGCCCGAATG    19200

GATGAGTAGG GGGGGTGTTG AAAGGGCAAA ATGCTCCATA AAATAGCCCT CAATTTTTTG    19260

AGCGATTAAG GGAAAATGCG TGCAACCTAA AATAATCACT TCGGGAAAAT CTTTAAGGGA    19320

GTGAAATAAT AACGCATGCA AGTTTCTAAC AATTCGCCCT CTAAAATACT TTCTTCAATC    19380

AAAGGCACAA AAAGAGAAGT GGCTAAATGC GAAACATTCA AATAGCCTTG TTGTTTCAGG    19440

GCATTGTCAT AAGCGTTGGA TTGGATCGTC GCTTTTGTCC CTAGCACTAA AATAGGGGCG    19500

TTTTTATCTT TTACTTGTCG CTTGATCGCT AAAATGCTTG GCTCAATCAC GCCCACAATA    19560

GGGATTTTGG AATGCTTTTG CATCTCTTCT AAAGCTAGAG CGCTCGCTGT GTTGCATGCC    19620
```

-continued

```
ACAATCAATA ATTCAATCTG GTGCGGTTTG AAAAAATCCA AAGCCTCTAA GCCAAATTGC       19680

TTGATCGTAG TGGGGTCTTT AGTGCCATAA GGCACTCTAG CCGTATCGCC ATAATAGATG       19740

ATTTCATCAA ATAATTGCGC TTTTAAAAGG CTTTTTAAAA CGCTAAACCC TCCCACACCG       19800

CTATCAAAAA CGCCTATTTT CATGACACTT TTTTAATTTA ATGGGATTAA TTAGGGATTT       19860

TATTTTTCAT TCATTAAGTT TAAAAATTCT TCATTGTCCT TAGTTTGTTG CATTTTAGAA       19920

TAGACAAAGC TT                                                          19932
```

(2) INFORMATION FOR SEQ ID NO:26:

(i) SEQUENCE CHARACTERISTICS:
        (A) LENGTH: 396 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Leu Leu Phe Arg Leu Pro Thr Lys Ala Ile Arg Lys Arg Leu Lys Glu
 1               5                  10                  15

Thr Tyr Phe Thr Met Gln Lys Val Leu Thr Gln Ile Lys His Gln Glu
             20                  25                  30

Lys Tyr His Tyr Leu Asn Glu Cys Asn Ser Gln Ser Leu Gln Met Ala
         35                  40                  45

Leu Arg Gln Leu Val Ser Ala Tyr Asp Asn Phe Phe Ser Lys Arg Ala
     50                  55                  60

Arg Tyr Pro Lys Phe Lys Ser Lys Lys Ala Lys Gln Ser Phe Ala
 65                  70                  75                  80

Ile Pro Gln Asn Ile Glu Ile Lys Thr Glu Thr Gln Thr Ile Ala Leu
                 85                  90                  95

Pro Lys Phe Lys Glu Gly Ile Lys Ala Lys Leu His Arg Glu Leu Pro
            100                 105                 110

Lys Asp Ser Val Ile Lys Gln Ala Phe Ile Ser Cys Ile Ala Gly Gln
        115                 120                 125

Tyr Phe Cys Ser Ile Ser Tyr Glu Thr Lys Glu Pro Ile Pro Lys Pro
    130                 135                 140

Thr Ile Ile Lys Lys Ala Val Gly Leu Asp Met Gly Leu Arg Thr Leu
145                 150                 155                 160

Ile Val Thr Ser Asp Lys Ile Glu Tyr Pro His Ile Arg Phe Tyr Gln
                165                 170                 175

Lys Leu Glu Lys Lys Leu Thr Lys Ala Glu Arg Arg Leu Ser Lys Lys
            180                 185                 190

Val Lys Gly Ser Asn Asn Arg Lys Lys Gln Ala Lys Val Ala Arg
        195                 200                 205

Leu His Leu Ala Cys Ser Asn Thr Arg Asp Asp Tyr Leu His Lys Ile
    210                 215                 220

Ser Asn Glu Ile Thr Asn Gln Tyr Asp Leu Ile Gly Val Glu Thr Leu
225                 230                 235                 240

Asn Val Lys Gly Leu Met Arg Thr Tyr His Ser Lys Ser Leu Ala Asn
                245                 250                 255

Ala Ser Trp Gly Lys Phe Leu Thr Met Leu Lys Tyr Lys Ala Gln Arg
            260                 265                 270

Lys Ala Lys Thr Leu Leu Gly Ile Asp Arg Phe Phe Pro Ser Ser Gln
        275                 280                 285

Leu Cys Ser Tyr Cys Gly Phe Asn Thr Gly Lys Lys His Glu Asn Ile
```

```
                290                 295                 300
    Thr Lys Phe Thr Cys Pro His Cys Asn Ile Thr His His Arg Asp Tyr
    305                 310                 315                 320

Asn Ala Ser Val Asn Ile Arg Asn Tyr Ala Leu Gly Met Leu Asp Asp
                    325                 330                 335

Arg His Lys Ile Lys Ile Asp Lys Ser Arg Val Gly Ile Ile Arg Thr
                    340                 345                 350

Asp Tyr Ala His Tyr Thr Asp Glu Arg Ile Lys Ala Cys Gly Ala Ser
                    355                 360                 365

Ser Asn Gly Val Ile Ser Lys Tyr Gly Asn Ile Leu Asp Leu Ala Ser
                    370                 375                 380

Tyr Gly Ala Met Lys Gln Glu Lys Ala Gln Ser Leu
    385                 390                 395

(2) INFORMATION FOR SEQ ID NO:27:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Glu Thr Leu Ile Leu Leu Ala Val Leu Ser Asp Leu Leu Pro Lys
    1               5                   10                  15

Pro Leu Pro Thr Lys Ala Asp Pro Met Phe Leu Ile Leu Ser Asn Pro
                    20                  25                  30

Phe Phe Ser Thr Ser Ser Ala Ile Lys Phe Leu Ile Leu Ser Ile Gly
                    35                  40                  45

Lys Leu Asn Phe Phe Pro Asn Ala Ser Leu Ser Pro Ile Ile Asn Ile
        50                  55                  60

Arg Lys Asn Lys Lys Phe Asn Ile Ile Glu Asn Lys Ser Leu Asp Lys
    65                  70                  75                  80

Pro Val Lys Arg Phe Val Pro Pro Asn Lys Glu Ala Lys Ile Phe Pro
                    85                  90                  95

Met Ile Ser Pro Phe Ile Phe Gly Cys Val Ser Ser Cys Leu Phe Leu
                    100                 105                 110

Ser Leu Met Arg Val Leu Val Gly Ser Ile Ser Gln
                115                 120

(2) INFORMATION FOR SEQ ID NO:28:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Gly Tyr Lys Asn Tyr Lys Met Leu Ala Lys Ile Val Phe Ser Ser Leu
    1               5                   10                  15

Val Ala Phe Gly Val Leu Ser Ala Asn Val Glu Gln Phe Gly Ser Phe
                    20                  25                  30

Phe Asn Glu Ile Lys Lys Glu Gln Glu Val Ala Ala Lys Glu Asp
                35                  40                  45

Ala Leu Lys Ala Arg Lys Lys Leu Leu Asn Asn Thr His Asp Phe Leu
```

```
            50                  55                  60
    Glu Asp Leu Ile Phe Arg Lys Gln Lys Ile Lys Glu Leu Met Asp His
    65                  70                  75                  80

Arg Ala Lys Val Leu Ser Asp Leu Glu Asn Lys Tyr Lys Lys Glu Lys
                    85                  90                  95

Glu Ala Leu Glu Lys Glu Thr Arg Gly Lys Ile Leu Thr Ala Lys Ser
                    100                 105                 110

Lys Ala Tyr Gly Asp Leu Glu Gln Ala Leu Lys Asp Asn Pro Leu Tyr
                    115                 120                 125

Lys Lys Leu Leu Pro Asn Pro Tyr Ala Tyr Val Leu Asn Gln Glu Thr
    130                 135                 140

Phe Thr Lys Glu Asp Lys Glu Arg Leu Ser Tyr Tyr Pro Gln Val
    145                 150                 155                 160

Lys Thr Ser Ser Ile Phe Glu Lys Thr Thr Ala Thr Thr Lys Asp Lys
                    165                 170                 175

Ala Gln Ala Leu Leu Gln Met Gly Val Phe Ser Leu Asp Glu Glu Gln
                    180                 185                 190

Asn Lys Lys Ala Ser Arg Leu Ala Leu Ser Tyr Lys Gln Ala Ile Glu
                    195                 200                 205

Glu Tyr Ser Asn Asn Ile Ser Asn Leu Leu Ser Arg Lys Glu Leu Asp
    210                 215                 220

Asn Ile Asp Tyr Tyr Leu Gln Leu Glu Arg Asn Lys Phe Asp Ser Lys
    225                 230                 235                 240

Ala Lys Asp Ile Ala Gln Lys Ala Thr Asn Thr Leu Ile Phe Asn Ser
                    245                 250                 255

Glu Arg Leu Ala Phe Ser Met Ala Ile Asp Lys Ile Asn Glu Lys Tyr
                    260                 265                 270

Leu Lys Gly Tyr Glu Ala Phe Ser Asn Leu Leu Lys Asn Val Lys Asp
                    275                 280                 285

Asp Val Glu Leu Asn Thr Leu Thr Lys Asn Phe Thr Asn Gln Lys Leu
                    290                 295                 300

Ser Phe Ala Gln Lys Gln Lys Leu Cys Leu Leu Val Leu Asp Ser Phe
    305                 310                 315                 320

Asn Phe Asp Thr Gln Ser Lys Lys Ser Ile Leu Lys Lys Thr Asn Glu
                    325                 330                 335

Tyr Asn Ile Phe Val Asp Ser Asp Pro Met Met Ser Asp Lys Thr Thr
                    340                 345                 350

Met Gln Lys Glu His Tyr Lys Ile Phe Asn Phe Lys Thr Val Val
                    355                 360                 365

Ser Ala Tyr Arg Asn Asn Val Ala Lys Asn Asn Pro Phe Glu
    370                 375                 380
```

(2) INFORMATION FOR SEQ ID NO:29:

(i) SEQUENCE CHARACTERISTICS:
      (A) LENGTH: 312 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:29:

```
    Ile Gly Lys Glu Thr Leu Leu Lys Ser Ile Phe Lys Lys Leu Gly Ser
    1               5                   10                  15

Val Ala Leu Tyr Ser Leu Val Val Tyr Gly Gly Leu Asn Ala Ile Asn
                    20                  25                  30
```

```
Thr Ala Leu Leu Pro Ser Glu Tyr Lys Glu Leu Val Ala Leu Gly Phe
        35                  40                  45

Lys Lys Ile Lys Thr Leu Tyr Gln Arg His Asp Asp Lys Glu Ile Thr
50                  55                  60

Lys Glu Glu Lys Glu Phe Ala Thr Asn Ala Leu Arg Glu Lys Leu Arg
65                  70                  75                  80

Asn Asp Arg Ala Arg Ala Glu Gln Ile Gln Lys Asn Ile Glu Ala Phe
                85                  90                  95

Glu Lys Lys Asn Asn Ser Ser Val Gln Lys Lys Ala Ala Lys His Lys
                100                 105                 110

Gly Leu Gln Glu Leu Asn Glu Ile Asn Ala Asn Pro Leu Asn Asp Asn
        115                 120                 125

Pro Asn Gly Asn Ser Ser Thr Glu Thr Lys Ser Asn Lys Asp Asp Asn
    130                 135                 140

Phe Asp Glu Met Ile Asn Lys Val Asn Glu Ser Phe Val Lys Pro Ala
145                 150                 155                 160

Ala Pro Leu Val Pro Asp Glu Trp Arg Thr Pro Glu Ile Glu Ile Ile
                165                 170                 175

Ile Asn Glu Cys Ile Ile Ser Ser Asn Asp Tyr Asp Gly Leu Arg Lys
                180                 185                 190

Cys Leu Ile Lys Asp Ile Lys Asp Gln Lys Ile Leu Ala Pro Leu Leu
        195                 200                 205

Glu Lys Ile Gln Glu Ile Glu Thr Glu Asn Asn Lys Phe Ser Arg Gln
    210                 215                 220

His Leu Ser Gly Leu Lys Leu Thr Leu Asn Asn Ser Asn Asn Arg Thr
225                 230                 235                 240

Phe Leu Ile Ala Ser Cys Ala Ile Cys Glu Lys Arg Lys Lys Glu Met
                245                 250                 255

Glu Gln Glu Asn Asn Tyr Gln Asp Thr Thr Asn Ala Ser Glu Phe Gly
                260                 265                 270

Thr Thr Asp Thr Lys Glu Asn Glu Ala Lys Asp Thr Ala Phe Ser Asn
        275                 280                 285

Asn Arg Ser Lys Ser Glu Leu Pro Asn Ser Val Ile Asn Gln Ile Glu
    290                 295                 300

Gln Ser Ile Ala His Gly Lys Lys
305                 310
```

(2) INFORMATION FOR SEQ ID NO:30:

(i) SEQUENCE CHARACTERISTICS:
        (A) LENGTH: 131 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Val Cys Tyr Cys Glu Met Leu Pro Thr Lys Thr Arg Ile Arg Asp Lys
1               5                   10                  15

Asn Lys Gln Glu Leu Thr Gln Pro Lys Ile Lys Gly Leu Ile Met Gly
                20                  25                  30

Lys Ile Leu Ala Ser Leu Leu Gly Gly Gly Thr Asn Leu Phe Thr Gly
        35                  40                  45

Leu Ser Ser Asp Leu Phe Ser Met Ile Leu Asn Phe Leu Phe Phe Leu
    50                  55                  60
```

-continued

```
Met Leu Met Met Gly Leu Asn Glu Ala Leu Gly Lys Lys Phe Asn Leu
 65              70                  75                  80

Pro Met Asp Met Ile Lys Asn Phe Met Ala Glu Val Leu Lys Asn Gly
             85                  90                  95

Phe Asp Ser Ile Lys Asn Met Gly Ser Ala Leu Val Gly Asn Gly Phe
            100                 105                 110

Gly Ser Ser Lys Ser Asp Lys Thr Ala Asn Lys Met Ser Val Ser Gln
            115                 120                 125

Val Arg Leu
        130
```

(2) INFORMATION FOR SEQ ID NO:31:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

```
Asn Ile Tyr Tyr Phe Met Leu Leu Tyr Lys Phe Thr Ala Leu Asn Tyr
  1              5                  10                  15

Phe Phe Lys Asn Gln Asn Gly Thr Asn Gln Ile Ser Lys Leu Lys Gln
             20                  25                  30

Asn Phe Leu Gln Phe Lys Tyr Ser Phe Asn Lys His Leu Asp Lys Tyr
             35                  40                  45

Ser Leu Tyr Tyr Arg Leu Phe Asn Ile Ser Ser Ile Val Ile Gly Phe
 50                  55                  60

Leu Ile Gly Leu Phe Ser Tyr Gly Ala Gly Val Ile Leu Val Tyr Pro
 65                  70                  75                  80

Ile Leu Phe Leu Phe Ala Leu Ile Ile Lys Pro Ser Phe Phe Tyr Tyr
             85                  90                  95

Thr Thr Tyr Leu Leu Leu Leu Val Ser Leu Ser Ile Ile Ser Lys Tyr
            100                 105                 110

Tyr Leu Leu Ser His Ala Lys Phe Thr Met Lys Leu Ile Ile Leu Met
            115                 120                 125

Thr Gln Trp Gln Asn Trp Phe Leu
            130                 135
```

(2) INFORMATION FOR SEQ ID NO:32:

(i) SEQUENCE CHARACTERISTICS:
        (A) LENGTH: 79 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

```
Ile Lys Ser Arg Ser Tyr Ser Val Met Phe Phe Leu Leu Val Cys Gly
  1              5                  10                  15

Leu Leu Val Phe Phe Lys Phe Leu Leu Arg Leu Phe Leu Tyr Asn Arg
             20                  25                  30

Phe Val Phe Phe Arg Trp Lys Thr Pro Leu Phe Phe Asn Arg Cys Phe
             35                  40                  45

Leu Phe Phe Val Trp His Lys Gln Thr Asn Arg Trp Phe Val Leu Tyr
 50                  55                  60
```

```
    His Met Leu Val Ser Ala Ser Gly Val Phe Phe Glu Ile Trp Ser
    65                  70                  75
```

(2) INFORMATION FOR SEQ ID NO:33:

(i) SEQUENCE CHARACTERISTICS:
        (A) LENGTH: 241 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

```
    Ser Tyr Cys Gln Met Lys Thr Leu Val Lys Asn Thr Ile Ser Ser Phe
    1               5                   10                  15

Leu Leu Leu Ser Val Leu Met Gly Glu Asp Ile Thr Ser Gly Leu Lys
                    20                  25                  30

Gln Leu Asp Ser Thr Tyr Gln Glu Thr Asn Gln Val Leu Lys Asn
                35                  40                  45

Leu Asp Glu Ile Phe Ser Thr Thr Ser Pro Ser Ala Asn Asn Glu Ile
    50                  55                  60

Gly Gln Glu Asp Ala Leu Asn Ile Lys Lys Ala Ile Ala Leu Arg
    65                  70                  75                  80

Gly Asp Leu Ala Leu Leu Lys Ala Asn Phe Glu Ala Asn Glu Leu Phe
                    85                  90                  95

Phe Ile Ser Glu Asp Val Ile Phe Lys Thr Tyr Met Ser Ser Pro Glu
                    100                 105                 110

Leu Leu Leu Thr Tyr Met Lys Ile Asn Pro Leu Asp Gln Asn Thr Ala
                    115                 120                 125

Glu Gln Gln Cys Gly Ile Ser Asp Lys Val Leu Val Leu Tyr Cys Glu
    130                 135                 140

Gly Lys Leu Lys Ile Glu Gln Glu Lys Gln Asn Ile Arg Glu Arg Leu
    145                 150                 155                 160

Glu Thr Ser Leu Lys Ala Tyr Gln Ser Asn Ile Gly Gly Thr Ala Ser
                        165                 170                 175

Leu Ile Thr Ala Ser Gln Thr Leu Val Glu Ser Leu Lys Asn Lys Asn
                    180                 185                 190

Phe Ile Lys Gly Ile Arg Lys Leu Met Leu Ala Gln Asn Lys Val Phe
                    195                 200                 205

Leu Asn Tyr Leu Glu Glu Leu Asp Ala Leu Glu Arg Ser Leu Glu Gln
                    210                 215                 220

Ser Lys Arg Gln Tyr Leu Gln Glu Arg Gln Ser Ser Lys Ile Ile Val
    225                 230                 235                 240

Lys
```

(2) INFORMATION FOR SEQ ID NO:34:

(i) SEQUENCE CHARACTERISTICS:
        (A) LENGTH: 131 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
    Phe Phe Phe Lys His Gly Arg Pro Phe Gly Ile Ile Glu Thr Phe Thr
    1               5                   10                  15

Leu Ala Pro Thr Lys Cys Pro Tyr Leu Asp Gly Leu Lys Ile Ser Ala
```

```
                      20                  25                  30
        Cys Leu Met Glu Gln Val Ile Gln Asn Tyr Arg Met Ile Val Ala Leu
                     35                  40                  45

Ile Gln Asn Lys Leu Ser Asp Ala Asp Phe Gln Asn Ile Ala Tyr Leu
         50                  55                  60

Asn Gly Ile Asn Gly Glu Ile Lys Thr Leu Lys Gly Ser Val Asp Leu
         65                  70                  75                  80

Asn Ala Leu Ile Glu Val Ala Ile Leu Asn Ala Glu Asn His Leu Asn
                     85                  90                  95

Tyr Ile Glu Asn Leu Glu Lys Lys Ala Asp Leu Trp Glu Glu Gln Leu
                    100                 105                 110

Lys Leu Glu Arg Glu Thr Thr Ala Arg Asn Ile Ala Ser Ser Lys Val
                    115                 120                 125

Ile Val Lys
                    130
```

(2) INFORMATION FOR SEQ ID NO:35:

(i) SEQUENCE CHARACTERISTICS:
        (A) LENGTH: 170 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
        Gln Gly Gly Phe Leu Gln Val Gln Thr Ser Cys Leu Ala Ser Trp Lys
          1               5                  10                  15

Gly Ile Gln Ala Ala Leu Ser Ala Leu Gly Gly Asn Val Lys Met Ile
                     20                  25                  30

Val Glu Lys Gln Lys Ile Asn Thr Gln Thr Glu Ile Gln Asn Met Gln
                     35                  40                  45

Ile Ala Leu Gln Lys Asn Asn Glu Met Ile Lys Leu Lys Met Asn Gln
         50                  55                  60

Gln Asn Ala Leu Leu Glu Ala Leu Lys Asn Ser Phe Glu Pro Arg Val
         65                  70                  75                  80

Thr Leu Lys Thr Gln Met Glu Ile Ser Gln Ala Leu Gly Ser Ser Ser
                     85                  90                  95

Asp Asn Ala Gln Tyr Ile Ala Tyr Asn Thr Ile Gly Ile Lys Ala Phe
                    100                 105                 110

Glu Glu Thr Leu Lys Gly Phe Glu Thr Trp Leu Lys Thr Ala Met Gln
                    115                 120                 125

Lys Ala Thr Leu Ile Asp Tyr Asn Ser Leu Thr Gly Gln Ala Leu Phe
                    130                 135                 140

Gln Ser Ala Ile Tyr Ala Pro Ala Leu Ser Phe Phe Ser Ser Met Gly
        145                 150                 155                 160

Asp His Leu Glu Ser Leu Lys His Ser Leu
                    165                 170
```

(2) INFORMATION FOR SEQ ID NO:36:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Ser Glu Glu Arg Asp Val Lys Cys Phe Leu Ser Ile Phe Ser Phe Leu
1               5                   10                  15

Thr Phe Cys Gly Leu Ser Leu Asn Gly Thr Glu Val Val Ile Thr Leu
            20                  25                  30

Glu Pro Ala Leu Lys Ala Ile Gln Ala Asp Ala Gln Ala Lys Gln Lys
        35                  40                  45

Thr Ala His Ala Glu Leu Lys Ala Ile Glu Ala Gln Ser Ser Ala Lys
    50                  55                  60

Glu Lys Ala Ile Gln Ala Gln Ile Glu Gly Leu Arg Thr Gln Leu
65                  70                  75                  80

Ala Thr Met Ser Ala Met Leu Lys Gly Ala Asn Gly Val Ile Asn Gly
            85                  90                  95

Val Asn Gly Met Thr Gly Gly Phe Phe Ala Gly Ser Asp Ile Leu Leu
            100                 105                 110

Gly Val Met Glu Gly Tyr Ser Ser Gly Ala
            115                 120

(2) INFORMATION FOR SEQ ID NO:37:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Arg Pro Met Ser Val Ser Met Pro Thr Val Tyr Ala Lys Tyr Gln Ala
1               5                   10                  15

Leu Arg Thr Asn Ala Leu Thr Ser Gly Val Asn Pro Ile Thr Thr Pro
            20                  25                  30

Ala Cys Pro Ile Gly Asp Lys Val Leu Ala Val Tyr Cys Tyr Ala Glu
        35                  40                  45

Lys Val Ala Glu Ile Leu Arg Glu Tyr Tyr Ile Glu Phe Val Lys Asn
    50                  55                  60

Asn Thr Asn Leu Leu Gln Asn Ala Ser Gln Met Ile Leu Asn Gln Ser
65                  70                  75                  80

Gly Leu Ala Thr Ser Thr Tyr Asp Thr Gln Ala Ile Ser Asn Ile Ser
            85                  90                  95

Ser Leu Tyr Asn Tyr Asn Ile Val Ala Asn Lys Ser Phe Leu Lys Ser
            100                 105                 110

His Leu Thr Tyr Leu Asp Tyr Ile Lys Asp Lys Leu Lys Gly Gln Lys
            115                 120                 125

Asp Ser Tyr Leu Thr Glu Arg Val Gln Thr Lys Ile Ile Val Lys
    130                 135                 140

(2) INFORMATION FOR SEQ ID NO:38:

(i) SEQUENCE CHARACTERISTICS:
        (A) LENGTH: 159 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Ile Ile Phe Cys Arg Leu Leu Ile Gly Ser Phe Leu Asn His Leu Asn

```
                 1               5                  10                 15
              Thr Ser Gly Val Ala Gly Pro Phe Ala Gly Ile Val Ala Gly Ala Met
                              20                 25                 30
              Thr Ala Ala Ile Ile Pro Ile Ile Val Gly Phe Thr Asn Pro Gln Met
                              35                 40                 45
              Thr Ala Ile Met Thr Gln Tyr Asn Gln Ser Ile Ala Glu Ala Val Ser
                              50                 55                 60
              Met Pro Met Lys Ala Ala Asn Gln Gln Tyr Asn Gln Leu Tyr Gln Gly
              65                           70                 75                 80
              Phe Asn Asp Gln Ser Met Ala Val Gly Asn Asn Ile Leu Asn Ile Ser
                                       85                 90                 95
              Lys Leu Thr Gly Glu Phe Asn Ala Gln Gly Asn Ser Gln Gly Ala Gln
                                  100                105                110
              Ile Gly Ala Val Asn Ser Gln Ile Ala Ser Ile Leu Ala Ser Asn Thr
                                  115                120                125
              Thr Pro Lys Asn Pro Ser Ala Ile Glu Ala Tyr Ala Thr Asn Gln Ile
                                  130                135                140
              Ala Val Pro Ser Val Pro Thr Val Glu Met Met Thr Val Tyr
                                  145                150                155
```

(2) INFORMATION FOR SEQ ID NO:39:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
              Lys Arg Ile Phe Ile Lys Leu Asn Tyr Tyr Leu Leu Gly Val Leu Ser
              1               5                  10                 15
              Leu Ala Cys Leu Gln Ser Val Asn Ala Asp Gln Asn Thr Asp Ile Lys
                              20                 25                 30
              Asp Ile Ser Pro Glu Asp Met Ala Leu Asn Ser Val Gly Leu Val Ser
                              35                 40                 45
              Arg Asp Gln Leu Lys Ile Glu Ile Pro Lys Glu Thr Leu Glu Gln Lys
              50                           55                 60
              Val Ala Ile Leu Asn Asp Tyr Asn Asp Lys Asn Val Asn Ile Lys Phe
              65                           70                 75                 80
              Asp Asp Ile Ser Leu Gly Ser Phe Gln Pro Asn Asp Asn Leu Gly Ile
                                       85                 90                 95
              Asn Ala Met Trp Gly Ile Gln Asn Leu Leu Met Ser Gln Met Met Gly
                                  100                105                110
              Asp Tyr Gly Pro Asn Asn Pro Phe Met Tyr Gly Tyr Ala Pro Thr Tyr
                                  115                120                125
              Ser Asp Ser Ser Phe Leu Pro Pro Ile Leu Gly Tyr
                                  130                135                140
```

(2) INFORMATION FOR SEQ ID NO:40:

(i) SEQUENCE CHARACTERISTICS:
        (A) LENGTH: 261 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

```
Thr Lys Ile Ile Gly Asn Phe Glu Asn Asp Val Leu Thr Ile Leu Asp
1               5                   10                  15

Ser Phe Ser Asn Tyr Leu Phe Glu Leu Lys Glu Glu Leu Asp Phe Ile
            20                  25                  30

Glu Glu Glu Met Glu Gly Glu Ile Thr Glu Gln Asn Leu Thr Thr Leu
        35                  40                  45

Tyr Asp Phe Ser Asn Phe Leu Glu Asp His Val Asn Val Phe Tyr Glu
    50                  55                  60

Asn Val Leu Asn Ile Asp Asp Val Lys Thr Glu His Leu Tyr Ser Gly
65                  70                  75                  80

Leu Ile Asp Ser Leu Asn Ala Asn Leu His Phe Val Lys Ser Phe Leu
                85                  90                  95

Ser Asn Gln Asp Leu Asp Phe Arg Phe Phe Lys Glu Ile Asn Asp Gly
            100                 105                 110

Gln Asp Pro Gln Lys Thr Leu Ser Arg Leu Ile Pro Leu Gln Ser Gly
        115                 120                 125

Lys Asn Asp Ala Ser Ser Phe Lys Ala Asn Asn Ser Phe Val Ser Leu
    130                 135                 140

Val Tyr Val Tyr Ala Tyr Phe Met Leu Glu Thr Ile Met Gln Ser Tyr
145                 150                 155                 160

Arg Ile Leu Arg Leu Leu Glu Lys Pro Ile Asn Asn Asn Ile Ser Glu
                165                 170                 175

Asp Met Gln Ser Asp Ile Glu Ile Phe Phe Val Gln Ala Asn Phe Leu
            180                 185                 190

Glu Tyr Tyr Val Gln Asn Lys Ile Tyr Pro Lys Asn His Ala Tyr Asp
        195                 200                 205

Phe Met His Leu Ile Met Asp Ser Ile Ile Pro Asn Trp Ile Gln Ile
    210                 215                 220

Asp Met Ser Val Glu Ala Lys Lys Glu Leu Phe Glu Lys Tyr Phe
225                 230                 235                 240

Gln Asn Ile Asp Glu Val Thr Asn Lys Met Leu Asp Gln Lys Asn Gln
                245                 250                 255

Asn Lys Asn Asn Asp
            260
```

(2) INFORMATION FOR SEQ ID NO:41:

(i) SEQUENCE CHARACTERISTICS:
        (A) LENGTH: 263 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

```
Tyr Ala Cys Ser Ala Val Thr Asn Leu Ile Thr Gly Asn Met Asn Leu
1               5                   10                  15

Asp Tyr Pro Ile Thr Gln Leu Ile Asn Ala Phe Gly Lys Asp His Asn
            20                  25                  30

Asp Pro Asn Gly Leu Val Ala Arg Leu Ala Pro Phe Cys Lys Ser Thr
        35                  40                  45

Asn Gly Glu Phe Gln Trp Leu Phe Asp Asn Lys Ala Thr Asp Arg Leu
    50                  55                  60

Asp Phe Ser Lys Thr Ile Ile Gly Val Asp Gly Ser Ser Phe Leu Asp
65                  70                  75                  80
```

```
Asn Asn Asp Val Ser Pro Phe Ile Cys Phe Tyr Leu Phe Ala Arg Ile
            85                  90                  95

Gln Glu Ala Met Asp Gly Arg Arg Phe Val Leu Asp Ile Asp Glu Ala
            100                 105                 110

Trp Lys Tyr Leu Gly Asp Pro Lys Val Ala Tyr Phe Val Arg Asp Met
            115                 120                 125

Leu Lys Thr Ala Arg Lys Arg Asn Ala Ile Val Arg Leu Ala Thr Gln
            130                 135                 140

Ser Ile Thr Asp Leu Leu Ala Cys Pro Ile Ala Asp Thr Ile Arg Glu
145                 150                 155                 160

Gln Cys Pro Thr Lys Ile Phe Leu Arg Asn Asp Gly Gly Asn Leu Ser
            165                 170                 175

Asp Tyr Gln Arg Leu Ala Asn Val Thr Glu Lys Glu Phe Glu Ile Ile
            180                 185                 190

Thr Lys Gly Leu Asp Arg Lys Ile Leu Tyr Lys Gln Asp Gly Ser Pro
            195                 200                 205

Ser Val Ile Ala Ser Phe Asn Leu Arg Gly Ile Pro Lys Glu Tyr Leu
            210                 215                 220

Lys Ile Leu Ser Thr Asp Thr Val Phe Val Lys Glu Ile Asp Lys Ile
225                 230                 235                 240

Ile Gln Asn His Ser Ile Ile Asp Lys Tyr Gln Ala Leu Arg Gln Met
            245                 250                 255

Tyr Gln Gln Ile Glu Glu Tyr
            260

(2) INFORMATION FOR SEQ ID NO:42:

(i) SEQUENCE CHARACTERISTICS:
        (A) LENGTH: 683 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

Ser Gly Ile Ser Ile Lys Arg Glu Val Phe Val Ala Ser Lys Gln Ala
    1               5                   10                  15

Asp Glu Gln Lys Lys Leu Ile Ile Glu Gln Glu Val Gln Lys Arg Gln
                    20                  25                  30

Phe Gln Lys Ile Glu Glu Leu Lys Ala Asp Met Gln Lys Gly Val Asn
                    35                  40                  45

Pro Phe Phe Lys Val Leu Phe Asp Gly Gly Asn Arg Leu Phe Gly Phe
    50                  55                  60

Pro Glu Thr Phe Ile Tyr Ser Ser Ile Phe Ile Leu Phe Val Thr Ile
    65                  70                  75                  80

Val Leu Ser Val Ile Leu Phe Gln Ala Tyr Glu Pro Val Leu Ile Val
                    85                  90                  95

Ala Ile Val Ile Val Leu Val Ala Leu Gly Phe Lys Lys Asp Tyr Arg
                    100                 105                 110

Leu Tyr Gln Arg Met Glu Arg Ala Met Lys Phe Lys Lys Pro Phe Leu
                    115                 120                 125

Phe Lys Gly Val Lys Asn Lys Ala Phe Met Ser Ile Phe Ser Met Lys
                    130                 135                 140

Pro Ser Lys Glu Met Ala Asn Asp Ile His Leu Asn Pro Asn Arg Glu
    145                 150                 155                 160
```

```
Asp Arg Leu Val Ser Ala Ala Asn Ser Tyr Leu Ala Asn Asn Tyr Glu
            165                 170                 175

Cys Phe Leu Asp Asp Gly Val Ile Leu Thr Asn Asn Tyr Ser Leu Leu
            180                 185                 190

Gly Thr Ile Lys Leu Gly Gly Ile Asp Phe Leu Thr Thr Ser Lys Lys
            195                 200                 205

Asp Leu Ile Glu Leu His Ala Ser Ile Tyr Ser Val Phe Arg Asn Phe
            210                 215                 220

Val Thr Pro Glu Phe Lys Phe Tyr His Thr Ile Lys Lys Lys Ile
225                 230                 235                 240

Val Ile Asp Glu Thr Asn Arg Asp Tyr Gly Leu Ile Phe Ser Asn Asp
                245                 250                 255

Phe Met Arg Ala Tyr Asn Glu Lys Gln Lys Arg Glu Ser Phe Tyr Asp
            260                 265                 270

Ile Ser Phe Phe Leu Thr Ile Glu Gln Asp Leu Leu Asp Thr Leu Asn
            275                 280                 285

Glu Pro Val Met Asn Lys Lys His Phe Ala Asp Asn Asn Phe Glu Glu
            290                 295                 300

Phe Gln Arg Ile Ile Arg Ala Lys Leu Glu Asn Phe Lys Asp Arg Ile
305                 310                 315                 320

Glu Leu Ile Glu Glu Leu Leu Ser Lys Tyr His Pro Thr Arg Leu Lys
            325                 330                 335

Glu Tyr Thr Lys Asp Gly Val Ile Tyr Ser Lys Gln Cys Glu Phe Tyr
            340                 345                 350

Asn Phe Leu Val Gly Met Asn Glu Ala Pro Phe Ile Cys Asn Arg Lys
            355                 360                 365

Asp Leu Tyr Leu Lys Glu Lys Met His Gly Gly Val Lys Glu Val Tyr
            370                 375                 380

Phe Ala Asn Lys His Gly Lys Ile Leu Asn Asp Asp Leu Ser Glu Lys
385                 390                 395                 400

Tyr Phe Ser Ala Ile Glu Ile Ser Glu Tyr Ala Pro Lys Ser Gln Ser
            405                 410                 415

Asp Leu Phe Asp Lys Ile Asn Ala Leu Asp Ser Glu Phe Ile Phe Met
            420                 425                 430

His Ala Tyr Ser Pro Lys Asn Ser Gln Val Leu Lys Asp Lys Leu Ala
            435                 440                 445

Phe Thr Ser Arg Arg Ile Ile Ile Ser Gly Gly Ser Lys Glu Gln Gly
            450                 455                 460

Met Thr Leu Gly Cys Leu Ser Glu Leu Val Gly Asn Gly Asp Ile Thr
465                 470                 475                 480

Leu Gly Ser Tyr Gly Asn Ser Leu Val Leu Phe Ala Asp Ser Phe Glu
            485                 490                 495

Lys Met Lys Gln Ser Val Lys Glu Cys Val Ser Ser Leu Asn Ala Lys
            500                 505                 510

Gly Phe Leu Ala Asn Ala Ala Thr Phe Ser Met Glu Asn Tyr Phe Phe
            515                 520                 525

Ala Lys His Cys Ser Phe Ile Thr Leu Pro Phe Ile Phe Asp Val Thr
            530                 535                 540

Ser Asn Asn Phe Ala Asp Phe Ile Ala Met Arg Ala Met Ser Phe Asp
545                 550                 555                 560

Gly Asn Gln Glu Asn Asn Ala Trp Gly Asn Ser Val Met Thr Leu Lys
            565                 570                 575

Ser Glu Ile Asn Ser Pro Phe Tyr Leu Asn Phe His Met Pro Thr Asp
            580                 585                 590
```

```
Phe Gly Ser Ala Ser Ala Gly His Ala Tyr Gly Asn Ile Val Ala Met
            595                 600                 605

Gly Gly Glu Tyr Val Lys Ile Glu Leu Gly Thr Asp Thr Gly Leu Asn
        610                 615                 620

Pro Phe Ala Trp Ala Ala Cys Val Gln Lys Thr Asn Ala Thr Met Glu
625                 630                 635                 640

Gln Lys Gln Thr Ala Ile Ser Val Val Lys Glu Leu Val Lys Asn Leu
                    645                 650                 655

Ala Thr Lys Ser Asp Glu Lys Asp Glu Asn Gly Asn Ser Ile Ser Phe
                660                 665                 670

Ser Leu Ala Asp Ser Asn Thr Leu Ala Ala Gln
            675                 680
```

(2) INFORMATION FOR SEQ ID NO:43:

(i) SEQUENCE CHARACTERISTICS:
        (A) LENGTH: 225 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

```
Ala Leu Ser Leu Ala Ser Ile Leu Ala Arg Val Glu Glu Leu Ala Lys
1               5                   10                  15

Leu Ile Asn Asn Asn Asn Ser Asn Lys Lys Leu Arg Gly Phe Phe
                20                  25                  30

Leu Lys Val Leu Leu Ser Leu Val Val Phe Ser Ser Tyr Gly Leu Ala
            35                  40                  45

Asn Asp Asp Lys Glu Ala Lys Lys Glu Ala Gln Glu Lys Glu Lys Asn
        50                  55                  60

Thr Pro Asn Gly Leu Val Tyr Thr Asn Leu Asp Phe Asp Ser Phe Lys
65                  70                  75                  80

Ala Thr Ile Lys Asn Leu Lys Asp Lys Lys Val Thr Phe Lys Glu Val
                85                  90                  95

Asn Pro Asp Ile Ile Lys Asp Glu Val Phe Asp Phe Val Ile Val Asn
                100                 105                 110

Arg Val Leu Lys Lys Ile Lys Asp Leu Lys His Tyr Asp Pro Val Ile
            115                 120                 125

Glu Lys Ile Phe Asp Glu Lys Gly Lys Glu Met Gly Leu Asn Val Glu
        130                 135                 140

Leu Gln Ile Asn Pro Glu Val Lys Asp Phe Phe Thr Phe Lys Ser Ile
145                 150                 155                 160

Ser Thr Thr Asn Lys Gln Arg Cys Phe Leu Ser Leu Arg Gly Glu Thr
                165                 170                 175

Arg Glu Ile Leu Cys Asp Asp Lys Leu Tyr Asn Val Leu Leu Ala Val
            180                 185                 190

Phe Asn Ser Tyr Asp Pro Asn Asp Leu Leu Lys His Ile Ser Thr Val
        195                 200                 205

Glu Ser Leu Lys Lys Ile Phe Tyr Thr Ile Thr Cys Glu Ala Val Tyr
    210                 215                 220

Leu

225
```

(2) INFORMATION FOR SEQ ID NO:44:

(i) SEQUENCE CHARACTERISTICS:
    (A) LENGTH: 122 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:44:

Phe Gln Phe Glu Arg Lys Arg Met Lys Phe Phe Thr Arg Ile Thr Asp
1               5                   10                  15

Ser Tyr Lys Lys Val Val Val Thr Leu Gly Leu Val Val Thr Thr Asn
            20                  25                  30

Pro Leu Asn Ala Val Ala Ser Pro Thr Glu Gly Val Thr Ala Thr Lys
        35                  40                  45

Gly Leu Val Ile Gln Ile Ile Ser Val Leu Ala Ile Val Gly Gly Cys
    50                  55                  60

Ala Leu Gly Val Lys Gly Ile Ala Asp Ile Trp Lys Ile Ser Asp Asp
65                  70                  75                  80

Ile Lys Arg Gly Gln Ala Thr Val Phe Arg Tyr Ala Gln Pro Ile Ala
                85                  90                  95

Met Leu Ala Val Ala Gly Gly Ile Ile Tyr Leu Ser Thr Lys Phe Gly
            100                 105                 110

Phe Asn Ile Gly Glu Gly Gly Gly Ala Ser
            115                 120

(2) INFORMATION FOR SEQ ID NO:45:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

Ala Phe Val Ile His Lys Ile His Met Gly Asn Lys Met Glu Asn Lys
1               5                   10                  15

Ser Ile Gly Gln Ile Phe Lys Asp Ser Leu Lys Ser Phe Phe Ser
            20                  25                  30

Gly Leu Trp Ser Cys Leu Lys Trp Ser Phe Ile Leu Thr Leu Ile Ser
            35                  40                  45

Leu Gly Leu Phe Leu Leu Val Phe Arg Phe Gln Pro Glu Thr Ile Lys
    50                  55                  60

Lys Tyr Ile Lys Asp Pro Lys Asp Leu Gln Phe Tyr Asn Asp Leu Arg
65                  70                  75                  80

Lys Lys Asn Gly Trp Asp Lys
            85

(2) INFORMATION FOR SEQ ID NO:46:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

Lys Ser Val Met Lys Ile Gly Val Phe Asp Ser Gly Val Gly Gly Phe

-continued

```
         1               5                    10                        15
    Ser Val Leu Lys Ser Leu Leu Lys Ala Gln Leu Phe Asp Glu Ile Ile
                    20                  25                  30

Tyr Tyr Gly Asp Thr Ala Arg Val Pro Tyr Gly Thr Lys Asp Pro Thr
                35                  40                  45

Thr Ile Lys Gln Phe Gly Leu Glu Ala Leu Asp Phe Phe Lys Pro His
            50                  55                  60

Gln Ile Glu Leu Leu Ile Val Ala Cys Asn Thr Ala Ser Ala Leu Ala
    65                      70                  75                  80

Leu Glu Glu Met Gln Lys His Ser Lys Ile Pro Ile Val Gly Val Ile
                    85                  90                  95

Glu Pro Ser Ile Leu Ala Ile Lys Arg Gln Val Lys Asp Lys Asn Ala
                100                 105                 110

Pro Ile Leu Val Leu Gly Thr Lys Ala Thr Ile Gln Ser Asn Ala Tyr
                115                 120                 125

Asp Asn Ala Leu Lys Gln Gln Gly Tyr Leu Asn Val Ser His Leu Ala
            130                 135                 140

Thr Ser Leu Phe Val Pro Leu Ile Glu Glu Ser Ile Leu Glu Gly Glu
    145                 150                 155                 160

Leu Leu Glu Thr Cys Met Arg Tyr Tyr Phe Thr Pro Leu Lys Ile Phe
                    165                 170                 175

Pro Lys
```

COMPOSITIONS COMPRISING ISOLATED HELICOBACTER PYLORI CAGI POLYNUCLEOTIDES AND METHOD OF PREPARATION THEREOF

CROSS-REFERENCE TO RELATED APPLICATIONS

This application is a continuation-in-part of U.S. Ser. No. 08/425,194 (attorney docket no. 00335.001), filed Apr. 20, 1995 now abandoned. This application is also a continuation-in-part of Covacci et al. copending application Ser. No. 08/471,491, filed Jun. 6, 1995, which is a divisional of application Ser. No. 08/256,848, filed Oct. 21, 1994 now abandoned, which is a U.S. national stage application of, PCT/EP93/00472, filed Mar. 2, 1993 and PCT/EP93/00158, filed Jan. 25, 1993, which PCT applications claimed priority benefit under 35 USC §119 of Italian application Serial No. FI92 A 000052, filed Mar. 2, 1992.

BACKGROUND OF THE INVENTION

1. Field of the Disclosure

The present invention relates generally to certain *Helicobacter pylori* genetic regions, to the proteins expressed by these regions, and to the use of these genes and proteins for diagnostic and vaccine applications.

2. Brief Description of Related Art

*Helicobacter pylori* is a curved, microaerophilic, gram negative bacterium that has been isolated for the first time in 1982 from stomach biopsies of patients with chronic gastritis, Warren et al., Lancet i: 1273–75 (1983). Originally named *Campylobacter pylori*, it has been recognized to be part of a separate genus named Helicobacter, Goodwin et al., Int. J. Syst. Bacteriol. 39: 397–405 (1989). The bacterium colonizes the human gastric mucosa, and infection can persist for decades. During the last few years, the presence of the bacterium has been associated with chronic gastritis type B, a condition that may remain asymptomatic in most infected persons but increases considerably the risk of peptic ulcer and gastric adenocarcinoma. The most recent studies strongly suggest that *H. pylori* infection may be either a cause or a cofactor of type B gastritis, peptic ulcers, and gastric tumors, see e.g., Blaser, Gastroenterology 93: 371–83 (1987); Dooley et al., New Engl. J. Med. 321: 1562–66 (1989); Parsonnet et al., New Engl. J. Med. 325: 1127–31 (1991). *H. pylori* is believed to be transmitted by the oral route, Thomas et al., Lancet i: 340, 1194 (1992), and the risk of infection increases with age, Graham et al., Gastroenterology 100: 1495–1501 (1991), and is facilitated by crowding, Drumm et al., New Engl. J. Med. 4322: 359–63 (1990); Blaser, Clin. Infect. Dis. 15: 386–93 (1992). In developed countries, the presence of antibodies against *H. pylori* antigens increases from less than 20% to over 50% in people 30 and 60 years old respectively, Jones et al., Med. Microbio. 22: 57–62 (1986); Morris et al., N. Z. Med. J. 99: 657–59 (1986), while in developing countries over 80% of the population are already infected by the age of 20, Graham et al., Digestive Diseases and Sciences 36: 1084–88 (1991).

*H. pylori* factors that have been identified so far include the flagella that are probably necessary to move across the mucus layer, see e.g., Leying et al., Mol. Microbiol. 6: 2863–74 (1992); the urease that is necessary to neutralize the acidic environment of the stomach and to allow initial colonization, see e.g., Cussac et al., J. Bacteriol. 174: 2466–73 (1992), Perez-Perez et al., J. Infect. Immun. 60: 3658–3663 (1992), Austin et al., J. Bacteriol. 174: 7470–73 (1992), PCT Publ. No. WO 90/04030; the *H. pylori* cytotoxin (sometimes referred to as VacA, as it causes vacuolation), see e.g., PCT Publ. No. WO 93/18150, Telford, J. L. et al., J. Exp. Med. 179: 1653–58 (1994), Cover et al., J. Bio. Chem. 267: 10570–75 (1992), Cover et al., J. Clin. Invest. 90: 913–18 (1992), Leunk, Rev. Infect. Dis. 13: 5686–89 (1991); the *H. pylori* heat shock protein, see e.g., PCT Publ. No. WO 93/18150, Evans et al., Infect. Immun. 60: 2125–27 (1992), Dunn et al., Infect. Immun. 60: 1946–51 (1992), Austin et al., J. Bacteriol. 174: 7470–73 (1992); and the cytotoxin-associated protein, CagA, see e.g., PCT Publ. No. WO 93/18150, Covacci, A., et al., Proc. Natl. Acad. Sci. USA 90: 5791–95 (1993), Tummuru, M. K. et al., Infect. Immun. 61: 1799–1809 (1994).

Currently, *H. pylori* strains can be partitioned into at least two major groups, which either express (Type I) or do not express (Type II) the cytotoxin and the CagA proteins. Type I strains contain the CagA and toxin genes and produce active forms of these antigens. Type II strains lack the CagA locus and fail to express the cytotoxin. The association between the presence of the CagA gene and cytotoxicity suggests that the product of the CagA gene is necessary for the transcription, folding, export or function of the cytotoxin. Epidemiological analysis indicate that Type I bacteria are associated with duodenal ulcerations, gastric ulceration and sever forms of active gastritis.

For a general review of the pathogenic role of *H. pylori* in peptic ulcer, see Telford, J. L., et al., TibTech 12: 420–426 (1994).

SUMMARY OF THE INVENTION

The present invention describes nucleotide sequences located at the 5' region of the CagA gene. It has been found that the absence of the CagA gene in Type I strains is associated with the absence of genetic sequences located 5' of the CagA locus. This general region has been designated CagI and may encode virulence factors restricted to Type I strains. Sequences from this region were able to recognize homologous sequences in all Type I strains but failed to hybridize with DNA from Type II strains. Thus, this region has important implications for diagnosis of pathogenic Type I bacteria.

The present invention pertains not only to this CagI region, but also to recombinant materials associated therewith, such as vectors, host cells, and proteins encoded by such regions. The understanding at the molecular level of the nature and the role of this region and the availability of recombinant production has important implications for the development of new diagnostics for *H. pylori* and for the design of vaccines that may prevent *H. pylori* infection and treat disease. As such, this region has applications for diagnostics and vaccines. The present invention includes methods for diagnosing those diseases associated with *H. pylori*. As *H. pylori* has been associated with type B gastritis, peptic ulcers, and gastric adenocarcinoma, it is hoped that the present invention will assist in early detection and alleviation of these disease states.

BRIEF DESCRIPTION OF THE DRAWINGS

FIG. 2 is the nucleotide (SEQ ID NOS 1 and 5 (for FIG. 2, Seq 1), SEQ ID NOS 9 and 13 (for FIG. 2, Seq 2) and SEQ ID NOS 17 and 21 (for FIG. 2, Seq. 3) and predicted amino acid sequences (SEQ ID NOS 2–4 and 6–8 (for FIG. 2, Seq 1), SEQ ID NOS 10–12 and 14–16 (for FIG. 2, Seq 2), and SEQ ID NOS 18–20 and 22–24 (for FIG. 2, Seq. 3), as well as restriction enzyme sites, for the *H. pylori* CagI locus, as represented by three sequence segments (see below).

FIGS. 3A through 3R is the complete nucleotide sequence for the *H. pylori* CagI locus (19,932 base pairs) (SEQ ID NO 25).

FIGS. 4A through 4N are the putative open reading frames (ORF) for the CagI locus and their possible homology with other proteins (SEQ ID NO 26–46).

DETAILED DESCRIPTION OF THE INVENTION

A. General Methodology

Figure 1:
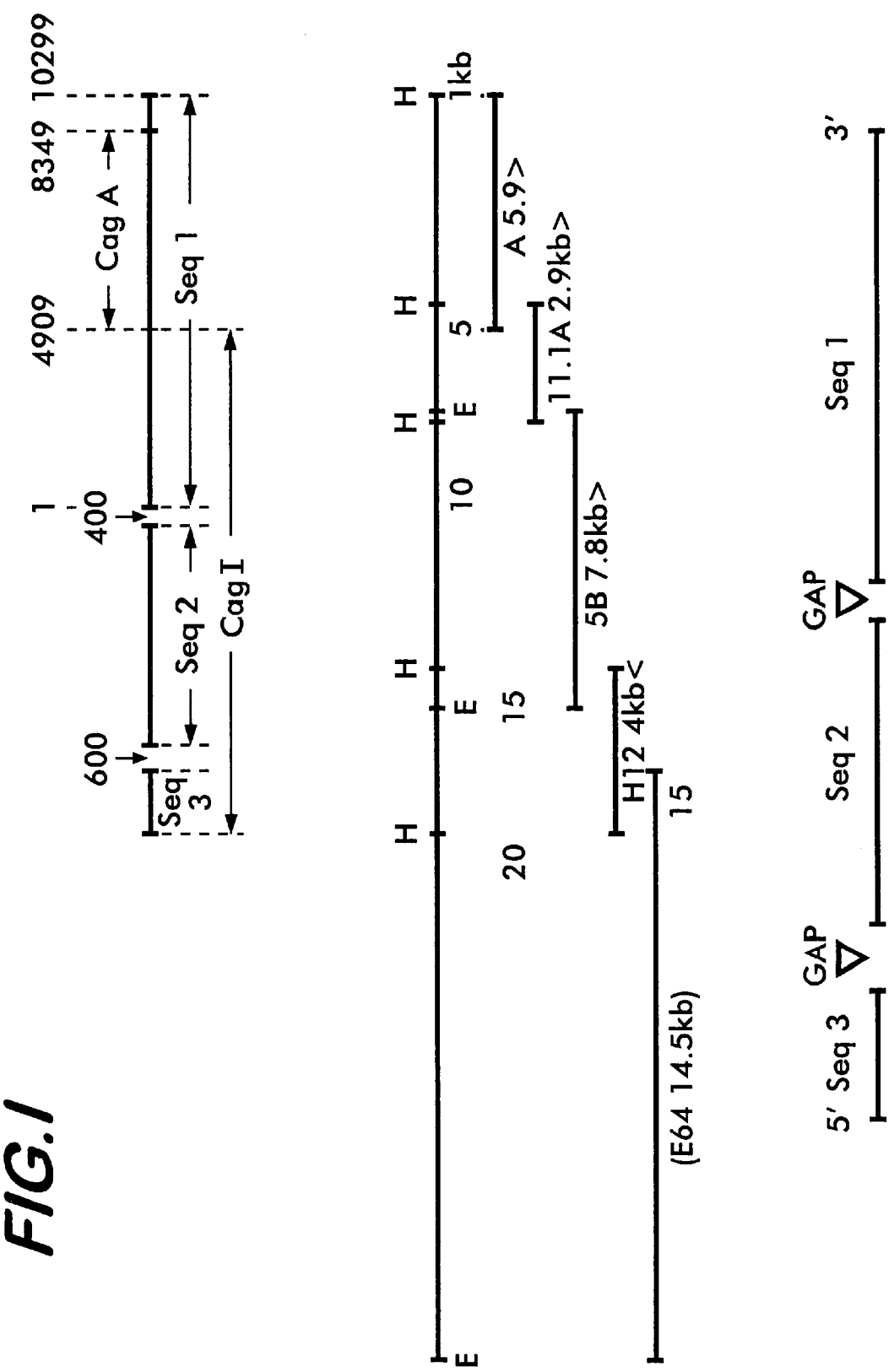
FIG. 1 is a schematic diagram of the *H. pylori* CagI region showing location of specific clones.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986).

Standard abbreviations for nucleotides and amino acids are used in this specification. All publications, patents, and patent applications cited herein are incorporated by reference.

B. Definitions

Figure 2:
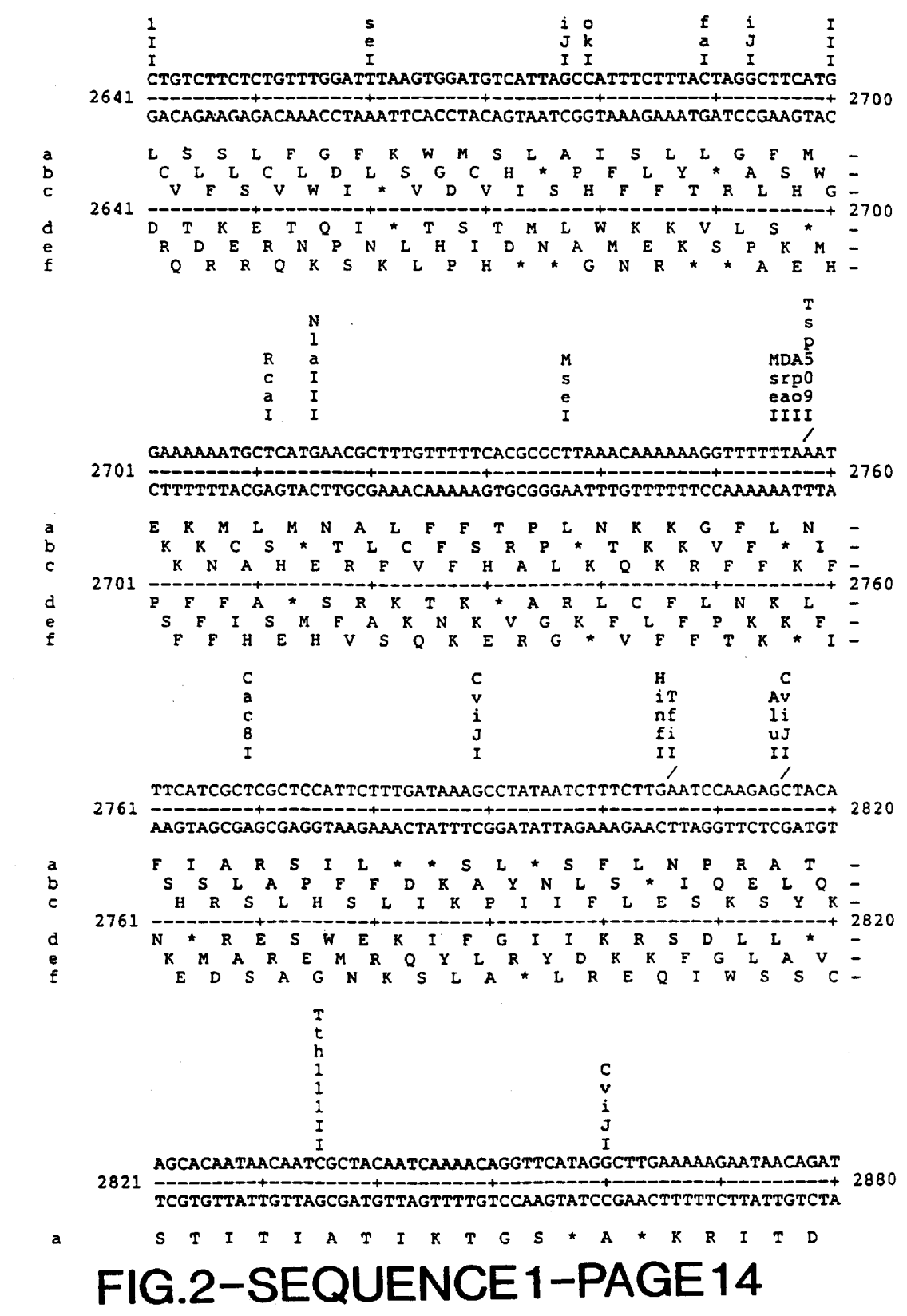
Figure 2:
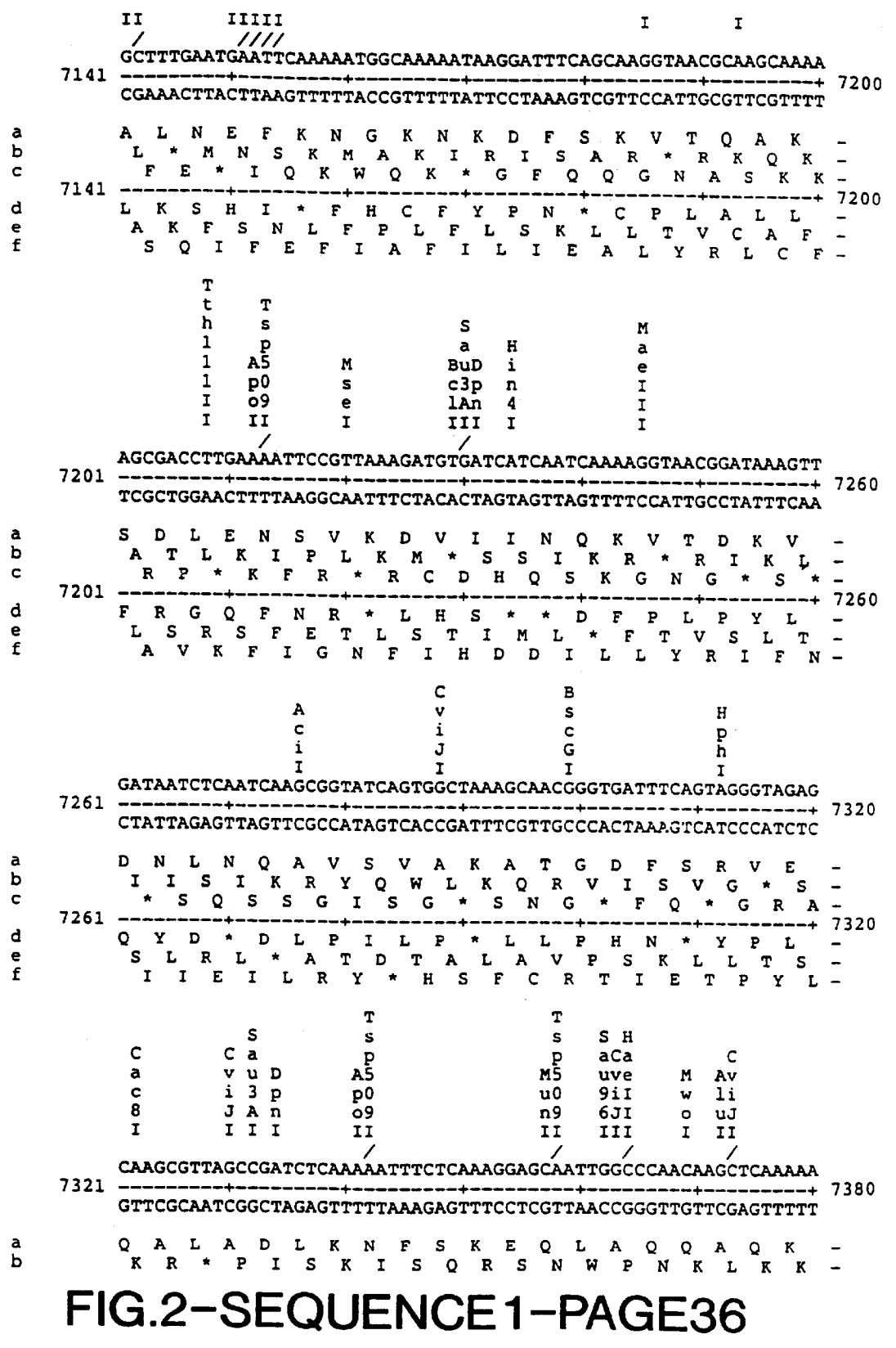
Figure 2:
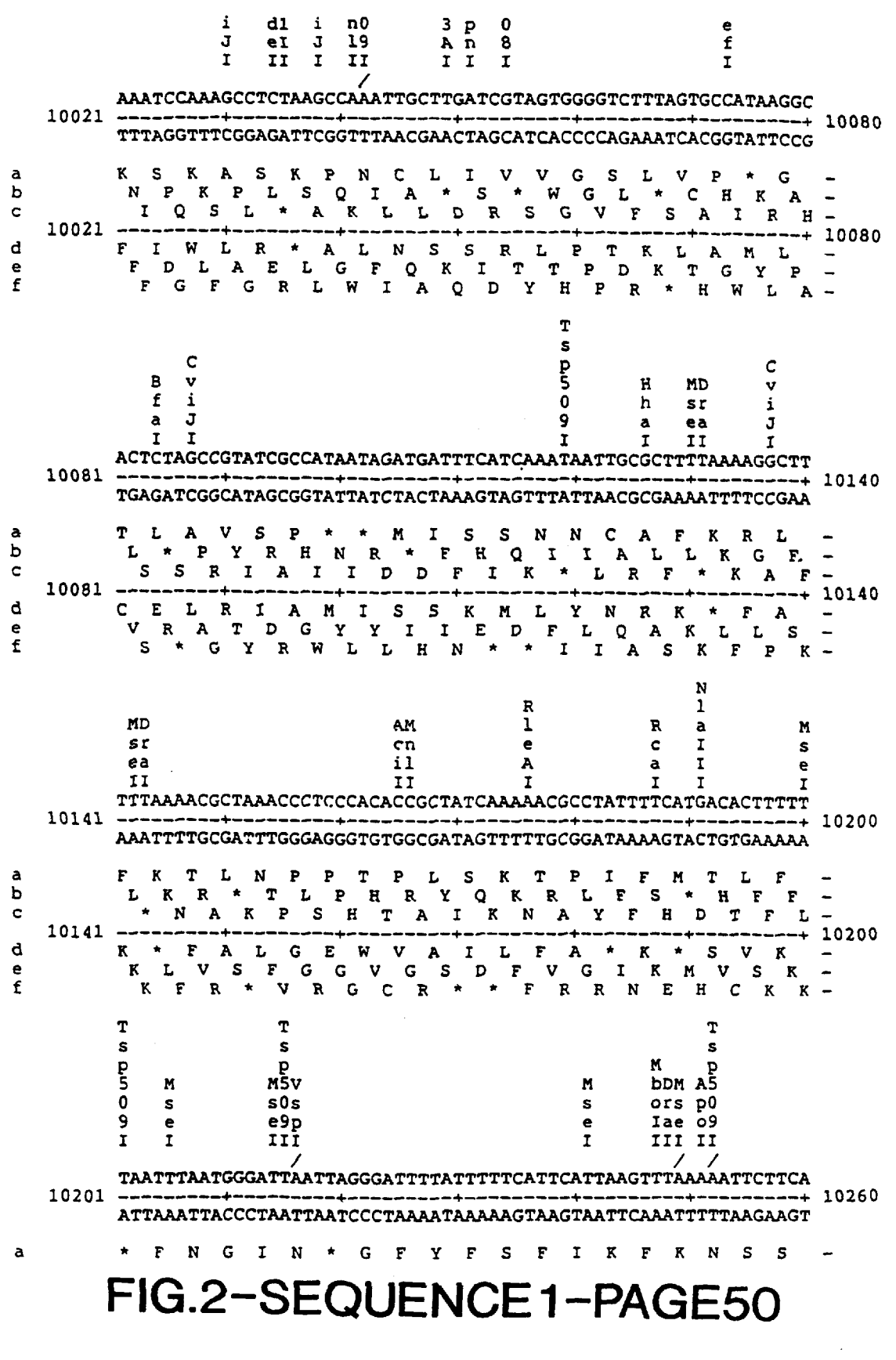
Figure 2:
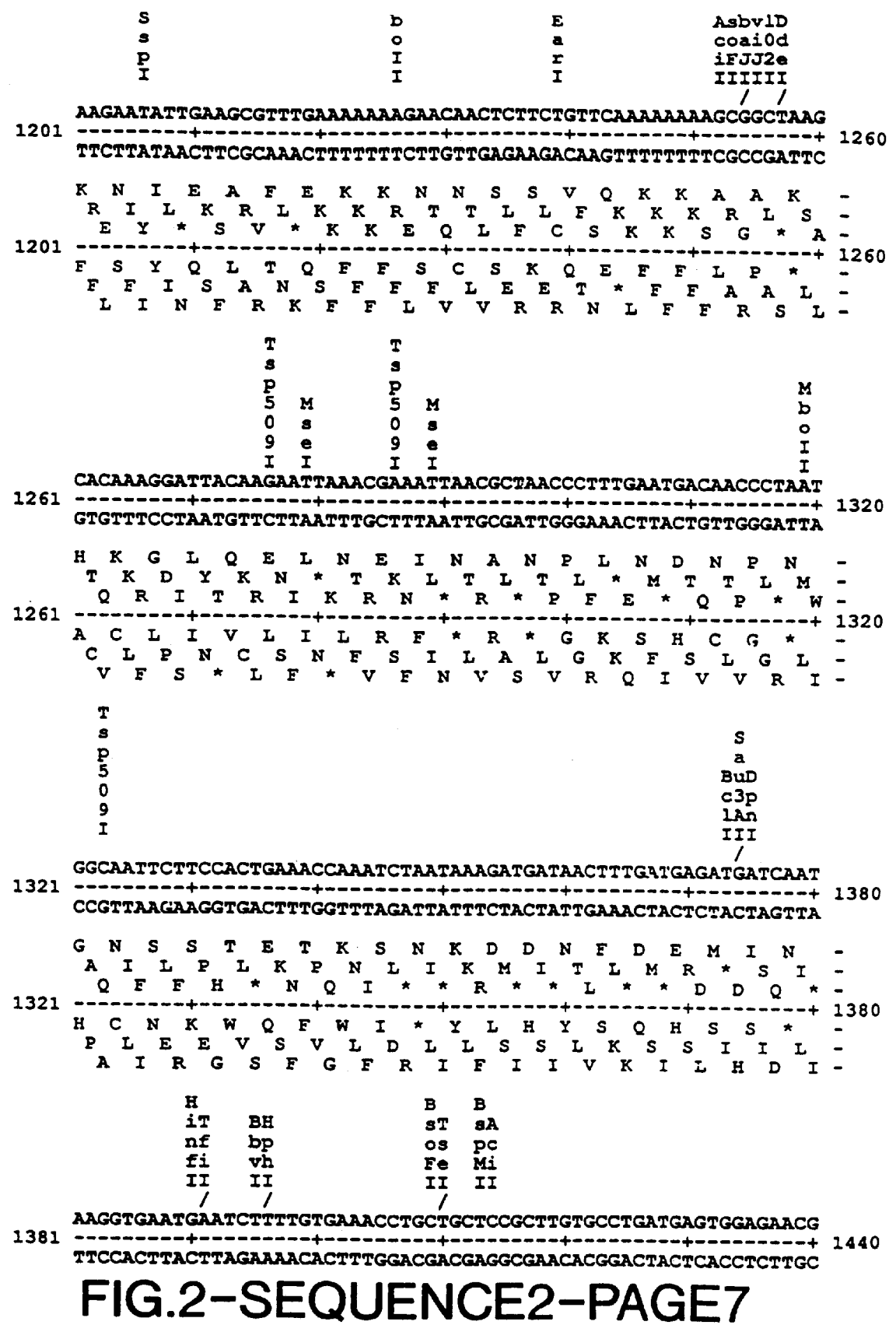

"CagI" refers to the genetic regions located 5' to the CagA locus, whose absence correlates with the absence of the CagA gene in Type II bacterial strains. The nucleotide and putative amino acid sequences of CagI are shown in FIGS. 2, 3, and 4(SEQ ID NOS 1–46).

Examples of proteins encoded by the CagI region that can be used in the present invention include polypeptides with minor amino acid variations from the natural amino acid sequence of the protein; in particular, conservative amino acid replacements are contemplated. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamate, cystine, serine, threonine, tyrosine. Phenylalanine, tryptophan, and tyrosine are sometimes classified jointly as aromatic amino acids. For example, it is reasonably predictable that an isolated replacement of a leucine with an isoleucine or valine, an aspartate with a glutamate, a threonine with a serine, or a similar conservative replacement of an amino acid with a structurally related amino acid will not have a major effect on the biological activity. Polypeptide molecules having substantially the same amino acid sequence as the protein but possessing minor amino acid substitutions that do not substantially affect the functional aspects are within the definition of the protein.

A significant advantage of producing the protein by recombinant DNA techniques rather than by isolating and purifying a protein from natural sources is that equivalent quantities of the protein can be produced by using less starting material than would be required for isolating the protein from a natural source. Producing the protein by recombinant techniques also permits the protein to be isolated in the absence of some molecules normally present in cells. Indeed, protein compositions entirely free of any trace of human protein contaminants can readily be produced because the only human protein produced by the recombinant non-human host is the recombinant protein at issue. Potential viral agents from natural sources and viral components pathogenic to humans are also avoided.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature. Thus, this term also encompasses the situation wherein the *H. pylori* bacterium genome is genetically modified (e.g., through mutagenesis) to produce one or more altered polypeptides.

The term "polynucleotide" as used herein refers to a polymeric form of a nucleotide of any length, preferably deoxyribonucleotides, and is used interchangeably herein with the terms "oligonucleotide" and "oligomer." The term refers only to the primary structure of the molecule. Thus, this term includes double- and single-stranded DNA, as well as antisense polynucleotides. It also includes known types of modifications, for example, the presence of labels which are known in the art, methylation, end "caps," substitution of one or more of the naturally occurring nucleotides with an analog, internucleotide modifications such as, for example, replacement with certain types of uncharged linkages (e.g., methyl phosphonates, phosphotriesters, phosphoamidates, carbamates, etc.) or charged linkages (e.g., phosphorothioates, phosphorodithioates, etc.), introduction of pendant moieties, such as, for example, proteins (including nucleases, toxins, antibodies, signal peptides, poly-L-lysine, etc.), intercalators (e.g., acridine, psoralen, etc.), chelators (e.g., metals, radioactive species, boron, oxidative moieties, etc.), alkylators (e.g., alpha anomeric nucleic acids, etc.).

By "genomic" is meant a collection or library of DNA molecules which are derived from restriction fragments that have been cloned in vectors. This may include all or part of the genetic material of an organism.

By "cDNA" is meant a complimentary mRNA sequence that hybridizes to a complimentary strand of mRNA.

As used herein, the term "oligomer" refers to both primers and probes and is used interchangeably herein with the term "polynucleotide." The term oligomer does not connote the size of the molecule. However, typically oligomers are no greater than 1000 nucleotides, more typically are no greater than 500 nucleotides, even more typically are no greater than 250 nucleotides; they may be no greater than 100 nucleotides, and may be no greater than 75 nucleotides, and also may be no greater than 50 nucleotides in length.

The term "primer" as used herein refers to an oligomer which is capable of acting as a point of initiation of synthesis of a polynucleotide strand when used under appropriate conditions. The primer will be completely or substantially complementary to a region of the polynucleotide strand to be copied. Thus, under conditions conducive to hybridization, the primer will anneal to the complementary region of the analyte strand. Upon addition of suitable reactants, (e.g., a polymerase, nucleotide triphosphates, and the like), the primer will be extended by the polymerizing agent to form a copy of the analyte strand. The primer may be single-stranded or alternatively may be partially or fully double-stranded.

The terms "analyte polynucleotide" and "analyte strand" refer to a single- or double-stranded nucleic acid molecule which is suspected of containing a target sequence, and which may be present in a biological sample.

As used herein, the term "probe" refers to a structure comprised of a polynucleotide which forms a hybrid structure with a target sequence, due to complementarily of at least one sequence in the probe with a sequence in the target region. The polynucleotide regions of probes may be composed of DNA, and/or RNA, and/or synthetic nucleotide analogs. Included within probes are "capture probes" and "label probes".

As used herein, the term "target region" refers to a region of the nucleic acid which is to be amplified and/or detected. The term "target sequence" refers to a sequence with which a probe or primer will form a stable hybrid under desired conditions.

The term "capture probe" as used herein refers to a polynucleotide probe comprised of a single-stranded polynucleotide coupled to a binding partner. The single-stranded polynucleotide is comprised of a targeting polynucleotide sequence, which is complementary to a target sequence in a target region to be detected in the analyte polynucleotide. This complementary region is of sufficient length and complementarily to the target sequence to afford a duplex of stability which is sufficient to immobilize the analyte polynucleotide to a solid surface (via the binding partners). The binding partner is specific for a second binding partner; the second binding partner can be bound to the surface of a solid support, or may be linked indirectly via other structures or binding partners to a solid support.

The term "targeting polynucleotide sequence" as used herein refers to a polynucleotide sequence which is comprised of nucleotides which are complementary to a target nucleotide sequence; the sequence is of sufficient length and complementarily with the target sequence to form a duplex which has sufficient stability for the purpose intended.

The term "binding partner" as used herein refers to a molecule capable of binding a ligand molecule with high specificity, as for example an antigen and an antibody specific therefor. In general, the specific binding partners must bind with sufficient affinity to immobilize the analyte copy/complementary strand duplex (in the case of capture probes) under the isolation conditions. Specific binding partners are known in the art, and include, for example, biotin and avidin or streptavidin, IgG and protein A, the numerous known receptor-ligand couples, and complementary polynucleotide strands. In the case of complementary polynucleotide binding partners, the partners are normally at least about 15 bases in length, and may be at least 40 bases in length; in addition, they have a content of Gs and Cs of at least about 40% and as much as about 60%. The polynucleotides may be composed of DNA, RNA, or synthetic nucleotide analogs.

The term "coupled" as used herein refers to attachment by covalent bonds or by strong non-covalent interactions (e.g., hydrophobic interactions, hydrogen bonds, etc.). Covalent bonds may be, for example, ester, ether, phosphoester, amide, peptide, imide, carbon-sulfur bonds, carbon-phosphorus bonds, and the like.

The term "support" refers to any solid or semi-solid surface to which a desired binding partner may be anchored. Suitable supports include glass, plastic, metal, polymer gels, and the like, and may take the form of beads, wells, dipsticks, membranes, and the like.

The term "label" as used herein refers to any atom or moiety which can be used to provide a detectable (preferably quantifiable) signal, and which can be attached to a polynucleotide or polypeptide.

As used herein, the term "label probe" refers to a polynucleotide probe which is comprised of a targeting polynucleotide sequence which is complementary to a target sequence to be detected in the analyte polynucleotide. This complementary region is of sufficient length and complementarily to the target sequence to afford a duplex comprised of the "label probe" and the "target sequence" to be detected by the label. The label probe is coupled to a label either directly, or indirectly via a set of ligand molecules with high specificity for each other, including multimers.

The term "multimer," as used herein, refers to linear or branched polymers of the same repeating single-stranded polynucleotide unit or different single-stranded polynucleotide units. At least one of the units has a sequence, length, and composition that permits it to hybridize specifically to a first single-stranded nucleotide sequence of interest, typically an analyte or a polynucleotide probe (e.g., a label probe) bound to an analyte. In order to achieve such specificity and stability, this unit will normally be at least about 15 nucleotides in length, typically no more than about 50 nucleotides in length, and preferably about 30 nucleotides in length; moreover, the content of Gs and Cs will normally be at least about 40%, and at most about 60%. In addition to such unit(s), the multimer includes a multiplicity of units that are capable of hybridizing specifically and stably to a second single-stranded nucleotide of interest, typically a labeled polynucleotide or another multimer. These units are generally about the same size and composition as the multimers discussed above. When a multimer is designed to be hybridized to another multimer, the first and second oligonucleotide units are heterogeneous (different), and do not hybridize with each other under the conditions of the selected assay. Thus, multimers may be label probes, or may be ligands which couple the label to the probe.

A "replicon" is any genetic element, e.g., a plasmid, a chromosome, a virus, a cosmid, etc. that behaves as an autonomous unit of polynucleotide replication within a cell; i.e., capable of replication under its own control. This may include selectable markers.

"PCR" refers to the technique of polymerase chain reaction as described in Saiki, et al., Nature 324: 163 (1986); and Scharf et al., Science (1986) 233: 1076–1078; and U.S. Pat. No. 4,683,195; and U.S. Pat. No. 4,683,202.

As used herein, x is "heterologous" with respect to y if x is not naturally associated with y in the identical manner; i.e., x is not associated with y in nature or x is not associated with y in the same manner as is found in nature.

"Homology" refers to the degree of similarity between x and y. The correspondence between the sequence from one form to another can be determined by techniques known in the art. For example, they can be determined by a direct comparison of the sequence information of the polynucleotide. Alternatively, homology can be determined by hybridization of the polynucleotides under conditions which form stable duplexes between homologous regions (for example, those which would be used prior to $S_1$ digestion), followed by digestion with single-stranded specific nuclease(s), followed by size determination of the digested fragments.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

"Immunogenic" refers to the ability of a polypeptide to cause a humoral and/or cellular immune response, whether alone or when linked to a carrier, in the presence or absence of an adjuvant. "Neutralization" refers to an immune response that blocks the infectivity, either partially or fully, of an infectious agent.

"Epitope" refers to an antigenic determinant of a peptide, polypeptide, or protein; an epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance. Antibodies that recognize the same epitope can be identified in a simple immunoassay showing the ability of one antibody to block the binding of another antibody to a target antigen.

"Treatment," as used herein, refers to prophylaxis and/or therapy (i.e., the modulation of any disease symptoms). An "individual" indicates an animal that is susceptible to infection by *H. pylori* and includes, but is not limited to, primates, including humans. A "vaccine" is an immunogenic, or otherwise capable of eliciting protection against *H. pylori*, whether partial or complete, composition useful for treatment of an individual. As such, it may include but is not limited to a modified bacterium (e.g., chemical or genetic alterations); bacterial protein subunits, whether recombinantly produced or purified from cell lysates; bacterial genetic material employed in polynucleotide vaccines, etc.

*H. pylori* proteins may be used for producing antibodies, either monoclonal or polyclonal, specific to the proteins. The methods for producing these antibodies are known in the art.

"Recombinant host cells", "host cells," "cells," "cell cultures," and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

Specifically, as used herein, "cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells. Preferably, cell lines include nonhybrid cell lines or hybridomas to only two cell types.

As used herein, the term "microorganism" includes prokaryotic and eukaryotic microbial species such as bacteria and fungi, the latter including yeast and filamentous fungi.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

C. Nucleic Acid Assays

Using as a basis the genome of *H. pylori*, and more particularly, the genetic region of CagI, polynucleotide probes of approximately 8 nucleotides or more can be prepared which hybridize with the positive strand(s) of the RNA or its complement, as well as to cDNAs. These polynucleotides serve as probes for the detection, isolation and/or labeling of polynucleotides which contain nucleotide sequences, and/or as primers for the transcription and/or replication of the targeted sequences. Each probe contains a targeting polynucleotide sequence, which is comprised of nucleotides which are complementary to a target nucleotide sequence; the sequence is of sufficient length and complementarily with the sequence to form a duplex which has sufficient stability for the purpose intended. For example, if the purpose is the isolation, via immobilization, of an analyte containing a target sequence, the probes will contain a polynucleotide region which is of sufficient length and complementarily to the targeted sequence to afford sufficient duplex stability to immobilize the analyte on a solid surface under the isolation conditions. For example, also, if the polynucleotide probes are to serve as primers for the transcription and/or replication of target sequences, the probes will contain a polynucleotide region of sufficient length and complementarily to the targeted sequence to allow for replication. For example, also, if the polynucleotide probes are to be used as label probes, or are to bind to multimers, the targeting polynucleotide region would be of sufficient length and complementarily to form stable hybrid duplex structures with the label probes and/or multimers to allow detection of the duplex. The probes may contain a minimum of about 4 contiguous nucleotides which are complementary to the targeted sequence; usually the oligomers will contain a minimum of about 8 continuous nucleotides which are complementary to the targeted sequence, and preferably will contain a minimum of about 14 contiguous nucleotides which are complementary to the targeted sequence.

The probes, however, need not consist only of the sequence which is complementary to the targeted sequence. They may contain additional nucleotide sequences or other moieties. For example, if the probes are to be used as primers for the amplification of sequences via PCR, they may contain sequences which, when in duplex, form restriction enzyme sites which facilitate the cloning of the amplified sequences. For example, also, if the probes are to be used as "capture probes" in hybridization assays, they will be coupled to a "binding partner" as defined above. Preparation of the probes is by means known in the art, including, for example, by methods which include excision, transcription or chemical synthesis.

D. Expression Systems

Once the appropriate *H. pylori* coding sequence is isolated, it can be expressed in a variety of different expression systems; for example those used with mammalian cells, baculoviruses, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation, Sambrook et al., *Molecular Cloning: A Laboratory Manual*, 2nd ed (1989).

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter, Maniatis et al., Science 236: 1237 (1989); Alberts et al. *Molecular Biology of the Cell*, 2nd ed (1989). Enhancer elements derived from viruses may be particularly useful, because they usually have a broader host range. Examples include the SV40 early gene enhancer, Dijkema et al (1985) EMBO J. 4: 761, and the enhancer/promoters derived from the long terminal repeat (LTR) of the Rous Sarcoma Virus, Gorman et al. (1982) Proc. Natl. Acad. Sci. 79: 6777, and from human cytomegalovirus, Boshart et al. (1985) Cell 41: 5221. Additionally, some enhancers are regulatable and become active only in the presence of an inducer, such as a hormone or metal ion, Sassone-Corsi et al. (1986) Trends Genet. 2: 215; Maniatis et al. (1987) Science 236: 1237.

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved eiLher in vivo or in vitro. The leader sequence fragment usually encodes a signal peptide comprised of hydrophobic amino acids which direct the secretion of the protein from the cell. The adenovirus tripartite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation, Birnstiel et al. (1985) Cell 41: 349; Proudfoot and Whitelaw (1988) "Termination and 3' end processing of eukaryotic RNA. In *Transcription and splicing* (ed. B. D. Hames and D. M. Glover); Proudfoot (1989) Trends Biochem. Sci. 14: 105. These sequences direct the transcription of an mRNA which can be translated into the polypeptide encoded by the DNA. Examples of transcription terminator/polyadenylation signals include those derived from SV40, Sambrook et al (1989), *Molecular Cloning: A Laboratory Manual*.

Some genes may be expressed more efficiently when introns (also called intervening sequences) are present. Several cDNAs, however, have been efficiently expressed from vectors that lack splicing signals (also called splice donor and acceptor sites), see e.g., Gething and Sambrook (1981) Nature 293: 620. Introns are intervening noncoding sequences within a coding sequence that contain splice donor and acceptor sites. They are removed by a process called "splicing," following polyadenylation of the primary transcript, Nevins (1983) Annu. Rev. Biochem. 52: 441; Green (1986) Annu. Rev. Genet. 20: 671; Padgett et al. (1986) Annu. Rev. Biochem. 55: 1119; Krainer and Maniatis (1988) "RNA splicing," In Transcription and splicing (ed. B. D. Hames and D. M. Glover).

Usually, the above-described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40, Gluzman (1981) Cell 23: 175, or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a procaryotic host for cloning and amplification. Examples of such mammalian-bacteria shuttle vectors include pMT2, Kaufman et al. (1989) Mol. Cell. Biol. 9: 946, and pHEBO, Shimizu et al. (1986) Mol. Cell. Biol. 6: 1074.

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, Texas Agricultural Experiment Station Bulletin No. 1555 (1987) (hereinafter "Summers and Smith").

Prior to inserting the DNA sequence encoding the protein into the baculovirus genome, the above-described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, Virology (1989) 17: 31.

The plasmid usually also contains the polyhedron polyadenylation signal (Miller et al. (1988) Ann. Rev. Microbiol., 42: 177) and a procaryotic ampicillin-resistance (amp) gene and origin of replication for selection and propagation in *E. coli*.

Baculovirus transfer vectors usually contain a baculovirus, promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), J. Gen. Virol. 69: 765.

DNA encoding suitable signal sequences can be derived from genes for secreted insect or baculovirus proteins, such as the baculovirus polyhedrin gene (Carbonell et al. (1988) Gene, 73: 409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), Nature 315: 592; human gastrin-releasing peptide, Lebacq-Verheyden et al., (1988), Molec. Cell. Biol. 8: 3129; human IL-2, Smith et al., (1985) Proc. Nat'l Acad. Sci. USA, 82: 8404; mouse IL-3, (Miyajima et al., (1987) Gene 58: 273; and human glucocerebrosidase, Martin et al. (1988) DNA 7: 99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2–5kb section of the baculovirus genome. Methods for introducing heterologous DNA into the desired site in the baculovirus virus are known in the art. (See Summers and Smith; Ju et al. (1987); Smith et al., Mol. Cell. Biol. (1983) 3: 2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), Bioessays 4: 91.

The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skill.ed in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda*, and *Trichoplusia ni* (PCT Pub. No. WO 89/046699; Carbonell et al., (1985) J. Virol. 56: 153; Wright (1986) Nature 321: 718; Smith et al., (1983) Mol. Cell. Biol. 3: 2156; and see generally, Fraser, et al. (1989) In Vitro Cell. Dev. Biol. 25: 225).

Cells and cell culture media are commercially available for both direct and fusion expression of heterologous polypeptides in a baculovirus/expression system; cell culture technology is generally known to those skilled in the art. See, e.g., Summers and Smith.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Bacterial Systems

Bacterial expression techniques are known in the art. A bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli*, Raibaud et al. (1984) Annu. Rev. Genet. 18: 173. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac), Chang et al. (1977) Nature 198: 1056, and maltose. Additional examples include promoter sequences derived from biosynthetic enzymes such as tryptophan (trp), Goeddel et al. (1980) Nuc. Acids Res. 8: 4057; Yelverton et al. (1981) Nucl. Acids Res. 9: 731; U.S. Pat. No. 4,738,921; EPO Publ. Nos. 036 776 and 121 775. The beta-glacotamase (bla) promoter system, Weissmann (1981) "The cloning of interferon and other mistakes." In *Interferon* 3 (ed. I. Gresser), bacteriophage lambda PL, Shimatake et al. (1981) Nature 292: 128, and T5, U.S. Pat. No. 4,689,406, promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter, U.S. Pat. No. 4,551,433. For example, the tac promoter is a hybrid trp-lac promoter comprised of both trp promoter and lac operon sequences that is regulated by the lac repressor, Amann et al. (1983) Gene 25: 167; de Boer et al. (1983) Proc. Natl. Acad. Sci. 80: 21. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system, Studier et al. (1986) J. Mol. Biol. 189: 113; Tabor et al. (1985) Proc Natl. Acad. Sci. 82: 1074. In addition, a hybrid promoter can also be comprised of a bacteriophage promoter and an *E. coli* operator region (EPO Publ. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon, Shine et al. (1975) Nature 254: 34. The SD sequence is thought to promote binding of mRNA to the ribosome by the pairing of bases between the SD sequence and the 3' and of *E. coli* 16S rRNA, Steitz et al. (1979) "Genetic signals and nucleotide sequences in messenger RNA." In *Biological Regulation and Development: Gene Expression* (ed. R. F. Goldberger). To express eukaryotic genes and prokaryotic genes with weak ribosome-binding site, Sambrook et al. (1989), *Molecular Cloning: A Laboratory Manual*.

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO Publ. No. 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene, Nagai et al. (1984) Nature 309: 810. Fusion proteins can also be made with sequences from the lacZ, Jia et al. (1987) Gene 60: 197, trpE, Allen et al. (1987) J. Biotechnol. 5: 93; Makoff et al. (1989) J. Gen. Microbiol. 135: 11, and EPO Publ. No. 324 647, genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated. Miller et al. (1989) Bio/Technology 7: 698.

Alternatively, foreign proteins can also be secreted from the cell by creating chimeric DNA molecules that encode a fusion protein comprised of a signal peptide sequence fragment that provides for secretion of the foreign protein in bacteria, U.S. Pat. No. 4,336,336. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA). Masui et al. (1983), in: *Experimental Manipulation of Gene Expression*; Ghrayeb et al. (1984) EMBO J. 3: 2437 and the *E. coli* alkaline phosphatase signal sequence (phoA), Oka et al. (1985) Proc. Natl. Acad. Sci. 82: 7212. As an additional example, the signal sequence of the alpha-amylase gene from various Bacillus strains can be used to secrete heterologous proteins from *B. subtilis*. Palva et al. (1982) Proc. Natl. Acad. Sci. USA 79: 5582; EPO Publ. No. 244 042.

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above-described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a procaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EPO Publ. No. 127 328). Integrating vectors may also be comprised of bacteriophage or transpose sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline. Davies et al. (1978) Annu. Rev. Microbiol. 32: 469. Selectable markers may also include biosynthetic genes, such as those in the histidine, tryptophan, and leucine biosynthetic pathways.

Alternatively, some of the above-described components can be put together in transformation vectors. Transformation vectors are usually comprised of a selectable marker that is either maintained in a replicon or developed into an integrating vector.

Expression and transformation vectors, either extrachromosomal replicons or integrating vectors, have been developed for transformation into many bacteria. For example, expression vectors have been developed for, inter alia, the following bacteria: *Bacillus subtilis*, Palv et al. (1982) Proc. Natl. Acad. Sci. USA 79: 5582; EPO Publ. Nos. 036 259 and 063 953; PCT Publ. No. WO 84/04541; *E. coli*, Shimatake et al. (1981) Nature 292: 128; Amann et al. (1985) Gene 40: 183; Studier et al. (1986) J. Mol. Biol. 189: 113; EPO Publ. Nos. 036 776, 136 829 and 136 907; *Streptococcus cremoris*, Powell et al. (1988) Appl. Environ. Microbiol. 54: 655; *Streptococcus lividans*, Powell et al. (1988) Appl. Environ. Microbiol. 54: 655; and *Streptomyces lividans*, U.S. Pat. No. 4,745,056.

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See, e.g., Masson et al. (1989) FEMS Microbiol. Lett. 60: 273; Palva et al. (1982) Proc. Natl. Acad. Sci. USA 79: 5582; EPO Publ. Nos. 036 259 and 063 953; PCT Publ. No. WO 84/04541, for Bacillus; Miller et al. (1988) Proc. Natl. Acad. Sci. 85: 856; Wang et al. (1990) J. Bacteriol. 172: 949, for Campylobacter; Cohen et al. (1973) Proc. Natl. Acad. Sci. 69: 2110; Dower et al. (1988) Nucleic Acids Res. 16:, 6127; Kushner (1978) "An improved method for transformation of *E. coli* with ColE1-derived plasmids," In *Genetic Engineering: Proceedings of the International Symposium on Genetic Engineering* (eds. H. W. Boyer and S. Nicosia); Mandel et al. (1970) J. Mol. Biol. 53: 159; Taketo (1988) Biochim. Biophys. Acta 949: 318, for Escherichia; Chassy et al. (1987) FEMS Microbiol. Lett. 44: 173, for Lactobacillus; Fiedler et al. (1988) Anal. Biochem 170: 38, for Pseudomonas; Augustin et al. (1990) FEMS Microbiol. Lett. 66: 203, for Staphylococcus; Barany et al. (1980) J. Bacteriol. 144: 698; Harlander (1987) "Transformation of *Streptococcus lactis* by electroporation, in: Streptococcal Genetics (ed. J. Ferretti and R. Curtiss III); Perry et al. (1981) Infec. Immun. 32: 1295; Powell et al. (1988) Appl. Environ. Microbiol. 54: 655; Somkuti et al. (1987) Proc. 4th Evr. Cong. Biotechnology 1: 412, for Streptococcus.

iv. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EPO Publ. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publ. No. 329 203). The yeast PHO5 gene, encoding acid phosphatase, also provides useful promoter sequences, Myanohara et al. (1983) Proc. Natl. Acad. Sci. USA 80: 1.

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. No. 4,876,197 and U.S. Pat. No. 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters include, inter alia, Cohen et al. (1980) Proc. Natl. Acad. Sci. USA 77: 1078; Henikoff et al. (1981) Nature 283: 835; Hollenberg et al. (1981) Curr. Topics Microbiol. Immunol. 96: 119; Hollenberg et al. (1979) "The Expression of Bacterial Antibiotic Resistance Genes in the Yeast *Saccharomyces cerevisiae,*" in: *Plasmids of Medical, Environmental and Commercial Importance* (eds. K. N. Timmis and A. Puhler); Mercerau-Puigalon et al. (1980) Gene 11: 163; Panthier et al. (1980) Curr. Genet. 2: 109.

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EPO Publ. No. 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (see, e.g., PCT Publ. No. WO 88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EPO Publ. No. 012 873; JPO Publ. No. 62,096,086) and the A-factor gene (U.S. Pat. No. 4,588, 684). Alternatively, leaders of non-yeast origin, such as an interferon leader, exist that also provide for secretion in yeast (EPO Publ. No. 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. No. 4,546,083 and U.S. Pat. No. 4,870,008; EPO Publ. No. 324 274). Additional leaders employing an alpha-factor leader fragment that provides for secretion include hybrid alpha-factor leaders made with a presequence of a first yeast, but a pro-region from a second yeast alphafactor. (See e.g., PCT Publ. No. WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above-described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24, Botstein et al. (1979) Gene 8: 17–24; pCl/1, Brake et al. (1984) Proc. Natl. Acad. Sci USA 81: 4642–4646; and YRp17, Stinchcomb et al. (1982) J. Mol. Biol. 158: 157. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. A high or low copy number vector may be selected, depending upon the effect of the vector and the foreign protein on the host.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome, Orr-Weaver et al. (1983) Methods in Enzymol. 101: 228–245. An integrating vector may be directed to a specific locus in yeast by selecting the appropriate homologous sequence for inclusion in the vector. One or more expression construct may integrate, possibly affecting levels of recombinant protein produced, Rine et al. (1983) Proc. Natl. Acad. Sci. USA 80: 6750. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions. Butt et al. (1987) Microbiol, Rev. 51: 351.

Alternatively, some of the above-described components can be put together into transformation vectors. Transformation vectors are usually comprised of a selectable marker that is either maintained in a replicon or developed into an integrating vector.

Expression and transformation vectors, either extrachromosomal replicons or integrating vectors, have been developed for transformation into many yeasts. For example, expression vectors have been developed for, inter alia, the following yeasts: *Candida albicans*, Kurtz, et al. (1986) Mol. Cell. Biol. 6: 142; *Candida maltosa*, Kunze, et al. (1985) J. Basic Microbiol. 25: 141; *Hansenula polymorpha*, Gleeson, et al. (1986) J. Gen. Microbiol. 132: 3459; Roggenkamp et al. (1986) Mol. Gen. Genet. 202: 302; *Kluyveromyces fragilis*, Das, et al. (1984) J. Bacteriol. 158: 1165; *Kluyveromyces lactis*, De Louvencourt et al. (1983) J. Bacteriol. 154: 737; Van den Berg et al. (1990) Bio/Technology 8: 135; *Pichia guillerimondii*, Kunze et al. (1985) J. Basic Microbiol. 25: 141; *Pichia pastoris*, Cregg, et al. (1985) Mol. Cell. Biol. 5: 3376; U.S. Pat. No. 4,837,148 and U.S. Pat. No. 4,929,555; *Saccharomyces cerevisiae*, Hinnen et al. (1978) Proc. Natl. Acad. Sci. USA 75: 1929; Ito et al. (1983) J. Bacteriol. 153: 163; *Schizosaccharomyces pombe*, Beach et al. (1981) Nature 300: 706; and *Yarrowia lipolytica*, Davidow, et al. (1985) Curr. Genet. 10: 380471 Gaillardin, et al. (1985) Curr. Genet. 10: 49.

Methods of introducing exogenous DNA into yeast hosts are well-known in the art, and usually include either the transformation of spheroplasts or of intact yeast cells treated with alkali cations. Transformation procedures usually vary with the yeast species to be transformed. See e.g., Kurtz et al. (1986) Mol. Cell. Biol. 6: 142; Kunze et al. (1985) J. Basic Microbiol. 25: 141, for Candida; Gleeson et al. (1986) J. Gen. Microbioy. 132: 3459; Roggenkamp et al. (1986) Mol. Gen. Genet. 202: 302, for Hansenula; Das et al. (1984) J. Bacteriol. 158: 1165; De Louvencourt et al. (1983) J. Bacteriol. 154: 1165; Van den Berg et al. (1990) Bio/Technology 8: 135, for Kluyveromyces; Cregg et al. (1985) Mol. Cell. Biol. 5: 3376; Kunze et al. (1985) J. Basic Microbiol. 25: 141; U.S. Pat. No. 4,837,148 and U.S. Pat. No. 4,929,555, for Pichia; Hinnen et al. (1978) Proc. Natl. Acad. Sci. USA 75; 1929; Ito et al. (1983) J. Bacteriol. 153: 163, for Saccharomyces; Beach et al. (1981) Nature 300: 706, for Schizosaccharomvces; Davidow et al. (1985) Curr. Genet. 10: 39; Gaillardin et al. (1985) Curr. Genet. 10: 49, for Yarrowia.

E. Vaccines

Proteins encoded by the CagI region (as well as DNA from the region itself in the form of polynucleotide vaccines) may be used as a sole vaccine candidate or in combination with one or more other antigens, the latter either from *H. pylori* or other pathogenic sources. Preferred are "cocktail" vaccines comprising, for example, the cytotoxin (CT or VacA) antigen, the CagA protein, and the urease. Additionally, the hsp can be added to one or more of these components. These vaccines may either be prophylactic (to prevent infection) or therapeutic (to treat disease after infection).

Such vaccines comprise *H. pylori* antigen or antigens, usually in combination with "pharmaceutically acceptable carriers", which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (and other submicron oil-in-water emulsions described in PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc; and (6) other substances that act as immunostimulating agents to enhance the effectiveness of the composition. Alum and MF59 are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-huydroxyphosphoryloxy)-ethylamine (MTP-PE), etc.

The immunogenic compositions (e.g., the antigen or polynucleotide, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic polypeptides or nucleotides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g., by injection, either subcutaneously or intramuscularly. Additional formulations suitable for other modes of administration include oral and pulmonary formulations, suppositories, and transdermal applications. Oral formulations are most preferred for the *H. pylori* proteins. Dosage treatment may be a single dose schedule or a multiple dose schedule. The vaccine may be administered in conjunction with other immunoregulatory agents.

F. Immunodiagnostic Assays

*H. pylori* antigens encoded by the CagI regions can be used in immunoassays to detect antibody levels (or conversely *H. pylori* antibodies can be used to detect antigen levels) and correlation can be made with gastroduodenal disease and with duodenal ulcer in particular. Immunoassays based on well defined, recombinant antigens can be developed to replace the invasive diagnostics methods that are used today. Antibodies to *H. pylori* proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

G. Examples

The examples presented below are provided as a further guide to the practitioner of ordinary skill in the art and are not to be construed as limiting the invention in any way.

1. Materials and methods a. Growth of *H. pylori* and DNA isolation

*H. pylori* strains can be cultured in solid or liquid media for 3 days at 37° C., both in microaerophilic atmosphere using Oxoid (Basingstoke, England) or Becton and Dickinson (Cockeysville, Md.) gas pack generators or in an incubator containing air supplemented with 50% $CO_2$, (26). The bacteria can be harvested and resuspended in STE (NaCl 0.1M, Tris-HCl 10 mM pH 8, EDTA 1 mM pH 8) containing lysozyme at a final concentration of 100 micrograms/ml and incubated at room temperature for 5 min. To lyse the bacteria SDS can be added to a final concentration 1% and heated at 65° C. After the addition of proteinase K at final concentration of 25 micrograms/ml, the solution can be incubated at 50° for 2 hours. The DNA can be purified by CsCl gradient in the presence of ethidium bromide, precipitated with 77% ethanol and recovered with a sealed glass capillary.

b. Construction and screening of a lambda gt11 expression library

To generate a lambda gt11 expression library, genomic DNA from the CCUG 17874 strain partially digested with restriction enzymes can be used. After fractionation on 0.8% agarose gel, the DNA between 0.6 and 8 Kb in size can be eluted using a Costar Spin-X (0.22 micron) microcentrifuge filter. The products from each digestion can be combined, and used to construct an expression library, using the lambda gt11 cloning system kit (Bethesda Research Laboratories) and the Gigapack II Gold packaging kit (Stratagene, La Jolla, Calif.).

c. Cloning

Using overlapping libraries of *H. pylori* DNA from strain CCUG 17874 digested with EcoRI and HindIII, cloned into vector Bluscript SK+, contiguous clones covering more than 31,000 bases of the *H. pylori* chromosome were identified, containing a full-length copy of the CagI region. Using random transpose mutagenesis and ad hoc deletions in different subclones, phenotypic variants were produced by allelic exchange.

As can be seen from FIG. 1, four clones, E64 (14,500 bases), H12 (4000 bases), 5B (7800 bases), and 11.1A (5900 bases), generated from the plasmid library, contain the entire CagI region and these four clones have been deposited with the American Type Culture Collection (ATCC), see below. These clones overlap with the CagA region (see PCT Publ. No. WO 93/18150 for the sequence for CagA). If one looks at the sequences on FIG. 1 designated 1, 2, and 3, the following is noted: Sequence 1 (10299 bases) (SEQ ID NOS 1 and 5) contains the 3'-terminus of CagA, the entire CagA gene, and part of CagI. This sequence starts with nucleotide 1 and terminates at nucleotide 10299 (SEQ ID NOS 1 and 5). Within this region, from nucleotides 4909 to 10299 is the CagA locus. From nucleotide 1 to 4908 is the 3'-terminus of CagI. Sequence 2 (5599 bases) starts with nucleotide 1 and terminates at 5599 (SEQ ID NOS 9 and 13); there is a minor gap of 400 base pairs between nucleotide 5599 of sequence 2 and nucleotide 1 of sequence 1. Sequence 3 (1529 bases) starts with nucleotide 1 and terminates at 1529 (SEQ ID NOS 17 and 21). Again, there is a minor gap of 400 base pairs between nucleotide 1529 of sequence 3 and nucleotide 1 of sequence 2. By assembling sequences 1, 2, and 3, the CagI region is covered from the 5'-terminus to the 3'-terminus. Furthermore, FIG. 3 is the complete nucleotide sequence of the CagI locus (19,932 base pairs) (SEQ ID NO 25), including the true 5'-terminus of CagI, contained in clone E64, which is about 2500 bases upstream from the beginning of sequence 3.

d. Sequencing

The nucleotide sequences of the overlapping clones was determined by manual and automated sequencing using nested deletions and primer walking. The produced data were subjected to computer analysis using the Wisconsin Genetic Group package running on parallel supercomputers. FIGS. 2 and 3 show the nucleotide (SEQ ID NOS 1, 5, 9, 13, 17, and 21 for FIG. 2 and SEQ ID NO 25 for FIG. 3) and predicted amino acid sequences of the CagI region. (SEQ ID NOS 2–4, 6–8, 10–12, 14–16, 18–20, and 22–24 for FIG. 2)

e. Structure of the CagI region

The CagI region contains clusters of putative open reading frames (ORFs) with different polarity. FIG. 4 shows the putative open reading frames (ORF) for this region and homologies with known proteins (SEQ ID NOS 26–46). It is hypothesized that some of these ORFs may encode exporter molecules with homology to the ptl genes of *Bordetella pertussis* and VIR B4 genes of *Agrobacterium tumefaciens* and for proteins with motifs shared by purported invasion factors of Salmonella genus. Predicted amino acid sequences for the various frameshifts are shown in FIGS. 2 and 4.

f. Hybridizations

All the clones were tested by Southern blotting on the DNA isolated from 44 well-characterized clinical isolates of *H. pylori*. The contiguous fragments located in the CagI region were able to recognize homologous sequences in all Type I strains of *H. pylori* but failed to hybridize with the DNA from Type II strains of *H. pylori*. It is possible that the approximately 120 base pair DNA segment ("MAK") present at both the 5'- and 3'-terminus of the CagI region may account for evolutionary divergence of Type I and Type II *H. pylori* bacteria.

H. Deposit of Biological Materials

The following materials were deposited on Apr. 7, 1995, with the American Type Culture Collection (ATCC), 12301 Parklawn Drive, Rockville, Md., phone (301) 231-5519, under the terms of the Budapest Treaty on the International Recognition of the Deposit of Microorganisms for Purposes of Patent Procedure.

ATCC No. 69781 *E. coli* host strain TG1 containing plasmid 11.1A (CMCC #4411);

ATCC No. 69782 *E. coli* host strain TG1 containing plasmid 5B (CMCC #4412);

ATCC No. 69783 *E. coli* host strain TG1 containing plasmid H12 (CMCC #4413); and ATCC No. 69784 *E. coli* host strain DH10B containing plasmid E64 (CMCC #4421).

These deposits are provided as convenience to those of skill in the art, and are not an admission that a deposit is required under 35 U.S.C. §112. The nucleic acid sequences of these deposits, as well as the amino acid sequences of the polypeptides encoded thereby, are incorporated herein by reference and should be referred to in the event of any error in the sequences described herein as compared with the sequences of the deposits. A license may be required to make, use, or sell the deposited materials, and no such license is granted hereby.

What is claimed is:

1. A composition comprising an isolated *Helicobacter pylori* CagI polynucleotide selected from the group consisting of SEQUENCE ID Nos. 9, 13, 17 and 21, or a polynucleotide encoding a polypeptide selected from the group consisting of SEQUENCE ID Nos. 3, 4, 10–12, 14–16, 18–20, 22–24, 26–40, and 45–46.

2. A composition comprising a probe comprising the polynucleotide of claim 1.

3. A diagnostic nucleic acid assay kit containing the probe of claim 2.

4. A composition comprising a vector comprising the polynucleotide of claim 1.

5. A composition comprising a host cell transformed with the vector of claim 4.

6. A method for recombinately producing an *H. pylori* protein comprising culturing the host cell of claim 5 and isolating the recombinant polypeptide.

* * * * *

UNITED STATES PATENT AND TRADEMARK OFFICE
CERTIFICATE OF CORRECTION

PATENT NO. : 5,928,865
DATED : July 27, 1999
INVENTOR(S) : Antonello Covacci

It is certified that error appears in the above-identified patent and that said Letters Patent is hereby corrected as shown below:

At column 24, line 32, delete "These clones overlap" and insert --Clone 11.1A overlaps--.

At column 24, line 36, delete "CagA," (first occurrence), and insert --CagI and--.

At column 24, line 46, delete "400" and insert --600--.

Signed and Sealed this

Tenth Day of October, 2000

Attest:

Q. TODD DICKINSON

Attesting Officer

Director of Patents and Trademarks